US012648572B2

(12) United States Patent
Schneider et al.

(10) Patent No.: US 12,648,572 B2
(45) Date of Patent: Jun. 9, 2026

(54) PROTEOLYTICALLY STABLE U1-AGATOXIN-TA1B VARIANT POLYPEPTIDES FOR PEST CONTROL

(71) Applicant: Vestaron Corporation, Kalamazoo, MI (US)

(72) Inventors: Kyle Schneider, Kalamazoo, MI (US); Alexandra Haase, Kalamazoo, MI (US); Breck Davis, Kalamazoo, MI (US); Ryan Garrett, Kalamazoo, MI (US)

(73) Assignee: Vestaron Corporation, Kalamazoo, MI (US)

( * ) Notice: Subject to any disclaimer, the term of this patent is extended or adjusted under 35 U.S.C. 154(b) by 790 days.

(21) Appl. No.: 17/919,940

(22) PCT Filed: Apr. 20, 2021

(86) PCT No.: PCT/US2021/028254
§ 371 (c)(1),
(2) Date: Oct. 19, 2022

(87) PCT Pub. No.: WO2021/216621
PCT Pub. Date: Oct. 28, 2021

(65) Prior Publication Data
US 2023/0337684 A1 Oct. 26, 2023

Related U.S. Application Data

(60) Provisional application No. 63/012,755, filed on Apr. 20, 2020.

(51) Int. Cl.
| | |
|---|---|
| *A01N 63/50* | (2020.01) |
| *A01N 25/08* | (2006.01) |
| *C12N 1/16* | (2026.01) |
| *C12N 15/63* | (2006.01) |
| *C12R 1/87* | (2006.01) |

(52) U.S. Cl.
CPC ............. *A01N 63/50* (2020.01); *A01N 25/08* (2013.01); *C12N 1/16* (2013.01); *C12N 15/63* (2013.01); *C12R 2001/87* (2021.05)

(58) Field of Classification Search
CPC .......... A01N 63/50; A01N 25/08; C12N 1/16; C12N 15/63; C12R 2001/87
See application file for complete search history.

(56) References Cited

U.S. PATENT DOCUMENTS

| | | |
|---|---|---|
| 683,106 A | 9/1901 | Du Buit |
| 1,029,203 A | 6/1912 | Loewenthal |
| 1,636,688 A | 7/1927 | Harris |
| 3,714,140 A | 1/1973 | Sipos |
| 3,933,590 A | 1/1976 | Oguma et al. |
| 3,946,780 A | 3/1976 | Sellers |
| 4,363,798 A | 12/1982 | D'Orazio |
| 4,411,994 A | 10/1983 | Gilbert et al. |
| 4,943,434 A | 7/1990 | Lidert |
| 4,945,050 A | 7/1990 | Sanford et al. |
| 4,959,221 A | 9/1990 | Holmes |
| 4,988,623 A | 1/1991 | Schwarz et al. |
| 4,996,155 A | 2/1991 | Sick et al. |
| 5,023,182 A | 6/1991 | Vail |
| 5,045,469 A | 9/1991 | Payne et al. |
| 5,055,294 A | 10/1991 | Gilroy |
| 5,073,632 A | 12/1991 | Donovan |
| 5,104,974 A | 4/1992 | Sick et al. |
| 5,135,867 A | 8/1992 | Payne et al. |
| 5,153,131 A | 10/1992 | Wolf et al. |
| 5,153,133 A | 10/1992 | Schwarz et al. |
| 5,155,034 A | 10/1992 | Wolf et al. |
| 5,187,091 A | 2/1993 | Donovan et al. |
| 5,236,843 A | 8/1993 | Narva et al. |
| 5,281,530 A | 1/1994 | Sick et al. |
| 5,316,905 A | 5/1994 | Mori et al. |
| 5,322,687 A | 6/1994 | Donovan et al. |
| 5,330,908 A | 7/1994 | Spaulding |
| 5,356,623 A | 10/1994 | Von Tersch et al. |
| 5,372,817 A | 12/1994 | Locke et al. |

(Continued)

FOREIGN PATENT DOCUMENTS

| | | |
|---|---|---|
| AU | 2001285900 B2 | 2/2005 |
| AU | 784649 B2 | 5/2006 |

(Continued)

OTHER PUBLICATIONS

Drumm et al, Genetic Variation and Clinical Heterogeneity in Cystic Fibrosis, Annu. Rev. Pathol. Mech. Dis., 2012, 7, pp. 267-282.*
Yampolsky et al, The Exchangeability of Amino Acids in Proteins, Genetics, 2005, 170, pp. 1459-1472.*
Ayres, Nicola M. et al., Genetic Transformation of Rice, Critical Reviews in Plant Science, 1994, vol. 13, No. 3 pp. 219-239.
Barloy, F. et al., Distribution of Clostridial cry-Like Genes Among Bacillus thuringiensis and Clostridium Strains, Current Microbiology, 1998, vol. 36, pp. 232-237.
Benchabane, Meriem, et al. Preventing unintended proteolysis in plant protein biofactories, Plant Biotechnology Journal, No. 6, 2008, pp. 633-648.
Borovsky, D., Trypsin-modulating oostatic factor: a potential new larvicide for mosquito control, Journal of Experimental Biology, 2003 vol. 206, No. 21, pp. 3869-3875.

(Continued)

*Primary Examiner* — Li N Komatsu
(74) *Attorney, Agent, or Firm* — Honigman LLP; Jeffrey I. Lehrberg; Johnathan P. O'Brien

(57) ABSTRACT

New insecticidal proteins, nucleotides, peptides, and their expression in plants. Methods of producing new nucleotides and new peptides, new processes, new production techniques, new formulations, and new organisms. The present disclosure is also related to and describes novel peptides called TVPs, which are non-natural peptide variations based upon the U1-agatoxin-Ta1b toxin derived from the Hobo spider. Here, we describe: genes encoding TVPs; formulations and combinations comprising TVP genes and/or peptides; and methods using the same that are useful for the control of pests.

10 Claims, 31 Drawing Sheets

Specification includes a Sequence Listing.

(56) References Cited

U.S. PATENT DOCUMENTS

| | | | |
|---|---|---|---|
| 5,378,625 A | 1/1995 | Donovan et al. |
| 5,407,825 A | 4/1995 | Payne et al. |
| 5,411,736 A | 5/1995 | Locke et al. |
| 5,424,409 A | 6/1995 | Ely et al. |
| 5,436,136 A | 7/1995 | Hinnen et al. |
| 5,441,934 A | 8/1995 | Krapcho et al. |
| 5,530,195 A | 6/1996 | Kramer et al. |
| 5,545,820 A | 8/1996 | Gatehouse et al. |
| 5,560,909 A | 10/1996 | Rheaume et al. |
| 5,593,881 A | 1/1997 | Thompson et al. |
| 5,616,319 A | 4/1997 | Donovan et al. |
| 5,670,365 A | 9/1997 | Feitelson |
| 5,679,343 A | 10/1997 | Donovan et al. |
| 5,683,691 A | 11/1997 | Peferoen et al. |
| 5,688,764 A | 11/1997 | Johnson et al. |
| 5,723,756 A | 3/1998 | Peferoen et al. |
| 5,723,758 A | 3/1998 | Payne et al. |
| 5,736,135 A | 4/1998 | Goeddel et al. |
| 5,736,145 A | 4/1998 | Murali |
| 5,741,669 A | 4/1998 | Krapcho et al. |
| 5,743,477 A | 4/1998 | Walsh et al. |
| 5,753,492 A | 5/1998 | Schnepf et al. |
| 5,763,568 A | 6/1998 | Atkinson et al. |
| 5,766,927 A | 6/1998 | Baker et al. |
| 5,824,792 A | 10/1998 | Payne et al. |
| 5,831,011 A | 11/1998 | Payne et al. |
| 5,837,237 A | 11/1998 | Peferoen et al. |
| 5,858,353 A | 1/1999 | Miller et al. |
| 5,871,780 A | 2/1999 | Moss |
| 5,874,288 A | 2/1999 | Thompson et al. |
| 5,932,209 A | 8/1999 | Thompson et al. |
| 5,942,664 A | 8/1999 | Baum et al. |
| 5,959,182 A | 9/1999 | Atkinson et al. |
| 5,973,231 A | 10/1999 | Bradfisch et al. |
| 5,985,831 A | 11/1999 | Bradfisch et al. |
| 6,007,832 A | 12/1999 | Stapleton |
| 6,028,246 A | 2/2000 | Lambert et al. |
| 6,042,843 A | 3/2000 | McIntosh |
| 6,043,415 A | 3/2000 | Strizhov et al. |
| 6,048,839 A | 4/2000 | Bradfisch et al. |
| 6,063,605 A | 5/2000 | Ely et al. |
| 6,063,756 A | 5/2000 | Donovan et al. |
| 6,077,937 A | 6/2000 | Payne et al. |
| 6,096,708 A | 8/2000 | Payne et al. |
| 6,107,278 A | 8/2000 | Schnepf et al. |
| 6,110,707 A | 8/2000 | Newgard et al. |
| 6,130,074 A | 10/2000 | Brennan |
| 6,143,550 A | 11/2000 | Lambert et al. |
| 6,150,165 A | 11/2000 | Payne et al. |
| 6,150,589 A | 11/2000 | Payne et al. |
| 6,156,573 A | 12/2000 | Malvar et al. |
| 6,159,724 A | 12/2000 | Ehret |
| 6,165,715 A | 12/2000 | Collins et al. |
| 6,165,981 A | 12/2000 | Flaa et al. |
| 6,166,195 A | 12/2000 | Schnepf et al. |
| 6,171,586 B1 | 1/2001 | Lam et al. |
| 6,172,281 B1 | 1/2001 | Van Mellaert et al. |
| 6,177,075 B1 | 1/2001 | Christian et al. |
| 6,261,553 B1 | 7/2001 | Bradley et al. |
| 6,281,413 B1 | 8/2001 | Kramer et al. |
| 6,312,738 B1 | 11/2001 | O'Shea et al. |
| 6,320,100 B1 | 11/2001 | Koziel et al. |
| 6,326,351 B1 | 12/2001 | Donovan et al. |
| 6,391,649 B1 | 5/2002 | Chait et al. |
| 6,399,330 B1 | 6/2002 | Donovan et al. |
| 6,448,226 B1 | 9/2002 | Lambert et al. |
| 6,468,523 B1 | 10/2002 | Mettus et al. |
| 6,528,484 B1 | 3/2003 | Ensign et al. |
| 6,537,756 B1 | 3/2003 | Rupar et al. |
| 6,548,285 B1 | 4/2003 | Swinkels et al. |
| 6,570,005 B1 | 5/2003 | Schnepf et al. |
| 6,573,240 B1 | 6/2003 | Payne et al. |
| 6,583,264 B2 | 6/2003 | King et al. |
| 6,630,619 B1 | 10/2003 | East |
| 6,645,739 B2 | 11/2003 | Clark |
| 6,686,452 B2 | 2/2004 | Rupar et al. |
| 6,727,409 B1 | 4/2004 | Lambert et al. |
| 6,737,273 B2 | 5/2004 | Payne et al. |
| 6,780,408 B1 | 8/2004 | Bosch et al. |
| 6,784,337 B1 | 8/2004 | Atkinson et al. |
| 6,811,790 B1 | 11/2004 | Damaria et al. |
| 6,831,062 B2 | 12/2004 | Thompson et al. |
| 6,855,873 B1 | 2/2005 | Van Mellaert et al. |
| 6,949,626 B2 | 9/2005 | Donovan et al. |
| 6,962,705 B2 | 11/2005 | Malvar et al. |
| 6,991,790 B1 | 1/2006 | Lam et al. |
| 7,019,197 B1 | 3/2006 | Christou et al. |
| 7,138,568 B2 | 11/2006 | Payne et al. |
| 7,161,062 B2 | 1/2007 | Ffrench-Constant et al. |
| 7,173,106 B2 | 2/2007 | King et al. |
| 7,208,474 B2 | 4/2007 | Bermudez et al. |
| 7,208,656 B2 | 4/2007 | Isaac et al. |
| 7,214,788 B2 | 5/2007 | Guzov et al. |
| 7,227,056 B2 | 6/2007 | English et al. |
| 7,241,612 B2 | 7/2007 | Shapiro-Ilan et al. |
| 7,244,880 B2 | 7/2007 | Arnaut et al. |
| 7,250,501 B2 | 7/2007 | Malvar et al. |
| 7,268,275 B2 | 9/2007 | Ffrench-Constant et al. |
| 7,271,002 B2 | 9/2007 | Kotin et al. |
| 7,279,547 B2 | 10/2007 | King et al. |
| 7,304,206 B2 | 12/2007 | Malvar et al. |
| 7,332,594 B2 | 2/2008 | Baum et al. |
| 7,332,650 B2 | 2/2008 | Ali et al. |
| 7,354,993 B2 | 4/2008 | King et al. |
| 7,355,099 B2 | 4/2008 | Carozzi et al. |
| 7,361,808 B2 | 4/2008 | Boets et al. |
| 7,419,801 B2 | 9/2008 | Barr et al. |
| 7,476,781 B2 | 1/2009 | Abad et al. |
| 7,491,698 B2 | 2/2009 | Hey et al. |
| 7,504,229 B2 | 3/2009 | Donovan et al. |
| 7,504,253 B2 | 3/2009 | Reed et al. |
| 7,510,878 B2 | 3/2009 | Abad et al. |
| 7,511,188 B2 | 3/2009 | Ali et al. |
| 7,528,293 B2 | 5/2009 | Ali et al. |
| 7,572,587 B2 | 8/2009 | Rupar et al. |
| 7,582,147 B1 | 9/2009 | Parker et al. |
| 7,595,173 B2 | 9/2009 | Krebs et al. |
| 7,655,838 B2 | 2/2010 | Guzov et al. |
| 7,678,764 B2 | 3/2010 | Garigapati et al. |
| 7,777,100 B2 | 8/2010 | Ffrench-Constant et al. |
| 7,785,832 B2 | 8/2010 | Pan et al. |
| 7,943,819 B2 | 5/2011 | Baum et al. |
| 7,956,028 B2 | 6/2011 | Garigapati et al. |
| 8,226,938 B1 | 7/2012 | Meikle et al. |
| 8,314,208 B2 | 11/2012 | Collins |
| 8,541,366 B2 | 9/2013 | Carozzi et al. |
| 8,709,399 B2 | 4/2014 | Vidal et al. |
| 8,778,372 B2 | 7/2014 | Lloyd et al. |
| 8,993,295 B2 | 3/2015 | Seed et al. |
| 9,201,073 B2 | 12/2015 | Finley et al. |
| 9,217,140 B2 | 12/2015 | Ryali et al. |
| 9,320,816 B2 | 4/2016 | Zhou et al. |
| 9,429,566 B2 | 8/2016 | Marinier et al. |
| 9,567,381 B2 | 2/2017 | Kennedy et al. |
| 9,635,858 B2 | 5/2017 | Newberry et al. |
| 9,714,408 B2 | 7/2017 | Tanaka et al. |
| 10,023,836 B2 | 7/2018 | Akada |
| 10,273,333 B2 | 4/2019 | Maynard |
| 10,442,834 B2 | 10/2019 | Sajiki et al. |
| 10,563,169 B2 | 2/2020 | Von Hagen |
| 10,588,957 B2 | 3/2020 | Scholz et al. |
| 11,535,653 B2 * | 12/2022 | Carlson .................. C12N 15/80 |
| 2001/0010932 A1 | 8/2001 | Schnepf et al. |
| 2001/0026939 A1 | 10/2001 | Rice et al. |
| 2001/0026941 A1 | 10/2001 | Held et al. |
| 2002/0015066 A1 | 2/2002 | Siwinski et al. |
| 2002/0152496 A1 | 10/2002 | Fischhoff et al. |
| 2003/0017967 A1 | 1/2003 | Asano et al. |
| 2003/0046726 A1 | 3/2003 | Koziel et al. |
| 2003/0054391 A1 | 3/2003 | Bulla, Jr. |
| 2003/0134310 A1 | 7/2003 | Cujec |
| 2003/0144192 A1 | 7/2003 | Donovan et al. |
| 2003/0167517 A1 | 9/2003 | Arnaut et al. |
| 2003/0167522 A1 | 9/2003 | Narva et al. |

(56)    References Cited

U.S. PATENT DOCUMENTS

| | | |
|---|---|---|
| 2003/0207806 A1 | 11/2003 | Ensign et al. |
| 2003/0229919 A1 | 12/2003 | Isaac et al. |
| 2004/0018982 A1 | 1/2004 | Schnepf et al. |
| 2004/0033523 A1 | 2/2004 | English et al. |
| 2004/0058860 A1 | 3/2004 | Payne et al. |
| 2004/0093637 A1 | 5/2004 | Malvar et al. |
| 2004/0123343 A1 | 6/2004 | La Rosa et al. |
| 2004/0194165 A1 | 9/2004 | Payne et al. |
| 2005/0091714 A1 | 4/2005 | Sunchis et al. |
| 2005/0097635 A1 | 5/2005 | Lambert et al. |
| 2005/0165215 A1 | 7/2005 | Bigelow |
| 2005/0227321 A1 | 10/2005 | Krebs et al. |
| 2006/0040352 A1 | 2/2006 | Retallack |
| 2006/0051822 A1 | 3/2006 | Donovan et al. |
| 2006/0174372 A1 | 8/2006 | Malvar et al. |
| 2006/0218666 A1 | 9/2006 | Isaac et al. |
| 2006/0242734 A1 | 10/2006 | King et al. |
| 2007/0020625 A1 | 1/2007 | Duchaud et al. |
| 2007/0061919 A1 | 3/2007 | Baum et al. |
| 2007/0074308 A1 | 3/2007 | Boets et al. |
| 2007/0163000 A1 | 7/2007 | Rupar et al. |
| 2007/0208168 A1 | 9/2007 | Guzov et al. |
| 2007/0245430 A1 | 10/2007 | Abad et al. |
| 2007/0277263 A1 | 11/2007 | Anderson et al. |
| 2008/0016596 A1 | 1/2008 | Abad et al. |
| 2008/0020968 A1 | 1/2008 | Abad et al. |
| 2008/0040827 A1 | 2/2008 | Donovan et al. |
| 2008/0047034 A1 | 2/2008 | Arnaut et al. |
| 2008/0109924 A1 | 5/2008 | Ali et al. |
| 2008/0120742 A1 | 5/2008 | Ali et al. |
| 2008/0120744 A1 | 5/2008 | Ali et al. |
| 2008/0120745 A1 | 5/2008 | Ali et al. |
| 2008/0120746 A1 | 5/2008 | Ali et al. |
| 2008/0120747 A1 | 5/2008 | Ali et al. |
| 2008/0127375 A1 | 5/2008 | Ali et al. |
| 2009/0099081 A1 | 4/2009 | Carozzi et al. |
| 2009/0183278 A1 | 7/2009 | Abad et al. |
| 2010/0055761 A1 | 3/2010 | Seed et al. |
| 2010/0081619 A1 | 4/2010 | Tedford et al. |
| 2012/0028286 A1 | 2/2012 | Saller |
| 2015/0148288 A1 | 5/2015 | Kennedy et al. |
| 2015/0257383 A1 | 9/2015 | Deisenroth et al. |
| 2018/0362598 A1 | 12/2018 | Carlson et al. |
| 2019/0261634 A1 | 8/2019 | Carlson et al. |
| 2020/0255482 A1 | 8/2020 | Kennedy et al. |

FOREIGN PATENT DOCUMENTS

| | | | |
|---|---|---|---|
| CA | 2410153 A1 | 6/2004 |
| CN | 1260397 A | 7/2000 |
| CN | 1366822 A | 9/2002 |
| CN | 1401772 A | 3/2003 |
| CN | 1199569 C | 5/2005 |
| CN | 1952151 A | 4/2007 |
| CN | 101003789 A | 7/2007 |
| CN | 104411714 A | 3/2015 |
| CN | 105420316 A | 3/2016 |
| CN | 106172504 A | 12/2016 |
| CN | 106367361 A | 2/2017 |
| CN | 106367361 B | 8/2019 |
| EP | 0431829 A1 | 6/1991 |
| EP | 0473645 B1 | 3/1998 |
| EP | 0834254 A1 | 4/1998 |
| EP | 1681351 A1 | 7/2006 |
| EP | 1812464 B1 | 10/2008 |
| EP | 3528617 A4 | 11/2020 |
| JP | 2005139167 A | 6/2005 |
| JP | 2007006895 A | 1/2007 |
| JP | 2008518624 A | 6/2008 |
| JP | 2009286708 A | 12/2009 |
| JP | 2012504623 A | 2/2012 |
| JP | 7227957 B2 | 2/2023 |
| MX | 9606262 A | 1/1998 |
| MX | 01004361 A | 6/2003 |
| MX | PA02008705 A | 12/2004 |
| MX | 03006130 A | 2/2005 |
| RU | 2278161 C1 | 6/2006 |
| RU | 2278181 C2 | 6/2006 |
| UA | 75317 C2 | 4/2006 |
| UA | 75570 C2 | 5/2006 |
| WO | 86/03777 A1 | 7/1986 |
| WO | 9100915 A1 | 1/1991 |
| WO | 9202139 A1 | 2/1992 |
| WO | 9315192 A1 | 8/1993 |
| WO | 9502962 A1 | 2/1995 |
| WO | 9534656 A1 | 12/1995 |
| WO | 9708197 A1 | 3/1997 |
| WO | 9808932 A1 | 3/1998 |
| WO | 199840490 A1 | 9/1998 |
| WO | 199840491 A2 | 9/1998 |
| WO | 2000026371 A1 | 5/2000 |
| WO | 2000026378 A1 | 5/2000 |
| WO | 2001014562 A1 | 3/2001 |
| WO | 2001034811 A2 | 5/2001 |
| WO | 2001047952 A2 | 7/2001 |
| WO | 2002014517 A1 | 2/2002 |
| WO | 2002015701 A2 | 2/2002 |
| WO | 2002057664 A2 | 7/2002 |
| WO | 2003042369 A2 | 5/2003 |
| WO | 2003082910 A1 | 10/2003 |
| WO | 2004016653 A2 | 2/2004 |
| WO | 2004020636 A1 | 3/2004 |
| WO | 2005066202 A2 | 7/2005 |
| WO | 2005082077 A2 | 9/2005 |
| WO | 2006052806 A2 | 5/2006 |
| WO | 2006053473 A1 | 5/2006 |
| WO | 2007027776 A2 | 3/2007 |
| WO | 2007045160 A1 | 4/2007 |
| WO | 2007062064 A2 | 5/2007 |
| WO | 2007087567 A2 | 8/2007 |
| WO | 2007107302 A2 | 9/2007 |
| WO | 2008036138 A2 | 3/2008 |
| WO | 2008132743 A2 | 11/2008 |
| WO | 2008153551 A1 | 12/2008 |
| WO | 2009155557 A2 | 12/2009 |
| WO | 2010/039652 A2 | 4/2010 |
| WO | 2010133644 A2 | 11/2010 |
| WO | 2011084634 A1 | 7/2011 |
| WO | 2011117351 A1 | 9/2011 |
| WO | 2012038950 A1 | 3/2012 |
| WO | 2013040142 A2 | 3/2013 |
| WO | 2013134734 A2 | 9/2013 |
| WO | 2013166211 A2 | 11/2013 |
| WO | 2014173716 A1 | 10/2014 |
| WO | 2014200910 A2 | 12/2014 |
| WO | 2016044575 A1 | 3/2016 |
| WO | 2018075269 A1 | 4/2018 |
| WO | 2018175677 A1 | 9/2018 |
| WO | 2018207036 A1 | 11/2018 |
| WO | 2019176676 A1 | 9/2019 |
| WO | 2020056315 A1 | 3/2020 |
| WO | 2021216621 A2 | 10/2021 |

OTHER PUBLICATIONS

Bosmans, Frank et al, Sea Anemone Venom as a Source of Insecticidal Peptides Acting on Voltage-Gated Na+ Channels, Toxicon, V 49, No. 4, pp. 550-560, Mar. 2007; XP002705659, ISN:0041-0101.

De Loose, M., et al., The extensin signal peptide allows secretion of a heterologous protein from protoplasts, Gene, 1991, vol. 99, pp. 95-100.

Hernandez-Campuzano et al., Expression of a spider venom peptide in transgenic tobacco confers insect resistance, Toxicon, 2009, vol. 53, No. 1, pp. 122-128.

Hiei et al., "Efficient transformation of rice (Oryza sativa L.) mediated by Agrobacterium and sequence analysis of the boundaries of the T-NDA", The Plant Journal, 1994, vol. 6, No. 2, pp. 271-282.

Jones et al., "The Cys-Loop Ligand-Gated Ion Channel Gene Superfamily of the Nematode, Caenorhabditis Elegans", Invert Neurosci, 2008, vol. 8, pp. 41-47.

Sambrook and Russell, Molecular Cloning: A Laboratory Manual, 2001, Table of Contents.

(56) References Cited

OTHER PUBLICATIONS

Stalker et al., Purification and Properties of a Nitrilase Specific for the Herbicide Bromoxynil and Corresponding Nucleotide Sequence Analysis of the bxn Gene, J. Biol. Chem., May 5, 1988, vol. 263, No. 13, pp. 6310-6314.

Van Damme, E.J.M., et al., "Biosynthesis, primary structure and molecular cloning of snowdrop (*Galanthus nivalis* L.) lectin", European Journal of Biochemistry, 1991, vol. 202, pp. 23-30.

Yokoyama et al., "Novel cry gene from Paenibacillus lentimorbus strain Semadara inhibits ingestion and promotes insecticidal activity in Anomala cuprea larvae", J of Invertebrate Pathology, 2004, vol. 85, pp. 25-32.

Anthony Shelton, Ph.D., "Biological Control a Guide to Natural Enemies in North America", as an update dated "Last updated Feb. 25, 2015" by Zachary P. Cohen, Cornell University.

Moran et al., "Molecular analysis of the sea anemone toxin Av3 reveals selectivity to insects and demonstrates the heterogeneity of receptor site-3 on voltage-gated Na+ channels", Biochem. J., 406:41-48, 2007.

Midoro-Horiuti et al., "Variable Expression of Pathogenesis-Related Protein Allergen in Mountain Cedar (*Juniperas ashei*) Pollen", J Immunol, 164(4):2188-2192, 2000.

PCT International Search Report for PCT/US2013/030042, mailed Oct. 28, 2013, 6 pages.

Raymond, Ben et al., "The impact of strain diversity and mixed infections on the evolution of resistance to Bacillus thuringiensis", Proceedings of the Royal Society B, 280:1-9 (http://dx.doi.org/10.1098/rspb.2013.1497), 2013. cited byapplicant.

Svab, et al., High-frequency plastid transformation in tobacco by selection for a chimeric aadA gene, Proc. Natl. Acad. Sci., Feb. 1993, vol. 90, pp. 913-917.

Svab, et al., Stable Transformation of Plastids in Higher Plants, Proc. Natl. Acad. Sci., Nov. 1990, vol. 87, pp. 8526-8530.

Barloy, F. et al., Cloning and Expression of the First Anaerobic Toxin Gene from Clostridium bifermentans subsp. Malaysia, Encoding a New Mosquitocidal Protein with Homologies to Bscillus thuringiensis Delta-Endotoxins, J of Bacteriology, Jun. 1996, vol. 178, No. 11, pp. 3099-3105.

BBC New Article: May 10, 2016, "Kew report makes new tally for nmber of world's plants", Retrieved from < https://www.bbc.com/ news/science-environment-36230858 > on Sep. 23, 2019.

Borovsky, D., et al., Expression of Aedes trypsin-modulating oostatic factor on the virion of TMV: A potential larvicide, Proc Natl Acad Sci, Dec. 12, 2006, vol. 103, No. 50, pp. 18963-18968.

Broderick, N.A et al., Midgut Bacteria Required for Bacillus Thuringiensis Insecticidal Activity, PNAS, Oct. 10, 2006, vol. 103, No. 41., pp. 15196-15199.

Cavallini, C., Biological Action of Two Tomato Cysteine-Rich Miniproteins, Ph.D. Thesis; Dept of Biotechnology; University of Verona, 2010; XP002705655, retrieved from the internet: URL:http://www.univr.it/documenti/AllegaiOA/allegatooa.sub.--5484.pdf.

Chang, H.C., et al., De novo folding of GFP fusion proteins: high efficiency in eukaryotes but not in bacteria, Journal of Molecular Biology, Oct. 21, 2005, vol. 353, No. 2, pp. 397-409.

Chen, M.H., et al., Signal peptide-dependent targeting of a rice alpha-amylase and cargo proteins to plastids and extracellular compartments of plant cells, Plant Physiology, Jul. 2004, vol. 135, No. 3, pp. 1367-1377.

Czapla, T.H. et al., Effect of Plant Lectins on the Larval Development of Europran Corn Borer (Lepidoptera: *Pyralidae*) and Southern Corn Rootworm (Coleoptera: *Chrysomelidae*) J. Econ. Entomol., Dec. 1990, vol. 83, No. 6, pp. 2480-2485.

Dauplais, M., et al., "On the convergent evolution of animal toxins", Journal of Biological Chemistry, Feb. 14, 1997; vol. 272, No. 7, pp. 4302-4309.

Jennings et al., "Biosynthesis and insecticidal properties of plant cyclotides: The cyclic knotted proteins from Oldenlandia affinis", PNAS, 98(19):10614-10619, 2001.

Kumari et al., "Cysteine-Rich Peptide Family with Unusual Disulfide Connectivity from Jasminum sambac", Journal of Natural Products, 78:2791-2799, 2015.

Li, WP et al., Expression and Characterization of a Recombinant Cry1Ac Crystal Protein Fused with an Insect-Specific Neurotoxin Omega-ACTX-Hv1a in Bacillus Thuringiensis, GENE (Amsterdam), V 498, No. 2, pp. 323-327, Feb. 2012, XP002705660.

Anonymous: GSP: BAY44659, Retrieved from the Internet: 1-4 URL:http://ibis.internal.epo.org/exam/dbfetch.jsp?id= GSP:BAY44659 [retrieved on Oct. 15, 2020], 1 page.

Chambaud, I. et al. "The complete genome sequence of the murine respiratory pathogen Mycoplasma pulmonis", Nucleic Acids Research, Information Retrieval Ltd, vol. 29, No. 10, Jan. 1, 2001 (Jan. 1, 2001), pp. 2145-2153.

NCBI, UniProtKB/Swiss-Prot. S0F209.1, Omega/Kappa-hexatoxin-Hv1h [Hydronyche versuta], Oct. 2014, 2 pages.

PCT International Search Report, PCT/US2017/055596, mailed Feb. 23, 2018 (6 pages).

UniProt P07984 GUNA_CELFI—Endoglucanse A from C. fimi, Retrieved from < https://www.unitprot.org/uniprotkb/P07984/ entry > on Aug. 4, 2022.

Angsuthanasombat, C. et al., "Directed Mutagenesis of the Bacillus Thuringiensis Cry11A Toxin Reveals a Crucial Role in Larvicidal Activity of Arginine-136 in Helix 4," Journal of Biochemistry and Molecular Biology, Sep. 2001, vol. 34, No. 5, pp. 402-407.

Aronson, A. et al., "Why Bacillus thuringiensis insecticidal toxins are so effective: unique features of their mode of action," FEMS Microbiology Letters, 2001, vol. 195, pp. 1-8.

De Dianous, S. et al., "The Effect of the Mode of Application on the Toxicity of Androctonus australis Hector Insect Toxin", Pestic. Sci., 23:35-40, 1988.

Guo, H. et al., "Protein tolerance to random amino acid change," PNAS, Jun. 2004, Vo. 101, No. 25, pp. 9205-9210.

Guo, L. et al., "Fractionation and identification of Alaska pollock skin collagen-derived mineral chelating peptides" Food Chemistry 173: 536-542, 2015.

Hallquiist, N. et al., "Lipopolysaccharide regulates cysteine-rich intestinal protein, a zincfinger protein, in immune cells and plasma", Journal of Leukocyte Biology, 59(2):172-177, 1996 (abstract only).

Harris, J. et al., "Rapid and general profiling of protease specificity by using combinatorial fluorogenic substrate libraries", PNAS, 97(14):7754-7759, 2000.

Helting, T. et al., "Structure of Tetanus Toxin," The Journal of Biological Chemistry, Jan. 1977, vol. 252, No. 1, pp. 187-193.

Pineda, S. et al., "Diversification of a single ancestral gene into a successful toxin superfamily in highly venomous Australian funnel-web spiders," BCM Genomics, 2014, vol. 15, pp. 177-177.

Sainsbury, F. et al., "Multimodal Protein Constructs for Herbivore Insect Control", Toxins, vol. 4, Jun. 12, 2012 (Jun. 12, 2012), pp. 455-475.

Seltzer, J. et al., "Cleavage Specificity of Human Skin Type IV Collagenase (Gelatinase)," The Journal of Biological Chemistry 265(33): 20409-20413, 1990.

Johnson Janice H. et al, "Novel insecticidal peptides from Tegenaria agrestis spider venom may have a direct effect on the insect central nervous system", Archives of Insect Biochemistry and Physiology., vol. {0} 38, No. {0} 1, Dec. 6, 1998 (Dec. 6, 1998), p. 19-31.

Herzig Volker et al, "Evaluation of Chemical Strategies for Improving the Stability and Oral Toxicity of Insecticidal Peptides", Biomedicines, vol. {0} 6, No. {0} 3, Aug. 28, 2018 (Aug. 28, 2018), p. 90.

Jai K. Kaushik et al, "Why Is Trehalose an Exceptional Protein Stabilizer? : An Analysis of the Thermal Stability of Proteins in the Presence of the Compatible Osmolyte Trehalose", Journal of Biological Chemistry, vol. {0} 278, No. {0} 29, Jul. 18, 2003 (Jul. 18, 2003), p. 26458-26465.

Windley Monique J. et al, "Spider-Venom Peptides as Bioinsecticides", Toxins, vol. {0} 4, No. {0} 3, Mar. 22, 2012 (Mar. 22, 2012), p. 191-227.

Hassett Kimberly J et al, "Stabilization of a recombinant ricin toxin A subunit vaccine through lyophilization", European Journal of

(56)        References Cited

OTHER PUBLICATIONS

Pharmaceutics and Biopharmaceutics, Elsevier Science Publishers B. V., Amsterdam, NL, vol. {0} 85, No. {0} 2, Apr. 10, 2013 (Apr. 10, 2013), p. 279-286.

EBI accession No. GSP:BFF54949, Database accession No. BFF54949, "Eratigena agrestis toxic protein (TP), SEQ ID 1765", Sequence information for W02018075269, Jun. 14, 2018 (Jun. 14, 2018).

EBI accession No. GSP:BFF54948, Database accession No. BFF54948, "Eratigena agrestis toxic protein (TP), SEQ ID 1764", Sequence information for W02018075269, Jun. 14, 2018 (Jun. 14, 2018).

International Search Report and Written Opinion issued in related PCT Application No. PCT/US2021/028254, dated. Nov. 19, 2021.

Undheim Eivind A.B. et al, "Weaponization of a Hormone: Convergent Recruitment of Hyperglycemic Hormone into the Venom of Arthropod Predators", Structure, vol. 23, Issue 7, Jul. 7, 2015 (Jul. 7, 2015), pp. 1283-1292.

Venkatraman Ramanujam et al, "Residual Dipolar Couplings for Resolving Cysteine Bridges in Disulfide-Rich Peptides", Frontiers in Chemistry, vol. 7, Jan. 22, 2020 (Jan. 22, 2020), ISSN: 2296-2646, DOI:10.3389/fchem.2019.00889.

Shu, C. et al., "Current Patents Related to Bacillus thuringiensis Insecticidal Crystal Proteins", Recent Patents on DNA Gene Sequences, 2009, vol. 3, No. 1, pp. 26-28.

Tounsi, S. et al., "Cloning and study of the expression of a novel cry1la-type gene from *Bacillus thuringiensis* subsp. Kurstaki," J. Appl. Microbial., 2003, vol. 95, No. 1, pp. 23-28.

Tyndall, J. et al., "Proteases Universally Recognize Beta Strands in Their Active Sites", Chem. Rev., 105:973-999, 2005.

Walters, F. et al., "An Engineered Chymotrypsin/Cathepsin G Site in Domain I Renders Bacillus thuringiensis Cry3A Active against Western Corn Rootworm Larvae", Applied and Environmental Microbiology, 74(2):367-374, 2008.

Gill, G. et al., "Mutants of GAL4 Protein Altered in an Activation Function", Cell, 1987, vol. 51, pp. 121-126.

Clark et al. "Environmental Fate and Effects of Bacillus thuringiensis," 2005, J. Agric. Food Chem., vol. 53, No. 12, pp. 4643-4653.

Ding et al., "Improving the Insecticidal Activity by Expression of a Recombnant cry1Ac Gene with Chitinase-Encoding Gene in Acrystalliferous Bascillus thuringiensis," 2008, Curr Microbiol vol. 56, pp. 442-446.

Godfrey et al., "Microorganisms and their byproducts, nematodes, oils," 2005, California Agriculture, vol. 59, No. 1, pp. 35-40.

Sadeghi et al., Ferritin acts as a target site for the snowdrop lectin (GNA) in the midgut of the cotton leafworm *Spodoptera littoralis*, 2008, Insect Science, vol. 15, pp. 513-519.

Yan, F. et al., "Improved Insecticidal Toxicity by Fusing Cry1Ac of Bacillus thuringiensis with Av3 of Anemonia viridis", Current Microbiology, Published online Dec. 29, 2013 (May 2014), vol. 68, No. 5, p. 604-609.

US EPA: "Pesticide Product Lable, MADEX HP", Aug. 2, 2013 (Aug. 2, 2013), XP055836696, Retrieved from the Internet: URL:https://www3.epa.gov/pesticides/chem_search/ppls/069553-00001-20130802.pdf.

Andrews et al., "Characterizatino of the lipid acyl hydrolase activity of the major potato (*Solanum tuberosum*) tuber protein, patatin, by cloning and abundant expression in a baculovirus vector", Biochem. J., (1988), vol. 252, pp. 199-206.

Anonymous, "Electroporation Methods in Neuroscience", Cold Spring Harbor Laboratory Press, (2015), Editor Saito, T.

Baptista, R. P. et al., "Thermodynamics and mechanism of cutinase stabilization by trehaloseBiopolymers", (Jun. 1, 2008), vol. 89, pp. 538-547.

Beattie, G.M., et al., "Trehalose: a cryoprotectant that enhances recovery and preserves function of human pancreatic islets after long-term storage" Diabetes, (Mar. 1, 1997), vol. 46, pp. 519-523.

Berge, S. M. et al., "Pharmaceutically acceptable salts in detail", J. Pharmaceutical Sciences, (1977), vol. 66, pp. 1-19.

Bonnardel et al., "UniLectin3D, a database of carbohydrate binding proteins with curated information on 3D structures and interacting ligands", Nucleic Acids Res., (Jan. 8, 2019), vol. 47, No. D1, pp. D1236-D1244.

Buchanan et al., "Cycloheximide Chase Analysis of Protein Degradation in Saccharomyces cerevisiae", J Vis Exp., (Apr. 18, 2016), No. 110, p. 53975.

Chang, L.L., et al., "Mechanism of protein stabilization by sugars during freeze-drying and storage: native structure preservation, specific interaction, and/or immobilization in a glassy matrix?" Journal of Pharmaceutical Sciences, (Jul. 1, 2005) American Chemical Society and American Pharmaceutical Association, US vol. 94, No. 7, pp. 1427-1444.

Conrad, U. and Fielder, U., "Compartment-specific accumulations of recombinant immunoglobulins in plant cells: an essential tool for antibody production and immunomodulation of physiological functions and pathogen activity", Plant Mol Bio (1998) 38: pp. 101-109.

Crickmore et al., "Revision of the Nomenclature for the Bacillus thuringiensis Pesticidal Crystal Proteins", Microbiology and Molecular Biology Reviews, vol. 62, No. 3, Sep. 1998, pp. 807-813.

Crowe, J.H., et al., "Preservation of membranes in anhydrobiotic organisms: the role of trehaloseScience", J.H., (Feb. 17, 1984), vol. 223, pp. 701-703.

Daskalova et al., "Engineering of *N. benthamiana* L. plants for production of N-acetylgalactosamine-glycosylated proteins", BMC Biotechnology, Aug. 24, 2010, vol. 10, No. 62.

Davis, B.D. and Mingioli, E.S., "Mutants of *Escherichia coli* requiring methionine or vitamin B12", J. Bact., (1950), vol. 60, pp. 17-28.

De Maagd et al., "How Bacillus thuringiensis has evolved specific toxins to colonize the insect world," Trends in Genetics, Apr. 2001, vol. 17, No. 4, pp. 193-199.

De Maagd et al., "Identification of Bacillus Thuringiensis Delta-Endotoxin Cry1C Domain III Amino Acid Residues Involved in Insect Specificity," Applied and Environmental Microbiology, Oct. 1999, vol. 65, No. 10, pp. 4369-4374.

Deloose et al., "The extensin signal peptide allows secretion of a heterologous protein from protoplasts", Gene, (Mar. 1, 1991) Elsevier Amsterdam, NL, vol. 99, No. 1, pp. 95-100.

Down et al., "Insecticidal Spider Venom Toxin Fused to Snowdrop Lectin is Toxic to the Peach-potato Aphid, *Myzus Persicae* (Hemiptera: Aphididae) and the Rice Brown Planthopper, *Nilaparvata lugens* (Hemiptera: Delphacidae)", Pest Manag. Sci., Jan. 2006, vol. 62, pp. 77-85.

Dymond, J.S. and Lorsch, J. "*Saccharomyces cerevisiae* Growth Media, Laboratory methods in enzymology: cell, lipid and carbohydrate"; IN: Methods in enzymology, (Dec. 18, 2013) ISSN 0076-6879 ; vol. 533; pp. 191-204.

Elbein, A.D., et al., "New insights on trehalose: a multifunctional molecule", Glycobiology, (Apr. 1, 2003) Oxford University Press, US Source info: vol. 13, No. 4, pp. 17R-27R.

Eldeeb et al., "A molecular toolbox for studying protein degradation in mammalian cells", J Neurochem, (Nov. 2019), vol. 151, No. 4, pp. 520-533.

Escoubas et al., "Structure and pharmacology of spider venom neurotoxins", Biochimie, vol. 82, Issues 9-10, Sep. 10, 2000, pp. 893-907.

European Extended Search Report, EP Application No. 17862582.8, dated Oct. 26, 2020, p. 22.

European Extended Search Report, EP Application No. 20191154.2, dated Oct. 21, 2020, 9 pages.

Figueiredo et al., "Heterologous Expression of an Insecticidal Gene from the Armed Spider (*Phoneutria nigriventer*)", Journal of Venomous Animals and Toxins Including Tropical Diseases, vol. 14, No. 2, pp. 274-293, 2008 XP002705657, ISSN: 1678-9199.

Fitches et al., "An evaluation of garlic lectin as an alternative carrier domain for insecticidal fusion proteins", Insect Science, 2008, vol. 15, pp. 483-495.

Fitches et al., "Fusion proteins containing insect-specific toxins as pest control agents: snowdrop lectin delivers fused insecticidal spider venom toxin to insect haemolymph following oral ingestion", J. Insect Physiol., Feb. 2004, vol. 50, pp. 61-71.

(56)     References Cited

OTHER PUBLICATIONS

Fitches et al., "The insecticidal activity of recombinant garlic lectins towards aphids", Insect Biochem. Mol. Biol., 2008, vol. 38, pp. 905-915.

Fletcher et al., "The Structure of a Novel Insecticidal Neurotoxin, w-atracotoxin-HV1, from the venom of an Australian funnel web spider", Nature Structural Biology vol. 4, No. 7, pp. 559-566, 1997.

Galvez et al., "Purification and characterization of a unique, potent, peptidyl probe for the high conductance calcium-activated potassium channel from venom of the scorpion *Buthus tamulus*", Journal of Biological Chemistry, Jul. 5, 1990; vol. 265, No. 19, pp. 11083-11090.

Gillespie, A.T. and Claydon, N., "The use of entomogenous fungi for pest control and the role of toxins in pathogenesis", Pestic. Sci., (1989), vol. 27, pp. 203-215.

Gimenez-Gallego et al., "Purification, sequence, and model structure of charybdotoxin, a potent selective inhibitor of calcium-activated potassium channels", Proc. Natl. Acad. Sci., May 1988, vol. 85, No. 10, pp. 3329-3333.

Goldstein I.J. and Hayes C.E., "The Lectins: Carbohydrate-binding proteins of plants and animals", Adv. Carbohydr. Chem. Biochem., (1978), vol. 35, pp. 127-340.

Gressent et al., "Pea Albumin 1 Subunit b (PA1b), a Promising Bioinsecticide of Plant Origin", Toxins, vol. 3, No. 12, pp. 1502-1517, Dec. 2011; XP002705656, ISSN: 2072-6651.

Guardia et al., "Structural basis of redox-dependent modulation of galectin-1 dynamics and function", Glycobiology, 2014, vol. 24, No. 5, pp. 424-441.

Guo, N., et al., "Trehalose expression confers desiccation tolerance on human cells", Nat. Biotechnol., (Feb. 1, 2000), vol. 18, pp. 168-171.

Hajek, A., "Interactions between fungal pathogens and insect hosts", Annu. Rev. Entomol, (Jan. 1, 1994) Annual Reviews Inc.

Hashimoto, Y. et al., "Location and nucleotide sequence of the gene encoding the viral enhancing factor of the Trichoplusia ni granulosis virus", Journal of General Virology, (1991), vol. 72, pp. 2645-2651.

Heath et al., "Characterization of the protease processing sites in a multidomain proteinase inhibitor precursor from Nicotiana alata", European Journal of Biochemistry, (1995), vol. 230, pp. 250-257.

Hellens et al., "A Guide to Agrobacterium Binary Ti Vectors", Trends in Plant Science, Oct. 2000, vol. 5, No. 10 pp. 446-451.

Terra, W.R. and Ferreira, C., Insect digestive enzymes: properties, compartmentalization and function, Comn. Biochem. Physiol., (1994), vol. 109B, pp. 1-62.

Tolmachov, O., "Designing plasmid vectors", Methods in Molecular Biology, Gene Therapy of Cancer (2009), vol. 542, pp. 117-129.

Turcanu V. and Williams N.A., "Cell identification and isolation on the basis of cytokine secretion: A novel tool for investigating immune responses", Nature Medicine, (Mar. 1, 2001) Nature Publishing Group US, New York, vol. 7, No. 3, pp. 373-376.

UniProt entry MYPU_2440, 2001.

UniProt entry X1P169, 2014.

UniProt P04824, Alpha-glactosidase 1, MEL1, Retrieved from < https://www.uniprot.org/uniprot/P04824 > on Apr. 6, 2022.

Wolfson, J.L. and Murdock, L.L., "Diversity in digestive proteinase activity among insects", J. Chem. Ecol., (1990), vol. 16, pp. 1089-1102.

Wong, T.K. and Neumann, E., "Biochemical and Biophysical Research Communications", (Jul. 30, 1982) vol. 107, No. 2, pp. 584-587.

Yu et al., "Glutathionylation-triggered conformational changes of glutaredoxin Grx1 from the yeast *Saccharomyces cerevisiae*", Proteins, 2008, vol. 72, No. 3, pp. 1077-1083.

Zhang et al., "Cloning and Analysis of the First cry Gene from Bacillus popilliae", J of Bacteriology, Jul. 1997, vol. 179, No. 13, pp. 4336-4341.

Zhu et al., "Evolutionary origin of inhibitor cystine knot peptides", FASEB Jour., Sep. 2003, vol. 17, pp. 1765-1767.

Zimmermann, et al., "Protein translocation across the ER membrane", Biochimica et Biophysica Acta, (Jun. 27, 2010) Elsevier, Amsterdam, vol. 1808, No. 3, pp. 912-924.

International Search Report and Written Opinion issued in related PCT Application No. PCT/US2022/023079, dated Jul. 20, 2022.

Anonymous: "Liposome—Wikipedia", Jan. 15, 2021 (Jan. 15, 2021), XP055939036, URL:https://en.wikipedia.org/w/index.php?title=Liposome&oldid=1000611753.

Hengherr, S. et al., "Trehalose and anhydrobiosis in tardigrades-evidence for divergence in responses to dehydration", FEBS J., (2008), vol. 275, pp. 281-288.

Hofte et al., "Insecticidal Crystal Proteins of Bacillus thuringiensis", Microbiological Reviews, vol. 53, No. 2, Jun. 1989, pp. 242-255.

Hurst, M.R.H. et al., "The Main Virulence Determinant of Yersinia entomophaga MH96 Is a Broad-Host-Range Toxin Complex Active against Insects" Journal of Bacteriology, (Apr. 15, 2011) American Society for Microbiology, US, vol. 193, No. 8, pp. 1966-1980.

Ishida et al., "High efficiency transformation of maize (*Zea mays* L.) mediated by Agrobacterium tumefaciens", Nature Biotechnology, Jun. 1996, vol. 14, pp. 745-750.

Khan et al., "Spider venom toxin protects plants from insect attack", Transgenic Research, 2006, vol. 15, pp. 349-357.

Kim, T.K. and Eberwine, J.H., "Mammalian cell transfection: the present and the future", (Jun. 13, 2010), vol. 397, No. 8, pp. 3173-3178.

Konishi T. and Harata, M. "Improvement of the transformation efficiency of *Saccharomyces cerevisiae* by altering carbon sources in pre-culture", Biosci Biotechnol Biochem., (Feb. 4, 2014), vol. 78, No. 6, pp. 1090-1093.

Kramer, K.J.et al., "Sequence of a cDNA and expression of the gene encoding epidermal and gut chitinases of Manduca sexta", Insects Biochemistry and Molecular Biology, (Sep. 1, 1993) Elsevier Ltd, vol. 23, No. 6, pp. 691-701.

Kumar et al., "Biological role of lectins: A review", J. Orofac. Sci., (2012), vol. 4, pp. 20-25.

Kwok et al., "GFP-labelled Rubisco and aspartate aminotransferase are present in plastid stromules and traffic between plastids", Journal of Experimental Botany, Mar. 2004, vol. 55, No. 397, pp. 595-604.

Lakhtin, V. et al., "Lectins of living organisms; The overview, Anaerobe", (Jun. 9, 2011) Elsevier, Amsterdam, NL, vol. 17, No. 6, pp. 452-455.

Lambert et al., "A Bacillus thuringiensis Insecticidal Crystal Protein with a High Activity against Members of the Family Noctuidae", Applied & Environmental Microbiology, Jan. 1996, vol. 62, No. 1, pp. 80-86.

Landsberg, M.J. et al., "3D structure of the Yersinia entomophaga toxin complex and implications for insecticidal activity", Proceedings of the National Academy of Sciences, (Dec. 20, 2011), vol. 108, No. 51, pp. 20544-20549.

Lew et al., "Structure-Function Relationships of ?-Conotoxin GVIA" Journal of Biological Chemistry, 1997, vol. 272, No. 18, pp. 12014-12023.

Lindbo JA, "TRBO: A high-efficiency tobacco mosiac virus RNA-based overexpression vector", Plant Physiology, (2007), vol. 145, pp. 1232-1240.

Lipperte, K. and Galinski, E.A., "Enzyme stabilization be ectoine-type compatible solutes: protection against heating, freezing and drying", Appl. Microbiol. Biotechnol., (Apr. 1, 1992), vol. 37, pp. 61-65.

Looke et al., "Extraction of genomic DNA from yeasts for PCR-based applications", Biotechniques, (May 2011), vol. 50, No. 5, pp. 325-328.

Lugue et al., "The complete sequence of the Cydia pomonella granulovirus genome", J Gen Virol, (Oct. 1, 2001), vol. 82, pp. 2531-2547.

Marrone et al., "Improvements in laboratory rearing of the southern corn rootworm, Diabrotica undecimpuncta howardi Barber (Coleoptera: Chrysomelidae), on an artificial diet and corn", J. of Economic Entomology, (1985), vol. 78, pp. 290-293.

Martinez et al., "Toxin III From Anemonia-Sulcata Primary Structure", Febs Letters, V 84, No. 2, pp. 247-252; 1977; XP002705658, ISSN: 0014-5793.

(56) References Cited

OTHER PUBLICATIONS

McBride et al., "Controlled expression of plastid transgenes in plants based on a nuclear DNA-encoded and plastid-targeted T7 RNA polymerase", Proc. Natl. Acad. Sci. USA, (Jul. 1, 1994), vol. 91, pp. 7301-7305.

McCormick et al., "Leaf Disc Transformation of Cultivated Tomato (L. esculentum) using Agrobacterium Trumefaciens", Plant Cell Reports, 1986, vol. 5, pp. 81-84.

McCormick et al., "Rapid production of specific vaccines for lymphoma by expression of the tumor-derived single-chain Fv epitopes in tobacco plants", Proc. Natl. Acad. Sci. USA, (1999), vol. 96, No. 2, pp. 703-708.

Memelink et al., "Structure and regulation of tobacco extensin", Plant Journal, (1993), vol. 4, No. 6, pp. 1011-1022.

Mensink, M.A., et al., "How sugars protect proteins in the solid state and during drying (review): Mechanisms of stabilization in relation to stress conditions", European journal of pharmaceutics and biopharmaceutics, (May 1, 2017) Elsevier Science Publishers B.V., Amsterdam, NL, vol. 114, pp. 288-295.

Mukherjee et al., "Orally active acaricidal peptide toxins from spider venom", Toxicon, 2006, vol. 47, pp. 182-187.

NCBI, Database accession No. NC_002816.1 (https://www.ncbi.nlm.nih.gov/nuccore/NC_002816.1), 2018.

Norton et al., "The Cystine Knot Structure of Ion Channel Toxins and Related Polypeptides", Toxicon, vol. 36, No. 11, pp. 1573-1583, 1998.

Ostergaard et al., "Increasing galactose consumption by Saccharomyces cerevisiae through metabolic engineering of the GAL gene regulatory network," Nature Biotechnology, 2000, vol. 18, pp. 1283-1286.

Ostergaard et al., "Physiological Studies in Aerobic Batch Cultivations of Saccharomyces cerevisiae Strains Harboring the MEL1," Biotechnology and Bioengineering, 2000, vol. 68, No. 3, pp. 252-259.

Pence, "The antimetabolite imidazole as a pesticide", California Agric., Jan. 1965, pp. 13-15.

Peña et al., "A Bacillus thuringiensis S-Layer Protein Involved in Toxicity against Epilachna varivestis (Coleoptera: Coccinellidae)", App & Environ Microbiology, Jan. 2006, vol. 72, No. 1, pp. 353-360.

Pogue et al., "Production of Pharmaceutical-Grade Recombinant Aprotinin and a Monoclonal Antibody Product Using Plant-Based Transient Expression Systems", Plant Biotechnology Journal, 2010, vol. 8, pp. 638-654.

Poinar, G.O. Jr and Hess, R., "Ultrastructure of 40-million-year-old insect tissue", Science, (Mar. 5, 1982), vol. 80, No. 215, pp. 1241-1242.

Potter, H. and Heller, R., "Transfection by Electroporation", Curr Protoc Mol Biol, (May 1, 2003).

Quintero-Hernandez et al., "Scorpion and Spider Venom Peptides: Gene Cloning and Peptide Expression", Toxicon, 2011, vol. 58, pp. 644-663.

Romanos, M.A. and Clare, J.J. "Culture of yeast for the production of heterologous proteins", Curr Protoc Prot Sci., (2015), 5.8.1-5.8.17, supplement 2.

Rowell et al., "Bt Basics for Vegetable Integrated Pest Management", University of Kentucky—College of Agriculture, UK Cooperative Extension Service, Jul. 2005.

Sathasivan et al., "Nucleotide sequence of a mutant acetolactate synthase gene from an imidazolinone-resistant Arabidopsis thaliana var. Columbia", Nucl. Acids Res., (1990), vol. 18, No. 8, p. 2188.

Shi et al., "Construction of Plant Expression Vector of Fusion Gene Ubiquitin and Signal peptide Sequence of Pathogenesis-related Protein 1a", Journal of Shihezi University (Natural Science), 2006, vol. 24, No. 3, pp. 265-269.

Shim et al., "NeuroBactrus, a Novel, Highly Effective, and Environmentally Friendly Recombinant Baculovirus Insecticide," Applied and Environmental Microbiology, 2013, vol. 79, No. 1, pp. 141-149.

Slade, L. and Levine, H., "Beyond Water Activity: Recent Advances Based on an Alternative Approach to the Assessment of Food Quality and Safety, Critical reviews in food science and nutrition", (Jan. 1, 1991) Taylor & Francis, USA, vol. 30, No. 2-3, pp. 115-360.

Smith, P.K. et al., "Measurement of protein using bicinchoninic acid", Analy Biochem (1985) vol. 150, pp. 76-85.

Staub, J.M. and Maliga, P., "Accumulation of D1 polypeptidde in tobacco plastids is regulated via the untranslated region of the psbA mRNA", The EMBO J. (1993) vol. 12 No. 2, pp. 601-606.

Staub, J.M. et al., "High-yield production of a human therapeuctic protein in tobacco chloroplasts", Nature Biotech. (Mar. 1, 2000), vol. 18, pp. 333-338.

Stoger et al., "Cereal crops as viable production and storage systems for pharmaceutical scFv antibodies", Plant Mol. Biol., (2000), vol. 42, pp. 583-590.

Sundaramurthi, P. and Suryanarayanan, R., "Trehalose Crystallization During Freeze-Drying: Implications on Lyoprotection", J. Phys. Chem. Lett., (Dec. 28, 2009), vol. 1, pp. 510-514.

Tabashnik et al., "Insect resistance to Bt crops: lessons from the first billion acres", Nature Biotechnology, 31(6):510-521, 2013.

Takahashi et al., "Solution structure of hanatoxin1, a gating modifier of voltage-dependent K+ channels: common surface features of gating modifier toxins", Journal of Molecular Biology, Mar. 31, 2000, vol. 297, Issue 3, pp. 771-780.

Office Action issued in related Chinese Patent Application No. 202180045271.7, dated Dec. 10, 2024.

Dipel® DF label, Valent BioSciences, LLC (2018).

Office Action issued in Japanese Patent Application No. JP2022-566417, dated Jun. 24, 2025.

Bommoneni, V.R., et al., An Evaluation of Target Cells and Tissues used in Genetic Transformation of Cereals, Maydica, Apr. 1997, vol. 42, pp. 107-120.

Pena et al., "Effects of high medium pH on growth, metabolism and transport in Saccharomyces cerevisiae", FEMS Yeast Res, (Mar. 1, 2015), vol. 15, No. 2, page.

Petit et al., Etude Structure/Fonction d'une Albumine Entomotoxique de Type Alb du Pois Chez le rix: Application GBP a la Protection Contre le Ravageur Sitophilus Oryzae. ["Structure-function study of an Alb-type entomotoxic albumin, isolated from garden pea, in rice : application to post-harvest protection again"], Ph.D. Dissertation. Etude Struction/Fonctition D'Une Albumine Entomotoxique de Type A1B du Pois Chez le Riz: Application GBP a la Protection Contre le Ravageur Sitophilus Oryzae, Universite 2008.

* cited by examiner

1

PROTEOLYTICALLY STABLE U1-AGATOXIN-TA1B VARIANT POLYPEPTIDES FOR PEST CONTROL

CROSS REFERENCE TO RELATED APPLICATIONS

This application is a 35 U.S.C. § 371 United States National Phase Application which claims the benefit of priority to PCT Application No. PCT/US2021/028254, filed Apr. 20, 2021, which claims the benefit of, and priority to, U.S. Provisional Application Ser. No. 63/012,755, filed on Apr. 20, 2020, the disclosures of which are incorporated by reference herein in their entireties.

SEQUENCE LISTING

This application incorporates by reference in its entirety the Sequence Listing entitled "277702-541286_ST.25.txt" (70,969 bytes), which was created on Dec. 10, 2025, and filed electronically herewith.

TECHNICAL FIELD

New insecticidal proteins, nucleotides, peptides, their expression in plants, methods of producing the peptides, new processes, production techniques, new peptides, new formulations, and combinations of new and known organisms that produce greater yields than would be expected of related peptides for the control of insects are described and claimed.

BACKGROUND

Numerous insects are vectors for disease. Mosquitoes in the genus *Anopheles* are the principle vectors of Zika virus, Chikungunya virus, and malaria, a disease caused by protozoa in the genus *Trypanosoma*. *Aedes aegypti* is the main vector of the viruses that cause Yellow fever and Dengue. Other viruses, the causal agents of various types of encephalitis, are also carried by *Aedes* spp. mosquitoes. *Wuchereria bancrofti* and *Brugia malayi*, parasitic roundworms that cause filariasis, are usually spread by mosquitoes in the genera *Culex, Mansonia,* and *Anopheles.*

Horse flies and deer flies may transmit the bacterial pathogens of tularemia (*Pasteurella tularensis*) and anthrax (*Bacillus anthracis*), as well as a parasitic roundworm (*Loa loa*) that causes loiasis in tropical Africa.

Eye gnats in the genus *Hippelates* can carry the spirochaete pathogen that causes yaws (*Treponema* pertenue), and may also spread conjunctivitis (pinkeye). Tsetse flies in the genus *Glossina* transmit the protozoan pathogens that cause African sleeping sickness (*Trypanosoma gambiense* and *T. rhodesiense*). Sand flies in the genus *Phlebotomus* are vectors of a bacterium (*Bartonella baciliformis*) that causes Carrion's disease (oroyo fever) in South America. In parts of Asia and North Africa, they spread a viral agent that causes sand fly fever (pappataci fever) as well as protozoan pathogens (*Leishmania* spp.) that cause Leishmaniasis.

SUMMARY

The present disclosure provides for U1-agatoxin-Ta1b variant polypeptide (TVP), compositions comprising a TVP, insecticidal proteins comprising one or more TVPs optionally with other proteins, and methods for their use to eradicate, kill, control, inhibit, injure, confuse, render sterile, or combinations thereof, one or more insect species. The TVPs described herein have insecticidal activity against one or more insect species. TVPs of the present disclosure have an amino acid sequence that is at least 95% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-K-X$_6$ (SEQ ID NO: 151), wherein the polypeptide comprises at least one amino acid substitution relative to the wild-type sequence of U1-agatoxin-Ta1b as set forth in SEQ ID NO: 1, and wherein X$_1$ is A, S, or N; X$_2$ is R, Q, N, A, G, N, L, D, V, M, I, Q, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; and wherein X$_6$ is G or absent. The TVPs described herein have been shown to have a knockdown of 50% of the population concentration (KD$_{50}$) of lower than 200 pmol/g against houseflies at 24-hours, and cause 100% mortality of *thrips* at day 4.

The present disclosure describes an insecticidal U1-agatoxin-Ta1b variant polypeptide (TVP), said TVP comprising an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-agatoxin-Ta1b as set forth in SEQ ID NO:1, and wherein X$_1$ is A, S, or N; X$_2$ is R, Q, N, A, G, N, L, D, V, M, I, Q, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; or a pharmaceutically acceptable salt thereof.

In addition, present disclosure describes a composition consisting of a TVP, and one or more excipients; wherein the TVP comprises an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-agatoxin-Ta1b as set forth in SEQ ID NO:1, and wherein X$_1$ is A, S, or N; X$_2$ is R, Q, N, A, G, N, L, D, V, M, I, Q, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; and wherein the one or more excipients is selected from the group consisting of: trehalose; maltodextrin; maltose; potassium phosphate dibasic (K$_2$HPO$_4$); potassium phosphate monobasic (KH$_2$PO$_4$); lignosulfonate; gypsum; sorbitol; sodium benzoate; potassium sorbate; EDTA; benzisothiazolinone (BIT); and fermentation solids.

In addition, the present disclosure describes a composition consisting of a TVP, and a plurality of excipients; wherein the TVP comprises an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-agatoxin-Ta1b as set forth in SEQ ID NO:1, and wherein X$_1$ is A, S, or N; X$_2$ is R, Q, N, A, G, N, L, D, V, M, I, Q, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; wherein the composition consists of an amount of TVP that is 8.5% wt/wt of the total weight of the composition; and wherein the plurality of excipients consists of the following: an amount of trehalose that is 25% wt/wt; an amount of BIT that is 0.05% wt/wt; an amount of maltodextrin that is 36.3% wt/wt; an amount of potassium phosphate dibasic anhydrous ($K_2HPO_4$) that is 2.6% wt/wt; an amount of potassium phosphate monobasic ($KH_2PO_4$) that is 0.4% wt/wt; and an amount of fermentation solids that is 26.85% wt/wt, of the total weight of the composition.

In addition, the present disclosure describes a polynucleotide encoding a TVP, said TVP comprising an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the TVP comprises at least one amino acid substitution relative to the wild-type sequence of U1-agatoxin-Ta1b as set forth in SEQ ID NO: 1, and wherein X$_1$ is A, S, or N; X$_2$ is R, Q, N, A, G, N, L, D, V, M, I, Q, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; or a complementary nucleotide sequence thereof.

In addition, the present disclosure describes a method of producing a TVP, the method comprising: (a) preparing a vector comprising a first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-agatoxin-Ta1b as set forth in SEQ ID NO:1, and wherein X$_1$ is A, S, or N; X$_2$ is R, Q, N, A, G, N, L, D, V, M, I, Q, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; (b) introducing the vector into a host cell; and (c) growing the host cell in a growth medium under conditions operable to enable expression of the TVP and secretion into the growth medium.

In addition, the present disclosure describes a method of using the compositions described above to control insects comprising, providing the compositions to the locus of an insect.

In addition, the present disclosure describes a method of protecting a plant from insects comprising, providing a plant which expresses a TVP, or polynucleotide encoding the same.

In addition, the present disclosure describes a method of combating, controlling, or inhibiting a pest comprising, applying a pesticidally effective amount of the compositions described above to the locus of the pest, or to a plant or animal susceptible to an attack by the pest.

In addition, the present disclosure describes a vector comprising a polynucleotide operable to encode a TVP having an amino acid sequence with 90% similarity to a sequence as set forth in any one of SEQ ID NOs: 2-15, 49-53, or 77-110.

In addition, the present disclosure describes a yeast strain comprising: a first expression cassette comprising a polynucleotide operable to encode a TVP, said TVP comprising an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-

X$_6$-X$_7$ (SEQ ID NO: 151), wherein the polypeptide comprises at least one amino acid substitution relative to the wild-type sequence of U1-agatoxin-Ta1b as set forth in SEQ ID NO: 1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; or complementary nucleotide sequence thereof.

In addition, the present disclosure describes an insecticidal U1-agatoxin-Ta1b variant polypeptide (TVP), said TVP comprising an amino acid sequence that is at least 90% identical to the amino acid sequence according to Formula (II): E-P-D-E-I-C-R-A-X$_1$-M-T-N-K-E-F-T-Y-K-S-N-V-C-N-N-C-G-D-Q-V-A-A-C-E-A-E-C-F-R-N-D-V-Y-Z$_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein X$_1$ is R or Q; and Z$_1$ is T or A; or a pharmaceutically acceptable salt thereof.

In addition, the present disclosure describes a composition consisting of a TVP, and one or more excipients; wherein the TVP comprises an amino acid sequence that is at least 90% identical to the amino acid sequence according to Formula (II): E-P-D-E-I-C-R-A-X$_1$-M-T-N-K-E-F-T-Y-K-S-N-V-C-N-N-C-G-D-Q-V-A-A-C-E-A-E-C-F-R-N-D-V-Y-Z$_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein X$_1$ is R or Q; and Z$_1$ is T or A; or a pharmaceutically acceptable salt thereof; and wherein the one or more excipients is selected from the group consisting of: trehalose; maltodextrin; maltose; potassium phosphate dibasic ($K_2HPO_4$); potassium phosphate monobasic ($KH_2PO_4$); lignosulfonate; gypsum; sorbitol; sodium benzoate; potassium sorbate; EDTA; benzisothiazolinone (BIT); and fermentation solids.

In addition, the present disclosure describes a composition consisting of a TVP, and a plurality of excipients; wherein the TVP comprises an amino acid sequence that is at least 90% identical to the amino acid sequence according to Formula (II): E-P-D-E-I-C-R-A-X$_1$-M-T-N-K-E-F-T-Y-K-S-N-V-C-N-N-C-G-D-Q-V-A-A-C-E-A-E-C-F-R-N-D-V-Y-Z$_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein X$_1$ is R or Q; and Z$_1$ is T or A; or a pharmaceutically acceptable salt thereof; wherein the composition consists of an amount of TVP that is 8.5% w/w of the total weight of the composition; and wherein the plurality of excipients consists of the following: an amount of trehalose that is 25% w/w; an amount of BIT that is 0.05% w/w; an amount of maltodextrin that is 36.3% w/w; an amount of potassium phosphate dibasic anhydrous ($K_2HPO_4$) that is 2.6% w/w; an amount of potassium phosphate monobasic ($KH_2PO_4$) that is 0.4% w/w; and an amount of fermentation solids that is 26.85% w/w, of the total weight of the composition.

In addition, the present disclosure describes an insecticidal U1-agatoxin-Ta1b variant polypeptide (TVP), said TVP comprising an amino acid sequence that is at least 90% identical to the amino acid sequence set forth in any one of SEQ ID NOs: 2, 49, or 51; or a pharmaceutically acceptable salt thereof.

In addition, the present disclosure describes an insecticidal U1-agatoxin-Ta1b variant polypeptide (TVP), said TVP comprising an amino acid sequence set forth in any one of SEQ ID NOs: 2, 49, or 51; or a pharmaceutically acceptable salt thereof.

In addition, the present disclosure describes an insecticidal U1-agatoxin-Ta1b variant polypeptide (TVP), said TVP consisting of an amino acid sequence set forth in any one of SEQ ID NOs: 2, 49, or 51; or a pharmaceutically acceptable salt thereof.

In addition, the present disclosure describes an insecticidal U1-agatoxin-Ta1b variant polypeptide (TVP), said TVP comprising an amino acid sequence that is at least 90% identical to the amino acid sequence set forth in SEQ ID NO 51, or a pharmaceutically acceptable salt thereof.

In addition, the present disclosure describes an insecticidal U1-agatoxin-Ta1b variant polypeptide (TVP), said TVP comprising an amino acid sequence set forth in SEQ ID NO: 51, or a pharmaceutically acceptable salt thereof.

In addition, the present disclosure describes an insecticidal U1-agatoxin-Ta1b variant polypeptide (TVP), said TVP consisting of an amino acid sequence set forth in SEQ ID NO: 51, or a pharmaceutically acceptable salt thereof.

DETAILED DESCRIPTION

Definitions

Figure 1:
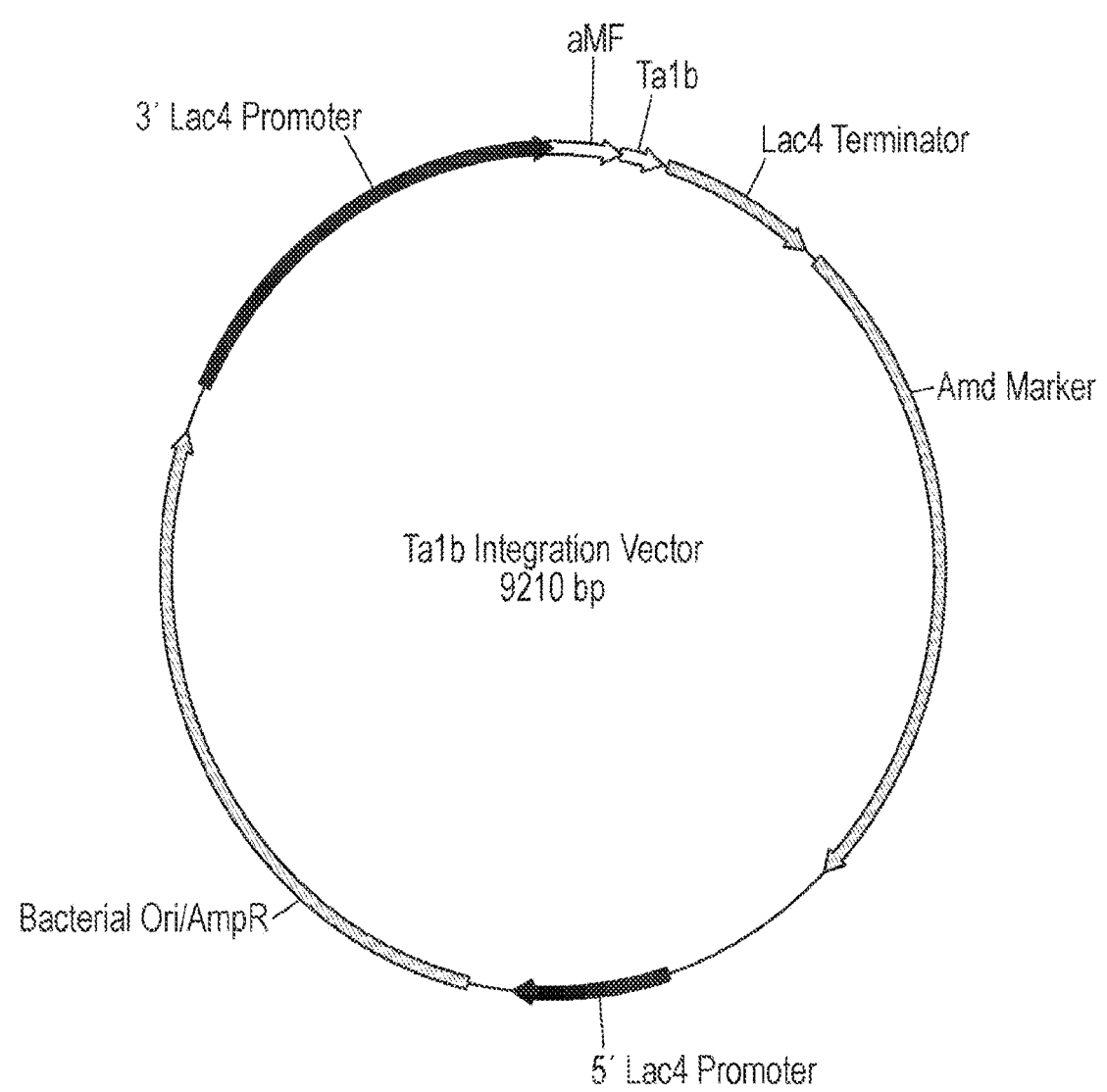
FIG. 1 depicts the Ta1b integration vector map comprising a 9210 base pair circular vector that contains the following sequences: a Bacterial Ori/AmpR; a 3' Lac4 promoter; an α-MF signal sequence (labeled as "a-MF" in the figure); the polynucleotide encoding a U1-agatoxin-Ta1b variant polypeptide (labeled as "Ta1b" in the figure); Lac4 terminator; an amdS marker (indicated as "Amd Marker); and a 5' Lac4 promoter.

"5'-end" and "3'-end" refers to the directionality, i.e., the end-to-end orientation of a nucleotide polymer (e.g., DNA). The 5'-end of a polynucleotide is the end of the polynucleotide that has the fifth carbon.

"5'- and 3'-homology arms" or "5' and 3' arms" or "left and right arms" refers to the polynucleotide sequences in a vector and/or targeting vector that homologously recombine with the target genome sequence and/or endogenous gene of interest in the host organism in order to achieve successful genetic modification of the host organism's chromosomal locus.

"ADN1 promoter" refers to the DNA segment comprised of the promoter sequence derived from the *Schizosaccharomyces pombe* adhesion defective protein 1 gene.

"Affect" refers to how a something influences another thing, e.g., how a peptide, polypeptide, protein, drug, or chemical influences an insect, e.g., a pest.

"Agent" refers to one or more chemical substances, molecules, nucleotides, polynucleotides, peptides, polypeptides, proteins, toxins, toxicants, poisons, insecticides, pesticides, organic compounds, inorganic compounds, prokaryote organisms, or eukaryote organisms (and the agents produced from said prokaryote or eukaryote organisms).

"Agriculturally-acceptable carrier" covers all adjuvants, inert components, dispersants, surfactants, tackifiers, binders, etc. that are ordinarily used in pesticide formulation technology; these are well known to those skilled in pesticide formulation.

"Agriculturally acceptable salt" is used herein synonymously with the term "pharmaceutically acceptable salt."

"Agroinfection" means a plant transformation method where DNA is introduced into a plant cell by using *Agrobacteria tumefaciens* or *Agrobacteria rhizogenes*.

"Alignment" refers to a method of comparing two or more sequences (e.g., nucleotide, polynucleotide, amino acid, peptide, polypeptide, or protein sequences) for the purpose of determining their relationship to each other. Alignments are typically performed by computer programs that apply various algorithms, however, it is also possible to perform an alignment by hand. Alignment programs typically iterate through potential alignments of sequences and score the alignments using substitution tables, employing a variety of strategies to reach a potential optimal alignment score. Commonly-used alignment algorithms include, but are not limited to, CLUSTALW (see Thompson J. D., Higgins D. G., Gibson T. J., CLUSTAL W: improving the sensitivity of progressive multiple sequence alignment through sequence weighting, position-specific gap penalties and weight matrix choice, Nucleic Acids Research 22: 4673-4680, 1994); CLUSTALV (see Larkin M. A., et al., CLUSTALW2, Clust-alW and ClustalX version 2, Bioinformatics 23(21): 2947-2948, 2007); Mafft; Kalign; ProbCons; and T-Coffee (see Notredame et al., T-Coffee: A novel method for multiple sequence alignments, Journal of Molecular Biology 302: 205-217, 2000). Exemplary programs that implement one or more of the foregoing algorithms include, but are not limited to, MegAlign from DNAStar (DNAStar, Inc. 3801 Regent St. Madison, Wis. 53705), MUSCLE, T-Coffee, CLUST-ALX, CLUSTALV, JalView, Phylip, and Discovery Studio from Accelrys (Accelrys, Inc., 10188 Telesis Ct, Suite 100, San Diego, Calif. 92121). In some embodiments, an align-ment will introduce "phase shifts" and/or "gaps" into one or both of the sequences being compared in order to maximize the similarity between the two sequences, and scoring refers to the process of quantitatively expressing the relatedness of the aligned sequences.

"Alpha-MF signal" or "αMF secretion signal" refers to a protein that directs nascent recombinant polypeptides to the secretory pathway.

"Arachnid" refers to a class of arthropods. For example in some embodiments, arachnid can mean spiders, scorpions, ticks, mites, harvestmen, or solifuges.

"BAAS" means barley alpha-amylase signal peptide, and is an example of an ERSP. One example of a BAAS is a BAAS having the amino acid sequence of SEQ ID NO:37 (NCBI Accession No. AAA32925.1).

"Biomass" refers to any measured plant product.

"Binary vector" or "binary expression vector" means an expression vector which can replicate itself in both *E. coli* strains and *Agrobacterium* strains. Also, the vector contains a region of DNA (often referred to as t-DNA) bracketed by left and right border sequences that is recognized by viru-lence genes to be copied and delivered into a plant cell by *Agrobacterium.*

"bp" or "base pair" refers to a molecule comprising two chemical bases bonded to one another. For example, a DNA molecule consists of two winding strands, wherein each strand has a backbone made of an alternating deoxyribose and phosphate groups. Attached to each deoxyribose is one of four bases, i.e., adenine (A), cytosine (C), guanine (G), or thymine (T), wherein adenine forms a base pair with thy-mine, and cytosine forms a base pair with guanine.

"C-terminal" refers to the free carboxyl group (i.e., —COOH) that is positioned on the terminal end of a polypeptide.

"cDNA" or "copy DNA" or "complementary DNA" refers to a molecule that is complementary to a molecule of RNA. In some embodiments, cDNA may be either single-stranded or double-stranded. In some embodiments, cDNA can be a double-stranded DNA synthesized from a single stranded RNA template in a reaction catalyzed by a reverse transcriptase. In yet other embodiments, "cDNA" refers to all nucleic acids that share the arrangement of sequence elements found in native mature mRNA species, where sequence elements are exons and 3' and 5' non-coding regions. Normally mRNA species have contiguous exons, with the intervening introns removed by nuclear RNA splicing, to create a continuous open reading frame encoding the protein. In some embodiments, "cDNA" refers to a DNA that is complementary to and derived from an mRNA template.

"CEW" refers to Corn earworm.

"Cleavable Linker" see Linker.

"Cloning" refers to the process and/or methods concern-ing the insertion of a DNA segment (e.g., usually a gene of interest, for example tvp) from one source and recombining it with a DNA segment from another source (e.g., usually a vector, for example, a plasmid) and directing the recombined DNA, or "recombinant DNA" to replicate, usually by trans-forming the recombined DNA into a bacteria or yeast host.

"Coding sequence" or "CDS" refers to a polynucleotide or nucleic acid sequence that can be transcribed (e.g., in the case of DNA) or translated (e.g., in the case of mRNA) into a peptide, polypeptide, or protein, when placed under the control of appropriate regulatory sequences and in the presence of the necessary transcriptional and/or translational molecular factors. The boundaries of the coding sequence are determined by a translation start codon at the 5' (amino) terminus and a translation stop codon at the 3' (carboxy) terminus. A transcription termination sequence will usually be located 3' to the coding sequence. In some embodiments, a coding sequence may be flanked on the 5' and/or 3' ends by untranslated regions. In some embodiments, a coding sequence can be used to produce a peptide, a polypeptide, or a protein product. In some embodiments, the coding sequence may or may not be fused to another coding sequence or localization signal, such as a nuclear localiza-tion signal. In some embodiments, the coding sequence may be cloned into a vector or expression construct, may be integrated into a genome, or may be present as a DNA fragment.

"Codon optimization" refers to the production of a gene in which one or more endogenous, native, and/or wild-type codons are replaced with codons that ultimately still code for the same amino acid, but that are of preference in the corresponding host.

"Complementary" refers to the topological compatibility or matching together of interacting surfaces of two poly-nucleotides as understood by those of skill in the art. Thus, two sequences are "complementary" to one another if they are capable of hybridizing to one another to form a stable anti-parallel, double-stranded nucleic acid structure. A first polynucleotide is complementary to a second polynucleotide if the nucleotide sequence of the first polynucleotide is substantially identical to the nucleotide sequence of the polynucleotide binding partner of the second polynucle-otide, or if the first polynucleotide can hybridize to the second polynucleotide under stringent hybridization condi-tions. Thus, the polynucleotide whose sequence 5'-TATAC-3' is complementary to a polynucleotide whose sequence is 5'-GTATA-3'.

"Conditioned medium" means the cell culture medium which has been used by cells and is enriched with cell derived materials but does not contain cells.

"Copy number" refers to the number of identical copies of a vector, an expression cassette, an amplification unit, a gene or indeed any defined nucleotide sequence, that are present in a host cell at any time. For example, in some embodi-ments, a gene or another defined chromosomal nucleotide sequence may be present in one, two, or more copies on the chromosome. An autonomously replicating vector may be present in one, or several hundred copies per host cell.

"Culture" or "cell culture" refers to the maintenance of cells in an artificial, in vitro environment.

"Culturing" refers to the propagation of organisms on or in various kinds of media. For example, the term "culturing" can mean growing a population of cells under suitable conditions in a liquid or solid medium. In some embodiments, culturing refers to fermentative recombinant production of a heterologous polypeptide of interest and/or other desired end products (typically in a vessel or reactor).

"Cystine" refers to an oxidized cysteine-dimer. Cystines are sulfur-containing amino acids obtained via the oxidation of two cysteine molecules, and are linked with a disulfide bond.

"Defined medium" means a medium that is composed of known chemical components but does not contain crude proteinaceous extracts or by-products such as yeast extract or peptone.

"Disulfide bond" means a covalent bond between two cysteine amino acids derived by the coupling of two thiol groups on their side chains.

"Degeneracy" or "codon degeneracy" refers to the phenomenon that one amino acid can be encoded by different nucleotide codons. Thus, the nucleic acid sequence of a nucleic acid molecule that encodes a protein or polypeptide can vary due to degeneracies. As a result of the degeneracy of the genetic code, many nucleic acid sequences can encode a given polypeptide with a particular activity; such functionally equivalent variants are contemplated herein.

"DNA" refers to deoxyribonucleic acid, comprising a polymer of one or more deoxyribonucleotides or nucleotides (i.e., adenine [A], guanine [G], thymine [T], or cytosine [C]), which can be arranged in single-stranded or double-stranded form. For example, one or more nucleotides creates a polynucleotide.

"dNTPs" refers to the nucleoside triphosphates that compose DNA and RNA.

"Double expression cassette" refers to two TVP expression cassettes contained on the same vector.

"Double transgene peptide expression vector" or "double transgene expression vector" means a yeast expression vector that contains two copies of the TVP expression cassette.

"Endogenous" refers to a polynucleotide, peptide, polypeptide, protein, or process that naturally occurs and/or exists in an organism, e.g., a molecule or activity that is already present in the host cell before a particular genetic manipulation.

"Enhancer element" refers to a DNA sequence operably linked to a promoter, which can exert increased transcription activity on the promoter relative to the transcription activity that results from the promoter in the absence of the enhancer element.

"ER" or "Endoplasmic reticulum" is a subcellular organelle common to all eukaryotes where some post translation modification processes occur.

"ERSP" or "endoplasmic reticulum signal peptide" is an N-terminus sequence of amino acids that—during protein translation of the mRNA molecule encoding a TVP—is recognized and bound by a host cell signal-recognition particle, which moves the protein translation ribosome/mRNA complex to the ER in the cytoplasm. The result is the protein translation is paused until it docks with the ER where it continues and the resulting protein is injected into the ER.

"ersp" refers to a polynucleotide encoding the peptide, ERSP.

"ER trafficking" means transportation of a cell expressed protein into ER for post-translational modification, sorting and transportation.

"Excipient" refers to any pharmacologically inactive, natural, or synthetic, component or substance that is formulated alongside (e.g., concomitantly), or subsequent to, the active ingredient of the present invention (i.e., a TVP or TVP-insecticidal protein). In some embodiments, an excipient can be any additive, adjuvant, binder, bulking agent, carrier, coating, diluent, disintegrant, filler, glidant, lubricant, preservative, vehicle, or combination thereof, with which a TVP or TVP-insecticidal protein of the present invention can be administered, and or which is useful in preparing a composition of the present invention. Excipients, include any such materials known in the art that are nontoxic and do not interact with other components of a composition. In some embodiments, excipients can be formulated alongside a TVP or TVP-insecticidal protein when preparing a composition for the purpose of bulking up compositions (thus often referred to as bulking agents, fillers or diluents). In other embodiments, an excipient can be used to confer an enhancement on the active ingredient in the final dosage form, such as facilitating absorption and/or solubility. In yet other embodiments, an excipient can be used to provide stability, or prevent contamination (e.g., microbial contamination). In other embodiments, an excipient can be used to confer a physical property to a composition (e.g., a composition that is a dry granular, or dry flowable powder physical form). Reference to an excipient includes both one and more than one such excipients. Suitable pharmaceutical excipients are described in Remington's Pharmaceutical Sciences, by E. W. Martin, the disclosure of which is incorporated herein by reference in its entirety.

"Expression cassette" refers to (1) a DNA sequence of interest, e.g., a polynucleotide operable to encode a TVP; and one or more of the following: (2) promoters, terminators, and/or enhancer elements; (3) an appropriate mRNA stabilizing polyadenylation signal; (4) an internal ribosome entry site (IRES); (5) introns; and/or (6) post-transcriptional regulatory elements. The combination (1) with at least one of (2)-(6) is called an "expression cassette." In some embodiments, there can be numerous expression cassettes cloned into a vector. For example, in some embodiments, there can be a first expression cassette comprising a polynucleotide operable to encode a TVP. In alternative embodiments, there are two expression cassettes, each comprising a polynucleotide operable to encode a TVP (i.e., a double expression cassette). In other embodiments, there are three expression cassettes operable to encode a TVP (i.e., a triple expression cassette). In some embodiments, a double expression cassette can be generated by subcloning a second expression cassette into a vector containing a first expression cassette. In some embodiments, a triple expression cassette can be generated by subcloning a third expression cassette into a vector containing a first and a second expression cassette. Methods concerning expression cassettes and cloning techniques are well-known in the art and described herein. See also TVP expression cassette.

"Expression ORF" means a nucleotide encoding a protein complex and is defined as the nucleotides in the ORF.

"FECT" means a transient plant expression system using Foxtail mosaic virus with elimination of coating protein gene and triple gene block.

"Fermentation beer" refers to spent fermentation medium, i.e., fermentation medium supernatant after removal of organisms, that has been inoculated with and consumed by a transformed host cell (e.g., a yeast cell operable to express a TVP of the present invention). In some embodiments, fermentation beer refers to the solution that is recovered following the fermentation of the transformed host cell. The term "fermentation" refers broadly to the enzymatic and anaerobic or aerobic breakdown of organic substances (e.g., a carbon substrate) nutrient substances by microorganisms under controlled conditions (e.g., temperature, oxygen, pH, nutrients, and the like) to produce fermentation products (e.g., one or more peptides of the present invention). While fermentation typically describes processes that occur under anaerobic conditions, as used herein it is not intended that the term be solely limited to strict anaerobic conditions, as the term "fermentation" used herein may also occur processes that occur in the presence of oxygen.

"Fermentation solid(s)" refers to solids (including dissolved) that remain from fermentation beer during the yeast-based fermentation process, and consists essentially of salts, complex protein source, vitamins, and additional yeast byproducts having a molecular weight cutoff of from about 200 kDa to about 1 kDA.

"GFP" means a green fluorescent protein from the jellyfish *Aequorea victoria.*

"Homologous" refers to the sequence similarity or sequence identity between two polypeptides or between two nucleic acid molecules. When a position in both of the two compared sequences is occupied by the same base or amino acid monomer subunit, e.g., if a position in each of two DNA molecules is occupied by adenine, then the molecules are homologous at that position. The percent of homology between two sequences is a function of the number of matching or homologous positions shared by the two sequences divided by the number of positions compared× 100. Thus, in some embodiments, the term "homologous" refers to the sequence similarity between two polypeptide molecules, or between two nucleic acid molecules. When a position in both of the two compared sequences is occupied by the same base or amino acid monomeric subunit, e.g., if a position in each of two DNA molecules is occupied by adenine, then the molecules are homologous at that position. The homology between two sequences is a function of the number of matching or homologous positions shared by the two sequences. For example, if 6 of 10 of the positions in two sequences are matched or homologous then the two sequences are 60% homologous. By way of example, the DNA sequences ATTGCC and TATGGC share 50% homology.

The term "homology," when used in relation to nucleic acids, refers to a degree of complementarity. There may be partial homology, or complete homology and thus identical. "Sequence identity" refers to a measure of relatedness between two or more nucleic acids, and is given as a percentage with reference to the total comparison length. The identity calculation takes into account those nucleotide residues that are identical and in the same relative positions in their respective larger sequences.

"Homologous recombination" refers to the event of substitution of a segment of DNA by another one that possesses identical regions (homologous) or nearly so. For example, in some embodiments, "homologous recombination" refers to a type of genetic recombination in which nucleotide sequences are exchanged between two similar or identical molecules of DNA. Briefly, homologous recombination is most widely used by cells to accurately repair harmful breaks that occur on both strands of DNA, known as double-strand breaks. Although homologous recombination varies widely among different organisms and cell types, most forms involve the same basic steps: after a double-strand break occurs, sections of DNA around the 5' ends of the break are cut away in a process called resection. In the strand invasion step that follows, an overhanging 3' end of the broken DNA molecule then "invades" a similar or identical DNA molecule that is not broken. After strand invasion, the further sequence of events may follow either of two main pathways, i.e., the double-strand break repair pathway, or the synthesis-dependent strand annealing pathway. Homologous recombination is conserved across all three domains of life as well as viruses, suggesting that it is a nearly universal biological mechanism. For example, in some embodiments, homologous recombination can occur using a site-specific integration (SSI) sequence, whereby there is a strand exchange crossover event between nucleic acid sequences substantially similar in nucleotide composition. These crossover events can take place between sequences contained in the targeting construct of the invention (i.e., the SSI sequence) and endogenous genomic nucleic acid sequences (e.g., the polynucleotide encoding the peptide subunit). In addition, in some embodiments, it is possible that more than one site-specific homologous recombination event can occur, which would result in a replacement event in which nucleic acid sequences contained within the targeting construct have replaced specific sequences present within the endogenous genomic sequences.

"Identity" refers to a relationship between two or more polypeptide sequences or two or more polynucleotide sequences, as determined by comparing said sequences. The term "identity" also means the degree of sequence relatedness between polypeptide or polynucleotide sequences, as the case may be, as determined by the match between strings of such sequences. "Identity" and "similarity" can be readily calculated by any one of the myriad methods known to those having ordinary skill in the art, including but not limited to those described in: Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part 1, Griffin, A. M., and Griffin, H. G., eds., Humana Press, New Jersey, 1994, Sequence Analysis in Molecular Biology, von Heinje, G., Academic Press, 1987; and Sequence Analysis Primer, Gribskov, M. and Devereux, J., eds., M Stockton Press, New York, 1991; and Carillo, H., and Lipman, D., SIAM J. Applied Math., 48: 1073 (1988), the disclosures of which are incorporated herein by reference in their entireties. Furthermore, methods to determine identity and similarity are codified in publicly available computer programs. For example in some embodiments, methods to determine identity and similarity between two sequences include, but are not limited to, the GCG program package (Devereux, J., et al., Nucleic Acids Research 12(1): 387 (1984)), BLASTP, BLASTN, and FASTA (Altschul, S. F. et al., J. Molec. Biol. 215: 403-410 (1990). The BLAST X program is publicly available from NCBI and other sources (BLAST Manual, Altschul, S., et al., NCBI NLM NIH Bethesda, Md. 20894; Altschul, S., et al., J. Mol. Biol. 215: 403-410 (1990), the disclosures of which are incorporated herein by reference in their entireties.

"in vivo" refers to the natural environment (e.g., an animal or a cell) and to processes or reactions that occur within a natural environment.

"Inactive" refers to a condition wherein something is not in a state of use, e.g., lying dormant and/or not working. For example, when used in the context of a gene or when referring to a gene, the term inactive means said gene is no longer actively synthesizing a gene product, having said gene product translated into a protein, or otherwise having the gene perform its normal function. For example, in some embodiments, the term inactive can refer the failure of a gene to transcribe RNA, a failure of RNA processing (e.g., pre-mRNA processing; RNA splicing; or other post-transcriptional modifications); interference with non-coding RNA maturation; interference with RNA export (e.g., from the nucleus to the cytoplasm); interference with translation; protein folding; translocation; protein transport; and/or inhibition and/or interference with any of the molecules polynucleotides, peptides, polypeptides, proteins, transcription factors, regulators, inhibitors, or other factors that take part in any of the aforementioned processes.

"Inoperable" refers to the condition of a thing not functioning, malfunctioning, or no longer able to function. For example, when used in the context of a gene or when referring to a gene, the term inoperable means said gene is no longer able to operate as it normally would, either permanently or transiently. For example, "inoperable," in some embodiments, means that a gene is no longer able to synthesize a gene product, having said gene product translated into a protein, or is otherwise unable to gene perform its normal function. For example, in some embodiments, the term inoperable can refer the failure of a gene to transcribe RNA, a failure of RNA processing (e.g., pre-mRNA processing; RNA splicing; or other post-transcriptional modifications); interference with non-coding RNA maturation; interference with RNA export (e.g., from the nucleus to the cytoplasm); interference with translation; protein folding; translocation; protein transport; and/or inhibition and/or interference with any of the molecules polynucleotides, peptides, polypeptides, proteins, transcription factors, regulators, inhibitors, or other factors that take part in any of the aforementioned processes.

"Insect" includes all organisms in the class "Insecta." The term "pre-adult" insects refers to any form of an organism prior to the adult stage, including, for example, eggs, larvae, and nymphs. As used herein, the term "insect refers to any arthropod and nematode, including acarids, and insects known to infest all crops, vegetables, and trees and includes insects that are considered pests in the fields of forestry, horticulture and agriculture. Examples of specific crops that might be protected with the methods disclosed herein are soybean, corn, cotton, alfalfa and the vegetable crops. A list of specific crops and insects is enclosed herein.

"Insecticidal activity" means that upon or after exposing the insect to compounds, agents, or peptides, the insect either dies stops or slows its movement; stops or slows its feeding; stops or slows its growth; becomes confused (e.g., with regard to navigation, locating food, sleeping behaviors, and/or mating); fails to pupate; interferes with reproduction; and/or precludes the insect from producing offspring and/or precludes the insect from producing fertile offspring.

"Insect gut environment" or "gut environment" means the specific pH and proteinase conditions found within the fore, mid or hind gut of an insect or insect larva.

"Insect hemolymph environment" means the specific pH and proteinase conditions of found within an insect or insect larva.

"Integrative expression vector" or "integrative vector" means a yeast expression vector which can insert itself into a specific locus of the yeast cell genome and stably becomes a part of the yeast genome.

"Intervening linker" refers to a short peptide sequence in the protein separating different parts of the protein, or a short DNA sequence that is placed in the reading frame in the ORF to separate the upstream and downstream DNA sequences. For example, in some embodiments, an intervening linker may be used allowing proteins to achieve their independent secondary and tertiary structure formation during translation. In some embodiments, the intervening linker can be either resistant or susceptible to cleavage in plant cellular environments, in the insect and/or lepidopteran gut environment, and in the insect hemolymph and lepidopteran hemolymph environment.

"Isolated" refers to separating a thing and/or a component from its natural environment, e.g., a toxin isolated from a given genus or species means that toxin is separated from its natural environment.

"kb" refers to kilobase, i.e., 1000 bases. As used herein, the term "kb" means a length of nucleic acid molecules. For example, 1 kb refers to a nucleic acid molecule that is 1000 nucleotides long. A length of double-stranded DNA that is 1 kb long, contains two thousand nucleotides (i.e., one thousand on each strand). Alternatively, a length of single-stranded RNA that is 1 kb long, contains one thousand nucleotides.

"kDa" refers to kilodalton, a unit equaling 1,000 daltons; a "Dalton" is a unit of molecular weight (MW).

"Knock in" or "knock-in" or "knocks-in" or "knocking-in" refers to the replacement of an endogenous gene with an exogenous or heterologous gene, or part thereof. For example, in some embodiments, the term "knock-in" refers to the introduction of a nucleic acid sequence encoding a desired protein to a target gene locus by homologous recombination, thereby causing the expression of the desired protein. In some embodiments, a "knock-in" mutation can modify a gene sequence to create a loss-of-function or gain-of-function mutation. The term "knock-in" can refer to the procedure by which a exogenous or heterologous polynucleotide sequence or fragment thereof is introduced into the genome, (e.g., "they performed a knock-in" or "they knocked-in the heterologous gene"), or the resulting cell and/or organism (e.g., "the cell is a "knock-in" or "the animal is a "knock-in").

"Knock out" or "knockout" or "knock-out" or "knocks-out" or "knocking-out" refers to a partial or complete suppression of the expression gene product (e.g., mRNA) of a protein encoded by an endogenous DNA sequence in a cell. In some embodiments, the "knock-out" can be effectuated by targeted deletion of a whole gene, or part of a gene encoding a peptide, polypeptide, or protein. As a result, the deletion may render a gene inactive, partially inactive, inoperable, partly inoperable, or otherwise reduce the expression of the gene or its products in any cell in the whole organism and/or cell in which it is normally expressed. The term "knock-out" can refer to the procedure by which an endogenous gene is made completely or partially inactive or inoperable (e.g., "they performed a knock-out" or "they knocked-out the endogenous gene"), or the resulting cell and/or organism (e.g., "the cell is a "knock-out" or "the animal is a "knock-out").

"Knockdown dose 50" or "$KD_{50}$" refers to the median dose required to cause paralysis or cessation of movement in 50% of a population, for example a population of *Musca domestica* (common housefly) and/or *Aedes aegypti* (mosquito).

"l" or "linker" refers to a nucleotide encoding intervening linker peptide.

"L" in the proper context refers to an intervening linker peptide, which links a translational stabilizing protein (STA) with an additional polypeptide, e.g., a TVP, and/or multiple TVPs. When referring to amino acids, "L" can also mean leucine.

"LAC4 promoter" or "Lac4 promoter" refers to a DNA segment comprised of the promoter sequence derived from the *K. lactis* β-galactosidase gene. The LAC4 promoters is strong and inducible reporter that is used to drive expression of exogenous genes transformed into yeast.

"LAC4 terminator" or "Lac4 terminator" refers to a DNA segment comprised of the transcriptional terminator sequence derived from the *K. lactis* β-galactosidase gene.

"$LD_{20}$" refers to a dose required to kill 20% of a population.

"$LD_{50}$" refers to lethal dose 50 which means the dose required to kill 50% of a population.

"Lepidopteran gut environment" means the specific pH and proteinase conditions found within the fore, mid or hind gut of a lepidopteran insect or larva.

"Lepidopteran hemolymph environment" means the specific pH and proteinase conditions of found within lepidopteran insect or larva.

"Linker" or "LINKER" or "peptide linker" or "L" or "intervening linker" refers to a short peptide sequence operable to link two peptides together. Linker can also refer to a short DNA sequence that is placed in the reading frame of an ORF to separate an upstream and downstream DNA sequences. In some embodiments, a linker can be cleavable by an insect protease. In some embodiments, a linker may allow proteins to achieve their independent secondary and tertiary structure formation during translation. In some embodiments, the linker can be either resistant or susceptible to cleavage in plant cellular environments, in the insect and/or lepidopteran gut environment, and/or in the insect hemolymph and lepidopteran hemolymph environment. In some embodiments, a linker can be cleaved by a protease, e.g., in some embodiments, a linker can be cleaved by a plant protease (e.g., papain, bromelain, ficin, actinidin, zingibain, and/or cardosins), an insect protease, a fungal protease, a vertebrate protease, an invertebrate protease, a bacteria protease, a mammal protease, a reptile protease, or an avian protease. In some embodiments, a linker can be cleavable or non-cleavable. In some embodiments, a linker comprises a binary or tertiary region, wherein each region is cleavable by at least two types of proteases: one of which is an insect and/or nematode protease and the other one of which is a human protease. In some embodiments, a linker can have one of (at least) three roles: to cleave in the insect gut environment, to cleave in the plant cell, or to be designed not to intentionally cleave.

"Medium" (plural "media") refers to a nutritive solution for culturing cells in cell culture.

"MOA" refers to mechanism of action.

"Molecular weight (MW)" refers to the mass or weight of a molecule, and is typically measured in "daltons (Da)" or kilodaltons (kDa). In some embodiments, MW can be calculated using sodium dodecyl sulfate polyacrylamide gel electrophoresis (SDS-PAGE), analytical ultracentrifugation, or light scattering. In some embodiments, the SDS-PAGE method is as follows: the sample of interest is separated on a gel with a set of molecular weight standards. The sample is run, and the gel is then processed with a desired stain, followed by destaining for about 2 to 14 hours. The next step is to determine the relative migration distance (Rf) of the standards and protein of interest. The migration distance can be determined using the following equation:

$$Rf = \frac{\text{Migration distance of the protein}}{\text{Migration distance of the dye front}} \qquad \text{(Formula III)}$$

Next, the logarithm of the MW can be determined based on the values obtained for the bands in the standard; e.g., in some embodiments, the logarithm of the molecular weight of an SDS-denatured polypeptide and its relative migration distance (Rf) is plotted into a graph. After plotting the graph, interpolating the value derived will provide the molecular weight of the unknown protein band.

"Motif" refers to a polynucleotide or polypeptide sequence that is implicated in having some biological significance and/or exerts some effect or is involved in some biological process.

"Multiple cloning site" or "MCS" refers to a segment of DNA found on a vector that contains numerous restriction sites in which a DNA sequence of interest can be inserted.

"Mutant" refers to an organism, DNA sequence, amino acid sequence, peptide, polypeptide, or protein, that has an alteration or variation (for example, in the nucleotide sequence or the amino acid sequence), which causes said organism and/or sequence to be different from the naturally occurring or wild-type organism, wild-type sequence, and/or reference sequence with which the mutant is being compared. In some embodiments, this alteration or variation can be one or more nucleotide and/or amino acid substitutions or modifications (e.g., deletion or addition). In some embodiments, the one or more amino acid substitutions or modifications can be conservative; here, such a conservative amino acid substitution and/or modification in a "mutant" does not substantially diminish the activity of the mutant in relation to its non-mutant form. For example, in some embodiments, a "mutant" possesses one or more conservative amino acid substitutions when compared to a peptide with a disclosed and/or claimed sequence, as indicated by a SEQ ID NO.

"N-terminal" refers to the free amine group (i.e., $-NH_2$) that is positioned on beginning or start of a polypeptide.

"NCBI" refers to the National Center for Biotechnology Information.

"nm" refers to nanometers.

"Normalized peptide yield" means the peptide yield in the conditioned medium divided by the corresponding cell density at the point the peptide yield is measured. The peptide yield can be represented by the mass of the produced peptide in a unit of volume, for example, mg per liter or mg/L, or by the UV absorbance peak area of the produced peptide in the HPLC chromatograph, for example, mAu·sec. The cell density can be represented by visible light absorbance of the culture at wavelength of 600 nm (OD600).

"OD" refers to optical density. Typically, OD is measured using a spectrophotometer. When measuring growth over time of a cell population, OD600 is preferable to UV spectroscopy; this is because at a 600 nm wavelength, the cells will not be harmed as they would under too much UV light.

"OD660 nm" or "$OD_{660nm}$" refers to optical densities at 660 nanometers (nm).

"One letter code" means the peptide sequence which is listed in its one letter code to distinguish the various amino acids in the primary structure of a protein: alanine=A, arginine=R, asparagine=N, aspartic acid=D, asparagine or aspartic acid=B, cysteine=C, glutamic acid=E, glutamine=Q, glutamine or glutamic acid=Z, glycine=G, histidine=H, isoleucine=I, leucine=L, lysine=K, methionine=M, phenylalanine=F, proline=P, serine=S, threonine=T, tryptophan=W, tyrosine=Y, and valine=V.

"Operable" refers to the ability to be used, the ability to do something, and/or the ability to accomplish some function or result. For example, in some embodiments, "operable" refers to the ability of a polynucleotide, DNA sequence, RNA sequence, or other nucleotide sequence or gene to encode a peptide, polypeptide, and/or protein. For example, in some embodiments, a polynucleotide may be operable to encode a protein, which means that the polynucleotide contains information that imbues it with the ability to create a protein (e.g., by transcribing mRNA, which is in turn translated to protein).

"Operably linked" refers to a juxtaposition wherein components so described are in a relationship permitting them to function in their intended manner. For example, in some embodiments, operably linked can refer to two or more DNA, peptide, or polypeptide sequences. For example, in some embodiments, operably linked can mean that the two adjacent DNA sequences are placed together such that the transcriptional activation of one can act on the other. In other embodiments, the term "operably linked" can refer to peptide and/or polypeptide molecules, e.g., wherein operably linked means that two or more peptide and/or polypeptide molecules are connected in such a way as to yield a single polypeptide chain, or connected in such a way inasmuch that one peptide exerts some effect on the other. In yet other embodiments, operably linked can refer to two adjacent DNA sequences are placed together such that the transcriptional activation of one can act on the other. In other embodiments, operably linked can refer to peptide and/or polypeptide molecules, wherein two or more peptide and/or polypeptide molecules are connected in such a way as to yield a single polypeptide chain, or connected in such a way inasmuch that one peptide exerts some effect on the other.

"ORF" or "open reading frame" refers to a length of RNA or DNA sequence, between a translation start signal (e.g., AUG or ATG, respectively) and any one or more of the known termination codons, which encodes one or more polypeptide sequences. Put another way, the ORF describes the frame of reference as seen from the point of view of a ribosome translating the RNA code, insofar that the ribosome is able to keep reading (i.e., adding amino acids to the nascent protein) because it has not encountered a stop codon. Thus, "open reading frame" or "ORF" refers to the amino acid sequence encoded between translation initiation and termination codons of a coding sequence. Here, the terms "initiation codon" and "termination codon" refer to a unit of three adjacent nucleotides (i.e., a codon) in a coding sequence that specifies initiation and chain termination, respectively, of protein synthesis (mRNA translation).

In some embodiments, an ORF is a continuous stretch of codons that begins with a start codon (usually ATG for DNA, and AUG for RNA) and ends at a stop codon (usually UAA, UAG or UGA). In other embodiments, an ORF can be a length of RNA or DNA sequence, between a translation start signal (e.g., AUG or ATG) and any one or more of the known termination codons, wherein said length of RNA or DNA sequence encodes one or more polypeptide sequences. In some other embodiments, an ORF can be a DNA sequence encoding a protein which begins with an ATG start codon and ends with a TGA, TAA or TAG stop codon. ORF can also mean the translated protein that the DNA encodes. Generally, those having ordinary skill in the art distinguish the terms "open reading frame" and "ORF," from the term "coding sequence," based upon the fact that the broadest definition of "open reading frame" simply contemplates a series of codons that does not contain a stop codon. Accordingly, while an ORF may contain introns, the coding sequence is distinguished by referring to those nucleotides (e.g., concatenated exons) that can be divided into codons that are actually translated into amino acids by the ribosomal translation machinery (i.e., a coding sequence does not contain introns); however, as used herein, the terms "coding sequence"; "CDS"; "open reading frame"; and "ORF," are used interchangeably.

"Out-recombined" or "out-recombination" refers to the removal of a gene and/or polynucleotide sequence (e.g., an endogenous gene) that is flanked by two site-specific recombination sites (e.g., the 5'- and 3'-nucleotide sequence of a target gene that is homologous to the homology arms of a target vector) during in vivo homologous recombination. See "knockout."

"Pest" includes, but is not limited to: insects, fungi, bacteria, nematodes, mites, ticks, and the like.

"Pesticidally-effective amount" refers to an amount of the pesticide that is able to bring about death to at least one pest, or to noticeably reduce pest growth, feeding, or normal physiological development. This amount will vary depending on such factors as, for example, the specific target pests to be controlled, the specific environment, location, plant, crop, or agricultural site to be treated, the environmental conditions, and the method, rate, concentration, stability, and quantity of application of the pesticidally-effective polypeptide composition. The formulations may also vary with respect to climatic conditions, environmental considerations, and/or frequency of application and/or severity of pest infestation.

"Pharmaceutically acceptable salt" is synonymous with agriculturally acceptable salt, and as used herein refers to a compound that is modified by making acid or base salts thereof.

"Plant" shall mean whole plants, plant tissues, plant organs (e.g., leaves, stems, roots, etc.), seeds, plant cells, propagules, embryos and progeny of the same. Plant cells can be differentiated or undifferentiated (e.g. callus, suspension culture cells, protoplasts, leaf cells, root cells, phloem cells, and pollen).

"Plant transgenic protein" means a protein from a heterologous species that is expressed in a plant after the DNA or RNA encoding it was delivered into one or more of the plant cells.

"Plasmid" refers to a DNA segment that acts as a carrier for a gene of interest (e.g., tvp) and, when transformed or transfected into an organism, can replicate and express the DNA sequence contained within the plasmid independently of the host organism. Plasmids are a type of vector, and can be "cloning vectors" (i.e., simple plasmids used to clone a DNA fragment and/or select a host population carrying the plasmid via some selection indicator) or "expression plasmids" (i.e., plasmids used to produce large amounts of polynucleotides and/or polypeptides).

"Polynucleotide" refers to a polymeric-form of nucleotides (e.g., ribonucleotides, deoxyribonucleotides, or analogs thereof) of any length; e.g., a sequence of two or more ribonucleotides or deoxyribonucleotides. As used herein, the term "polynucleotide" includes double- and single-stranded DNA, as well as double- and single-stranded RNA; it also includes modified and unmodified forms of a polynucleotide (modifications to and of a polynucleotide, for example, can include methylation, phosphorylation, and/or capping). In some embodiments, a polynucleotide can be one of the following: a gene or gene fragment (for example, a probe, primer, EST, or SAGE tag); genomic DNA; genomic DNA fragment; exon; intron; messenger RNA (mRNA); transfer RNA; ribosomal RNA; ribozyme; cDNA; recombinant polynucleotide; branched polynucleotide; plasmid; vector; isolated DNA of any sequence; isolated RNA of any sequence; nucleic acid probe; primer or amplified copy of any of the foregoing.

In yet other embodiments, a polynucleotide can refer to a polymeric-form of nucleotides operable to encode the open reading frame of a gene.

In some embodiments, a polynucleotide can refer to cDNA.

In some embodiments, polynucleotides can have any three-dimensional structure and may perform any function, known or unknown. The structure of a polynucleotide can also be referenced to by its 5'- or 3'-end or terminus, which indicates the directionality of the polynucleotide. Adjacent nucleotides in a single-strand of polynucleotides are typically joined by a phosphodiester bond between their 3' and 5' carbons. However, different internucleotide linkages could also be used, such as linkages that include a methylene, phosphoramidate linkages, etc. This means that the respective 5' and 3' carbons can be exposed at either end of the polynucleotide, which may be called the 5' and 3' ends or termini. The 5' and 3' ends can also be called the phosphoryl ($PO_4$) and hydroxyl (OH) ends, respectively, because of the chemical groups attached to those ends. The term polynucleotide also refers to both double- and single-stranded molecules. Unless otherwise specified or required, any embodiment that makes or uses a polynucleotide encompasses both the double-stranded form and each of two complementary single-stranded forms known or predicted to make up the double-stranded form.

In some embodiments, a polynucleotide can include modified nucleotides, such as methylated nucleotides and nucleotide analogs (including nucleotides with non-natural bases, nucleotides with modified natural bases such as aza- or deaza-purines, etc.). If present, modifications to the nucleotide structure can be imparted before or after assembly of the polynucleotide.

In some embodiments, a polynucleotide can also be further modified after polymerization, such as by conjugation with a labeling component. Additionally, the sequence of nucleotides in a polynucleotide can be interrupted by non-nucleotide components. One or more ends of the poly-nucleotide can be protected or otherwise modified to prevent that end from interacting in a particular way (e.g. forming a covalent bond) with other polynucleotides.

In some embodiments, a polynucleotide can be composed of a specific sequence of four nucleotide bases: adenine (A); cytosine (C); guanine (G); and thymine (T). Uracil (U) can also be present, for example, as a natural replacement for thymine when the polynucleotide is RNA. Uracil can also be used in DNA. Thus, the term "sequence" refers to the alphabetical representation of a polynucleotide or any nucleic acid molecule, including natural and non-natural bases.

The term "RNA molecule" or ribonucleic acid molecule refers to a polynucleotide having a ribose sugar rather than deoxyribose sugar and typically uracil rather than thymine as one of the pyrimidine bases. An RNA molecule of the invention is generally single-stranded, but can also be double-stranded. In the context of an RNA molecule from an RNA sample, the RNA molecule can include the single-stranded molecules transcribed from DNA in the cell nucleus, mitochondrion or chloroplast, which have a linear sequence of nucleotide bases that is complementary to the DNA strand from which it is transcribed.

In some embodiments, a polynucleotide can further comprise one or more heterologous regulatory elements. For example, in some embodiments, the regulatory element is one or more promoters; enhancers; silencers; operators; splicing signals; polyadenylation signals; termination signals; RNA export elements, internal ribosomal entry sites (IRES); poly-U sequences; or combinations thereof.

"Post-transcriptional regulatory elements" are DNA segments and/or mechanisms that affect mRNA after it has been transcribed. Mechanisms of post-transcriptional mechanisms include splicing events; capping, splicing, and addition of a Poly (A) tail, and other mechanisms known to those having ordinary skill in the art.

"Promoter" refers to a region of DNA to which RNA polymerase binds and initiates the transcription of a gene.

"Protein" has the same meaning as "peptide" and/or "polypeptide" in this document.

"Ratio" refers to the quantitative relation between two amounts showing the number of times one value contains or is contained within the other.

"Reading frame" refers to one of the six possible reading frames, three in each direction, of the double stranded DNA molecule. The reading frame that is used determines which codons are used to encode amino acids within the coding sequence of a DNA molecule. In some embodiments, a reading frame is a way of dividing the sequence of nucleotides in a polynucleotide and/or nucleic acid (e.g., DNA or RNA) into a set of consecutive, non-overlapping triplets.

"Recombinant DNA" or "rDNA" refers to DNA that is comprised of two or more different DNA segments.

"Recombinant vector" means a DNA plasmid vector into which foreign DNA has been inserted.

"Regulatory elements" refers to a genetic element that controls some aspect of the expression and/or processing of nucleic acid sequences. For example, in some embodiments, a regulatory element can be found at the transcriptional and post-transcriptional level. Regulatory elements can be cis-regulatory elements (CREs), or trans-regulatory elements (TREs). In some embodiments, a regulatory element can be one or more promoters; enhancers; silencers; operators; splicing signals; polyadenylation signals; termination signals; RNA export elements, internal ribosomal entry sites (IRES); poly-U sequences; and/or other elements that influence gene expression, for example, in a tissue-specific manner; temporal-dependent manner; to increase or decrease expression; and/or to cause constitutive expression.

"Restriction enzyme" or "restriction endonuclease" refers to an enzyme that cleaves DNA at a specified restriction site. For example, a restriction enzyme can cleave a plasmid at an EcoRI, SacII or BstXI restriction site allowing the plasmid to be linearized, and the DNA of interest to be ligated.

"Restriction site" refers to a location on DNA comprising a sequence of 4 to 8 nucleotides, and whose sequence is recognized by a particular restriction enzyme.

"Selection gene" means a gene which confers an advantage for a genetically modified organism to grow under the selective pressure.

"Serovar" or "serotype" refers to a group of closely related microorganisms distinguished by a characteristic set of antigens. In some embodiments, a serovar is an antigenically and serologically distinct variety of microorganism "sp." refers to species.

"ssp." or "subsp." refers to subspecies.

"Subcloning" or "subcloned" refers to the process of transferring DNA from one vector to another, usually advantageous vector. For example, polynucleotide encoding a mutant TVP can be subcloned into a pKlac1 plasmid subsequent to selection of yeast colonies transformed with pKLAC1 plasmids.

"SSI" is an acronym that is context dependent. In some contexts, it can refer to "Site-specific integration," which is used to refer to a sequence that will permit in vivo homologous recombination to occur. However, in other contexts, SSI can refer to "Surface spraying indoors," which is a technique of applying a variable volume sprayable volume of an insecticide onto indoor surfaces where vectors rest, such as on walls, windows, floors and ceilings. The term "site-specific integration" refers to the process directing a transgene to a target site in a host-organism's genome; thus, SSI allows the integration of genes of interest into preselected genome locations of a host-organism.

"STA" or "Translational stabilizing protein" or "stabilizing domain" or "stabilizing protein" (used interchangeably herein) means a peptide or protein with sufficient tertiary structure that it can accumulate in a cell without being targeted by the cellular process of protein degradation. The protein can be between 5 and 50 amino acids long. The translational stabilizing protein is coded by a DNA sequence for a protein that is operably linked with a sequence encoding an insecticidal protein or a TVP in the ORF. The operably-linked STA can either be upstream or downstream of the TVP and can have any intervening sequence between the two sequences (STA and TVP) as long as the intervening sequence does not result in a frame shift of either DNA sequence. The translational stabilizing protein can also have an activity which increases delivery of the TVP across the gut wall and into the hemolymph of the insect.

"sta" means a nucleotide encoding a translational stabilizing protein.

"Structural motif" refers to the three-dimensional arrangement of peptides and/or polypeptides, and/or the arrangement of operably linked polypeptide segments. For example, a polypeptide having an ERSP motif, an STA motif, a LINKER motif, and a TVP polypeptide motif, has an overall "structural motif" of ERSP-STA-L-TVP. See also "TVP construct"

"Ta1b" or "U1-agatoxin-Ta1b" or "Ta1bWT" or "wild-type U1-agatoxin-Ta1b" refers to a polypeptide isolated from the Hobo spider, *Eratigena agrestis*. One example of a U1-agatoxin-Ta1b is a polypeptide having the amino acid sequence of SEQ ID NO:1 (NCBI Accession No. 046167.1).

"Ta1b variant polynucleotide" or "U1-agatoxin-Ta1b variant polynucleotide" refers to a polynucleotide or group of polynucleotides operable to express and/or encode an insecticidal protein comprising one or more TVPs. The term "U1-agatoxin-Ta1b variant polynucleotide" when used to describe the U1-agatoxin-Ta1b variant polynucleotide sequence contained in a TVP expression ORF, its inclusion in a vector, and/or when describing the polynucleotides encoding an insecticidal protein, is described as "tvp" and/or "Tvp."

"Toxin" refers to a venom and/or a poison, especially a protein or conjugated protein produced by certain animals, higher plants, and pathogenic bacteria. Generally, the term "toxin" is reserved natural products, e.g., molecules and peptides found in scorpions, spiders, snakes, poisonous mushrooms, etc., whereas the term "toxicant" is reserved for man-made products and/or artificial products e.g., man-made chemical pesticides. However, as used herein, the terms "toxin" and "toxicant" are used synonymously "Transfection" and "transformation" both refer to the process of introducing exogenous and/or heterologous DNA or RNA (e.g., a vector containing a polynucleotide that encodes a TVP) into a host organism (e.g., a prokaryote or a eukaryote). Generally, those having ordinary skill in the art sometimes reserve the term "transformation" to describe processes where exogenous and/or heterologous DNA or RNA are introduced into a bacterial cell; and reserve the term "transfection" for processes that describe the introduction of exogenous and/or heterologous DNA or RNA into eukaryotic cells. However, as used herein, the term "transformation" and "transfection" are used synonymously, regardless of whether a process describes the introduction exogenous and/or heterologous DNA or RNA into a prokaryote (e.g., bacteria) or a eukaryote (e.g., yeast, plants, or animals).

"Transgene" means a heterologous DNA sequence encoding a protein which is transformed into a plant.

"Transgenic host cell" means a cell which is transformed with a gene and has been selected for its transgenic status via an additional selection gene.

"Transgenic plant" means a plant that has been derived from a single cell that was transformed with foreign DNA such that every cell in the plant contains that transgene.

"Transient expression system" means an *Agrobacterium tumefaciens*-based system which delivers DNA encoding a disarmed plant virus into a plant cell where it is expressed. The plant virus has been engineered to express a protein of interest at high concentrations, up to 40% of the TSP.

"Triple expression cassette refers to three TVP expression cassettes contained on the same vector.

"TRBO" means a transient plant expression system using Tobacco mosaic virus with removal of the viral coating protein gene.

"TSP" or "total soluble protein" means the total amount of protein that can be extracted from a plant tissue sample and solubilized into the extraction buffer.

"TVP" or "U1-agatoxin-Ta1b Variant Polypeptides (TVPs)" or "Ta1b Variant Polypeptides (TVPs)" refers to mutants or variants of the wild-type U1-agatoxin-Ta1b polypeptide sequence and/or a polynucleotide sequence encoding a wild-type U1-agatoxin-Ta1b polypeptide, that have been altered to produce a non-naturally occurring polypeptide and/or polynucleotide sequence. An exemplary wild-type U1-agatoxin-Ta1b polypeptide sequence is provided herein, having the amino acid sequence of SEQ ID NO: 1. An exemplary wild-type U1-agatoxin-Ta1b precursor polypeptide sequence is provided herein, having the amino acid sequence of SEQ ID NO: 48 (NCBI Accession No. 046167.1), which includes the signal sequence "MKLQLMICLVLLPCFFC" (SEQ ID NO: 59). In some embodiments, a TVP can have an amino acid sequence according to any of the amino acid sequences listed in Table 1. Accordingly, the term "TVP" refers to peptides having one or more mutations relative to the amino acid sequence set forth in SEQ ID NO: 1. In some embodiments, a TVP can have an amino acid sequence according to Formula (I):

Formula (I)
E-P-D-E-I-C-R-$X_1$-$X_2$-M-$X_3$-N-K-E-F-T-Y-$X_4$-S-N-V-C-N-

N-C-G-D-Q-V-A-A-C-E-A-E-C-F-$X_5$-N-D-V-Y-$Z_1$-A-C-H-E-

A-Q-$X_6$-$X_7$ wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $\lambda_6$ is K or absent; and $X_7$ is G or absent.

In some embodiments, a TVP can have an amino acid sequence according to Formula (II):

Formula (II)
E-P-D-E-I-C-R-A-X₁-M-T-N-K-E-F-T-Y-K-S-N-V-C-N-N-

C-G-D-Q-V-A-A-C-E-A-E-C-F-R-N-D-V-Y-Z₁-A-C-H-E-A-

Q-K-G wherein the polypeptide comprises at least one amino acid substitution relative to the wild-type sequence of U1-aga-toxin-Ta1b as set forth in SEQ ID NO:1, and wherein $X_1$ is R or Q; and $Z_1$ is T or A; or a pharmaceutically acceptable salt thereof.

"TVP ORF diagram" refers to the composition of one or more TVP ORFs, as written out in diagram or equation form. For example, a "TVP ORF diagram" can be written out as using acronyms or short-hand references to the DNA segments contained within the expression ORF. Accordingly, in one example, a "TVP ORF diagram" may describe the polynucleotide segments encoding the ERSP, LINKER, STA, and TVP, by diagramming in equation form the DNA segments as "ersp" (i.e., the polynucleotide sequence that encodes the ERSP polypeptide); "linker" or "L" (i.e., the polynucleotide sequence that encodes the LINKER poly-peptide); "sta" (i.e., the polynucleotide sequence that encodes the STA polypeptide), and "tvp" (i.e., the poly-nucleotide sequence encoding a TVP), respectively. An example of a TVP ORF diagram is "ersp-sta-(linker$_i$-tvp$_j$)$_N$," or "ersp-(tvp$_j$-linker$_i$)$_N$-sta" and/or any combination of the DNA segments thereof.

"TVP polynucleotide" refers to a polynucleotide or group of polynucleotides operable to express and/or encode a TVP or a TVP-insecticidal protein.

"TVP-insecticidal protein" refers to any protein, peptide, polypeptide, amino acid sequence, configuration, or arrange-ment, consisting of: (1) at least one TVP, or two or more TVPs; and (2) additional non-toxin peptides, polypeptides, or proteins, wherein said additional non-toxin peptides, polypeptides, or proteins e.g., in some embodiments, have the ability to do one or more of the following: increase the mortality and/or inhibit the growth of insects when the insects are exposed to a TVP-insecticidal protein, relative to a TVP alone; increase the expression of said TVP-insecti-cidal protein, e.g., in a host cell or an expression system; and/or affect the post-translational processing of the TVP-insecticidal protein. In some embodiments, a TVP-insecti-cidal protein can be a polymer comprising two or more TVPs. In some embodiments, a TVP-insecticidal protein can be a polymer comprising two or more TVPs, wherein the TVPs are operably linked via a linker peptide, e.g., a cleavable and/or non-cleavable linker. In some embodi-ments, a TVP-insecticidal protein can refer to a one or more TVPs operably linked with one or more proteins such as a stabilizing domain (STA); an endoplasmic reticulum signal-ing protein (ERSP); an insect cleavable or insect non-cleavable linker (L); and/or any other combination thereof. In some embodiments, a TVP-insecticidal protein can be a non-naturally occurring protein comprising (1) a wild-type Ta1b protein; and (2) additional non-toxin peptides, poly-peptides, or proteins, e.g., an ERSP; a linker; a STA; a UBI; or a histidine tag or similar marker.

"TVP construct" refers to the three-dimensional arrange-ment/orientation of peptides, polypeptides, and/or motifs of operably linked polypeptide segments (e.g., a TVP-insecti-cidal protein). For example, a TVP expression ORF can include one or more of the following components or motifs: a TVP; an endoplasmic reticulum signal peptide (ERSP); a linker peptide (L); a translational stabilizing protein (STA); or any combination thereof. And, as used herein, the term "TVP construct" is used to describe the designation and/or orientation of the structural motif. In other words, the TVP construct describes the arrangement and orientation of the components or motifs contained within a given TVP expres-sion ORF. For example, in some embodiments, a TVP construct describes, without limitation, the orientation of one of the following TVP-insecticidal proteins: ERSP-TVP; ERSP-(TVP)$_N$; ERSP-TVP-L; ERSP-(TVP)$_N$-L; ERSP-(TVP-L)$_N$; ERSP-L-TVP; ERSP-L-(TVP)$_N$; ERSP-(L-TVP)$_N$; ERSP-STA-TVP; ERSP-STA-(TVP)$_N$; ERSP-TVP-STA; ERSP-(TVP)$_N$-STA; ERSP-(STA-TVP)$_N$; ERSP-(TVP-STA)$_N$; ERSP-L-TVP-STA; ERSP-L-STA-TVP; ERSP-L-(TVP-STA)$_N$; ERSP-L-(STA-TVP)$_N$; ERSP-L-(TVP)$_N$—STA; ERSP-(L-TVP)$_N$—STA; ERSP-(L-STA-TVP)$_N$; ERSP-(L-TVP-STA)$_N$; ERSP-(L-STA)$_N$-TVP; ERSP-(L-TVP)$_N$—STA; ERSP-STA-L-TVP; ERSP-STA-TVP-L; ERSP-STA-L-(TVP)$_N$; ERSP-(STA-L)$_N$-TVP; ERSP-STA-(L-TVP)$_N$; ERSP-(STA-L-TVP)$_N$; ERSP-STA-(TVP)$_N$-L; ERSP-STA-(TVP-L)$_N$; ERSP-(STA-TVP)$_N$-L; ERSP-(STA-TVP-L)$_N$; ERSP-TVP-L-STA; ERSP-TVP-STA-L; ERSP-(TVP)$_N$—STA-L ERSP-(TVP-L)$_N$-STA; ERSP-(TVP-STA)$_N$-L; ERSP-(TVP-L-STA)$_N$; or ERSP-(TVP-STA-L)$_N$; wherein N is an integer ranging from 1 to 200. See also "Structural motif."

"var." refers to varietas or variety. The term "var." is used to indicate a taxonomic category that ranks below the species level and/or subspecies (where present). In some embodiments, the term "var." represents members differing from others of the same subspecies or species in minor but permanent or heritable characteristics.

"Variant" or "variant sequence" or "variant peptide" refers to an amino acid sequence that possesses one or more conservative amino acid substitutions or conservative modi-fications. The conservative amino acid substitutions in a "variant" does not substantially diminish the activity of the variant in relation to its non-varied form. For example, in some embodiments, a "variant" possesses one or more conservative amino acid substitutions when compared to a peptide with a disclosed and/or claimed sequence, as indi-cated by a SEQ ID NO.

"Vector" refers to the DNA segment that accepts a foreign gene of interest (e.g., tvp). The gene of interest is known as an "insert" or "transgene."

"Vitrification" refers to a process of converting a material into a glass-like amorphous material. The glass-like amor-phous solid may be free of any crystalline structure. Solidi-fication of a vitreous solid occurs at the glass transition temperature (Tg).

"Wild type" or "WT" refers to the phenotype and/or genotype (i.e., the appearance or sequence) of an organism, polynucleotide sequence, and/or polypeptide sequence, as it is found and/or observed in its naturally occurring state or condition.

"Yeast expression vector" or "expression vector" or "vec-tor" means a plasmid which can introduce a heterologous gene and/or expression cassette into yeast cells to be tran-scribed and translated.

"Yield" refers to the production of a peptide, and increased yields can mean increased amounts of production, increased rates of production, and an increased average or median yield and increased frequency at higher yields. The term "yield" when used in reference to plant crop growth and/or production, as in "yield of the plant" refers to the quality and/or quantity of biomass produced by the plant.

Throughout this specification, unless specifically stated otherwise or the context requires otherwise, reference to a single step, composition of matter, group of steps or group of compositions of matter shall be taken to encompass one and a plurality (i.e., one or more) of those steps, compositions of matter, groups of steps or group of compositions of matter.

The present disclosure is performed without undue experimentation using, unless otherwise indicated, conventional techniques of molecular biology, microbiology, virology, recombinant DNA technology, solid phase and liquid nucleic acid synthesis, peptide synthesis in solution, solid phase peptide synthesis, immunology, cell culture, and formulation. Such procedures are described, for example, in Sambrook, Fritsch & Maniatis, Molecular Cloning: A Laboratory Manual, Cold Spring Harbor Laboratories, New York, Second Edition (1989), whole of Vols I, II, and III; DNA Cloning: A Practical Approach, Vols. I and II (D. N. Glover, ed., 1985), IRL Press, Oxford, whole of text; Oligonucleotide Synthesis: A Practical Approach (M. J. Gait, ed, 1984) IRL Press, Oxford, whole of text, and particularly the papers therein by Gait, pp 1-22; Atkinson et al, pp 35-81; Sproat et al, pp 83-115; and Wu et al, pp 135-151; 4. Nucleic Acid Hybridization: A Practical Approach (B. D. Hames & S. J. Higgins, eds., 1985) IRL Press, Oxford, whole of text; Immobilized Cells and Enzymes: A Practical Approach (1986) IRL Press, Oxford, whole of text; Perbal, B., A Practical Guide to Molecular Cloning (1984); Methods In Enzymology (S. Colowick and N. Kaplan, eds., Academic Press, Inc.), whole of series; J. F. Ramalho Ortigao, "The Chemistry of Peptide Synthesis" In: Knowledge database of Access to Virtual Laboratory website (Interactiva, Germany); Sakakibara, D., Teichman, J., Lien, E. Land Fenichel, R. L. (1976). Biochem. Biophys. Res. Commun. 73 336-342; Merrifield, R. B. (1963). J. Am. Chem. Soc. 85, 2149-2154; Barany, G. and Merrifield, R. B. (1979) in The Peptides (Gross, E. and Meienhofer, 3. eds.), vol. 2, pp. 1-284, Academic Press, New York. 12. Wiinsch, E., ed. (1974) Synthese von Peptiden in Houben-Weyls Metoden der Organischen Chemie (Muler, E., ed.), vol. 15, 4th edn., Parts 1 and 2, Thieme, Stuttgart; Bodanszky, M. (1984) Principles of Peptide Synthesis, Springer-Verlag, Heidelberg; Bodanszky, M. & Bodanszky, A. (1984) The Practice of Peptide Synthesis, Springer-Verlag, Heidelberg; Bodanszky, M. (1985) Int. J. Peptide Protein Res. 25, 449-474; Handbook of Experimental Immunology, Vols. I-IV (D. M. Weir and C. C. Blackwell, eds., 1986, Blackwell Scientific Publications); and Animal Cell Culture: Practical Approach, Third Edition (John R. W. Masters, ed., 2000); each of these references are incorporated herein by reference in their entireties.

Throughout this specification, unless the context requires otherwise, the word "comprise," or variations such as "comprises" or "comprising," will be understood to imply the inclusion of a stated step or element or integer or group of steps or elements or integers but not the exclusion of any other step or element or integer or group of elements or integers.

All patent applications, patents, and printed publications referred to herein are incorporated by reference in their entirety to the same extent as if each individual publication, patent, or patent application was specifically and individually indicated to be incorporated by reference in its entirety. And, all patent applications, patents, and printed publications cited herein are incorporated herein by reference in the entireties, except for any definitions, subject matter disclaimers, or disavowals, and except to the extent that the incorporated material is inconsistent with the express disclosure herein, in which case the language in this disclosure controls.

Wild-Type U1-Agatoxins and TVPS

"Hobo spiders" (*Eratigena agrestis*, formerly *Tegenaria agrestis*) are venomous spiders that are members of the Agelenidae family of spiders, or funnel web weavers. See Ingale A, Antigenic epitopes prediction and MHC binder of a paralytic insecticidal toxin (ITX-1) of *Tegenaria agrestis* (hobo spider). 4 Aug. 2010 Volume 2010:2 pp 97-103. The venom of Hobo spiders has been implicated as possessing insecticidal activity. See Johnson et al., Novel insecticidal peptides from *Tegenaria agrestis* spider venom may have a direct effect on the insect central nervous system. Arch Insect Biochem Physiol. 1998; 38(1):19-31; Klint et al., Production of Recombinant Disulfide-Rich Venom Peptides for Structural and Functional Analysis via Expression in the Periplasm of *E. coli*. PLoS One. 2013; 8(5): e63865.

The Hobo spider—along with several other spiders in the Agelenidae family, produce venom containing agatoxins—which exhibit insecticidal activity. Agatoxins are a chemically diverse group of toxins that can induce various insecticidal effects depending on the target species; e.g., agatoxins cause slow-onset spastic paralysis in coleopterans, lepidopterans, and dipterans; increase the rate of neuron firing in the central nervous system (CNS) of houseflies (*Musca domestica*); and are lethal to other insects (e.g., the blowfly, *Lucilia cuprina*). Accordingly, agatoxins are implicated in targeting the CNS. See Undheim et al., Weaponization of a hormone: convergent recruitment of hyperglycemic hormone into the venom of arthropod predators. Structure 23: 1283-1292, and Johnson et al., Novel insecticidal peptides from *Tegenaria agrestis* spider venom may have a direct effect on the insect central nervous system. Arch. Insect Biochem. Physiol. 38:19-31(1998).

Two types of agatoxins include U1-agatoxin-Ta1a and U1-agatoxin-Ta1b, which are both members of the helical arthropod-neuropeptide-derived (HAND) toxins family. In addition to spiders, these toxins can also be found in the venom of centipedes. The agatoxins are evolutionary offshoots of an ancient ecdysozoan hormone family, i.e., the ion transport peptide/crustacean hyperglycemic hormone (ITP/CHH) family. See Undheim et al., Weaponization of a hormone: convergent recruitment of hyperglycemic hormone into the venom of arthropod predators. Structure 23: 1283-1292, and Johnson et al., Novel insecticidal peptides from *Tegenaria agrestis* spider venom may have a direct effect on the insect central nervous system. Arch. Insect Biochem. Physiol. 38:19-31(1998).

The Hobo-spider-derived U1-agatoxin-Ta1b toxin has a full amino acid sequence of "MKLQLMICLVLLPCFFCEP-DEICRARMTNKEFTYKSNVCNNCGDQVAACE-AECFRNDVYTACHEAQKG" (SEQ ID NO:48)" which includes a signal peptide from amino acid positions 1-17, and the mature toxin from positions 18-68. Id. The protein comprises four tightly packed α-helices, with no β-strands present, and the molecular mass of the mature toxin is 5700.39 Daltons (Da). Id.

An exemplary mature wild-type U1-agatoxin-Ta1b polypeptide from *Eratigena agrestis* is provided having the amino acid sequence:

(SEQ ID NO: 1)

"EPDEICRARMTNKEFTYKSNVCNNCGDQVAACEAECFRNDVYTACH

EAQKG"

During protein processing, the mature wild-type U1-aga-toxin-Ta1b toxin undergoes an excision event of the C-terminal glycine, yielding the following amino acid sequence: EPDEICRARMTNKEFTYKSNVCNNCGDQVAACE-AECFRNDVYTACHEAQK (SEQ ID NO: 60). A subsequent post-translational event result in the mature wild-type U1-agatoxin-Ta1b toxin having a C-terminal amidation.

U1-agatoxin-Ta1b Variant Polypeptides (TVPs) are mutants or variants that differ from the wild-type U1-aga-toxin-Ta1b (SEQ ID NO: 1) in some way, e.g., in some embodiments, this variance can be an amino acid substitution, deletion, or addition; or a change to the polynucleotide encoding the wild-type U1-agatoxin-Ta1b resulting in an amino acid substitution, deletion, or addition. The result of this variation is a non-naturally occurring polypeptide and/or polynucleotide sequence encoding the same that possesses enhanced insecticidal activity against one or more insect species relative to the wild-type U1-agatoxin-Ta1b.

In some embodiments, a TVP can have an amino acid sequence according to SEQ ID NOs: 2-15, 49-53, or 77-110, as shown in Table 1.

TABLE 1

| | | | |
|---|---|---|---|
| | | TVPs of the present invention. | |
| Amino Acid SEQ ID NO | Name | Amino Acid Sequence | Nucleotide Sequence |
| 1 | WT-Ta1b | EPDEICRARMTNKEF TYKSNVCNNCGDQVA ACEAECFRNDVYTAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 2 | TVP-R9Q | EPDEICRAQMTNKEF TYKSNVCNNCGDQVA ACEAECFRNDVYTAC HEAQKG | GAACCAGACGAGATATGCAGAGCAcaaATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 3 | TVP-R9QΔG | EPDEICRAQMTNKEF TYKSNVCNNCGDQVA ACEAECFRNDVYTAC HEAQK | GAACCAGACGAGATATGCAGAGCAcaaATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAA |
| 4 | TVP-K18A | EPDEICRARMTNKEF TYASNVCNNCGDQVA ACEAECFRNDVYTAC HEAQKG | GAACCAGACGAGATATGCAGAGCAAGGATGACC AACAAAGAATTTACCTATgctTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 5 | TVP-K18AΔG | EPDEICRARMTNKEF TYASNVCNNCGDQVA ACEAECFRNDVYTAC HEAQK | GAACCAGACGAGATATGCAGAGCAAGGATGACC AACAAAGAATTTACCTATgctTCCAACGTATGC AATAATTGTGGCGACCAGGTGGCAGCCTGCGAG GCAGAGTGCTTTCGTAATGACGTTTACACAGCT TGTCACGAGGCTCAGAAA |
| 6 | TVP-R38A | EPDEICRARMTNKEF TYKSNVCNNCGDQVA ACEAECFANDVYTAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTgctAATGACGTTTACACAGCT TGTCACGAGGCTCAGAAAGGT |
| 7 | TVP-R38AΔG | EPDEICRARMTNKEF TYKSNVCNNCGDQVA ACEAECFANDVYTAC HEAQK | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTgctAATGACGTTTACACAGCT TGTCACGAGGCTCAGAAA |
| 8 | TVP-A8N | EPDEICRNRMTNKEF TYKSNVCNNCGDQVA ACEAECFRNDVYTAC HEAQKG | GAACCAGACGAGATATGCAGAaacAGGATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 9 | TVP-A8NΔG | EPDEICRNRMTNKEF TYKSNVCNNCGDQVA ACEAECFRNDVYTAC HEAQK | GAACCAGACGAGATATGCAGAaacAGGATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAA |

TABLE 1-continued

TVPs of the present invention.

| Amino Acid SEQ ID NO | Name | Amino Acid Sequence | Nucleotide Sequence |
|---|---|---|---|
| 10 | TVP-A8S | EPDEICRSRMTNKEF TYKSNVCNNCGDQVA ACEAECFRNDVYTAC HEAQKG | GAACCAGACGAGATATGCAGAtcaAGGATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 11 | TVP-A8SΔG | EPDEICRSRMTNKEF TYKSNVCNNCGDQVA ACEAECFRNDVYTAC HEAQK | GAACCAGACGAGATATGCAGAtcaAGGATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAA |
| 12 | TVP-R9N | EPDEICRANMTNKEF TYKSNVCNNCGDQVA ACEAECFRNDVYTAC HEAQKG | GAACCAGACGAGATATGCAGAGCAaacATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 13 | TVP-R9NΔG | EPDEICRANMTNKEF TYKSNVCNNCGDQVA ACEAECFRNDVYTAC HEAQK | GAACCAGACGAGATATGCAGAGCAaacATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAA |
| 14 | TVP-T11P | EPDEICRARMPNKEF TYKSNVCNNCGDQVA ACEAECFRNDVYTAC HEAQKG | GAACCAGACGAGATATGCAGAGCAAGGATGcct AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 15 | TVP-T11PΔG | EPDEICRARMPNKEF TYKSNVCNNCGDQVA ACEAECFRNDVYTAC HEAQK | GAACCAGACGAGATATGCAGAGCAAGGATGcct AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAA |
| 49 | TVP-T43A | EPDEICRARMTNKEF TYKSNVCNNCGDQVA ACEAECFRNDVYAAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACgctGCT TGTCACGAGGCTCAGAAAGGT |
| 50 | TVP-T43AΔG | EPDEICRARMTNKEF TYKSNVCNNCGDQVA ACEAECFRNDVYAAC HEAQK | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACgctGCT TGTCACGAGGCTCAGAAA |
| 51 | TVP-R9Q/T43A | EPDEICRAQMTNKEF TYKSNVCNNCGDQVA ACEAECFRNDVYAAC HEAQKG | GAACCAGACGAGATATGCAGAGCAcaaATGACC AACAAAGAATTTACCTATAAGTCCAACGTATGC AATAATTGTGGCGACCAGGTGGCAGCCTGCGAG GCAGAGTGCTTTCGTAATGACGTTTACgcaGCT TGTCACGAGGCTCAGAAAGGT |
| 52 | TVP-R9Q/T43A/ΔG | EPDEICRAQMTNKEF TYKSNVCNNCGDQVA ACEAECFRNDVYAAC HEAQK | GAACCAGACGAGATATGCAGAGCAcaaATGACC AACAAAGAATTTACCTATAAGTCCAACGTATGC AATAATTGTGGCGACCAGGTGGCAGCCTGCGAG GCAGAGTGCTTTCGTAATGACGTTTACgctGCT TGTCACGAGGCTCAGAAA |
| 53 | TVP-R9Q/T43A/ΔK-G | EPDEICRAQMTNKEF TYKSNVCNNCGDQVA ACEAECFRNDVYAAC HEAQ | GAACCAGACGAGATATGCAGAGCAcaaATGACC AACAAAGAATTTACCTATAAGTCCAACGTATGC AATAATTGTGGCGACCAGGTGGCAGCCTGCGAG GCAGAGTGCTTTCGTAATGACGTTTACgctGCT TGTCACGAGGCTCAG |
| 77 | TVP-R9A | EPDEICRAAMTNKEF TYKSNVCNNCGDQVA ACEAECFRNDVYTAC HEAQKG | GAACCAGACGAGATATGCAGAGCAgcaATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |

TABLE 1-continued

TVPs of the present invention.

| Amino Acid SEQ ID NO | Name | Amino Acid Sequence | Nucleotide Sequence |
|---|---|---|---|
| 78 | TVP-R9G | EPDEICRAGMTNKEF TYKSNVCNNCGDQVA ACEAECFRNDVYTAC HEAQKG | GAACCAGACGAGATATGCAGAGCAggaATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 79 | TVP-R9N | EPDEICRANMTNKEF TYKSNVCNNCGDQVA ACEAECFRNDVYTAC HEAQKG | GAACCAGACGAGATATGCAGAGCAaatATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 80 | TVP-R9L | EPDEICRALMTNKEF TYKSNVCNNCGDQVA ACEAECFRNDVYTAC HEAQKG | GAACCAGACGAGATATGCAGAGCActaATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 81 | TVP-R9D | EPDEICRADMTNKEF TYKSNVCNNCGDQVA ACEAECFRNDVYTAC HEAQKG | GAACCAGACGAGATATGCAGAGCAgatATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 82 | TVP-R9V | EPDEICRAVMTNKEF TYKSNVCNNCGDQVA ACEAECFRNDVYTAC HEAQKG | GAACCAGACGAGATATGCAGAGCAgtcATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 83 | TVP-R9M | EPDEICRAMMTNKEF TYKSNVCNNCGDQVA ACEAECFRNDVYTAC HEAQKG | GAACCAGACGAGATATGCAGAGCAatgATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 84 | TVP-R9I | EPDEICRAIMTNKEF TYKSNVCNNCGDQVA ACEAECFRNDVYTAC HEAQKG | GAACCAGACGAGATATGCAGAGCAattATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 85 | TVP-R9Q/ T43A | EPDEICRAQMTNKEF TYKSNVCNNCGDQVA ACEAECFRNDVYAAC HEAQKG | GAACCAGACGAGATATGCAGAGCAcaaATGACC AACAAAGAATTTACCTATAAGTCCAACGTATGC AATAATTGTGGCGACCAGGTGGCAGCCTGCGAG GCAGAGTGCTTTCGTAATGACGTTTACgcaGCT TGTCACGAGGCTCAGAAAGGT |
| 86 | TVP-R9Q | EPDEICRAQMTNKEF TYKSNVCNNCGDQVA ACEAECFRNDVYTAC HEAQKG | GAACCAGACGAGATATGCAGAGCAcaaATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 87 | TVP-R9C | EPDEICRACMTNKEF TYKSNVCNNCGDQVA ACEAECFRNDVYTAC HEAQKG | GAACCAGACGAGATATGCAGAGCAtctATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 88 | TVP-R9E | EPDEICRAEMTNKEF TYKSNVCNNCGDQVA ACEAECFRNDVYTAC HEAQKG | GAACCAGACGAGATATGCAGAGCAgaaATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 89 | TVP-R9T | EPDEICRATMTNKEF TYKSNVCNNCGDQVA ACEAECFRNDVYTAC HEAQKG | GAACCAGACGAGATATGCAGAGCAactATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |

TABLE 1-continued

TVPs of the present invention.

| Amino Acid SEQ ID NO | Name | Amino Acid Sequence | Nucleotide Sequence |
|---|---|---|---|
| 90 | TVP-R9S | EPDEICRASMTNKEF TYKSNVCNNCGDQVA ACEAECFRNDVYTAC HEAQKG | GAACCAGACGAGATATGCAGAGCAtctATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 91 | TVP-T43F | EPDEICRARMTNKEF TYKSNVCNNCGDQVA ACEAECFRNDVYFAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACtttGCT TGTCACGAGGCTCAGAAAGGT |
| 92 | TVP-T43P | EPDEICRARMTNKEF TYKSNVCNNCGDQVA ACEAECFRNDVYPAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACcctGCT TGTCACGAGGCTCAGAAAGGT |
| 93 | TVP-T43Y | EPDEICRARMTNKEF TYKSNVCNNCGDQVA ACEAECFRNDVYYAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACtatGCT TGTCACGAGGCTCAGAAAGGT |
| 94 | TVP-T43K | EPDEICRARMTNKEF TYKSNVCNNCGDQVA ACEAECFRNDVYKAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACaaaGCT TGTCACGAGGCTCAGAAAGGT |
| 95 | TVP-T43W | EPDEICRARMTNKEF TYKSNVCNNCGDQVA ACEAECFRNDVYWAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACtggGCT TGTCACGAGGCTCAGAAAGGT |
| 96 | TVP-T43H | EPDEICRARMTNKEF TYKSNVCNNCGDQVA ACEAECFRNDVYHAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACcatGCT TGTCACGAGGCTCAGAAAGGT |
| 97 | TVP-T43A | EPDEICRARMTNKEF TYKSNVCNNCGDQVA ACEAECFRNDVYAAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACgctGCT TGTCACGAGGCTCAGAAAGGT |
| 98 | TVP-T43G | EPDEICRARMTNKEF TYKSNVCNNCGDQVA ACEAECFRNDVYGAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACggtGCT TGTCACGAGGCTCAGAAAGGT |
| 99 | TVP-T43N | EPDEICRARMTNKEF TYKSNVCNNCGDQVA ACEAECFRNDVYNAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACaatGCT TGTCACGAGGCTCAGAAAGGT |
| 100 | TVP-T43L | EPDEICRARMTNKEF TYKSNVCNNCGDQVA ACEAECFRNDVYLAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACttaGCT TGTCACGAGGCTCAGAAAGGT |
| 101 | TVP-T43D | EPDEICRARMTNKEF TYKSNVCNNCGDQVA ACEAECFRNDVYDAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACgatGCT TGTCACGAGGCTCAGAAAGGT |

TABLE 1-continued

TVPs of the present invention.

| Amino Acid SEQ ID NO | Name | Amino Acid Sequence | Nucleotide Sequence |
|---|---|---|---|
| 102 | TVP-T43V | EPDEICRARMTNKEF TYKSNVCNNCGDQVA ACEAECFRNDVYVAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACgtcGCT TGTCACGAGGCTCAGAAAGGT |
| 103 | TVP-T43M | EPDEICRARMTNKEF TYKSNVCNNCGDQVA ACEAECFRNDVYMAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACatgGCT TGTCACGAGGCTCAGAAAGGT |
| 104 | TVP-T43I | EPDEICRARMTNKEF TYKSNVCNNCGDQVA ACEAECFRNDVYIAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACattGCT TGTCACGAGGCTCAGAAAGGT |
| 105 | TVP-T43Q | EPDEICRARMTNKEF TYKSNVCNNCGDQVA ACEAECFRNDVYQAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACcaaGCT TGTCACGAGGCTCAGAAAGGT |
| 106 | TVP-T43C | EPDEICRARMTNKEF TYKSNVCNNCGDQVA ACEAECFRNDVYCAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACtctGCT TGTCACGAGGCTCAGAAAGGT |
| 107 | TVP-T43E | EPDEICRARMTNKEF TYKSNVCNNCGDQVA ACEAECFRNDVYEAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACgaaGCT TGTCACGAGGCTCAGAAAGGT |
| 108 | TVP-T43T | EPDEICRARMTNKEF TYKSNVCNNCGDQVA ACEAECFRNDVYTAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACACAGCT TGTCACGAGGCTCAGAAAGGT |
| 109 | TVP-T43S | EPDEICRARMTNKEF TYKSNVCNNCGDQVA ACEAECFRNDVYSAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACtcaGCT TGTCACGAGGCTCAGAAAGGT |
| 110 | TVP-T43R | EPDEICRARMTNKEF TYKSNVCNNCGDQVA ACEAECFRNDVYRAC HEAQKG | GAACCAGACGAGATATGCAGAGCAAGGATGACC AACAAAGAATTTACCTATAAGTCCAACGTATGC AATAATTGTGGCGACCAGGTGGCAGCCTGCGAG GCAGAGTGCTTTCGTAATGACGTTTACagaGCT TGTCACGAGGCTCAGAAAGGT |

In some embodiments, a polynucleotide sequence can be operable to encode a TVP having an amino acid sequence according to SEQ ID NOs: 2-15, 49-53, or 77-110, is operable to encode a TVP. For example, in some embodiments, a polynucleotide as shown in Table 2 is operable to encode a TVP.

TABLE 2

Polynucleotides of the present invention.

| Polynucleotide SEQ ID NO | Name | Sequence |
|---|---|---|
| 16 | WT-Ta1b | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAAGGT |

TABLE 2-continued

| Polynucleotide SEQ ID NO | Name | Sequence |
|---|---|---|
| 17 | TVP-R9Q | GAACCAGACGAGATATGCAGAGCAcaaATGACCAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAAGGT |
| 18 | TVP-R9QΔG | GAACCAGACGAGATATGCAGAGCAcaaATGACCAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAA |
| 19 | TVP-K18A | GAACCAGACGAGATATGCAGAGCAAGGATGACCAACAAAGA ATTTACCTATgctTCCAACGTATGCAATAATTGTGGCGACC AGGTGGCAGCCTGCGAGGCAGAGTGCTTTCGTAATGACGTT TACACAGCTTGTCACGAGGCTCAGAAAGGT |
| 20 | TVP-K18AΔG | GAACCAGACGAGATATGCAGAGCAAGGATGACCAACAAAGA ATTTACCTATgctTCCAACGTATGCAATAATTGTGGCGACC AGGTGGCAGCCTGCGAGGCAGAGTGCTTTCGTAATGACGTT TACACAGCTTGTCACGAGGCTCAGAAA |
| 21 | TVP-R38A | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTgctAATGACGTT TACACAGCTTGTCACGAGGCTCAGAAAGGT |
| 22 | TVP-R38AΔG | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTgctAATGACGTT TACACAGCTTGTCACGAGGCTCAGAAA |
| 23 | TVP-A8N | GAACCAGACGAGATATGCAGAaacAGGATGACCAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAAGGT |
| 24 | TVP-A8NΔG | GAACCAGACGAGATATGCAGAaacAGGATGACCAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAA |
| 25 | TVP-A8S | GAACCAGACGAGATATGCAGAtcaAGGATGACCAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAAGGT |
| 26 | TVP-A8SΔG | GAACCAGACGAGATATGCAGAtcaAGGATGACCAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAA |
| 27 | TVP-R9N | GAACCAGACGAGATATGCAGAGCAaaaCATGACCAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAAGGT |
| 28 | TVP-R9NΔG | GAACCAGACGAGATATGCAGAGCAaaaCATGACCAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAA |
| 29 | TVP-T11P | GAACCAGACGAGATATGCAGAGCAAGGATGcctAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAAGGT |
| 30 | TVP-T11PΔG | GAACCAGACGAGATATGCAGAGCAAGGATGcctAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAA |
| 54 | TVP-T43A | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACgctGCTTGTCACGAGGCTCAGAAAGGT |

TABLE 2-continued

Polynucleotides of the present invention.

| Polynucleotide SEQ ID NO | Name | Sequence |
|---|---|---|
| 55 | TVP-T43AΔG | GAACCAGACGAGATATGCAGAGCAAGGATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACgctGCTTGTCACGAGGCTCAGAAA |
| 56 | TVP-R9Q/T43A | GAACCAGACGAGATATGCAGAGCAcaaATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACgcaGCTTGTCACGAGGCTCAGAAAGGT |
| 57 | TVP-R9Q/T43A/<br>ΔG | GAACCAGACGAGATATGCAGAGCAcaaATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACgctGCTTGTCACGAGGCTCAGAAA |
| 58 | TVP-<br>R9Q/T43A/ΔK-G | GAACCAGACGAGATATGCAGAGCAcaaATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACgctGCTTGTCACGAGGCTCAG |
| 117 | TVP-R9A | GAACCAGACGAGATATGCAGAGCAgcaATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACACAGCTTGTCACGAGGCTCAGAAAGGT |
| 118 | TVP-R9G | GAACCAGACGAGATATGCAGAGCAggaATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACACAGCTTGTCACGAGGCTCAGAAAGGT |
| 119 | TVP-R9N | GAACCAGACGAGATATGCAGAGCAaatATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACACAGCTTGTCACGAGGCTCAGAAAGGT |
| 120 | TVP-R9L | GAACCAGACGAGATATGCAGAGCActaATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACACAGCTTGTCACGAGGCTCAGAAAGGT |
| 121 | TVP-R9D | GAACCAGACGAGATATGCAGAGCAgatATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACACAGCTTGTCACGAGGCTCAGAAAGGT |
| 122 | TVP-R9V | GAACCAGACGAGATATGCAGAGCAgtcATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACACAGCTTGTCACGAGGCTCAGAAAGGT |
| 123 | TVP-R9M | GAACCAGACGAGATATGCAGAGCAatgATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACACAGCTTGTCACGAGGCTCAGAAAGGT |
| 124 | TVP-R9I | GAACCAGACGAGATATGCAGAGCAattATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACACAGCTTGTCACGAGGCTCAGAAAGGT |
| 125 | TVP-R9Q/T43A | GAACCAGACGAGATATGCAGAGCAcaaATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACgcaGCTTGTCACGAGGCTCAGAAAGGT |
| 126 | TVP-R9Q | GAACCAGACGAGATATGCAGAGCAcaaATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACACAGCTTGTCACGAGGCTCAGAAAGGT |
| 127 | TVP-R9C | GAACCAGACGAGATATGCAGAGCAtctATGACCAACAAAGA<br>ATTTACCTATAAGTCCAACGTATGCAATAATTGTGGCGACC<br>AGGTGGCAGCCTGCGAGGCAGAGTGCTTTCGTAATGACGTT<br>TACACAGCTTGTCACGAGGCTCAGAAAGGT |

TABLE 2-continued

Polynucleotides of the present invention.

| Polynucleotide SEQ ID NO | Name | Sequence |
|---|---|---|
| 128 | TVP-R9E | GAACCAGACGAGATATGCAGAGCAgaaATGACCAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAAGGT |
| 129 | TVP-R9T | GAACCAGACGAGATATGCAGAGCAactATGACCAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAAGGT |
| 130 | TVP-R9S | GAACCAGACGAGATATGCAGAGCAtctATGACCAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAAGGT |
| 131 | TVP-T43F | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACtttGCTTGTCACGAGGCTCAGAAAGGT |
| 132 | TVP-T43P | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACcctGCTTGTCACGAGGCTCAGAAAGGT |
| 133 | TVP-T43Y | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACtatGCTTGTCACGAGGCTCAGAAAGGT |
| 134 | TVP-T43K | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACaaaGCTTGTCACGAGGCTCAGAAAGGT |
| 135 | TVP-T43W | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACtggGCTTGTCACGAGGCTCAGAAAGGT |
| 136 | TVP-T43H | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACcatGCTTGTCACGAGGCTCAGAAAGGT |
| 137 | TVP-T43A | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACgctGCTTGTCACGAGGCTCAGAAAGGT |
| 138 | TVP-T43G | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACggtGCTTGTCACGAGGCTCAGAAAGGT |
| 139 | TVP-T43N | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACaatGCTTGTCACGAGGCTCAGAAAGGT |
| 140 | TVP-T43L | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACttaGCTTGTCACGAGGCTCAGAAAGGT |
| 141 | TVP-T43D | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACgatGCTTGTCACGAGGCTCAGAAAGGT |
| 142 | TVP-T43V | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACgtcGCTTGTCACGAGGCTCAGAAAGGT |

TABLE 2-continued

Polynucleotides of the present invention.

| Polynucleotide SEQ ID NO | Name | Sequence |
|---|---|---|
| 143 | TVP-T43M | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACatgGCTTGTCACGAGGCTCAGAAAGGT |
| 144 | TVP-T43I | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACattGCTTGTCACGAGGCTCAGAAAGGT |
| 145 | TVP-T43Q | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACcaaGCTTGTCACGAGGCTCAGAAAGGT |
| 146 | TVP-T43C | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACtctGCTTGTCACGAGGCTCAGAAAGGT |
| 147 | TVP-T43E | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACgaaGCTTGTCACGAGGCTCAGAAAGGT |
| 148 | TVP-T43T | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACACAGCTTGTCACGAGGCTCAGAAAGGT |
| 149 | TVP-T43S | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACtcaGCTTGTCACGAGGCTCAGAAAGGT |
| 150 | TVP-T43R | GAACCAGACGAGATATGCAGAGCAAGGATGACCAACAAAGA ATTTACCTATAAGTCCAACGTATGCAATAATTGTGGCGACC AGGTGGCAGCCTGCGAGGCAGAGTGCTTTCGTAATGACGTT TACagaGCTTGTCACGAGGCTCAGAAAGGT |

In some embodiments, a TVP comprises one or more mutations relative to the wild-type sequence of U1-agatoxin-Ta1b as set forth in SEQ ID NO:1. For example, in some embodiments, a TVP can have a first, second, or third mutation relative to the wild-type sequence of U1-agatoxin-Ta1b as set forth in SEQ ID NO:1.

In some embodiments, a TVP can have a first mutation relative to the wild-type sequence of U1-agatoxin-Ta1b as set forth in SEQ ID NO:1 wherein the first mutation is an amino acid substitution of R9Q; K18A; R38A; A8N; A8S; R9N; T11P; or T43A.

In some embodiments, a TVP can have a first and second mutation relative to the wild-type sequence of U1-agatoxin-Ta1b as set forth in SEQ ID NO:1, e.g., R9QΔG; K18AΔG; R38AΔG; A8NΔG; A8SΔG; R9NΔG; T11PΔG; or T43AΔG; wherein the first mutation is an amino acid substitution of R9Q; K18A; R38A; A8N; A8S; R9N; or T11P; and wherein the second mutation is a deletion of the C-terminal Glycine.

In some embodiments, a TVP can have a first and second mutation relative to the wild-type sequence of U1-agatoxin-Ta1b as set forth in SEQ ID NO: 1, e.g., R9QT43A; K18AT43A; R38AT43A; A8NT43A; A8ST43A; R9NT43A; or T11PT43A; wherein the first mutation is an amino acid substitution of R9Q; K18A; R38A; A8N; A8S; R9N; T11P; and wherein the second mutation is a T43A amino acid substitution that results in a TVP that is not glycosylated.

In some embodiments, a TVP can have a first, second, and third mutation relative to the wild-type sequence of U1-aga-toxin-Ta1b as set forth in SEQ ID NO: 1, e.g., R9QT43AΔG; K18AT43AΔG; R38AT43AΔG; A8NT43AΔG; A8ST43AΔG; R9NT43AΔG; or T11PT43AΔG; wherein the first mutation is an amino acid substitution of R9Q; K18A; R38A; A8N; A8S; R9N; or T11P; and wherein the second mutation is a T43A amino acid substitution that results in a TVP that is not glycosylated; and wherein the third mutation is a deletion of the C-terminal Glycine.

In some preferred embodiments, a TVP can be a TVP-R9Q/T43A (SEQ ID NO: 51).

In various embodiments, polynucleotides encoding TVPs can be used to transform plant cells, yeast cells, or bacteria cells. In some embodiments, the insecticidal TVP transgenic proteins may be formulated into compositions that can be sprayed or otherwise applied in any manner known to those skilled in the art to the surface of plants or parts thereof. Accordingly, DNA constructs are provided herein, operable to encode one or more TVPs under the appropriate conditions in a host cell, for example, a plant cell. Methods for controlling a pest infection by a parasitic insect of a plant cell comprises administering or introducing a polynucle-otide encoding a TVP as described herein to a plant, plant tissue, or a plant cell by recombinant techniques and grow-ing said recombinantly altered plant, plant tissue or plant cell in a field exposed to the pest. Alternatively, TVPs can be formulated into a sprayable composition consisting of a TVP and an excipient, and applied directly to susceptible plants by direct application, such that upon ingestion of the TVP by the infectious insect results in a deleterious effect.

In some embodiments, a TVP may have an amino acid sequence of any one of SEQ ID NOs: 2-15, 49-53, and 77-110. In some embodiments, the TVP may comprise an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to of SEQ ID NOs: 2-15, 49-53, or 77-110.

In some embodiments, the TVP may comprise an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence set forth in SEQ ID NOs: 2-15, 49-53, or 77-110.

In some embodiments, the TVP may comprise an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence: "EPDEI-CRAQMTNKEFTYKSNVCNNCGDQVAACE-AECFRNDVYAACHEAQKG" (SEQ ID NO: 51).

In some embodiments, a TVP can be encoded by a polynucleotide. For example, in some embodiments, a polynucleotide encoding a TVP, can comprise an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the TVP comprises at least one amino acid substitution relative to the wild-type sequence of U1-agatoxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; or a complementary nucleotide sequence thereof.

In some embodiments, a polynucleotide encoding a TVP can comprise a polynucleotide, wherein the TVP has one amino acid substitution at X$_1$, X$_2$, X$_3$, X$_4$, or X$_5$.

In some embodiments, a polynucleotide encoding a TVP can comprise a polynucleotide, wherein the TVP has one amino acid substitution at X$_1$, X$_2$, X$_3$, X$_4$, or X$_5$; and wherein X$_7$ is Glycine.

In some embodiments, a polynucleotide encoding a TVP can comprise a polynucleotide, wherein the TVP has one amino acid substitution at X$_1$, X$_2$, X$_3$, X$_4$, or X$_5$; and wherein X$_7$ is absent.

In some embodiments, a polynucleotide encoding a TVP can comprise a polynucleotide, wherein the TVP has one amino acid substitution at X$_1$, X$_2$, X$_3$, X$_4$, or X$_5$; and wherein X$_6$ and X$_7$ are absent.

In some embodiments, a polynucleotide encoding a TVP can comprise a polynucleotide, wherein the TVP comprises an amino sequence as set forth in any one of SEQ ID NOs: 2-15, 49-53, or 77-110.

In some embodiments, a polynucleotide encoding a TVP can comprise a polynucleotide, wherein the polynucleotide sequence has a sequence as set forth in any one of SEQ ID NOs: 17-30, 54-58, or 117-150, or a complementary nucleotide sequence thereof.

In some embodiments, a polynucleotide encoding a TVP can comprise a polynucleotide, wherein if Z$_1$ is T or S, then the TVP is glycosylated.

In some embodiments, a polynucleotide encoding a TVP can encode a TVP having an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to an amino acid sequence set forth in SEQ ID NOs: 2-15, 49-53, or 77-110.

In some embodiments, a vector can comprise a polynucleotide operable to encode a TVP.

In some embodiments, a vector can comprise a polynucleotide operable to encode a TVP having an amino acid sequence with 90% similarity to a sequence as set forth in any one of SEQ ID NOs: 2-15, 49-53, or 77-110.

In some embodiments, a vector can comprise a polynucleotide has a nucleotide sequence as set forth in any one of SEQ ID NOs: 17-30, 54-58, or 117-150, or a complementary nucleotide sequence thereof.

Exemplary TVPs

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent, or a pharmaceutically acceptable salt thereof.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; and wherein the TVP has one amino acid substitution at $X_1$, $X_2$, $X_3$, $X_4$, or $X_5$, or a pharmaceutically acceptable salt thereof.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; and wherein the TVP has one amino acid substitution at $X_1$, $X_2$, $X_3$, $X_4$, or $X_5$; and wherein $X_7$ is Glycine, or a pharmaceutically acceptable salt thereof.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; and wherein the TVP has one amino acid substitution at $X_1$, $X_2$, $X_3$, $X_4$, or $X_5$; and wherein $X_7$ is absent, or a pharmaceutically acceptable salt thereof.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; and wherein the TVP has one amino acid substitution at $X_1$, $X_2$, $X_3$, $X_4$, or $X_5$; and wherein $X_6$ and $X_7$ are absent, or a pharmaceutically acceptable salt thereof.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; and wherein the TVP comprises an amino sequence as set forth in any one of SEQ ID NOs: 2-15, 49-53, or 77-110, or a pharmaceutically acceptable salt thereof.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; and wherein the TVP is encoded by a polynucleotide sequence as set forth in any one of SEQ ID NOs: 17-30, 54-58, or 117-150, or a complementary nucleotide sequence thereof.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; and wherein the TVP further comprises a homopolymer or heteropolymer of two or more TVPs, wherein the amino acid sequence of each TVP is the same or different.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; and wherein the TVP is a fused protein comprising two or more TVPs separated by a cleavable or non-cleavable linker, and wherein the amino acid sequence of each TVP may be the same or different.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; and wherein the TVP is a fused protein comprising two or more TVPs separated by a cleavable or non-cleavable linker, and wherein the amino acid sequence of each TVP may be the same or different, and wherein the linker is cleavable inside the gut or hemolymph of an insect.

In some embodiments, the linker has an amino acid sequence as set forth in any one of SEQ ID NOs: 61-70.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (I): E-P-D-E-I-C-R-A-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; and wherein if $Z_1$ is T or S, then the TVP is glycosylated, or a pharmaceutically acceptable salt thereof.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence "EPDEI-CRAQMTNKEFTYKSNVCNNCGDQVAACE-AECFRNDVYAACHEAQKG" (SEQ ID NO: 51).

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof; wherein if $Z_1$ is T then the TVP is glycosylated.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof, wherein $X_1$ is Q; and $Z_1$ is A.

In some embodiments, an insecticidal U1-agatoxin-Ta1b variant polypeptide (TVP), can be a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence to the amino acid sequence as set forth in any one of SEQ ID NOs: 2, 49, or 51, or a pharmaceutically acceptable salt thereof.

TVP-Insecticidal Proteins

TVP-insecticidal proteins are any protein, peptide, polypeptide, amino acid sequence, configuration, or arrangement, consisting of: (1) at least one TVP, or two or more TVPs; and (2) additional non-toxin peptides, polypeptides, or proteins that, e.g., in some embodiments, have the ability to do the following: increase the mortality and/or inhibit the growth of insects when the insects are exposed to a TVP-insecticidal protein, relative to a TVP alone; increase the expression of said TVP-insecticidal protein, e.g., in a host cell or an expression system; and/or affect the post-translational processing of the TVP-insecticidal protein. In some embodiments, a TVP-insecticidal protein can be a polymer comprising two or more TVPs. In some embodiments, a TVP-insecticidal protein can be a polymer comprising two or more TVPs, wherein the TVPs are operably linked via a linker peptide, e.g., a cleavable and/or non-cleavable linker. In some embodiments, a TVP-insecticidal protein can refer to a one or more TVPs operably linked with one or more proteins such as a stabilizing domain (STA); an endoplasmic reticulum signaling protein (ERSP); an insect cleavable or insect non-cleavable linker (L); and/or any other combination thereof. In some embodiments, a TVP-insecticidal protein can be a non-naturally occurring protein comprising (1) a wild-type Ta1b protein; and (2) additional peptides, polypeptides, or proteins, e.g., an ERSP; a linker; a STA; a UBI; or a histidine tag or similar marker.

In some embodiments, a TVP-insecticidal protein can comprise a one or more TVPs found in Table 1, e.g., SEQ ID NOs: 2-15, 49-53, and 77-110. In some embodiments, the insecticidal protein can comprise a TVP homopolymer, e.g., two or more TVP monomers that are the same TVP. In some embodiments, the insecticidal protein can comprise a TVP heteropolymer, e.g., two or more TVP monomers, wherein the TVP monomers are different.

In some embodiments, a TVP-insecticidal protein can comprise a homopolymer of two or more TVPs, wherein the amino acid sequence of each TVP is the same. For example, in some embodiments, a TVP can have one polypeptide comprising a R9Q; K18A; R38A; A8N; A8S; R9N; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG amino acid substitution relative to relative to the wild-type sequence of U1-agatoxin-Ta1b as set forth in SEQ ID NO:1, linked to another polypeptide comprising one or more of the same TVPs with the same amino acid substitutions: i.e., R9Q; K18A; R38A; A8N; A8S; R9N; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A;

T11PT43A; R9QT43AΔG; K18AT43AΔG; R38AT43AΔG; A8NT43AΔG; A8ST43AΔG; R9NT43AΔG; and/or T11PT43AΔG amino acid substitutions relative to relative to the wild-type sequence of U1-agatoxin-Ta1b as set forth in SEQ ID NO:1

In some embodiments, a TVP-insecticidal protein can comprise a heteropolymer of two or more TVPs, wherein the amino acid sequence of each TVP is the same or different. For example, in some embodiments, a TVP can have one polypeptide comprising an amino acid substitution relative to the wild-type sequence of U1-agatoxin-Ta1b as set forth in SEQ ID NO:1 of R9Q; K18A; R38A; A8N; A8S; R9N; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG; linked to another polypeptide comprising one or more of the following amino acid substitutions: R9Q; K18A; R38A; A8N; A8S; R9N; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG; relative to the wild-type sequence of U1-agatoxin-Ta1b as set forth in SEQ ID NO:1.

In some embodiments, a TVP-insecticidal protein can comprise a heteropolymer of two or more TVPs, wherein the amino acid sequence of each TVP is the same or different. For example, in some embodiments, a TVP can have one polypeptide comprising an amino acid substitution relative to the wild-type sequence of U1-agatoxin-Ta1b as set forth in SEQ ID NO:1 of R9Q; linked to another polypeptide comprising one or more of the following amino acid substitutions: R9Q; K18A; R38A; A8N; A8S; R9N; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG; relative to the wild-type sequence of U1-agatoxin-Ta1b as set forth in SEQ ID NO:1.

In some embodiments, a TVP-insecticidal protein can comprise a heteropolymer of two or more TVPs, wherein the amino acid of each TVP is different, e.g., one polypeptide comprising a R9QΔG amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; A8S; R9N; T11P; T43A; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a K18A amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; R38A; A8N; A8S; R9N; T11P; T43A;

R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a K18AΔG amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; A8S; R9N; T11P; T43A; R9QΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a R38A amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; A8N; A8S; R9N; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a R38AΔG amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; A8S; R9N; T11P; T43A; R9QΔG; K18AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a A8N amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8S; R9N; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a A8NΔG amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; A8S; R9N; T11P; T43A; R9QΔG; K18AΔG; R38AΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a A8S amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; R9N; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG In some embodiments, a TVP-insecticidal protein can comprise a heteropolymer of two or more TVPs, wherein the amino acid of each TVP is different, e.g., one polypeptide comprising a A8SΔG amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; A8S; R9N; T11P; T43A; R9QΔG; K18AΔG; R38AΔG; A8NΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a R9N amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; A8S; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a R9NΔG amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; A8S; R9N; T11P; T43A; R9QΔG; K18AΔG; R38AΔG; A8NΔG; A8SΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a T11P amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; A8S; R9N; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a T11PΔG amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; A8S; R9N; T11P; T43A; R9QΔG; K18AΔG; R38AΔG; A8NΔG; A8SΔG; R9NΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a T43A amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; A8S; R9N; T11P; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A; R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a T43AΔG amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; A8S; R9N; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a RQ9/T43A amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; A8S; R9N; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A R9QT43AΔG; K18AT43AΔG; R38AT43AΔG; A8NT43AΔG; A8ST43AΔG; R9NT43AΔG; and/or T11PT43AΔG.

In some embodiments, a TVP-insecticidal protein can comprise a heteropolymer of two or more TVPs, wherein the amino acid of each TVP is different, e.g., one polypeptide comprising a RQ9/T43A amino acid substitution relative to the wild-type sequence of U1-agatoxin-Ta1b as set forth in SEQ ID NO:1, linked to another polypeptide comprising one or more of the following amino acid substitutions relative to the wild-type sequence of U1-agatoxin-Ta1b as set forth in SEQ ID NO:1: R9Q; K18A; R38A; A8N; A8S; R9N; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; T11PT43A R9QT43AΔG; K18AT43AΔG; R38AT43AΔG; A8NT43AΔG; A8ST43AΔG; R9NT43AΔG; T11PT43AΔG; and/or any combination thereof.

In some embodiments, a TVP-insecticidal protein can comprise a fused protein comprising two or more TVPs separated by a cleavable or non-cleavable linker, and wherein the amino acid sequence of each TVP may be the same or different. For example, in some embodiments, a first TVP polymer can have an amino acid substitution relative to the wild-type sequence of U1-agatoxin-Ta1b as set forth in SEQ ID NO:1 of R9Q; K18A; R38A; A8N; A8S; R9N; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; or T11PT43A R9QT43AΔG; K18AT43AΔG; R38AT43AΔG; A8NT43AΔG; A8ST43AΔG; R9NT43AΔG; and/or T11PT43AΔG; and/or T11PT43AΔG that is fused a second TVP polymer that can have an amino acid substitution relative to the wild-type sequence of U1-agatoxin-Ta1b as set forth in SEQ ID NO:1: R9Q; K18A; R38A; A8N; A8S; R9N; T11P; T43A; R9QΔG; K18AΔG; R38AΔG; A8NΔG; A8SΔG; R9NΔG; T11PΔG; T43AΔG; R9QT43A; K18AT43A; R38AT43A; A8NT43A; A8ST43A; R9NT43A; or T11PT43A R9QT43AΔG; K18AT43AΔG; R38AT43AΔG; A8NT43AΔG; A8ST43AΔG; R9NT43AΔG; and/or T11PT43AΔG.

In some embodiments, an insecticidal protein can comprise a fused protein comprising two or more TVPs separated by a cleavable linker or non-cleavable linker, and wherein the amino acid sequence of each TVP may be the same or different, wherein the linker is cleavable inside the gut or hemolymph of an insect. Exemplary methods for the generation of cleavable and non-cleavable linkers can be found in U.S. patent application Ser. No. 15/727,277; and PCT Application No. PCT/US2013/030042, the disclosure of which are incorporated by reference herein in their entirety.

In some embodiments, a TVP-insecticidal protein can comprise one or more TVPs having an amino acid sequence of SEQ ID NOs: 2-15, 49-53, and 77-110. In some embodiments, the TVP may comprise an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence identity to of SEQ ID NOs: 2-15, 49-53, or 77-110.

In some embodiments, a TVP-insecticidal protein can comprise one or more TVPs having an amino acid sequence of SEQ ID NOs: 2-15, 49-53, and 77-110. In some embodiments, the TVP may comprise an amino acid sequence having at least 50%, at least 55%, at least 60%, at least 65%, at least 70%, at least 75%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, at least 99.5%, at least 99.6%, at least 99.7%, at least 99.8%, at least 99.9%, or 100% amino acid sequence "EPDEI-CRAQMTNKEFTYKSNVCNNCGDQVAACE-AECFRNDVYAACHEAQKG" (SEQ ID NO: 51).

Methods for Producing a TVP

Methods of producing proteins are well known in the art, and there are a variety of techniques available. For example, in some embodiments, proteins can be produced using recombinant methods, or chemically synthesized.

In some embodiments, a TVP of the present invention can be created using any known method for producing a protein. For example, in some embodiments, and without limitation, a TVP can be created using a recombinant expression system, such as yeast expression system or a bacterial expression system. However, those having ordinary skill in the art will recognize that other methods of protein production are available.

In some embodiments, the present invention provides a method of producing a TVP using a recombinant expression system.

In some embodiments, the present invention comprises, consists essentially of, or consists of, a method of producing a TVP, said method comprising: (a) preparing a vector comprising a first expression cassette comprising, consisting essentially of, or consisting of, a polynucleotide operable to encode a TVP, or a complementary nucleotide sequence thereof, (b) introducing the vector into a host cell, for example a bacteria or a yeast, or an insect, or a plant cell, or an animal cell; and (c) growing the yeast strain in a growth medium under conditions operable to enable expression of the TVP and secretion into the growth medium. In some related embodiments, the host cell, is a yeast cell.

The invention is practicable in a wide variety of host cells (see host cell section below). Indeed, an end-user of the invention can practice the teachings thereof in any host cell of his or her choosing. Thus, in some embodiments, the host cell can be any host cell that satisfies the requirements of the end-user; i.e., in some embodiments, the expression of a TVP may be accomplished using a variety of host cells, and pursuant to the teachings herein. For example, in some embodiments, a user may desire to use one specific type of host cell (e.g., a yeast cell or a bacteria cell) as opposed to another; the preference of a given host cell can range from availability to cost.

For example, in some embodiments, in some embodiments, the present invention comprises, consists essentially of, or consists of, a method of producing a TVP, said method comprising: (a) preparing a vector comprising a first expression cassette comprising, consisting essentially of, or consisting of, a polynucleotide operable to encode a TVP, or a complementary nucleotide sequence thereof; (b) introducing the vector into a host cell, for example a bacteria or a yeast, or an insect, or a plant cell, or an animal cell; and (c) growing the yeast strain in a growth medium under conditions operable to enable expression of the TVP and secretion into the growth medium. In some related embodiments, the host cell, is a yeast cell.

Isolating and Mutating Wild-Type U1-Agatoxin-Ta1b

A TVP can be obtained by creating a mutation in the wild-type U1-agatoxin-Ta1b polynucleotide sequence; inserting that U1-agatoxin-Ta1b variant polynucleotide (tvp) sequence into the appropriate vector; transforming a host organism in such a way that the polynucleotide encoding a TVP is expressed; culturing the host organism to generate the desired amount of TVP; and then purifying the TVP from in and/or around host organism.

Producing a mutation in wild-type U1-agatoxin-Ta1b polynucleotide sequence can be achieved by various means that are well known to those having ordinary skill in the art. Methods of mutagenesis include Kunkel's method; cassette mutagenesis; PCR site-directed mutagenesis; the "perfect murder" technique (delitto perfetto); direct gene deletion and site-specific mutagenesis with PCR and one recyclable marker; direct gene deletion and site-specific mutagenesis with PCR and one recyclable marker using long homologous regions; transplacement "pop-in pop-out" method; and CRISPR-Cas 9. Exemplary methods of site-directed mutagenesis can be found in Ruvkun & Ausubel, A general method for site-directed mutagenesis in prokaryotes. Nature. 1981 Jan. 1; 289(5793):85-8; Wallace et al., Oligonucleotide directed mutagenesis of the human beta-globin gene: a general method for producing specific point mutations in cloned DNA. Nucleic Acids Res. 1981 Aug. 11; 9(15):3647-56; Dalbadie-McFarland et al., Oligonucleotide-directed mutagenesis as a general and powerful method for studies of protein function. Proc Natl Acad Sci USA. 1982 November; 79(21):6409-13; Bachman. Site-directed mutagenesis. Methods Enzymol. 2013; 529:241-8; Carey et al., PCR-mediated site-directed mutagenesis. Cold Spring Harb Protoc. 2013 Aug. 1; 2013(8):738-42; and Cong et al., Multiplex genome engineering using CRISPR/Cas systems. Science. 2013 Feb. 15; 339(6121):819-23, the disclosures of all of the aforementioned references are incorporated herein by reference in their entireties.

Wild-type U1-agatoxin-Ta1b toxins can be isolated from spider venom. Spider venom can be isolated from the venom glands of spiders (e.g., spiders such as *Eratigena agrestis*), using any of the techniques known to those having ordinary skill in the art. For example, in some embodiments, venom can be isolated from spiders according to the methods described in U.S. Pat. No. 5,688,764, the disclosure of which is incorporated herein by reference in its entirety.

A wild-type U1-agatoxin-Ta1b polynucleotide sequence can be obtained by screening a genomic library using primer probes directed to the U1-agatoxin-Ta1b polynucleotide sequence. Alternatively, wild-type U1-agatoxin-Ta1b polynucleotide sequence and/or TVP polynucleotide sequences can be chemically synthesized. For example, a wild-type U1-agatoxin-Ta1b polynucleotide sequence and/or TVP polynucleotide sequence can be generated using the oligonucleotide synthesis methods such as the phosphoramidite;

triester, phosphite, or H-Phosphonate methods (see Engels, J. W. and Uhlmann, E. (1989), Gene Synthesis [New Synthetic Methods (77)]. Angew. Chem. Int. Ed. Engl., 28: 716-734, the disclosure of which is incorporated herein by reference in its entirety).

Chemically Synthesizing TVP Polynucleotides

In some embodiments, the polynucleotide sequence encoding the TVP can be chemically synthesized using commercially available polynucleotide synthesis services such as those offered by GENEWIZ® (e.g., TurboGENE™; PriorityGENE; and FragmentGENE), or SIGMA-AL-DRICH® (e.g., Custom DNA and RNA Oligos Design and Order Custom DNA Oligos). Exemplary method for generating DNA and or custom chemically synthesized polynucleotides are well known in the art, and are illustratively provided in U.S. Pat. No. 5,736,135, Ser. No. 08/389,615, filed on Feb. 13, 1995, the disclosure of which is incorporated herein by reference in its entirety. See also Agarwal, et al., Chemical synthesis of polynucleotides. Angew Chem Int Ed Engl. 1972 June; 11(6):451-9; Ohtsuka et al., Recent developments in the chemical synthesis of polynucleotides. Nucleic Acids Res. 1982 Nov. 11; 10(21): 6553-6570; Sondek & Shortle. A general strategy for random insertion and substitution mutagenesis: substoichiometric coupling of trinucleotide phosphoramidites. Proc Natl Acad Sci USA. 1992 Apr. 15; 89(8): 3581-3585; Beaucage S. L., et al., Advances in the Synthesis of Oligonucleotides by the Phosphoramidite Approach. Tetrahedron, Elsevier Science Publishers, Amsterdam, NL, vol. 48, No. 12, 1992, pp. 2223-2311; Agrawal (1993) Protocols for Oligonucleotides and Analogs: Synthesis and Properties; Methods in Molecular Biology Vol. 20, the disclosures of which are incorporated herein by reference in their entirety.

Chemically synthesizing polynucleotides allows for a DNA sequence to be generated that is tailored to produce a desired polypeptide based on the arrangement of nucleotides within said sequence (i.e., the arrangement of cytosine [C], guanine [G], adenine [A] or thymine [T] molecules); the mRNA sequence that is transcribed from the chemically synthesized DNA polynucleotide can be translated to a sequence of amino acids, each amino acid corresponding to a codon in the mRNA sequence. Accordingly, the amino acid composition of a polypeptide chain that is translated from an mRNA sequence can be altered by changing the underlying codon that determines which of the 20 amino acids will be added to the growing polypeptide; thus, mutations in the DNA such as insertions, substitutions, deletions, and frameshifts may cause amino acid insertions, substitutions, or deletions, depending on the underlying codon.

Obtaining a TVP from a chemically synthesized DNA polynucleotide sequence and/or a wild-type DNA polynucleotide sequence that has been altered via mutagenesis can be achieved by cloning the DNA sequence into an appropriate vector. There are a variety of expression vectors available, host organisms, and cloning strategies known to those having ordinary skill in the art. For example, the vector can be a plasmid, which can introduce a heterologous gene and/or expression cassette into yeast cells to be transcribed and translated. The term "vector" is used to refer to a carrier nucleic acid molecule into which a nucleic acid sequence can be inserted for introduction into a cell where it can be replicated. A vector may contain "vector elements" such as an origin of replication (ORI); a gene that confers antibiotic resistance to allow for selection; multiple cloning sites; a promoter region; a selection marker for non-bacterial transfection; and a primer binding site. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques, which are described in Sambrook et al., 1989 and Ausubel et al., 1996, both incorporated herein by reference. In addition to encoding an Ta1b variant polynucleotide, a vector may encode a targeting molecule. A targeting molecule is one that directs the desired nucleic acid to a particular tissue, cell, or other location.

Vectors and Transformation

In some embodiments, a TVP polynucleotide can be cloned into a vector using a variety of cloning strategies, and commercial cloning kits and materials readily available to those having ordinary skill in the art. For example, the TVP polynucleotide can be cloned into a vector using such strategies as the SnapFast; Gateway; TOPO; Gibson; LIC; InFusionHD; or Electra strategies. There are numerous commercially available vectors that can be used to produce TVP. For example, a TVP polynucleotide can be generated using polymerase chain reaction (PCR), and combined with a pCR™II-TOPO vector, or a PCR™2.1-TOPO® vector (commercially available as the TOPO® TA Cloning® Kit from Invitrogen) for 5 minutes at room temperature; the TOPO® reaction can then be transformed into competent cells, which can subsequently be selected based on color change (see Janke et al., A versatile toolbox for PCR-based tagging of yeast genes: new fluorescent proteins, more markers and promoter substitution cassettes. Yeast. 2004 August; 21(11):947-62; see also, Adams et al. Methods in Yeast Genetics. Cold Spring Harbor, NY, 1997, the disclosure of which is incorporated herein by reference in its entirety).

In some embodiments, a polynucleotide encoding a TVP can be cloned into a vector such as a plasmid, cosmid, virus (bacteriophage, animal viruses, and plant viruses), and/or artificial chromosome (e.g., YACs).

In some embodiments, a polynucleotide encoding a TVP can be inserted into a vector, for example, a plasmid vector using *E. coli* as a host, by performing the following: digesting about 2 to 5 μg of vector DNA using the restriction enzymes necessary to allow the DNA segment of interest to be inserted, followed by overnight incubation to accomplish complete digestion (alkaline phosphatase may be used to dephosphorylate the 5'-end in order to avoid self-ligation/recircularization); gel purify the digested vector. Next, amplify the DNA segment of interest, for example, a polynucleotide encoding a TVP, via PCR, and remove any excess enzymes, primers, unincorporated dNTPs, short-failed PCR products, and/or salts from the PCR reaction using techniques known to those having ordinary skill in the art (e.g., by using a PCR clean-up kit). Ligate the DNA segment of interest to the vector by creating a mixture comprising: about 20 ng of vector; about 100 to 1,000 ng or DNA segment of interest; 2 μL 10× buffer (i.e., 30 mM Tris-HCl 4 mM MgCl$_2$, 26 μM NAD, 1 mM DTT, 50 μg/ml BSA, pH 8, stored at 25° C.); 1 μL T4 DNA ligase; all brought to a total volume of 20 μL by adding H$_2$O. The ligation reaction mixture can then be incubated at room temperature for 2 hours, or at 16° C. for an overnight incubation. The ligation reaction (i.e., about 1 μL) can then be transformed to competent cell, for example, by using electroporation or chemical methods, and a colony PCR can then be performed to identify vectors containing the DNA segment of interest.

In some embodiments a polynucleotide encoding a TVP, along with other DNA segments together composing a TVP expression ORF can be designed for secretion from host yeast cells. An illustrative method of designing a TVP expression ORF is as follows: the ORF can begin with a signal peptide sequence, followed by a DNA sequence encoding a Kex2 cleavage site (Lysine-Arginine), and subsequently followed by the TVP polynucleotide transgene, with the addition of glycine-serine codons at the 5'-end, and finally a stop codon at the 3'-end. All these elements will then be expressed to a fusion peptide in yeast cells as a single open reading frame (ORF). An α-mating factor (αMF) signal sequence is most frequently used to facilitate metabolic processing of the recombinant insecticidal peptides through the endogenous secretion pathway of the recombinant yeast, i.e. the expressed fusion peptide will typically enter the Endoplasmic Reticulum, wherein the α-mating factor signal sequence is removed by signal peptidase activity, and then the resulting pro-insecticidal peptide will be trafficked to the Golgi Apparatus, in which the Lysine-Arginine dipeptide mentioned above is completely removed by Kex2 endoprotease, after which the mature, polypeptide (i.e., TVP), is secreted out of the cells.

In some embodiments, polypeptide expression levels in recombinant yeast cells can be enhanced by optimizing the codons based on the specific host yeast species. Naturally occurring frequencies of codons observed in endogenous open reading frames of a given host organism need not necessarily be optimized for high efficiency expression. Furthermore, different yeast species (for example, *Kluyveromyces lactis, Pichia pastoris, Saccharomyces cerevisiae,* etc.) have different optimal codons for high efficiency expression. Hence, codon optimization should be considered for the TVP expression ORF, including the sequence elements encoding the signal sequence, the Kex2 cleavage site and the TVP, because they are initially translated as one fusion peptide in the recombinant yeast cells.

In some embodiments, a codon-optimized TVP expression ORF can be ligated into a yeast-specific expression vectors for yeast expression. There are many expression vectors available for yeast expression, including episomal vectors and integrative vectors, and they are usually designed for specific yeast strains. One should carefully choose the appropriate expression vector in view of the specific yeast expression system which will be used for the peptide production. In some embodiments, integrative vectors can be used, which integrate into chromosomes of the transformed yeast cells and remain stable through cycles of cell division and proliferation. The integrative DNA sequences are homologous to targeted genomic DNA loci in the transformed yeast species, and such integrative sequences include pLAC4, 25S rDNA, pAOX1, and TRP2, etc. The locations of insecticidal peptide transgenes can be adjacent to the integrative DNA sequence (Insertion vectors) or within the integrative DNA sequence (replacement vectors).

In some embodiments, the expression vectors can contain *E. coli* elements for DNA preparation in *E. coli,* for example, *E. coli* replication origin, antibiotic selection marker, etc. In some embodiments, vectors can contain an array of the sequence elements needed for expression of the transgene of interest, for example, transcriptional promoters, terminators, yeast selection markers, integrative DNA sequences homologous to host yeast DNA, etc. There are many suitable yeast promoters available, including natural and engineered promoters, for example, yeast promoters such as pLAC4, pAOX1, pUPP, pADH1, pTEF, pGal1, etc., and others, can be used in some embodiments.

In some embodiments, selection methods such as acetamide prototrophy selection; zeocin-resistance selection; geneticin-resistance selection; nourseothricin-resistance selection; uracil deficiency selection; and/or other selection methods may be used. For example, in some embodiments, the *Aspergillus nidulans* amdS gene can be used as selectable marker. Exemplary methods for the use of selectable markers can be found in U.S. Pat. No. 6,548,285 (filed Apr. 3, 1997); U.S. Pat. No. 6,165,715 (filed Jun. 22, 1998); and 6,110,707 (filed Jan. 17, 1997), the disclosures of which are incorporated herein by reference in its entirety.

In some embodiments, a polynucleotide encoding a TVP can be inserted into a pKLAC1 plasmid. The pKLAC1 is commercially available from New England Biolabs® Inc., (item no. (NEB #E1000). The pKLAC1 is designed to accomplish high-level expression of recombinant protein (e.g., TVP) in the yeast *Kluyveromyces lactis*. The pKLAC1 plasmid can be ordered alone, or as part of a *K. lactis* Protein Expression Kit. The pKLAC1 plasmid can be linearized using the SacII or BstXI restriction enzymes, and possesses a MCS downstream of an αMF secretion signal. The αMF secretion signal directs recombinant proteins to the secretory pathway, which is then subsequently cleaved via Kex2 resulting in peptide of interest, for example, a TVP. Kex2 is a calcium-dependent serine protease, which is involved in activating proproteins of the secretory pathway, and is commercially available (PeproTech®; item no. 450-45).

In some embodiments, a polynucleotide encoding a TVP can be inserted into a pKlac1 plasmid, or subcloned into a pKlac1 plasmid subsequent to selection of yeast colonies transformed with pKLAC1 plasmids ligated with polynucleotide encoding a TVP. Yeast, for example *K. lactis*, transformed with a pKLAC1 plasmids ligated with polynucleotide encoding a TVP can be selected based on acetamidase (amdS), which allows transformed yeast cells to grow in YCB medium containing acetamide as its only nitrogen source. Once positive yeast colonies transformed with a pKLAC1 plasmids ligated with polynucleotide encoding a TVP are identified.

In some embodiments, a polynucleotide encoding a TVP can be inserted into other commercially available plasmids and/or vectors that are readily available to those having skill in the art, e.g., plasmids are available from Addgene (a non-profit plasmid repository); GenScript®; Takara®; Qiagen®; and Promega™.

In some embodiments, a yeast cell transformed with one or more TVP expression cassettes can produce a TVP in a yeast culture with a yield of: at least 70 mg/L, at least 80 mg/L, at least 90 mg/L, at least 100 mg/L, at least 110 mg/L, at least 120 mg/L, at least 130 mg/L, at least 140 mg/L, at least 150 mg/L, at least 160 mg/L, at least 170 mg/L, at least 180 mg/L, at least 190 mg/L 200 mg/L, at least 500 mg/L, at least 750 mg/L, at least 1,000 mg/L, at least 1,250 mg/L, at least 1,500 mg/L, at least 1,750 mg/L, at least 2,000 mg/L, at least 2,500 mg/L, at least 3,000 mg/L, at least 3,500 mg/L, at least 4,000 mg/L, at least 4,500 mg/L, at least 5,000 mg/L, at least 5,500 mg/L, at least at least 6,000 mg/L, at least 6,500 mg/L, at least 7,000 mg/L, at least 7,500 mg/L, at least 8,000 mg/L, at least 8,500 mg/L, at least 9,000 mg/L, at least 9,500 mg/L, at least 10,000 mg/L, at least 11,000 mg/L, at least 12,000 mg/L, at least 12,500 mg/L, at least 13,000 mg/L, at least 14,000 mg/L, at least 15,000 mg/L, at least 16,000 mg/L, at least 17,000 mg/L, at least 17,500 mg/L, at least 18,000 mg/L, at least 19,000 mg/L, at least 20,000 mg/L, at least 25,000 mg/L, at least 30,000 mg/L, at least 40,000 mg/L, at least 50,000 mg/L, at least 60,000 mg/L, at least 70,000 mg/L, at least 80,000 mg/L, at least 90,000 mg/L, or at least 100,000 mg/L of TVP per liter of medium.

In some embodiments, one or more expression cassettes comprising a polynucleotide operable to express a TVP can be inserted into a vector, resulting in a yield ranging from about 100 mg/L of TVP to about 100,000 mg/L; from about 110 mg/L to about 100,000 mg/L; from about 120 mg/L to about 100,000 mg/L; from about 130 mg/L to about 100,000 mg/L; from about 140 mg/L to about 100,000 mg/L; from about 150 mg/L to about 100,000 mg/L; from about 160 mg/L to about 100,000 mg/L; from about 170 mg/L to about 100,000 mg/L; from about 180 mg/L to about 100,000 mg/L; from about 190 mg/L to about 100,000 mg/L; from about 200 mg/L to about 100,000 mg/L; from about 250 mg/L to about 100,000 mg/L; from about 500 mg/L to about 100,000 mg/L; from about 750 mg/L to about 100,000 mg/L; from about 1000 mg/L to about 100,000 mg/L; from about 1000 mg/L to about 100,000 mg/L; from about 1500 mg/L to about 100,000 mg/L; from about 2000 mg/L to about 100,000 mg/L; from about 2500 mg/L to about 100,000 mg/L; from about 3000 mg/L to about 100,000 mg/L; from about 3500 mg/L to about 100,000 mg/L; from about 4000 mg/L to about 100,000 mg/L; from about 4500 mg/L to about 100,000 mg/L; from about 5000 mg/L to about 100,000 mg/L; from about 5500 mg/L to about 100,000 mg/L; from about 6000 mg/L to about 100,000 mg/L; from about 6500 mg/L to about 100,000 mg/L; from about 7000 mg/L to about 100,000 mg/L; from about 7500 mg/L to about 100,000 mg/L; from about 8000 mg/L to about 100,000 mg/L; from about 8500 mg/L to about 100,000 mg/L; from about 9000 mg/L to about 100,000 mg/L; from about 9500 mg/L to about 100,000 mg/L; from about 10000 mg/L to about 100,000 mg/L; from about 10500 mg/L to about 100,000 mg/L; from about 11000 mg/L to about 100,000 mg/L; from about 11500 mg/L to about 100,000 mg/L; from about 12000 mg/L to about 100,000 mg/L; from about 12500 mg/L to about 100,000 mg/L; from about 13000 mg/L to about 100,000 mg/L; from about 13500 mg/L to about 100,000 mg/L; from about 14000 mg/L to about 100,000 mg/L; from about 14500 mg/L to about 100,000 mg/L; from about 15000 mg/L to about 100,000 mg/L; from about 15500 mg/L to about 100,000 mg/L; from about 16000 mg/L to about 100,000 mg/L; from about 16500 mg/L to about 100,000 mg/L; from about 17000 mg/L to about 100,000 mg/L; from about 17500 mg/L to about 100,000 mg/L; from about 18000 mg/L to about 100,000 mg/L; from about 18500 mg/L to about 100,000 mg/L; from about 19000 mg/L to about 100,000 mg/L; from about 19500 mg/L to about 100,000 mg/L; from about 20000 mg/L to about 100,000 mg/L; from about 20500 mg/L to about 100,000 mg/L; from about 21000 mg/L to about 100,000 mg/L; from about 21500 mg/L to about 100,000 mg/L; from about 22000 mg/L to about 100,000 mg/L; from about 22500 mg/L to about 100,000 mg/L; from about 23000 mg/L to about 100,000 mg/L; from about 23500 mg/L to about 100,000 mg/L; from about 24000 mg/L to about 100,000 mg/L; from about 24500 mg/L to about 100,000 mg/L; from about 25000 mg/L to about 100,000 mg/L; from about 25500 mg/L to about 100,000 mg/L; from about 26000 mg/L to about 100,000 mg/L; from about 26500 mg/L to about 100,000 mg/L; from about 27000 mg/L to about 100,000 mg/L; from about 27500 mg/L to about 100,000 mg/L; from about 28000 mg/L to about 100,000 mg/L; from about 28500 mg/L to about 100,000 mg/L; from about 29000 mg/L to about 100,000 mg/L; from about 29500 mg/L to about 100,000 mg/L; from about 30000 mg/L to about 100,000 mg/L; from about 30500 mg/L to about 100,000 mg/L; from about 31000 mg/L to about 100,000 mg/L; from about 31500 mg/L to about 100,000 mg/L; from about 32000 mg/L to about 100,000 mg/L; from about 32500 mg/L to about 100,000 mg/L; from about 33000 mg/L to about 100,000 mg/L; from about 33500 mg/L to about 100,000 mg/L; from about 34000 mg/L to about 100,000 mg/L; from about 34500 mg/L to about 100,000 mg/L; from about 35000 mg/L to about 100,000 mg/L; from about 35500 mg/L to about 100,000 mg/L; from about 36000 mg/L to about 100,000 mg/L; from about 36500 mg/L to about 100,000 mg/L; from about 37000 mg/L to about 100,000 mg/L; from about 37500 mg/L to about 100,000 mg/L; from about 38000 mg/L to about 100,000 mg/L; from about 38500 mg/L to about 100,000 mg/L; from about 39000 mg/L to about 100,000 mg/L; from about 39500 mg/L to about 100,000 mg/L; from about 40000 mg/L to about 100,000 mg/L; from about 40500 mg/L to about 100,000 mg/L; from about 41000 mg/L to about 100,000 mg/L; from about 41500 mg/L to about 100,000 mg/L; from about 42000 mg/L to about 100,000 mg/L; from about 42500 mg/L to about 100,000 mg/L; from about 43000 mg/L to about 100,000 mg/L; from about 43500 mg/L to about 100,000 mg/L; from about 44000 mg/L to about 100,000 mg/L; from about 44500 mg/L to about 100,000 mg/L; from about 45000 mg/L to about 100,000 mg/L; from about 45500 mg/L to about 100,000 mg/L; from about 46000 mg/L to about 100,000 mg/L; from about 46500 mg/L to about 100,000 mg/L; from about 47000 mg/L to about 100,000 mg/L; from about 47500 mg/L to about 100,000 mg/L; from about 48000 mg/L to about 100,000 mg/L; from about 48500 mg/L to about 100,000 mg/L; from about 49000 mg/L to about 100,000 mg/L; from about 49500 mg/L to about 100,000 mg/L; from about 50000 mg/L to about 100,000 mg/L; from about 50500 mg/L to about 100,000 mg/L; from about 51000 mg/L to about 100,000 mg/L; from about 51500 mg/L to about 100,000 mg/L; from about 52000 mg/L to about 100,000 mg/L; from about 52500 mg/L to about 100,000 mg/L; from about 53000 mg/L to about 100,000 mg/L; from about 53500 mg/L to about 100,000 mg/L; from about 54000 mg/L to about 100,000 mg/L; from about 54500 mg/L to about 100,000 mg/L; from about 55000 mg/L to about 100,000 mg/L; from about 55500 mg/L to about 100,000 mg/L; from about 56000 mg/L to about 100,000 mg/L; from about 56500 mg/L to about 100,000 mg/L; from about 57000 mg/L to about 100,000 mg/L; from about 57500 mg/L to about 100,000 mg/L; from about 58000 mg/L to about 100,000 mg/L; from about 58500 mg/L to about 100,000 mg/L; from about 59000 mg/L to about 100,000 mg/L; from about 59500 mg/L to about 100,000 mg/L; from about 60000 mg/L to about 100,000 mg/L; from about 60500 mg/L to about 100,000 mg/L; from about 61000 mg/L to about 100,000 mg/L; from about 61500 mg/L to about 100,000 mg/L; from about 62000 mg/L to about 100,000 mg/L; from about 62500 mg/L to about 100,000 mg/L; from about 63000 mg/L to about 100,000 mg/L; from about 63500 mg/L to about 100,000 mg/L; from about 64000 mg/L to about 100,000 mg/L; from about 64500 mg/L to about 100,000 mg/L; from about 65000 mg/L to about 100,000 mg/L; from about 65500 mg/L to about 100,000 mg/L; from about 66000 mg/L to about 100,000 mg/L; from about 66500 mg/L to about 100,000 mg/L; from about 67000 mg/L to about 100,000 mg/L; from about 67500 mg/L to about 100,000 mg/L; from about 68000 mg/L to about 100,000 mg/L; from about 68500 mg/L to about 100,000 mg/L; from about 69000 mg/L to about 100,000 mg/L; from about 69500 mg/L to about 100,000 mg/L; from about 70000 mg/L to about 100,000 mg/L; from about 70500 mg/L to about 100,000 mg/L; from about 71000 mg/L to about 100,000 mg/L; from about 71500 mg/L to about 100,000 mg/L; from about 72000 mg/L to about 100,000 mg/L; from about 72500 mg/L to about 100,000 mg/L; from about 73000 mg/L to about 100,000 mg/L; from about 73500 mg/L to about 100,000 mg/L; from about 74000 mg/L to about 100,000 mg/L; from about 74500 mg/L to about 100,000 mg/L; from about 75000 mg/L to about 100,000 mg/L; from about 75500 mg/L to about 100,000 mg/L; from about 76000 mg/L to about 100,000 mg/L; from about 76500 mg/L to about 100,000 mg/L; from about 77000 mg/L to about 100,000 mg/L; from about 77500 mg/L to about 100,000 mg/L; from about 78000 mg/L to about 100,000 mg/L; from about 78500 mg/L to about 100,000 mg/L; from about 79000 mg/L to about 100,000 mg/L; from about 79500 mg/L to about 100,000 mg/L; from about 80000 mg/L to about 100,000 mg/L; from about 80500 mg/L to about 100,000 mg/L; from about 81000 mg/L to about 100,000 mg/L; from about 81500 mg/L to about 100,000 mg/L; from about 82000 mg/L to about 100,000 mg/L; from about 82500 mg/L to about 100,000 mg/L; from about 83000 mg/L to about 100,000 mg/L; from about 83500 mg/L to about 100,000 mg/L; from about 84000 mg/L to about 100,000 mg/L; from about 84500 mg/L to about 100,000 mg/L; from about 85000 mg/L to about 100,000 mg/L; from about 85500 mg/L to about 100,000 mg/L; from about 86000 mg/L to about 100,000 mg/L; from about 86500 mg/L to about 100,000 mg/L; from about 87000 mg/L to about 100,000 mg/L; from about 87500 mg/L to about 100,000 mg/L; from about 88000 mg/L to about 100,000 mg/L; from about 88500 mg/L to about 100,000 mg/L; from about 89000 mg/L to about 100,000 mg/L; from about 89500 mg/L to about 100,000 mg/L; from about 90000 mg/L to about 100,000 mg/L; from about 90500 mg/L to about 100,000 mg/L; from about 91000 mg/L to about 100,000 mg/L; from about 91500 mg/L to about 100,000 mg/L; from about 92000 mg/L to about 100,000 mg/L; from about 92500 mg/L to about 100,000 mg/L; from about 93000 mg/L to about 100,000 mg/L; from about 93500 mg/L to about 100,000 mg/L; from about 94000 mg/L to about 100,000 mg/L; from about 94500 mg/L to about 100,000 mg/L; from about 95000 mg/L to about 100,000 mg/L; from about 95500 mg/L to about 100,000 mg/L; from about 96000 mg/L to about 100,000 mg/L; from about 96500 mg/L to about 100,000 mg/L; from about 97000 mg/L to about 100,000 mg/L; from about 97500 mg/L to about 100,000 mg/L; from about 98000 mg/L to about 100,000 mg/L; from about 98500 mg/L to about 100,000 mg/L; from about 99000 mg/L to about 100,000 mg/L; or from about 99500 mg/L to about 100,000 mg/L of TVP per liter of medium (supernatant of yeast fermentation broth).

In some In some embodiments, one or more expression cassettes comprising a polynucleotide operable to express a TVP can be inserted into a vector, resulting in a yield ranging from about 100 mg/L of TVP to about 100,000 mg/L; from about 100 mg/L to about 99500 mg/L; from about 100 mg/L to about 99000 mg/L; from about 100 mg/L to about 98500 mg/L; from about 100 mg/L to about 98000 mg/L; from about 100 mg/L to about 97500 mg/L; from about 100 mg/L to about 97000 mg/L; from about 100 mg/L to about 96500 mg/L; from about 100 mg/L to about 96000 mg/L; from about 100 mg/L to about 95500 mg/L; from about 100 mg/L to about 95000 mg/L; from about 100 mg/L to about 94500 mg/L; from about 100 mg/L to about 94000 mg/L; from about 100 mg/L to about 93500 mg/L; from about 100 mg/L to about 93000 mg/L; from about 100 mg/L to about 92500 mg/L; from about 100 mg/L to about 92000 mg/L; from about 100 mg/L to about 91500 mg/L; from about 100 mg/L to about 91000 mg/L to about 90500 mg/L; from about 100 mg/L to about 90000 mg/L; from about 100 mg/L to about 89500 mg/L; from about 100 mg/L to about 89000 mg/L; from about 100 mg/L to about 88500 mg/L; from about 100 mg/L to about 88000 mg/L; from about 100 mg/L to about 87500 mg/L; from about 100 mg/L to about 87000 mg/L; from about 100 mg/L to about 86500 mg/L; from about 100 mg/L to about 86000 mg/L; from about 100 mg/L to about 85500 mg/L; from about 100 mg/L to about 85000 mg/L; from about 100 mg/L to about 84500 mg/L; from about 100 mg/L to about 84000 mg/L; from about 100 mg/L to about 83500 mg/L; from about 100 mg/L to about 83000 mg/L; from about 100 mg/L to about 82500 mg/L; from about 100 mg/L to about 82000 mg/L; from about 100 mg/L to about 81500 mg/L; from about 100 mg/L to about 81000 mg/L; from about 100 mg/L to about 80500 mg/L; from about 100 mg/L to about 80000 mg/L; from about 100 mg/L to about 79500 mg/L; from about 100 mg/L to about 79000 mg/L; from about 100 mg/L to about 78500 mg/L; from about 100 mg/L to about 78000 mg/L; from about 100 mg/L to about 77500 mg/L; from about 100 mg/L to about 77000 mg/L; from about 100 mg/L to about 76500 mg/L; from about 100 mg/L to about 76000 mg/L; from about 100 mg/L to about 75500 mg/L; from about 100 mg/L to about 75000 mg/L; from about 100 mg/L to about 74500 mg/L; from about 100 mg/L to about 74000 mg/L; from about 100 mg/L to about 73500 mg/L; from about 100 mg/L to about 73000 mg/L; from about 100 mg/L to about 72500 mg/L; from about 100 mg/L to about 72000 mg/L; from about 100 mg/L to about 71500 mg/L; from about 100 mg/L to about 71000 mg/L; from about 100 mg/L to about 70500 mg/L; from about 100 mg/L to about 70000 mg/L; from about 100 mg/L to about 69500 mg/L; from about 100 mg/L to about 69000 mg/L; from about 100 mg/L to about 68500 mg/L; from about 100 mg/L to about 68000 mg/L; from about 100 mg/L to about 67500 mg/L; from about 100 mg/L to about 67000 mg/L; from about 100 mg/L to about 66500 mg/L; from about 100 mg/L to about 66000 mg/L; from about 100 mg/L to about 65500 mg/L; from about 100 mg/L to about 65000 mg/L; from about 100 mg/L to about 64500 mg/L; from about 100 mg/L to about 64000 mg/L; from about 100 mg/L to about 63500 mg/L; from about 100 mg/L to about 63000 mg/L; from about 100 mg/L to about 62500 mg/L; from about 100 mg/L to about 62000 mg/L; from about 100 mg/L to about 61500 mg/L; from about 100 mg/L to about 61000 mg/L; from about 100 mg/L to about 60500 mg/L; from about 100 mg/L to about 60000 mg/L; from about 100 mg/L to about 59500 mg/L; from about 100 mg/L to about 59000 mg/L; from about 100 mg/L to about 58500 mg/L; from about 100 mg/L to about 58000 mg/L; from about 100 mg/L to about 57500 mg/L; from about 100 mg/L to about 57000 mg/L; from about 100 mg/L to about 56500 mg/L; from about 100 mg/L to about 56000 mg/L; from about 100 mg/L to about 55500 mg/L; from about 100 mg/L to about 55000 mg/L; from about 100 mg/L to about 54500 mg/L; from about 100 mg/L to about 54000 mg/L; from about 100 mg/L to about 53500 mg/L; from about 100 mg/L to about 53000 mg/L; from about 100 mg/L to about 52500 mg/L; from about 100 mg/L to about 52000 mg/L; from about 100 mg/L to about 51500 mg/L; from about 100 mg/L to about 51000 mg/L; from about 100 mg/L to about 50500 mg/L; from about 100 mg/L to about 50000 mg/L; from about 100 mg/L to about 49500 mg/L; from about 100 mg/L to about 49000 mg/L; from about 100 mg/L to about 48500 mg/L; from about 100 mg/L to about 48000 mg/L; from about 100 mg/L to about 47500 mg/L; from about 100 mg/L to about 47000 mg/L; from about 100 mg/L to about 46500 mg/L; from about 100 mg/L to about 46000 mg/L; from about 100 mg/L to about 45500 mg/L; from about 100 mg/L to about 45000 mg/L; from about 100 mg/L to about 44500 mg/L; from about 100 mg/L to about 44000 mg/L; from about 100 mg/L to about 43500 mg/L; from about 100 mg/L to about 43000 mg/L; from about 100 mg/L to about 42500 mg/L; from about 100 mg/L to about 42000 mg/L; from about 100 mg/L to about 41500 mg/L; from about 100 mg/L to about 41000 mg/L; from about 100 mg/L to about 40500 mg/L; from about 100 mg/L to about 40000 mg/L; from about 100 mg/L to about 39500 mg/L; from about 100 mg/L to about 39000 mg/L; from about 100 mg/L to about 38500 mg/L; from about 100 mg/L to about 38000 mg/L; from about 100 mg/L to about 37500 mg/L; from about 100 mg/L to about 37000 mg/L; from about 100 mg/L to about 36500 mg/L; from about 100 mg/L to about 36000 mg/L; from about 100 mg/L to about 35500 mg/L; from about 100 mg/L to about 35000 mg/L; from about 100 mg/L to about 34500 mg/L; from about 100 mg/L to about 34000 mg/L; from about 100 mg/L to about 33500 mg/L; from about 100 mg/L to about 33000 mg/L; from about 100 mg/L to about 32500 mg/L; from about 100 mg/L to about 32000 mg/L; from about 100 mg/L to about 31500 mg/L; from about 100 mg/L to about 31000 mg/L; from about 100 mg/L to about 30500 mg/L; from about 100 mg/L to about 30000 mg/L; from about 100 mg/L to about 29500 mg/L; from about 100 mg/L to about 29000 mg/L; from about 100 mg/L to about 28500 mg/L; from about 100 mg/L to about 28000 mg/L; from about 100 mg/L to about 27500 mg/L; from about 100 mg/L to about 27000 mg/L; from about 100 mg/L to about 26500 mg/L; from about 100 mg/L to about 26000 mg/L; from about 100 mg/L to about 25500 mg/L; from about 100 mg/L to about 25000 mg/L; from about 100 mg/L to about 24500 mg/L; from about 100 mg/L to about 24000 mg/L; from about 100 mg/L to about 23500 mg/L; from about 100 mg/L to about 23000 mg/L; from about 100 mg/L to about 22500 mg/L; from about 100 mg/L to about 22000 mg/L; from about 100 mg/L to about 21500 mg/L; from about 100 mg/L to about 21000 mg/L; from about 100 mg/L to about 20500 mg/L; from about 100 mg/L to about 20000 mg/L; from about 100 mg/L to about 19500 mg/L; from about 100 mg/L to about 19000 mg/L; from about 100 mg/L to about 18500 mg/L; from about 100 mg/L to about 18000 mg/L; from about 100 mg/L to about 17500 mg/L; from about 100 mg/L to about 17000 mg/L; from about 100 mg/L to about 16500 mg/L; from about 100 mg/L to about 16000 mg/L; from about 100 mg/L to about 15500 mg/L; from about 100 mg/L to about 15000 mg/L; from about 100 mg/L to about 14500 mg/L; from about 100 mg/L to about 14000 mg/L; from about 100 mg/L to about 13500 mg/L; from about 100 mg/L to about 13000 mg/L; from about 100 mg/L to about 12500 mg/L; from about 100 mg/L to about 12000 mg/L; from about 100 mg/L to about 11500 mg/L; from about 100 mg/L to about 11000 mg/L; from about 100 mg/L to about 10500 mg/L; from about 100 mg/L to about 10000 mg/L; from about 100 mg/L to about 9500 mg/L; from about 100 mg/L to about 9000 mg/L; from about 100 mg/L to about 8500 mg/L; from about 100 mg/L to about 8000 mg/L; from about 100 mg/L to about 7500 mg/L; from about 100 mg/L to about 7000 mg/L; from about 100 mg/L to about 6500 mg/L; from about 100 mg/L to about 6000 mg/L; from about 100 mg/L to about 5500 mg/L; from about 100 mg/L to about 5000 mg/L; from about 100 mg/L to about 4500 mg/L; from about 100 mg/L to about 4000 mg/L; from about 100 mg/L to about 3500 mg/L; from about 100 mg/L to about 3000 mg/L; from about 100 mg/L to about 2500 mg/L;

from about 100 mg/L to about 2000 mg/L; from about 100 mg/L to about 1500 mg/L; from about 100 mg/L to about 1000 mg/L; from about 100 mg/L to about 1000 mg/L; from about 100 mg/L to about 750 mg/L; from about 100 mg/L to about 500 mg/L; from about 100 mg/L to about 250 mg/L; from about 100 mg/L to about 100 mg/L; or from about 100 mg/L to about 110 mg/L of TVP per liter of medium (supernatant of yeast fermentation broth).

In addition to the DNA polynucleotide sequence that encodes a TVP, additional DNA segments known as regulatory elements can be cloned into a vector that allow for enhanced expression of the foreign DNA or transgene; examples of such additional DNA segments include (1) promoters, terminators, and/or enhancer elements; (2) an appropriate mRNA stabilizing polyadenylation signal; (3) an internal ribosome entry site (IRES); (4) introns; and (5) post-transcriptional regulatory elements. The combination of a DNA segment of interest (e.g., tvp) with any one of the foregoing cis-acting elements is called an "expression cassette."

A single expression cassette can contain one or more of the aforementioned regulatory elements, and a polynucleotide operable to express a TVP. For example, in some embodiments, a TVP expression cassette can comprise polynucleotide operable to express a TVP, and an α-MF signal; Kex2 site; LAC4 terminator; ADN1 promoter; and an acetamidase (amdS) selection marker—flanked by LAC4 promoters on the 5'-end and 3'-end.

In some embodiments, there can be numerous expression cassettes cloned into a vector. For example, in some embodiments, there can be a first expression cassette comprising a polynucleotide operable to express a TVP. In alternative embodiments, there are two expression cassettes operable to encode a TVP (i.e., a double expression cassette). In other embodiments, there are three expression cassettes operable to encode a TVP (i.e., a triple expression cassette).

In some embodiments, a double expression cassette can be generated by subcloning a second TVP expression cassette into a vector containing a first TVP expression cassette.

In some embodiments, a triple expression cassette can be generated by subcloning a third TVP expression cassette into a vector containing a first and a second TVP expression cassette.

In some embodiments, a yeast cell transformed with one or more TVP expression cassettes can produce TVP in a yeast culture with a yield of: at least 70 mg/L, at least 80 mg/L, at least 90 mg/L, at least 100 mg/L, at least 110 mg/L, at least 120 mg/L, at least 130 mg/L, at least 140 mg/L, at least 150 mg/L, at least 160 mg/L, at least 170 mg/L, at least 180 mg/L, at least 190 mg/L 200 mg/L, at least 500 mg/L, at least 750 mg/L, at least 1,000 mg/L, at least 1,250 mg/L, at least 1,500 mg/L, at least 1,750 mg/L, at least 2,000 mg/L, at least 2,500 mg/L, at least 3,000 mg/L, at least 3,500 mg/L, at least 4,000 mg/L, at least 4,500 mg/L, at least 5,000 mg/L, at least 5,500 mg/L, at least at least 6,000 mg/L, at least 6,500 mg/L, at least 7,000 mg/L, at least 7,500 mg/L, at least 8,000 mg/L, at least 8,500 mg/L, at least 9,000 mg/L, at least 9,500 mg/L, at least 10,000 mg/L, at least 11,000 mg/L, at least 12,000 mg/L, at least 12,500 mg/L, at least 13,000 mg/L, at least 14,000 mg/L, at least 15,000 mg/L, at least 16,000 mg/L, at least 17,000 mg/L, at least 17,500 mg/L, at least 18,000 mg/L, at least 19,000 mg/L, at least 20,000 mg/L, at least 25,000 mg/L, at least 30,000 mg/L, at least 40,000 mg/L, at least 50,000 mg/L, at least 60,000 mg/L, at least 70,000 mg/L, at least 80,000 mg/L, at least 90,000 mg/L, or at least 100,000 mg/L of TVP per liter of yeast culture medium.

In some embodiments, one or more expression cassettes comprising a polynucleotide operable to express a TVP can be inserted into a vector, for example a pKlac1 plasmid, resulting in a yield of about 100 mg/L of TVP (supernatant of yeast fermentation broth). For example, in some embodiments, two expression cassettes comprising a polynucleotide operable to express a TVP can be inserted into a vector, for example a pKS482 plasmid, resulting in a yield of about 2 g/L of TVP (supernatant of yeast fermentation broth). Alternatively, in some embodiments, three expression cassettes comprising a polynucleotide operable to express a TVP can be inserted into a vector, for example a pKlac1T plasmid.

In some embodiments, multiple TVP expression cassettes can be transfected into yeast in order to enable integration of one or more copies of the optimized TVP transgene into the K. lactis genome. An exemplary method of introducing multiple TVP expression cassettes into a K. lactis genome is as follows: a TVP expression cassette DNA sequence is synthesized, comprising an intact LAC4 promoter element, a codon-optimized TVP expression ORF element and a pLAC4 terminator element; the intact expression cassette is ligated into the pKlac1 vector between Sal I and Kpn I restriction sites, downstream of the pLAC4 terminator of pKS477, resulting in the double transgene TVP expression vector, pKS482; the double transgene vectors, pKS482, are then linearized using Sac II restriction endonuclease and transformed into YCT306 strain of K. lactis by electroporation. The resulting yeast colonies are then grown on YCB agar plate supplemented with 5 mM acetamide, which only the acetamidase-expressing cells could use efficiently as a metabolic source of nitrogen. To evaluate the yeast colonies, about 100 to 400 colonies can be picked from the pKS482 yeast plates. Inoculates from the colonies are each cultured in 2.2 mL of the defined K. lactis media with 2% sugar alcohol added as a carbon source. Cultures are incubated at 23.5° C., with shaking at 280 rpm, for six days, at which point cell densities in the cultures will reach their maximum levels as indicated by light absorbance at 600 nm (OD600). Cells are then removed from the cultures by centrifugation at 4,000 rpm for 10 minutes, and the resulting supernatants (conditioned media) are filtered through 0.2 μM membranes for HPLC yield analysis.

In some embodiments, a vector comprises a polynucleotide operable to encode a TVP having an amino acid sequence with 90% similarity to a sequence as set forth in any one of SEQ ID NOs: 2-15, 49-53, or 77-110.

In other embodiments, a vector comprises a polynucleotide having amino sequence as set forth in any one of SEQ ID NOs: 17-30, 54-58, or 117-150, or a complementary nucleotide sequence thereof.

Chemically Synthesizing TVPs

Peptide synthesis or the chemical synthesis or peptides and/or polypeptides can be used to generate TVPs: these methods can be performed by those having ordinary skill in the art, and/or through the use of commercial vendors (e.g., GenScript®; Piscataway, New Jersey). For example, in some embodiments, chemical peptide synthesis can be achieved using Liquid phase peptide synthesis (LPPS), or solid phase peptide synthesis (SPPS).

In some embodiments, peptide synthesis can generally be achieved by using a strategy wherein the coupling the carboxyl group of a subsequent amino acid to the N-terminus of a preceding amino acid generates the nascent polypeptide chain—a process that is opposite to the type of polypeptide synthesis that occurs in nature.

Peptide deprotection is an important first step in the chemical synthesis of polypeptides. Peptide deprotection is the process in which the reactive groups of amino acids are blocked through the use of chemicals in order to prevent said amino acid's functional group from taking part in an unwanted or non-specific reaction or side reaction; in other words, the amino acids are "protected" from taking part in these undesirable reactions.

Prior to synthesizing the peptide chain, the amino acids must be "deprotected" to allow the chain to form (i.e., amino acids to bind). Chemicals used to protect the N-termini include 9-fluorenylmethoxycarbonyl (Fmoc), and tert-butoxycarbonyl (Boc), each of which can be removed via the use of a mild base (e.g., piperidine) and a moderately strong acid (e.g., trifluoracetic acid (TFA)), respectively.

The C-terminus protectant required is dependent on the type of chemical peptide synthesis strategy used: e.g., LPPS requires protection of the C-terminal amino acid, whereas SPPS does not owing to the solid support which acts as the protecting group. Side chain amino acids require the use of several different protecting groups that vary based on the individual peptide sequence and N-terminal protection strategy; typically, however, the protecting group used for side chain amino acids are based on the tert-butyl (tBu) or benzyl (Bzl) protecting groups.

Amino acid coupling is the next step in a peptide synthesis procedure. To effectuate amino acid coupling, the incoming amino acid's C-terminal carboxylic acid must be activated: this can be accomplished using carbodiimides such as diisopropylcarbodiimide (DIC), or dicyclohexylcarbodiimide (DCC), which react with the incoming amino acid's carboxyl group to form an O-acylisourea intermediate. The O-acylisourea intermediate is subsequently displaced via nucleophilic attack via the primary amino group on the N-terminus of the growing peptide chain. The reactive intermediate generated by carbodiimides can result in the racemization of amino acids. To avoid racemization of the amino acids, reagents such as 1-hydroxybenzotriazole (HOBt) are added in order to react with the O-acylisourea intermediate. Other couple agents that may be used include 2-(1H-benzotriazol-1-yl)-1,1,3,3-tetramethyluronium hexafluorophosphate (HBTU), and benzotriazol-1-yl-oxy-tris(dimethylamino)phosphonium hexafluorophosphate (BOP), with the additional activating bases. Finally, following amino acid deprotection and coupling, At the end of the synthesis process, removal of the protecting groups from the polypeptide must occur—a process that usually occurs through acidolysis. Determining which reagent is required for peptide cleavage is a function of the protection scheme used and overall synthesis method. For example, in some embodiments, hydrogen bromide (HBr); hydrogen fluoride (HF); or trifluoromethane sulfonic acid (TFMSA) can be used to cleave Bzl and Boc groups. Alternatively, in other embodiments, a less strong acid such as TFA can effectuate acidolysis of tBut and Fmoc groups. Finally, peptides can be purified based on the peptide's physiochemical characteristics (e.g., charge, size, hydrophobicity, etc.). Techniques that can be used to purify peptides include Purification techniques include Reverse-phase chromatography (RPC); Size-exclusion chromatography; Partition chromatography; High-performance liquid chromatography (HPLC); and Ion exchange chromatography (IEC).

Exemplary methods of peptide synthesis can be found in Anderson G. W. and McGregor A. C. (1957) T-butyloxy-carbonylamino acids and their use in peptide synthesis. Journal of the American Chemical Society. 79, 6180-3; Carpino L. A. (1957) Oxidative reactions of hydrazines. Iv. Elimination of nitrogen from 1,1-disubstituted-2-arene-sulfonhydrazides1-4. Journal of the American Chemical Society. 79, 4427-31; McKay F. C. and Albertson N. F. (1957) New amine-masking groups for peptide synthesis. Journal of the American Chemical Society. 79, 4686-90; Merrifield R. B. (1963) Solid phase peptide synthesis. I. The synthesis of a tetrapeptide. Journal of the American Chemical Society. 85, 2149-54; Carpino L. A. and Han G. Y. (1972) 9-fluorenylmethoxycarbonyl amino-protecting group. The Journal of Organic Chemistry. 37, 3404-9; and A Lloyd-Williams P. et al. (1997) Chemical approaches to the synthesis of peptides and proteins. Boca Raton: CRC Press. 278; U.S. Pat. No. 3,714,140 (filed Mar. 16, 1971); U.S. Pat. No. 4,411,994 (filed Jun. 8, 1978); U.S. Pat. No. 7,785,832 (filed Jan. 20, 2006); U.S. Pat. No. 8,314,208 (filed Feb. 10, 2006); and 10,442,834 (filed Oct. 2, 2015); and United States Patent Application 2005/0165215 (filed Dec. 23, 2004), the disclosures of which are incorporated herein by reference in their entirety.

Illustrative Methods

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the TVP has one amino acid substitution at $X_1$, $X_2$, $X_3$, $X_4$, or $X_5$.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-

A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the TVP has one amino acid substitution at X1, X2, X3, X4, or X5; and wherein X7 is Glycine.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the TVP has one amino acid substitution at $X_1$, $X_2$, $X_3$, $X_4$, or $X_5$; and wherein $X_7$ is absent.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the TVP has one amino acid substitution at $X_1$, $X_2$, $X_3$, $X_4$, or $X_5$; and wherein $X_6$ and $X_7$ are absent.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the TVP comprises an amino sequence as set forth in any one of SEQ ID NOs: 2-15, 49-53, or 77-110

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the TVP is encoded by a polynucleotide sequence as set forth in any one of SEQ ID NOs: 17-30, 54-58, or 117-150, or a complementary nucleotide sequence thereof.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the vector is a plasmid comprising an alpha-MF signal.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the alpha-MF signal is operable to express an alpha-MF signal peptide.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the vector is transformed into a host cell.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the host cell is a eukaryotic cell or a prokaryotic cell.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the host cell is a yeast cell.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the host cell is a yeast cell selected from any species of the genera *Saccharomyces, Pichia, Kluyveromyces, Hansenula, Yarrowia* or *Schizosaccharomyces*.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the host cell is *Kluyveromyces lactis* or *Kluyveromyces marxianus*.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the TVP is secreted into the growth medium.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the TVP is secreted into the growth medium, wherein the TVP is operably linked to the alpha-MF signal peptide.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the expression of the TVP provides a yield of: at least 70 mg/L, at least 80 mg/L, at least 90 mg/L, at least 100 mg/L, at least 110 mg/L, at least 120 mg/L, at least 130 mg/L, at least 140 mg/L, at least 150 mg/L, at least 160 mg/L, at least 170 mg/L, at least 180 mg/L, at least 190 mg/L 200 mg/L, at least 500 mg/L, at least 750 mg/L, at least 1,000 mg/L, at least 1,250 mg/L, at least 1,500 mg/L, at least 1,750 mg/L, at least 2,000 mg/L, at least 2,500 mg/L, at least 3,000 mg/L, at least 3,500 mg/L, at least 4,000 mg/L, at least 4,500 mg/L, at least 5,000 mg/L, at least 5,500 mg/L, at least 6,000 mg/L, at least 6,500 mg/L, at least 7,000 mg/L, at least 7,500 mg/L, at least 8,000 mg/L, at least 8,500 mg/L, at least 9,000 mg/L, at least 9,500 mg/L, at least 10,000 mg/L, at least 12,500 mg/L, at least 15,000 mg/L, at least 17,500 mg/L, at least 20,000 mg/L, at least 25,000 mg/L, at least 30,000 mg/L, at least 40,000 mg/L, at least 50,000 mg/L, or at least 100,000 mg/L of TVP per liter of yeast culture medium.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the expression of the TVP provides a yield of at least 100 mg/L of TVP per liter of medium.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the expression of the TVP in the medium results in the expression of a single TVP in the medium.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the expression of the TVP in the medium results in the expression of a TVP fusion polymer comprising two or more TVP polypeptides in the medium In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the vector comprises two or three expression cassettes, each expression cassette operable to encode the TVP of the first expression cassette.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the vector comprises two or three expression cassettes, each expression cassette operable to encode the TVP of the first expression cassette, or a TVP of a different expression cassette.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the expression cassette is operable to encode a TVP as set forth in any one of SEQ ID NOs: 2-15, 49-53, or 77-110

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein the TVP is encoded by a polynucleotide sequence as set forth in any one of SEQ ID NOs: 17-30, 54-58, or 117-150, or a complementary nucleotide sequence thereof.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; (b) introducing the vector into a host cell; and (c) growing the host cell in a growth medium under conditions operable to enable expression of the TVP; wherein if $Z_1$ is T or S, then the TVP is glycosylated.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein if $Z_1$ is T then the TVP is glycosylated.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein $X_1$ is Q; and $Z_1$ is A.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the TVP comprises an amino sequence as set forth in any one of SEQ ID NOs: 2, 49, or 51.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the TVP is encoded by a polynucleotide sequence as set forth in any one of SEQ ID NOs: 17, 54, or 56, or a complementary nucleotide sequence thereof.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the vector is a plasmid comprising an alpha-MF signal.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the alpha-MF signal is operable to express an alpha-MF signal peptide.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the vector is transformed into a host cell.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the host cell is a eukaryotic cell or a prokaryotic cell.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the host cell is a yeast cell.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the host cell is a yeast cell selected from any species of the genera *Saccharomyces, Pichia, Kluyveromyces, Hansenula, Yarrowia* or *Schizosaccharomyces*.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the host cell is *Kluyveromyces lactis* or *Kluyveromyces marxianus*.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the TVP is secreted into the growth medium.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the TVP is operably linked to the alpha-MF signal peptide.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the expression of the TVP provides a yield of: at least 70 mg/L, at least 80 mg/L, at least 90 mg/L, at least 100 mg/L, at least 110 mg/L, at least 120 mg/L, at least 130 mg/L, at least 140 mg/L, at least 150 mg/L, at least 160 mg/L, at least 170 mg/L, at least 180 mg/L, at least 190 mg/L 200 mg/L, at least 500 mg/L, at least 750 mg/L, at least 1,000 mg/L, at least 1,250 mg/L, at least 1,500 mg/L, at least 1,750 mg/L, at least 2,000 mg/L, at least 2,500 mg/L, at least 3,000 mg/L, at least 3,500 mg/L, at least 4,000 mg/L, at least 4,500 mg/L, at least 5,000 mg/L, at least 5,500 mg/L, at least at least 6,000 mg/L, at least 6,500 mg/L, at least 7,000 mg/L, at least 7,500 mg/L, at least 8,000 mg/L, at least 8,500 mg/L, at least 9,000 mg/L, at least 9,500 mg/L, at least 10,000 mg/L, at least 12,500 mg/L, at least 15,000 mg/L, at least 17,500 mg/L, at least 20,000 mg/L, at least 25,000 mg/L, at least 30,000 mg/L, at least 40,000 mg/L, at least 50,000 mg/L, or at least 100,000 mg/L of TVP per liter of yeast culture medium.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the expression of the TVP provides a yield of at least 100 mg/L of TVP per liter of medium.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the expression of the TVP in the medium results in the expression of a single TVP in the medium.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the expression of the TVP in the medium results in the expression of a TVP fusion polymer comprising two or more TVP polypeptides in the medium In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the vector comprises two or three expression cassettes, each expression cassette operable to encode the TVP of the first expression cassette.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the vector comprises two or three expression cassettes, each expression cassette operable to encode the TVP of the first expression cassette, or a TVP of a different expression cassette.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-

N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the expression cassette is operable to encode a TVP as set forth in any one of SEQ ID NOs: 2, 49, or 51.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein the TVP is encoded by a polynucleotide sequence as set forth in any one of SEQ ID NOs: 17, 54, or 56, or a complementary nucleotide sequence thereof.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein if $Z_1$ is T then the TVP is glycosylated.

In some embodiments, a method of producing a TVP or TVP-insecticidal protein comprises: (a) preparing a vector comprising a first expression cassette, the first expression cassette comprising a polynucleotide operable to encode a TVP, or complementary nucleotide sequence thereof, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; (b) introducing the vector into a host cell; and (c) growing the host cell in a growth medium under conditions operable to enable expression of the TVP; wherein $X_1$ is Q; and $Z_1$ is A.

Cell Culture and Transformation Techniques

The terms "transformation" and "transfection" both describe the process of introducing exogenous and/or heterologous DNA or RNA to a host organism. Generally, those having ordinary skill in the art sometimes reserve the term "transformation" to describe processes where exogenous and/or heterologous DNA or RNA are introduced into a bacterial cell; and reserve the term "transfection" for processes that describe the introduction of exogenous and/or heterologous DNA or RNA into eukaryotic cells. However, as used herein, the term "transformation" and "transfection" are used synonymously, regardless of whether a process describes the introduction exogenous and/or heterologous DNA or RNA into a prokaryote (e.g., bacteria) or a eukaryote (e.g., yeast, plants, or animals).

In some embodiments, a host cell can be transformed using the following methods: electroporation; cell squeezing; microinjection; impalefection; the use of hydrostatic pressure; sonoporation; optical transfection; continuous infusion; lipofection; through the use of viruses such as adenovirus, adeno-associated virus, lentivirus, herpes simplex virus, and retrovirus; the chemical phosphate method; endocytosis via DEAE-dextran or polyethylenimine (PEI); protoplast fusion; hydrodynamic deliver; magnetofection; nucleoinfection; and/or others. Exemplary methods regarding transfection and/or transformation techniques can be found in Makrides (2003), Gene Transfer and Expression in Mammalian Cells, Elvesier; Wong, TK & Neumann, E. Electric field mediated gene transfer. Biochem. Biophys. Res. Commun. 107, 584-587 (1982); Potter & Heller, Transfection by Electroporation. Curr Protoc Mol Biol. 2003 May; CHAPTER: Unit-9.3; Kim & Eberwine, Mammalian cell transfection: the present and the future. Anal Bioanal Chem. 2010 August; 397(8): 3173-3178, each of these references are incorporated herein by reference in their entireties.

Electroporation is a technique in which electricity is applied to cells causing the cell membrane to become permeable; this in turn allows exogenous DNA to be introduced into the cells. Electroporation is readily known to those having ordinary skill in the art, and the tools and devices required to achieve electroporation are commercially available (e.g., Gene Pulser Xcell™ Electroporation Systems, Bio-Rad®; Neon® Transfection System for Electroporation, Thermo-Fisher Scientific; and other tools and/or devices). Exemplary methods of electroporation are illustrated in Potter & Heller, Transfection by Electroporation. Curr Protoc Mol Biol. 2003 May; CHAPTER: Unit-9.3; Saito (2015) Electroporation Methods in Neuroscience. Springer press; Pakhomov et al., (2017) Advanced Electroporation Techniques in Biology and Medicine. Taylor & Francis; the disclosure of which is incorporated herein by reference in its entirety.

In some embodiments, electroporation can be used to introduce a vector containing a polynucleotide encoding a TVP into yeast, for example, a TVP cloned into a pKlac1 plasmid, and transformed into *K. lactis* cells via electroporation, can be accomplished by inoculating about 10-200 mL of yeast extract peptone dextrose (YEPD) with a suitable yeast species, for example, *Kluyveromyces lactis, Kluyveromyces marxianus, Saccharomyces cerevisiae, Pichia pastoris*, etc., and incubate on a shaker at 30° C. until the early exponential phase of yeast culture (e.g. about 0.6 to $2 \times 10^8$ cells/mL); harvesting the yeast in sterile centrifuge tube and centrifuging at 3000 rpm for 5 minutes at 4° C. (note: keep cells chilled during the procedure) washing cells with 40 mL of ice cold, sterile deionized water, and pelleting the cells a 23,000 rpm for 5 minutes; repeating the wash step, and the resuspending the cells in 20 mL of 1M fermentable sugar, e.g. galactose, maltose, latotriose, sucrose, fructose or glucose and/or sugar alcohol, for example, erythritol, hydrogenated starch hydrolysates, isomalt, lactitol, maltitol, mannitol, and xylitol, followed by spinning down at 3,000 rpm for 5 minutes; resuspending the cells with proper volume of ice cold 1M fermentable sugar, e.g. galactose, maltose, latotriose, sucrose, fructose or glucose and/or a sugar alcohol, for example, erythritol, hydrogenated starch hydrolysates, isomalt, lactitol, maltitol, mannitol, and xylitol to final cell density of $3\times10^9$ cell/mL; mixing 40 μl of the yeast suspension with about 1-4 μl of the vector containing a linear polynucleotide encoding a TVP (~1 μg) in a prechilled 0.2 cm electroporation cuvette (note: ensure the sample is in contact with both sides of the aluminum cuvette); providing a single pulse at 2000 V, for optimal time constant of 5 ms of the RC circuit, the cells was then let recovered in 0.5 ml YED and 0.5 mL 1M fermentable sugar, e.g. galactose, maltose, latotriose, sucrose, fructose or glucose and/or a sugar alcohol, for example, erythritol, hydrogenated starch hydrolysates, isomalt, lactitol, maltitol, mannitol, and xylitol mixture, and then spreading onto selective plates.

In some embodiments, electroporation can be used to introduce a vector containing a polynucleotide encoding a TVP into plant protoplasts by incubating sterile plant material in a protoplast solution (e.g., around 8 mL of 10 mM 2-[N-morpholino]ethanesulfonic acid (MES), pH 5.5; 0.01% (w/v) pectylase; 1% (w/v) macerozyme; 40 mM $CaCl_2$; and 0.4 M mannitol) and adding the mixture to a rotary shaker for about 3 to 6 hours at 30° C. to produce protoplasts; removing debris via 80-μm-mesh nylon screen filtration; rinsing the screen with about 4 ml plant electroporation buffer (e.g., 5 mM $CaCl_2$; 0.4 M mannitol; and PBS); combining the protoplasts in a sterile 15 mL conical centrifuge tube, and then centrifuging at about 300×g for about 5 minutes; subsequent to centrifugation, discarding the supernatant and washing with 5 mL of plant electroporation buffer; resuspending the protoplasts in plant electroporation buffer at about $1.5\times10^6$ to $2\times10^6$ protoplasts per mL of liquid; transferring about 0.5-mL of the protoplast suspension into one or more electroporation cuvettes, set on ice, and adding the vector (note: for stable transformation, the vector should be linearized using anyone of the restriction methods described above, and about 1 to 10 μg of vector may be used; for transient expression, the vector may be retained in its supercoiled state, and about 10 to 40 μg of vector may be used); mixing the vector and protoplast suspension; placing the cuvette into the electroporation apparatus, and shocking for one or more times at about 1 to 2 kV (a 3- to 25-μF capacitance may be used initially while optimizing the reaction); returning the cuvette to ice; diluting the transformed cells 20-fold in complete medium; and harvesting the protoplasts after about 48 hours.

Host Cells

The methods, compositions, and TVPs of the present invention may be implemented in any cell type, e.g., a eukaryotic or prokaryotic cell.

In some embodiments, the host cell used to produce a TVP or a TVP-insecticidal protein is a prokaryote. For example, in some embodiments, the host cell may be an Archaebacteria or Eubacteria, such as Gram-negative or Gram-positive organisms. Examples of useful bacteria include *Escherichia* (e.g., *E. coli*), Bacilli (e.g., *B. subtilis*), Enterobacteria, *Pseudomonas* species (e.g., *P. aeruginosa*), *Salmonella typhimurium*, *Serratia marcescans*, *Klebsiella*, *Proteus*, *Shigella*, *Rhizobia*, *Vitreoscilla*, or *Paracoccus*.

In some embodiments, the host cell used to produce a TVP or a TVP-insecticidal protein may be a unicellular cell. For example, in some embodiments, the host cell may be bacterial cells such as gram positive bacteria.

In some embodiments, the host cell may be a bacteria selected from the following genuses: consisting of *Candidatus chloracidobacterium*, *Arthrobacter*, *Corynebacterium*, *Frankia*, *Micrococcus*, *Mycobacterium*, *Propionibacterium*, *Streptomyces*, *Aquifex Bacteroides*, *Porphyromonas*, *Bacteroides*, *Porphyromonas*, *Flavobacterium*, *Chlamydia*, *Prosthecobacter*, *Verrucomicrobium*, *Chloroflexus*, *Chroococcus*, *Merismopedia*, *Synechococcus*, *Anabaena*, *Nostoc*, *Spirulina*, *Trichodesmium*, *Pleurocapsa*, *Prochlorococcus*, *Prochloron*, *Bacillus*, *Listeria*, *Staphylococcus*, *Clostridium*, *Dehalobacter*, *Epulopiscium*, *Ruminococcus*, *Enterococcus*, *Lactobacillus*, *Streptococcus*, *Erysipelothrix*, *Mycoplasma*, *Leptospirillum*, *Nitrospira*, *Thermodesulfobacterium*, *Gemmata*, *Pirellula*, *Planctomyces*, *Caulobacter*, *Agrobacterium*, *Bradyrhizobium*, *Brucella*, *Methylobacterium*, *Prosthecomicrobium*, *Rhizobium*, *Rhodopseudomonas*, *Sinorhizobium*, *Rhodobacter*, *Roseobacter*, *Acetobacter*, *Rhodospirillum*, *Rickettsia*, *Rickettsia conorii*, *Mitochondria*, *Wolbachia*, *Erythrobacter*, *Erythromicrobium*, *Sphingomonas*, *Alcaligenes*, *Burkholderia*, *Leptothrix*, *Sphaerotilus*, *Thiobacillus*, *Neisseria*, *Nitrosomonas*, *Gallionella*, *Spirillum*, *Azoarcus*, *Aeromonas*, *Succinomonas*, *Succinivibrio*, *Ruminobacter*, *Nitrosococcus*, *Thiocapsa*, *Enterobacter*, *Escherichia*, *Klebsiella*, *Salmonella*, *Shigella*, *Wigglesworthia*, *Yersinia*, *Coxiella*, *Legionella*, *Halomonas*, *Pasteurella*, *Acinetobacter*, *Azotobacter*, *Pseudomonas*, *Psychrobacter*, *Beggiatoa*, *Thiomargarita*, *Vibrio*, *Xanthomonas*, *Bdellovibrio*, *Campylobacter*, *Helicobacter*, *Myxococcus*, *Desulfosarcina*, *Geobacter*, *Desulfuromonas*, *Borrelia*, *Leptospira*, *Treponema*, *Petrotoga*, *Thermotoga*, *Deinococcus*, or *Thermus*.

In some embodiments, the host cell used to produce a TVP or a TVP-insecticidal protein may be selected from one of the following bacteria species: *Bacillus alkalophilus*, *Bacillus amyloliquefaciens*, *Bacillus brevis*, *Bacillus circulans*, *Bacillus coagulans*, *Bacillus lautus*, *Bacillus lentus*, *Bacillus licheniformis*, *Bacillus megaterium*, *Bacillus stearothermophilus*, *Bacillus subtilis*, *Bacillus thuringiensis*, *Streptomyces lividans*, *Streptomyces murinus*, *Streptomyces coelicolor*, *Streptomyces albicans*, *Streptomyces griseus*, *Streptomyces plicatosporus*, *Escherichia albertii*, *Escherichia blattae*, *Escherichia coli*, *Escherichia fergusonii*, *Escherichia hermannii*, *Escherichia senegalensis*, *Escherichia vulneris*, *Pseudomonas abietaniphila*, *Pseudomonas agarici*, *Pseudomonas agarolyticus*, *Pseudomonas alcaliphila*, *Pseudomonas alginovora*, *Pseudomonas andersonii*, *Pseudomonas antarctica*, *Pseudomonas asplenii*, *Pseudomonas azelaica*, *Pseudomonas batumici*, *Pseudomonas borealis*, *Pseudomonas brassicacearum*, *Pseudomonas chloritidismutans*, *Pseudomonas cremoricolorata*, *Pseudomonas diterpeniphila*, *Pseudomonas filiscindens*, *Pseudomonas frederiksbergensis*, *Pseudomonas gingeri*, *Pseudomonas graminis*, *Pseudomonas grimontii*, *Pseudomonas halodenitrificans*, *Pseudomonas halophila*, *Pseudomonas hibiscicola*, *Pseudomonas hydrogenovora*, *Pseudomonas indica*, *Pseudomonas japonica*, *Pseudomonas jessenii*, *Pseudomonas kilonensis*, *Pseudomonas koreensis*, *Pseudomonas lini*, *Pseudomonas lurida*, *Pseudomonas lutea*, *Pseudomonas marginata*, *Pseudomonas meridiana*, *Pseudomonas mesoacidophila*, *Pseudomonas pachastrellae*, *Pseudomonas palleroniana*, *Pseudomonas parafulva*, *Pseudomonas pavonanceae*, *Pseudomonas proteolyica*, *Pseudomonas psychrophila*, *Pseudomonas psychrotolerans*, *Pseudomonas pudica*, *Pseudomonas rathonis*, *Pseudomonas reactans*, *Pseudomonas rhizosphaerae*, *Pseudomonas salmononii*, *Pseudomonas thermaerum*, *Pseudomonas thermocarboxydovorans*, *Pseudomonas thermotolerans*,

*Pseudomonas thivervalensis, Pseudomonas umsongensis, Pseudomonas vancouverensis, Pseudomonas wisconsinensis, Pseudomonas xanthomarina Pseudomonas xiamenensis, Pseudomonas aeruginosa, Pseudomonas alcaligenes, Pseudomonas anguilliseptica, Pseudomonas citronellolis, Pseudomonas flavescens, Pseudomonas jinjuensis, Pseudomonas mendocina, Pseudomonas nitroreducens, Pseudomonas oleovorans, Pseudomonas pseudoalcaligenes, Pseudomonas resinovorans, Pseudomonas straminae, Pseudomonas aurantiaca, Pseudomonas chlororaphis, Pseudomonas fragi, Pseudomonas lundensis, Pseudomonas taetrolens Pseudomonas azotoformans, Pseudomonas brenneri, Pseudomonas cedrina, Pseudomonas congelans, Pseudomonas corrugata, Pseudomonas costantinii, Pseudomonas extremorientalis, Pseudomonas fluorescens, Pseudomonas fulgida, Pseudomonas gessardii, Pseudomonas libanensis, Pseudomonas mandelii, Pseudomonas marginalis, Pseudomonas mediterranea, Pseudomonas migulae, Pseudomonas mucidolens, Pseudomonas orientalis, Pseudomonas poae, Pseudomonas rhodesiae, Pseudomonas synxantha, Pseudomonas tolaasii, Pseudomonas trivialis, Pseudomonas veronii Pseudomonas denitrificans, Pseudomonas pertucinogena, Pseudomonas fulva, Pseudomonas monteiii, Pseudomonas mosselii, Pseudomonas oryzihabitans, Pseudomonas plecoglossicida, Pseudomonas putida, Pseudomonas balearica, Pseudomonas luteola,* or *Pseudomonas stutzeri, Pseudomonas avellanae, Pseudomonas cannabina, Pseudomonas caricapapyae, Pseudomonas cichorii, Pseudomonas coronafaciens, Pseudomonas fuscovaginae, Pseudomonas tremae,* or *Pseudomonas viridiflava*

In some embodiments, the host cell used to produce a TVP or a TVP-insecticidal protein can be eukaryote.

In some embodiments, the host cell used to produce a TVP or a TVP-insecticidal protein may be a cell belonging to the clades: Opisthokonta; Viridiplantae (e.g., algae and plant); Amebozoa; Cercozoa; Alveolata; Marine flagellates; Heterokonta; Discicristata; or Excavata.

In some embodiments, the procedures and methods described here can be accomplished using a host cell that is, e.g., a Metazoan, a Choanoflagellata, or a fungi.

In some embodiments, the procedures and methods described here can be accomplished using a host cell that is a fungi. For example, in some embodiments, the host cell may be a cell belonging to the eukaryote phyla: Ascomycota, Basidiomycota, Chytridiomycota, Microsporidia, or Zygomycota In some embodiments, the procedures and methods described here can be accomplished using a host cell that is a fungi belonging to one of the following genera: *Aspergillus, Cladosporium, Magnaporthe, Morchella, Neurospora, Penicillium, Saccharomyces, Cryptococcus,* or *Ustilago.*

In some embodiments, the procedures and methods described here can be accomplished using a host cell that is a fungi belonging to one of the following species: *Saccharomyces cerevisiae, Saccharomyces boulardi, Saccharomyces uvarum; Aspergillus flavus, A. terreus, A. awamori; Cladosporium elatum, Cl. Herbarum, Cl. Sphaerospermum,* and *Cl. Cladosporioides; Magnaporthe grise, Magnaporthe oryzae, Magnaporthe rhizophila; Morchella deliciosa, Morchella esculenta, Morchella conica; Neurospora crassa, Neurospora intermedia, Neurospora tetrasperma; Penicillium notatum, Penicillium chrysogenum, Penicillium roquefortii,* or *Penicillium simplicissimum.*

In some embodiments, the procedures and methods described here can be accomplished using a host cell that is a *Kluyveromyces lactis, Kluyveromyces marxianus, Saccharomyces cerevisiae,* or *Pichia pastoris.*

In some embodiments, the host cell used to produce a TVP or a TVP-insecticidal protein may be a fungi belonging to one of the following genera: *Aspergillus, Cladosporium, Magnaporthe, Morchella, Neurospora, Penicillium, Saccharomyces, Cryptococcus,* or *Ustilago.*

In some embodiments, the host cell used to produce a TVP or a TVP-insecticidal protein may be a member of the Saccharomycetaceae family. For example, in some embodiments, the host cell may be one of the following genera within the Saccharomycetaceae family: *Brettanomyces, Candida, Citeromyces, Cyniclomyces, Debaryomyces, Issatchenkia, Kazachstania, Kluyveromyces, Komagataella, Kuraishia, Lachancea, Lodderomyces, Nakaseomyces, Pachysolen, Pichia, Saccharomyces, Spathaspora, Tetrapisispora, Vanderwaltozyma, Torulaspora, Williopsis, Zygosaccharomyces,* or *Zygotorulaspora.*

In some embodiments, the host cell used to produce a TVP or a TVP-insecticidal protein may be one of the following: *Aspergillus flavus, Aspergillus terreus, Aspergillus awamori, Cladosporium elatum, Cladosporium Herbarum, Cladosporium Sphaerospermum, Cladosporium cladosporioides, Magnaporthe grisea, Magnaporthe oryzae, Magnaporthe rhizophila, Morchella deliciosa, Morchella esculenta, Morchella conica, Neurospora crassa, Neurospora intermedia, Neurospora tetrasperma, Penicillium notatum, Penicillium chrysogenum, Penicillium roquefortii,* or *Penicillium simplicissimum.*

In some embodiments, the host cell used to produce a TVP or a TVP-insecticidal protein may be a species within the *Candida* genus. For example, the host cell may be one of the following: *Candida albicans, Candida ascalaphidarum, Candida amphixiae, Candida antarctica, Candida argentea, Candida atlantica, Candida atmosphaerica, Candida auris, Candida blankii, Candida blattae, Candida bracarensis, Candida bromeliacearum, Candida carpophila, Candida carvajalis, Candida cerambycidarum, Candida chauliodes, Candida corydalis, Candida dosseyi, Candida dubliniensis, Candida ergatensis, Candida fructus, Candida glabrata, Candida fermentati, Candida guilliermondii, Candida haemulonii, Candida humilis, Candida insectamens, Candida insectorum, Candida intermedia, Candida jeffresii,* or *Candida kefyr.*

In some embodiments, the host cell used to produce a TVP or a TVP-insecticidal protein may be a species within the *Kluyveromyces* genus. For example, the host cell may be one of the following: *Kluyveromyces aestuarii, Kluyveromyces dobzhanskii, Kluyveromyces lactis, Kluyveromyces marxianus, Kluyveromyces nonfermentans,* or *Kluyveromyces wickerhamii.*

In some embodiments, the host cell used to produce a TVP or a TVP-insecticidal protein may be a species within the *Pichia* genus. For example, the host cell may be one of the following: *Pichia farinose, Pichia anomala, Pichia heedii, Pichia guilliermondii, Pichia kluyveri, Pichia membranifaciens, Pichia norvegensis, Pichia ohmeri, Pichia pastoris, Pichia methanolica,* or *Pichia subpelliculosa.*

In some embodiments, the host cell used to produce a TVP or a TVP-insecticidal protein may be a species within the *Saccharomyces* genus. For example, the host cell may be one of the following: *Saccharomyces arboricolus, Saccharomyces bayanus, Saccharomyces bulderi, Saccharomyces cariocanus, Saccharomyces cariocus, Saccharomyces cerevisiae, Saccharomyces cerevisiae* var *boulardii, Saccharomyces chevalieri, Saccharomyces dairenensis, Saccharomyces ellipsoideus, Saccharomyces eubayanus, Saccharomyces*

*exiguous, Saccharomyces florentinus, Saccharomyces fragilis, Saccharomyces kudriavzevii, Saccharomyces martiniae, Saccharomyces mikatae, Saccharomyces monacensis, Saccharomyces norbensis, Saccharomyces paradoxus, Saccharomyces pastorianus, Saccharomyces spencerorum, Saccharomyces turicensis, Saccharomyces unisporus, Saccharomyces uvarum,* or *Saccharomyces zonatus.*

In some embodiments, the host cell used to produce a TVP or a TVP-insecticidal protein may be one of the following: *Saccharomyces cerevisiae, Pichia pastoris, Pichia methanolica, Schizosaccharomyces pombe,* or *Hansenula anomala.*

The use of yeast cells as a host organism to generate recombinant TVP is an exceptional method, well known to those having ordinary skill in the art. In some embodiments, the methods and compositions described herein can be performed with any species of yeast, including but not limited to any species of the genus *Saccharomyces, Pichia, Kluyveromyces, Hansenula, Yarrowia* or *Schizosaccharomyces* and the species *Saccharomyces* includes any species of *Saccharomyces,* for example *Saccharomyces cerevisiae* species selected from following strains: INVSc1, YNN27, S150-2B, W303-1B, CG25, W3124, JRY188, BJ5464, AH22, GRF18, W303-1A and BJ3505. In some embodiments, members of the *Pichia* species including any species of *Pichia,* for example the *Pichia* species, *Pichia pastoris,* for example, the *Pichia pastoris* is selected from following strains: Bg08, Y-11430, X-33, GS115, GS190, JC220, JC254, GS200, JC227, JC300, JC301, JC302, JC303, JC304, JC305, JC306, JC307, JC308, YJN165, KM71, MC100-3, SMD1163, SMD1165, SMD1168, GS241, MS105, any pep4 knock-out strain and any prb1 knock-out strain, as well as *Pichia pastoris* selected from following strains: Bg08, X-33, SMD1168 and KM71. In some embodiments, any *Kluyveromyces* species can be used to accomplish the methods described here, including any species of *Kluyveromyces,* for example, *Kluyveromyces lactis,* and we teach that the stain of *Kluyveromyces lactis* can be but is not required to be selected from following strains: GG799, YCT306, YCT284, YCT389, YCT390, YCT569, YCT598, NRRL Y-1140, MW98-8C, MS1, CBS293.91, Y721, MD2/1, PM6-7A, WM37, K6, K7, 22AR1, 22A295-1, SD11, MG1/2, MSK110, JA6, CMK5, HP101, HP108 and PM6-3C, in addition to *Kluyveromyces lactis* species is selected from GG799, YCT306 and NRRL Y-1140.

In some embodiments, the host cell used to produce a TVP or a TVP-insecticidal protein can be an *Aspergillus oryzae.*

In some embodiments, the host cell used to produce a TVP or a TVP-insecticidal protein can be an *Aspergillus japonicas.*

In some embodiments, the host cell used to produce a TVP or a TVP-insecticidal protein can be an *Aspergillus niger.*

In some embodiments, the host cell used to produce a TVP or a TVP-insecticidal protein can be a *Bacillus licheniformis.*

In some embodiments, the host cell used to produce a TVP or a TVP-insecticidal protein can be a *Bacillus subtilis.*

In some embodiments, the host cell used to produce a TVP or a TVP-insecticidal protein can be a *Trichoderma reesei.*

In some embodiments, the procedures and methods described here can be accomplished using a host cell that is a yeast, including but not limited to any species of *Hansenula* species including any species of *Hansenula* and preferably *Hansenula polymorpha.* In some embodiments, the procedures and methods described here can be accomplished with any species of yeast, including but not limited to any species of *Yarrowia* species for example, *Yarrowia lipolytica.* In some embodiments, the procedures and methods described here can be accomplished with any species of yeast, including but not limited to any species of *Schizosaccharomyces* species including any species of *Schizosaccharomyces* and preferably *Schizosaccharomyces pombe.*

In some embodiments, yeast species such as *Kluyveromyces lactis, Saccharomyces cerevisiae, Pichia pastoris,* and others, can be used as a host organism. Yeast cell culture techniques are well known to those having ordinary skill in the art. Exemplary methods of yeast cell culture can be found in Evans, Yeast Protocols. Springer (1996); Bill, Recombinant Protein Production in Yeast. Springer (2012); Hagan et al., Fission Yeast: A Laboratory Manual, CSH Press (2016); Konishi et al., Improvement of the transformation efficiency of *Saccharomyces cerevisiae* by altering carbon sources in pre-culture. Biosci Biotechnol Biochem. 2014; 78(6):1090-3; Dymond, *Saccharomyces cerevisiae* growth media. Methods Enzymol. 2013; 533:191-204; Looke et al., Extraction of genomic DNA from yeasts for PCR-based applications. Biotechniques. 2011 May; 50(5): 325-8; and Romanos et al., Culture of yeast for the production of heterologous proteins. Curr Protoc Cell Biol. 2014 Sep. 2; 64:20.9.1-16, the disclosure of which is incorporated herein by reference in its entirety.

Recipes for yeast cell fermentation media and stocks are described as follows: (1) MSM media recipe: 2 g/L sodium citrate dihydrate; 1 g/L calcium sulfate dihydrate (0.79 g/L anhydrous calcium sulfate); 42.9 g/L potassium phosphate monobasic; 5.17 g/L ammonium sulfate; 14.33 g/L potassium sulfate; 11.7 g/L magnesium sulfate heptahydrate; 2 mL/L PTM1 trace salt solution; 0.4 ppm biotin (from 500×, 200 ppm stock); 1-2% pure glycerol or other carbon source. (2) PTM1 trace salts solution: Cupric sulfate-5H2O 6.0 g; Sodium iodide 0.08 g; Manganese sulfate-H2O 3.0 g; Sodium molybdate-$2H_2O$ 0.2 g; Boric Acid 0.02 g; Cobalt chloride 0.5 g; Zinc chloride 20.0 g; Ferrous sulfate-$7H_2O$ 65.0 g; Biotin 0.2 g; Sulfuric Acid 5.0 ml; add Water to a final volume of 1 liter. An illustrative composition for *K. lactis* defined medium (DMSor) is as follows: 11.83 g/L $KH_2PO_4$, 2.299 g/L $K_2HPO_4$, 20 g/L of a fermentable sugar, e.g., galactose, maltose, latotriose, sucrose, fructose or glucose and/or a sugar alcohol, for example, erythritol, hydrogenated starch hydrolysates, isomalt, lactitol, maltitol, mannitol, and xylitol, 1 g/L $MgSO_4 \cdot 7H_2O$, 10 g/L $(NH_4)SO_4$, 0.33 g/L $CaCl_2 \cdot 2H_2O$, 1 g/L NaCl, 1 g/L KCl, 5 mg/L $CuSO_4 \cdot 5H_2O$, 30 mg/L $MnSO_4 \cdot H_2O$, 10 mg/L, $ZnCl_2$, 1 mg/L KI, 2 mg/L $CoCl_2 \cdot 6H_2O$, 8 mg/L $Na_2MoO_4 \cdot 2H_2O$, 0.4 mg/L $H_3BO_3$, 15 mg/L $FeCl_3 \cdot 6H_2O$, 0.8 mg/L biotin, 20 mg/L Ca-pantothenate, 15 mg/L thiamine, 16 mg/L myo-inositol, 10 mg/L nicotinic acid, and 4 mg/L pyridoxine.

Yeast cells can be cultured in 48-well Deep-well plates, sealed after inoculation with sterile, air-permeable cover. Colonies of yeast, for example, *K. lactis* cultured on plates can be picked and inoculated the deep-well plates with 2.2 mL media per well, composed of DMSor. Inoculated deep-well plates can be grown for 6 days at 23.5° C. with 280 rpm shaking in a refrigerated incubator-shaker. On day 6 post-inoculation, conditioned media should be harvested by centrifugation at 4000 rpm for 10 minutes, followed by filtration using filter plate with 0.22 µM membrane, with filtered media are subject to HPLC analyses.

Illustrative Yeast Strains

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO: 1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or complementary nucleotide sequence thereof.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO: 1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or complementary nucleotide sequence thereof; wherein the TVP has one amino acid substitution at $X_1$, $X_2$, $X_3$, $X_4$, or $X_5$.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO: 1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or complementary nucleotide sequence thereof; wherein the TVP has one amino acid substitution at $X_1$, $X_2$, $X_3$, $X_4$, or $X_5$; and wherein $X_7$ is Glycine.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO: 1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or complementary nucleotide sequence thereof; wherein the TVP has one amino acid substitution at $X_1$, $X_2$, $X_3$, $X_4$, or $X_5$; and wherein $X_7$ is absent.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO: 1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or complementary nucleotide sequence thereof; wherein the TVP has one amino acid substitution at $X_1$, $X_2$, $X_3$, $X_4$, or $X_5$; and wherein $X_6$ and $X_7$ are absent.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO: 1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or complementary nucleotide sequence thereof; wherein the TVP comprises an amino sequence as set forth in any one of SEQ ID NOs: 2-15, 49-53, or 77-110.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO: 1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or complementary nucleotide sequence thereof; wherein the TVP is encoded by a polynucleotide sequence as set forth in any one of SEQ ID NOs: 17-30, 54-58, or 117-150, or a complementary nucleotide sequence thereof.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO: 1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or complementary nucleotide sequence thereof; wherein the yeast strain is selected from any species of the genera *Saccharomyces, Pichia, Kluyveromyces, Hansenula, Yarrowia* or *Schizosaccharomyces*

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO: 1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or complementary nucleotide sequence thereof; wherein the yeast strain the yeast cell is selected from the group consisting of *Kluyveromyces lactis, Kluyveromyces marxianus, Saccharomyces cerevisiae*, and *Pichia pastoris*.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO: 1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or complementary nucleotide sequence thereof; wherein the yeast strain is *Kluyveromyces lactis* or *Kluyveromyces marxianus*.

Form (II)

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or complementary nucleotide sequence thereof.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or complementary nucleotide sequence thereof; wherein if $Z_1$ is T then the TVP is glycosylated.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or complementary nucleotide sequence thereof; wherein $X_1$ is Q; and $Z_1$ is A.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or complementary nucleotide sequence thereof; wherein the TVP comprises an amino sequence as set forth in any one of SEQ ID NOs: 2, 49, or 51.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or complementary nucleotide sequence thereof; wherein the TVP is encoded by a polynucleotide sequence as set forth in any one of SEQ ID NOs: 17, 54, or 56, or a complementary nucleotide sequence thereof.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or complementary nucleotide sequence thereof; wherein the yeast strain is selected from any species of the genera *Saccharomyces, Pichia, Kluyveromyces, Hansenula, Yarrowia* or *Schizosaccharomyces*

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or complementary nucleotide sequence thereof; wherein the yeast strain the yeast cell is selected from the group consisting of *Kluyveromyces lactis, Kluyveromyces marxianus, Saccharomyces cerevisiae*, and *Pichia pastoris*.

In some embodiments, a yeast strain of the present invention can comprise: a first expression cassette comprising a polynucleotide operable to encode a TVP, said TVP comprising an amino acid sequence that is at least 90% identical to the amino acid sequence according to Formula (II): E-P-D-E-I-C-R-A-X₁-M-T-N-K-E-F-T-Y-K-S-N-V-C-N-N-C-G-D-Q-V-A-A-C-E-A-E-C-F-R-N-D-V-Y-Z₁-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or complementary nucleotide sequence thereof; wherein the yeast strain is *Kluyveromyces lactis* or *Kluyveromyces marxianus*.

Yeast Transformation, TVP Purification, and Analysis

An exemplary method of yeast transformation is as follows: the expression vectors carrying a TVP expression ORF are transformed into yeast cells. First, the expression vectors are usually linearized by specific restriction enzyme cleavage to facilitate chromosomal integration via homologous recombination. The linear expression vector is then transformed into yeast cells by a chemical or electroporation method of transformation and integrated into the targeted locus of the yeast genome by homologous recombination. The integration can happen at the same chromosomal locus multiple times; therefore, the genome of a transformed yeast cell can contain multiple copies of TVP expression cassettes. The successfully transformed yeast cells can be identified using growth conditions that favor a selective marker engineered into the expression vector and co-integrated into yeast chromosomes with the TVP expression ORF; examples of such markers include, but are not limited to, acetamide prototrophy, zeocin resistance, geneticin resistance, nourseothricin resistance, and uracil prototrophy.

Due to the influence of unpredictable and variable factors-such as epigenetic modification of genes and networks of genes, and variation in the number of integration events that occur in individual cells in a population undergoing a transformation procedure-individual yeast colonies of a given transformation process will differ in their capacities to produce a TVP expression ORF. Therefore, transgenic yeast colonies carrying the TVP transgenes should be screened for high yield strains. Two effective methods for such screening—each dependent on growth of small-scale cultures of the transgenic yeast to provide conditioned media samples for subsequent analysis—use reverse-phase HPLC or housefly injection procedures to analyze conditioned media samples from the positive transgenic yeast colonies.

The transgenic yeast cultures can be performed using 14 mL round bottom polypropylene culture tubes with 5 to 10 mL defined medium added to each tube, or in 48-well deep well culture plates with 2.2 mL defined medium added to each well. The defined medium, not containing crude proteinaceous extracts or by-products such as yeast extract or peptone, is used for the cultures to reduce the protein background in the conditioned media harvested for the later screening steps. The cultures are performed at the optimal temperature, for example, 23.5° C. for *K. lactis*, for about 5-6 days, until the maximum cell density is reached. TVPs will now be produced by the transformed yeast cells and secreted out of cells to the growth medium. To prepare samples for the screening, cells are removed from the cultures by centrifugation and the supernatants are collected as the conditioned media, which are then cleaned by filtration through 0.22 μm filter membrane and then made ready for strain screening.

In some embodiments, positive yeast colonies transformed with TVP can be screened via reverse-phase HPLC (rpHPLC) screening of putative yeast colonies. In this screening method, an HPLC analytic column with bonded phase of C18 can be used. Acetonitrile and water are used as mobile phase solvents, and a UV absorbance detector set at 220 nm is used for the peptide detection. Appropriate amounts of the conditioned medium samples are loaded into the rpHPLC system and eluted with a linear gradient of mobile phase solvents. The corresponding peak area of the insecticidal peptide in the HPLC chromatograph is used to quantify the TVP concentrations in the conditioned media. Known amounts of pure TVP are run through the same rpHPLC column with the same HPLC protocol to confirm the retention time of the peptide and to produce a standard peptide HPLC curve for the quantification.

An exemplary reverse-phase HPLC screening process of positive *K. lactis* cells is as follows: a TVP expression ORF can be inserted into the expression vector, pKLAC1, and transformed into the *K. lactis* strain, YCT306, from New England Biolabs, Ipswich, MA, USA. pKLAC1 vector is an integrative expression vector. Once the TVP transgenes were cloned into pKLAC1 and transformed into YCT306, their expression was controlled by the LAC4 promoter. The resulting transformed colonies produced pre-propeptides comprising an α-mating factor signal peptide, a Kex2 cleavage site and mature TVPs. The α-Mating factor signal peptide guides the pre-propeptides to enter the endogenous secretion pathway, and mature TVPs are released into the growth media.

In some embodiments, codon optimization for TVP expression can be performed in two rounds, for example, in the first round, based on some common features of high expression DNA sequences, multiple variants of the TVP expression ORF, expressing an α-Mating factor signal peptide, a Kex2 cleavage site and the TVP, are designed and their expression levels are evaluated in the YCT306 strain of *K. lactis*, resulting in an initial *K. lactis* expression algorithm; in a second round of optimization, additional variant TVP expression ORFs can be designed based on the initial *K. lactis* expression algorithm to further fine-tuned the *K. lactis* expression algorithm, and identify the best ORF for TVP expression in *K. lactis*. In some embodiments, the resulting DNA sequence from the foregoing optimization can have an open reading frame encoding an α-MF signal peptide, a Kex2 cleavage site and a TVP, which can be cloned into the pKLAC1 vector using Hind III and Not I restriction sites, resulting in TVP expression vectors.

In some embodiments, the yeast, *Pichia pastoris*, can be transformed with a TVP expression cassette. An exemplary method for transforming *P. pastoris* is as follows: the vectors, pJUGαKR and pJUZαKR, can be used to transform the TVP into *P. pastoris*. The pJUGαKR and pJUZαKR vectors are available from Biogrammatics, Carlsbad, California, USA. Both vectors are integrative vectors and use the uracil phosphoribosyltransferase promoter (pUPP) to enhance the heterologous transgene expression. The only difference between the vectors is that pJUGαKR provides G418 resistance to the host yeast, while pJUZαKR provides Zeocin resistance. Pairs of complementary oligonucleotides, encoding the TVP are designed and synthesized for sub-cloning into the two yeast expression vectors. Hybridization reactions are performed by mixing the corresponding complementary oligonucleotides to a final concentration of 20 µM in 30 mM NaCl, 10 mM Tris-Cl (all final concentrations), pH 8, and then incubating at 95° C. for 20 min, followed by a 9-hour incubation starting at 92° C. and ending at 17° C., with 3° C. drops in temperature every 20 min. The hybridization reactions will result in DNA fragments encoding TVP. The two *P. pastoris* vectors are digested with BsaI-HF restriction enzymes, and the double stranded DNA products of the reactions are then subcloned into the linearized *P. pastoris* vectors using standard procedures. Following verification of the sequences of the subclones, plasmid aliquots are transfected by electroporation into the *P. pastoris* strain, Bg08. The resulting transformed yeast, selected based on resistance to Zeocin or G418 conferred by elements engineered into vectors pJUZαKR and pJUGαKR, respectively, can be cultured and screened as described herein.

Yeast Peptide Yield Screening and Evaluation

Peptide yield can be determined by any of the methods known to those of skill in the art (e.g., capillary gel electrophoresis (CGE), Western blot analysis, and the like). Activity assays, as described herein and known in the art, can also provide information regarding peptide yield. In some embodiments, these or any other methods known in the art can be used to evaluate peptide yield.

Quantification Assays

In some embodiments, and without limitation, TVP peptide yield can be measured using: HPLC; Mass spectrometry (MS) and related techniques; LC/MS/MS; reverse phase protein arrays (RPPA); immunohistochemistry; ELISA; suspension bead array, mass spectrometry; dot blot; SDS-PAGE; capillary gel electrophoresis (CGE); Western blot analysis; Bradford assay; measuring UV absorption at 260 nm; Lowry assay; Smith copper/bicinchoninic assay; a secretion assay; Pierce protein assay; Biuret reaction; and the like. Exemplary methods of protein quantification are provided in Stoscheck, C. 1990 "Quantification of Protein" *Methods in Enzymology,* 182:50-68; Lowry, O. Rosebrough, A., Farr, A. and Randall, R. 1951 *J. Biol. Chem.* 193:265; Smith, P. et al., (1985) Anal. Biochem. 150:76-85; Bradford, M. 1976 "A Rapid and Sensitive Method for the Quantitation of Microgram Quantities of Protein Utilizing the Principle of Protein-Dye Binding" Anal. Biochem. 72:248-254; Cabib, E. and Polacheck, I. 1984 "Protein assay for dilute solutions." Methods in Enzymology, 104:318-328; Turcanu, Victor; Williams, Neil A. (2001). "Cell identification and isolation on the basis of cytokine secretion: A novel tool for investigating immune responses." Nature Medicine. 7 (3): 373-376; U.S. Pat. No. 6,391,649; the disclosures of which are incorporated herein by reference in their entireties.

In other embodiments, TVP peptide yield can be quantified and/or assessed using methods that include, without limitation: recombinant protein mass per volume of culture (e.g., gram or milligrams protein per liter culture); percent or fraction of recombinant protein insoluble precipitate obtained after cell lysis determined in (e.g., recombinant protein extracted supernatant in an amount/amount of protein in the insoluble components); percentage or fraction of active protein (e.g., an amount/analysis of the active protein for use in protein amount); total cell protein (tcp) percentage or fraction; and/or the amount of protein/cell and the dry biomass of a percentage or ratio.

In some embodiments, wherein yield is expressed in terms of culture volume, the culture cell density may be taken into account, particularly when yields between different cultures are being compared.

In some embodiments, the present invention provides a method of producing a heterologous polypeptide that is at least about 5%, at least about 10%, about 15%, about 20%, about 25%, about 30%, about 40%, about 45%, about 50%, about 55%, about 60%, about 65%, about 70%, about 75%, or greater of total cell protein (tcp). "Percent total cell protein" is the amount of heterologous polypeptide in the host cell as a percentage of aggregate cellular protein. The determination of the percent total cell protein is well known in the art.

"Total cell protein (tcp)" or "Percent total cell protein (% tcp)" is the amount of protein or polypeptide in the host cell as a percentage of aggregate cellular protein. Methods for the determination of the percent total cell protein are well known in the art.

In some embodiments, HPLC can be used to quantify peptide yield. For example, in some embodiments, peptide yield can be quantified using an Agilent 1100 HPLC system equipped with an Onyx monolithic 4.5×100 mm, C18 reverse-phase analytical HPLC column and an auto-injector. An illustrative use of the Agilent 1100 HPLC system equipped with an Onyx monolithic 4.5×100 mm, C18 reverse-phase analytical HPLC column and an auto-injector is as follows: filtered conditioned media samples from transformed *K. lactis* cells are analyzed using Agilent 1100 HPLC system equipped with an Onyx monolithic 4.5×100 mm, C18 reverse-phase analytical HPLC column and an auto-injector by analyzing HPLC grade water and acetonitrile containing 0.1% trifluoroacetic acid, constituting the two mobile phase solvents used for the HPLC analyses; the peak areas of both the TVP or TVP-insecticidal protein are analyzed using HPLC chromatographs, and then used to calculate the peptide concentration in the conditioned media, which can be further normalized to the corresponding final cell densities (as determined by OD600 measurements) as normalized peptide yield.

Activity Assays

In some embodiments, positive yeast colonies transformed with TVP or TVP-insecticidal protein can be screened using a housefly injection assay. TVP or TVP-insecticidal protein can paralyze/kill houseflies when injected in measured doses through the body wall of the dorsal thorax. The efficacy of the TVP or TVP-insecticidal protein can be defined by the median paralysis/lethal dose of the peptide ($PD_{50}/LD_{50}$), which causes 50% knock-down ratio or mortality of the injected houseflies respectively. The pure TVP or TVP-insecticidal protein is normally used in the housefly injection assay to generate a standard dose-response curve, from which a $PD_{50}/LD_{50}$ value can be determined. Using a $PD_{50}/LD_{50}$ value from the analysis of a standard dose-response curve of the pure TVP or TVP-insecticidal protein, quantification of the TVP or TVP-insecticidal protein produced by the transformed yeast can be achieved using a housefly injection assay performed with serial dilutions of the corresponding conditioned media.

An exemplary housefly injection bioassay is as follows: conditioned media is serially diluted to generate full dose-response curves from the housefly injection bioassay. Before injection, adult houseflies (*Musca domestica*) are immobilized with $CO_2$, and 12-18 mg houseflies are selected for injection. A microapplicator, loaded with a 1 cc syringe and 30-gauge needle, is used to inject 0.5 µL per fly, doses of serially diluted conditioned media samples into houseflies through the body wall of the dorsal thorax. The injected houseflies are placed into closed containers with moist filter paper and breathing holes on the lids, and they are examined by knock-down ratio or by mortality scoring at 24 hours post-injection. Normalized yields are calculated. Peptide yield means the peptide concentration in the conditioned media in units of mg/L. However, peptide yields are not always sufficient to accurately compare the strain production rate. Individual strains may have different growth rates, hence when a culture is harvested, different cultures may vary in cell density. A culture with a high cell density may produce a higher concentration of the peptide in the media, even though the peptide production rate of the strain is lower than another strain which has a higher production rate. Accordingly, the term "normalized yield" is created by dividing the peptide yield with the cell density in the corresponding culture and this allows a better comparison of the peptide production rate between strains. The cell density is represented by the light absorbance at 600 nm with a unit of "A" (Absorbance unit).

Screening yeast colonies that have undergone a transformation with TVP can identify the high yield yeast strains from hundreds of potential colonies. These strains can be fermented in bioreactor to achieve at least up to 4 g/L or at least up to 3 g/L or at least up to 2 g/L yield of the TVP when using optimized fermentation media and fermentation conditions described herein. The higher rates of production (expressed in mg/L) can be anywhere from about 100 mg/L to about 100,000 mg/L; or from about 100 mg/L to about 90,000 mg/L; or from about 100 mg/L to about 80,000 mg/L; or from about 100 mg/L to about 70,000 mg/L; or from about 100 mg/L to about 60,000 mg/L; or from about 100 mg/L to about 50,000 mg/L; or from about 100 mg/L to about 40,000 mg/L; or from about 100 mg/L to about 30,000 mg/L; or from about 100 mg/L to about 20,000 mg/L; or from about 100 mg/L to about 17,500 mg/L; or from about 100 mg/L to about 15,000 mg/L; or from about 100 mg/L to about 12,500 mg/L; or from about 100 mg/L to about 10,000 mg/L; or from about 100 mg/L to about 9,000 mg/L; or from about 100 mg/L to about 8,000 mg/L; or from about 100 mg/L to about 7,000 mg/L; or from about 100 mg/L to about 6,000 mg/L; or from about 100 mg/L to about 5,000 mg/L; or from about 100 mg/L to about 3,000 mg/L; or from about 100 mg/L to 2,000 mg/L; or from about 100 mg/L to 1,500 mg/L; or from about 100 mg/L to 1,000 mg/L; or from about 100 mg/L to 750 mg/L; or from about 100 mg/L to 500 mg/L; or from about 150 mg/L to 100,000 mg/L; or from about 200 mg/L to 100,000 mg/L; or from about 300 mg/L to 100,000 mg/L; or from about 400 mg/L to 100,000 mg/L; or from about 500 mg/L to 100,000 mg/L; or from about 750 mg/L to 100,000 mg/L; or from about 1,000 mg/L to 100,000 mg/L; or from about 1,250 mg/L to 100,000 mg/L; or from about 1,500 mg/L to 100,000 mg/L; or from about 2,000 mg/L to 100,000 mg/L; or from about 2,500 mg/L to 100,000 mg/L; or from about 3,000 mg/L to 100,000 mg/L; or from about 3,500 mg/L to 100,000 mg/L; or from about 4,000 mg/L to 100,000 mg/L; or from about 4,500 mg/L to 100,000 mg/L; or from about 5,000 mg/L to 100,000 mg/L; or from about 6,000 mg/L to 100,000 mg/L; or from about 7,000 mg/L to 100,000 mg/L; or from about 8,000 mg/L to 100,000 mg/L; or from about 9,000 mg/L to 100,000 mg/L; or from about 10,000 mg/L to 100,000 mg/L; or from about 12,500 mg/L to 100,000 mg/L; or from about 15,000 mg/L to 100,000 mg/L; or from about 17,500 mg/L to 100,000 mg/L; or from about 20,000 mg/L to 100,000 mg/L; or from about 30,000 mg/L to 100,000 mg/L; or from about 40,000 mg/L to 100,000 mg/L; or from about 50,000 mg/L to 100,000 mg/L; or from about 60,000 mg/L to 100,000 mg/L; or from about 70,000 mg/L to 100,000 mg/L; or from about 80,000 mg/L to 100,000 mg/L; or from about 90,000 mg/L to 100,000 mg/L; or any range of any value provided or even greater yields than can be achieved with a peptide before conversion, using the same or similar production methods that were used to produce the peptide before conversion.

Culture and Fermentation Conditions

Cell culture techniques are well-known in the art. In some embodiments, the culture method and/or materials will necessarily require adaption based on the host cell selected; and, such adaptions (e.g., modifying pH, temperature, medium contents, and the like) are well known to those having ordinary skill in the art. In some embodiments, any known culture technique may be employed to produce a TVP or TVP-insecticidal protein of the present invention.

Exemplary culture methods are provided in U.S. Pat. Nos. 3,933,590; 3,946,780; 4,988,623; 5,153,131; 5,153,133; 5,155,034; 5,316,905; 5,330,908; 6,159,724; 7,419,801; 9,320,816; 9,714,408; and 10,563,169; the disclosures of which are incorporated herein by reference in their entireties.

Yeast Culture

Yeast cell culture techniques are well known to those having ordinary skill in the art. Exemplary methods of yeast cell culture can be found in Evans, Yeast Protocols. Springer (1996); Bill, Recombinant Protein Production in Yeast. Springer (2012); Hagan et al., Fission Yeast: A Laboratory Manual, CSH Press (2016); Konishi et al., Improvement of the transformation efficiency of *Saccharomyces cerevisiae* by altering carbon sources in pre-culture. Biosci Biotechnol Biochem. 2014; 78(6):1090-3; Dymond, *Saccharomyces cerevisiae* growth media. Methods Enzymol. 2013; 533:191-204; Looke et al., Extraction of genomic DNA from yeasts for PCR-based applications. Biotechniques. 2011 May; 50(5):325-8; and Romanos et al., Culture of yeast for the production of heterologous proteins. Curr Protoc Cell Biol. 2014 Sep. 2; 64:20.9.1-16, the disclosure of which is incorporated herein by reference in its entirety.

Yeast can be cultured in a variety of media, e.g., in some embodiments, yeast can be cultured in minimal medium; YPD medium; yeast synthetic drop-out medium; Yeast Nitrogen Base (YNB with or without amino acids); YEPD medium; ADE D medium; ADE DS" medium; LEU D medium; HIS D medium; or Mineral salts medium.

In some embodiments, yeast can be cultured in minimal medium. In some embodiments, minimal medium ingredients can comprise: 2% Sugar; Phosphate Buffer, pH 6.0; Magnesium Sulfate; Calcium Chloride; Ammonium Sulfate; Sodium Chloride; Potassium Chloride; Copper Sulfate; Manganese Sulfate; Zinc Chloride; Potassium Iodide; Cobalt Chloride; Sodium Molybdate; Boric Acid; Iron Chloride; Biotin; Calcium pantothenate; Thiamine; Myo-inositol; Nicotinic Acid; and Pyridoxine.

In some embodiments, yeast can be cultured in YPD medium. YPD medium comprises a bacteriological peptone, yeast extract, and glucose.

In some embodiments, yeast can be cultured in yeast synthetic drop-out medium, which can be used to differentiate auxotrophic mutant strains that cannot grow without a specific medium component transformed with a plasmid that allows said transformant to grow on a medium lacking the required component.

In some embodiments, yeast can be cultured using Yeast Nitrogen Base (YNB with or without amino acids), which comprises nitrogen, vitamins, trace elements, and salts.

In some embodiments, the medium can be YEPD medium, e.g., a medium comprising 2% D-glucose, 2% BACTO Peptone (Difco Laboratories, Detroit, MI), 1% BACTO yeast extract (Difco), 0.004% adenine, and 0.006% L-leucine; or, a variation thereof, wherein the carbon source is a sugar alcohol, e.g., glycerol or sorbitol In some embodiments, the medium can be ADE D medium, e.g., a medium comprising 0.056%-Ade-Trp-Thr powder, 0.67% yeast nitrogen base without amino acids, 2% D-glucose, and 0.5% 200× tryptophan, threonine solution; or, a variation thereof, wherein the carbon source is a sugar alcohol, e.g., glycerol or sorbitol In some embodiments, the medium can be ADE DS" medium, e.g., a medium comprising 0.056%-Ade-Trp-Thr powder, 0.67% yeast nitrogen base without amino acids, 2% D-glucose, 0.5% 200× tryptophan, threonine solution, and 18.22% D-sorbitol; or, a variation thereof, wherein the carbon source is entirely a sugar alcohol, e.g., glycerol or sorbitol In some embodiments, the medium can be LEU D medium e.g., a medium comprising 0.052%-Leu-Trp-Thr powder, 0.67% yeast nitrogen base without amino acids, 2% D-glucose, and 0.5% 200× tryptophan, threonine solution; or, a variation thereof, wherein the carbon source is a sugar alcohol, e.g., glycerol or sorbitol.

In some embodiments, the medium can be HIS D medium, e.g., a medium comprising 0.052%-His-Trp-Thr powder, 0.67% yeast nitrogen base without amino acids, 2% D-glucose, and 0.5% 200× tryptophan, threonine solution; or, a variation thereof, wherein the carbon source is a sugar alcohol, e.g., glycerol or sorbitol.

In some embodiments, a mineral salts medium can be used. Mineral salts media consists of mineral salts and a carbon source such as, e.g., glucose, sucrose, or glycerol. Examples of mineral salts media include, e.g., M9 medium, *Pseudomonas* medium (ATCC 179), and Davis and Mingioli medium. See, Davis & Mingioli (1950) J. Bact. 60:17-28. The mineral salts used to make mineral salts media include those selected from among, e.g., potassium phosphates, ammonium sulfate or chloride, magnesium sulfate or chloride, and trace minerals such as calcium chloride, borate, and sulfates of iron, copper, manganese, and zinc. Typically, no organic nitrogen source, such as peptone, tryptone, amino acids, or a yeast extract, is included in a mineral salts medium. Instead, an inorganic nitrogen source is used and this may be selected from among, e.g., ammonium salts, aqueous ammonia, and gaseous ammonia. A mineral salts medium will typically contain glucose or glycerol as the carbon source.

In comparison to mineral salts media, minimal media can also contain mineral salts and a carbon source, but can be supplemented with, e.g., low levels of amino acids, vitamins, peptones, or other ingredients, though these are added at very minimal levels. Media can be prepared using the methods described in the art, e.g., in U.S. Pat. App. Pub. No. 2006/0040352, the disclosure of which is incorporated herein by reference in its entirety. Details of cultivation procedures and mineral salts media useful in the methods of the present invention are described by Riesenberg, D et al., 1991, "High cell density cultivation of *Escherichia coli* at controlled specific growth rate," J. Biotechnol. 20 (1):17-27.

In some embodiments, *Kluyveromyces lactis* are grown in minimal media supplemented with 2% glucose, galactose, sorbitol, or glycerol as the sole carbon source. Cultures are incubated at 30° C. until mid-log phase (24-48 hours) for β-galactosidase measurements, or for 6 days at 23.5° C. for heterologous protein expression.

In some embodiments, yeast cells can be cultured in 48-well Deep-well plates, sealed after inoculation with sterile, air-permeable cover. Colonies of yeast, for example, *K. lactis* cultured on plates can be picked and inoculated the deep-well plates with 2.2 mL media per well, composed of DMSor. Inoculated deep-well plates can be grown for 6 days at 23.5° C. with 280 rpm shaking in a refrigerated incubator-shaker. On day 6 post-inoculation, conditioned media should be harvested by centrifugation at 4000 rpm for 10 minutes, followed by filtration using filter plate with 0.22 μM membrane, with filtered media are subject to HPLC analyses.

In some embodiments, yeast species such as *Kluyveromyces lactis, Saccharomyces cerevisiae, Pichia pastoris*, and others, can be used as a host organism, and/or the yeast to be modified using the methods described herein.

Temperature and pH conditions will vary depending on the stage of culture and the host cell species selected. Variables such as temperature and pH in cell culture are readily known to those having ordinary skill in the art.

The pH level is important in the culturing of yeast. One of skill in the art will appreciate that the culturing process includes not only the start of the yeast culture but the maintenance of the culture as well. The yeast culture may be started at any pH level, however, since the media of a yeast culture tends to become more acidic (i.e., lowering the pH) over time, care must be taken to monitor the pH level during the culturing process.

In some embodiments of the invention, the yeast is grown in a medium at a pH level that is dictated based on the species of yeast used, the stage of culture, and/or the temperature. Thus, in some embodiments, the pH level can fall within a range from about 2 to about 10. Those having ordinary skill in the art will recognize that the optimum pH for most microorganisms is near the neutral point (pH 7.0). However, in some embodiments, some fungal species prefer an acidic environment: accordingly, in some embodiments, the pH can range from 2 to 6.5. In some embodiments, the pH can range from about 4 to about 4.5. Some fungal species (e.g., molds) can grow can grow in a pH of from about 2 to about 8.5, but favor an acid pH. See Mountney & Gould, Practical food microbiology and technology. 1988. Ed. 3; and Pena et al., Effects of high medium pH on growth, metabolism and transport in *Saccharomyces cerevisiae*. FEMS Yeast Res. 2015 March; 15(2):fou005.

In other embodiments, the pH is about 5.7 to 5.9, 5.8 to 6.0, 5.9 to 6.1, 6.0 to 6.2, 6.1 to 6.3, 6.2 to 6.5, 6.4 to 6.7, 6.5 to 6.8, 6.6 to 6.9, 6.7 to 7.0, 6.8 to 7.1, 6.9 to 7.2, 7.0 to 7.3, 7.1 to 7.4, 7.2 to 7.5, 7.3 to 7.6, 7.4 to 7.7, 7.5 to 7.8, 7.6 to 7.9, 7.7 to 8.0, 7.8 to 8.1, 7.9 to 8.2, 8.0 to 8.3, 8.1 to 8.4, 8.2 to 8.5, 8.3 to 8.6, 8.4 to 8.7, or 8.5 to 8.8.

In some embodiments, the pH of the medium can be at least 5.5. In other aspects, the medium can have a pH level of about 5.5. In other aspects, the medium can have a pH level of between 4 and 8. In some cases, the culture is maintained at a pH level of between 5.5 and 8. In other aspects, the medium has a pH level of between 6 and 8. In some cases, medium has a pH level that is maintained at a pH level of between 6 and 8. In some embodiments, the yeast is grown and/or maintained at a pH level of between 6.1 and 8.1. In some embodiments, the yeast is grown and/or maintained at a pH level of between 6.2 and 8.2. In some embodiments, the yeast is grown and/or maintained at a pH level of between 6.3 and 8.3. In some embodiments, the yeast is grown and/or maintained at a pH level of between 6.4 and 8.4. In some embodiments, the yeast is grown and/or maintained at a pH level of between 5.5 and 8.5. In some embodiments, the yeast is grown and/or maintained at a pH level of between 6.5 and 8.5. In some embodiments, the yeast is grown at a pH level of about 5.6, 5.7, 5.8 or 5.9. In some embodiments, the yeast is grown at a pH level of about 6. In some embodiments, the yeast is grown at a pH level of about 6.5. In some embodiments, the yeast is grown at a pH level of about 6, 6.1, 6.2, 6.3, 6.4, 6.5, 6.6, 6.7, 6.8, 6.9 or 7.0. In some embodiments, the yeast is grown at a pH level of about 7, 7.1, 7.2, 7.3, 7.4, 7.5, 7.6, 7.7, 7.8, 7.9, or 8.0. In some embodiments, the yeast is grown at a level of above 8.

In some embodiments, the pH of the medium can range from a pH of 2 to 8.5. In certain embodiments, the pH is about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, or 8.8.

Exemplary methods of yeast culture can be found in U.S. Pat. No. 5,436,136, entitled "Repressible yeast promoters" (filed Dec. 20, 1991; assignee Ciba-Geigy Corporation); U.S. Pat. No. 6,645,739, entitled "Yeast expression systems, methods of producing polypeptides in yeast, and compositions relating to same" (filed Jul. 26, 2001; assignee Phoenix Pharmacologies, Inc., Lexington, KY); and U.S. Pat. No. 10,023,836, entitled "Medium for yeasts" (filed Aug. 23, 2013; assignee Yamaguchi University); the disclosures of which are incorporated herein by reference in their entirety.

Fermentation

The present invention contemplates the culture of host organisms in any fermentation format. For example, batch, fed-batch, semi-continuous, and continuous fermentation modes may be employed herein.

Fermentation may be performed at any scale. The methods and techniques contemplated according to the present invention are useful for recombinant protein expression at any scale. Thus, in some embodiments, e.g., microliter-scale, milliliter scale, centiliter scale, and deciliter scale fermentation volumes may be used, and 1 Liter scale and larger fermentation volumes can be used.

In some embodiments, the fermentation volume is at or above about 1 Liter. For example, in some embodiments, the fermentation volume is about 1 liter to about 100 liters. In some embodiments, the fermentation volume is about 1 liter, about 2 liters, about 3 liters, about 4 liters, about 5 liters, about 6 liters, about 7 liters, about 8 liters, about 9 liters, or about 10 liters. In some embodiments, the fermentation volume is about 1 liter to about 5 liters, about 1 liter to about 10 liters, about 1 liter to about 25 liters, about 1 liter to about 50 liters, about 1 liter to about 75 liters, about 10 liters to about 25 liters, about 25 liters to about 50 liters, or about 50 liters to about 100 liters In other embodiments, the fermentation volume is at or above 5 Liters, 10 Liters, 15 Liters, 20 Liters, 25 Liters, 50 Liters, 75 Liters, 100 Liters, 200 Liters, 500 Liters, 1,000 Liters, 2,000 Liters, 5,000 Liters, 10,000 Liters, or 50,000 Liters.

In some embodiments, the fermentation medium can be a nutrient solution used for growing and or maintaining cells. Without limitation, this solution ordinarily provides at least one component from one or more of the following categories: (1) an energy source, usually in the form of a carbon source, e.g., glucose; (2) all essential amino acids, and usually the basic set of twenty amino acids; (3) vitamins and/or other organic compounds required at low concentrations; (4) free fatty acids or lipids, for example linoleic acid; and (5) trace elements, where trace elements are defined as inorganic compounds or naturally occurring elements that are typically required at very low concentrations, usually in the micromolar range.

In some embodiments, the fermentation medium can be the same as the cell culture medium or any other media described herein. In some embodiments, the fermentation medium can be different from the cell culture medium. In some embodiments, the fermentation medium can be modified in order to accommodate the large-scale production of proteins.

In some embodiments, the fermentation medium can be supplemented electively with one or more components from any of the following categories: (1) hormones and other growth factors such as, serum, insulin, transferrin, and the like; (2) salts, for example, magnesium, calcium, and phosphate; (3) buffers, such as HEPES; (4) nucleosides and bases such as, adenosine, thymidine, etc.; (5) protein and tissue hydrolysates, for example peptone or peptone mixtures which can be obtained from purified gelatin, plant material, or animal byproducts; (6) antibiotics, such as gentamycin; and (7) cell protective agents, for example pluronic polyol.

In some embodiments, the pH of the fermentation medium can be maintained using pH buffers and methods known to those of skill in the art. Control of pH during fermentation can also can be achieved using aqueous ammonia. In some embodiments, the pH of the fermentation medium will be selected based on the preferred pH of the organism used. Thus, in some embodiments, and depending on the host cell and temperature, the pH can range from about to 1 to about 10.

In some embodiments, the pH of the fermentation medium can range from a pH of 2 to 8.5. In certain embodiments, the pH is about 4.0, 4.1, 4.2, 4.3, 4.4, 4.5, 4.6, 4.7, 4.8, 4.9, 5.0, 5.1, 5.2, 5.3, 5.4, 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, or 8.8.

In other embodiments, the pH is about 5.7 to 5.9, 5.8 to 6.0, 5.9 to 6.1, 6.0 to 6.2, 6.1 to 6.3, 6.2 to 6.5, 6.4 to 6.7, 6.5 to 6.8, 6.6 to 6.9, 6.7 to 7.0, 6.8 to 7.1, 6.9 to 7.2, 7.0 to 7.3, 7.1 to 7.4, 7.2 to 7.5, 7.3 to 7.6, 7.4 to 7.7, 7.5 to 7.8, 7.6 to 7.9, 7.7 to 8.0, 7.8 to 8.1, 7.9 to 8.2, 8.0 to 8.3, 8.1 to 8.4, 8.2 to 8.5, 8.3 to 8.6, 8.4 to 8.7, or 8.5 to 8.8

In some embodiments, e.g., where *Escherichia coli* (*E. coli*) is used, the optimal pH range is between 6.5 and 7.5, depending on the temperature.

In other embodiments, e.g., where a yeast strain is used, the pH can range from about 4.0 to 8.0.

In some embodiments, neutral pH, i.e., a pH of about 7.0 can be used.

Those having ordinary skill in the art will recognize that during fermentation, the pH levels may drift as result of conversion and production of substrates and metabolic compounds.

In some embodiments, the fermentation medium can be supplemented with a buffer or other chemical in order to avoid changes to the pH. For example, in some embodiments, the addition of $Ca(OH)_2$, $CaCO_3$, NaOH, or $NH_4OH$ can be added to the fermentation medium to neutralize the production of acidic compounds that occur, e.g., in some yeast species during industrial processes.

Temperature is another important consideration in the fermentation process; and, like pH considerations, temperature will depend on the type of host cell selected.

In some embodiments, the fermentation temperature is maintained at about 4° C. to about 42° C. In certain embodiments, the fermentation temperature is about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., or about 42° C.

In other embodiments, the fermentation temperature is maintained at about 25° C. to about 27° C., about 25° C. to about 28° C., about 25° C. to about 29° C., about 25° C. to about 30° C., about 25° C. to about 31° C., about 25° C. to about 32° C., about 25° C. to about 33° C., about 26° C. to about 28° C., about 26° C. to about 29° C., about 26° C. to about 30° C., about 26° C. to about 31° C., about 26° C. to about 32° C., about 27° C. to about 29° C., about 27° C. to about 30° C., about 27° C. to about 31° C., about 27° C. to about 32° C., about 26° C. to about 33° C., about 28° C. to about 30° C., about 28° C. to about 31° C., about 28° C. to about 32° C., about 29° C. to about 31° C., about 29° C. to about 32° C., about 29° C. to about 33° C., about 30° C. to about 32° C., about 30° C. to about 33° C., about 31° C. to about 32° C., about 30° C. to about 33° C., about 31° C. to about 32° C., about 30° C. to about 33° C., or about 32° C. to about 33° C.

In other embodiments, the temperature is changed during fermentation, e.g., depending on the stage of fermentation.

Fermentation can be achieved with a variety of microorganisms known to those having ordinary skill in the art. Suitable microorganisms for up-scaled production of a TVP or TVP-insecticidal protein include any microorganism listed herein. In some embodiments, non-limiting examples of microorganisms include strains of the genus *Saccharomyces* spp. (including, but not limited to, *S. cerevisiae* (baker's yeast), *S. distaticus, S. uvarum*), the genus *Kluyveromyces*, (including, but not limited to, *K. marxianus, K. fragilis*), the genus *Candida* (including, but not limited to, *C. pseudotropicalis*, and *C. brassicae*), *Pichia stipitis* (a relative of *Candida shehatae*), the genus *Clavispora* (including, but not limited to, *C. lusitaniae* and *C. opuntiae*), the genus *Pachysolen* (including, but not limited to, *P. tannophilus*), the genus *Bretannomyces* (including, but not limited to, e.g., *B. clausenii*. Other suitable microorganisms include, for example, *Zymomonas mobilis, Clostridium* spp. (including, but not limited to, *C. thermocellum; C. saccharobutylacetonicum, C. saccharobutylicum, C. Puniceum, C. beijernckii*, and *C. acetobutylicum*), *Moniliella pollinis, Moniliella megachiliensis, Lactobacillus* spp. *Yarrowia lipolytica, Aureobasidium* sp., *Trichosporonoides* sp., *Trigonopsis variabilis, Trichosporon* sp., *Moniliellaacetoabutans* sp., *Typhula variabilis, Candida magnolias, Ustilaginomycetes* sp., *Pseudozyma tsukubaensis*, yeast species of genera *Zygosaccharomyces, Debaryomyces, Hansenula* and *Pichia*, and fungi of the dematioid genus *Torula*. See, e.g., Philippidis, G. P., 1996, Cellulose bioconversion technology, in Handbook on Bioethanol: Production and Utilization, Wyman, C. E., ed., Taylor & Francis, Washington, D.C., 179-212.

Fermentation medium may be selected depending on the host cell and/or needs of the end-user. Any necessary supplements besides, e.g., carbon, may also be included at appropriate concentrations introduced alone or as a mixture with another supplement or medium such as a complex nitrogen source.

Yeast Fermentation

Fermentation methods using yeast are well known to those having ordinary skill in the art. In some embodiments, batch fermentation can be used according to the methods provided herein; in other embodiments, continuous fermentation procedures can be used.

In some embodiments, the batch method of fermentation can be used to produce TVPs of the present invention. Briefly, the batch method of fermentation refers to a type of fermentation that is performed with a closed system, wherein the composition of the medium is determined at the beginning of the fermentation and is not subject to artificial alterations during the fermentation (i.e., the medium is inoculated with one or more yeast cells at the start of fermentation, and fermentation is allowed to proceed, uninterrupted by the user). Typically, in batch fermentation systems, the metabolite and biomass compositions of the system change constantly up to the time the fermentation is stopped. Within batch cultures, yeast cells pass through a static lag phase to a high growth log phase, and, finally, to a stationary phase, in which the growth rate is diminished or stopped. If untreated, yeast cells in the stationary phase will eventually die. In a batch method, yeast cells in log phase generally are responsible for the bulk of synthesis of end product.

In some embodiments, fed-batch fermentation can be used to produce TVPs of the present invention. Briefly, fed-batch fermentation is similar to typical batch method (described above), however, the substrate in the fed-batch method is added in increments as the fermentation progresses. Fed-batch fermentation is useful when catabolite repression may inhibit yeast cell metabolism, and when it is desirable to have limited amounts of substrate in the medium. Generally, the measurement of the substrate concentration in a fed-batch system is estimated on the basis of the changes of measurable factors reflecting metabolism, such as pH, dissolved oxygen, the partial pressure of waste gases (e.g., $CO_2$), and the like.

In some embodiments, the fed-batch fermentation procedure can be used to produce TVPs as follows: culturing a production organism (e.g., a modified yeast cell) in a 10 L bioreactor sparged with an $N_2/CO_2$ mixture, using 5 L broth containing 5 g/L potassium phosphate, 2.5 g/L ammonium chloride, 0.5 g/L magnesium sulfate, and 30 g/L corn steep liquor, and an initial first and second carbon source concentration of 20 g/L. As the modified yeast cells grow and utilize the carbon sources, additional 70% carbon source mixture is then fed into the bioreactor at a rate approximately balancing carbon source consumption. The temperature of the bioreactor is generally maintained at 30° C. Growth continues for approximately 24 hours or more, and the heterologous peptides reach a desired concentration, e.g., with the cell density being between about 5 and 10 g/L. Upon completion of the cultivation period, the fermenter contents can be passed through a cell separation unit such as a centrifuge to remove cells and cell debris, and the fermentation broth can be transferred to a product separations unit. Isolation of the heterologous peptides can take place by standard separations procedures well known in the art.

In some embodiments, continuous fermentation can be used to produce TVPs of the present invention. Briefly, continuous fermentation refers to fermentation with an open system, wherein a fermentation medium is added continuously to a bioreactor, and an approximately equal amount of conditioned medium is removed simultaneously for processing. Continuous fermentation generally maintains the cultures at a high density, in which yeast cells are primarily in log phase growth. Typically, continuous fermentation methods are performed to maintain steady state growth conditions, and yeast cell loss, due to medium withdrawal, should be balanced against the cell growth rate in the fermentation.

In some embodiments, the continuous fermentation method can be used to produce TVPs as follows: a modified yeast strain can be cultured using a bioreactor apparatus and a medium composition, albeit where the initial first and second carbon source is about, e.g., 30-50 g/L. When the carbon source is exhausted, feed medium of the same composition is supplied continuously at a rate of between about 0.5 L/hr and 1 L/hr, and liquid is withdrawn at the same rate. The heterologous peptide concentration in the bioreactor generally remains constant along with the cell density. Temperature is generally maintained at 30° C., and the pH is generally maintained at about 4.5 using concentrated NaOH and HCl, as required.

In some embodiments, when producing TVPs, the bioreactor can be operated continuously, for example, for about one month, with samples taken every day or as needed to assure consistency of the target chemical compound concentration. In continuous mode, fermenter contents are constantly removed as new feed medium is supplied. The exit stream, containing cells, medium, and heterologous peptides, can then be subjected to a continuous product separations procedure, with or without removing cells and cell debris, and can be performed by continuous separations methods well known in the art to separate organic products from peptides of interest.

In some embodiments, a yeast cell operable to express a TVP or TVP-insecticidal protein can be grown, e.g., using a fed batch process in aerobic bioreactor. Briefly, reactors are filled to about 20% to about 70% capacity with medium comprising a carbon source and other reagents. Temperature and pH is maintained using one or more chemicals as described herein. Oxygen level is maintained by sparging air intermittently in concert with agitation.

For example, in some embodiments, the present invention provides a method of using a fed batch process in aerobic bioreactor, wherein the reactor is filled to about 20%; 21%; 22%; 23%; 24%; 25%; 26%; 27%; 28%; 29%; 30%; 31%; 32%; 33%; 34%; 35%; 36%; 37%; 38%; 39%; 40%; 41%; 42%; 43%; 44%; 45%; 46%; 47%; 48%; 49%; 50%; 51%; 52%; 53%; 54%; 55%; 56%; 57%; 58%; 59%; 60%; 61%; 62%; 63%; 64%; 65%; 66%; 67%; 68%; 69%; or 70% capacity.

In some embodiments, the present invention provides a fed batch fermentation method using an aerobic bioreactor to produce TVPs, wherein the medium is a rich culture medium. For example, in some embodiments, the carbon source can be glucose, sorbitol, or lactose.

In some embodiments, the amount of glucose can be about 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; or 30 g/L of the medium.

In some embodiments, the amount of sorbitol can be about 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; or 30 g/L of the medium.

In some embodiments, the amount of lactose can be about 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; or 30 g/L of the medium.

In some embodiments, the present invention provides a fed batch fermentation method using an aerobic bioreactor, wherein the medium is supplemented with one or more of phosphoric acid, calcium sulfate, potassium sulfate, magnesium sulfate heptahydrate, potassium hydroxide, and/or corn steep liquor.

In some embodiments, the medium can be supplemented with phosphoric acid in an amount of about 2 g/L; 3 g/L; 4 g/L; 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; or 30 g/L to the medium.

In some embodiments, the medium can be supplemented with calcium sulfate in an amount of about 0.05 g/L; 0.15 g/L; 0.25 g/L; 0.35 g/L; 0.45 g/L; 0.55 g/L; 0.65 g/L; 0.75 g/L; 0.85 g/L; 0.95 g/L; 1.05 g/L; 1.15 g/L; 1.25 g/L; 1.35 g/L; 1.45 g/L; 1.55 g/L; 1.65 g/L; 1.75 g/L; 1.85 g/L; 1.95 g/L; 2.05 g/L; 2.15 g/L; 2.25 g/L; 2.35 g/L; 2.45 g/L; 2.55 g/L; 2.65 g/L; 2.75 g/L; 2.85 g/L; or 2.95 g/L to the medium.

In some embodiments, the medium can be supplemented with potassium sulfate in an amount of about 2 g/L; 2.5 g/L; 3 g/L; 3.5 g/L; 4 g/L; 4.5 g/L; 5 g/L; 5.5 g/L; 6 g/L; 6.5 g/L; 7 g/L; 7.5 g/L; 8 g/L; 8.5 g/L; 9 g/L; 9.5 g/L; 10 g/L; 10.5 g/L; 11 g/L; 11.5 g/L; 12 g/L; 12.5 g/L; 13 g/L; 13.5 g/L; 14 g/L; 14.5 g/L; 15 g/L; 15.5 g/L; 16 g/L; 16.5 g/L; 17 g/L; 17.5 g/L; 18 g/L; 18.5 g/L; 19 g/L; 19.5 g/L; or 20 g/L to the medium.

In some embodiments, the medium can be supplemented with magnesium sulfate heptahydrate in an amount of about 0.25 g/L; 0.5 g/L; 0.75 g/L; 1 g/L; 1.25 g/L; 1.5 g/L; 1.75 g/L; 2 g/L; 2.25 g/L; 2.5 g/L; 2.75 g/L; 3 g/L; 3.25 g/L; 3.5 g/L; 3.75 g/L; 4 g/L; 4.25 g/L; 4.5 g/L; 4.75 g/L; 5 g/L; 5.25 g/L; 5.5 g/L; 5.75 g/L; 6 g/L; 6.25 g/L; 6.5 g/L; 6.75 g/L; 7 g/L; 7.25 g/L; 7.5 g/L; 7.75 g/L; 8 g/L; 8.25 g/L; 8.5 g/L; 8.75 g/L; 9 g/L; 9.25 g/L; 9.5 g/L; 9.75 g/L; 10 g/L; 10.25 g/L; 10.5 g/L; 10.75 g/L; 11 g/L; 11.25 g/L; 11.5 g/L; 11.75 g/L; 12 g/L; 12.25 g/L; 12.5 g/L; 12.75 g/L; 13 g/L; 13.25 g/L; 13.5 g/L; 13.75 g/L; 14 g/L; 14.25 g/L; 14.5 g/L; 14.75 g/L; or 15 g/L to the medium.

In some embodiments, the medium can be supplemented with potassium hydroxide in an amount of about 0.25 g/L; 0.5 g/L; 0.75 g/L; 1 g/L; 1.25 g/L; 1.5 g/L; 1.75 g/L; 2 g/L; 2.25 g/L; 2.5 g/L; 2.75 g/L; 3 g/L; 3.25 g/L; 3.5 g/L; 3.75 g/L; 4 g/L; 4.25 g/L; 4.5 g/L; 4.75 g/L; 5 g/L; 5.25 g/L; 5.5 g/L; 5.75 g/L; 6 g/L; 6.25 g/L; 6.5 g/L; 6.75 g/L; or 7 g/L to the medium.

In some embodiments, the medium can be supplemented with corn steep liquor in an amount of about 5 g/L; 6 g/L; 7 g/L; 8 g/L; 9 g/L; 10 g/L; 11 g/L; 12 g/L; 13 g/L; 14 g/L; 15 g/L; 16 g/L; 17 g/L; 18 g/L; 19 g/L; 20 g/L; 21 g/L; 22 g/L; 23 g/L; 24 g/L; 25 g/L; 26 g/L; 27 g/L; 28 g/L; 29 g/L; 30 g/L; 31 g/L; 32 g/L; 33 g/L; 34 g/L; 35 g/L; 36 g/L; 37 g/L; 38 g/L; 39 g/L; 40 g/L; 41 g/L; 42 g/L; 43 g/L; 44 g/L; 45 g/L; 46 g/L; 47 g/L; 48 g/L; 49 g/L; 50 g/L; 51 g/L; 52 g/L; 53 g/L; 54 g/L; 55 g/L; 56 g/L; 57 g/L; 58 g/L; 59 g/L; 60 g/L; 61 g/L; 62 g/L; 63 g/L; 64 g/L; 65 g/L; 66 g/L; 67 g/L; 68 g/L; 69 g/L; or 70 g/L to the medium.

In some embodiments, the temperature of the reactor can be maintained between about 15° C. and about 45° C. In some embodiments, the reactor can have a temperature of about 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., or 40° C.

In some embodiments, the pH can have a level of about 3 to about 6. In some embodiments, the pH can be 3.0, 3.1, 3.2, 3.3, 3.4, 3.5, 3.6, 3.7, 3.8, 3.9, 4, 4.1, 4.2, 4.3, 4.4, 4.5, 4.6, 4.7, 4.8, 4.9, 5, 5.1, 5.2, 5.3, 5.4, 5.5, 5.6, 5.7, 5.8, 5.9, or 6.0.

In some embodiments, the pH can be maintained at a constant level via the addition of one or more chemicals. For example, in some embodiments, ammonium hydroxide can be added to maintain pH. In some embodiments, ammonium hydroxide can be added to a level of ammonium hydroxide in the medium that is about 5% 6%, 7% 8%, 9%, 10%, 11%, 12%, 13%, 14%, 16%, 17%, 18%, 19%, or 20%, of ammonium hydroxide In some embodiments, oxygen levels can be maintained by sparging. For example, in some embodiments, dissolved oxygen can be maintained at a constant level by sparging air between 0.5-1.5 volume/volume/min and by increasing agitation to maintain a set point of 10-30%.

In some embodiments, inoculation of the reactor can be accomplished based on an overnight seed culture comprising from about 2.5 g/L to about 50 g/L of a carbon source, e.g., glucose, sorbitol, or lactose. In some embodiments, the overnight seed culture can comprise corn steep liquor, e.g., from about 2.5 g/L to about 50 g/L of corn steep liquor.

In some embodiments, the inoculation percentage can range from about 5-20% of initial fill volume. Following inoculation, the reactor can be fed with from about a 50% to about an 80% solution of the selected carbon source up until the reactor is filled and/or the desired supernatant peptide concentration is achieved. In some embodiments, the time required to fill the reactor can range from about 86 hours to about 160 hours. In some embodiments, the quantity required to reach the desired peptide concentration can range from about 0.8 g/L to about 1.2 g/L. Upon completion of the fermentation, the contents can be passed through a cell separation unit and optionally concentrated, depending on intended use of the material.

Additional recipes for yeast fermentation media are provided herein.

Recipes for yeast cell fermentation media and stocks are described as follows: (1) MSM media recipe: 2 g/L sodium citrate dihydrate; 1 g/L calcium sulfate dihydrate (0.79 g/L anhydrous calcium sulfate); 42.9 g/L potassium phosphate monobasic; 5.17 g/L ammonium sulfate; 14.33 g/L potassium sulfate; 11.7 g/L magnesium sulfate heptahydrate; 2 mL/L PTM1 trace salt solution; 0.4 ppm biotin (from 500×, 200 ppm stock); 1-2% pure glycerol or other carbon source. (2) PTM1 trace salts solution: Cupric sulfate-5H2O 6.0 g; Sodium iodide 0.08 g; Manganese sulfate-H2O 3.0 g; Sodium molybdate-$2H_2O$ 0.2 g; Boric Acid 0.02 g; Cobalt chloride 0.5 g; Zinc chloride 20.0 g; Ferrous sulfate-$7H_2O$ 65.0 g; Biotin 0.2 g; Sulfuric Acid 5.0 ml; add Water to a final volume of 1 liter. An illustrative composition for *K. lactis* defined medium (DMSor) is as follows: 11.83 g/L $KH_2PO_4$, 2.299 g/L $K_2HPO_4$, 20 g/L of a fermentable sugar, e.g., galactose, maltose, latotriose, sucrose, fructose or glucose and/or a sugar alcohol, for example, erythritol, hydrogenated starch hydrolysates, isomalt, lactitol, maltitol, mannitol, and xylitol, 1 g/L $MgSO_4.7H_2O$, 10 g/L $(NH_4)SO_4$, 0.33 g/L $CaCl_2\cdot2H_2O$, 1 g/L NaCl, 1 g/L KCl, 5 mg/L $CuSO_4\cdot5H_2O$, 30 mg/L $MnSO_4\cdot H_2O$, 10 mg/L, $ZnCl_2$, 1 mg/L KI, 2 mg/L $CoCl_2\cdot6H_2O$, 8 mg/L $Na_2MoO_4\cdot2H_2O$, 0.4 mg/L $H_3BO_3$, 15 mg/L $FeCl_3\cdot6H_2O$, 0.8 mg/L biotin, 20 mg/L Ca-pantothenate, 15 mg/L thiamine, 16 mg/L myoinositol, 10 mg/L nicotinic acid, and 4 mg/L pyridoxine.

Peptide Degradation

Proteins, polypeptides, and peptides degrade in both biological samples and in solution (e.g., cell culture and/or during fermentation). Methods of detecting TVP peptide degradation are well known in the art. Any of the well-known methods of detecting peptide degradation (e.g., during fermentation) may be employed here.

In some embodiments, peptide degradation can be detected using isotope labeling techniques; liquid chromatography/mass spectrometry (LC/MS); HPLC; radioactive amino acid incorporation and subsequent detection, e.g., via scintillation counting; the use of a reporter protein, e.g., a protein that can be detected (e.g., by fluorescence, spectroscopy, luminometry, etc.); fluorescent intensity of one or more bioluminescent proteins and/or fluorescent proteins and/or fusions thereof; pulse-chase analysis (e.g., pulse-labeling a cell with radioactive amino acids and following the decay of the labeled protein while chasing with unlabeled precursor, and arresting protein synthesis and measuring the decay of total protein levels with time); cycloheximide-chase assays;

In some embodiments, an assay can be used to detect peptide degradation, wherein a sample is contacted with a non-fluorescent compound that is operable to react with free primary amine in said sample produced via the degradation of a peptide, and which then produces a fluorescent signal that can be quantified and compared to a standard. Examples of non-fluorescent compounds that can be utilized as fluorescent tags for free amines according to the present disclosure are 3-(4-carboxybenzoyl) quinoline-2-carboxaldehyde (CBQCA), fluorescamine, and o-phthaldialdehyde.

In some embodiments, the method to determine the readout signal from the reporter protein depends from the nature of the reporter protein. For example, for fluorescent reporter proteins, the readout signal corresponds to the intensity of the fluorescent signal. The readout signal may be measured using spectroscopy-, fluorometry-, photometry-, and/or luminometry-based methods and detection systems, for example. Such methods and detection systems are well known in the art.

In some embodiments, standard immunological procedures known to those having ordinary skill in the art can be used to detect peptide degradation. For example, in some embodiments, peptide degradation can be detected in a sample using immunoassays that employ a detectable antibody. Such immunoassays include, for example, agglutination assays, ELISA, Pandex microfluorimetric assay, flow cytometry, serum diagnostic assays, and immunohistochemical staining procedures, all of which are well-known in the art. In some embodiments, the levels (e.g., of fluorescence) in one sample can be compared to a standard. An antibody can be made detectable by various means well known in the art. For example, a detectable marker can be directly or indirectly attached to the antibody. Useful markers include, for example, radionucleotides, enzymes, fluorogens, chromogens and chemiluminescent labels.

Exemplary methods of detecting peptide degradation is provided in U.S. Pat. Nos. 5,766,927; 7,504,253; 9,201,073; 9,429,566; United States Patent Application 20120028286; Eldeeb et al., A molecular toolbox for studying protein degradation in mammalian cells. J Neurochem. 2019 November; 151(4):520-533; and Buchanan et al., Cycloheximide Chase Analysis of Protein Degradation in *Saccharomyces cerevisiae*. J Vis Exp. 2016; (110): 53975, the disclosures of which are incorporated herein by reference in their entireties.

Pharmaceutically Acceptable Salts

As used herein, the term "pharmaceutically acceptable salt" and "agriculturally acceptable salt" are synonymous. In some embodiments, pharmaceutically acceptable salts, hydrates, solvates, crystal forms and individual isomers, enantiomers, tautomers, diastereomers and prodrugs of the TVP described herein can be utilized.

In some embodiments, a pharmaceutically acceptable salt of the present invention possesses the desired pharmacological activity of the parent compound. Such salts include: acid addition salts, formed with inorganic acids; acid addition salts formed with organic acids; or salts formed when an acidic proton present in the parent compound is replaced by a metal ion, e.g., an alkali metal ion, aluminum ion; or coordinates with an organic base such as ethanolamine, and the like.

In some embodiments, pharmaceutically acceptable salts include conventional toxic or non-toxic salts. For example, in some embodiments, convention non-toxic salts include those such as fumarate, phosphate, citrate, chlorydrate, and the like. In some embodiments, the pharmaceutically acceptable salts of the present invention can be synthesized from a parent compound by conventional chemical methods. In some embodiments, such salts can be prepared by reacting the free acid or base forms of these compounds with a stoichiometric amount of the appropriate base or acid in water or in an organic solvent, or in a mixture of the two. In some embodiments, non-aqueous media like ether, ethyl acetate, ethanol, isopropanol, or acetonitrile are preferred. Lists of suitable salts are found in Remington's Pharmaceutical Sciences, 17th ed., Mack Publishing Company, Easton, Pa., 1985, p. 1418, the disclosure of which is incorporated herein by reference in its entirety.

In some embodiments, a pharmaceutically acceptable salt can be one of the following: hydrochloride; sodium; sulfate; acetate; phosphate or diphosphate; chloride; potassium; maleate; calcium; citrate; mesylate; nitrate; tartrate; aluminum; or gluconate.

In some embodiments, a list of pharmaceutically acceptable acids that can be used to form salts can be: glycolic acid; hippuric acid; hydrobromic acid; hydrochloric acid; isobutyric acid; lactic acid (DL); lactobionic acid; lauric acid; maleic acid; malic acid (−L); malonic acid; mandelic acid (DL); methanesulfonic acid; naphthalene-1,5-disulfonic acid; naphthalene-2-sulfonic acid; nicotinic acid; nitric acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); undecylenic acid; a 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; or glycerophosphoric acid.

In some embodiments, pharmaceutically acceptable salt can be any organic or inorganic addition salt.

In some embodiments, the salt may use an inorganic acid and an organic acid as a free acid. The inorganic acid may be hydrochloric acid, bromic acid, nitric acid, sulfuric acid, perchloric acid, phosphoric acid, etc. The organic acid may be citric acid, acetic acid, lactic acid, maleic acid, fumaric acid, gluconic acid, methane sulfonic acid, gluconic acid, succinic acid, tartaric acid, galacturonic acid, embonic acid, glutamic acid, aspartic acid, oxalic acid, (D) or (L) malic acid, maleic acid, methane sulfonic acid, ethane sulfonic acid, 4-toluene sulfonic acid, salicylic acid, citric acid, benzoic acid, malonic acid, etc.

In some embodiments, the salts include alkali metal salts (sodium salts, potassium salts, etc.) and alkaline earth metal salts (calcium salts, magnesium salts, etc.). For example, the acid addition salt may include acetate, aspartate, benzoate, besylate, bicarbonate/carbonate, bisulfate/sulfate, borate, camsylate, citrate, edisilate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methyl sulfate, naphthalate, 2-napsylate, nicotinate, nitrate, orotate, oxalate, palmitate, pamoate, phosphate/hydrogen phosphate/dihydrogen phosphate, saccharate, stearate, succinate, tartrate, tosylate, trifluoroacetate, aluminum, arginine, benzathine, calcium, choline, diethylamine, diolamine, glycine, lysine, magnesium, meglumine, olamine, potassium, sodium, tromethamine, zinc salt, etc., and among them, hydrochloride or trifluoroacetate may be used.

In yet other embodiments, the pharmaceutically acceptable salt can be a salt with an acid such as acetic acid, propionic acid, butyric acid, formic acid, trifluoroacetic acid, maleic acid, tartaric acid, citric acid, stearic acid, succinic acid, ethylsuccinic acid, lactobionic acid, gluconic acid, glucoheptonic acid, benzoic acid, methanesulfonic acid, ethanesulfonic acid, 2-hydroxyethanesulfonic acid, benzenesulfonic acid, p-toluenesulfonic acid, laurylsulfuric acid, malic acid, aspartic acid, glutaminic acid, adipic acid, cysteine, N-acetylcysteine, hydrochloric acid, hydrobromic acid, phosphoric acid, sulfuric acid, hydroiodic acid, nicotinic acid, oxalic acid, picric acid, thiocyanic acid, undecanoic acid, polyacrylate or carboxyvinyl polymer.

In some embodiments, the pharmaceutically acceptable salt can be prepared from either inorganic or organic bases. Salts derived from inorganic bases include, but are not limited to, the sodium, potassium, lithium, ammonium, calcium, magnesium, ferrous, zinc, copper, manganous, aluminum, ferric, manganic salts, and the like. Preferred inorganic salts are the ammonium, sodium, potassium, calcium, and magnesium salts. Salts derived from organic bases include, but are not limited to, salts of primary, secondary, and tertiary amines, substituted amines including naturally-occurring substituted amines, and cyclic amines, including isopropylamine, trimethylamine, diethylamine, triethylamine, tripropylamine, ethanolamine, 2-dimethylaminoethanol, tromethamine, lysine, arginine, histidine, caffeine, procaine, hydrabamine, choline, betaine, ethylenediamine, glucosamine, N-alkylglucamines, theobromine, purines, piperazine, piperidine, N-ethylpiperidine, and the like. Preferred organic bases are isopropylamine, diethylamine, ethanolamine, piperidine, tromethamine, and choline.

In some embodiments, pharmaceutically acceptable salt refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in J. Pharmaceutical Sciences, 66: 1-19 (1977), the disclosure of which is incorporated herein by reference in its entirety.

In some embodiments, the salts of the present invention can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, lower alkyl sulfonate and aryl sulfonate.

Exemplary descriptions of pharmaceutically acceptable salts is provided in P. H. Stahl and C. G. Wermuth, (editors), *Handbook of Pharmaceutical Salts: Properties, Selection and Use*, John Wiley & Sons, August 23, (2002), the disclosure of which is incorporated herein by reference in its entirety.

TVP Incorporation into Plants or Parts Thereof

The TVPs described herein, and/or an insecticidal protein consisting of one or more TVPs as described herein, can be incorporated into plants, plant tissues, plant cells, plant seeds, and/or plant parts thereof, for either the stable, or transient expression of a TVP or TVP-insecticidal protein, and/or a polynucleotide sequence encoding the same.

In some embodiments, the TVP (or an insecticidal protein consisting of one or more TVPs) can be incorporated into a plant using recombinant techniques known in the art. In some embodiments, the TVP or insecticidal protein consisting of one or more TVPs may be in the form of an insecticidal protein which may consist of one or more TVP monomers.

As used herein, with respect to transgenic plants, plant tissues, plant cells, and plant seeds, the term "TVP" also encompasses a TVP-insecticidal protein, and a "TVP polynucleotide" is similarly also used to encompass a polynucleotide or group of polynucleotides operable to express and/or encode an insecticidal protein consisting of one or more TVPs.

The goal of incorporating a TVP into plants (i.e., to make transgenic plants that express U1-agatoxin-Ta1b Variant polynucleotide, and/or a TVP-insecticidal protein) is to deliver TVP containing insecticidal proteins to the pest via the insect's consumption of the transgenic TVP expressed in a plant tissue consumed by the insect. Upon the consumption of the TVP by the insect from its food (e.g., via an insect feeding upon a transgenic plant transformed with a TVP), the consumed TVP may have the ability to inhibit the growth, impair the movement, or even kill an insect. Accordingly, transgenic plants expressing a TVP polynucleotide and/or a TVP polypeptide may express said TVP polynucleotide/polypeptide in a variety of plant tissues, including but not limited to: the epidermis (e.g., mesophyll); periderm; phloem; xylem; parenchyma; collenchyma; sclerenchyma; and primary and secondary meristematic tissues. For example, in some embodiments, a polynucleotide sequence encoding a TVP can be operably linked to a regulatory region containing a phosphoenolpyruvate carboxylase promoter, resulting in the expression of a TVP in a plant's mesophyll tissue.

Transgenic plants expressing a TVP and/or a polynucleotide operable to express TVP can be generated by any one of the various methods and protocols well known to those having ordinary skill in the art; such methods of the invention do not require that a particular method for introducing a nucleotide construct to a plant be used, only that the nucleotide construct gains access to the interior of at least one cell of the plant. Methods for introducing nucleotide constructs into plants are known in the art including, but not limited to, stable transformation methods, transient transformation methods, and virus-mediated methods. "Transgenic plants" or "transformed plants" or "stably transformed" plants or cells or tissues refers to plants that have incorporated or integrated exogenous nucleic acid sequences or DNA fragments into the plant cell. These nucleic acid sequences include those that are exogenous, or not present in the untransformed plant cell, as well as those that may be endogenous, or present in the untransformed plant cell. "Heterologous" generally refers to the nucleic acid sequences that are not endogenous to the cell or part of the native genome in which they are present, and have been added to the cell by infection, transfection, microinjection, electroporation, microprojection, or the like.

Transformation of plant cells can be accomplished by one of several techniques known in the art. Typically, a construct that expresses an exogenous or heterologous peptide or polypeptide of interest (e.g., a TVP), would contain a promoter to drive transcription of the gene, as well as a 3' untranslated region to allow transcription termination and polyadenylation. The design and organization of such constructs is well known in the art. In some embodiments, a gene can be engineered such that the resulting peptide is secreted, or otherwise targeted within the plant cell to a specific region and/or organelle. For example, the gene can be engineered to contain a signal peptide to facilitate transfer of the peptide to the endoplasmic reticulum. It may also be preferable to engineer the plant expression cassette to contain an intron, such that mRNA processing of the intron is required for expression.

Typically, a plant expression cassette can be inserted into a plant transformation vector. This plant transformation vector may comprise one or more DNA vectors needed for achieving plant transformation. For example, it is a common practice in the art to utilize plant transformation vectors that are comprise more than one contiguous DNA segment. These vectors are often referred to in the art as "binary vectors." Binary vectors as well as vectors with helper plasmids are most often used for *Agrobacterium*-mediated transformation, where the size and complexity of DNA segments needed to achieve efficient transformation is quite large, and it is advantageous to separate functions onto separate DNA molecules. Binary vectors typically contain a plasmid vector that contains the cis-acting sequences required for T-DNA transfer (such as left border and right border), a selectable marker that is engineered to be capable of expression in a plant cell, and a "gene of interest" (a gene engineered to be capable of expression in a plant cell for which generation of transgenic plants is desired). Also present on this plasmid vector are sequences required for bacterial replication. The cis-acting sequences are arranged in a fashion to allow efficient transfer into plant cells and expression therein. For example, the selectable marker gene and the TVP are located between the left and right borders. Often a second plasmid vector contains the trans-acting factors that mediate T-DNA transfer from *Agrobacterium* to plant cells. This plasmid often contains the virulence functions (Vir genes) that allow infection of plant cells by *Agrobacterium*, and transfer of DNA by cleavage at border sequences and vir-mediated DNA transfer, as is understood in the art (Hellens and Mullineaux (2000) Trends in Plant Science 5:446-451). Several types of *Agrobacterium* strains (e.g. LBA4404, GV3101, EHA101, EHA105, etc.) can be used for plant transformation. The second plasmid vector is not necessary for transforming the plants by other methods such as microprojection, microinjection, electroporation, polyethylene glycol, etc.

In general, plant transformation methods involve transferring heterologous DNA into target plant cells (e.g. immature or mature embryos, suspension cultures, undifferentiated callus, protoplasts, etc.), followed by applying a maximum threshold level of appropriate selection (depending on the selectable marker gene) to recover the transformed plant cells from a group of untransformed cell mass. Explants are typically transferred to a fresh supply of the same medium and cultured routinely. Subsequently, the transformed cells are differentiated into shoots after placing on regeneration medium supplemented with a maximum threshold level of selecting agent. The shoots are then transferred to a selective rooting medium for recovering rooted shoot or plantlet. The transgenic plantlet then grows into a mature plant and produces fertile seeds (e.g. Hiei et al. (1994) The Plant Journal 6:271-282; Ishida et al. (1996) Nature Biotechnology 14:745-750). Explants are typically transferred to a fresh supply of the same medium and cultured routinely. A general description of the techniques and methods for generating transgenic plants are found in Ayres and Park (1994) Critical Reviews in Plant Science 13:219-239 and Bommineni and Jauhar (1997) Maydica 42:107-120. Because the transformed material contains many cells, both transformed and non-transformed cells are present in any piece of subjected target callus or tissue or group of cells. The ability to kill non-transformed cells and allow transformed cells to proliferate results in transformed plant cultures. Often, the ability to remove non-transformed cells is a limitation to rapid recovery of transformed plant cells and successful generation of transgenic plants.

Transformation protocols as well as protocols for introducing nucleotide sequences into plants may vary depending on the type of plant or plant cell, i.e., monocot or dicot, targeted for transformation. Generation of transgenic plants may be performed by one of several methods, including, but not limited to, microinjection, electroporation, direct gene transfer, introduction of heterologous DNA by *Agrobacterium* into plant cells (*Agrobacterium*-mediated transformation), bombardment of plant cells with heterologous foreign DNA adhered to particles, ballistic particle acceleration, aerosol beam transformation, Lec1 transformation, and various other non-particle direct-mediated methods to transfer DNA. Exemplary transformation protocols are disclosed in U.S. Published Application No. 20010026941; U.S. Pat. No. 4,945,050; International Publication No. WO 91/00915; and U.S. Published Application No. 2002015066, the disclosures of which are incorporated herein by reference in their entireties.

Chloroplasts can also be readily transformed, and methods concerning the transformation of chloroplasts are known in the art. See, for example, Svab et al. (1990) Proc. Natl. Acad. Sci. USA 87:8526-8530; Svab and Maliga (1993) Proc. Natl. Acad. Sci. USA 90:913-917; Svab and Maliga (1993) EMBO J. 12:601-606, the disclosure of which is incorporated herein by reference in its entirety. The method of chloroplast transformation relies on particle gun delivery of DNA containing a selectable marker and targeting of the DNA to the plastid genome through homologous recombination. Additionally, plastid transformation can be accomplished by transactivation of a silent plastid-borne transgene by tissue-preferred expression of a nuclear-encoded and plastid-directed RNA polymerase. Such a system has been reported in McBride et al. (1994) Proc. Natl. Acad. Sci. USA 91:7301-7305.

Following integration of heterologous foreign DNA into plant cells, one having ordinary skill may then apply a maximum threshold level of appropriate selection chemical/reagent (e.g., an antibiotic) in the medium to kill the untransformed cells, and separate and grow the putatively transformed cells that survive from this selection treatment by transferring said surviving cells regularly to a fresh medium. By continuous passage and challenge with appropriate selection, an artisan identifies and proliferates the cells that are transformed with the plasmid vector. Molecular and biochemical methods can then be used to confirm the presence of the integrated heterologous gene of interest into the genome of the transgenic plant.

The cells that have been transformed may be grown into plants in accordance with conventional methods known to those having ordinary skill in the art. See, for example, McCormick et al. (1986) Plant Cell Reports 5:81-84, the disclosure of which is incorporated herein by reference in its entirety. These plants may then be grown, and either pollinated with the same transformed strain or different strains, and the resulting hybrid having constitutive expression of the desired phenotypic characteristic identified. Two or more generations may be grown to ensure that expression of the desired phenotypic characteristic is stably maintained and inherited and then seeds harvested to ensure expression of the desired phenotypic characteristic has been achieved. In this manner, the present disclosure provides transformed seed (also referred to as "transgenic seed") having a nucleotide construct of the invention, for example, an expression cassette of the invention, stably incorporated into their genome.

In various embodiments, the present disclosure provides a TVP-insecticidal protein, that act as substrates for insect proteinases, proteases and peptidases (collectively referred to herein as "proteases") as described above.

In some embodiments, transgenic plants or parts thereof, that may be receptive to the expression of TVPs can include: alfalfa, banana, barley, bean, broccoli, cabbage, canola, carrot, cassava, castor, cauliflower, celery, chickpea, Chinese cabbage, citrus, coconut, coffee, corn, clover, cotton, a cucurbit, cucumber, Douglas fir, eucalyptus, flax, garlic, grape, hops, leek, lettuce, Loblolly pine, millets, melons, nut, oat, olive, onion, ornamental, palm, pasture grass, pea, peanut, pepper, pigeonpea, pine, potato, poplar, pumpkin, Radiata pine, radish, rapeseed, rice, rootstocks, rye, safflower, shrub, sorghum, Southern pine, soybean, spinach, squash, strawberry, sugar beet, sugarcane, sunflower, sweet corn, sweet gum, sweet potato, switchgrass, tea, tobacco, tomato, triticale, turf grass, watermelon, and a wheat plant.

In some embodiments the transgenic plant may be grown from cells that were initially transformed with the DNA constructs described herein. In other embodiments, the transgenic plant may express the encoded TVP in a specific tissue, or plant part, for example, a leaf, a stem a flower, a sepal, a fruit, a root, a seed, or combinations thereof.

In some embodiments, the plant, plant tissue, plant cell, or plant seed can be transformed with a TVP or a polynucleotide encoding the same, wherein the TVP comprises a TVP polypeptide with an amino acid sequence that is at least 95% identical to the amino acid sequence according to Formula (I): E-P-D-E-I-C-R-$X_1$-$X_2$-M-$X_3$-N-K-E-F-T-Y-$X_4$-S—N-V-C-N-N-C-G-D-Q-V-A-A-C-E-A-E-C-F-$X_5$-N-

D-V-Y-$Z_1$-A-C-H-E-A-Q-K-$X_6$ (SEQ ID NO: 151), wherein the polypeptide comprises at least one amino acid substitution relative to the wild-type sequence of U1-agatoxin-Ta1b as set forth in SEQ ID NO: 1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; and wherein $X_6$ is G or absent.

In some embodiments, the plant, plant tissue, plant cell, or plant seed can be transformed with a TVP or a polynucleotide encoding the same, wherein the TVP comprises a TVP polypeptide with an the amino acid sequence that is at least 95% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-K-$X_6$ (SEQ ID NO: 151), wherein the polypeptide comprises at least one amino acid substitution relative to the wild-type sequence of U1-agatoxin-Ta1b as set forth in SEQ ID NO: 1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is G or absent; and wherein if $Z_1$ is T or S, then the TVP is glycosylated.

In some embodiments, the plant, plant tissue, plant cell, or plant seed can be transformed with a TVP or a polynucleotide encoding the same, wherein the TVP comprises a TVP polypeptide with an the amino acid sequence selected from the group consisting of SEQ NOs 17, 18, 19, 20, 21, 22, 23, 24, 25, 26, 27, 28, 29, and 30.

In some embodiments, the plant, plant tissue, plant cell, or plant seed can be transformed with a polynucleotide encoding the TVP, wherein the TVP encoding polynucleotide or a complementary nucleotide sequence thereof selected from the group consisting of SEQ NOs 2, 3, 4, 5, 6, 7, 8, 9, 10, 11, 12, 13, 14, and 15.

In some embodiments, the plant, plant tissue, plant cell, or plant seed can be transformed with a TVP or a polynucleotide encoding the same, wherein the TVP wherein the TVP further comprises a homopolymer or heteropolymer of two or more TVP polypeptides, wherein the amino acid sequence of each TVP is the same or different.

Proteins with Cleavable Linkers and Non-Cleavable Linkers

In some embodiments, the TVP-insecticidal protein comprises at least one TVP operably linked to a cleavable peptide. In other embodiments, the TVP-insecticidal protein comprises at least one TVP operably linked to a non-cleavable peptide.

In some embodiments, the TVP-insecticidal protein can have two or more cleavable peptides, wherein the insecticidal protein comprises an insect cleavable linker (L), the insect cleavable linker being fused in frame with a construct comprising (TVP-L)$_n$, wherein "n" is an integer ranging from 1 to 200, or from 1 to 100, or from 1 to 10. In another embodiment, the TVP-insecticidal protein, and described herein, comprises an endoplasmic reticulum signal peptide (ERSP) operably linked with a TVP, which is operably linked with an insect cleavable linker (L) and/or a repeat construct (L-TVP)$_n$ or (TVP-L)$_n$, wherein n is an integer ranging from 1 to 200, or from 1 to 100, or from 1 to 10.

In various embodiments, an exemplary insecticidal protein can include a protein construct comprising: (ERSP)-(TVP-L)$_n$; (ERSP)-(L)-(TVP-L)$_n$; (ERSP)-(L-TVP)$_n$; (ERSP)-(L-TVP)$_n$-(L); wherein n is an integer ranging from 1 to 200 or from 1 to 100, or from 1 to 10. In various related embodiments described above, a TVP is the aforementioned U1-agatoxin-Ta1b Variant Polypeptides, L is a non-cleavable or cleavable peptide, and n is an integer ranging from 1 to 200, preferably an integer ranging from 1 to 100, and more preferably an integer ranging from 1 to 10. In some embodiments, the TVP-insecticidal protein may contain TVP peptides that are the same or different, and insect cleavable peptides that are the same or different. In some embodiments, the C-terminal TVP is operably linked at its C-terminus with a cleavable peptide that is operable to be cleaved in an insect gut environment. In some embodiments, the N-terminal TVP is operably linked at its N-terminus with a cleavable peptide that is operable to be cleaved in an insect gut environment.

Some of the available proteases and peptidases found in the insect gut environment are dependent on the life-stage of the insect, as these enzymes are often spatially and temporally expressed. The digestive system of the insect is composed of the alimentary canal and associated glands. Food enters the mouth and is mixed with secretions that may or may not contain digestive proteases and peptidases. The foregut and the hind gut are ectodermal in origin. The foregut serves generally as a storage depot for raw food. From the foregut, discrete boluses of food pass into the midgut (mesenteron or ventriculus). The midgut is the site of digestion and absorption of food nutrients. Generally, the presence of certain proteases and peptidases in the midgut follow the pH of the gut. Certain proteases and peptidases in the human gastrointestinal system may include: pepsin, trypsin, chymotrypsin, elastase, carboxypeptidase, aminopeptidase, and dipeptidase.

The insect gut environment includes the regions of the digestive system in the herbivore species where peptides and proteins are degraded during digestion. Some of the available proteases and peptidases found in insect gut environments may include: (1) serine proteases; (2) cysteine proteases; (3) aspartic proteases, and (4) metalloproteases.

The two predominant protease classes in the digestive systems of phytophagous insects are the serine and cysteine proteases. Murdock et al. (1987) carried out an elaborate study of the midgut enzymes of various pests belonging to Coleoptera, while Srinivasan et al. (2008) have reported on the midgut enzymes of various pests belonging to Lepidoptera. Serine proteases are known to dominate the larval gut environment and contribute to about 95% of the total digestive activity in Lepidoptera, whereas the Coleopteran species have a wider range of dominant gut proteases, including cysteine proteases.

The papain family contains peptidases with a wide variety of activities, including endopeptidases with broad specificity (such as papain), endopeptidases with very narrow specificity (such as glycyl endopeptidases), aminopeptidases, dipeptidyl-peptidase, and peptidases with both endopeptidase and exopeptidase activities (such as cathepsins B and H). Other exemplary proteinases found in the midgut of various insects include trypsin-like enzymes, e.g. trypsin and chymotrypsin, pepsin, carboxypeptidase-B and aminotripeptidases.

Serine proteases are widely distributed in nearly all animals and microorganisms (Joanitti et al., 2006). In higher organisms, nearly 2% of genes code for these enzymes (Barrette-Ng et al., 2003). Being essentially indispensable to the maintenance and survival of their host organism, serine proteases play key roles in many biological processes. Serine proteases are classically categorized by their substrate specificity, notably by whether the residue at P1: trypsin-like (Lys/Arg preferred at P1), chymotrypsin-like (large hydrophobic residues such as Phe/Tyr/Leu at P1), or elastase-like (small hydrophobic residues such as Ala/Val at P1) (revised by Tyndall et. al., 2005). Serine proteases are a class of proteolytic enzymes whose central catalytic machinery is composed of three invariant residues, an aspartic acid, a histidine and a uniquely reactive serine, the latter giving rise to their name, the "catalytic triad". The Asp-His-Ser triad can be found in at least four different structural contexts (Hedstrom, 2002). These four clans of serine proteases are typified by chymotrypsin, subtilisin, carboxypeptidase Y, and Clp protease. The three serine proteases of the chymotrypsin-like clan that have been studied in greatest detail are chymotrypsin, trypsin, and elastase. More recently, serine proteases with novel catalytic triads and dyads have been discovered for their roles in digestion, including Ser-His-Glu, Ser-Lys/His, His-Ser-His, and N-terminal Ser.

One class of well-studied digestive enzymes found in the gut environment of insects is the class of cysteine proteases. The term "cysteine protease" is intended to describe a protease that possesses a highly reactive thiol group of a cysteine residue at the catalytic site of the enzyme. There is evidence that many phytophagous insects and plant parasitic nematodes rely, at least in part, on midgut cysteine proteases for protein digestion. These include but are not limited to Hemiptera, especially squash bugs (*Anasa tristis*); green stink bug (*Acrosternum hilare*); *Riptortus clavatus*; and almost all Coleoptera examined to date, especially, Colorado potato beetle (*Leptinotarsa deaemlineata*); three-lined potato beetle (*Lema trilineata*); asparagus beetle (*Crioceris asparagi*); Mexican bean beetle (*Epilachna varivestis*); red flour beetle (*Triolium castaneum*); confused flour beetle (*Tribolium confusum*); the flea beetles (*Chaetocnema* spp., *Haltica* spp., and *Epitrix* spp.); corn rootworm (*Diabrotica* Spp.); cowpea weevil (*Callosobruchus aculatue*); boll weevil (*Antonomus grandis*); rice weevil (*Sitophilus oryza*); maize weevil (*Sitophilus zeamais*); granary weevil (*Sitophilus granarius*); Egyptian alfalfa weevil (*Hypera postica*); bean weevil (*Acanthoseelides obtectus*); lesser grain borer (*Rhyzopertha dominica*); yellow meal worm (*Tenebrio molitor*); Thysanoptera, especially, western flower thrips (*Franklini ella occidentalis*); Diptera, especially, leafminer spp. (*Liriomyza trifolii*); plant parasitic nematodes especially the potato cyst nematodes (*Globodera* spp.), the beet cyst nematode (*Heterodera schachtii*) and root knot nematodes (*Meloidogyne* spp.).

Another class of digestive enzymes is the aspartic proteases. The term "aspartic protease" is intended to describe a protease that possesses two highly reactive aspartic acid residues at the catalytic site of the enzyme and which is most often characterized by its specific inhibition with pepstatin, a low molecular weight inhibitor of nearly all known aspartic proteases. There is evidence that many phytophagous insects rely, in part, on midgut aspartic proteases for protein digestion most often in conjunction with cysteine proteases. These include but are not limited to Hemiptera especially (*Rhodnius prolixus*) and bedbug (*Cimex* spp.) and members of the families Phymatidae, Pentatomidae, Lygaeidae and Belostomatidae; Coleoptera, in the families of the Meloidae, Chrysomelidae, Coccinelidae and Bruchidae all belonging to the series Cucujiformia, especially, Colorado potato beetle (*Leptinotarsa decemlineata*) three-lined potato beetle (*Lematri lineata*); southern and western corn rootworm (*Diabrotica undecimpunctata* and *D. virgifera*), boll weevil (*Anthonomus grandis*), squash bug (*Anasatristis*); flea beetle (*Phyllotreta crucifera*), bruchid beetle (*Callosobruchus maculatus*), Mexican bean beetle (*Epilachna varivestis*), soybean leafminer (*Odontota horni*), margined blister beetle (*Epicauta pestifera*) and the red flour beetle (*Triolium castaneum*); Diptera, especially housefly (*Musca domestica*).

See Terra and Ferreira (1994) Comn. Biochem. Physiol. 109B: 1-62; Wolfson and Murdock (1990) J. Chem. Ecol. 16: 1089-1102.

Polynucleotide Incorporation into Plants

A challenge regarding the expression of heterogeneous polypeptides in transgenic plants is maintaining the desired effect (e.g., insecticidal activity) of the introduced polypeptide upon expression in the host organism; one way to maintain such an effect is to increase the chance of proper protein folding through the use of an operably linked Endoplasmic Reticulum Signal Peptide (ERSP). Another method to maintain the effect of a transgenic protein is to incorporate a Translational Stabilizing Protein (STA).

Plants can be transiently or stably transfected with the DNA sequence that encodes a TVP or a TVP-insecticidal protein comprising one or more TVPs, using any of the transfection methods described above. Alternatively, plants can be transfected with a polynucleotide that encodes a TVP, wherein said TVP is operably linked to a polynucleotide operable to encode an Endoplasmic Reticulum Signal Peptide (ERSP); linker, Translational Stabilizing Protein (STA); or combination thereof. For example, in some embodiments, a transgenic plant or plant genome can be transformed with a polynucleotide sequence that encodes the Endoplasmic Reticulum Signal Peptide (ERSP); TVP; and/or intervening linker peptide (LINKER or L), thus causing mRNA transcribed from the heterogeneous DNA to be expressed in the transformed plant, and subsequently, said mRNA to be translated into a peptide.

Endoplasmic Reticulum Signal Peptide (ERSP)

The subcellular targeting of a recombinant protein to the ER can be achieved through the use of an ERSP operably linked to said recombinant protein; this allows for the correct assembly and/or folding of such proteins, and the high level accumulation of these recombinant proteins in plants. Exemplary methods concerning the compartmentalization of host proteins into intracellular storage are disclosed in McCormick et al., Proc. Natl. Acad. Sci. USA 96(2):703-708, 1999; Staub et al., Nature Biotechnology 18:333-338, 2000; Conrad et al., Plant Mol. Biol. 38:101-109, 1998; and Stoger et al., Plant Mol. Biol. 42:583-590, 2000, the disclosures of which are incorporated herein by reference in their entireties. Accordingly, one way to achieve the correct assembly and/or folding of recombinant proteins, is to operably link an endoplasmic reticulum signal peptide (ERSP) to the recombinant protein of interest.

In some embodiments, a peptide comprising an Endoplasmic Reticulum Signal Peptide (ERSP) can be operably linked to a TVP (designated as ERSP-TVP), wherein said ERSP is the N-terminal of said peptide. In some embodiments, the ERSP peptide is between 3 to 60 amino acids in length, between 5 to 50 amino acids in length, between 20 to 30 amino acids in length.

In some embodiments, the ERSP can include, but is not limited to, one of the following: a BAAS; a tobacco extensin signal peptide; a modified tobacco extensin signal peptide; or a Jun a 3 signal peptide from *Juniperus ashei*. For example, in some embodiments, a plant can be transformed with a nucleotide that encodes any of the peptides that are described herein as Endoplasmic Reticulum Signal Peptides (ERSP), and a TVP.

In some embodiments, a protein comprising an Endoplasmic Reticulum Signal Peptide (ERSP) can be operably linked to a TVP and an intervening linker peptide (L or Linker); such a construct is designated as ERSP-L-TVP, or ERSP-TVP-L, wherein said ERSP is the N-terminal of said protein, and said L or Linker may be either on the N-terminal side (upstream) of the TVP, or the C-terminal side (downstream) of the TVP. A protein designated as ERSP-L-TVP, or ERSP-TVP-L, comprising any of the ERSPs or TVPs described herein, can have a Linker "L" that can be an uncleavable linker peptide, or a cleavable linker peptide, and which may be cleavable in a plant cells during protein expression process, or may be cleavable in an insect gut environment and/or hemolymph environment.

In some embodiments, a TVP-insecticidal protein can comprise any of the intervening linker peptides (LINKER or L) described herein, or taught by this document, including but not limited to following sequences: IGER (SEQ ID NO:31), EEKKN, (SEQ ID NO:32), and ETMFKHGL (SEQ ID NO:33), ALKFLV (SEQ ID NO: 61), or combinations thereof.

In some embodiments, a protein comprising an Endoplasmic Reticulum Signal Peptide (ERSP) can be operably linked to a TVP, which is in turn operably linked to a Translational Stabilizing Protein (STA). Here, this configuration is designated as ERSP-STA-TVP or ERSP-TVP-STA, wherein said ERSP is the N-terminal of said protein and said STA may be either on the N-terminal side (upstream) of the TVP, or of the C-terminal side (downstream) of the TVP. In some embodiments, a protein designated as ERSP-STA-TVP or ERSP-TVP-STA, comprising any of the ERSPs or TVPs described herein, can be operably linked to a STA, for example, any of the translational stabilizing proteins described, or taught by this document including GFP (Green Fluorescent Protein; SEQ ID NO:34; NCBI Accession No. P42212), or Jun a 3, (*Juniperus ashei*; SEQ ID NO:36; NCBI Accession No. P81295.1).

Plants can be transiently or stably transfected with the DNA sequence that encodes a TVP or an insecticidal protein comprising one or more TVPs using anyone of the transfection methods described above. Alternatively, plants can be transfected with a polynucleotide that encodes a TVP operably linked to an ERSP, LINKER, and/or a STA protein encoding polynucleotide. For example, in some embodiments, a transgenic plant or plant genome can be transfected to incorporate the polynucleotide sequence that encodes the Endoplasmic Reticulum Signal Peptide (ERSP); TVP; and/or intervening linker peptide (LINKER or L), thus causing mRNA transcribed from the heterogeneous DNA to be expressed in the transformed plant.

The present disclosure may be used for transformation of any plant species, including, but not limited to, monocots and dicots. Crops for which a transgenic approach or PEP would be an especially useful approach include, but are not limited to: alfalfa, cotton, tomato, maize, wheat, corn, sweet corn, lucerne, soybean, sorghum, field pea, linseed, safflower, rapeseed, oil seed rape, rice, soybean, barley, sunflower, trees (including coniferous and deciduous), flowers (including those grown commercially and in greenhouses), field lupins, switchgrass, sugarcane, potatoes, tomatoes, tobacco, crucifers, peppers, sugarbeet, barley, and oilseed rape, *Brassica* sp., rye, millet, peanuts, sweet potato, cassaya, coffee, coconut, pineapple, citrus trees, cocoa, tea, banana, avocado, fig, guava, mango, olive, papaya, cashew, macadamia, almond, oats, vegetables, ornamentals, and conifers.

In some embodiments, the TVP expression open reading frame (ORF) described herein is a polynucleotide sequence that will enable the plant to express mRNA, which in turn will be translated into peptides be expressed, folded properly, and/or accumulated to such an extent that said proteins provide a dose sufficient to inhibit and/or kill one or more pests. In one embodiment, an example of a protein TVP expression ORF can be a U1-agatoxin-Ta1b variant polynucleotide (tvp), an "ersp" (i.e., the polynucleotide sequence that encodes the ERSP polypeptide) a "linker" (i.e., the polynucleotide sequence that encodes the LINKER polypeptide), a "sta" (i.e., the polynucleotide sequence that encodes the STA polypeptide), or any combination thereof, and can be described in the following equation format:

$$\text{ersp-sta-(linker}_i\text{-tvp}_j)_n\text{, or ersp-(tvp}_j\text{-linker}_i)_n\text{-sta}$$

The foregoing illustrative embodiment of a polynucleotide equation would result in the following protein complex being expressed: ERSP-STA-$(\text{LINKER}_I\text{-TVP}_J)_N$, containing four possible peptide components with dash signs to separate each component. The nucleotide component of ersp is a polynucleotide segment encoding a plant endoplasmic reticulum trafficking signal peptide (ERSP). The component of sta is a polynucleotide segment encoding a translation stabilizing protein (STA), which helps the accumulation of the TVP expressed in plants, however, in some embodiments, the inclusion of sta may not be necessary in the TVP expression ORF. The component of linker$_i$ is a polynucleotide segment encoding an intervening linker peptide (L OR LINKER) to separate the TVP from other components contained in ORF, and from the translation stabilizing protein. The subscript letter "i" indicates that in some embodiments, different types of linker peptides can be used in the TVP expression ORF. The component "tvp" indicates the polynucleotide segment encoding the TVP (also known as the U1-agatoxin-Ta1b variant polynucleotide sequence). The subscript "j" indicates different U1-agatoxin-Ta1b variant polynucleotides may be included in the TVP expression ORF. For example, in some embodiments, the U1-agatoxin-Ta1b variant polynucleotide sequence can encode a TVP with an amino acid substitution, or an amino acid deletion. The subscript "n" as shown in "(linker$_i$-tvp$_j$)$_n$," indicates that the structure of the nucleotide encoding an intervening linker peptide and a TVP can be repeated "n" times in the same open reading frame in the same TVP expression ORF, where "n" can be any integrate number from 1 to 10; "n" can be from 1 to 10, specifically "n" can be 1, 2, 3, 4, or 5, and in some embodiments "n" is 6, 7, 8, 9 or 10. The repeats may contain polynucleotide segments encoding different intervening linkers (LINKER) and different TVPs. The different polynucleotide segments including the repeats within the same TVP expression ORF are all within the same translation frame. In some embodiments, the inclusion of a sta polynucleotide in the TVP expression ORF may not be required. For example, an ersp polynucleotide sequence can be directly be linked to the polynucleotide encoding a TVP variant polynucleotide without a linker.

In the foregoing exemplary equation, the polynucleotide "tvp" encoding the polypeptide "TVP" can be the polynucleotide sequence that encodes any variant U1-agatoxin-Ta1b variant polypeptide. For example, in some embodiments, the "tvp" polynucleotide can encode a TVP having an amino acid sequence that is at least 95% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-K-X$_6$ (SEQ ID NO: 151), wherein the polypeptide comprises at least one amino acid substitution relative to the wild-type sequence of U1-agatoxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; and wherein X$_6$ is G or absent.

In some embodiments, the "tvp" polynucleotide can encode a TVP having an amino acid sequence as set forth in any one of SEQ ID NOs: 2, 3, 4, 5, 6, 7, 8, 9, 10, 11, 12, 13, 14, and 15.

In some embodiments, the "tvp" polynucleotide or complementary nucleotide sequence thereof, as set forth in any one of SEQ NOs 17, 18, 19, 20, 21, 22, 23, 24, 25, 26, 27, 28, 29, and 30.

In the foregoing exemplary equation, the polynucleotide "tvp" encoding the polypeptide "TVP" can be the polynucleotide sequence that encodes any variant U1-agatoxin-Ta1b variant polypeptide. For example, in some embodiments, the "tvp" polynucleotide can encode a TVP having an amino acid sequence that is at least 95% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-K-X$_6$ (SEQ ID NO: 151), wherein the polypeptide comprises at least one amino acid substitution relative to the wild-type sequence of U1-agatoxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is G or absent; and wherein if Z$_1$ is T then the TVP is glycosylated.

In some embodiments, TVP expression ORF starts with an ersp at its 5'-end. For the TVP to be properly folded and functional when it is expressed from a transgenic plant, it must have an ersp nucleotide fused in frame with the polynucleotide encoding a TVP. During the cellular translation process, translated ERSP can direct the TVP being translated to insert into the Endoplasmic Reticulum (ER) of the plant cell by binding with a cellular component called a signal-recognition particle. Within the ER the ERSP peptide is cleaved by signal peptidase and the TVP is released into the ER, where the TVP is properly folded during the post-translation modification process, for example, the formation of disulfide bonds. Without any additional retention protein signals, the protein is transported through the ER to the Golgi apparatus, where it is finally secreted outside the plasma membrane and into the apoplastic space. TVP can accumulate at apoplastic space efficiently to reach the insecticidal dose in plants.

The ERSP peptide is at the N-terminal region of the plant-translated TVP complex and the ERSP portion is composed of about 3 to 60 amino acids. In some embodiments it is 5 to 50 amino acids. In some embodiments it is 10 to 40 amino acids but most often is composed of 15 to 20; 20 to 25; or 25 to 30 amino acids. The ERSP is a signal peptide so called because it directs the transportation of a protein. Signal peptides may also be called targeting signals, signal sequences, transit peptides, or localization signals. The signal peptides for ER trafficking are often 15 to 30 amino acid residues in length and have a tripartite organization, comprising a core of hydrophobic residues flanked by a positively charged amino terminal and a polar, but uncharged carboxyterminal region. (Zimmermann, et al, "Protein translocation across the ER membrane," Biochimica et Biohysica Acta, 2011, 1808: 912-924).

Many ERSPs are known. It is NOT required that the ERSP be derived from a plant ERSP, non-plant ERSPs will work with the procedures described herein. Many plant ERSPs are however well known and we describe some plant derived ERSPs here. For example, ins some embodiments, the ERSP can be a barley alpha-amylase signal peptide (BAAS), which is derived from the plant, *Hordeum vulgare*, and has an amino acid sequence as follows: MANKHLSLSLFLVLLGLSASLASG (SEQ ID NO:37).

Plant ERSPs, which are selected from the genomic sequence for proteins that are known to be expressed and released into the apoplastic space of plants, include examples such as BAAS, carrot extensin, and tobacco PRI. The following references provide further descriptions, and are incorporated by reference herein in their entirety: De Loose, M. et al. "The extensin signal peptide allows secretion of a heterologous protein from protoplasts" Gene, 99 (1991) 95-100; De Loose, M. et al. described the structural analysis of an extension-encoding gene from *Nicotiana plumbaginifolia*, the sequence of which contains a typical signal peptide for translocation of the protein to the endoplasmic reticulum; Chen, M. H. et al. "Signal peptide-dependent targeting of a rice alpha-amylase and cargo proteins to plastids and extracellular compartments of plant cells" Plant Physiology, 2004 July; 135(3): 1367-77. Epub 2004 Jul. 2. Chen, M. H. et al. studied the subcellular localization of α-amylases in plant cells by analyzing the expression of α-amylase, with and without its signal peptide, in transgenic tobacco. These references and others teach and disclose the signal peptide that can be used in the methods, procedures and peptide, protein and nucleotide complexes and constructs described herein.

The tobacco extensin signal peptide motif is another exemplary type of ERSP. See Memelink et al, the Plant Journal, 1993, V4: 1011-1022; Pogue G P et al, Plant Biotechnology Journal, 2010, V8: 638-654, the disclosures of which are incorporated herein by reference in their entireties.

In some embodiments, a TVP expression ORF can have a tobacco extensin signal peptide motif. In one embodiment, the TVP expression ORF can have an extensin motif according to SEQ ID NO:38. In another embodiment, the TVP expression ORF can have an extensin motif according to SEQ ID NO:39.

An illustrative example of how to generate an embodiment with an extensin signal motif is as follows: A DNA sequence encoding an extensin motif is designed (for example, the DNA sequence shown in SEQ ID NO:40 or SEQ ID NO:41) using oligo extension PCR with four synthetic DNA primers; ends sites such as a restriction site, for example, a Pac I restriction site at the 5'-end, and a 5'-end of a GFP sequence at the 3'-end, can be added using PCR with the extensin DNA sequence serving as a template, and resulting in a fragment; the fragment is used as the forward PCR primer to amplify the DNA sequence encoding a TVP expression ORF, for example "gfp-l-tvp" contained in a pFECT vector, thus producing a TVP expression ORF encoding (from N' to C' terminal) "ERSP-GFP-L-TVP" wherein the ERSP is extensin. The resulting DNA sequence can then be cloned into Pac I and Avr II restriction sites of a FECT vector to generate the pFECT-TVP vector for transient plant expression of GFP fused TVP.

In some embodiments, an illustrative expression system can include the FECT expression vectors containing TVP expression ORF is transformed into *Agrobacterium*, GV3101, and the transformed GV3101 is injected into tobacco leaves for transient expression of TVP expression ORF.

Translational Stabilizing Protein (STA)

A translational stabilizing protein (STA) can increase the amount of TVP in plant tissues. One of the TVP expression ORFs, ERSP-TVP, is sufficient to express a properly folded TVP in the transfected plant, but in some embodiments, effective protection of a plant from pest damage may require that the plant expressed TVP accumulate. With transfection of a properly constructed TVP expression ORF, a transgenic plant can express and accumulate greater amounts of the correctly folded TVP. When a plant accumulates greater amounts of properly folded TVP, it can more easily resist, inhibit, and/or kill the pests that attack and eat the plants. One method of increasing the accumulation of a polypeptide in transgenic tissues is through the use of a translational stabilizing protein (STA). The translational stabilizing protein can be used to significantly increase the accumulation of TVP in plant tissue, and thus increase the efficacy of a plant transfected with TVP with regard to pest resistance. The translational stabilizing protein is a protein with sufficient tertiary structure that it can accumulate in a cell without being targeted by the cellular process of protein degradation. The following equations describe two examples of a TVP expression ORF that encodes a stabilizing protein fused with U1-agatoxin-Ta1b Variant polynucleotide sequence:

ersp-sta-l-tvp or ersp-tvp-l-sta

In some embodiments, the translational stabilizing protein can be a domain of another protein, or it can comprise an entire protein sequence. In some embodiments, the translational stabilizing protein can be between 5 and 50 amino acids, 50 to 250 amino acids (e.g., GNA), 250 to 750 amino acids (e.g., chitinase) and 750 to 1500 amino acids (e.g., enhancin).

One embodiment of the translational stabilizing protein can be a polymer of fusion proteins comprising at least one TVP. A specific example of a translational stabilizing protein is provided here to illustrate the use of a translational stabilizing protein. The example is not intended to limit the disclosure or claims in any way. Useful translational stabilizing proteins are well known in the art, and any proteins of this type could be used as disclosed herein. Procedures for evaluating and testing production of peptides are both known in the art and described herein. One example of one translational stabilizing protein is Green-Fluorescent Protein (GFP) (SEQ ID NO:34; NCBI Accession No. P42212.1).

Additional examples of translational stabilizing proteins can be found in the following references, the disclosures of which are incorporated by reference in their entirety: Kramer, K. J. et al. "Sequence of a cDNA and expression of the gene encoding epidermal and gut chitinases of *Manduca sexta*" Insect Biochemistry and Molecular Biology, Vol. 23, Issue 6, September 1993, pp. 691-701. Kramer, K. J. et al. isolated and sequenced a chitinase-encoding cDNA from the tobacco hornworm, *Manduca sexta*. Hashimoto, Y. et al. "Location and nucleotide sequence of the gene encoding the viral enhancing factor of the *Trichoplusia ni* granulosis virus" Journal of General Virology, (1991), 72, 2645-2651. These references and others teach and disclose translational stabilizing proteins that can be used in the methods, procedures and peptide, protein and nucleotide complexes and constructs described herein.

In some embodiments, a TVP expression ORF can be transformed into a plant, for example, in the tobacco plant, *Nicotiana benthamiana*, using a TVP expression ORF that contains a STA. For example, in some embodiments, the STA can be Jun a 3. The mature Jun a 3 is a ~30 kDa plant defending protein that is also an allergen for some people. Jun a 3 is produced by *Juniperus ashei* trees and can be used in some embodiments as a translational stabilizing protein (STA). In some embodiments, the Jun a 3 amino acid sequence can be the sequence shown in SEQ ID NO:36. In other embodiments, the Jun a 3 amino acid sequence can be the sequence shown in SEQ ID NO:42.

Linkers

Linker proteins assist in the proper folding of the different motifs composing a TVP expression ORF. The TVP expression ORF described in this invention also incorporates polynucleotide sequences encoding intervening linker peptides between the polynucleotide sequences encoding the TVP (tvp) and the translational stabilizing protein (sta), or between polynucleotide sequence encoding multiple polynucleotide sequences encoding TVP, i.e., $(l\text{-}tvp)_N$ or $(tvp\text{-}l)_N$, if the expression ORF involves multiple TVP domain expression. The intervening linker peptides (LINKERS or L or $L_{INK}$) separate the different parts of the expressed TVP construct, and help proper folding of the different parts of the complex during the expression process. In the expressed TVP construct, different intervening linker peptides can be involved to separate different functional domains. In some embodiments, the LINKER is attached to a TVP and this bivalent group can be repeated up to 10 (N=1-10) and possibly even more than 10 times (e.g., N=200) in order to facilitate the accumulation of properly folded TVP in the plant that is to be protected.

In some embodiments the intervening linker peptide can be between 1 and 30 amino acids in length. However, it is not necessarily an essential component in the expressed TVP in plants. A cleavable linker peptide can be designed to the TVP expression ORF to release the properly TVP from the expressed TVP complex in the transformed plant to improve the protection the TVP affords the plant with regard to pest damage. One type of the intervening linker peptide is the plant cleavable linker peptide. This type of linker peptides can be completely removed from the expressed TVP expression ORF complex during plant post-translational modification. Therefore, in some embodiments, the properly folded TVP linked by this type of intervening linker peptides can be released in the plant cells from the expressed TVP expression ORF complex during post-translational modification in the plant.

Another type of the cleavable intervening linker peptide is not cleavable during the expression process in plants. However, it has a protease cleavage site specific to serine, threonine, cysteine, aspartate proteases or metalloproteases. The type of cleavable linker peptide can be digested by proteases found in the insect and lepidopteran gut environment and/or the insect hemolymph and lepidopteran hemolymph environment to release the TVP in the insect gut or hemolymph. Using the information taught by this disclosure it should be a matter of routine for one skilled in the art to make or find other examples of LINKERS that will be useful in this invention.

In some embodiments, the TVP expression ORF can contain a cleavable type of intervening linker, for example, the type listed in SEQ ID NO:31, having the amino acid code of "IGER" (SEQ ID NO:31). The molecular weight of this intervening linker or LINKER is 473.53 Daltons. In other embodiments, the intervening linker peptide (LINKER) can also be one without any type of protease cleavage site, i.e. an uncleavable intervening linker peptide, for example, the linker "ETMFKHGL" (SEQ ID NO:33).

In some embodiments, the TVP-insecticidal protein can have two or more cleavable peptides, wherein the insecticidal protein comprises an insect cleavable linker (L), the insect cleavable linker being fused in frame with a construct comprising $(TVP\text{-}L)_n$, wherein "n" is an integer ranging from 1 to 200, or from 1 to 100, or from 1 to 10. In another embodiment, the TVP-insecticidal protein, and described herein, comprises an endoplasmic reticulum signal peptide (ERSP) operably linked with a TVP, which is operably linked with an insect cleavable linker (L) and/or a repeat construct (L-TVP)$_n$ or (TVP-L)$_n$, wherein n is an integer ranging from 1 to 200, or from 1 to 100, or from 1 to 10.

In some embodiments, a protein comprising an Endoplasmic Reticulum Signal Peptide (ERSP) can be operably linked to a TVP and an intervening linker peptide (L or Linker); such a construct is designated as ERSP-L-TVP, or ERSP-TVP-L, wherein said ERSP is the N-terminal of said protein, and said L or Linker may be either on the N-terminal side (upstream) of the TVP, or the C-terminal side (downstream) of the TVP. A protein designated as ERSP-L-TVP, or ERSP-TVP-L, comprising any of the ERSPs or TVPs described herein, can have a Linker "L" that can be an uncleavable linker peptide, or a cleavable linker peptide, and which may be cleavable in a plant cells during protein expression process, or may be cleavable in an insect gut environment and/or hemolymph environment.

In some embodiments, a TVP-insecticidal protein can comprise any of the intervening linker peptides (LINKER or L) described herein, or taught by this document, including but not limited to following sequences: IGER (SEQ ID NO:181), EEKKN, (SEQ ID NO:182), and ETMFKHGL (SEQ ID NO: 183), or combinations thereof.

In some embodiments, the linker can be one or more of the following: ALKFLV (SEQ ID NO: 61), ALKLFV (SEQ ID NO: 62), IFVRLR (SEQ ID NO: 63), LFAAPF (SEQ ID NO: 64), ALKFLVGS (SEQ ID NO: 65), ALKLFVGS (SEQ ID NO: 66), IFVRLRGS (SEQ ID NO: 67), LFAAPFGS (SEQ ID NO: 68), LFVRLRGS (SEQ ID NO: 69), and/or LGERGS (SEQ ID NO: 70).

An exemplary description of the foregoing linkers, and methods of making and using the same, are provided in U.S. Patent Application Publication No. US20180362598A1, the disclosure of which is incorporated herein by reference in its entirety.

In various embodiments, an exemplary insecticidal protein can include a protein construct comprising: (ERSP)-(TVP-L)$_n$; (ERSP)-(L)-(TVP-L)$_n$; (ERSP)-(L-TVP)$_n$; (ERSP)-(L-TVP)$_n$-(L); wherein n is an integer ranging from 1 to 200 or from 1 to 100, or from 1 to 10. In various related embodiments described above, a TVP is the Ta1b variant peptide, L is a non-cleavable or cleavable peptide, and n is an integer ranging from 1 to 200, preferably an integer ranging from 1 to 100, and more preferably an integer ranging from 1 to 10. In some embodiments, the TVP-insecticidal protein may contain TVP peptides that are the same or different, and insect cleavable peptides that are the same or different. In some embodiments, the C-terminal TVP is operably linked at its C-terminus with a cleavable peptide that is operable to be cleaved in an insect gut environment. In some embodiments, the N-terminal TVP is operably linked at its N-terminus with a cleavable peptide that is operable to be cleaved in an insect gut environment.

Some of the available proteases and peptidases found in the insect gut environment are dependent on the life-stage of the insect, as these enzymes are often spatially and temporally expressed. The digestive system of the insect is composed of the alimentary canal and associated glands. Food enters the mouth and is mixed with secretions that may or may not contain digestive proteases and peptidases. The foregut and the hind gut are ectodermal in origin. The foregut serves generally as a storage depot for raw food. From the foregut, discrete boluses of food pass into the midgut (mesenteron or ventriculus). The midgut is the site of digestion and absorption of food nutrients. Generally, the presence of certain proteases and peptidases in the midgut follow the pH of the gut. Certain proteases and peptidases in the human gastrointestinal system may include: pepsin, trypsin, chymotrypsin, elastase, carboxypeptidase, aminopeptidase, and dipeptidase.

The insect gut environment includes the regions of the digestive system in the herbivore species where peptides and proteins are degraded during digestion. Some of the available proteases and peptidases found in insect gut environments may include: (1) serine proteases; (2) cysteine proteases; (3) aspartic proteases, and (4) metalloproteases.

The two predominant protease classes in the digestive systems of phytophagous insects are the serine and cysteine proteases. Murdock et al. (1987) carried out an elaborate study of the midgut enzymes of various pests belonging to Coleoptera, while Srinivasan et al. (2008) have reported on the midgut enzymes of various pests belonging to Lepidoptera. Serine proteases are known to dominate the larval gut environment and contribute to about 95% of the total digestive activity in Lepidoptera, whereas the Coleopteran species have a wider range of dominant gut proteases, including cysteine proteases.

The papain family contains peptidases with a wide variety of activities, including endopeptidases with broad specificity (such as papain), endopeptidases with very narrow specificity (such as glycyl endopeptidases), aminopeptidases, dipeptidyl-peptidase, and peptidases with both endopeptidase and exopeptidase activities (such as cathepsins B and H). Other exemplary proteinases found in the midgut of various insects include trypsin-like enzymes, e.g. trypsin and chymotrypsin, pepsin, carboxypeptidase-B and aminotripeptidases.

Serine proteases are widely distributed in nearly all animals and microorganisms (Joanitti et al., 2006). In higher organisms, nearly 2% of genes code for these enzymes (Barrette-Ng et al., 2003). Being essentially indispensable to the maintenance and survival of their host organism, serine proteases play key roles in many biological processes. Serine proteases are classically categorized by their substrate specificity, notably by whether the residue at P1: trypsin-like (Lys/Arg preferred at P1), chymotrypsin-like (large hydrophobic residues such as Phe/Tyr/Leu at P1), or elastase-like (small hydrophobic residues such as Ala/Val at P1) (revised by Tyndall et. al., 2005). Serine proteases are a class of proteolytic enzymes whose central catalytic machinery is composed of three invariant residues, an aspartic acid, a histidine and a uniquely reactive serine, the latter giving rise to their name, the "catalytic triad". The Asp-His-Ser triad can be found in at least four different structural contexts (Hedstrom, 2002). These four clans of serine proteases are typified by chymotrypsin, subtilisin, carboxypeptidase Y, and Cip protease. The three serine proteases of the chymotrypsin-like clan that have been studied in greatest detail are chymotrypsin, trypsin, and elastase. More recently, serine proteases with novel catalytic triads and dyads have been discovered for their roles in digestion, including Ser-His-Glu, Ser-Lys/His, His-Ser-His, and N-terminal Ser.

One class of well-studied digestive enzymes found in the gut environment of insects is the class of cysteine proteases. The term "cysteine protease" is intended to describe a protease that possesses a highly reactive thiol group of a cysteine residue at the catalytic site of the enzyme. There is evidence that many phytophagous insects and plant parasitic nematodes rely, at least in part, on midgut cysteine proteases for protein digestion. These include but are not limited to Hemiptera, especially squash bugs (*Anasa tristis*); green stink bug (*Acrosternum hilare*); *Riptortus clavatus*; and almost all Coleoptera examined to date, especially, Colorado potato beetle (*Leptinotarsa deaemlineata*); three-lined potato beetle (*Lema trilineata*); asparagus beetle (*Crioceris*

*asparagi*); Mexican bean beetle (*Epilachna varivestis*); red flour beetle (*Triolium castaneum*); confused flour beetle (*Tribolium confusum*); the flea beetles (*Chaetocnema* spp., *Haltica* spp., and *Epitrix* spp.); corn rootworm (*Diabrotica* Spp.); cowpea weevil (*Callosobruchus aculatue*); boll weevil (*Antonomus grandis*); rice weevil (*Sitophilus oryza*); maize weevil (*Sitophilus zeamais*); granary weevil (*Sitophilus granarius*); Egyptian alfalfa weevil (*Hypera postica*); bean weevil (*Acanthoseelides obtectus*); lesser grain borer (*Rhyzopertha dominica*); yellow meal worm (*Tenebrio molitor*); Thysanoptera, especially, western flower thrips (*Franklini ella occidentalis*); Diptera, especially, leafminer spp. (*Liriomyza trifolii*); plant parasitic nematodes especially the potato cyst nematodes (*Globodera* spp.), the beet cyst nematode (*Heterodera schachtii*) and root knot nematodes (*Meloidogyne* spp.).

Another class of digestive enzymes is the aspartic proteases. The term "aspartic protease" is intended to describe a protease that possesses two highly reactive aspartic acid residues at the catalytic site of the enzyme and which is most often characterized by its specific inhibition with pepstatin, a low molecular weight inhibitor of nearly all known aspartic proteases. There is evidence that many phytophagous insects rely, in part, on midgut aspartic proteases for protein digestion most often in conjunction with cysteine proteases. These include but are not limited to Hemiptera especially (*Rhodnius prolixus*) and bedbug (*Cimex* spp.) and members of the families Phymatidae, Pentatomidae, Lygaeidae and Belostomatidae; Coleoptera, in the families of the Meloidae, Chrysomelidae, Coccinelidae and Bruchidae all belonging to the series Cucujiformia, especially, Colorado potato beetle (*Leptinotarsa decemlineata*) three-lined potato beetle (*Lematri lineata*); southern and western corn rootworm (*Diabrotica undecimpunctata* and *D. virgifera*), boll weevil (*Anthonomus grandis*), squash bug (*Anasatristis*); flea beetle (*Phyllotreta crucifera*), bruchid beetle (*Callosobruchus maculatus*), Mexican bean beetle (*Epilachna varivestis*), soybean leafminer (*Odontota horni*), margined blister beetle (*Epicauta pestifera*) and the red flour beetle (*Triolium castaneum*); Diptera, especially housefly (*Musca domestica*). See Terra and Ferreira (1994) Comn. Biochem. Physiol. 109B: 1-62; Wolfson and Murdock (1990) J. Chem. Ecol. 16: 1089-1102.

Other examples of intervening linker peptides can be found in the following references, which are incorporated by reference herein in their entirety: a plant expressed serine proteinase inhibitor precursor was found to contain five homogeneous protein inhibitors separated by six same linker peptides, as disclosed in Heath et al. "Characterization of the protease processing sites in a multidomain proteinase inhibitor precursor from *Nicotiana alata*" European Journal of Biochemistry, 1995; 230: 250-257. A comparison of the folding behavior of green fluorescent proteins through six different linkers is explored in Chang, H. C. et al. "De novo folding of GFP fusion proteins: high efficiency in eukaryotes but not in bacteria" Journal of Molecular Biology, 2005 Oct. 21; 353(2): 397-409. An isoform of the human GalNAc-Ts family, GalNAc-T2, was shown to retain its localization and functionality upon expression in *N. benthamiana* plants by Daskalova, S. M. et al. "Engineering of *N. benthamiana* L. plants for production of N-acetylgalactosamine-glycosylated proteins" BMC Biotechnology, 2010 Aug. 24; 10: 62. The ability of endogenous plastid proteins to travel through stromules was shown in Kwok, E. Y. et al. "GFP-labelled Rubisco and aspartate aminotransferase are present in plastid stromules and traffic between plastids" Journal of Experimental Botany, 2004 March; 55(397): 595-604. Epub 2004

Jan. 30. A report on the engineering of the surface of the tobacco mosaic virus (TMV), virion, with a mosquito decapeptide hormone, trypsin-modulating oostatic factor (TMOF) was made by Borovsky, D. et al. "Expression of *Aedes* trypsin-modulating oostatic factor on the virion of TMV: A potential larvicide" Proc Natl Acad Sci, 2006 December 12; 103(50): 18963-18968. These references and others teach and disclose the intervening linkers that can be used in the methods, procedures and peptide, protein and nucleotide complexes and constructs described herein.

The TVP ORF and TVP Constructs

"TVP ORF" refers to a nucleotide encoding a TVP, and/or one or more stabilizing proteins, secretory signals, or target directing signals, for example, ERSP or STA, and is defined as the nucleotides in the ORF that has the ability to be translated. Thus, a "TVP ORF diagram" refers to the composition of one or more TVP ORFs, as written out in diagram or equation form. For example, a "TVP ORF diagram" can be written out as using acronyms or short-hand references to the DNA segments contained within the expression ORF. Accordingly, in one example, a "TVP ORF diagram" may describe the polynucleotide segments encoding the ERSP, LINKER, STA, and TVP, by diagramming in equation form the DNA segments as "ersp" (i.e., the polynucleotide sequence that encodes the ERSP polypeptide); "linker" or "L" (i.e., the polynucleotide sequence that encodes the LINKER polypeptide); "sta" (i.e., the polynucleotide sequence that encodes the STA polypeptide), and "tvp" (i.e., the polynucleotide sequence encoding a TVP), respectively. An example of a TVP ORF diagram is "ersp-sta-(linker$_i$-tvp$_j$)$_N$," or "ersp-(tvp$_j$-linker$_i$)$_N$-sta" and/or any combination of the DNA segments thereof.

The following equations describe two examples of a TVP ORF that encodes an ERSP, a STA, a linker, and a TVP:

ersp-sta-l-tvp or ersp-tvp-l-sta

In some embodiments, the TVP open reading frame (ORF) described herein is a polynucleotide sequence that will enable the plant to express mRNA, which in turn will be translated into peptides that will folded properly, and/or accumulated to such an extent that said proteins provide a dose sufficient to inhibit and/or kill one or more pests. In one embodiment, an example of a protein TVP ORF can be a polynucleotide encoding a TVP (tvp), an "ersp" (i.e., the polynucleotide sequence that encodes the ERSP polypeptide) a "linker" (i.e., the polynucleotide sequence that encodes the LINKER polypeptide), a "sta" (i.e., the polynucleotide sequence that encodes the STA polypeptide), or any combination thereof, and can be described in the following equation format:

$$\text{ersp-sta-(linker}_i\text{-tvp}_j)_n, \text{ or ersp-(tvp}_j\text{-linker}_i)_n\text{-sta}$$

The foregoing illustrative embodiment of a polynucleotide equation would result in the following protein complex being expressed: ERSP-STA-(LINKER$_i$-TVP$_j$)$_N$, containing four possible peptide components with dash signs to separate each component. The nucleotide component of ersp is a polynucleotide segment encoding a plant endoplasmic reticulum trafficking signal peptide (ERSP). The component of sta is a polynucleotide segment encoding a translation stabilizing protein (STA), which helps the accumulation of the TVP expressed in plants, however, in some embodiments, the inclusion of sta may not be necessary in the TVP ORF. The component of linker$_i$ is a polynucleotide segment encoding an intervening linker peptide (L OR LINKER) to separate the TVP from other components contained in ORF, and from the translation stabilizing protein. The subscript letter "i" indicates that in some embodiments, different types of linker peptides can be used in the TVP ORF. The component "tvp" indicates the polynucleotide segment encoding the TVP. The subscript "j" indicates different polynucleotides may be included in the TVP ORF. For example, in some embodiments, the polynucleotide sequence can encode a TVP with a different amino acid substitution. The subscript "n" as shown in "(linker$_i$-tvp$_j$)$_n$," indicates that the structure of the nucleotide encoding an intervening linker peptide and a TVP can be repeated "n" times in the same open reading frame in the same TVP ORF, where "n" can be any integrate number from 1 to 10; "n" can be from 1 to 10, specifically "n" can be 1, 2, 3, 4, or 5, and in some embodiments "n" is 6, 7, 8, 9 or 10. The repeats may contain polynucleotide segments encoding different intervening linkers (LINKER) and different TVPs. The different polynucleotide segments including the repeats within the same TVP ORF are all within the same translation frame. In some embodiments, the inclusion of a sta polynucleotide in the TVP ORF may not be required. For example, an ersp polynucleotide sequence can be directly be linked to the polynucleotide encoding a TVP variant polynucleotide without a linker.

In the foregoing exemplary equation, the polynucleotide "tvp" encoding the polypeptide "TVP" can be the polynucleotide sequence that encodes any TVP as described herein, e.g., a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-A-Q-X$_6$-X$_7$ (SEQ ID NO: 151), wherein the polypeptide comprises at least one amino acid substitution relative to the wild-type sequence of U1-agatoxin-Ta1b as set forth in SEQ ID NO: 1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent, or a complementary nucleotide sequence thereof.

In some embodiments, the TVP has one amino acid substitution at X$_1$, X$_2$, X$_3$, X$_4$, or X$_5$.

In some embodiments, the TVP has one amino acid substitution at X$_1$, X$_2$, X$_3$, X$_4$, or X$_5$; and wherein X$_7$ is Glycine.

In some embodiments, the TVP has one amino acid substitution at X$_1$, X$_2$, X$_3$, X$_4$, or X$_5$; and wherein X$_7$ is absent.

In some embodiments, the TVP has one amino acid substitution at X$_1$, X$_2$, X$_3$, X$_4$, or X$_5$; and wherein X$_6$ and X$_7$ are absent.

In some embodiments, if Z$_1$ is T or S, then the TVP is glycosylated.

In some embodiments, the tvp polynucleotide, or polynucleotide operable to encode a TVP, can encode a TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence set forth in any one of SEQ ID NOs: 2-15, 49-53, or 77-110.

In some embodiments, a polynucleotide is operable to encode a TVP-insecticidal protein having the following TVP construct orientation and/or arrangement: ERSP-TVP; ERSP-(TVP)$_N$; ERSP-TVP-L; ERSP-(TVP)$_N$-L; ERSP-(TVP-L)$_N$; ERSP-L-TVP; ERSP-L-(TVP)$_N$; ERSP-(L-TVP)$_N$; ERSP-STA-TVP; ERSP-STA-(TVP)$_N$; ERSP-TVP-STA; ERSP-(TVP)$_N$-STA; ERSP-(STA-TVP)$_N$; ERSP-(TVP-STA)$_N$; ERSP-L-TVP-STA; ERSP-L-STA-TVP; ERSP-L-(TVP-STA)$_N$; ERSP-L-(STA-TVP)$_N$; ERSP-L-(TVP)$_N$-STA; ERSP-(L-TVP)$_N$-STA; ERSP-(L-STA-TVP)$_N$; ERSP-(L-TVP-STA)$_N$; ERSP-(L-STA)$_N$-TVP; ERSP-(L-TVP)$_N$-STA; ERSP-STA-L-TVP; ERSP-STA-TVP-L; ERSP-STA-L-(TVP)$_N$; ERSP-(STA-L)$_N$-TVP; ERSP-STA-(L-TVP)$_N$; ERSP-(STA-L-TVP)$_N$; ERSP-STA-(TVP)$_N$-L; ERSP-STA-(TVP-L)$_N$; ERSP-(STA-TVP)$_N$-L; ERSP-(STA-TVP-L)$_N$; ERSP-TVP-L-STA; ERSP-TVP-STA-L; ERSP-(TVP)$_N$-STA-L ERSP-(TVP-L)$_N$-STA; ERSP-(TVP-STA)$_N$-L; ERSP-(TVP-L-STA)$_N$; or ERSP-(TVP-STA-L)$_N$; wherein N is an integer ranging from 1 to 200.

In some embodiments, any of the TVP ORFs and/or TVP constructs described herein can be produced recombinantly, e.g., in some embodiments, any of the TVP ORFs and/or TVP constructs described herein can be produced in cell culture, e.g., by a yeast cell.

Any of the aforementioned methods, and/or any of the methods described herein, can be used to incorporate into a plant or a plant part thereof, one or more polynucleotides operable to express any one or more of the TVPs or TVP-insecticidal proteins as described herein; e.g., one or more TVPs or TVP-insecticidal protein having the amino acid sequence of SEQ ID NOs: 2-15, 49-53, or 77-110, which are likewise described herein.

The present disclosure may be used for transformation of any plant species, including, but not limited to, monocots and dicots. Crops for which a transgenic approach or PEP would be an especially useful approach include, but are not limited to: alfalfa, cotton, tomato, maize, wheat, corn, sweet corn, lucerne, soybean, sorghum, field pea, linseed, safflower, rapeseed, oil seed rape, rice, soybean, barley, sunflower, trees (including coniferous and deciduous), flowers (including those grown commercially and in greenhouses), field lupins, switchgrass, sugarcane, potatoes, tomatoes, tobacco, crucifers, peppers, sugarbeet, barley, and oilseed rape, *Brassica* sp., rye, millet, peanuts, sweet potato, cassaya, coffee, coconut, pineapple, citrus trees, cocoa, tea, banana, avocado, fig, guava, mango, olive, papaya, cashew, macadamia, almond, oats, vegetables, ornamentals, and conifers.

Transforming Plants with Polynucleotides

In some embodiments, the TVP expression ORFs and TVP constructs described above and herein can be cloned into any plant expression vector for TVP to be expressed in plants, either transiently or stably.

Transient plant expression systems can be used to promptly optimize the structure of the TVP expression ORF for some specific TVP expression in plants, including the necessity of some components, codon optimization of some components, optimization of the order of each component, etc. A transient plant expression vector is often derived from a plant virus genome. Plant virus vectors provide advantages in quick and high level of foreign gene expression in plant due to the infection nature of plant viruses. The full length of the plant viral genome can be used as a vector, but often a viral component is deleted, for example the coat protein, and transgenic ORFs are subcloned in that place. The TVP expression ORF can be subcloned into such a site to create a viral vector. These viral vectors can be introduced into plant mechanically since they are infectious themselves, for example through plant wound, spray-on etc. They can also be transfected into plants via agroinfection, by cloning the virus vector into the T-DNA of the crown gall bacterium, *Agrobacterium tumefaciens*, or the hairy root bacterium, *Agrobacterium rhizogenes*. The expression of the TVP in this vector is controlled by the replication of the RNA virus, and the virus translation to mRNA for replication is controlled by a strong viral promoter, for example, 35S promoter from Cauliflower mosaic virus. Viral vectors with TVP expression ORF are usually cloned into T-DNA region in a binary vector that can replicate itself in both *E. coli* strains and *Agrobacterium* strains. The transient transfection of a plant can be done by infiltration of the plant leaves with the *Agrobacterium* cells which contain the viral vector for TVP expression. In the transient transformed plant, it is common for the foreign protein expression to be ceased in a short period of time due to the post-transcriptional gene silencing (PTGS). Sometimes a PTGS suppressing protein gene is necessary to be co-transformed into the plant transiently with the same type of viral vector that drives the expression of with the TVP expression ORF. This improves and extends the expression of the TVP in the plant. The most commonly used PTGS suppressing protein is P19 protein discovered from tomato bushy stunt virus (TBSV).

In some embodiments, transient transfection of plants can be achieved by recombining a polynucleotide encoding a TVP with any one of the readily available vectors (see above and described herein), and confirmed, using a marker or signal (e.g., GFP emission). In some embodiments, a transiently transfected plant can be created by recombining a polynucleotide encoding a TVP with a DNA encoding a GFP-Hybrid fusion protein in a vector, and transfection said vector into a plant (e.g., tobacco) using different FECT vectors designed for targeted expression. In some embodiments, a polynucleotide encoding a TVP can be recombined with a pFECT vector for APO (apoplast localization) accumulation; a pFECT vector for CYTO (cytoplasm localization) accumulation; or pFECT with ersp vector for ER (endoplasm reticulum localization) accumulation.

An exemplary transient plant transformation strategy is agroinfection using a plant viral vector due to its high efficiency, ease, and low cost. In some embodiments, a tobacco mosaic virus overexpression system can be used to transiently transform plants with TVP. See TRBO, Lindbo J A, Plant Physiology, 2007, V145: 1232-1240, the disclosure of which is incorporated herein by reference in its entirety.

The TRBO DNA vector has a T-DNA region for agroinfection, which contains a CaMV 35S promoter that drives expression of the tobacco mosaic virus RNA without the gene encoding the viral coating protein. Moreover, this system uses the "disarmed" virus genome, therefore viral plant to plant transmission can be effectively prevented.

In another embodiment, the FECT viral transient plant expression system can be used to transiently transform plants with TVP. See Liu Z & Kearney C M, BMC Biotechnology, 2010, 10:88, the disclosure of which is incorporated herein by reference in its entirety. The FECT vector contains a T-DNA region for agroinfection, which contains a CaMV 35S promoter that drives the expression of the foxtail mosaic virus RNA without the genes encoding the viral coating protein and the triple gene block. Moreover, this system uses the "disarmed" virus genome, therefore viral plant to plant transmission can be effectively prevented. To efficiently express the introduced heterologous gene, the FECT expression system additionally needs to co-express P19, a RNA silencing suppressor protein from tomato bushy stunt virus, to prevent the post-transcriptional gene silencing (PTGS) of the introduced T-DNA (the TRBO expression system does not need co-expression of P19).

In some embodiments, the TVP expression ORF can be designed to encode a series of translationally fused structural motifs that can be described as follows: N'-ERSP-STA-L-TVP-C' wherein the "N'" and "C'" indicating the N-terminal and C-terminal amino acids, respectively, and the ERSP motif can be the Barley Alpha-Amylase Signal peptide (BAAS) (SEQ ID NO:37); the stabilizing protein (STA) can be GFP (SEQ ID NO:34); the linker peptide "L" can be IGER (SEQ ID NO:31) In some embodiments, the ersp-sta-l-tvp ORF can chemically synthesized to include restrictions sites, for example a Pac I restriction site at its 5'-end, and an Avr II restriction site at its 3'-end. In some embodiments, the TVP expression ORF can be cloned into the Pac I and Avr II restriction sites of a FECT expression vector (pFECT) to create an U1-agatoxin-Ta1b variant expression vector for the FECT transient plant expression system (pFECT-TVP). To maximize expression in the FECT expression system, some embodiments may have a FECT vector expressing the RNA silencing suppressor protein P19 (pFECT-P19) generated for co-transformation.

In some embodiments, a U1-agatoxin-Ta1b variant expression vector can be recombined for use in a TRBO transient plant expression system, for example, by performing a routine PCR procedure and adding a Not I restriction site to the 3'-end of the TVP expression ORF described above, and then cloning the TVP expression ORF into Pac I and Not I restriction sites of the TRBO expression vector (pTRBO-TVP).

In some embodiments, an *Agrobacterium tumefaciens* strain, for example, commercially available GV3101 cells, can be used for the transient expression of a TVP expression ORF in a plant tissue (e.g., tobacco leaves) using one or more transient expression systems, for example, the FECT and TRBO expression systems. An exemplary illustration of such a transient transfection protocol includes the following: an overnight culture of GV3101 can be used to inoculate 200 mL Luria-Bertani (LB) medium; the cells can be allowed to grow to log phase with OD600 between 0.5 and 0.8; the cells can then be pelleted by centrifugation at 5000 rpm for 10 minutes at 4° C.; cells can then be washed once with 10 mL prechilled TE buffer (Tris-HCl 10 mM, EDTA 1 mM, pH8.0), and then resuspended into 20 mL LB medium; GV3101 cell resuspension can then be aliquoted in 250 µL fractions into 1.5 mL microtubes; aliquots can then be snap-frozen in liquid nitrogen and stored at −80° C. freezer for future transformation. The pFECT-TVP and pTRBO-TVP vectors can then be transformed into the competent GV3101 cells using a freeze-thaw method as follows: the stored competent GV3101 cells are thawed on ice and mixed with 1 to 5 µg pure DNA (pFECT-TVP or pTRBO-TVP vector). The cell-DNA mixture is kept on ice for 5 minutes, transferred to −80° C. for 5 minutes, and incubated in a 37° C. water bath for 5 minutes. The freeze-thaw treated cells are then diluted into 1 mL LB medium and shaken on a rocking table for 2 to 4 hours at room temperature. A 200 μL aliquot of the cell-DNA mixture is then spread onto LB agar plates with the appropriate antibiotics (10 μg/mL rifampicin, 25 μg/mL gentamycin, and 50 μg/mL kanamycin can be used for both pFECT-TVP transformation and pTRBO-TVP transformation) and incubated at 28° C. for two days. Resulting transformed colonies are then picked and cultured in 6 mL aliquots of LB medium with the appropriate antibiotics for transformed DNA analysis and making glycerol stocks of the transformed GV3101 cells.

In some embodiments, the transient transformation of plant tissues, for example, tobacco leaves, can be performed using leaf injection with a 3-mL syringe without needle. In one illustrative example, the transformed GV3101 cells are streaked onto an LB plate with the appropriate antibiotics (as described above) and incubated at 28° C. for two days. A colony of transformed GV3101 cells are inoculated to 5 ml of LB-MESA medium (LB media supplemented with 10 mM MES, and 20 μM acetosyringone) and the same antibiotics described above, and grown overnight at 28° C. The cells of the overnight culture are collected by centrifugation at 5000 rpm for 10 minutes and resuspended in the induction medium (10 mM MES, 10 mM MgCl$_2$, 100 μM acetosyringone) at a final OD600 of 1.0. The cells are then incubated in the induction medium for 2 hours to overnight at room temperature and are then ready for transient transformation of tobacco leaves. The treated cells can be infiltrated into the underside of attached leaves of *Nicotiana benthamiana* plants by injection, using a 3-mL syringe without a needle attached.

In some embodiments, the transient transformation can be accomplished by transfecting one population of GV3101 cells with pFECT-TVP or pTRBO-TVP and another population with pFECT-P19, mixing the two cell populations together in equal amounts for infiltration of tobacco leaves by injection with a 3-mL syringe.

Stable integration of polynucleotide operable to encode TVP is also possible with the present disclosure, for example, the TVP expression ORF can also be integrated into plant genome using stable plant transformation technology, and therefore TVPs can be stably expressed in plants and protect the transformed plants from generation to generation. For the stable transformation of plants, the TVP expression vector can be circular or linear. The TVP expression ORF, the TVP expression cassette, and/or the vector with polynucleotide encoding a TVP for stable plant transformation should be carefully designed for optimal expression in plants based on what is known to those having ordinary skill in the art, and/or by using predictive vector design tools such as Gene Designer 2.0 (Atum Bio); VectorBuilder (Cyagen); SnapGene® viewer; GeneArt™ Plasmid Construction Service (Thermo-Fisher Scientific); and/or other commercially available plasmid design services. See Tolmachov, Designing plasmid vectors. Methods Mol Biol. 2009; 542:117-29. The expression of TVP is usually controlled by a promoter that promotes transcription in some, or all the cells of the transgenic plant. The promoter can be a strong plant viral promoter, for example, the constitutive 35S promoter from Cauliflower Mosaic Virus (CaMV); it also can be a strong plant promoter, for example, the hydroperoxide lyase promoter (pHPL) from *Arabidopsis thaliana*; the *Glycine max* polyubiquitin (Gmubi) promoter from soybean; the ubiquitin promoters from different plant species (rice, corn, potato, etc.), etc. A plant transcriptional terminator often occurs after the stop codon of the ORF to halt the RNA polymerase and transcription of the mRNA. To evaluate the TVPs expression, a reporter gene can be included in the TVP expression vector, for example, beta-glucuronidase gene (GUS) for GUS straining assay, green fluorescent protein (GFP) gene for green fluorescence detection under UV light, etc. For selection of transformed plants, a selection marker gene is usually included in the TVP expression vector. In some embodiments, the marker gene expression product can provide the transformed plant with resistance to specific antibiotics, for example, kanamycin, hygromycin, etc., or specific herbicide, for example, glyphosate etc. If agroinfection technology is adopted for plant transformation, T-DNA left border and right border sequences are also included in the TVP expression vector to transport the T-DNA portion into the plant.

The constructed TVP expression vector can be transfected into plant cells or tissues using many transfection technologies. Agroinfection is a very popular way to transform a plant using an *Agrobacterium tumefaciens* strain or an *Agrobacterium rhizogenes* strain. Particle bombardment (also called Gene Gun, or Biolistics) technology is also very common method of plant transfection. Other less common transfection methods include tissue electroporation, silicon carbide whiskers, direct injection of DNA, etc. After transfection, the transfected plant cells or tissues placed on plant regeneration media to regenerate successfully transfected plant cells or tissues into transgenic plants.

Evaluation of a transformed plant can be accomplished at the DNA level, RNA level and protein level. A stably transformed plant can be evaluated at all of these levels and a transiently transformed plant is usually only evaluated at protein level. To ensure that the TVP expression ORF integrates into the genome of a stably transformed plant, the genomic DNA can be extracted from the stably transformed plant tissues for and analyzed using PCR or Southern blot. The expression of the TVP in the stably transformed plant can be evaluated at the RNA level, for example, by analyzing total mRNA extracted from the transformed plant tissues using northern blot or RT-PCR. The expression of the TVP in the transformed plant can also be evaluated in protein level directly. There are many ways to evaluate expression of TVP in a transformed plant. If a reporter gene included in the TVP expression ORF, a reporter gene assay can be performed, for example, in some embodiments a GUS straining assay for GUS reporter gene expression, a green fluorescence detection assay for GFP reporter gene expression, a luciferase assay for luciferase reporter gene expression, and/or other reporter techniques may be employed.

In some embodiments total protein can be extracted from the transformed plant tissues for the direct evaluation of the expression of the TVP using a Bradford assay to evaluate the total protein level in the sample.

In some embodiments, analytical HPLC chromatography technology, Western blot technique, or iELISA assay can be adopted to qualitatively or quantitatively evaluate the TVP in the extracted total protein sample from the transformed plant tissues. TVP expression can also be evaluated by using the extracted total protein sample from the transformed plant tissues in an insect bioassay, for example, in some embodiments, the transformed plant tissue or the whole transformed plant itself can be used in insect bioassays to evaluate TVP expression and its ability to provide protection for the plant.

Illustrative Transgenic Plants

In some embodiments, a plant, plant tissue, plant cell, plant seed, or part thereof of the present invention, can comprise one or more TVPs, or a polynucleotide encoding the same, said TVP comprising an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-aga-toxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent.

In some embodiments, a plant, plant tissue, plant cell, plant seed, or part thereof of the present invention, can comprise one or more TVPs, or a polynucleotide encoding the same, said TVP comprising an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-aga-toxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; wherein the TVP has one amino acid substitution at X$_1$, X$_2$, X$_3$, X$_4$, or X$_5$.

In some embodiments, a plant, plant tissue, plant cell, plant seed, or part thereof of the present invention, can comprise one or more TVPs, or a polynucleotide encoding the same, said TVP comprising an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-aga-toxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; wherein the TVP has one amino acid substitution at X$_1$, X$_2$, X$_3$, X$_4$, or X$_5$; and wherein X$_7$ is Glycine.

In some embodiments, a plant, plant tissue, plant cell, plant seed, or part thereof of the present invention, can comprise one or more TVPs, or a polynucleotide encoding the same, said TVP comprising an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-aga-toxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; wherein the TVP has one amino acid substitution at X$_1$, X$_2$, X$_3$, X$_4$, or X$_5$; and wherein X$_7$ is absent.

In some embodiments, a plant, plant tissue, plant cell, plant seed, or part thereof of the present invention, can comprise one or more TVPs, or a polynucleotide encoding the same, said TVP comprising an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-aga-toxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; wherein the TVP has one amino acid substitution at X$_1$, X$_2$, X$_3$, X$_4$, or X$_5$; and wherein X$_6$ and X$_7$ are absent.

In some embodiments, a plant, plant tissue, plant cell, plant seed, or part thereof of the present invention, can comprise one or more TVPs, or a polynucleotide encoding the same, said TVP comprising an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-aga-toxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; wherein the TVP comprises an amino sequence as set forth in any one of SEQ ID NOs: 2-15, 49-53, or 77-110.

In some embodiments, a plant, plant tissue, plant cell, plant seed, or part thereof of the present invention, can comprise one or more TVPs, or a polynucleotide encoding the same, said TVP comprising an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-aga-toxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; wherein the TVP is encoded by a polynucleotide sequence as set forth in any one of SEQ ID NOs: 17-30, 54-58, or 117-150, or a complementary nucleotide sequence thereof.

In some embodiments, a plant, plant tissue, plant cell, plant seed, or part thereof of the present invention, can comprise one or more TVPs, or a polynucleotide encoding the same, said TVP comprising an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-aga-toxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; wherein the TVP or polynucleotide or complementary sequence thereof comprises at least two or more TVPs.

In some embodiments, a plant, plant tissue, plant cell, plant seed, or part thereof of the present invention, can comprise one or more TVPs, or a polynucleotide encoding the same, said TVP comprising an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-agatoxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; wherein if Z$_1$ is T or S, then the TVP is glycosylated.

Confirming Successful Transformation with TVP

Following introduction of heterologous foreign DNA into plant cells, the transformation or integration of heterologous gene in the plant genome is confirmed by various methods such as analysis of nucleic acids, proteins and metabolites associated with the integrated gene.

PCR analysis is a rapid method to screen transformed cells, tissue or shoots for the presence of incorporated gene at the earlier stage before transplanting into the soil (Sambrook and Russell (2001) Molecular Cloning: A Laboratory Manual. Cold Spring Harbor Laboratory Press, Cold Spring Harbor, N.Y.). PCR is carried out using oligonucleotide primers specific to the gene of interest or *Agrobacterium* vector background, etc.

Plant transformation may be confirmed by Southern blot analysis of genomic DNA (Sambrook and Russell, 2001, supra). In general, total DNA is extracted from the transformed plant, digested with appropriate restriction enzymes, fractionated in an agarose gel and transferred to a nitrocellulose or nylon membrane. The membrane or "blot" is then probed with, for example, radiolabeled $^{32}$P target DNA fragment to confirm the integration of introduced gene into the plant genome according to standard techniques (Sambrook and Russell, 2001, supra).

In Northern blot analysis, RNA is isolated from specific tissues of transformed plant, fractionated in a formaldehyde agarose gel, and blotted onto a nylon filter according to standard procedures that are routinely used in the art (Sambrook and Russell, 2001, supra). Expression of RNA encoded by the polynucleotide encoding a TVP is then tested by hybridizing the filter to a radioactive probe derived from a TVP, by methods known in the art (Sambrook and Russell, 2001, supra).

Western blot, biochemical assays and the like may be carried out on the transgenic plants to confirm the presence of protein encoded by the TVP gene by standard procedures (Sambrook and Russell, 2001, supra) using antibodies that bind to one or more epitopes present on the TVP.

A number of markers have been developed to determine the success of plant transformation, for example, resistance to chloramphenicol, the aminoglycoside G418, hygromycin, or the like. Other genes that encode a product involved in chloroplast metabolism may also be used as selectable markers. For example, genes that provide resistance to plant herbicides such as glyphosate, bromoxynil, or imidazolinone may find particular use. Such genes have been reported (Stalker et al. (1985) J. Biol. Chem. 263:6310-6314 (bromoxynil resistance nitrilase gene); and Sathasivan et al. (1990) Nucl. Acids Res. 18:2188 (AHAS imidazolinone resistance gene). Additionally, the genes disclosed herein are useful as markers to assess transformation of bacterial, yeast, or plant cells. Methods for detecting the presence of a transgene in a plant, plant organ (e.g., leaves, stems, roots, etc.), seed, plant cell, propagule, embryo or progeny of the same are well known in the art. In one embodiment, the presence of the transgene is detected by testing for pesticidal activity.

Fertile plants expressing a TVP and/or U1-agatoxin-Ta1b variant polynucleotide may be tested for pesticidal activity, and the plants showing optimal activity selected for further breeding. Methods are available in the art to assay for pest activity. Generally, the protein is mixed and used in feeding assays. See, for example Marrone et al. (1985) J. of Economic Entomology 78:290-293.

In some embodiments, evaluating the success of a transient transfection procedure can be determined based on the expression of a reporter gene, for example, GFP. In some embodiments, GFP can be detected under U.V. light in tobacco leaves transformed with the FECT and/or TRBO vectors.

In some embodiments, TVP expression can be quantitatively evaluated in a plant (e.g., tobacco). An exemplary procedure that illustrates TVP quantification in a tobacco plant is as follows: 100 mg disks of transformed leaf tissue is collected by punching leaves with the large opening of a 1000 μL pipette tip. The collected leaf tissue is place into a 2 mL microtube with 5/32" diameter stainless steel grinding balls, and frozen in −80° C. for 1 hour, and then homogenized using a Troemner-Talboys High Throughput Homogenizer. Next, 750 μL ice-cold TSP-SE1 extraction solutions (sodium phosphate solution 50 mM, 1:100 diluted protease inhibitor cocktail, EDTA 1 mM, DIECA 10 mM, PVPP 8%, pH 7.0) is added into the tube and vortexed. The microtube is then left still at room temperature for 15 minutes and then centrifuged at 16,000 g for 15 minutes at 4° C.; 100 μL of the resulting supernatant is taken and loaded into pre-Sephadex G-50-packed column in 0.45 μm Millipore MultiScreen filter microtiter plate with empty receiving Costar microtiter plate on bottom. The microtiter plates are then centrifuged at 800 g for 2 minutes at 4° C. The resulting filtrate solution, herein called total soluble protein extract (TSP extract) of the tobacco leaves, is then ready for the quantitative analysis.

In some embodiments, the total soluble protein concentration of the TSP extract can be estimated using Pierce Coomassie Plus protein assay. BSA protein standards with known concentrations can be used to generate a protein quantification standard curve. For example, 2 μL of each TSP extract can be mixed into 200 μL of the chromogenic reagent (CPPA reagent) of the Coomassie Plus protein assay kits and incubated for 10 minutes. The chromogenic reaction can then be evaluated by reading OD595 using a SpectroMax-M2 plate reader using SoftMax Pro as control software. The concentrations of total soluble proteins can be about 0.788±0.20 μg/μL or about 0.533±0.03 μg/μL in the TSP extract from plants transformed via FECT and TRBO, respectively, and the results can be used to calculate the percentage of the expressed U1-agatoxin-Ta1b Variant peptide in the TSP (% TSP) for the iELISA assay In some embodiments, an indirect ELISA (iELISA) assay can be used to quantitatively evaluate the TVP content in the tobacco leaves transiently transformed with the FECT and/or TRBO expression systems. An illustrative example of using iELISA to quantify TVP is as follows: 5 μL of the leaf TSP extract is diluted with 95 μL of CB2 solution (Immunochemistry Technologies) in the well of an Immulon 2HD 96-well plate, with serial dilutions performed as necessary; leaf proteins obtained from extract samples are then allowed to coat the well walls for 3 hours in the dark, at room temperature, and the CB2 solution is then subsequently removed; each well is washed twice with 200 μL PBS (Gibco); 150 μL blocking solution (Block BSA in PBS with 5% non-fat dry milk) is added into each well and incubated for 1 hour, in the dark, at room temperature; after the removal of the blocking solution, a PBS wash of the wells, 100 μL of primary antibodies directed against TVP (custom antibodies are commercially available from ProMab Bio-technologies, Inc.; GenScript®; or raised using the knowl-edge readily available to those having ordinary skill in the art); the antibodies diluted at 1:250 dilution in blocking solution are added to each well and incubated for 1 hour in the dark at room temperature; the primary antibody is removed and each well is washed with PBS 4 times; 100 μL of HRP-conjugated secondary antibody (i.e., antibody directed against host species used to generate primary anti-body, used at 1:1000 dilution in the blocking solution) is added into each well and incubated for 1 hour in the dark at room temperature; the secondary antibody is removed and the wells are washed with PBS, 100 μL; substrate solution (a 1:1 mixture of ABTS peroxidase substrate solution A and solution B, KPL) is added to each well, and the chromogenic reaction proceeds until sufficient color development is apparent; 100 μL of peroxidase stop solution is added to each well to stop the reaction; light absorbance of each reaction mixture in the plate is read at 405 nm using a SpectroMax-M2 plate reader, with SoftMax Pro used as control software; serially diluted known concentrations of pure TVPs samples can be treated in the same manner as described above in the iELISA assay to generate a mass-absorbance standard curve for quantities analysis. The expressed TVP can be detected by iELISA at about 3.09±1.83 ng/μL in the leaf TSP extracts from the FECT transformed tobacco; and about 3.56±0.74 ng/μL in the leaf TSP extract from the TRBO transformed tobacco. Alterna-tively, the expressed TVP can be about 0.40% total soluble protein (% TSP) for FECT transformed plants and about 0.67% TSP in TRBO transformed plants.

Compositions and Formulations

As used herein, the terms "composition" and "formula-tions" are used interchangeably.

As used herein, "v/v" or "% v/v" or "volume per volume" refers to the volume concentration of a solution ("v/v" stands for volume per volume). Here, v/v can be used when both components of a solution are liquids. For example, when 50 mL of ingredient X is diluted with 50 mL of water, there will be 50 mL of ingredient X in a total volume of 100 mL; therefore, this can be expressed as "ingredient X 50% v/v." Percent volume per volume (% v/v) is calculated as follows: (volume of solute (mL)/volume of solution (100 mL)); e.g., % v/v=mL of solute/100 mL of solution.

As used herein, "w/w" or "% w/w" or "weight per weight" or "wt/wt" or "% wt/wt" refers to the weight concentration of a formulation or solution, i.e., percent weight in weight ("w/w" stands for weight per weight). Here, w/w expresses the number of grams (g) of a constitu-ent in 100 g of solution or mixture. For example, a mixture consisting of 30 g of ingredient X, and 70 g of water would be expressed as "ingredient X 30% w/w." Percent weight per weight (% w/w) is calculated as follows: (weight of solute (g)/weight of solution (g))×100; or (mass of solute (g)/mass of solution (g))×100.

As used herein, "w/v" or "% w/v" or "weight per volume" refers to the mass concentration of a solution, i.e., percent weight in volume ("w/v" stands for weight per volume). Here, w/v expresses the number of grams (g) of a constituent in 100 mL of solution. For example, if 1 g of ingredient X is used to make up a total volume of 100 mL, then a "1% w/v solution of ingredient X" has been made. Percent weight per volume (% w/v) is calculated as follows: (Mass of solute (g)/Volume of solution (mL))×100.

Any of the aforementioned U1-agatoxin-Ta1b Variant Polypeptides (TVPs) or TVP-insecticidal proteins described herein (e.g., those found in Table 1) can be used to create a composition, wherein said composition consists of at least one TVP, and/or at least one TVP-insecticidal protein.

In some embodiments, a composition can consist of a TVP-insecticidal protein and an excipient.

In some embodiments, the composition consists of a TVP having insecticidal activity against one or more insect spe-cies, said TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences provided in Table 1, or a pharmaceu-tically acceptable salt thereof, and an excipient.

In some embodiments, the composition consists of one or more TVPs disclosed in Table 1, and an excipient.

In some embodiments, the composition consists of a TVP having insecticidal activity against one or more insect spe-cies, said TVP comprising an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences set forth in SEQ ID NOs: 2-15, 49-53, or 77-110, or a pharmaceutically acceptable salt thereof, and an excipient.

In some embodiments, the composition consists of a TVP, wherein said TVP has an amino acid sequence as set forth in SEQ ID NOs: 2-15, 49-53, and 77-110, and an excipient.

Compositions consisting of a TVP, a TVP-insecticidal protein, or a pharmaceutically acceptable salt thereof, for example, agrochemical compositions, can include, but are not limited to, aerosols and/or aerosolized products, e.g., sprays, fumigants, powders, dusts, and/or gases; seed dress-ings; oral preparations (e.g., insect food, etc.); transgenic organisms expressing and/or producing a TVP, a TVP-insecticidal protein, and/or a TVP ORF (either transiently and/or stably), e.g., a plant or an animal.

The composition may be formulated as a powder, dust, pellet, granule, spray, emulsion, colloid, solution, or such like, and may be prepared by such conventional means as desiccation, lyophilization, homogenization, extraction, fil-tration, centrifugation, sedimentation, or concentration of a culture of cells comprising the polypeptide. In all such compositions that contain at least one such pesticidal polypeptide, the polypeptide may be present in a concentration of from about 1% to about 99% by weight.

In some embodiments, the pesticide compositions described herein may be made by formulating either the TVP, TVP-insecticidal protein, or pharmaceutically acceptable salt thereof, with the desired agriculturally-acceptable carrier. The compositions may be formulated prior to administration in an appropriate means such as lyophilized, freeze-dried, desiccated, or in an aqueous carrier, medium or suitable diluent, such as saline and/or other buffer. In some embodiments, the formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. In some embodiments, the formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, the disclosure of which is incorporated by reference herein in its entirety.

In some embodiments, the composition consists of a TVP and an excipient.

In some embodiments, the composition consists of a TVP-insecticidal protein and an excipient.

In some embodiments, a composition can consist of a TVP, a TVP-insecticidal protein, or a pharmaceutically acceptable salt thereof; and an excipient.

Sprayable Compositions

Examples of spray products of the present invention can include field sprayable formulations for agricultural usage and indoor sprays for use in interior spaces in a residential or commercial space. In some embodiments, residual sprays or space sprays consisting of a TVP, a TVP-insecticidal protein, or a pharmaceutically acceptable salt thereof can be used to reduce or eliminate insect pests in an interior space.

Surface spraying indoors (SSI) is the technique of applying a variable volume sprayable volume of an insecticide onto indoor surfaces where vectors rest, such as on walls, windows, floors and ceilings. The primary goal of variable volume sprayable volume is to reduce the lifespan of the insect pest, (for example, a fly, a flea, a tick, or a mosquito vector) and thereby reduce or interrupt disease transmission. The secondary impact is to reduce the density of insect pests within the treatment area. SSI can be used as a method for the control of insect pest vector diseases, such as Lyme disease, *Salmonella*, Chikungunya virus, Zika virus, and malaria, and can also be used in the management of parasites carried by insect vectors, such as Leishmaniasis and Chagas disease. Many mosquito vectors that harbor Zika virus, Chikungunya virus, and malaria include endophilic mosquito vectors, resting inside houses after taking a blood meal. These mosquitoes are particularly susceptible to control through surface spraying indoors (SSI) with a sprayable composition consisting of a TVP, a TVP-insecticidal protein, or a pharmaceutically acceptable salt thereof, and an excipient. As its name implies, SSI involves applying the composition onto the walls and other surfaces of a house with a residual insecticide.

In one embodiment, the composition consisting of a TVP, a TVP-insecticidal protein, or a pharmaceutically acceptable salt thereof, and an excipient will knock down insect pests that come in contact with these surfaces. SSI does not directly prevent people from being bitten by mosquitoes. Rather, it usually controls insect pests after they have blood fed, if they come to rest on the sprayed surface. SSI thus prevents transmission of infection to other persons. To be effective, SSI must be applied to a very high proportion of households in an area (usually greater than 40-80 percent). Therefore, sprays in accordance with the invention having good residual efficacy and acceptable odor are particularly suited as a component of integrated insect pest vector management or control solutions.

In contrast to SSI, which requires that the active TVP or TVP-insecticidal protein be bound to surfaces of dwellings, such as walls or ceilings, as with a paint, for example, space spray products of the invention rely on the production of a large number of small insecticidal droplets intended to be distributed through a volume of air over a given period of time. When these droplets impact on a target insect pest, they deliver a knockdown effective dose of the TVP or TVP-insecticidal protein effective to control the insect pest. The traditional methods for generating a space-spray include thermal fogging (whereby a dense cloud of a composition consisting of a TVP, a TVP-insecticidal protein, or a pharmaceutically acceptable salt thereof is produced giving the appearance of a thick fog) and Ultra Low Volume (ULV), whereby droplets are produced by a cold, mechanical aerosol-generating machine. Ready-to-use aerosols such as aerosol cans may also be used.

Because large areas can be treated at any one time, the foregoing method is a very effective way to rapidly reduce the population of flying insect pests in a specific area. And, because there is very limited residual activity from the application, it must be repeated at intervals of 5-7 days in order to be fully effective. This method can be particularly effective in epidemic situations where rapid reduction in insect pest numbers is required. As such, it can be used in urban dengue control campaigns.

Effective space-spraying is generally dependent upon the following specific principles. Target insects are usually flying through the spray cloud (or are sometimes impacted whilst resting on exposed surfaces). The efficiency of contact between the spray droplets and target insects is therefore crucial. This is achieved by ensuring that spray droplets remain airborne for the optimum period of time and that they contain the right dose of insecticide. These two issues are largely addressed through optimizing the droplet size. If droplets are too big they drop to the ground too quickly and don't penetrate vegetation or other obstacles encountered during application (limiting the effective area of application). If one of these big droplets impacts an individual insect then it is also "overkill," because a high dose will be delivered per individual insect. If droplets are too small then they may either not deposit on a target insect (no impaction) due to aerodynamics or they can be carried upwards into the atmosphere by convection currents. The optimum size of droplets for space-spray application are droplets with a Volume Median Diameter (VMD) of 10-25 microns.

In some embodiments, a sprayable composition may contain an amount of a TVP, or a pharmaceutically acceptable salt thereof, ranging from about 0.005 wt % to about 99 wt %.

In some embodiments, a sprayable composition may contain an amount of a TVP-insecticidal protein, or a pharmaceutically acceptable salt thereof, ranging from about 0.005 wt % to about 99 wt %.

Foams

The active compositions of the present invention consisting of a TVP, a TVP-insecticidal protein, or a pharmaceutically acceptable salt thereof, and an excipient, may be made available in a spray product as an aerosol-based application, including aerosolized foam applications. Pressurized cans are the typical vehicle for the formation of aerosols. An aerosol propellant that is compatible with the TVP or TVP-insecticidal protein used. Preferably, a liquefied-gas type propellant is used.

Suitable propellants include compressed air, carbon dioxide, butane and nitrogen. The concentration of the propellant in the active compound composition is from about 5 percent to about 40 percent by weight of the pyridine composition, preferably from about 15 percent to about 30 percent by weight of the composition consisting of a TVP, a TVP-insecticidal protein, or a pharmaceutically acceptable salt thereof, and an excipient.

In one embodiment, formulations consisting of a TVP, a TVP-insecticidal protein, or a pharmaceutically acceptable salt thereof can also include one or more foaming agents. Foaming agents that can be used include sodium laureth sulfate, cocamide DEA, and cocamidopropyl betaine. Preferably, the sodium laureth sulfate, cocamide DEA and cocamidopropyl are used in combination. The concentration of the foaming agent(s) in the active compound composition is from about 10 percent to about 25 percent by weight, more preferably 15 percent to 20 percent by weight of the composition.

When such formulations are used in an aerosol application not containing foaming agents, the active compositions of the present invention can be used without the need for mixing directly prior to use. However, aerosol formulations containing the foaming agents do require mixing (i.e., shaking) immediately prior to use. In addition, if the formulations containing foaming agents are used for an extended time, they may require additional mixing at periodic intervals during use.

In some embodiments, an aerosolized foam may contain an amount of a TVP, or a pharmaceutically acceptable salt thereof, ranging from about 0.005 wt % to about 99 wt %.

In some embodiments, an aerosolized foam may contain an amount of a TVP-insecticidal protein, or a pharmaceutically acceptable salt thereof, ranging from about 0.005 wt % to about 99 wt %.

Burning Formulations

In some embodiments, a dwelling area may also be treated with an active TVP or TVP-insecticidal protein composition by using a burning formulation, such as a candle, a smoke coil or a piece of incense containing the composition. For example, the composition may be formulated into household products such as "heated" air fresheners in which insecticidal compositions are released upon heating, e.g., electrically, or by burning. The active compound compositions of the present invention consisting of a TVP, a TVP-insecticidal protein, or a pharmaceutically acceptable salt thereof may be made available in a spray product as an aerosol, a mosquito coil, and/or a vaporizer or fogger.

In some embodiments, a burning formulation may contain an amount of a TVP, or a pharmaceutically acceptable salt thereof, ranging from about 0.005 wt % to about 99 wt %.

In some embodiments, a burning formulation may contain an amount of a TVP-insecticidal protein, or a pharmaceutically acceptable salt thereof, ranging from about 0.005 wt % to about 99 wt %.

Fabric Treatments

In some embodiments, fabrics and garments may be made containing a pesticidal effective composition consisting of a TVP, a TVP-insecticidal protein, or a pharmaceutically acceptable salt thereof, and an excipient. In some embodiments, the concentration of the TVP or TVP-insecticidal protein in the polymeric material, fiber, yarn, weave, net, or substrate described herein, can be varied within a relatively wide concentration range from, for example, 0.05 to 15 percent by weight, preferably 0.2 to 10 percent by weight, more preferably 0.4 to 8 percent by weight, especially 0.5 to 5, such as 1 to 3, percent by weight.

Similarly, the concentration of the composition consisting of a TVP, a TVP-insecticidal protein, or a pharmaceutically acceptable salt thereof, and an excipient (whether for treating surfaces or for coating a fiber, yarn, net, weave) can be varied within a relatively wide concentration range from, for example 0.1 to 70 percent by weight, such as 0.5 to 50 percent by weight, preferably 1 to 40 percent by weight, more preferably 5 to 30 percent by weight, especially 10 to 20 percent by weight.

The concentration of the TVP or TVP-insecticidal protein may be chosen according to the field of application such that the requirements concerning knockdown efficacy, durability and toxicity are met. Adapting the properties of the material can also be accomplished and so custom-tailored textile fabrics are obtainable in this way.

Accordingly, an effective amount of a TVP, a TVP-insecticidal protein, or a pharmaceutically acceptable salt thereof can depend on the specific use pattern, the insect pest against which control is most desired and the environment in which the TVP or TVP-insecticidal protein will be used. Therefore, an effective amount of a TVP, a TVP-insecticidal protein, or a pharmaceutically acceptable salt thereof is sufficient that control of an insect pest is achieved.

In some embodiments, a fabric treatment may contain an amount of a TVP, or a pharmaceutically acceptable salt thereof, ranging from about 0.005 wt % to about 99 wt %.

In some embodiments, a fabric treatment may contain an amount of a TVP-insecticidal protein, or a pharmaceutically acceptable salt thereof, ranging from about 0.005 wt % to about 99 wt %.

Surface-Treatment Compositions

In some embodiments, the present disclosure provides compositions or formulations consisting of a TVP and an excipient, or consisting of a TVP-insecticidal protein and an excipient, for coating walls, floors and ceilings inside of buildings, and for coating a substrate or non-living material. The inventive compositions consisting of a TVP, a TVP-insecticidal protein, or a pharmaceutically acceptable salt thereof, and an excipient, can be prepared using known techniques for the purpose in mind. Preparations of compositions consisting of a TVP-insecticidal protein and an excipient, could be so formulated to also contain a binder to facilitate the binding of the compound to the surface or other substrate. Agents useful for binding are known in the art and tend to be polymeric in form. The type of binder suitable for a compositions to be applied to a wall surface having particular porosities and/or binding characteristics would be different compared to a fiber, yarn, weave or net-thus, a skilled person, based on known teachings, would select a suitable binder based on the desired surface and/or substrate.

Typical binders are poly vinyl alcohol, modified starch, poly vinyl acrylate, polyacrylic, polyvinyl acetate co polymer, polyurethane, and modified vegetable oils. Suitable binders can include latex dispersions derived from a wide variety of polymers and co-polymers and combinations thereof. Suitable latexes for use as binders in the inventive compositions comprise polymers and copolymers of styrene, alkyl styrenes, isoprene, butadiene, acrylonitrile lower alkyl acrylates, vinyl chloride, vinylidene chloride, vinyl esters of lower carboxylic acids and alpha, beta-ethylenically unsaturated carboxylic acids, including polymers containing three or more different monomer species copolymerized therein, as well as post-dispersed suspensions of silicones or polyurethanes. Also suitable may be a polytetrafluoroethylene (PTFE) polymer for binding the active ingredient to other surfaces.

In some embodiments, a surface-treatment composition may contain an amount of a TVP, or a pharmaceutically acceptable salt thereof, ranging from about 0.005 wt % to about 99 wt %.

In some embodiments, a surface-treatment composition may contain an amount of a TVP-insecticidal protein, or a pharmaceutically acceptable salt thereof, ranging from about 0.005 wt % to about 99 wt %.

Dispersants

In some exemplary embodiments, an insecticidal formulation according to the present disclosure may consist of a TVP, a TVP-insecticidal protein, or a pharmaceutically acceptable salt thereof, and an excipient, diluent or carrier (e.g., such as water), a polymeric binder, and/or additional components such as a dispersing agent, a polymerizing agent, an emulsifying agent, a thickener, an alcohol, a fragrance, or any other inert excipients used in the preparation of sprayable insecticides known in the art.

In some embodiments, a composition consisting of a TVP, a TVP-insecticidal protein, or a pharmaceutically acceptable salt thereof, and an excipient, can be prepared in a number of different forms or formulation types, such as suspensions or capsules suspensions. And a person skilled in the art can prepare the relevant composition based on the properties of the particular TVP or TVP-insecticidal protein, its uses, and also its application type. For example, the TVP or TVP-insecticidal protein used in the methods, embodiments, and other aspects of the present disclosure, may be encapsulated in a suspension or capsule suspension formulation. An encapsulated TVP or TVP-insecticidal protein can provide improved wash-fastness, and also a longer period of activity. The formulation can be organic based or aqueous based, preferably aqueous based.

In some embodiments, a dispersant may contain an amount of a TVP, or a pharmaceutically acceptable salt thereof, ranging from about 0.005 wt % to about 99 wt %.

In some embodiments, a dispersant may contain an amount of a TVP-insecticidal protein, or a pharmaceutically acceptable salt thereof, ranging from about 0.005 wt % to about 99 wt %.

Microencapsulation

Microencapsulated TVP or TVP-insecticidal protein suitable for use in the compositions and methods according to the present disclosure may be prepared with any suitable technique known in the art. For example, various processes for microencapsulating material have been previously developed. These processes can be divided into three categories: physical methods, phase separation, and interfacial reaction. In the physical methods category, microcapsule wall material and core particles are physically brought together and the wall material flows around the core particle to form the microcapsule. In the phase separation category, microcapsules are formed by emulsifying or dispersing the core material in an immiscible continuous phase in which the wall material is dissolved and caused to physically separate from the continuous phase, such as by coacervation, and deposit around the core particles. In the interfacial reaction category, microcapsules are formed by emulsifying or dispersing the core material in an immiscible continuous phase and then an interfacial polymerization reaction is caused to take place at the surface of the core particles. The concentration of the TVP or TVP-insecticidal protein present in the microcapsules can vary from 0.1 to 60% by weight of the microcapsule.

In some embodiments, a microencapsulation may contain an amount of a TVP, or a pharmaceutically acceptable salt thereof, ranging from about 0.005 wt % to about 99 wt %.

In some embodiments, a microencapsulation may contain an amount of a TVP-insecticidal protein, or a pharmaceutically acceptable salt thereof, ranging from about 0.005 wt % to about 99 wt %.

Kits, Formulations, Dispersants, and the Ingredients Thereof

The formulation used in the compositions (consisting of a TVP, a TVP-insecticidal protein, or a pharmaceutically acceptable salt thereof, and an excipient), methods, embodiments and other aspects according to the present disclosure, may be formed by mixing all ingredients together with water, and optionally using suitable mixing and/or dispersing aggregates. In general, such a formulation is formed at a temperature of from 10 to 70° C., preferably 15 to 50° C., more preferably 20 to 40° C. Generally, a formulation comprising one or more of (A), (B), (C), and/or (D) is possible, wherein it is possible to use: a TVP, a TVP-insecticidal protein, or a pharmaceutically acceptable salt thereof (as pesticide) (A); solid polymer (B); optional additional additives (D); and to disperse them in the aqueous component (C). If a binder is present in a composition of the present invention (consisting of a TVP, a TVP-insecticidal protein, or a pharmaceutically acceptable salt thereof, and an excipient), it is preferred to use dispersions of the polymeric binder (B) in water as well as aqueous formulations of the TVP or TVP-insecticidal protein (A) in water which have been separately prepared before. Such separate formulations may contain additional additives for stabilizing (A) and/or (B) in the respective formulations and are commercially available. In a second process step, such raw formulations and optionally additional water (component (C)) are added. Also, combinations of the abovementioned ingredients based on the foregoing scheme are likewise possible, e.g., using a pre-formed dispersion of (A) and/or (B) and mixing it with solid (A) and/or (B). A dispersion of the polymeric binder (B) may be a pre-manufactured dispersion already made by a chemicals manufacturer.

Moreover, it is also within the scope of the present invention to use "hand-made" dispersions, i.e., dispersions made in small-scale by an end-user. Such dispersions may be made by providing a mixture of about 20 percent of the binder (B) in water, heating the mixture to temperature of 90° C. to 100° C. and intensively stirring the mixture for several hours. It is possible to manufacture the formulation as a final product so that it can be readily used by the end-user for the process according to the present invention. And, it is of course similarly possible to manufacture a concentrate, which may be diluted by the end-user with additional water (C) to the desired concentration for use.

In an embodiment, a composition (consisting of a TVP, a TVP-insecticidal protein, or a pharmaceutically acceptable salt thereof, and an excipient) suitable for SSI application or a coating formulation (consisting of a TVP, a TVP-insecticidal protein, or a pharmaceutically acceptable salt thereof, and an excipient), contains the active ingredient and a carrier, such as water, and may also one or more co-formulants selected from a dispersant, a wetter, an anti-freeze, a thickener, a preservative, an emulsifier and a binder or sticker.

In some embodiments, an exemplary solid formulation of a TVP, a TVP-insecticidal protein, or a pharmaceutically acceptable salt thereof, is generally milled to a desired particle size, such as the particle size distribution d(0.5) is generally from 3 to 20, preferably 5 to 15, especially 7 to 12, μm.

Furthermore, it may be possible to ship the formulation to the end-user as a kit comprising at least a first component consisting of a TVP, a TVP-insecticidal protein, or a pharmaceutically acceptable salt thereof (A); and a second component comprising at least one polymeric binder (B). Further additives (D) may be a third separate component of the kit, or may be already mixed with components (A) and/or (B). The end-user may prepare the formulation for use by just adding water (C) to the components of the kit and mixing. The components of the kit may also be formulations in water. Of course it is possible to combine an aqueous formulation of one of the components with a dry formulation of the other component(s). As an example, the kit can consist of one formulation of a TVP, a TVP-insecticidal protein, or a pharmaceutically acceptable salt thereof (A) and optionally water (C); and a second, separate formulation of at least one polymeric binder (B), water as component (C) and optionally components (D).

The concentrations of the components (A), (B), (C) and optionally (D) will be selected by the skilled artisan depending of the technique to be used for coating/treating. In general, the amount of a TVP, a TVP-insecticidal protein, or a pharmaceutically acceptable salt thereof (A) may be up to 50, preferably 1 to 50, such as 10 to 40, especially 15 to 30, percent by weight, based on weight of the composition. The amount of polymeric binder (B) may be in the range of 0.01 to 30, preferably 0.5 to 15, more preferably 1 to 10, especially 1 to 5, percent by weight, based on weight of the composition. If present, in general the amount of additional components (D) is from 0.1 to 20, preferably 0.5 to 15, percent by weight, based on weight of the composition. If present, suitable amounts of pigments and/or dyestuffs and/or fragrances are in general 0.01 to 5, preferably 0.1 to 3, more preferably 0.2 to 2, percent by weight, based on weight of the composition. A typical formulation ready for use comprises 0.1 to 40, preferably 1 to 30, percent of components (A), (B), and optionally (D), the residual amount being water (C). A typical concentration of a concentrate to be diluted by the end-user may comprise 5 to 70, preferably 10 to 60, percent of components (A), (B), and optionally (D), the residual amount being water (C).

Any of the U1-agatoxin-Ta1b Variant Polypeptides (TVPs) as described herein (e.g., those found in Table 1), and/or any of the TVP-insecticidal proteins described here; and/or any of the methods regarding the same, can be used to create any of the foregoing sprayable compositions, formulations, and/or kits as described herein.

Vitrification

Vitrification describes a process wherein the reaction kinetics of a peptide are slowed down via immobilization of the peptide in a rigid, amorphous glassy sugar matrix: this results in drastically slowing down degradation of the peptide. See Slade et al., Beyond water activity: recent advances based on an alternative approach to the assessment of food quality and safety, Crit. Rev. Food Sci. Nutr. 30 (1991) 115-360. The unfolding of peptides, and other mechanisms of degradation, are dependent on molecular mobility of a peptide; thus, vitrification slows down such degradation. See Change et al., Mechanism of protein stabilization by sugars during freeze-drying and storage: native structure preservation, specific interaction, and/or immobilization in a glassy matrix?, J Pharm. Sci. 94 (2005) 1427-1444; and G. O. Poinar and R. Hess, Ultrastructure of 40-million-year-old insect tissue, Science 80 (215) (1982) 1241-1242.

An exemplary description of vitrification, and considerations thereof in the stabilization of peptides, is provided in Mensink et al., How sugars protect proteins in the solid state and during drying (review): Mechanisms of stabilization in relation to stress conditions. Eur J Pharm Biopharm. 2017 May; 114:288-295; the disclosure of which is incorporated herein by reference in its entirety.

In some embodiments, a TVP of the present invention can be vitrified. For example, in some embodiments, a TVP of the present invention can be stabilized using the process of vitrification.

In some embodiments, vitrification can occur via the use of sugar. In some embodiments, the sugar can be trehalose.

Trehalose

Trehalose is a disaccharide formed by a 1,1-glycosidic bond between two α-glucose units. In some embodiments, the molecular formula for trehalose is $C_{12}H_{22}O_{11}$; having a molecular weight of 342.3 g/mol.

Trehalose is found in nature as a disaccharide and also as a monomer in some polymers; however, some trehalose isomers exist that are not found in nature. See Elbein et al., New insights on trehalose: a multifunctional molecule. Glycobiology. 2003 April; 13(4):17R-27R.

Trehalose has been shown to stabilize proteins and cells against stresses such as heat, freezing, and desiccation. See K. Lippert and E. Galinski, Appl. Microbiol. Biotechnol., 1992, 37, 61-65; J. K. Kaushik and R. Bhat, J. Biol. Chem., 2003, 278, 26458-26465; R. P. Baptista, S. Pedersen, G. J. Cabrita, D. E. Otzen, J. M. Cabral and E. P. Melo, Biopolymers, 2008, 89, 538-547; Guo et al., Nat. Biotechnol., 2000, 18, 168-171; Hengherr et al., FEBS J., 2008, 275, 281-288; Crowe et al., Science, 1984, 223, 701-703; Beattie et al., Diabetes, 1997, 46, 519-523; P. Sundaramurthi and R. Suryanarayanan, J. Phys. Chem. Lett., 2009, 1, 510-514; Duong et al., Appl. Environ. Microbiol., 2006, 72, 1218-1225.

Indeed, some animals accumulate trehalose to significant levels in response to environmental stresses, thus emphasizing the ability of trehalose to stabilize biological molecules. See P. Westh and H. Ramlev, J. Exp. Zool., 1991, 258, 303-311; and K. A. C. Madin and J. H. Crowe, J. Exp. Zool., 1975, 193, 335-342. Furthermore, trehalose is generally regarded as safe, and is used in several pharmaceutical drugs as stabilizers. See N. K. Jain and I. Roy, Protein Sci., 2009, 18, 24-36; and S. Ohtake and Y. J. Wang, J. Pharm. Sci., 2011, 100, 2020-2053.

The use of trehalose is well known in the art. Trehalose is readily available from commercial sources. For example, D-(+)-Trehalose dihydrate (Product No. T9531); and Trehalose (Product Nos. PHR1344 and 1673715) are available from Sigma Aldrich (Sigma-Aldrich Corp. St. Louis, MO, USA).

Exemplary trehalose molecules are provided herein, having an Chemical Abstracts Service (CAS) Reg. No. 99-20-7 (anhydrous); and CAS Reg. No. 6138-23-4 (dihydrous). An exemplary trehalose compound of the present disclosure has a PubChem CID No. 7427.

Exemplary descriptions of the use of trehalose to stabilize peptides is provided in U.S. Pat. Nos. 6,165,981; 6,171,586; 6,991,790; 7,956,028; 10,273,333; and 10,588,957; the disclosures of which are incorporated herein by reference in their entireties.

Exemplary descriptions of the preparation and use of trehalose in compositions is provided in U.S. Pat. No. 7,678,764, the disclosure of which is incorporated herein by reference in its entirety.

Illustrative Compositions and Formulations

As used herein, "formulation" and "composition" are synonymous.

Ranges and Descriptions Composition and Formulation Components

In some embodiments, a formulation of the present invention be a liquid concentrate, a wettable powder, or a granule formulation. In some embodiments, any of the TVPs, TVP-insecticidal proteins, or pharmaceutically acceptable salts thereof, as described herein, can be used in the any of the formulations described below, e.g., any of the foregoing TVPs, TVP-insecticidal proteins, or pharmaceutically acceptable salts thereof, can be used in the formulation of: a wettable powder or granule formulation; or a liquid concentrate formulation.

In some embodiments, a formulation consists of: (1) a TVP, a TVP-insecticidal protein, or a pharmaceutically acceptable salt thereof; and (2) one or more excipients; wherein the excipients comprise, consist essentially of, or consist of: trehalose; potassium phosphate dibasic (K$_2$HPO$_4$); potassium phosphate monobasic (KH$_2$PO$_4$); maltodextrin; and BIT.

In some embodiments, a formulation of the present invention consists of, a concentration of trehalose ranging from about 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% by weight of the total formulation.

In some embodiments, a formulation of the present invention consists of, a concentration of trehalose ranging from about 0.1% to about 99.9%; from about 1% to about 99.9%; from about 2% to about 99.9%; from about 3% to about 99.9%; from about 4% to about 99.9%; from about 5% to about 99.9%; from about 6% to about 99.9%; from about 7% to about 99.9%; from about 8% to about 99.9%; from about 9% to about 99.9%; from about 10% to about 99.9%; from about 11% to about 99.9%; from about 12% to about 99.9%; from about 13% to about 99.9%; from about 14% to about 99.9%; from about 15% to about 99.9%; from about 16% to about 99.9%; from about 17% to about 99.9%; from about 18% to about 99.9%; from about 19% to about 99.9%; from about 20% to about 99.9%; from about 21% to about 99.9%; from about 22% to about 99.9%; from about 23% to about 99.9%; from about 24% to about 99.9%; from about 25% to about 99.9%; from about 26% to about 99.9%; from about 27% to about 99.9%; from about 28% to about 99.9%; from about 29% to about 99.9%; from about 30% to about 99.9%; from about 31% to about 99.9%; from about 32% to about 99.9%; from about 33% to about 99.9%; from about 34% to about 99.9%; from about 35% to about 99.9%; from about 36% to about 99.9%; from about 37% to about 99.9%; from about 38% to about 99.9%; from about 39% to about 99.9%; from about 40% to about 99.9%; from about 41% to about 99.9%; from about 42% to about 99.9%; from about 43% to about 99.9%; from about 44% to about 99.9%; from about 45% to about 99.9%; from about 46% to about 99.9%; from about 47% to about 99.9%; from about 48% to about 99.9%;

from about 49% to about 99.9%; from about 50% to about 99.9%; from about 51% to about 99.9%; from about 52% to about 99.9%; from about 53% to about 99.9%; from about 54% to about 99.9%; from about 55% to about 99.9%; from about 56% to about 99.9%; from about 57% to about 99.9%; from about 58% to about 99.9%; from about 59% to about 99.9%; from about 60% to about 99.9%; from about 61% to about 99.9%; from about 62% to about 99.9%; from about 63% to about 99.9%; from about 64% to about 99.9%; from about 65% to about 99.9%; from about 66% to about 99.9%; from about 67% to about 99.9%; from about 68% to about 99.9%; from about 69% to about 99.9%; from about 70% to about 99.9%; from about 71% to about 99.9%; from about 72% to about 99.9%; from about 73% to about 99.9%; from about 74% to about 99.9%; from about 75% to about 99.9%; from about 76% to about 99.9%; from about 77% to about 99.9%; from about 78% to about 99.9%; from about 79% to about 99.9%; from about 80% to about 99.9%; from about 81% to about 99.9%; from about 82% to about 99.9%; from about 83% to about 99.9%; from about 84% to about 99.9%; from about 85% to about 99.9%; from about 86% to about 99.9%; from about 87% to about 99.9%; from about 88% to about 99.9%; from about 89% to about 99.9%; from about 90% to about 99.9%; from about 91% to about 99.9%; from about 92% to about 99.9%; from about 93% to about 99.9%; from about 94% to about 99.9%; from about 95% to about 99.9%; from about 96% to about 99.9%; from about 97% to about 99.9%; from about 98% to about 99.9%; or from about 99% to about 99.9%, wt/wt of the total formulation.

In some embodiments, a formulation of the present invention consists of, a concentration of trehalose ranging from about 0.1% to about 99%; from about 0.1% to about 98%; from about 0.1% to about 97%; from about 0.1% to about 96%; from about 0.1% to about 95%; from about 0.1% to about 94%; from about 0.1% to about 93%; from about 0.1% to about 92%; from about 0.1% to about 91%; from about 0.1% to about 90%; from about 0.1% to about 89%; from about 0.1% to about 88%; from about 0.1% to about 87%; from about 0.1% to about 86%; from about 0.1% to about 85%; from about 0.1% to about 84%; from about 0.1% to about 83%; from about 0.1% to about 82%; from about 0.1% to about 81%; from about 0.1% to about 80%; from about 0.1% to about 79%; from about 0.1% to about 78%; from about 0.1% to about 77%; from about 0.1% to about 76%; from about 0.1% to about 75%; from about 0.1% to about 74%; from about 0.1% to about 73%; from about 0.1% to about 72%; from about 0.1% to about 71%; from about 0.1% to about 70%; from about 0.1% to about 69%; from about 0.1% to about 68%; from about 0.1% to about 67%; from about 0.1% to about 66%; from about 0.1% to about 65%; from about 0.1% to about 64%; from about 0.1% to about 63%; from about 0.1% to about 62%; from about 0.1% to about 61%; from about 0.1% to about 60%; from about 0.1% to about 59%; from about 0.1% to about 58%; from about 0.1% to about 57%; from about 0.1% to about 56%; from about 0.1% to about 55%; from about 0.1% to about 54%; from about 0.1% to about 53%; from about 0.1% to about 52%; from about 0.1% to about 51%; from about 0.1% to about 50%; from about 0.1% to about 49%; from about 0.1% to about 48%; from about 0.1% to about 47%; from about 0.1% to about 46%; from about 0.1% to about 45%; from about 0.1% to about 44%; from about 0.1% to about 43%; from about 0.1% to about 42%; from about 0.1% to about 41%; from about 0.1% to about 40%; from about 0.1% to about 39%; from about 0.1% to about 38%; from about 0.1% to about 37%; from about 0.1% to about 36%; from about 0.1% to about 35%; from about 0.1% to about 34%; from about 0.1% to about 33%; from about 0.1% to about 32%; from about 0.1% to about 31%; from about 0.1% to about 30%; from about 0.1% to about 29%; from about 0.1% to about 28%; from about 0.1% to about 27%; from about 0.1% to about 26%; from about 0.1% to about 25%; from about 0.1% to about 24%; from about 0.1% to about 23%; from about 0.1% to about 22%; from about 0.1% to about 21%; from about 0.1% to about 20%; from about 0.1% to about 19%; from about 0.1% to about 18%; from about 0.1% to about 17%; from about 0.1% to about 16%; from about 0.1% to about 15%; from about 0.1% to about 14%; from about 0.1% to about 13%; from about 0.1% to about 12%; from about 0.1% to about 11%; from about 0.1% to about 10%; from about 0.1% to about 9%; from about 0.1% to about 8%; from about 0.1% to about 7%; from about 0.1% to about 6%; from about 0.1% to about 5%; from about 0.1% to about 4%; from about 0.1% to about 3%; from about 0.1% to about 2%; from about 0.1% to about 1%; or from about 0.1% to about 0.5%, wt/wt of the total formulation.

In some embodiments, a formulation of the present invention consists of, a concentration of potassium phosphate dibasic ($K_2HPO_4$) ranging from about 0.1% to about 40%; from about 0.5% to about 40%; from about 1% to about 40%; from about 2% to about 40%; from about 3% to about 40%; from about 4% to about 40%; from about 5% to about 40%; from about 6% to about 40%; from about 7% to about 40%; from about 8% to about 40%; from about 9% to about 40%; from about 10% to about 40%; from about 11% to about 40%; from about 12% to about 40%; from about 13% to about 40%; from about 14% to about 40%; from about 15% to about 40%; from about 16% to about 40%; from about 17% to about 40%; from about 18% to about 40%; from about 19% to about 40%; from about 20% to about 40%; from about 21% to about 40%; from about 22% to about 40%; from about 23% to about 40%; from about 24% to about 40%; from about 25% to about 40%; from about 26% to about 40%; from about 27% to about 40%; from about 28% to about 40%; from about 29% to about 40%; from about 30% to about 40%; from about 31% to about 40%; from about 32% to about 40%; from about 33% to about 40%; from about 34% to about 40%; from about 35% to about 40%; from about 36% to about 40%; from about 37% to about 40%; from about 38% to about 40%; or from about 39% to about 40%; wt/wt of the total formulation.

In some embodiments, a formulation of the present invention consists of a concentration of potassium phosphate dibasic ($K_2HPO_4$) ranging from about 0.1% to about 40%; from about 0.1% to about 39%; from about 0.1% to about 38%; from about 0.1% to about 37%; from about 0.1% to about 36%; from about 0.1% to about 35%; from about 0.1% to about 34%; from about 0.1% to about 33%; from about 0.1% to about 32%; from about 0.1% to about 31%; from about 0.1% to about 30%; from about 0.1% to about 29%; from about 0.1% to about 28%; from about 0.1% to about 27%; from about 0.1% to about 26%; from about 0.1% to about 25%; from about 0.1% to about 24%; from about 0.1% to about 23%; from about 0.1% to about 22%; from about 0.1% to about 21%; from about 0.1% to about 20%; from about 0.1% to about 19%; from about 0.1% to about 18%; from about 0.1% to about 17%; from about 0.1% to about 16%; from about 0.1% to about 15%; from about 0.1% to about 14%; from about 0.1% to about 13%; from about 0.1% to about 12%; from about 0.1% to about 11%; from about 0.1% to about 10%; from about 0.1% to about 9%; from about 0.1% to about 8%; from about 0.1% to about 7%; from about 0.1% to about 6%; from about 0.1% to about 5%; from about 0.1% to about 4%; from about 0.1% to about 3%; from about 0.1% to about 2%; from about 0.1% to about 1%; or from about 0.1% to about 0.5%, wt/wt of the total formulation.

In some embodiments, a formulation of the present invention consists of a concentration of potassium phosphate monobasic ($KH_2PO_4$) ranging from about 0.1% to about 20%; from about 0.5% to about 20%; from about 1% to about 20%; from about 2% to about 20%; from about 3% to about 20%; from about 4% to about 20%; from about 5% to about 20%; from about 6% to about 20%; from about 7% to about 20%; from about 8% to about 20%; from about 9% to about 20%; from about 10% to about 20%; from about 11% to about 20%; from about 12% to about 20%; from about 13% to about 20%; from about 14% to about 20%; from about 15% to about 20%; from about 16% to about 20%; from about 17% to about 20%; from about 18% to about 20%; or from about 19% to about 20%; wt/wt of the total formulation.

In some embodiments, a formulation of the present invention consists of a concentration of potassium phosphate monobasic ($KH_2PO_4$) ranging from about 0.1% to about 20%; from about 0.1% to about 19%; from about 0.1% to about 18%; from about 0.1% to about 17%; from about 0.1% to about 16%; from about 0.1% to about 15%; from about 0.1% to about 14%; from about 0.1% to about 13%; from about 0.1% to about 12%; from about 0.1% to about 11%; from about 0.1% to about 10%; from about 0.1% to about 9%; from about 0.1% to about 8%; from about 0.1% to about 7%; from about 0.1% to about 6%; from about 0.1% to about 5%; from about 0.1% to about 4%; from about 0.1% to about 3%; from about 0.1% to about 2%; from about 0.1% to about 1%; or from about 0.1% to about 0.5%, wt/wt of the total formulation.

In some embodiments, a formulation of the present invention consists of a concentration of maltodextrin ranging from about 0.1% to about 99.9%; from about 1% to about 99.9%; from about 2% to about 99.9%; from about 3% to about 99.9%; from about 4% to about 99.9%; from about 5% to about 99.9%; from about 6% to about 99.9%; from about 7% to about 99.9%; from about 8% to about 99.9%; from about 9% to about 99.9%; from about 10% to about 99.9%; from about 11% to about 99.9%; from about 12% to about 99.9%; from about 13% to about 99.9%; from about 14% to about 99.9%; from about 15% to about 99.9%; from about 16% to about 99.9%; from about 17% to about 99.9%; from about 18% to about 99.9%; from about 19% to about 99.9%; from about 20% to about 99.9%; from about 21% to about 99.9%; from about 22% to about 99.9%; from about 23% to about 99.9%; from about 24% to about 99.9%; from about 25% to about 99.9%; from about 26% to about 99.9%; from about 27% to about 99.9%; from about 28% to about 99.9%; from about 29% to about 99.9%; from about 30% to about 99.9%; from about 31% to about 99.9%; from about 32% to about 99.9%; from about 33% to about 99.9%; from about 34% to about 99.9%; from about 35% to about 99.9%; from about 36% to about 99.9%; from about 37% to about 99.9%; from about 38% to about 99.9%; from about 39% to about 99.9%; from about 40% to about 99.9%; from about 41% to about 99.9%; from about 42% to about 99.9%; from about 43% to about 99.9%; from about 44% to about 99.9%; from about 45% to about 99.9%; from about 46% to about 99.9%; from about 47% to about 99.9%; from about 48% to about 99.9%; from about 49% to about 99.9%; from about 50% to about 99.9%; from about 51% to about 99.9%; from about 52% to about 99.9%; from about 53% to about 99.9%; from about 54% to about 99.9%; from about 55% to about 99.9%; from about 56% to about 99.9%; from about 57% to about 99.9%;

from about 58% to about 99.9%; from about 59% to about 99.9%; from about 60% to about 99.9%; from about 61% to about 99.9%; from about 62% to about 99.9%; from about 63% to about 99.9%; from about 64% to about 99.9%; from about 65% to about 99.9%; from about 66% to about 99.9%; from about 67% to about 99.9%; from about 68% to about 99.9%; from about 69% to about 99.9%; from about 70% to about 99.9%; from about 71% to about 99.9%; from about 72% to about 99.9%; from about 73% to about 99.9%; from about 74% to about 99.9%; from about 75% to about 99.9%; from about 76% to about 99.9%; from about 77% to about 99.9%; from about 78% to about 99.9%; from about 79% to about 99.9%; from about 80% to about 99.9%; from about 81% to about 99.9%; from about 82% to about 99.9%; from about 83% to about 99.9%; from about 84% to about 99.9%; from about 85% to about 99.9%; from about 86% to about 99.9%; from about 87% to about 99.9%; from about 88% to about 99.9%; from about 89% to about 99.9%; from about 90% to about 99.9%; from about 91% to about 99.9%; from about 92% to about 99.9%; from about 93% to about 99.9%; from about 94% to about 99.9%; from about 95% to about 99.9%; from about 96% to about 99.9%; from about 97% to about 99.9%; from about 98% to about 99.9%; or from about 99% to about 99.9%, wt/wt of the total formulation.

In some embodiments, a formulation of the present invention consists of a concentration of maltodextrin ranging from about 0.1% to about 99%; from about 0.1% to about 98%; from about 0.1% to about 97%; from about 0.1% to about 96%; from about 0.1% to about 95%; from about 0.1% to about 94%; from about 0.1% to about 93%; from about 0.1% to about 92%; from about 0.1% to about 91%; from about 0.1% to about 90%; from about 0.1% to about 89%; from about 0.1% to about 88%; from about 0.1% to about 87%; from about 0.1% to about 86%; from about 0.1% to about 85%; from about 0.1% to about 84%; from about 0.1% to about 83%; from about 0.1% to about 82%; from about 0.1% to about 81%; from about 0.1% to about 80%; from about 0.1% to about 79%; from about 0.1% to about 78%; from about 0.1% to about 77%; from about 0.1% to about 76%; from about 0.1% to about 75%; from about 0.1% to about 74%; from about 0.1% to about 73%; from about 0.1% to about 72%; from about 0.1% to about 71%; from about 0.1% to about 70%; from about 0.1% to about 69%; from about 0.1% to about 68%; from about 0.1% to about 67%; from about 0.1% to about 66%; from about 0.1% to about 65%; from about 0.1% to about 64%; from about 0.1% to about 63%; from about 0.1% to about 62%; from about 0.1% to about 61%; from about 0.1% to about 60%; from about 0.1% to about 59%; from about 0.1% to about 58%; from about 0.1% to about 57%; from about 0.1% to about 56%; from about 0.1% to about 55%; from about 0.1% to about 54%; from about 0.1% to about 53%; from about 0.1% to about 52%; from about 0.1% to about 51%; from about 0.1% to about 50%; from about 0.1% to about 49%; from about 0.1% to about 48%; from about 0.1% to about 47%; from about 0.1% to about 46%; from about 0.1% to about 45%; from about 0.1% to about 44%; from about 0.1% to about 43%; from about 0.1% to about 42%; from about 0.1% to about 41%; from about 0.1% to about 40%; from about 0.1% to about 39%; from about 0.1% to about 38%; from about 0.1% to about 37%; from about 0.1% to about 36%; from about 0.1% to about 35%; from about 0.1% to about 34%; from about 0.1% to about 33%; from about 0.1% to about 32%; from about 0.1% to about 31%; from about 0.1% to about 30%; from about 0.1% to about 29%; from about 0.1% to about 28%; from about 0.1% to about 27%; from about 0.1% to about 26%; from about 0.1% to about 25%; from about 0.1% to about 24%; from about 0.1% to about 23%; from about 0.1% to about 22%; from about 0.1% to about 21%; from about 0.1% to about 20%; from about 0.1% to about 19%; from about 0.1% to about 18%; from about 0.1% to about 17%; from about 0.1% to about 16%; from about 0.1% to about 15%; from about 0.1% to about 14%; from about 0.1% to about 13%; from about 0.1% to about 12%; from about 0.1% to about 11%; from about 0.1% to about 10%; from about 0.1% to about 9%; from about 0.1% to about 8%; from about 0.1% to about 7%; from about 0.1% to about 6%; from about 0.1% to about 5%; from about 0.1% to about 4%; from about 0.1% to about 3%; from about 0.1% to about 2%; from about 0.1% to about 1%; or from about 0.1% to about 0.5%, wt/wt of the total formulation.

In some embodiments, the maltodextrin can have a dextrose equivalent ranging from about 2% to about 20%; from about 3% to about 20%; from about 4% to about 20%; from about 5% to about 20%; from about 6% to about 20%; from about 7% to about 20%; from about 8% to about 20%; from about 9% to about 20%; from about 10% to about 20%; from about 11% to about 20%; from about 12% to about 20%; from about 13% to about 20%; from about 14% to about 20%; from about 15% to about 20%; from about 16% to about 20%; from about 17% to about 20%; from about 18% to about 20%; or from about 19% to about 20%; wt/wt of the total formulation.

In some embodiments, the maltodextrin can have a dextrose equivalent ranging from about 2% to about 20%; from about 2% to about 19%; from about 2% to about 18%; from about 2% to about 17%; from about 2% to about 16%; from about 2% to about 15%; from about 2% to about 14%; from about 2% to about 13%; from about 2% to about 12%; from about 2% to about 11%; from about 2% to about 10%; from about 2% to about 9%; from about 2% to about 8%; from about 2% to about 7%; from about 2% to about 6%; from about 2% to about 5%; from about 2% to about 4%; or from about 2% to about 3%; wt/wt of the total formulation.

In some embodiments, a formulation of the present invention consists of a concentration of benzisothiazolinone (BIT) ranging from about 0.01% to about 1%; from about 0.025% to about 1%; from about 0.05% to about 1%; from about 0.075% to about 1%; from about 0.1% to about 1%; from about 0.125% to about 1%; from about 0.15% to about 1%; from about 0.175% to about 1%; from about 0.2% to about 1%; from about 0.225% to about 1%; from about 0.25% to about 1%; from about 0.275% to about 1%; from about 0.3% to about 1%; from about 0.325% to about 1%; from about 0.35% to about 1%; from about 0.375% to about 1%; from about 0.4% to about 1%; from about 0.425% to about 1%; from about 0.45% to about 1%; from about 0.475% to about 1%; from about 0.5% to about 1%; from about 0.525% to about 1%; from about 0.55% to about 1%; from about 0.575% to about 1%; from about 0.6% to about 1%; from about 0.625% to about 1%; from about 0.65% to about 1%; from about 0.675% to about 1%; from about 0.7% to about 1%; from about 0.725% to about 1%; from about 0.75% to about 1%; from about 0.775% to about 1%; from about 0.8% to about 1%; from about 0.825% to about 1%; from about 0.85% to about 1%; from about 0.875% to about 1%; from about 0.9% to about 1%; from about 0.925% to about 1%; from about 0.95% to about 1%; or from about 0.975% to about 1%; wt/wt of the total formulation.

In some embodiments, a formulation of the present invention consists of a concentration of benzisothiazolinone (BIT) ranging from about 0.01% to about 1%; from about 0.01% to about 0.975%; from about 0.01% to about 0.95%; from about 0.01% to about 0.925%; from about 0.01% to about 0.9%; from about 0.01% to about 0.875%; from about 0.01% to about 0.85%; from about 0.01% to about 0.825%; from about 0.01% to about 0.8%; from about 0.01% to about 0.775%; from about 0.01% to about 0.75%; from about 0.01% to about 0.725%; from about 0.01% to about 0.7%; from about 0.01% to about 0.675%; from about 0.01% to about 0.65%; from about 0.01% to about 0.625%; from about 0.01% to about 0.6%; from about 0.01% to about 0.575%; from about 0.01% to about 0.55%; from about 0.01% to about 0.525%; from about 0.01% to about 0.5%; from about 0.01% to about 0.475%; from about 0.01% to about 0.45%; from about 0.01% to about 0.425%; from about 0.01% to about 0.4%; from about 0.01% to about 0.375%; from about 0.01% to about 0.35%; from about 0.01% to about 0.325%; from about 0.01% to about 0.3%; from about 0.01% to about 0.275%; from about 0.01% to about 0.25%; from about 0.01% to about 0.225%; from about 0.01% to about 0.2%; from about 0.01% to about 0.175%; from about 0.01% to about 0.15%; from about 0.01% to about 0.125%; from about 0.01% to about 0.1%; from about 0.01% to about 0.075%; from about 0.01% to about 0.05%; or from about 0.01% to about 0.025%; wt/wt of the total formulation.

In some embodiments, the BIT can be 1,2-Benzisothiazolin-3-one. An exemplary 1,2-Benzisothiazolin-3-one is provided herein, having a CAS No. 2634-33-5. An exemplary description describing how to make 1,2-Benzisothiazolin-3-one is provided in WIPO Publication No. WO2014173716A1, the disclosure of which is incorporated herein by reference in its entirety. In addition, 1,2-Benzisothiazolin-3-one is readily available from commercial vendors, e.g., PROXEL® AQ Preservative; 9.25% aqueous solution of 1,2-benzisothiazolin-3-one; available from Lonza Group Ltd. Muenchensteinerstrasse 38, CH-4002 Basel, Switzerland.

In some embodiments, a formulation of the present invention consists of a concentration of lignosulfonate ranging from about 0.1% to about 1%; from about 0.125% to about 1%; from about 0.15% to about 1%; from about 0.175% to about 1%; from about 0.2% to about 1%; from about 0.225% to about 1%; from about 0.25% to about 1%; from about 0.275% to about 1%; from about 0.3% to about 1%; from about 0.325% to about 1%; from about 0.35% to about 1%; from about 0.375% to about 1%; from about 0.4% to about 1%; from about 0.425% to about 1%; from about 0.45% to about 1%; from about 0.475% to about 1%; from about 0.5% to about 1%; from about 0.525% to about 1%; from about 0.55% to about 1%; from about 0.575% to about 1%; from about 0.6% to about 1%; from about 0.625% to about 1%; from about 0.65% to about 1%; from about 0.675% to about 1%; from about 0.7% to about 1%; from about 0.725% to about 1%; from about 0.75% to about 1%; from about 0.775% to about 1%; from about 0.8% to about 1%; from about 0.825% to about 1%; from about 0.85% to about 1%; from about 0.875% to about 1%; from about 0.9% to about 1%; from about 0.925% to about 1%; from about 0.95% to about 1%; or from about 0.975% to about 1%; wt/wt of the total formulation.

In some embodiments, a formulation of the present invention consists of a concentration of lignosulfonate from about 0.1% to about 1%; from about 0.1% to about 0.975%; from about 0.1% to about 0.95%; from about 0.1% to about 0.925%; from about 0.1% to about 0.9%; from about 0.1% to about 0.875%; from about 0.1% to about 0.85%; from about 0.1% to about 0.825%; from about 0.1% to about 0.8%; from about 0.1% to about 0.775%; from about 0.1% to about 0.75%; from about 0.1% to about 0.725%; from about 0.1% to about 0.7%; from about 0.1% to about 0.675%; from about 0.1% to about 0.65%; from about 0.1% to about 0.625%; from about 0.1% to about 0.6%; from about 0.1% to about 0.575%; from about 0.1% to about 0.55%; from about 0.1% to about 0.525%; from about 0.1% to about 0.5%; from about 0.1% to about 0.475%; from about 0.1% to about 0.45%; from about 0.1% to about 0.425%; from about 0.1% to about 0.4%; from about 0.1% to about 0.375%; from about 0.1% to about 0.35%; from about 0.1% to about 0.325%; from about 0.1% to about 0.3%; from about 0.1% to about 0.275%; from about 0.1% to about 0.25%; from about 0.1% to about 0.225%; from about 0.1% to about 0.2%; from about 0.1% to about 0.175%; from about 0.1% to about 0.15%; or from about 0.1% to about 0.125%; wt/wt of the total formulation.

In some embodiments, a formulation of the present invention consists of a concentration of gypsum ranging from about 0.1% to about 1%; from about 0.125% to about 1%; from about 0.15% to about 1%; from about 0.175% to about 1%; from about 0.2% to about 1%; from about 0.225% to about 1%; from about 0.25% to about 1%; from about 0.275% to about 1%; from about 0.3% to about 1%; from about 0.325% to about 1%; from about 0.35% to about 1%; from about 0.375% to about 1%; from about 0.4% to about 1%; from about 0.425% to about 1%; from about 0.45% to about 1%; from about 0.475% to about 1%; from about 0.5% to about 1%; from about 0.525% to about 1%; from about 0.55% to about 1%; from about 0.575% to about 1%; from about 0.6% to about 1%; from about 0.625% to about 1%; from about 0.65% to about 1%; from about 0.675% to about 1%; from about 0.7% to about 1%; from about 0.725% to about 1%; from about 0.75% to about 1%; from about 0.775% to about 1%; from about 0.8% to about 1%; from about 0.825% to about 1%; from about 0.85% to about 1%; from about 0.875% to about 1%; from about 0.9% to about 1%; from about 0.925% to about 1%; from about 0.95% to about 1%; or from about 0.975% to about 1%; wt/wt of the total formulation.

In some embodiments, a formulation of the present invention consists of a concentration of gypsum ranging from about 0.1% to about 1%; from about 0.1% to about 0.975%; from about 0.1% to about 0.95%; from about 0.1% to about 0.925%; from about 0.1% to about 0.9%; from about 0.1% to about 0.875%; from about 0.1% to about 0.85%; from about 0.1% to about 0.825%; from about 0.1% to about 0.8%; from about 0.1% to about 0.775%; from about 0.1% to about 0.75%; from about 0.1% to about 0.725%; from about 0.1% to about 0.7%; from about 0.1% to about 0.675%; from about 0.1% to about 0.65%; from about 0.1% to about 0.625%; from about 0.1% to about 0.6%; from about 0.1% to about 0.575%; from about 0.1% to about 0.55%; from about 0.1% to about 0.525%; from about 0.1% to about 0.5%; from about 0.1% to about 0.475%; from about 0.1% to about 0.45%; from about 0.1% to about 0.425%; from about 0.1% to about 0.4%; from about 0.1% to about 0.375%; from about 0.1% to about 0.35%; from about 0.1% to about 0.325%; from about 0.1% to about 0.3%; from about 0.1% to about 0.275%; from about 0.1% to about 0.25%; from about 0.1% to about 0.225%; from about 0.1% to about 0.2%; from about 0.1% to about 0.175%; from about 0.1% to about 0.15%; or from about 0.1% to about 0.125%; wt/wt of the total formulation.

In some embodiments, a formulation of the present invention consists of a concentration of sorbitol ranging from about 0.5% to about 8%; from about 0.75% to about 8%; from about 1% to about 8%; from about 1.25% to about 8%; from about 1.5% to about 8%; from about 1.75% to about 8%; from about 2% to about 8%; from about 2.25% to about 8%; from about 2.5% to about 8%; from about 2.75% to about 8%; from about 3% to about 8%; from about 3.25% to about 8%; from about 3.5% to about 8%; from about 3.75% to about 8%; from about 4% to about 8%; from about 4.25% to about 8%; from about 4.5% to about 8%; from about 4.75% to about 8%; from about 5% to about 8%; from about 5.25% to about 8%; from about 5.5% to about 8%; from about 5.75% to about 8%; from about 6% to about 8%; from about 6.25% to about 8%; from about 6.5% to about 8%; from about 6.75% to about 8%; from about 7% to about 8%; from about 7.25% to about 8%; from about 7.5% to about 8%; or from about 7.75% to about 8%; wt/wt of the total formulation.

In some embodiments, a formulation of the present invention consists of a concentration of sorbitol ranging from about 0.5% to about 8%; from about 0.5% to about 7.75%; from about 0.5% to about 7.5%; from about 0.5% to about 7.25%; from about 0.5% to about 7%; from about 0.5% to about 6.75%; from about 0.5% to about 6.5%; from about 0.5% to about 6.25%; from about 0.5% to about 6%; from about 0.5% to about 5.75%; from about 0.5% to about 5.5%; from about 0.5% to about 5.25%; from about 0.5% to about 5%; from about 0.5% to about 4.75%; from about 0.5% to about 4.5%; from about 0.5% to about 4.25%; from about 0.5% to about 4%; from about 0.5% to about 3.75%; from about 0.5% to about 3.5%; from about 0.5% to about 3.25%; from about 0.5% to about 3%; from about 0.5% to about 2.75%; from about 0.5% to about 2.5%; from about 0.5% to about 2.25%; from about 0.5% to about 2%; from about 0.5% to about 1.75%; from about 0.5% to about 1.5%; from about 0.5% to about 1.25%; from about 0.5% to about 1%; or from about 0.5% to about 0.75%; wt/wt of the total formulation.

In some embodiments, a formulation of the present invention consists of a concentration of sodium benzoate ranging from about 0.1% to about 1%; from about 0.125% to about 1%; from about 0.15% to about 1%; from about 0.175% to about 1%; from about 0.2% to about 1%; from about 0.225% to about 1%; from about 0.25% to about 1%; from about 0.275% to about 1%; from about 0.3% to about 1%; from about 0.325% to about 1%; from about 0.35% to about 1%; from about 0.375% to about 1%; from about 0.4% to about 1%; from about 0.425% to about 1%; from about 0.45% to about 1%; from about 0.475% to about 1%; from about 0.5% to about 1%; from about 0.525% to about 1%; from about 0.55% to about 1%; from about 0.575% to about 1%; from about 0.6% to about 1%; from about 0.625% to about 1%; from about 0.65% to about 1%; from about 0.675% to about 1%; from about 0.7% to about 1%; from about 0.725% to about 1%; from about 0.75% to about 1%; from about 0.775% to about 1%; from about 0.8% to about 1%; from about 0.825% to about 1%; from about 0.85% to about 1%; from about 0.875% to about 1%; from about 0.9% to about 1%; from about 0.925% to about 1%; from about 0.95% to about 1%; or from about 0.975% to about 1%; wt/wt of the total formulation.

In some embodiments, a formulation of the present invention consists of a concentration of sodium benzoate ranging from about 0.1% to about 1%; from about 0.1% to about 0.975%; from about 0.1% to about 0.95%; from about 0.1% to about 0.925%; from about 0.1% to about 0.9%; from about 0.1% to about 0.875%; from about 0.1% to about 0.85%; from about 0.1% to about 0.825%; from about 0.1% to about 0.8%; from about 0.1% to about 0.775%; from about 0.1% to about 0.75%; from about 0.1% to about 0.725%; from about 0.1% to about 0.7%; from about 0.1% to about 0.675%; from about 0.1% to about 0.65%; from about 0.1% to about 0.625%; from about 0.1% to about 0.6%; from about 0.1% to about 0.575%; from about 0.1% to about 0.55%; from about 0.1% to about 0.525%; from about 0.1% to about 0.5%; from about 0.1% to about 0.475%; from about 0.1% to about 0.45%; from about 0.1% to about 0.425%; from about 0.1% to about 0.4%; from about 0.1% to about 0.375%; from about 0.1% to about 0.35%; from about 0.1% to about 0.325%; from about 0.1% to about 0.3%; from about 0.1% to about 0.275%; from about 0.1% to about 0.25%; from about 0.1% to about 0.225%; from about 0.1% to about 0.2%; from about 0.1% to about 0.175%; from about 0.1% to about 0.15%; or from about 0.1% to about 0.125%; wt/wt of the total formulation.

In some embodiments, a formulation of the present invention consists of a concentration of potassium sorbate ranging from about 0.1% to about 1%; from about 0.125% to about 1%; from about 0.15% to about 1%; from about 0.175% to about 1%; from about 0.2% to about 1%; from about 0.225% to about 1%; from about 0.25% to about 1%; from about 0.275% to about 1%; from about 0.3% to about 1%; from about 0.325% to about 1%; from about 0.35% to about 1%; from about 0.375% to about 1%; from about 0.4% to about 1%; from about 0.425% to about 1%; from about 0.45% to about 1%; from about 0.475% to about 1%; from about 0.5% to about 1%; from about 0.525% to about 1%; from about 0.55% to about 1%; from about 0.575% to about 1%; from about 0.6% to about 1%; from about 0.625% to about 1%; from about 0.65% to about 1%; from about 0.675% to about 1%; from about 0.7% to about 1%; from about 0.725% to about 1%; from about 0.75% to about 1%; from about 0.775% to about 1%; from about 0.8% to about 1%; from about 0.825% to about 1%; from about 0.85% to about 1%; from about 0.875% to about 1%; from about 0.9% to about 1%; from about 0.925% to about 1%; from about 0.95% to about 1%; or from about 0.975% to about 1%; wt/wt of the total formulation.

In some embodiments, a formulation of the present invention consists of a concentration of potassium sorbate ranging from about 0.1% to about 1%; from about 0.1% to about 0.975%; from about 0.1% to about 0.95%; from about 0.1% to about 0.925%; from about 0.1% to about 0.9%; from about 0.1% to about 0.875%; from about 0.1% to about 0.85%; from about 0.1% to about 0.825%; from about 0.1% to about 0.8%; from about 0.1% to about 0.775%; from about 0.1% to about 0.75%; from about 0.1% to about 0.725%; from about 0.1% to about 0.7%; from about 0.1% to about 0.675%; from about 0.1% to about 0.65%; from about 0.1% to about 0.625%; from about 0.1% to about 0.6%; from about 0.1% to about 0.575%; from about 0.1% to about 0.55%; from about 0.1% to about 0.525%; from about 0.1% to about 0.5%; from about 0.1% to about 0.475%; from about 0.1% to about 0.45%; from about 0.1% to about 0.425%; from about 0.1% to about 0.4%; from about 0.1% to about 0.375%; from about 0.1% to about 0.35%; from about 0.1% to about 0.325%; from about 0.1% to about 0.3%; from about 0.1% to about 0.275%; from about 0.1% to about 0.25%; from about 0.1% to about 0.225%; from about 0.1% to about 0.2%; from about 0.1% to about 0.175%; from about 0.1% to about 0.15%; or from about 0.1% to about 0.125%; wt/wt of the total formulation.

In some embodiments, a formulation of the present invention consists of a concentration of EDTA ranging from about 0.1% to about 1%; from about 0.125% to about 1%; from about 0.15% to about 1%; from about 0.175% to about 1%; from about 0.2% to about 1%; from about 0.225% to about 1%; from about 0.25% to about 1%; from about 0.275% to about 1%; from about 0.3% to about 1%; from about 0.325% to about 1%; from about 0.35% to about 1%; from about 0.375% to about 1%; from about 0.4% to about 1%; from about 0.425% to about 1%; from about 0.45% to about 1%; from about 0.475% to about 1%; from about 0.5% to about 1%; from about 0.525% to about 1%; from about 0.55% to about 1%; from about 0.575% to about 1%; from about 0.6% to about 1%; from about 0.625% to about 1%; from about 0.65% to about 1%; from about 0.675% to about 1%; from about 0.7% to about 1%; from about 0.725% to about 1%; from about 0.75% to about 1%; from about 0.775% to about 1%; from about 0.8% to about 1%; from about 0.825% to about 1%; from about 0.85% to about 1%; from about 0.875% to about 1%; from about 0.9% to about 1%; from about 0.925% to about 1%; from about 0.95% to about 1%; or from about 0.975% to about 1%; wt/wt of the total formulation.

In some embodiments, a formulation of the present invention consists of a concentration of EDTA ranging from about 0.1% to about 1%; from about 0.1% to about 0.975%; from about 0.1% to about 0.95%; from about 0.1% to about 0.925%; from about 0.1% to about 0.9%; from about 0.1% to about 0.875%; from about 0.1% to about 0.85%; from about 0.1% to about 0.825%; from about 0.1% to about 0.8%; from about 0.1% to about 0.775%; from about 0.1% to about 0.75%; from about 0.1% to about 0.725%; from about 0.1% to about 0.7%; from about 0.1% to about 0.675%; from about 0.1% to about 0.65%; from about 0.1% to about 0.625%; from about 0.1% to about 0.6%; from about 0.1% to about 0.575%; from about 0.1% to about 0.55%; from about 0.1% to about 0.525%; from about 0.1% to about 0.5%; from about 0.1% to about 0.475%; from about 0.1% to about 0.45%; from about 0.1% to about 0.425%; from about 0.1% to about 0.4%; from about 0.1% to about 0.375%; from about 0.1% to about 0.35%; from about 0.1% to about 0.325%; from about 0.1% to about 0.3%; from about 0.1% to about 0.275%; from about 0.1% to about 0.25%; from about 0.1% to about 0.225%; from about 0.1% to about 0.2%; from about 0.1% to about 0.175%; from about 0.1% to about 0.15%; or from about 0.1% to about 0.125%; wt/wt of the total formulation.

In some embodiments a formulation of the present invention can be formulated at a pH ranging from about 5 to about 11; from about 5.5 to about 11; from about 6 to about 11; from about 6.5 to about 11; from about 7 to about 11; from about 7.5 to about 11; from about 8 to about 11; from about 8.5 to about 11; from about 9 to about 11; from about 9.5 to about 11; from about 10 to about 11; or from about 10.5 to about 11.

In some embodiments a formulation of the present invention can be formulated at a pH ranging from about 5 to about 11; from about 5 to about 10.5; from about 5 to about 10; from about 5 to about 9.5; from about 5 to about 9; from about 5 to about 8.5; from about 5 to about 8; from about 5 to about 7.5; from about 5 to about 7; from about 5 to about 6.5; from about 5 to about 6; or from about 5 to about 5.5.

In some embodiments the formulation can be formulated into a granule form (granular formulation). Methods of generating a granular formulation are well known in the art, and include: crystallization, precipitation, pan-coating, fluid bed coating, agglomeration (e.g., fluid bed agglomeration), rotary atomization, extrusion, prilling, spheronization, size reduction methods, drum granulation, and/or high shear granulation, and the like.

In some embodiments, the granular formulation can be generated via agglomeration, e.g., spray-drying agglomeration; rewet agglomeration; fluid bed agglomeration; and the like.

In some embodiments, the type of agglomeration can be fluid bed agglomeration. Exemplary methods of fluid bed agglomeration are provided in U.S. Pat. No. 7,582,147; the disclosure of which is incorporated herein by reference in its entirety.

In some embodiments, the granular formulation can be generated via fluid bed agglomeration.

In some embodiments, the granular formulation can be generated by spraying the active and inert ingredients onto a blank carrier in a fluid bed.

In some embodiments, the granular formulation can be generated by spraying the active and inert ingredients (excipients) onto a blank carrier and granulated in pan granulator.

In some embodiments, the granular formulation can be generated by mixing the active and inert powders (i.e., one or more excipients described herein) and water, and subsequently granulated by passing the ingredients through an extruder.

In some embodiments, the granular formulation can be generated by mixing the active and inert powders (i.e., one or more excipients described herein) with water, and granulated by roll compaction.

Any of the foregoing TVPs, TVP-insecticidal proteins, or pharmaceutically acceptable salts thereof, can be used in the any of the formulations described herein and below, e.g., any of the foregoing TVPs, TVP-insecticidal proteins, or pharmaceutically acceptable salts thereof, can be used in the formulation of: a wettable powder or granule formulation; or a liquid concentrate formulation.

Illustrative Embodiments of the Present Invention

The present disclosure contemplates compositions, products, and transgenic organisms that contain—or, in the case of transgenic organisms, express or otherwise produce—one or more TVPs, or one or more TVP-insecticidal proteins.

In some embodiments, the illustrative composition consists of: (1) a TVP, a TVP-insecticidal protein, or a combination thereof; and (2) an excipient (e.g., any of the excipients described herein).

In some embodiments, the illustrative composition consists of: (1) a TVP, or a pharmaceutically acceptable salt thereof; a TVP-insecticidal protein, or a pharmaceutically acceptable salt thereof; or a combination thereof; and (2) an excipient (e.g., any of the excipients described herein).

In some embodiments, the illustrative composition consists of: (1) one or more TVPs, one or more a TVP-insecticidal proteins, or a combination thereof; and (2) one or more excipient (e.g., any of the excipients described herein).

In some embodiments, the illustrative composition consists of: (1) one or more TVPs, or a pharmaceutically acceptable salt thereof; one or more a TVP-insecticidal proteins, or a pharmaceutically acceptable salt thereof; or a combination thereof; and (2) one or more excipients (e.g., any of the excipients described herein).

In some embodiments, the compositions of the present invention consist of: (1) one or more TVPs, or one or more TVP-insecticidal proteins; and (2) one or more excipients (e.g., any of the excipients described herein).

In some embodiments, the compositions of the present invention consist of: (1) one or more TVPs, or one or more TVP-insecticidal proteins; and (2) one or more excipients (e.g., any of the excipients described herein); wherein either of the foregoing (1) or (2) can be used concomitantly, or sequentially.

Any of the compositions, products, polypeptides and/or plants utilizing a TVP, or a TVP-insecticidal protein (as described herein), can be used to control pests, their growth, and/or the damage caused by their actions, especially their damage to plants.

Compositions consisting of a TVP or a TVP-insecticidal protein, and an excipient, can include agrochemical compositions. For example, in some embodiments, agrochemical compositions can include, but is not limited to, aerosols and/or aerosolized products (e.g., sprays, fumigants, powders, dusts, and/or gases); seed dressings; oral preparations (e.g., insect food, etc.); or a transgenic organisms (e.g., a cell, a plant, or an animal) expressing and/or producing a TVP or a TVP-insecticidal protein, either transiently and/or stably.

In some embodiments, the active ingredients of the present disclosure can be applied in the form of compositions and can be applied to the crop area or plant to be treated, simultaneously or in succession, with other non-active compounds. These compounds can be fertilizers, weed killers, cryoprotectants, surfactants, detergents, soaps, dormant oils, polymers, and/or time-release or biodegradable carrier formulations that permit long-term dosing of a target area following a single application of the formulation. One or more of these non-active compounds can be prepared, if desired, together with further agriculturally acceptable carriers, surfactants or application-promoting adjuvants customarily employed in the art of formulation. Suitable carriers and adjuvants can be solid or liquid and correspond to the substances ordinarily employed in formulation technology, e.g. natural or regenerated mineral substances, solvents, dispersants, wetting agents, tackifiers, binders or fertilizers. Likewise, the formulations may be prepared into edible "baits" or fashioned into pest "traps" to permit feeding or ingestion by a target pest of the pesticidal formulation.

Methods of applying an active ingredient of the present disclosure or an agrochemical composition of the present disclosure that consists of a TVP or TVP-insecticidal protein, and an excipient, as produced by the methods described herein of the present disclosure, include leaf application, seed coating and soil application. In some embodiments, the number of applications and the rate of application depend on the intensity of infestation by the corresponding pest.

The composition consisting of a TVP or a TVP-insecticidal protein and an excipient may be formulated as a powder, dust, pellet, granule, spray, emulsion, colloid, solution, or such like, and may be prepared by such conventional means as desiccation, lyophilization, homogenization, extraction, filtration, centrifugation, sedimentation, or concentration of a culture of cells comprising the polypeptide. In all such compositions that contain at least one such pesticidal polypeptide, the polypeptide may be present in a concentration of from about 1% to about 99% by weight.

In some embodiments, compositions consisting of TVPs or TVP-insecticidal proteins may be prophylactically applied to an environmental area to prevent infestation by a susceptible pest, for example, a lepidopteran and/or coleopteran pest, which may be killed or reduced in numbers in a given area by the methods of the invention. In some embodiments, the pest ingests, or comes into contact with, a pesticidally-effective amount of the polypeptide.

In some embodiments, the pesticide compositions described herein may be made by formulating either the TVP or TVP-insecticidal-protein transformed bacterial, yeast, or other cell, crystal and/or spore suspension, or isolated protein component with the desired agriculturally-acceptable carrier. The compositions may be formulated prior to administration in an appropriate means such as lyophilized, freeze-dried, desiccated, or in an aqueous carrier, medium or suitable diluent, such as saline and/or other buffer. In some embodiments, the formulated compositions may be in the form of a dust or granular material, or a suspension in oil (vegetable or mineral), or water or oil/water emulsions, or as a wettable powder, or in combination with any other carrier material suitable for agricultural application. Suitable agricultural carriers can be solid or liquid and are well known in the art. In some embodiments, the formulations may be mixed with one or more solid or liquid adjuvants and prepared by various means, e.g., by homogeneously mixing, blending and/or grinding the pesticidal composition with suitable adjuvants using conventional formulation techniques. Suitable formulations and application methods are described in U.S. Pat. No. 6,468,523, herein incorporated by reference in its entirety.

In some embodiments, a formulation consists of, a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; and one or more of the following excipients: maltodextrin; trehalose; maltose; potassium phosphate dibasic ($K_2HPO_4$); potassium phosphate monobasic ($KH_2PO_4$); lignosulfonate; gypsum; sorbitol; sodium benzoate; potassium sorbate; EDTA; and/or benzisothiazolinone (BIT).

In some embodiments, a formulation consists of a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-agatoxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; wherein the TVP has one amino acid substitution at X$_1$, X$_2$, X$_3$, X$_4$, or X$_5$; and one or more of the following excipients: maltodextrin; trehalose; maltose; potassium phosphate dibasic (K$_2$HPO$_4$); potassium phosphate monobasic (KH$_2$PO$_4$); lignosulfonate; gypsum; sorbitol; sodium benzoate; potassium sorbate; EDTA; and/or benzisothiazolinone (BIT).

In some embodiments, a formulation consists of a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-agatoxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; wherein the TVP has one amino acid substitution at X$_1$, X$_2$, X$_3$, X$_4$, or X$_5$; and wherein X$_7$ is Glycine; and one or more of the following excipients: maltodextrin; trehalose; maltose; potassium phosphate dibasic (K$_2$HPO$_4$); potassium phosphate monobasic (KH$_2$PO$_4$); lignosulfonate; gypsum; sorbitol; sodium benzoate; potassium sorbate; EDTA; and/or benzisothiazolinone (BIT).

In some embodiments, a formulation consists of a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): E-P-D-E-I-

C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-agatoxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; wherein the TVP has one amino acid substitution at X$_1$, X$_2$, X$_3$, X$_4$, or X$_5$; and wherein X$_7$ is absent; and one or more of the following excipients: maltodextrin; trehalose; maltose; potassium phosphate dibasic (K$_2$HPO$_4$); potassium phosphate monobasic (KH$_2$PO$_4$); lignosulfonate; gypsum; sorbitol; sodium benzoate; potassium sorbate; EDTA; and/or benzisothiazolinone (BIT).

In some embodiments, a formulation consists of a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences set forth in SEQ ID NOs: 2-15, 49-53, or 77-110; and one or more of the following excipients: maltodextrin; trehalose; maltose; potassium phosphate dibasic (K$_2$HPO$_4$); potassium phosphate monobasic (KH$_2$PO$_4$); lignosulfonate; gypsum; sorbitol; sodium benzoate; potassium sorbate; EDTA; and/or benzisothiazolinone (BIT).

In some embodiments, a formulation consisting of a TVP, a TVP-insecticidal protein, or a pharmaceutically acceptable salt thereof, and an excipient, can have a TVP that is 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% by weight of the formulation.

In some embodiments, a composition of the present invention consists of a TVP, and one or more excipients; wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-agatoxin-Ta1b as set forth in SEQ ID NO: 1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; or a pharmaceutically acceptable salt thereof; and wherein the one or more excipients is selected from the group consisting of: trehalose; maltodextrin; maltose; potassium phosphate dibasic (K$_2$HPO$_4$); potassium phosphate monobasic (KH$_2$PO$_4$); lignosulfonate; gypsum; sorbitol; sodium benzoate; potassium sorbate; EDTA; benzisothiazolinone (BIT); and fermentation solids.

In some embodiments, a composition of the present invention consists of a TVP, wherein the TVP has one amino acid substitution at X$_1$, X$_2$, X$_3$, X$_4$, or X$_5$, or a pharmaceutically acceptable salt thereof.

In some embodiments, a composition of the present invention consists of a TVP, wherein the TVP has one amino acid substitution at X$_1$, X$_2$, X$_3$, X$_4$, or X$_5$; and wherein X$_7$ is Glycine, or a pharmaceutically acceptable salt thereof.

In some embodiments, a composition of the present invention consists of a TVP, wherein the TVP has one amino acid substitution at X$_1$, X$_2$, X$_3$, X$_4$, or X$_5$; and wherein X$_7$ is absent, or a pharmaceutically acceptable salt thereof.

In some embodiments, a composition of the present invention consists of a TVP, wherein the TVP has one amino acid substitution at X$_1$, X$_2$, X$_3$, X$_4$, or X$_5$; and wherein X$_6$ and X$_7$ are absent, or a pharmaceutically acceptable salt thereof.

In some embodiments, a composition of the present invention consists of a TVP, wherein the TVP comprises an amino sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any of the amino acid sequences set forth in any one of SEQ ID NOs: 2-15, 49-53, or 77-110.

In some embodiments, a composition of the present invention consists of a TVP, wherein the TVP is encoded by a polynucleotide sequence as set forth in any one of SEQ ID NOs: 17-30, 54-58, or 117-150, or a complementary nucleotide sequence thereof.

In some embodiments, a composition of the present invention consists of a TVP, wherein the TVP further comprises a homopolymer or heteropolymer of two or more TVPs, wherein the amino acid sequence of each TVP is the same or different.

In some embodiments, a composition of the present invention consists of a TVP, wherein the TVP is a fused protein comprising two or more TVPs separated by a cleavable linker or non-cleavable linker, and wherein the amino acid sequence of each TVP may be the same or different.

In some embodiments, a composition of the present invention consists of a TVP having a linker, wherein the linker is a cleavable linker.

In some embodiments, a composition of the present invention consists of a TVP having a cleavable linker, wherein the cleavable linker is cleavable inside the gut or hemolymph of an insect.

In some embodiments, a composition of the present invention consists of a TVP having a linker, wherein the linker has an amino acid sequence as set forth in any one of SEQ ID NOs: 61-70.

In some embodiments, a composition of the present invention consists of a TVP, and one or more excipients; wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-agatoxin-Ta1b as set forth in SEQ ID NO: 1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; or a pharmaceutically acceptable salt thereof; and wherein the one or more excipients is selected from the group consisting of: trehalose; maltodextrin; maltose; potassium phosphate dibasic (K$_2$HPO$_4$); potassium phosphate monobasic (KH$_2$PO$_4$); lignosulfonate; gypsum; sorbitol; sodium benzoate; potassium sorbate; EDTA; benzisothiazolinone (BIT); and fermentation solids, wherein if Z$_1$ is T or S, then the TVP is glycosylated.

In some embodiments, a composition of the present invention consists of one or more excipients.

In some embodiments, a composition of the present invention consists of one or more excipients, wherein the one or more excipients is selected from the group consisting of: trehalose; maltodextrin; potassium phosphate dibasic anhydrous (K$_2$HPO$_4$); potassium phosphate monobasic (KH$_2$PO$_4$); BIT; and fermentation solids.

In some embodiments, a composition of the present invention consists of (1) a TVP, a TVP-insecticidal protein, or a combination thereof; and (2) one or more excipients; wherein the TVP or TVP-insecticidal protein ranges from about 2% to about 16% wt/wt; and wherein trehalose ranges from about 5% to about 40% wt/wt; BIT ranges from about 0.01% to about 0.1% wt/wt; maltodextrin ranges from about 10% to about 50% wt/wt; potassium phosphate dibasic anhydrous (K$_2$HPO$_4$) ranges from about 1% to about 5% wt/wt; and potassium phosphate monobasic (KH$_2$PO$_4$) ranges from about 0.10% to about 1% wt/wt; and fermentation solids range from about 15% to about 40% wt/wt; of the total weight of the composition.

In some embodiments, a composition of the present invention consists of (1) a TVP, a TVP-insecticidal protein, or a combination thereof; and (2) one or more excipients; wherein the TVP or TVP-insecticidal protein ranges from about 7% to about 9% wt/wt; and wherein trehalose ranges from about 20% to about 30% wt/wt; BIT ranges from about 0.025% to about 0.075% wt/wt; maltodextrin ranges from about 30% to about 40% wt/wt; potassium phosphate dibasic anhydrous (K$_2$HPO$_4$) ranges from about 2% to about 3% wt/wt; potassium phosphate monobasic (KH$_2$PO$_4$) ranges from about 0.2% to about 0.6%; and fermentation solids range from about 20% to about 30%, of the total weight of the composition.

In some embodiments, a composition of the present invention consists of (1) a TVP, a TVP-insecticidal protein, or a combination thereof; and (2) one or more excipients; wherein the TVP or TVP-insecticidal protein is about 8.5% wt/wt; and wherein trehalose is about 25% wt/wt; BIT is about 0.05% wt/wt; maltodextrin is about 36.3% wt/wt; potassium phosphate dibasic anhydrous (K$_2$HPO$_4$) is about 2.6% wt/wt; potassium phosphate monobasic (KH$_2$PO$_4$) is about 0.4% wt/wt; and fermentation solids are about 26.85% wt/wt, of the total weight of the composition.

In some embodiments, a composition of the present invention consists essentially of the following: an amount of a TVP or a TVP-insecticidal protein that is 8.5% wt/wt; an amount of trehalose that is 25% wt/wt; an amount of BIT that is 0.05% wt/wt; an amount of maltodextrin that is 36.3% wt/wt; an amount of potassium phosphate dibasic anhydrous (K$_2$HPO$_4$) that is 2.6% wt/wt; an amount of potassium phosphate monobasic (KH$_2$PO$_4$) that is 0.4% wt/wt; and an amount of fermentation solids that is 26.85% wt/wt, of the total weight of the composition.

In some embodiments, a composition of the present invention consists of the following: an amount of a TVP or a TVP-insecticidal protein that is 8.5% wt/wt; an amount of trehalose that is 25% wt/wt; an amount of BIT that is 0.05% wt/wt; an amount of maltodextrin that is 36.3% wt/wt; an amount of potassium phosphate dibasic anhydrous (K$_2$HPO$_4$) that is 2.6% wt/wt; an amount of potassium phosphate monobasic (KH$_2$PO$_4$) that is 0.4% wt/wt; and an amount of fermentation solids that is 26.85% wt/wt, of the total weight of the composition.

In some embodiments, a composition of the present invention consists of (1) a TVP, a TVP-insecticidal protein, or a combination thereof; and (2) a plurality of excipients; wherein the TVP or TVP-insecticidal protein comprises an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-agatoxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; or a pharmaceutically acceptable salt thereof; wherein the composition consists of an amount of TVP that is 8.5% wt/wt of the total weight of the composition; and wherein the plurality of excipients consists of the following: an amount of trehalose that is 25% wt/wt; an amount of BIT that is 0.05% wt/wt; an amount of maltodextrin that is 36.3% wt/wt; an amount of potassium phosphate dibasic anhydrous (K$_2$HPO$_4$) that is 2.6% wt/wt; an amount of potassium phosphate monobasic (KH$_2$PO$_4$) that is 0.4% wt/wt; and an amount of fermentation solids that is 26.85% wt/wt, of the total weight of the composition.

In some embodiments, a composition of the present invention consists of (1) a TVP, a TVP-insecticidal protein, or a combination thereof; and (2) a plurality of excipients; wherein the TVP or TVP-insecticidal protein; wherein the TVP has one amino acid substitution at X$_1$, X$_2$, X$_3$, X$_4$, or X$_5$, or a pharmaceutically acceptable salt thereof.

In some embodiments, a composition of the present invention consists of (1) a TVP, a TVP-insecticidal protein, or a combination thereof; and (2) a plurality of excipients; wherein the TVP or TVP-insecticidal protein; wherein the TVP has one amino acid substitution at X$_1$, X$_2$, X$_3$, X$_4$, or X$_5$; and wherein X$_7$ is Glycine, or a pharmaceutically acceptable salt thereof.

In some embodiments, a composition of the present invention consists of (1) a TVP, a TVP-insecticidal protein, or a combination thereof; and (2) a plurality of excipients; wherein the TVP or TVP-insecticidal protein; wherein the TVP has one amino acid substitution at X$_1$, X$_2$, X$_3$, X$_4$, or X$_5$; and wherein X$_7$ is absent, or a pharmaceutically acceptable salt thereof.

In some embodiments, a composition of the present invention consists of (1) a TVP, a TVP-insecticidal protein, or a combination thereof; and (2) a plurality of excipients; wherein the TVP or TVP-insecticidal protein; wherein the TVP has one amino acid substitution at X$_1$, X$_2$, X$_3$, X$_4$, or X$_5$; and wherein X$_6$ and X$_7$ are absent, or a pharmaceutically acceptable salt thereof.

In some embodiments, a composition of the present invention consists of (1) a TVP, a TVP-insecticidal protein, or a combination thereof; and (2) a plurality of excipients; wherein the TVP or TVP-insecticidal protein; wherein the TVP comprises an amino sequence as set forth in any one of SEQ ID NOs: 2-15, 49-53, or 77-110.

In some embodiments, a composition of the present invention consists of (1) a TVP, a TVP-insecticidal protein, or a combination thereof; and (2) a plurality of excipients; wherein the TVP or TVP-insecticidal protein; wherein the TVP is encoded by a polynucleotide sequence as set forth in any one of SEQ ID NOs: 17-30, 54-58, or 117-150, or a complementary nucleotide sequence thereof.

In some embodiments, a composition of the present invention consists of (1) a TVP, a TVP-insecticidal protein, or a combination thereof; and (2) a plurality of excipients; wherein the TVP or TVP-insecticidal protein; wherein the TVP further comprises a homopolymer or heteropolymer of two or more TVPs, wherein the amino acid sequence of each TVP is the same or different.

In some embodiments, a composition of the present invention consists of (1) a TVP, a TVP-insecticidal protein, or a combination thereof; and (2) a plurality of excipients; wherein the TVP or TVP-insecticidal protein; wherein the TVP is a fused protein comprising two or more TVPs separated by a cleavable or non-cleavable linker, and wherein the amino acid sequence of each TVP may be the same or different.

In some embodiments, a composition of the present invention consists of (1) a TVP, a TVP-insecticidal protein, or a combination thereof; and (2) a plurality of excipients; wherein the TVP or TVP-insecticidal protein; wherein the linker is a cleavable linker.

In some embodiments, a composition of the present invention consists of (1) a TVP, a TVP-insecticidal protein, or a combination thereof; and (2) a plurality of excipients; wherein the TVP or TVP-insecticidal protein; wherein the cleavable linker is cleavable inside the gut or hemolymph of an insect.

In some embodiments, a composition of the present invention consists of (1) a TVP, a TVP-insecticidal protein, or a combination thereof; and (2) a plurality of excipients; wherein the TVP or TVP-insecticidal protein; wherein the linker has an amino acid sequence as set forth in any one of SEQ ID NOs: 61-70.

In some embodiments, a composition of the present invention consists of (1) a TVP, a TVP-insecticidal protein, or a combination thereof; and (2) a plurality of excipients; wherein the TVP or TVP-insecticidal protein comprises an amino acid sequence that is at least 90% identical to the amino acid sequence according to Formula (I): E-P-D-E-I-C-R-X$_1$-X$_2$-M-X$_3$-N-K-E-F-T-Y-X$_4$-S-N-V-C-N-N-C-G-D-Q-V-A-A-C-E-A-E-C-F-X$_5$-N-D-V-Y-Z$_1$-A-C-H-E-A-Q-X$_6$-X$_7$ (SEQ ID NO: 151), wherein the polypeptide comprises at least one amino acid substitution relative to the wild-type sequence of U1-agatoxin-Ta1b as set forth in SEQ ID NO:1, and wherein X$_1$ is A, S, or N; X$_2$ is R, Q, N, A, G, N, L, D, V, M, I, C, E, T, or S; X$_3$ is T or P; X$_4$ is K or A; X$_5$ is R or A; Z$_1$ is T, S, A, F, P, Y, K, W, H, A, G, N, L, V, M, I, Q, C, E, or R; X$_6$ is K or absent; and X$_7$ is G or absent; or a pharmaceutically acceptable salt thereof; wherein the composition consists of an amount of TVP that is 8.5% wt/wt of the total weight of the composition; and wherein the plurality of excipients consists of the following: an amount of trehalose that is 25% wt/wt; an amount of BIT that is 0.05% wt/wt; an amount of maltodextrin that is 36.3% wt/wt; an amount of potassium phosphate dibasic anhydrous (K$_2$HPO$_4$) that is 2.6% wt/wt; an amount of potassium phosphate monobasic (KH$_2$PO$_4$) that is 0.4% wt/wt; and an amount of fermentation solids that is 26.85% wt/wt, of the total weight of the composition; wherein if Z$_1$ is T or S, then the TVP is glycosylated.

Any of the foregoing TVPs, TVP-insecticidal proteins, or pharmaceutically acceptable salts thereof, can be used in the any of the formulations described herein and below, e.g., any of the foregoing TVPs, TVP-insecticidal proteins, or pharmaceutically acceptable salts thereof, can be used in the formulation of: a wettable powder or granule formulation; or a liquid concentrate formulation.

In some embodiments, a formulation consists of, a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-X$_1$-M-T-N-K-E-F-T-Y-K-S-N-V-C-N-N-C-G-D-Q-V-A-A-C-E-A-E-C-F-R-N-D-V—Y-Z$_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein X$_1$ is R or Q; and Z$_1$ is T or A; and one or more of the following excipients: maltodextrin; trehalose; maltose; potassium phosphate dibasic (K$_2$HPO$_4$); potassium phosphate monobasic (KH$_2$PO$_4$); lignosulfonate; gypsum; sorbitol; sodium benzoate; potassium sorbate; EDTA; and/or benzisothiazolinone (BIT).

In some embodiments, a formulation consists of a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-X$_1$-M-T-N-K-E-F-T-Y-K-S-N-V-C-N-N-C-G-D-Q-V-A-A-C-E-A-E-C-F-R-N-D-V—Y-Z$_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein X$_1$ is R or Q; and Z$_1$ is T or A; wherein if Z$_1$ is T then the TVP is glycosylated; and one or more of the following excipients: maltodextrin; trehalose; maltose; potassium phosphate dibasic (K$_2$HPO$_4$); potassium phosphate monobasic (KH$_2$PO$_4$); lignosulfonate; gypsum; sorbitol; sodium benzoate; potassium sorbate; EDTA; and/or benzisothiazolinone (BIT).

In some embodiments, a formulation consists of a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-X$_1$-M-T-N-K-E-F-T-Y-K-S-N-V-C-N-N-C-G-D-Q-V-A-A-C-E-A-E-C-F-R-N-D-V—Y-Z$_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein X$_1$ is R or Q; and Z$_1$ is T or A; wherein the wherein X$_1$ is Q; and Z$_1$ is A; and one or more of the following excipients: maltodextrin; trehalose; maltose; potassium phosphate dibasic (K$_2$HPO$_4$); potassium phosphate monobasic (KH$_2$PO$_4$); lignosulfonate; gypsum; sorbitol; sodium benzoate; potassium sorbate; EDTA; and/or benzisothiazolinone (BIT).

In some embodiments, a formulation consists of a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any one of the amino acid sequences set forth in SEQ ID NOs: 2, 49, or 51; and one or more of the following excipients: maltodextrin; trehalose; maltose; potassium phosphate dibasic ($K_2HPO_4$); potassium phosphate monobasic ($KH_2PO_4$); lignosulfonate; gypsum; sorbitol; sodium benzoate; potassium sorbate; EDTA; and/or benzisothiazolinone (BIT).

In some embodiments, a formulation consisting of a TVP, a TVP-insecticidal protein, or a pharmaceutically acceptable salt thereof, and an excipient, can have a TVP that is 0.01%, 0.02%, 0.03%, 0.04%, 0.05%, 0.06%, 0.07%, 0.08%, 0.09%, 0.1%, 0.2%, 0.3%, 0.4%, 0.5%, 0.6%, 0.7%, 0.8%, 0.9%, 1%, 2%, 3%, 4%, 5%, 6%, 7%, 8%, 9%, 10%, 11%, 12%, 13%, 14%, 15%, 16%, 17%, 18%, 19%, 20%, 21%, 22%, 23%, 24%, 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, 99.1%, 99.2%, 99.3%, 99.4%, 99.5%, 99.6%, 99.7%, 99.8%, or 99.9% by weight of the formulation.

In some embodiments, a composition of the present invention consists of a TVP, and one or more excipients; wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-$X_1$-M-T-N-K-E-F-T-Y—K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO: 1, and wherein $X_1$ is R or Q; and $Z_1$ is T or A; wherein the wherein $X_1$ is Q; and $Z_1$ is A; or a pharmaceutically acceptable salt thereof; and wherein the one or more excipients is selected from the group consisting of: trehalose; maltodextrin; maltose; potassium phosphate dibasic ($K_2HPO_4$); potassium phosphate monobasic ($KH_2PO_4$); lignosulfonate; gypsum; sorbitol; sodium benzoate; potassium sorbate; EDTA; benzisothiazolinone (BIT); and fermentation solids.

In some embodiments, a composition of the present invention consists of a TVP, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any of the amino acid sequences set forth in any one of SEQ ID NOs: 2, 49, or 51.

In some embodiments, a composition of the present invention consists of a TVP, wherein the TVP is encoded by a polynucleotide sequence as set forth in any one of SEQ ID NOs: 17, 54, or 56, or a complementary nucleotide sequence thereof.

In some embodiments, a composition of the present invention consists of a TVP, and one or more excipients; wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO: 1, and wherein $X_1$ is R or Q; and $Z_1$ is T or A; or a pharmaceutically acceptable salt thereof; and wherein the one or more excipients is selected from the group consisting of: trehalose; maltodextrin; maltose; potassium phosphate dibasic ($K_2HPO_4$); potassium phosphate monobasic ($KH_2PO_4$); lignosulfonate; gypsum; sorbitol; sodium benzoate; potassium sorbate; EDTA; benzisothiazolinone (BIT); and fermentation solids, wherein if $Z_1$ is T or S, then the TVP is glycosylated.

In some embodiments, a composition of the present invention consists of one or more excipients.

In some embodiments, a composition of the present invention consists of one or more excipients, wherein the one or more excipients is selected from the group consisting of: trehalose; maltodextrin; potassium phosphate dibasic anhydrous ($K_2HPO_4$); potassium phosphate monobasic ($KH_2PO_4$); BIT; and fermentation solids.

In some embodiments, a composition of the present invention consists of (1) a TVP, a TVP-insecticidal protein, or a combination thereof; and (2) one or more excipients; wherein the TVP or TVP-insecticidal protein ranges from about 2% to about 16% wt/wt; and wherein trehalose ranges from about 5% to about 40% wt/wt; BIT ranges from about 0.01% to about 0.1% wt/wt; maltodextrin ranges from about 10% to about 50% wt/wt; potassium phosphate dibasic anhydrous ($K_2HPO_4$) ranges from about 1% to about 5% wt/wt; and potassium phosphate monobasic ($KH_2PO_4$) ranges from about 0.10% to about 1% wt/wt; and fermentation solids range from about 15% to about 40% wt/wt; of the total weight of the composition.

In some embodiments, a composition of the present invention consists of (1) a TVP, a TVP-insecticidal protein, or a combination thereof; and (2) one or more excipients; wherein the TVP or TVP-insecticidal protein ranges from about 7% to about 9% wt/wt; and wherein trehalose ranges from about 20% to about 30% wt/wt; BIT ranges from about 0.025% to about 0.075% wt/wt; maltodextrin ranges from about 30% to about 40% wt/wt; potassium phosphate dibasic anhydrous ($K_2HPO_4$) ranges from about 2% to about 3% wt/wt; potassium phosphate monobasic ($KH_2PO_4$) ranges from about 0.2% to about 0.6%; and fermentation solids range from about 20% to about 30%, of the total weight of the composition.

In some embodiments, a composition of the present invention consists of (1) a TVP, a TVP-insecticidal protein, or a combination thereof; and (2) one or more excipients; wherein the TVP or TVP-insecticidal protein is about 8.5% wt/wt; and wherein trehalose is about 25% wt/wt; BIT is about 0.05% wt/wt; maltodextrin is about 36.3% wt/wt; potassium phosphate dibasic anhydrous ($K_2HPO_4$) is about 2.6% wt/wt; potassium phosphate monobasic ($KH_2PO_4$) is about 0.4% wt/wt; and fermentation solids are about 26.85% wt/wt, of the total weight of the composition.

In some embodiments, a composition of the present invention consists essentially of the following: an amount of a TVP or a TVP-insecticidal protein that is 8.5% wt/wt; an amount of trehalose that is 25% wt/wt; an amount of BIT that is 0.05% wt/wt; an amount of maltodextrin that is 36.3% wt/wt; an amount of potassium phosphate dibasic anhydrous ($K_2HPO_4$) that is 2.6% wt/wt; an amount of potassium phosphate monobasic ($KH_2PO_4$) that is 0.4% wt/wt; and an amount of fermentation solids that is 26.85% wt/wt, of the total weight of the composition.

In some embodiments, a composition of the present invention consists of the following: an amount of a TVP or a TVP-insecticidal protein that is 8.5% wt/wt; an amount of trehalose that is 25% wt/wt; an amount of BIT that is 0.05% wt/wt; an amount of maltodextrin that is 36.3% wt/wt; an amount of potassium phosphate dibasic anhydrous ($K_2HPO_4$) that is 2.6% wt/wt; an amount of potassium phosphate monobasic ($KH_2PO_4$) that is 0.4% wt/wt; and an amount of fermentation solids that is 26.85% wt/wt, of the total weight of the composition.

In some embodiments, a composition of the present invention consists of (1) a TVP, a TVP-insecticidal protein, or a combination thereof; and (2) a plurality of excipients; wherein the TVP or TVP-insecticidal protein comprises an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof; wherein the composition consists of an amount of TVP that is 8.5% wt/wt of the total weight of the composition; and wherein the plurality of excipients consists of the following: an amount of trehalose that is 25% wt/wt; an amount of BIT that is 0.05% wt/wt; an amount of maltodextrin that is 36.3% wt/wt; an amount of potassium phosphate dibasic anhydrous ($K_2HPO_4$) that is 2.6% wt/wt; an amount of potassium phosphate monobasic ($KH_2PO_4$) that is 0.4% wt/wt; and an amount of fermentation solids that is 26.85% wt/wt, of the total weight of the composition.

In some embodiments, a composition of the present invention consists of (1) a TVP, a TVP-insecticidal protein, or a combination thereof; and (2) a plurality of excipients; wherein the TVP or TVP-insecticidal protein; wherein $Z_1$ is T and the TVP is glycosylated, or a pharmaceutically acceptable salt thereof.

In some embodiments, a composition of the present invention consists of (1) a TVP, a TVP-insecticidal protein, or a combination thereof; and (2) a plurality of excipients; wherein the TVP or TVP-insecticidal protein; wherein the TVP comprises an amino sequence as set forth in any one of SEQ ID NOs: 2, 49, or 51.

In some embodiments, a composition of the present invention consists of (1) a TVP, a TVP-insecticidal protein, or a combination thereof; and (2) a plurality of excipients; wherein the TVP or TVP-insecticidal protein; wherein the TVP is encoded by a polynucleotide sequence as set forth in any one of SEQ ID NOs: 17, 54, or 56, or a complementary nucleotide sequence thereof.

In some embodiments, a composition of the present invention consists of (1) a TVP, a TVP-insecticidal protein, or a combination thereof; and (2) a plurality of excipients; wherein the TVP or TVP-insecticidal protein comprises an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof; wherein the composition consists of an amount of TVP that is 8.5% wt/wt of the total weight of the composition; and wherein the plurality of excipients consists of the following: an amount of trehalose that is 25% wt/wt; an amount of BIT that is 0.05% wt/wt; an amount of maltodextrin that is 36.3% wt/wt; an amount of potassium phosphate dibasic anhydrous ($K_2HPO_4$) that is 2.6% wt/wt; an amount of potassium phosphate monobasic ($KH_2PO_4$) that is 0.4% wt/wt; and an amount of fermentation solids that is 26.85% wt/wt, of the total weight of the composition.

In some embodiments, a composition consists of, a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V—Y-$Z_1$-A-C-H-E-A-Q-

K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof; and wherein the one or more excipients is selected from the group consisting of: trehalose; maltodextrin; maltose; potassium phosphate dibasic ($K_2HPO_4$); potassium phosphate monobasic ($KH_2PO_4$); lignosulfonate; gypsum; sorbitol; sodium benzoate; potassium sorbate; EDTA; benzisothiazolinone (BIT); and fermentation solids.

In some embodiments, a composition consists of, a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V—Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof; and wherein the one or more excipients is selected from the group consisting of: trehalose; maltodextrin; maltose; potassium phosphate dibasic ($K_2HPO_4$); potassium phosphate monobasic ($KH_2PO_4$); lignosulfonate; gypsum; sorbitol; sodium benzoate; potassium sorbate; EDTA; benzisothiazolinone (BIT); and fermentation solids; wherein if $Z_1$ is T, and the TVP is glycosylated.

In some embodiments, a composition consists of, a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V—Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof; and wherein the one or more excipients is selected from the group consisting of:

trehalose; maltodextrin; maltose; potassium phosphate dibasic ($K_2HPO_4$); potassium phosphate monobasic ($KH_2PO_4$); lignosulfonate; gypsum; sorbitol; sodium benzoate; potassium sorbate; EDTA; benzisothiazolinone (BIT); and fermentation solids, wherein $X_1$ is Q; and $Z_1$ is A.

In some embodiments, a composition consists of, a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence in any one of SEQ ID NOs: 2, 49, or 51, or a pharmaceutically acceptable salt thereof; or a pharmaceutically acceptable salt thereof; and wherein the one or more excipients is selected from the group consisting of: trehalose; maltodextrin; maltose; potassium phosphate dibasic ($K_2HPO_4$); potassium phosphate monobasic ($KH_2PO_4$); lignosulfonate; gypsum; sorbitol; sodium benzoate; potassium sorbate; EDTA; benzisothiazolinone (BIT); and fermentation solids.

In some embodiments, a composition consists of, a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence in any one of SEQ ID NOs: 2, 49, or 51, or a pharmaceutically acceptable salt thereof; or a pharmaceutically acceptable salt thereof; and wherein the one or more excipients is selected from the group consisting of: trehalose; maltodextrin; potassium phosphate dibasic anhydrous ($K_2HPO_4$); potassium phosphate monobasic ($KH_2PO_4$); BIT; and fermentation solids.

In some embodiments, a composition consists of, a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V—Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof; and wherein the TVP ranges from about 2% to about 16% w/w; and wherein trehalose ranges from about 5% to about 40% w/w; BIT ranges from about 0.01% to about 0.1% w/w; maltodextrin ranges from about 10% to about 50% w/w; potassium phosphate dibasic anhydrous ($K_2HPO_4$) ranges from about 1% to about 5% w/w; and potassium phosphate monobasic ($KH_2PO_4$) ranges from about 0.10% to about 1% w/w; and fermentation solids range from about 15% to about 40% w/w; of the total weight of the composition.

In some embodiments, a composition consists of, a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V—Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof; and wherein the TVP ranges from about 7% to about 9% w/w; and wherein trehalose ranges from about 20% to about 30% w/w; BIT ranges from about 0.025% to about 0.075% w/w; maltodextrin ranges from about 30% to about 40% w/w; potassium phosphate dibasic anhydrous ($K_2HPO_4$) ranges from about 2% to about 3% w/w; potassium phosphate monobasic ($KH_2PO_4$) ranges from about 0.2% to about 0.6%; and fermentation solids range from about 20% to about 30%, of the total weight of the composition.

In some embodiments, a composition consists of, a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V—Y—$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof; and wherein the TVP is about 8.5% w/w; and wherein trehalose is about 25% w/w; BIT is about 0.05% w/w; maltodextrin is about 36.3% w/w; potassium phosphate dibasic anhydrous ($K_2HPO_4$) is about 2.6% w/w; potassium phosphate monobasic ($KH_2PO_4$) is about 0.4% w/w; and fermentation solids are about 26.85% w/w, of the total weight of the composition.

In some embodiments, a composition consists of, a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V—Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof; and wherein the composition consists essentially of the following: an amount of TVP that is 8.5% w/w; an amount of trehalose that is 25% w/w; an amount of BIT that is 0.05% w/w; an amount of maltodextrin that is 36.3% w/w; an amount of potassium phosphate dibasic anhydrous ($K_2HPO_4$) that is 2.6% w/w; an amount of potassium phosphate monobasic ($KH_2PO_4$) that is 0.4% w/w; and an amount of fermentation solids that is 26.85% w/w, of the total weight of the composition.

In some embodiments, a composition consists of, a TVP, a TVP-insecticidal protein, or a pharmaceutically acceptable salt thereof, wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V—Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof; and wherein the composition consists of the following: an amount of TVP that is 8.5% w/w; an amount of trehalose that is 25% w/w; an amount of BIT that is 0.05% w/w; an amount of maltodextrin that is 36.3% w/w; an amount of potassium phosphate dibasic anhydrous ($K_2HPO_4$) that is 2.6% w/w; an amount of potassium phosphate monobasic ($KH_2PO_4$) that is 0.4% w/w; and an amount of fermentation solids that is 26.85% w/w, of the total weight of the composition.

In some embodiments, a composition consists of a TVP, and a plurality of excipients; wherein the TVP comprises an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO: 1, and wherein $X_1$ is R or Q; and $Z_1$ is T or A; or a pharmaceutically acceptable salt thereof; wherein the composition consists of an amount of TVP that is 8.5% w/w of the total weight of the composition; and wherein the plurality of excipients consists of the following: an amount of trehalose that is 25% w/w; an amount of BIT that is 0.05% w/w; an amount of maltodextrin that is 36.3% w/w; an amount of potassium phosphate dibasic anhydrous ($K_2HPO_4$) that is 2.6% w/w; an amount of potassium phosphate monobasic ($KH_2PO_4$) that is 0.4% w/w; and an amount of fermentation solids that is 26.85% w/w, of the total weight of the composition.

In some embodiments, a composition consists of a TVP, and a plurality of excipients; wherein the TVP comprises an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO: 1, and wherein $X_1$ is R or Q; and $Z_1$ is T or A; or a pharmaceutically acceptable salt thereof; wherein the composition consists of an amount of TVP that is 8.5% w/w of the total weight of the composition; and wherein the plurality of excipients consists of the following: an amount of trehalose that is 25% w/w; an amount of BIT that is 0.05% w/w; an amount of maltodextrin that is 36.3% w/w; an amount of potassium phosphate dibasic anhydrous ($K_2HPO_4$) that is 2.6% w/w; an amount of potassium phosphate monobasic ($KH_2PO_4$) that is 0.4% w/w; and an amount of fermentation solids that is 26.85% w/w, of the total weight of the composition; wherein if $Z_1$ is T and the TVP is glycosylated.

In some embodiments, a composition consists of a TVP, and a plurality of excipients; wherein the TVP comprises an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO: 1, and wherein $X_1$ is R or Q; and $Z_1$ is T or A; or a pharmaceutically acceptable salt thereof; wherein the composition consists of an amount of TVP that is 8.5% w/w of the total weight of the composition; and wherein the plurality of excipients consists of the following: an amount of trehalose that is 25% w/w; an amount of BIT that is 0.05% w/w; an amount of maltodextrin that is 36.3% w/w; an amount of potassium phosphate dibasic anhydrous ($K_2HPO_4$) that is 2.6% w/w; an amount of potassium phosphate monobasic ($KH_2PO_4$) that is 0.4% w/w; and an amount of fermentation solids that is 26.85% w/w, of the total weight of the composition; wherein $X_1$ is Q; and $Z_1$ is A.

In some embodiments, a composition consists of a TVP, and a plurality of excipients; wherein the TVP comprises an amino acid sequence that is at least 90% identical to the amino acid sequence according to SEQ ID NOs: 2, 49, or 51; or a pharmaceutically acceptable salt thereof; wherein the composition consists of an amount of TVP that is 8.5% w/w of the total weight of the composition; and wherein the plurality of excipients consists of the following: an amount of trehalose that is 25% w/w; an amount of BIT that is 0.05% w/w; an amount of maltodextrin that is 36.3% w/w; an amount of potassium phosphate dibasic anhydrous ($K_2HPO_4$) that is 2.6% w/w; an amount of potassium phosphate monobasic ($KH_2PO_4$) that is 0.4% w/w; and an amount of fermentation solids that is 26.85% w/w, of the total weight of the composition.

Any of the foregoing TVPs, TVP-insecticidal proteins, or pharmaceutically acceptable salts thereof, can be used in the any of the formulations described herein and below, e.g., any of the foregoing TVPs, TVP-insecticidal proteins, or pharmaceutically acceptable salts thereof, can be used in the formulation of: a wettable powder or granule formulation; or a liquid concentrate formulation.

Methods of Using the Present Invention

Methods for Protecting Plants, Plant Parts, and Seeds

In some embodiments, the present disclosure provides a method for controlling an invertebrate pest in agronomic and/or nonagronomic applications, comprising contacting the invertebrate pest or its environment, a solid surface, including a plant surface or part thereof, with a biologically effective amount of one or more of the TVPs of the invention, or with an insecticidal protein comprising at least one TVP.

In some embodiments, the present disclosure provides a method for controlling an invertebrate pest in agronomic and/or nonagronomic applications, comprising contacting the invertebrate pest or its environment, a solid surface, including a plant surface or part thereof, with a biologically effective amount of a composition consisting of at least one TVP of the invention and an excipient.

In some embodiments, the present disclosure provides a method for controlling an invertebrate pest in agronomic and/or nonagronomic applications, comprising contacting the invertebrate pest or its environment, a solid surface, including a plant surface or part thereof, with a biologically effective amount of a composition consisting of at least one TVP-insecticidal protein of the invention and an excipient.

Examples of suitable compositions consisting of: (1) at least one TVP of the invention; two or more of the TVPs of the present invention; a TVP-insecticidal protein; and/or Two or more TVP-insecticidal proteins; and (2) an excipient; include said compositions formulated w in inactive ingredients to be delivered in the form of: a liquid solution, an emulsion, a powder, a granule, a nanoparticle, a micropart-icle, or a combination thereof.

In some embodiments, to achieve contact with a compound, mixture, or composition of the invention to protect a field crop from invertebrate pests, the compound or composition is typically applied to the seed of the crop before planting, to the foliage (e.g., leaves, stems, flowers, fruits) of crop plants, or to the soil or other growth medium before or after the crop is planted.

One embodiment of a method of contact is by spraying. Alternatively, a granular composition consisting of a TVP or a TVP-insecticidal protein, and an excipient, can be applied to the plant foliage or the soil. Compounds of this invention can also be effectively delivered through plant uptake by contacting the plant with a composition comprising a compound of this invention applied as a soil drench of a liquid formulation, a granular formulation to the soil, a nursery box treatment or a dip of transplants. Of note is a composition of the present disclosure in the form of a soil drench liquid formulation. Also of note is a method for controlling an invertebrate pest comprising contacting the invertebrate pest or its environment with a biologically effective amount of a TVP or TVP-insecticidal protein. Of further note, in some illustrative embodiments, the illustrative method contemplates a soil environment, wherein the composition is applied to the soil as a soil drench formulation. Of further note is that a TVP or a TVP-insecticidal protein is also effective by localized application to the locus of infestation. Other methods of contact include application of a compound or a composition of the invention by direct and residual sprays, aerial sprays, gels, seed coatings, microencapsulations, systemic uptake, baits, ear tags, boluses, foggers, fumigants, aerosols, dusts and many others. One embodiment of a method of contact is a dimensionally stable fertilizer granule, stick or tablet comprising a compound or composition of the invention. The compounds of this invention can also be impregnated into materials for fabricating invertebrate control devices (e.g., insect netting, application onto clothing, application into candle formulations and the like).

In some embodiments, a TVP or a TVP-insecticidal protein is also useful in seed treatments for protecting seeds from invertebrate pests. In the context of the present disclosure and claims, treating a seed means contacting the seed with a biologically effective amount of a TVP or a TVP-insecticidal protein, which is typically formulated as a composition of the invention. This seed treatment protects the seed from invertebrate soil pests and generally can also protect roots and other plant parts in contact with the soil of the seedling developing from the germinating seed. The seed treatment may also provide protection of foliage by translocation of the TVP or TVP-insecticidal protein within the developing plant. Seed treatments can be applied to all types of seeds, including those from which plants genetically transformed to express specialized traits will germinate. In addition, a TVP or a TVP-insecticidal protein can be transformed into a plant or part thereof, for example a plant cell, or plant seed, that is already transformed, e.g., those expressing herbicide resistance such as glyphosate acetyltransferase, which provides resistance to glyphosate.

One method of seed treatment is by spraying or dusting the seed with a TVP or a TVP-insecticidal protein (i.e. as a formulated composition consisting of a TVP or a TVP-insecticidal protein and an excipient) before sowing the seeds. Compositions formulated for seed treatment generally consist of a TVP or a TVP-insecticidal protein, and a film former or adhesive agent. Therefore, typically, a seed coating composition of the present disclosure consists of a biologically effective amount of a TVP or a TVP-insecticidal protein, and a film former or adhesive agent. Seed can be coated by spraying a flowable suspension concentrate directly into a tumbling bed of seeds and then drying the seeds. Alternatively, other formulation types such as wetted powders, solutions, suspoemulsions, emulsifiable concentrates and emulsions in water can be sprayed on the seed. This process is particularly useful for applying film coatings on seeds. Various coating machines and processes are available to one skilled in the art. Suitable processes include those listed in P. Kosters et al., Seed Treatment: Progress and Prospects, 1994 BCPC Monograph No. 57, and references listed therein, the disclosures of which are incorporated herein by reference in their entireties.

The treated seed typically comprises a TVP or a TVP-insecticidal protein in an amount ranging from about 0.01 g to 1 kg per 100 kg of seed (i.e. from about 0.00001 to 1% by weight of the seed before treatment). A flowable suspension formulated for seed treatment typically comprises from about 0.5 to about 70% of the active ingredient, from about 0.5 to about 30% of a film-forming adhesive, from about 0.5 to about 20% of a dispersing agent, from 0 to about 5% of a thickener, from 0 to about 5% of a pigment and/or dye, from 0 to about 2% of an antifoaming agent, from 0 to about 1% of a preservative, and from 0 to about 75% of a volatile liquid diluent.

Methods of Using Formulations and Compositions

In some embodiments, the present invention provides a method of using a composition consisting of: (1) a TVP or a TVP-insecticidal protein; and (2) an excipient; to control insects, wherein the TVP is selected from one or any combination of the TVPs described herein, e.g., an insecticidal U1-agatoxin-Ta1b variant polypeptide (TVP), said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO: 1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; wherein said method comprises, preparing the composition and then applying said composition to the locus of an insect.

In some embodiments, the present invention provides a method of using a composition consisting of: (1) a TVP or a TVP-insecticidal protein; and (2) an excipient; to control insects, wherein the TVP is selected from one or any combination of the TVPs described herein, e.g., an insecticidal U1-agatoxin-Ta1b variant polypeptide (TVP), said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; wherein said method comprises, preparing the composition and then applying said composition to the locus of an insect.

In some embodiments, the present invention provides a method of using a composition to control insects, said composition consisting of: (1) a TVP or a TVP-insecticidal protein, and (2) an excipient; wherein the insects are selected from the group consisting of: Achema Sphinx Moth (Hornworm) (*Eumorpha achemon*); Alfalfa Caterpillar (*Colias eurytheme*); Almond Moth (*Caudra cautella*); Amorbia Moth (*Amorbia humerosana*); Armyworm (*Spodoptera* spp., e.g. *exigua, frugiperda, littoralis, Pseudaletia unipuncta*); Artichoke Plume Moth (*Platyptilia carduidactyla*); Azalea Caterpillar (*Datana major*); Bagworm (*Thyridopteryx*); *ephemeraeformis*); Banana Moth (*Hypercompe scribonia*); Banana Skipper (*Erionota thrax*); Blackheaded Budworm (*Acleris gloverana*); California Oakworm (*Phryganidia californica*); Spring Cankerworm (*Paleacrita merriccata*); Cherry Fruitworm (*Grapholita packardi*); China Mark Moth (*Nymphula stagnata*); Citrus Cutworm (*Xylomyges curialis*); Codling Moth (*Cydia pomonella*); Cranberry Fruit-worm (*Acrobasis vaccinii*); Cross-striped Cabbageworm (*Evergestis rimosalis*); Cutworm (*Noctuid* species, *Agrotis ipsilon*); Douglas Fir Tussock Moth (*Orgyia pseudotsugata*); Ello Moth (Hornworm) (*Erinnyis ello*); Elm Spanworm (*Ennomos subsignaria*); European Grapevine Moth (*Lobesia botrana*); European Skipper (*Thymelicus lineola* (Essex Skipper); Fall Webworm (*Melissopus latiferreanus*; Filbert Leafroller (*Archips rosanus*; Fruittree Leafroller (*Archips argyrospilia*; Grape Berry Moth (*Paralobesia viteana*; Grape Leafroller (*Platynota stultana*; Grapeleaf Skeletonizer (*Harrisina americana* (ground only); Green Cloverworm (*Plathypena scabra*; Greenstriped Mapleworm (*Dryocampa rubicunda*; Gummosos-Batrachedra; Comosae (Hodges); Gypsy Moth (*Lymantria dispar*); Hemlock Looper (*Lambdina fiscellaria*); Hornworm (*Manduca* spp.); Imported Cabbageworm (*Pieris rapae*); Io Moth (*Automeris io*); Jack Pine Budworm (*Choristoneura pinus*); Light Brown Apple Moth (*Epiphyas postvittana*); Melonworm (*Diaphania hyalinata*); Mimosa Webworm (*Homadaula anisocentra*); Obliquebanded Leafroller (*Choristoneura rosaceana*); Oleander Moth (*Syntomeida epilais*); Omnivorous Leafroller (*Playnota stultana*); Omnivorous Looper (*Sabulodes aegrotata*); Orangedog (*Papilio cresphontes*); Orange Tortrix (*Argyrotaenia citrana*); Oriental Fruit Moth (*Grapholita molesta*); Peach Twig Borer (*Anarsia lineatella*); Pine Butterfly (*Neophasia menapia*); Podworm (*Heliocoverpa zea*); Redbanded Leafroller (*Argyrotaenia velutinana*); Redhumped Caterpillar (*Schizura concinna*); Rindworm Complex (Various Leps.); Saddleback Caterpillar (*Sibine stimulea*); Saddle Prominent Caterpillar *Heterocampa guttivitta*); Saltmarsh Caterpillar (*Estigmene acrea*); Sod Webworm (*Crambus* spp.); Spanworm (*Ennomos subsignaria*); Fall Cankerworm (*Alsophila pometaria*); Spruce Budworm (*Choristoneura fumiferana*); Tent Caterpillar (Various Lasiocampidae); Thecla-Thecla Basilides (Geyr) *Thecla basilides*); Tobacco Hornworm (*Manduca sexta*); Tobacco Moth (*Ephestia elutella*); Tufted Apple Budmoth (*Platynota idaeusalis*); Twig Borer (*Anarsia lineatella*); Variegated Cutworm (*Peridroma saucia*); Variegated Leafroller (*Platynota flavedana*); Velvetbean Caterpillar (*Anticarsia gemmatalis*); Walnut Caterpillar (*Datana integerrima*); Webworm (*Hyphantria cunea*); Western Tussock Moth (*Orgyia vetusta*); Southern Cornstalk Borer (*Diatraea crambidoides*); Corn Earworm; Sweet potato weevil; Pepper weevil; Citrus root weevil; Strawberry root weevil; Pecan weevil; Filbert weevil; Ricewater weevil; Alfalfa weevil; Clover weevil; Tea shot-hole borer; Root weevil; Sugarcane beetle; Coffee berry borer; Annual blue grass weevil (*Listronotus maculicollis*); Asiatic garden beetle (*Maladera castanea*); European chafer (*Rhizotroqus majalis*); Green June beetle (*Cotinis nitida*); Japanese beetle (*Popillia japonica*); May or June beetle (*Phyllophaga* sp.); Northern masked chafer (*Cyclocephala borealis*); Oriental beetle (*Anomala orientalis*); Southern masked chafer (*Cyclocephala lurida*); Billbug (Curculionoidea); *Aedes aegypti; Busseola fusca; Chilo suppressalis; Culex pipiens; Culex quinquefasciatus; Diabrotica virgifera; Diatraea saccharalis; Helicoverpa*

*armigera; Helicoverpa zea; Heliothis virescens; Leptinotarsa decemlineata; Ostrinia furnacalis; Ostrinia nubilalis; Pectinophora gossypiella; Plodia interpunctella; Plutella xylostella; Pseudoplusia includens; Spodoptera exigua; Spodoptera frugiperda; Spodoptera littoralis; Trichoplusia ni;* and *Xanthogaleruca luteola.*

In some embodiments, the present invention provides a method of protecting a plant from insects comprising, providing a plant which expresses one or more TVPs, or polynucleotides encoding the same.

In some embodiments, the present invention provides a method of protecting a plant from insects comprising, providing a plant that expresses a TVP, or polynucleotide encoding the same, wherein said TVP comprises an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent.

In some embodiments, the present invention provides a method of protecting a plant from insects comprising, providing a plant that expresses a TVP, or polynucleotide encoding the same, wherein the TVP has one amino acid substitution at $X_1$, $X_2$, $X_3$, $X_4$, or $X_5$.

In some embodiments, the present invention provides a method of protecting a plant from insects comprising, providing a plant that expresses a TVP, or polynucleotide encoding the same, wherein the TVP has one amino acid substitution at $X_1$, $X_2$, $X_3$, $X_4$, or $X_5$; and wherein $X_7$ is Glycine.

In some embodiments, the present invention provides a method of protecting a plant from insects comprising, providing a plant that expresses a TVP, or polynucleotide encoding the same, wherein the TVP has one amino acid substitution at $X_1$, $X_2$, $X_3$, $X_4$, or $X_5$; and wherein $X_7$ is absent.

In some embodiments, the present invention provides a method of protecting a plant from insects comprising, providing a plant that expresses a TVP, or polynucleotide encoding the same, wherein the TVP has one amino acid substitution at $X_1$, $X_2$, $X_3$, $X_4$, or $X_5$; and wherein $X_6$ and $X_7$ are absent.

In some embodiments, the present invention provides a method of protecting a plant from insects comprising, providing a plant that expresses a TVP, or polynucleotide encoding the same, wherein the TVP comprises an amino sequence as set forth in any one of SEQ ID NOs: 2-15, 49-53, or 77-110.

In some embodiments, the present invention provides a method of protecting a plant from insects comprising, providing a plant that expresses a TVP, or polynucleotide encoding the same, wherein the TVP is encoded by a polynucleotide sequence as set forth in any one of SEQ ID NOs: 17-30, 54-58, or 117-150, or a complementary nucleotide sequence thereof.

In some embodiments, the present invention provides a method of protecting a plant from insects comprising, providing a plant that expresses a TVP, or polynucleotide encoding the same, wherein the TVP further comprises a homopolymer or heteropolymer of two or more TVPs, wherein the amino acid sequence of each TVP is the same or different.

In some embodiments, the present invention provides a method of protecting a plant from insects comprising, providing a plant that expresses a TVP, or polynucleotide encoding the same, wherein the TVP is a fused protein comprising two or more TVPs separated by a cleavable or non-cleavable linker, and wherein the amino acid sequence of each TVP may be the same or different.

In some embodiments, the present invention provides a method of protecting a plant from insects comprising, providing a plant that expresses a TVP, or polynucleotide encoding the same, wherein the linker is cleavable inside the gut or hemolymph of an insect.

In some embodiments, the present invention provides a method of protecting a plant from insects comprising, providing a plant that expresses a TVP, or polynucleotide encoding the same, wherein the plant is protected from insects that are selected from the group consisting of: Achema Sphinx Moth (Hornworm) (*Eumorpha achemon*); Alfalfa Caterpillar (*Colias eurytheme*); Almond Moth (*Caudra cautella*); Amorbia Moth (*Amorbia humerosana*); Armyworm (*Spodoptera* spp., e.g. *exigua, frugiperda, littoralis, Pseudaletia unipuncta*); Artichoke Plume Moth (*Platyptilia carduidactyla*); Azalea Caterpillar (*Datana major*); Bagworm (*Thyridopteryx*); *ephemeraeformis*); Banana Moth (*Hypercompe scribonia*); Banana Skipper (*Erionota thrax*); Blackheaded Budworm (*Acleris gloverana*); California Oakworm (*Phryganidia californica*); Spring Cankerworm (*Paleacrita merriccata*); Cherry Fruitworm (*Grapholita packardi*); China Mark Moth (*Nymphula stagnata*); Citrus Cutworm (*Xylomyges curialis*); Codling Moth (*Cydia pomonella*); Cranberry Fruitworm (*Acrobasis vaccinii*); Cross-striped Cabbageworm (*Evergestis rimosalis*); Cutworm (*Noctuid* species, *Agrotis ipsilon*); Douglas Fir Tussock Moth (*Orgyia pseudotsugata*); Ello Moth (Hornworm) (*Erinnyis ello*); Elm Spanworm (*Ennomos subsignaria*); European Grapevine Moth (*Lobesia botrana*); European Skipper (*Thymelicus lineola* (Essex Skipper); Fall Webworm (*Melissopus latiferreanus*; Filbert Leafroller (*Archips rosanus*; Fruittree Leafroller (*Archips argyrospilia*; Grape Berry Moth (*Paralobesia viteana*; Grape Leafroller (*Platynota stultana*; Grapeleaf Skeletonizer (*Harrisina americana* (ground only); Green Cloverworm (*Plathypena scabra*; Greenstriped Mapleworm (*Dryocampa rubicunda*; Gummosos-Batrachedra; Comosae (Hodges); Gypsy Moth (*Lymantria dispar*); Hemlock Looper (*Lambdina fiscellaria*); Hornworm (*Manduca* spp.); Imported Cabbageworm (*Pieris rapae*); Io Moth (*Automeris io*); Jack Pine Budworm (*Choristoneura pinus*); Light Brown Apple Moth (*Epiphyas postvittana*); Melonworm (*Diaphania hyalinata*); Mimosa Webworm (*Homadaula anisocentra*); Obliquebanded Leafroller (*Choristoneura rosaceana*); Oleander Moth (*Syntomeida epilais*); Omnivorous Leafroller (*Playnota stultana*); Omnivorous Looper (*Sabulodes aegrotata*); Orangedog (*Papilio cresphontes*); Orange Tortrix (*Argyrotaenia citrana*); Oriental Fruit Moth (*Grapholita molesta*); Peach Twig Borer (*Anarsia lineatella*); Pine Butterfly (*Neophasia menapia*); Podworm (*Heliocoverpa zea*); Redbanded Leafroller (*Argyrotaenia velutinana*); Redhumped Caterpillar (*Schizura concinna*); Rindworm Complex (Various Leps.); Saddleback Caterpillar (*Sibine stimulea*); Saddle Prominent Caterpillar *Heterocampa guttivitta*); Saltmarsh Caterpillar (*Estigmene acrea*); Sod Webworm (*Crambus* spp.); Spanworm (*Ennomos subsignaria*); Fall Cankerworm (*Alsophila pometaria*); Spruce Budworm (*Choristoneura*

*fumiferana*); Tent Caterpillar (Various Lasiocampidae); Thecla-Thecla Basilides (Geyr) *Thecla basilides*); Tobacco Hornworm (*Manduca sexta*); Tobacco Moth (*Ephestia elutella*); Tufted Apple Budmoth (*Platynota idaeusalis*); Twig Borer (*Anarsia lineatella*); Variegated Cutworm (*Peridroma saucia*); Variegated Leafroller (*Platynota flavedana*); Velvetbean Caterpillar (*Anticarsia gemmatalis*); Walnut Caterpillar (*Datana integerrima*); Webworm (*Hyphantria cunea*); Western Tussock Moth (*Orgyia vetusta*); Southern Cornstalk Borer (*Diatraea crambidoides*); Corn Earworm; Sweet potato weevil; Pepper weevil; Citrus root weevil; Strawberry root weevil; Pecan weevil; Filbert weevil; Ricewater weevil; Alfalfa weevil; Clover weevil; Tea shot-hole borer; Root weevil; Sugarcane beetle; Coffee berry borer; Annual blue grass weevil (*Listronotus maculicollis*); Asiatic garden beetle (*Maladera castanea*); European chafer (*Rhizotroqus majalis*); Green June beetle (*Cotinis nitida*); Japanese beetle (*Popillia japonica*); May or June beetle (*Phyllophaga* sp.); Northern masked chafer (*Cyclocephala borealis*); Oriental beetle (*Anomala orientalis*); Southern masked chafer (*Cyclocephala lurida*); Billbug (Curculionoidea); *Aedes aegypti; Busseola fusca; Chilo suppressalis; Culex pipiens; Culex quinquefasciatus; Diabrotica virgifera; Diatraea saccharalis; Helicoverpa armigera; Helicoverpa zea; Heliothis virescens; Leptinotarsa decemlineata; Ostrinia furnacalis; Ostrinia nubilalis; Pectinophora gossypiella; Plodia interpunctella; Plutella xylostella; Pseudoplusia includens; Spodoptera exigua; Spodoptera frugiperda; Spodoptera littoralis; Trichoplusia ni*; and *Xanthogaleruca luteola*.

In some embodiments, the present invention provides a method for controlling insects comprising, providing to said insect a transgenic plant that comprises in its genome a stably incorporated nucleic acid construct, wherein said stably incorporated nucleic acid construct comprises polynucleotide operable to encode a TVP.

In some embodiments, the present invention provides a method of combating, controlling, or inhibiting a pest comprising, applying a pesticidally effective amount of a composition consisting of: (1) a TVP or a TVP-insecticidal protein; and (2) an excipient; wherein the TVP is selected from one or any combination of the TVPs described herein, e.g., an insecticidal U1-agatoxin-Ta1b variant polypeptide (TVP), said TVP comprising an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; and wherein the composition is applied to the locus of the pest, or to a plant or animal susceptible to an attack by the pest.

Any of the compositions described herein can be used in the method of method of combating, controlling, or inhibiting a pest comprising, applying a pesticidally effective amount of a composition consisting of: (1) a TVP or a TVP-insecticidal protein; and (2) an excipient.

For example, in some embodiments, the present invention provides a method of combating, controlling, or inhibiting a pest comprising, applying a pesticidally effective amount of a composition consisting of a TVP, and one or more excipients; wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or a pharmaceutically acceptable salt thereof; and wherein the one or more excipients is selected from the group consisting of: trehalose; maltodextrin; maltose; potassium phosphate dibasic ($K_2HPO_4$); potassium phosphate monobasic ($KH_2PO_4$); lignosulfonate; gypsum; sorbitol; sodium benzoate; potassium sorbate; EDTA; benzisothiazolinone (BIT); and fermentation solids.

In some embodiments, the present invention provides a method of combating, controlling, or inhibiting a pest comprising, applying a pesticidally effective amount of a composition consisting of a TVP, wherein the TVP has one amino acid substitution at $X_1$, $X_2$, $X_3$, $X_4$, or $X_5$, or a pharmaceutically acceptable salt thereof.

In some embodiments, the present invention provides a method of combating, controlling, or inhibiting a pest comprising, applying a pesticidally effective amount of a composition consisting of a TVP, wherein the TVP has one amino acid substitution at $X_1$, $X_2$, $X_3$, $X_4$, or $X_5$; and wherein $X_7$ is Glycine, or a pharmaceutically acceptable salt thereof.

In some embodiments, the present invention provides a method of combating, controlling, or inhibiting a pest comprising, applying a pesticidally effective amount of a composition consisting of a TVP, wherein the TVP has one amino acid substitution at $X_1$, $X_2$, $X_3$, $X_4$, or $X_5$; and wherein $X_7$ is absent, or a pharmaceutically acceptable salt thereof.

In some embodiments, a composition of the present invention consists of a TVP, wherein the TVP has one amino acid substitution at $X_1$, $X_2$, $X_3$, $X_4$, or $X_5$; and wherein $X_6$ and $X_7$ are absent, or a pharmaceutically acceptable salt thereof.

In some embodiments, the present invention provides a method of combating, controlling, or inhibiting a pest comprising, applying a pesticidally effective amount of a composition consisting of a TVP, wherein the TVP comprises an amino sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any of the amino acid sequences set forth in any one of SEQ ID NOs: 2-15, 49-53, or 77-110.

In some embodiments, the present invention provides a method of combating, controlling, or inhibiting a pest comprising, applying a pesticidally effective amount of a composition consisting of a TVP, wherein the TVP is encoded by a polynucleotide sequence as set forth in any one of SEQ ID NOs: 17-30, 54-58, or 117-150, or a complementary nucleotide sequence thereof.

In some embodiments, the present invention provides a method of combating, controlling, or inhibiting a pest comprising, applying a pesticidally effective amount of a composition consisting of a TVP, wherein the TVP further comprises a homopolymer or heteropolymer of two or more TVPs, wherein the amino acid sequence of each TVP is the same or different.

In some embodiments, the present invention provides a method of combating, controlling, or inhibiting a pest comprising, applying a pesticidally effective amount of a composition consisting of a TVP, wherein the TVP is a fused protein comprising two or more TVPs separated by a cleavable linker or non-cleavable linker, and wherein the amino acid sequence of each TVP may be the same or different.

In some embodiments, the present invention provides a method of combating, controlling, or inhibiting a pest comprising, applying a pesticidally effective amount of a composition consisting of a TVP having a linker, wherein the linker is a cleavable linker.

In some embodiments, a composition of the present invention consists of a TVP having a cleavable linker, wherein the cleavable linker is cleavable inside the gut or hemolymph of an insect.

In some embodiments, the present invention provides a method of combating, controlling, or inhibiting a pest comprising, applying a pesticidally effective amount of a composition consisting of a TVP having a linker, wherein the linker has an amino acid sequence as set forth in any one of SEQ ID NOs: 61-70.

In some embodiments, the present invention provides a method of combating, controlling, or inhibiting a pest comprising, applying a pesticidally effective amount of a composition consisting of a TVP, and one or more excipients; wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or a pharmaceutically acceptable salt thereof; and wherein the one or more excipients is selected from the group consisting of: trehalose; maltodextrin; maltose; potassium phosphate dibasic ($K_2HPO_4$); potassium phosphate monobasic ($KH_2PO_4$); lignosulfonate; gypsum; sorbitol; sodium benzoate; potassium sorbate; EDTA; benzisothiazolinone (BIT); and fermentation solids, wherein if $Z_1$ is T or S, then the TVP is glycosylated.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) one or more excipients.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) one or more excipients, wherein the one or more excipients is selected from the group consisting of: trehalose; maltodextrin; potassium phosphate dibasic anhydrous ($K_2HPO_4$); potassium phosphate monobasic ($KH_2PO_4$); BIT; and fermentation solids.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) one or more excipients; wherein the TVP or TVP-insecticidal protein ranges from about 2% to about 16% wt/wt; and wherein trehalose ranges from about 5% to about 40% wt/wt; BIT ranges from about 0.01% to about 0.1% wt/wt; maltodextrin ranges from about 10% to about 50% wt/wt; potassium phosphate dibasic anhydrous ($K_2HPO_4$) ranges from about 1% to about 5% wt/wt; and potassium phosphate monobasic ($KH_2PO_4$) ranges from about 0.10% to about 1% wt/wt; and fermentation solids range from about 15% to about 40% wt/wt; of the total weight of the composition.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) one or more excipients; wherein the TVP or TVP-insecticidal protein ranges from about 7% to about 9% wt/wt; and wherein trehalose ranges from about 20% to about 30% wt/wt; BIT ranges from about 0.025% to about 0.075% wt/wt; maltodextrin ranges from about 30% to about 40% wt/wt; potassium phosphate dibasic anhydrous ($K_2HPO_4$) ranges from about 2% to about 3% wt/wt; potassium phosphate monobasic ($KH_2PO_4$) ranges from about 0.2% to about 0.6%; and fermentation solids range from about 20% to about 30%, of the total weight of the composition.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) one or more excipients; wherein the TVP or TVP-insecticidal protein is about 8.5% wt/wt; and wherein trehalose is about 25% wt/wt; BIT is about 0.05% wt/wt; maltodextrin is about 36.3% wt/wt; potassium phosphate dibasic anhydrous ($K_2HPO_4$) is about 2.6% wt/wt; potassium phosphate monobasic ($KH_2PO_4$) is about 0.4% wt/wt; and fermentation solids are about 26.85% wt/wt, of the total weight of the composition.

In some embodiments, the present invention provides a method of combating, controlling, or inhibiting a pest comprising, applying a pesticidally effective amount of a composition consisting of essentially of the following: an amount of a TVP or a TVP-insecticidal protein that is 8.5% wt/wt; an amount of trehalose that is 25% wt/wt; an amount of BIT that is 0.05% wt/wt; an amount of maltodextrin that is 36.3% wt/wt; an amount of potassium phosphate dibasic anhydrous ($K_2HPO_4$) that is 2.6% wt/wt; an amount of potassium phosphate monobasic ($KH_2PO_4$) that is 0.4% wt/wt; and an amount of fermentation solids that is 26.85% wt/wt, of the total weight of the composition.

In some embodiments, the present invention provides a method of combating, controlling, or inhibiting a pest comprising, applying a pesticidally effective amount of a composition consisting of the following: an amount of a TVP or a TVP-insecticidal protein that is 8.5% wt/wt; an amount of trehalose that is 25% wt/wt; an amount of BIT that is 0.05% wt/wt; an amount of maltodextrin that is 36.3% wt/wt; an amount of potassium phosphate dibasic anhydrous ($K_2HPO_4$) that is 2.6% wt/wt; an amount of potassium phosphate monobasic ($KH_2PO_4$) that is 0.4% wt/wt; and an amount of fermentation solids that is 26.85% wt/wt, of the total weight of the composition.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein comprises an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or a pharmaceutically acceptable salt thereof; wherein the composition consists of an amount of TVP that is 8.5% wt/wt of the total weight of the composition; and wherein the plurality of excipients consists of the following: an amount of trehalose that is 25% wt/wt; an amount of BIT that is 0.05% wt/wt; an amount of maltodextrin that is 36.3% wt/wt; an amount of potassium phosphate dibasic anhydrous ($K_2HPO_4$) that is 2.6% wt/wt; an amount of potassium phosphate monobasic ($KH_2PO_4$) that is 0.4% wt/wt; and an amount of fermentation solids that is 26.85% wt/wt, of the total weight of the composition.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the TVP has one amino acid substitution at $X_1$, $X_2$, $X_3$, $X_4$, or $X_5$, or a pharmaceutically acceptable salt thereof.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the TVP has one amino acid substitution at $X_1$, $X_2$, $X_3$, $X_4$, or $X_5$; and wherein $X_7$ is Glycine, or a pharmaceutically acceptable salt thereof.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the TVP has one amino acid substitution at $X_1$, $X_2$, $X_3$, $X_4$, or $X_5$; and wherein $X_7$ is absent, or a pharmaceutically acceptable salt thereof.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the TVP has one amino acid substitution at $X_1$, $X_2$, $X_3$, $X_4$, or $X_5$; and wherein $X_6$ and $X_7$ are absent, or a pharmaceutically acceptable salt thereof.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the TVP comprises an amino sequence as set forth in any one of SEQ ID NOs: 2-15, 49-53, or 77-110.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the TVP is encoded by a polynucleotide sequence as set forth in any one of SEQ ID NOs: 17-30, 54-58, or 117-150, or a complementary nucleotide sequence thereof.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the TVP further comprises a homopolymer or heteropolymer of two or more TVPs, wherein the amino acid sequence of each TVP is the same or different.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the TVP is a fused protein comprising two or more TVPs separated by a cleavable or non-cleavable linker, and wherein the amino acid sequence of each TVP may be the same or different.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the linker is a cleavable linker.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the cleavable linker is cleavable inside the gut or hemolymph of an insect.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the linker has an amino acid sequence as set forth in any one of SEQ ID NOs: 61-70.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein comprises an amino acid sequence that is at least 90% identical to the amino acid sequence according to Formula (I): E-P-D-E-I-C-R-$X_1$-$X_2$-M-$X_3$-N-K-E-F-T-Y-$X_4$-S-N-V-C-N-N-C-G-D-Q-V-A-A-C-E-A-E-C-F-$X_5$-N-D-V-Y-$Z_1$-A-C-H-E-A-Q-$X_6$-$X_7$ (SEQ ID NO: 151), wherein the polypeptide comprises at least one amino acid substitution relative to the wild-type sequence of U1-agatoxin-Ta1b as set forth in SEQ ID NO:1, and wherein $X_1$ is A, S, or N; $X_2$ is R, Q, N, A, G, N, L, D, V, M, I, C, E, T, or S; $X_3$ is T or P; $X_4$ is K or A; $X_5$ is R or A; $Z_1$ is T, S, A, F, P, Y, K, W, H, A, G, N, L, V, M, I, Q, C, E, or R; $X_6$ is K or absent; and $X_7$ is G or absent; or a pharmaceutically acceptable salt thereof; wherein the composition consists of an amount of TVP that is 8.5% wt/wt of the total weight of the composition; and wherein the plurality of excipients consists of the following: an amount of trehalose that is 25% wt/wt; an amount of BIT that is 0.05% wt/wt; an amount of maltodextrin that is 36.3% wt/wt; an amount of potassium phosphate dibasic anhydrous ($K_2HPO_4$) that is 2.6% wt/wt; an amount of potassium phosphate monobasic ($KH_2PO_4$) that is 0.4% wt/wt; and an amount of fermentation solids that is 26.85% wt/wt, of the total weight of the composition; wherein if $Z_1$ is T or S, then the TVP is glycosylated.

Any of the foregoing TVPs, TVP-insecticidal proteins, or pharmaceutically acceptable salts thereof, can be used in any of the formulations described herein and below, e.g., any of the foregoing TVPs, TVP-insecticidal proteins, or pharmaceutically acceptable salts thereof, can be used in the formulation of: a wettable powder or granule formulation; or a liquid concentrate formulation.

In some embodiments, the present invention provides a method of combating, controlling, or inhibiting a pest comprising, applying a pesticidally effective amount of a composition consisting of: (1) a TVP or a TVP-insecticidal protein; and (2) an excipient; to the locus of a pest, wherein the pest is selected from the group consisting of: Achema Sphinx Moth (Hornworm) (*Eumorpha achemon*); Alfalfa Caterpillar (*Colias eurytheme*); Almond Moth (*Caudra cautella*); Amorbia Moth (*Amorbia humerosana*); Armyworm (*Spodoptera* spp., e.g. *exigua, frugiperda, littoralis, Pseudaletia unipuncta*); Artichoke Plume Moth (*Platyptilia carduidactyla*); Azalea Caterpillar (*Datana major*); Bagworm (*Thyridopteryx*); *ephemeraeformis*); Banana Moth (*Hypercompe scribonia*); Banana Skipper (*Erionota thrax*); Black-headed Budworm (*Acleris gloverana*); California Oakworm (*Phryganidia californica*); Spring Cankerworm (*Paleacrita merriccata*); Cherry Fruitworm (*Grapholita packardi*); China Mark Moth (*Nymphula stagnata*); Citrus Cutworm (*Xylomyges curialis*); Codling Moth (*Cydia pomonella*); Cranberry Fruitworm (*Acrobasis vaccinii*); Cross-striped Cabbageworm (*Evergestis rimosalis*); Cutworm (*Noctuid* species, *Agrotis ipsilon*); Douglas Fir Tussock Moth (*Orgyia pseudotsugata*); Ello Moth (Hornworm) (*Erinnyis ello*); Elm Spanworm (*Ennomos subsignaria*); European Grapevine Moth (*Lobesia botrana*); European Skipper (*Thymelicus lineola* (Essex Skipper); Fall Webworm (*Melissopus latiferreanus*; Filbert Leafroller (*Archips rosanus*; Fruittree Leafroller (*Archips argyrospilia*; Grape Berry Moth (*Paralobesia viteana*; Grape Leafroller (*Platynota stultana*; Grapeleaf Skeletonizer (*Harrisina americana* (ground only); Green Cloverworm (*Plathypena scabra*; Greenstriped Mapleworm (*Dryocampa rubicunda*; Gummosos-Batrachedra; Comosae (Hodges); Gypsy Moth (*Lymantria dispar*); Hemlock Looper (*Lambdina fiscellaria*); Hornworm (*Manduca* spp.); Imported Cabbageworm (*Pieris rapae*); Io Moth (*Automeris io*); Jack Pine Budworm (*Choristoneura pinus*); Light Brown Apple Moth (*Epiphyas postvittana*); Melonworm (*Diaphania hyalinata*); Mimosa Webworm (*Homadaula anisocentra*); Obliquebanded Leafroller (*Choristoneura rosaceana*); Oleander Moth (*Syntomeida epilais*); Omnivorous Leafroller (*Playnota stultana*); Omnivorous Looper (*Sabulodes aegrotata*); Orangedog (*Papilio cresphontes*); Orange Tortrix (*Argyrotaenia citrana*); Oriental Fruit Moth (*Grapholita molesta*); Peach Twig Borer (*Anarsia lineatella*); Pine Butterfly (*Neophasia menapia*); Podworm (*Heliocoverpa zea*); Redbanded Leafroller (*Argyrotaenia velutinana*); Redhumped Caterpillar (*Schizura concinna*); Rindworm Complex (Various Leps.); Saddleback Caterpillar (*Sibine stimulea*); Saddle Prominent Caterpillar *Heterocampa guttivitta*); Saltmarsh Caterpillar (*Estigmene acrea*); Sod Webworm (*Crambus* spp.); Spanworm (*Ennomos subsignaria*); Fall Cankerworm (*Alsophila pometaria*); Spruce Budworm (*Choristoneura fumiferana*); Tent Caterpillar (Various Lasiocampidae); Thecla-Thecla Basilides (Geyr) *Thecla basilides*); Tobacco Hornworm (*Manduca sexta*); Tobacco Moth (*Ephestia elutella*); Tufted Apple Budmoth (*Platynota idaeusalis*); Twig Borer (*Anarsia lineatella*); Variegated Cutworm (*Peridroma saucia*); Variegated Leafroller (*Platynota flavedana*); Velvetbean Caterpillar (*Anticarsia gemmatalis*); Walnut Caterpillar (*Datana integerrima*); Webworm (*Hyphantria cunea*); Western Tussock Moth (*Orgyia vetusta*); Southern Cornstalk Borer (*Diatraea crambidoides*); Corn Earworm; Sweet potato weevil; Pepper weevil; Citrus root weevil; Strawberry root weevil; Pecan weevil; Filbert weevil; Ricewater weevil; Alfalfa weevil; Clover weevil; Tea shot-hole borer; Root weevil; Sugarcane beetle; Coffee berry borer; Annual blue grass weevil (*Listronotus maculicollis*); Asiatic garden beetle (*Maladera castanea*); European chafer (*Rhizotroqus majalis*); Green June beetle (*Cotinis nitida*); Japanese beetle (*Popillia japonica*); May or June beetle (*Phyllophaga* sp.); Northern masked chafer (*Cyclocephala borealis*); Oriental beetle (*Anomala orientalis*); Southern masked chafer (*Cyclocephala lurida*); Billbug (Curculionoidea); *Aedes aegypti; Busseola fusca; Chilo suppressalis; Culex pipiens; Culex quinquefasciatus; Diabrotica virgifera; Diatraea saccharalis; Helicoverpa armigera; Helicoverpa zea; Heliothis virescens; Leptinotarsa decemlineata; Ostrinia furnacalis; Ostrinia nubilalis; Pectinophora gossypiella; Plodia interpunctella; Plutella xylostella; Pseudoplusia includens; Spodoptera exigua; Spodoptera frugiperda; Spodoptera littoralis; Trichoplusia ni*; and *Xanthogaleruca luteola.*

In some embodiments, the present invention provides a method of combating, controlling, or inhibiting a pest comprising, applying a pesticidally effective amount of a composition consisting of: (1) a TVP or a TVP-insecticidal protein; and (2) an excipient; wherein the TVP is selected from one or any combination of the TVPs described herein, e.g., an insecticidal U1-agatoxin-Ta1b variant polypeptide (TVP), said TVP comprising an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; and wherein the composition is applied to the locus of the pest, or to a plant or animal susceptible to an attack by the pest.

Any of the compositions described herein can be used in the method of method of combating, controlling, or inhibiting a pest comprising, applying a pesticidally effective amount of a composition consisting of: (1) a TVP or a TVP-insecticidal protein; and (2) an excipient.

For example, in some embodiments, the present invention provides a method of combating, controlling, or inhibiting a pest comprising, applying a pesticidally effective amount of a composition consisting of a TVP, and one or more excipients; wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof; and wherein the one or more excipients is selected from the group consisting of: trehalose; maltodextrin; maltose; potassium phosphate dibasic ($K_2HPO_4$); potassium phosphate monobasic ($KH_2PO_4$); lignosulfonate; gypsum; sorbitol; sodium benzoate; potassium sorbate; EDTA; benzisothiazolinone (BIT); and fermentation solids.

In some embodiments, the present invention provides a method of combating, controlling, or inhibiting a pest comprising, applying a pesticidally effective amount of a composition consisting of a TVP, wherein $Z_1$ is T and the TVP is glycosylated, or a pharmaceutically acceptable salt thereof.

In some embodiments, the present invention provides a method of combating, controlling, or inhibiting a pest comprising, applying a pesticidally effective amount of a composition consisting of a TVP, wherein $X_1$ is Q; and $Z_1$ is A, or a pharmaceutically acceptable salt thereof.

In some embodiments, the present invention provides a method of combating, controlling, or inhibiting a pest comprising, applying a pesticidally effective amount of a composition consisting of a TVP, wherein the TVP comprises an amino sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to any of the amino acid sequences set forth in any one of SEQ ID NOs: 2, 49, or 51.

In some embodiments, the present invention provides a method of combating, controlling, or inhibiting a pest comprising, applying a pesticidally effective amount of a composition consisting of a TVP, wherein the TVP is encoded by a polynucleotide sequence as set forth in any one of SEQ ID NOs: 17, 54, or 56, or a complementary nucleotide sequence thereof.

In some embodiments, the present invention provides a method of combating, controlling, or inhibiting a pest comprising, applying a pesticidally effective amount of a composition consisting of a TVP, wherein the TVP further comprises a homopolymer or heteropolymer of two or more TVPs, wherein the amino acid sequence of each TVP is the same or different.

In some embodiments, the present invention provides a method of combating, controlling, or inhibiting a pest comprising, applying a pesticidally effective amount of a composition consisting of a TVP, wherein the TVP is a fused protein comprising two or more TVPs separated by a cleavable linker or non-cleavable linker, and wherein the amino acid sequence of each TVP may be the same or different.

In some embodiments, the present invention provides a method of combating, controlling, or inhibiting a pest comprising, applying a pesticidally effective amount of a composition consisting of a TVP having a linker, wherein the linker is a cleavable linker.

In some embodiments, a composition of the present invention consists of a TVP having a cleavable linker, wherein the cleavable linker is cleavable inside the gut or hemolymph of an insect.

In some embodiments, the present invention provides a method of combating, controlling, or inhibiting a pest comprising, applying a pesticidally effective amount of a composition consisting of a TVP having a linker, wherein the linker has an amino acid sequence as set forth in any one of SEQ ID NOs: 61-70.

In some embodiments, the present invention provides a method of combating, controlling, or inhibiting a pest comprising, applying a pesticidally effective amount of a composition consisting of a TVP, and one or more excipients; wherein the TVP comprises an amino acid sequence that is at least 50% identical, at least 55% identical, at least 60% identical, at least 65% identical, at least 70% identical, at least 75% identical, at least 80% identical, at least 81% identical, at least 82% identical, at least 83% identical, at least 84% identical, at least 85% identical, at least 86% identical, at least 87% identical, at least 88% identical, at least 89% identical, at least 90% identical, at least 91% identical, at least 92% identical, at least 93% identical, at least 94% identical, at least 95% identical, at least 96% identical, at least 97% identical, at least 98% identical, at least 99% identical, at least 99.5% identical, at least 99.6% identical, at least 99.7% identical, at least 99.8% identical, at least 99.9% identical, or 100% identical to the amino acid sequence according to Formula (II): E-P-D-E-I-C-R-A-X$_1$-M-T-N-K-E-F-T-Y-K-S-N-V-C-N-N-C-G-D-Q-V-A-A-C-E-A-E-C-F-R-N-D-V-Y-Z$_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO: 1, and wherein X$_1$ is R or Q; and Z$_1$ is T or A; or a pharmaceutically acceptable salt thereof; and wherein the one or more excipients is selected from the group consisting of: trehalose; maltodextrin; maltose; potassium phosphate dibasic (K$_2$HPO$_4$); potassium phosphate monobasic (KH$_2$PO$_4$); lignosulfonate; gypsum; sorbitol; sodium benzoate; potassium sorbate; EDTA; benzisothiazolinone (BIT); and fermentation solids, wherein if Z$_1$ is T or S, then the TVP is glycosylated.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) one or more excipients.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) one or more excipients, wherein the one or more excipients is selected from the group consisting of: trehalose; maltodextrin; potassium phosphate dibasic anhydrous (K$_2$HPO$_4$); potassium phosphate monobasic (KH$_2$PO$_4$); BIT; and fermentation solids.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) one or more excipients; wherein the TVP or TVP-insecticidal protein ranges from about 2% to about 16% wt/wt; and wherein trehalose ranges from about 5% to about 40% wt/wt; BIT ranges from about 0.01% to about 0.1% wt/wt; maltodextrin ranges from about 10% to about 50% wt/wt; potassium phosphate dibasic anhydrous (K$_2$HPO$_4$) ranges from about 1% to about 5% wt/wt; and potassium phosphate monobasic (KH$_2$PO$_4$) ranges from about 0.10% to about 1% wt/wt; and fermentation solids range from about 15% to about 40% wt/wt; of the total weight of the composition.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) one or more excipients; wherein the TVP or TVP-insecticidal protein ranges from about 7% to about 9% wt/wt; and wherein trehalose ranges from about 20% to about 30% wt/wt; BIT ranges from about 0.025% to about 0.075% wt/wt; maltodextrin ranges from about 30% to about 40% wt/wt; potassium phosphate dibasic anhydrous (K$_2$HPO$_4$) ranges from about 2% to about 3% wt/wt; potassium phosphate monobasic (KH$_2$PO$_4$) ranges from about 0.2% to about 0.6%; and fermentation solids range from about 20% to about 30%, of the total weight of the composition.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) one or more excipients; wherein the TVP or TVP-insecticidal protein is about 8.5% wt/wt; and wherein trehalose is about 25% wt/wt; BIT is about 0.05% wt/wt; maltodextrin is about 36.3% wt/wt; potassium phosphate dibasic anhydrous ($K_2HPO_4$) is about 2.6% wt/wt; potassium phosphate monobasic ($KH_2PO_4$) is about 0.4% wt/wt; and fermentation solids are about 26.85% wt/wt, of the total weight of the composition.

In some embodiments, the present invention provides a method of combating, controlling, or inhibiting a pest comprising, applying a pesticidally effective amount of a composition consisting of essentially of the following: an amount of a TVP or a TVP-insecticidal protein that is 8.5% wt/wt; an amount of trehalose that is 25% wt/wt; an amount of BIT that is 0.05% wt/wt; an amount of maltodextrin that is 36.3% wt/wt; an amount of potassium phosphate dibasic anhydrous ($K_2HPO_4$) that is 2.6% wt/wt; an amount of potassium phosphate monobasic ($KH_2PO_4$) that is 0.4% wt/wt; and an amount of fermentation solids that is 26.85% wt/wt, of the total weight of the composition.

In some embodiments, the present invention provides a method of combating, controlling, or inhibiting a pest comprising, applying a pesticidally effective amount of a composition consisting of the following: an amount of a TVP or a TVP-insecticidal protein that is 8.5% wt/wt; an amount of trehalose that is 25% wt/wt; an amount of BIT that is 0.05% wt/wt; an amount of maltodextrin that is 36.3% wt/wt; an amount of potassium phosphate dibasic anhydrous ($K_2HPO_4$) that is 2.6% wt/wt; an amount of potassium phosphate monobasic ($KH_2PO_4$) that is 0.4% wt/wt; and an amount of fermentation solids that is 26.85% wt/wt, of the total weight of the composition.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein comprises an amino acid sequence that is at least 90% identical to the amino acid sequence according to Formula (II): E-P-D-E-I-C-R-A-$X_1$-M-T-N-K-E-F-T-Y-K-S-N-V-C-N-N-C-G-D-Q-V-A-A-C-E-A-E-C-F-R-N-D-V-Y-$Z_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein $X_1$ is R or Q; and $Z_1$ is T or A; or a pharmaceutically acceptable salt thereof; wherein the composition consists of an amount of TVP that is 8.5% wt/wt of the total weight of the composition; and wherein the plurality of excipients consists of the following: an amount of trehalose that is 25% wt/wt; an amount of BIT that is 0.05% wt/wt; an amount of maltodextrin that is 36.3% wt/wt; an amount of potassium phosphate dibasic anhydrous ($K_2HPO_4$) that is 2.6% wt/wt; an amount of potassium phosphate monobasic ($KH_2PO_4$) that is 0.4% wt/wt; and an amount of fermentation solids that is 26.85% wt/wt, of the total weight of the composition.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein $Z_1$ is T and the TVP is glycosylated, or a pharmaceutically acceptable salt thereof.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein $X_1$ is Q; and $Z_1$ is A, or a pharmaceutically acceptable salt thereof.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the TVP comprises an amino sequence as set forth in any one of SEQ ID NOs: 2, 49, or 51.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the TVP is encoded by a polynucleotide sequence as set forth in any one of SEQ ID NOs: 17, 54, or 56, or a complementary nucleotide sequence thereof.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the TVP further comprises a homopolymer or heteropolymer of two or more TVPs, wherein the amino acid sequence of each TVP is the same or different.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the TVP is a fused protein comprising two or more TVPs separated by a cleavable or non-cleavable linker, and wherein the amino acid sequence of each TVP may be the same or different.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the linker is a cleavable linker.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the cleavable linker is cleavable inside the gut or hemolymph of an insect.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients; wherein the TVP or TVP-insecticidal protein; wherein the linker has an amino acid sequence as set forth in any one of SEQ ID NOs: 61-70.

In some embodiments, the present invention provides a method of combating, controlling, or inhibiting a pest comprising, applying a pesticidally effective amount of a composition consisting of (1) a TVP, a TVP-insecticidal protein, or a combination thereof; and (2) a plurality of excipients;

wherein the TVP or TVP-insecticidal protein comprises an amino acid sequence that is at least 90% identical to the amino acid sequence according to Formula (II): E-P-D-E-I-C-R-A-X$_1$-M-T-N-K-E-F-T-Y-K-S-N-V-C-N-N-C-G-D-Q-V-A-A-C-E-A-E-C-F-R-N-D-V-Y-Z$_1$-A-C-H-E-A-Q-K-G (SEQ ID NO: 152); wherein the polypeptide comprises at least one amino acid substitution relative to the wild-type sequence of U1-agatoxin-Ta1b as set forth in SEQ ID NO:1, and wherein X$_1$ is R or Q; and Z$_1$ is T or A; or a pharmaceutically acceptable salt thereof; wherein the composition consists of an amount of TVP that is 8.5% wt/wt of the total weight of the composition; and wherein the plurality of excipients consists of the following: an amount of trehalose that is 25% wt/wt; an amount of BIT that is 0.05% wt/wt; an amount of maltodextrin that is 36.3% wt/wt; an amount of potassium phosphate dibasic anhydrous (K$_2$HPO$_4$) that is 2.6% wt/wt; an amount of potassium phosphate monobasic (KH$_2$PO$_4$) that is 0.4% wt/wt; and an amount of fermentation solids that is 26.85% wt/wt, of the total weight of the composition; wherein if Z$_1$ is T or S, then the TVP is glycosylated.

In some embodiments, the present invention provides a method of combating, controlling, or inhibiting a pest comprising, applying a pesticidally effective amount of an insecticidal U1-agatoxin-Ta1b variant polypeptide (TVP), said TVP comprising an amino acid sequence that is at least 90% identical to the amino acid sequence set forth in any one of SEQ ID NOs: 2, 49, or 51; or a pharmaceutically acceptable salt thereof, to the locus of the pest.

In some embodiments, the present invention provides a method of combating, controlling, or inhibiting a pest comprising, applying a pesticidally effective amount of an insecticidal U1-agatoxin-Ta1b variant polypeptide (TVP), said TVP comprising an amino acid sequence set forth in any one of SEQ ID NOs: 2, 49, or 51; or a pharmaceutically acceptable salt thereof, to the locus of the pest.

In some embodiments, the present invention provides a method of combating, controlling, or inhibiting a pest comprising, applying a pesticidally effective amount of an insecticidal U1-agatoxin-Ta1b variant polypeptide (TVP), said TVP consisting of an amino acid sequence set forth in any one of SEQ ID NOs: 2, 49, or 51; or a pharmaceutically acceptable salt thereof, to the locus of the pest.

In some embodiments, the present invention provides a method of combating, controlling, or inhibiting a pest comprising, applying a pesticidally effective amount of an insecticidal U1-agatoxin-Ta1b variant polypeptide (TVP), said TVP comprising an amino acid sequence that is at least 90% identical to the amino acid sequence set forth in SEQ ID NO 51, or a pharmaceutically acceptable salt thereof, to the locus of the pest.

In some embodiments, the present invention provides a method of combating, controlling, or inhibiting a pest comprising, applying a pesticidally effective amount of an insecticidal U1-agatoxin-Ta1b variant polypeptide (TVP), said TVP comprising an amino acid sequence set forth in SEQ ID NO: 51, or a pharmaceutically acceptable salt thereof, to the locus of the pest.

In some embodiments, the present invention provides a method of combating, controlling, or inhibiting a pest comprising, applying a pesticidally effective amount of an insecticidal U1-agatoxin-Ta1b variant polypeptide (TVP), said TVP consisting of an amino acid sequence set forth in SEQ ID NO: 51, or a pharmaceutically acceptable salt thereof, to the locus of the pest.

Any of the foregoing TVPs, TVP-insecticidal proteins, or pharmaceutically acceptable salts thereof, can be used in the any of the compositions described herein, e.g., any of the foregoing TVPs, TVP-insecticidal proteins, or pharmaceutically acceptable salts thereof, can be used to combat, control, or inhibit a pest and/or to apply to the locus of a pest, wherein the pest is selected from the group consisting of: Achema Sphinx Moth (Hornworm) (*Eumorpha achemon*); Alfalfa Caterpillar (*Colias eurytheme*); Almond Moth (*Caudra cautella*); Amorbia Moth (*Amorbia humerosana*); Armyworm (*Spodoptera* spp., e.g. *exigua, frugiperda, littoralis, Pseudaletia unipuncta*); Artichoke Plume Moth (*Platyptilia carduidactyla*); Azalea Caterpillar (*Datana major*); Bagworm (*Thyridopteryx*); *ephemeraeformis*); Banana Moth (*Hypercompe scribonia*); Banana Skipper (*Erionota thrax*); Blackheaded Budworm (*Acleris gloverana*); California Oakworm (*Phryganidia californica*); Spring Cankerworm (*Paleacrita merriccata*); Cherry Fruitworm (*Grapholita packardi*); China Mark Moth (*Nymphula stagnata*); Citrus Cutworm (*Xylomyges curialis*); Codling Moth (*Cydia pomonella*); Cranberry Fruitworm (*Acrobasis vaccinii*); Cross-striped Cabbageworm (*Evergestis rimosalis*); Cutworm (*Noctuid* species, *Agrotis ipsilon*); Douglas Fir Tussock Moth (*Orgyia pseudotsugata*); Ello Moth (Hornworm) (*Erinnyis ello*); Elm Spanworm (*Ennomos subsignaria*); European Grapevine Moth (*Lobesia botrana*); European Skipper (*Thymelicus lineola* (Essex Skipper); Fall Webworm (*Melissopus latiferreanus*; Filbert Leafroller (*Archips rosanus*; Fruittree Leafroller (*Archips argyrospilia*; Grape Berry Moth (*Paralobesia viteana*; Grape Leafroller (*Platynota stultana*); Grapeleaf Skeletonizer (*Harrisina americana* (ground only); Green Cloverworm (*Plathypena scabra*; Greenstriped Mapleworm (*Dryocampa rubicunda*; Gummosos-Batrachedra; Comosae (Hodges); Gypsy Moth (*Lymantria dispar*); Hemlock Looper (*Lambdina fiscellaria*); Hornworm (*Manduca* spp.); Imported Cabbageworm (*Pieris rapae*); Io Moth (*Automeris io*); Jack Pine Budworm (*Choristoneura pinus*); Light Brown Apple Moth (*Epiphyas postvittana*); Melonworm (*Diaphania hyalinata*); Mimosa Webworm (*Homadaula anisocentra*); Obliquebanded Leafroller (*Choristoneura rosaceana*); Oleander Moth (*Syntomeida epilais*); Omnivorous Leafroller (*Playnota stultana*); Omnivorous Looper (*Sabulodes aegrotata*); Orangedog (*Papilio cresphontes*); Orange Tortrix (*Argyrotaenia citrana*); Oriental Fruit Moth (*Grapholita molesta*); Peach Twig Borer (*Anarsia lineatella*); Pine Butterfly (*Neophasia menapia*); Podworm (*Heliocoverpa zea*); Redbanded Leafroller (*Argyrotaenia velutinana*); Redhumped Caterpillar (*Schizura concinna*); Rindworm Complex (Various Leps.); Saddleback Caterpillar (*Sibine stimulea*); Saddle Prominent Caterpillar *Heterocampa guttivitta*); Saltmarsh Caterpillar (*Estigmene acrea*); Sod Webworm (*Crambus* spp.); Spanworm (*Ennomos subsignaria*); Fall Cankerworm (*Alsophila pometaria*); Spruce Budworm (*Choristoneura fumiferana*); Tent Caterpillar (Various Lasiocampidae); Thecla-Thecla Basilides (Geyr) *Thecla basilides*); Tobacco Hornworm (*Manduca sexta*); Tobacco Moth (*Ephestia elutella*); Tufted Apple Budmoth (*Platynota idaeusalis*); Twig Borer (*Anarsia lineatella*); Variegated Cutworm (*Peridroma saucia*); Variegated Leafroller (*Platynota flavedana*); Velvetbean Caterpillar (*Anticarsia gemmatalis*); Walnut Caterpillar (*Datana integerrima*); Webworm (*Hyphantria cunea*); Western Tussock Moth (*Orgyia vetusta*); Southern Cornstalk Borer (*Diatraea crambidoides*); Corn Earworm; Sweet potato weevil; Pepper weevil; Citrus root weevil; Strawberry root weevil; Pecan weevil; Filbert weevil; Ricewater weevil; Alfalfa weevil; Clover weevil; Tea shot-hole borer; Root weevil; Sugarcane beetle; Coffee berry borer; Annual blue grass weevil (*Listronotus maculicollis*); Asiatic garden beetle (*Maladera castanea*); European chafer (*Rhizotroqus majalis*); Green June beetle (*Cotinis nitida*); Japanese beetle (*Popillia japonica*); May or June beetle (*Phyllophaga* sp.); Northern masked chafer (*Cyclocephala borealis*); Oriental beetle (*Anomala orientalis*); Southern masked chafer (*Cyclocephala lurida*); Billbug (Curculionoidea); *Aedes aegypti; Busseola fusca; Chilo suppressalis; Culex pipiens; Culex quinquefasciatus; Diabrotica virgifera; Diatraea saccharalis; Helicoverpa armigera; Helicoverpa zea; Heliothis virescens; Leptinotarsa decemlineata; Ostrinia furnacalis; Ostrinia nubilalis; Pectinophora gossypiella; Plodia interpunctella; Plutella xylostella; Pseudoplusia includens; Spodoptera exigua; Spodoptera frugiperda; Spodoptera littoralis; Trichoplusia ni*; and *Xanthogaleruca luteola.*

Crops and Pests

Specific crop pests and insects that may be controlled by these methods include the following: Dictyoptera (cockroaches); Isoptera (termites); Orthoptera (locusts, grasshoppers and crickets); Diptera (house flies, mosquito, tsetse fly, crane-flies and fruit flies); Hymenoptera (ants, wasps, bees, saw-flies, ichneumon flies and gall-wasps); Anoplura (biting and sucking lice); Siphonaptera (fleas); and Hemiptera (bugs and aphids), as well as arachnids such as Acari (ticks and mites), and the parasites that each of these organisms harbor.

"Pest" includes, but is not limited to: insects, fungi, bacteria, nematodes, mites, ticks, and the like.

Insect pests include, but are not limited to, insects selected from the orders Coleoptera, Diptera, Hymenoptera, Lepidoptera, Mallophaga, Homoptera, Hemiptera, Orthroptera, Thysanoptera, Dermaptera, Isoptera, Anoplura, Siphonaptera, Trichoptera, and the like. More particularly, insect pests include Coleoptera, Lepidoptera, and Diptera.

Insects of suitable agricultural, household and/or medical/veterinary importance for treatment with the insecticidal polypeptides include, but are not limited to, members of the following classes and orders:

The order Coleoptera includes the suborders Adephaga and Polyphaga. Suborder Adephaga includes the superfamilies Caraboidea and Gyrinoidea. Suborder Polyphaga includes the superfamilies Hydrophiloidea, Staphylinoidea, Cantharoidea, Cleroidea, Elateroidea, Dascilloidea, Dryopoidea, Byrrhoidea, Cucujoidea, Meloidea, Mordelloidea, Tenebrionoidea, Bostrichoidea, Scarabaeoidea, Cerambycoidea, Chrysomeloidea, and Curculionoidea. Superfamily Caraboidea includes the families Cicindelidae, Carabidae, and Dytiscidae. Superfamily Gyrinoidea includes the family Gyrinidae. Superfamily Hydrophiloidea includes the family Hydrophilidae. Superfamily Staphylinoidea includes the families Silphidae and Staphylinidae. Superfamily Cantharoidea includes the families Cantharidae and Lampyridae. Superfamily Cleroidea includes the families Cleridae and Dermestidae. Superfamily Elateroidea includes the families Elateridae and Buprestidae. Superfamily Cucujoidea includes the family Coccinellidae. Superfamily Meloidea includes the family Meloidae. Superfamily Tenebrionoidea includes the family Tenebrionidae. Superfamily Scarabaeoidea includes the families Passalidae and Scarabaeidae. Superfamily Cerambycoidea includes the family Cerambycidae. Superfamily Chrysomeloidea includes the family Chrysomelidae. Superfamily Curculionoidea includes the families Curculionidae and Scolytidae.

Examples of Coleoptera include, but are not limited to: the American bean weevil *Acanthoscelides obtectus*, the leaf beetle *Agelastica alni*, click beetles (*Agriotes lineatus, Agriotes obscurus, Agriotes bicolor*), the grain beetle *Ahasverus advena*, the summer schafer *Amphimallon solstitialis*, the furniture beetle *Anobium punctatum, Anthonomus* spp.

(weevils), the Pygmy mangold beetle *Atomaria linearis*, carpet beetles (*Anthrenus* spp., *Attagenus* spp.), the cowpea weevil *Callosobruchus maculates*, the fried fruit beetle *Carpophilus hemipterus*, the cabbage seedpod weevil *Ceutorhynchus assimilis*, the rape winter stem weevil *Ceutorhynchus picitarsis*, the wireworms *Conoderus vespertinus* and *Conoderus falli*, the banana weevil *Cosmopolites sordidus*, the New Zealand grass grub *Costelytra zealandica*, the June beetle *Cotinis nitida*, the sunflower stem weevil *Cylindrocopturus adspersus*, the larder beetle *Dermestes lardarius*, the corn rootworms *Diabrotica virgifera, Diabrotica virgifera virgifera*, and *Diabrotica barberi*, the Mexican bean beetle *Epilachna varivestis*, the old house borer *Hylotropes bajulus*, the lucerne weevil *Hypera postica*, the shiny spider beetle Gibbium psylloides, the cigarette beetle Lasioderma serricorne, the Colorado potato beetle *Leptinotarsa decemlineata*, Lyctus beetles (*Lyctus* spp.), the pollen beetle *Meligethes aeneus*, the common cockshafer *Melolontha melolontha*, the American spider beetle *Mezium americanum*, the golden spider beetle *Niptus hololeucus*, the grain beetles *Oryzaephilus surinamensis* and *Oryzaephilus mercator*, the black vine weevil *Otiorhynchus sulcatus*, the mustard beetle *Phaedon cochleariae*, the crucifer flea beetle *Phyllotreta cruciferae*, the striped flea beetle *Phyllotreta striolata*, the cabbage steam flea beetle *Psylliodes chrysocephala, Ptinus* spp. (spider beetles), the lesser grain borer *Rhizopertha dominica*, the pea and been weevil *Sitona lineatus*, the rice and granary beetles *Sitophilus oryzae* and *Sitophilus granaries*, the red sunflower seed weevil *Smicronyx fulvus*, the drugstore beetle *Stegobium paniceum*, the yellow mealworm beetle *Tenebrio molitor*, the flour beetles *Tribolium castaneum* and *Tribolium confusum*, warehouse and cabinet beetles (*Trogoderma* spp.), and the sunflower beetle *Zygogramma* exclamation's.

Examples of Dermaptera (earwigs) include, but are not limited to: the European earwig *Forficula auricularia*, and the striped earwig *Labidura riparia.*

Examples of Dictvontera include, but are not limited to: the oriental cockroach *Blatta orientalis*, the German cockroach *Blatella germanica*, the Madeira cockroach *Leucophaea maderae*, the American cockroach *Periplaneta americana*, and the smokybrown cockroach *Periplaneta fuliginosa.*

Examples of Diplonoda include, but are not limited to: the spotted snake millipede Blaniulus guttulatus, the flat-back millipede *Brachydesmus superus*, and the greenhouse millipede *Oxidus gracilis.*

The order Diptera includes the Suborders Nematocera, Brachycera, and Cyclorrhapha. Suborder Nematocera includes the families Tipulidae, Psychodidae, Culicidae, Ceratopogonidae, Chironomidae, Simuliidae, Bibionidae, and Cecidomyiidae. Suborder Brachycera includes the families Stratiomyidae, Tabanidae, Therevidae, Asilidae, Mydidae, Bombyliidae, and Dolichopodidae. Suborder Cyclorrhapha includes the Divisions Aschiza and Aschiza. Division Aschiza includes the families Phoridae, Syrphidae, and Conopidae. Division Aschiza includes the Sections Acalyptratae and Calyptratae. Section Acalyptratae includes the families Otitidae, Tephritidae, Agromyzidae, and Drosophilidae. Section Calyptratae includes the families Hippoboscidae, Oestridae, Tachinidae, Anthomyiidae, Muscidae, Calliphoridae, and Sarcophagidae.

Examples of Diptera include, but are not limited to: the house fly (*Musca domestica*), the African tumbu fly (*Cordylobia anthropophaga*), biting midges (*Culicoides* spp.), bee louse (*Braula* spp.), the beet fly *Pegomyia betae*, blackflies (*Cnephia* spp., *Eusimulium* spp., *Simulium* spp.), bot flies (*Cuterebra* spp., *Gastrophilus* spp., *Oestrus* spp.), craneflies (*Tipula* spp.), eye gnats (*Hippelates* spp.), filth-breeding flies (*Calliphora* spp., *Fannia* spp., *Hermetia* spp., *Lucilia* spp., *Musca* spp., *Muscina* spp., *Phaenicia* spp., *Phormia* spp.), flesh flies (*Sarcophaga* spp., *Wohlfahrtia* spp.); the flit fly *Oscinella frit*, fruit flies (*Dacus* spp., *Drosophila* spp.), head and canon flies (*Hydrotea* spp.), the hessian fly *Mayetiola destructor*, horn and buffalo flies (*Haematobia* spp.), horse and deer flies (*Chrysops* spp., *Haematopota* spp., *Tabanus* spp.), louse flies (*Lipoptena* spp., *Lynchia* spp., and *Pseudo-lynchia* spp.), medflies (*Ceratitus* spp.), mosquitoes (*Aedes* spp., *Anopheles* spp., *Culex* spp., *Psorophora* spp.), sand-flies (*Phlebotomus* spp., *Lutzomyia* spp.), screw-worm flies (*Chtysomya bezziana* and *Cochliomyia hominivorax*), sheep keds (*Melophagus* spp.); stable flies (*Stomoxys* spp.), tsetse flies (*Glossina* spp.), and warble flies (*Hypoderma* spp.).

Examples of Isontera (termites) include, but are not limited to: species from the families Hodotennitidae, Kalo-termitidae, Mastotermitidae, Rhinotennitidae, Serritermiti-dae, Termitidae, Termopsidae.

Examples of Heteroptera include, but are not limited to: the bed bug *Cimex lectularius*, the cotton stainer *Dysdercus intermedius*, the Sunn pest *Eurygaster integriceps*, the tar-nished plant bug *Lygus lineolaris*, the green stink bug *Nezara antennata*, the southern green stink bug *Nezara viridula*, and the triatomid bugs *Panstrogylus megistus, Rhodnius ecuadoriensis, Rhodnius pallescans, Rhodnius prolixus, Rhodnius robustus, Triatoma dimidiata, Triatoma infestans*, and *Triatoma sordida*.

Examples of Homoptera include, but are not limited to: the California red scale *Aonidiella aurantii*, the black bean aphid *Aphis fabae*, the cotton or melon aphid *Aphis gossypii*, the green apple aphid *Aphis pomi*, the citrus spiny whitefly *Aleurocanthus spiniferus*, the oleander scale *Aspidiotus hed-erae*, the sweet potato whitefly *Bemesia tabaci*, the cabbage aphid *Brevicoryne brassicae*, the pear psylla *Cacopsylla pyricola*, the currant aphid *Cryptomyzus ribis*, the grape phylloxera *Daktulosphaira vitifoliae*, the citrus psylla *Dia-phorina citri*, the potato leafhopper *Empoasca fabae*, the bean leafhopper *Empoasca solana*, the vine leafhopper *Empoasca vitis*, the woolly aphid *Eriosoma lanigerum*, the European fruit scale *Eulecanium corni*, the mealy plum aphid *Hyalopterus arundinis*, the small brown planthopper *Laodelphax striatellus*, the potato aphid *Macrosiphum euphorbiae*, the green peach aphid *Myzus persicae*, the green rice leafhopper *Nephotettix cinticeps*, the brown plan-thopper *Nilaparvata lugens*, gall-forming aphids (*Pemphi-gus* spp.), the hop aphid *Phorodon humuli*, the bird-cherry aphid *Rhopalosiphum padi*, the black scale *Saissetia oleae*, the greenbug *Schizaphis graminum*, the grain aphid *Sitobion avenae*, and the greenhouse whitefly *Trialeurodes vaporari-orum*.

Examples of Isopoda include, but are not limited to: the common pillbug *Armadillidium vulgare* and the common woodlouse Oniscus asellus.

The order Lepidoptera includes the families Papilionidae, Pieridae, Lycaenidae, Nymphalidae, Danaidae, Satyridae, Hesperiidae, Sphingidae, Saturniidae, Geometridae, Arcti-idae, Noctuidae, Lymantriidae, Sesiidae, and Tineidae.

Examples of Lepidoptera include, but are not limited to: *Adoxophyes orana* (summer fruit tortrix moth), *Agrotis ipsolon* (black cutworm), *Archips podana* (fruit tree tortrix moth), *Bucculatrix pyrivorella* (pear leafminer), *Bucculatrix thurberiella* (cotton leaf perforator), *Bupalus piniarius* (pine looper), *Carpocapsa pomonella* (codling moth), *Chilo sup-pressalis* (striped rice borer), *Choristoneura fumiferana* (eastern spruce budworm), *Cochylis hospes* (banded sunflower moth), *Diatraea grandiosella* (southwestern corn borer), *Earls insulana* (Egyptian bollworm), *Euphestia kue-hniella* (Mediterranean flour moth), *Eupoecilia ambiguella* (European grape berry moth), *Euproctis chrysorrhoea* (brown-tail moth), *Euproctis subflava* (oriental tussock moth), *Galleria mellonella* (greater wax moth), *Helicoverpa armigera* (cotton bollworm), *Helicoverpa zea* (cotton boll-worm), *Heliothis virescens* (tobacco budworm), *Hofmanno-phila pseudopretella* (brown house moth), *Homeosoma elec-tellum* (sunflower moth), *Homona magnanima* (oriental tea tree tortrix moth), *Lithocolletis blancardella* (spotted tenti-form leafminer), *Lymantria dispar* (gypsy moth), *Malaco-soma neustria* (tent caterpillar), *Mamestra brassicae* (cab-bage armyworm), *Mamestra configurata* (Bertha armyworm), the hornworms *Manduca sexta* and *Manduca quinquemaculata, Operophtera brumata* (winter moth), *Ostrinia nubilalis* (European corn borer), *Panolis flammea* (pine beauty moth), *Pectinophora gossypiella* (pink boll-worm), *Phyllocnistis citrella* (citrus leafminer), *Pieris bras-sicae* (cabbage white butterfly), *Plutella xylostella* (dia-mondback moth), *Rachiplusia ni* (soybean looper), *Spilosoma virginica* (yellow bear moth), *Spodoptera exigua* (beet armyworm), *Spodoptera frugiperda* (fall armyworm), *Spodoptera littoralis* (cotton leafworm), *Spodoptera litura* (common cutworm), *Spodoptera praefica* (yellowstriped armyworm), *Sylepta derogata* (cotton leaf roller), *Tineola bisselliella* (webbing clothes moth), *Tineola pellionella* (case-making clothes moth), *Tortrix viridana* (European oak leafroller), *Trichoplusia ni* (cabbage looper), and *Yponomeuta padella* (small ermine moth).

Examples of Orthoptera include, but are not limited to: the common cricket *Acheta domesticus*, tree locusts (*Ana-cridium* spp.), the migratory locust *Locusta migratoria*, the twostriped grasshopper *Melanoplus bivittatus*, the differen-tial grasshopper *Melanoplus dfferentialis*, the redlegged grasshopper *Melanoplus femurrubrum*, the migratory grass-hopper *Melanoplus sanguinipes*, the northern mole cricket *Neocurtilla hexadectyla*, the red locust *Nomadacris sep-temfasciata*, the shortwinged mole cricket *Scapteriscus abbreviatus*, the southern mole cricket *Scapteriscus borellii*, the tawny mole cricket *Scapteriscus vicinus*, and the desert locust *Schistocerca gregaria*.

Examples of Phthiraptera include, but are not limited to: the cattle biting louse *Bovicola bovis*, biting lice (*Damalinia* spp.), the cat louse *Felicola subrostrata*, the shortnosed cattle louse *Haematopinus eloysternus*, the tail-switch louse *Haematopinus quadriperiussus*, the hog louse *Haematopi-nus suis*, the face louse *Linognathus ovillus*, the foot louse *Linognathus pedalis*, the dog sucking louse *Linognathus setosus*, the long-nosed cattle louse *Linognathus vituli*, the chicken body louse *Menacanthus stramineus*, the poultry shaft louse *Menopon gallinae*, the human body louse *Pediculus humanus*, the pubic louse *Phthirus pubis*, the little blue cattle louse *Solenopotes capillatus*, and the dog biting louse *Trichodectes canis*.

Examples of Psocoptera include, but are not limited to: the booklice *Liposcelis bostrychophila, Liposcelis decolor, Liposcelis entomophila*, and *Trogium pulsatorium*. Examples of Siphonaptera include, but are not limited to: the bird flea *Ceratophyllus gallinae*, the dog flea *Ctenocepha-lides canis*, the cat flea *Ctenocephalides fells*, the human flea *Pulex irritans*, and the oriental rat flea *Xenopsylla cheopis*.

Examples of Symphyla include, but are not limited to: the garden symphylan Scutigerella immaculate.

Examples of Thysanura include, but are not limited to: the gray silverfish *Ctenolepisma longicaudata*, the four-lined silverfish *Ctenolepisma quadriseriata*, the common silverfish *Lepisma saccharina*, and the firebrat *Thennobia domestica;*

Examples of Thysanoptera include, but are not limited to: the tobacco thrips *Frankliniella fusca*, the flower thrips *Frankliniella intonsa*, the western flower thrips *Frankliniella occidentalis*, the cotton bud thrips *Frankliniella schultzei*, the banded greenhouse thrips *Hercinothrips femoralis*, the soybean thrips *Neohydatothrips variabilis*, Kelly's citrus thrips *Pezothrips kellyanus*, the avocado thrips *Scirtothrips perseae*, the melon thrips *Thrips palmi*, and the onion thrips *Thrips tabaci.*

Examples of Nematodes include, but are not limited to: parasitic nematodes such as root-knot, cyst, and lesion nematodes, including *Heterodera* spp., *Meloidogyne* spp., and *Globodera* spp.; particularly members of the cyst nematodes, including, but not limited to: *Heterodera glycines* (soybean cyst nematode); *Heterodera schachtii* (beet cyst nematode); *Heterodera avenae* (cereal cyst nematode); and *Globodera rostochiensis* and *Globodera pailida* (potato cyst nematodes). Lesion nematodes include, but are not limited to: *Pratylenchus* spp.

Other insect species susceptible to a TVP of the present disclosure includes: athropod pests which cause public and animal health concerns, for example, mosquitos for example, mosquitoes from the genera *Aedes, Anopheles* and *Culex*, from ticks, flea, and flies etc.

In one embodiment, the insecticidal compositions consisting of a TVP or a TVP-insecticidal protein, and an excipient, can be employed to treat ectoparasites. Ectoparasites include, but are not limited to: fleas, ticks, mange, mites, mosquitoes, nuisance and biting flies, lice, and combinations comprising one or more of the foregoing ectoparasites. The term "fleas" includes the usual or accidental species of parasitic flea of the order Siphonaptera, and in particular the species *Ctenocephalides*, in particular *C. fells* and *C. cams*, rat fleas (*Xenopsylla cheopis*) and human fleas (*Pulex irritans*).

Insect pests of the invention for the major crops include, but are not limited to: Maize: *Ostrinia nubilalis*, European corn borer; *Agrotis ipsilon*, black cutworm; *Helicoverpa zea*, corn earworm; *Spodoptera frugiperda*, fall armyworm; *Diatraea grandiosella*, southwestern corn borer; *Elasmopalpus lignosellus*, lesser cornstalk borer; *Diatraea saccharalis*, surgarcane borer; *Diabrotica virgifera*, western corn rootworm; *Diabrotica longicornis barberi*, northern corn rootworm; *Diabrotica undecimpunctata howardi*, southern corn rootworm; *Melanotus* spp., wireworms; *Cyclocephala borealis*, northern masked chafer (white grub); *Cyclocephala immaculata*, southern masked chafer (white grub); *Popillia japonica*, Japanese beetle; *Chaetocnema pulicaria*, corn flea beetle; *Sphenophorus maidis*, maize billbug; *Rhopalosiphum maidis*, corn leaf aphid; *Anuraphis maidiradicis*, corn root aphid; *Blissus leucopterus leucopterus*, chinch bug; *Melanoplus femurrubrum*, redlegged grasshopper; *Melanoplus sanguinipes*, migratory grasshopper; *Hylemya platura*, seedcorn maggot; *Agromyza parvicornis*, corn blot leafminer; *Anaphothrips obscrurus*, grass thrips; *Solenopsis milesta*, thief ant; *Tetranychus urticae*, twospotted spider mite; Sorghum: *Chilo partellus*, sorghum borer; *Spodoptera frugiperda*, fall armyworm; *Helicoverpa zea*, corn earworm; *Elasmopalpus lignosellus*, lesser cornstalk borer; *Feltia subterranea*, granulate cutworm; *Phyllophaga crinita*, white grub; *Eleodes, Conoderus*, and *Aeolus* spp., wireworms; *Oulema melanopus*, cereal leaf beetle; *Chaetocnema pulicaria*, corn flea beetle; *Sphenophorus maidis*, maize billbug; *Rhopalosiphum maidis*, corn leaf aphid; *Sipha flava*, yellow sugarcane aphid; *Blissus leucopterus leucopterus*, chinch bug; *Contarinia sorghicola*, sorghum midge; *Tetranychus cinnabarinus*, carmine spider mite; *Tetranychus urticae*, twospotted spider mite; Wheat: *Pseudaletia unipunctata*, army worm; *Spodoptera frugiperda*, fall armyworm; *Elasmopalpus lignosellus*, lesser cornstalk borer; *Agrotis orthogonia*, western cutworm; *Elasmopalpus lignosellus*, lesser cornstalk borer; *Oulema melanopus*, cereal leaf beetle; *Hypera punctata*, clover leaf weevil; *Diabrotica undecimpunctata howardi*, southern corn rootworm; Russian wheat aphid; *Schizaphis graminum*, greenbug; *Macrosiphum avenae*, English grain aphid; *Melanoplus femurrubrum*, redlegged grasshopper; *Melanoplus differentialis*, differential grasshopper; *Melanoplus sanguinipes*, migratory grasshopper; *Mayetiola destructor*, Hessian fly; Sitodiplosis mosellana, wheat midge; *Meromyza americana*, wheat stem maggot; *Hylemya coarctata*, wheat bulb fly; *Frankliniella fusca*, tobacco thrips; *Cephus cinctus*, wheat stem sawfly; *Aceria tulipae*, wheat curl mite; Sunflower: *Suleima helianthana*, sunflower bud moth; *Homoeosoma electellum*, sunflower moth; *Zygogramma exclamationis*, sunflower beetle; *Bothyrus gibbosus*, carrot beetle; *Neolasioptera murtfeldtiana*, sunflower seed midge; Cotton: *Heliothis virescens*, cotton budworm; *Helicoverpa zea*, cotton bollworm; *Spodoptera exigua*, beet armyworm; *Pectinophora gossypiella*, pink bollworm; *Anthonomus grandis*, boll weevil; *Aphis gossypii*, cotton aphid; *Pseudatomoscelis seriatus*, cotton fleahopper; *Trialeurodes abutilonea*, banded winged whitefly; *Lygus lineolaris*, tarnished plant bug; *Melanoplus femurrubrum*, redlegged grasshopper; *Melanoplus differentialis*, differential grasshopper; *Thrips tabaci*, onion thrips; *Franklinkiella fusca*, tobacco thrips; *Tetranychus cinnabarinus*, carmine spider mite; *Tetranychus urticae*, twospotted spider mite; Rice: *Diatraea saccharalis*, sugarcane borer; *Spodoptera frugiperda*, fall armyworm; *Helicoverpa zea*, corn earworm; *Colaspis brunnea*, grape colaspis; *Lissorhoptrus oryzophilus*, rice water weevil; *Sitophilus oryzae*, rice weevil; *Nephotettix nigropictus*, rice leafhopper; *Blissus leucopterus*, chinch bug; *Acrosternum hilare*, green stink bug; Soybean: *Pseudoplusia includens*, soybean looper; *Anticarsia gemmatalis*, velvet bean caterpillar; *Plathypena scabra*, green clover worm; *Ostrinia nubilalis*, European corn borer; *Agrotis ipsilon*, black cutworm; *Spodoptera exigua*, beet armyworm; *Heliothis virescens*, cotton budworm; *Helicoverpa zea*, cotton bollworm; *Epilachna varivestis*, Mexican bean beetle; *Myzus persicae*, green peach aphid; *Empoasca fabae*, potato leafhopper; *Acrosternum hilare*, green stink bug; *Melanoplus femurrubrum*, redlegged grasshopper; *Melanoplus differentialis*, differential grasshopper; *Hylemya platura*, seedcorn maggot; *Sericothrips variabilis*, soybean thrips; *Thrips tabaci*, onion thrips; *Tetranychus turkestani*, strawberry spider mite; *Tetranychus urticae*, twospotted spider mite; Barley: *Ostrinia nubilalis*, European corn borer; *Agrotis ipsilon*, black cutworm; *Schizaphis graminum*, greenbug; *Blissus leucopterus leucopterus*, chinch bug; *Acrosternum hilare*, green stink bug; *Euschistus servus*, brown stink bug; *Delia platura*, seedcorn maggot; *Mayetiola destructor*, Hessian fly; *Petrobia latens*, brown wheat mite; Oil Seed Rape: *Brevicoryne brassicae*, cabbage aphid; *Phyllotreta cruciferae*, Flea beetle; *Mamestra configurata*, Bertha armyworm; *Plutella xylostella*, Diamond-back moth; *Delia* ssp., Root maggots.

In some embodiments, the insecticidal compositions can be employed to treat combinations comprising one or more of the foregoing insects.

The insects that are susceptible to the peptides of this invention include but are not limited to the following:

families such as: Blattaria, Coleoptera, Collembola, Diptera, Echinostomida, Hemiptera, Hymenoptera, Isoptera, Lepidoptera, Neuroptera, Orthoptera, Rhabditida, Siphonoptera, Thysanoptera.

Genus-Species are indicated as follows: *Actebia-fennica, Agrotis-ipsilon, A.-segetum, Anticarsia-gemmatalis, Argyrotaenia-citrana, Artogeia-rapae, Bombyx-mori, Busseola-fusca, Cacyreus-marshall, Chilo-suppressalis, Christoneura-fumiferana, C.-occidentalis, C.-pinus pinus, C.-rosacena, Cnaphalocrocis-medinalis, Conopomorpha-cramerella, Ctenopsuestis-obliquana, Cydia-pomonella, Danaus-plexippus, Diatraea-saccharallis, D.-grandiosella, Earias-vittella, Elasmolpalpus-lignoselius, Eldana-saccharina, Ephestia-kuehniella, Epinotia-aporema, Epiphyas-postvittana, Galleria-mellonella*, Genus-Species, *Helicoverpa-zea, H.-punctigera, H.-armigera, Heliothis-virescens, Hyphantria-cunea, Lambdina-fiscellaria, Leguminivora-glycinivorella, Lobesia-botrana, Lymantria-dispar, Malacosoma-disstria, Mamestra-brassicae, M. configurata, Manduca-sexta, Marasmia-patnalis, Maruca-vitrata, Orgyia-leucostigma, Ostrinia-nubilalis, O.-furnacalis, Pandemis-pyrusana, Pectinophora-gossypiella, Perileucoptera-coffeella, Phthorimaea-opercullela, Pianotortrix-octo, Piatynota-stultana, Pieris-brassicae, Plodia-interpunctala, Plutella-xylostella, Pseudoplusia-includens, Rachiplusia-nu, Sciropophaga-incertulas, Sesamia-calamistis, Spilosoma-virginica, Spodoptera-exigua, S.-frugiperda, S.-littoralis, S.-exempta, S.-litura, Tecia-solanivora, Thaumetopoea-pityocampa, Trichoplusia-ni, Wiseana-cervinata, Wiseana-copularis, Wiseana-jocosa, Blattaria-blattella, Collembola-xenylla, C.-folsomia, Echinostomida-fasciola, Hemiptera-oncopeltrus, He.-bemisia, He.-macrosiphum, He.-rhopalosiphum, He.-myzus, Hymenoptera-diprion, Hy.-apis, Hy.-macrocentrus, Hy.-meteorus, Hy.-nasonia, Hy.-solenopsis, Isopoda-porcellio, Isoptera-reticulitermes, Orthoptera-achta, Prostigmata-tetranychus, Rhabitida-acrobeloides, R.-caenorhabditis, R.-distolabrellus, R.-panagrellus, R.-pristionchus, R.-pratylenchus, R.-ancylostoma, R.-nippostrongylus, R.-panagrellus, R.-haemonchus, R.-meloidogyne*, and *Siphonaptera-ctenocephalides*.

The present disclosure provides methods for plant transformation, which may be used for transformation of any plant species, including, but not limited to, monocots and dicots. Crops for which a transgenic approach or plant incorporated protectants (PIP) would be an especially useful approach include, but are not limited to: alfalfa, cotton, tomato, maize, wheat, corn, sweet corn, lucerne, soybean, sorghum, field pea, linseed, safflower, rapeseed, oil seed rape, rice, soybean, barley, sunflower, trees (including coniferous and deciduous), flowers (including those grown commercially and in greenhouses), field lupins, switchgrass, sugarcane, potatoes, tomatoes, tobacco, crucifers, peppers, sugarbeet, barley, and oilseed rape, *Brassica* sp., rye, millet, peanuts, sweet potato, cassaya, coffee, coconut, pineapple, citrus trees, cocoa, tea, banana, avocado, fig, guava, mango, olive, papaya, cashew, macadamia, almond, oats, vegetables, ornamentals, and conifers.

In some embodiments, the compositions and/or methods of the present invention can be applied to the locus of an insect and/or pest selected from the group consisting of: Loopers; Omnivorous Leafroller; Hornworms; Imported Cabbageworm; Diamondback Moth; Green Cloverworm; Webworm; Saltmarsh Caterpillar; Armyworms; Cutworms; Cross-Striped Cabbageworm; Podworms; Velvetbean Caterpillar; Soybean Looper; Tomato Fruitworm; Variegated Cutworm; Melonworms; Rindworm complex; Fruittree Leafroller; Citrus Cutworm; *Heliothis*; Orangedog; Citrus Cutworm; Redhumped Caterpillar; Tent Caterpillars; Fall Webworm; Walnut Caterpillar; Cankerworms; Gypsy Moth; Variegated Leafroller; Redbanded Leafroller; Tufted Apple Budmoth; Oriental Fruit Moth; Filbert Leafroller; Obliquebanded Leafroller; Codling Moth; Twig Borer; Grapeleaf Skeletonizer; Grape Leafroller; Achema Sphinx Moth (Hornworm); Orange Tortrix; Tobacco Budworm; Grape Berry Moth; Spanworm; Alfalfa Caterpillar; Cotton Bollworm; Head Moth; Amorbia Moth; Omnivorous Looper; Ello Moth (Hornworm); Io Moth; Oleander Moth; Azalea Caterpillar; Hornworm; Leafrollers; Banana Skipper; *Batrachedra comosae* (Hodges); Thecla Moth; Artichoke Plume Moth; Thistle Butterfly; Bagworm; Spring & Fall Cankerworm; Elm Spanworm; California Oakworm; Pine Butterfly; Spruce Budworms; Saddle Prominent Caterpillar; Douglas Fir Tussock Moth; Western Tussock Moth; Blackheaded Budworm; *Mimosa* Webworm; Jack Pine Budworm; Saddleback Caterpillar; Greenstriped Mapleworm; or Hemlock Looper.

In some embodiments, the compositions and/or methods of the present invention can be applied to the locus of an insect and/or pest selected from the group consisting of: Achema Sphinx Moth (Hornworm) (*Eumorpha achemon*); Alfalfa Caterpillar (*Colias eurytheme*); Almond Moth (*Caudra cautella*); Amorbia Moth (*Amorbia humerosana*); Armyworm (*Spodoptera* spp., e.g. *exigua, frugiperda, littoralis, Pseudaletia unipuncta*); Artichoke Plume Moth (*Platyptilia carduidactyla*); Azalea Caterpillar (*Datana major*); Bagworm (*Thyridopteryx*); *ephemeraeformis*); Banana Moth (*Hypercompe scribonia*); Banana Skipper (*Erionota thrax*); Blackheaded Budworm (*Acleris gloverana*); California Oakworm (*Phryganidia californica*); Spring Cankerworm (*Paleacrita merriccata*); Cherry Fruitworm (*Grapholita packardi*); China Mark Moth (*Nymphula stagnata*); Citrus Cutworm (*Xylomyges curialis*); Codling Moth (*Cydia pomonella*); Cranberry Fruitworm (*Acrobasis vaccinii*); Cross-striped Cabbageworm (*Evergestis rimosalis*); Cutworm (*Noctuid* species, *Agrotis ipsilon*); Douglas Fir Tussock Moth (*Orgyia pseudotsugata*); Ello Moth (Hornworm) (*Erinnyis ello*); Elm Spanworm (*Ennomos subsignaria*); European Grapevine Moth (*Lobesia botrana*); European Skipper (*Thymelicus lineola* (Essex Skipper); Fall Webworm (*Melissopus latiferreanus*; Filbert Leafroller (*Archips rosanus*; Fruittree Leafroller (*Archips argyrospilia*; Grape Berry Moth (*Paralobesia viteana*; Grape Leafroller (*Platynota stultana*; Grapeleaf Skeletonizer (*Harrisina americana* (ground only); Green Cloverworm (*Plathypena scabra*; Greenstriped Mapleworm (*Dryocampa rubicunda*; Gummosos-Batrachedra; Comosae (Hodges); Gypsy Moth (*Lymantria dispar*); Hemlock Looper (*Lambdina fiscellaria*); Hornworm (*Manduca* spp.); Imported Cabbageworm (*Pieris rapae*); Io Moth (*Automeris io*); Jack Pine Budworm (*Choristoneura pinus*); Light Brown Apple Moth (*Epiphyas postvittana*); Melonworm (*Diaphania hyalinata*); Mimosa Webworm (*Homadaula anisocentra*); Obliquebanded Leafroller (*Choristoneura rosaceana*); Oleander Moth (*Syntomeida epilais*); Omnivorous Leafroller (*Playnota stultana*); Omnivorous Looper (*Sabulodes aegrotata*); Orangedog (*Papilio cresphontes*); Orange Tortrix (*Argyrotaenia citrana*); Oriental Fruit Moth (*Grapholita molesta*); Peach Twig Borer (*Anarsia lineatella*); Pine Butterfly (*Neophasia menapia*); Podworm (*Heliocoverpa zea*); Redbanded Leafroller (*Argyrotaenia velutinana*); Redhumped Caterpillar (*Schizura concinna*); Rindworm Complex (Various Leps.); Saddleback Caterpillar (*Sibine stimulea*); Saddle Prominent Caterpillar *Heterocampa guttivitta*); Saltmarsh Caterpillar (*Estigmene acrea*); Sod Webworm (*Crambus* spp.); Spanworm (*Ennomos subsignaria*); Fall Cankerworm (*Alsophila pometaria*); Spruce Budworm (*Choristoneura fumiferana*); Tent Caterpillar (Various Lasiocampidae); Thecla-Thecla Basilides (Geyr) *Thecla basilides*); Tobacco Hornworm (*Manduca sexta*); Tobacco Moth (*Ephestia elutella*); Tufted Apple Budmoth (*Platynota idaeusalis*); Twig Borer (*Anarsia lineatella*); Variegated Cutworm (*Peridroma saucia*); Variegated Leafroller (*Platynota flavedana*); Velvetbean Caterpillar (*Anticarsia gemmatalis*); Walnut Caterpillar (*Datana integerrima*); Webworm (*Hyphantria cunea*); Western Tussock Moth (*Orgyia vetusta*); Southern Cornstalk Borer (*Diatraea crambidoides*); Corn Earworm; Sweet potato weevil; Pepper weevil; Citrus root weevil; Strawberry root weevil; Pecan weevil; Filbert weevil; Ricewater weevil; Alfalfa weevil; Clover weevil; Tea shot-hole borer; Root weevil; Sugarcane beetle; Coffee berry borer; Annual blue grass weevil (*Listronotus maculicollis*); Asiatic garden beetle (*Maladera castanea*); European chafer (*Rhizotroqus majalis*); Green June beetle (*Cotinis nitida*); Japanese beetle (*Popillia japonica*); May or June beetle (*Phyllophaga* sp.); Northern masked chafer (*Cyclocephala borealis*); Oriental beetle (*Anomala orientalis*); Southern masked chafer (*Cyclocephala lurida*); Billbug (Curculionoidea); *Aedes aegypti; Busseola fusca; Chilo suppressalis; Culex pipiens; Culex quinquefasciatus; Diabrotica virgifera; Diatraea saccharalis; Helicoverpa armigera; Helicoverpa zea; Heliothis virescens; Leptinotarsa decemlineata; Ostrinia furnacalis; Ostrinia nubilalis; Pectinophora gossypiella; Plodia interpunctella; Plutella xylostella; Pseudoplusia includens; Spodoptera exigua; Spodoptera frugiperda; Spodoptera littoralis; Trichoplusia ni;* or *Xanthogaleruca luteola.*

In some embodiments, the compositions and/or methods of the present invention can be applied to the locus of an adult beetle selected from the group consisting of: Asiatic garden beetle (*Maladera castanea*); Gold spotted oak borer (*Agrilus coxalis auroguttatus*); Green June beetle (*Cotinis nitida*); Japanese beetle (*Popillia japonica*); May or June beetle (*Phyllophaga* sp.); Oriental beetle (*Anomala orientalis*); and Soap berry-borer (*Agrilus prionurus*).

In some embodiments, the compositions and/or methods of the present invention can be applied to the locus of an insect and/or pest that is a larvae (annual white grub) selected from the group consisting of: Annual blue grass weevil (*Listronotus maculicollis*); Asiatic garden beetle (*Maladera castanea*); European chafer (*Rhizotroqus majalis*); Green June beetle (*Cotinis nitida*); Japanese beetle (*Popillia japonica*); May or June beetle (*Phyllophaga* sp.); Northern masked chafer (*Cyclocephala borealis*); Oriental beetle (*Anomala orientalis*); Southern masked chafer (*Cyclocephala lurida*); and Billbug (Curculionoidea).

EXAMPLES

The Examples in this specification are not intended to, and should not be used to, limit the invention; they are provided only to illustrate the invention.

Example 1: Generation of the TVP Expression Vector

A DNA construct of various TVPs were codon optimized and synthesized as a fusion with *Kluyveromyces lactis* alpha mating factor pre/pro sequence (αMF) and ligated into the NotI and HindIII restriction sites of pKlac1 (New England Biolabs). The vector was digested with SacII to linearize and remove the bacterial Ori and selection marker, then electroporated into electrocompetent *Kluyveromyces lactis* cells. Multiple gene copy transformants were selected on selection plates containing acetamide as the sole nitrogen source. Clones expressing TVPs were assessed by HPLC on a Chromolith C18 column (4.6×100 mm) and eluted at a flow rate of 2 mL min-1 and gradient of 15-33% acetonitrile over 8 min. FIG. 1.

Example 2: Digestion of TVPs and Alanine Scan of Basic Amino Acids

To determine the stability of TVPs when exposed to lepidopteran gut proteases. Briefly, 5th instar *Manduca sexta* were dissected by making a small incision to the intestinal lining such that gut contents could be collected in a tube. Multiple dissections were pooled and kept on ice for immediate use, or stored at –80° C. for future use. The isolated midgut (referred to hereinafter as *Manduca* Gut Extract, or MGE) was then for digest assays. Next, 1 mg/mL TVP was incubated with 0.1 mg/mL bovine trypsin, or 1/10 diluted MGE with 50 mM Tris-HCl, pH 8.8 to maintain alkaline pH. Time points were taken and the digest quenched with the addition of 200 mM HCl. Degradation was quantified by HPLC analysis and rates were determined by fit to a single exponential decay.

Lepidopteran gut contains trypsin-like proteases that cut after Arg or Lys amino acids; without wishing to be bound by any particular theory, we hypothesized that singly mutating these amino acids to alanine could identify the site(s) that are causing degradation in lepidopteran gut. To test the foregoing hypothesis, TVPs were created by individually mutating each basic amino acid to alanine present in the wild-type Ta1b amino acid sequence. Next, the stability of each of these TVPs was assessed by confronting the TVPs with the digestion conditions as described above. As a result of this experiment, it was revealed that substitution of arginine at amino acid position 9 with alanine (R9A) completely abolished trypsin digestion, while substitutions of K18A and R38A gave modest, albeit significant reduction in digestibility. Accordingly, R9A and R38A were further assessed for stability to lepidopteran gut proteases in the MGE assay, and the mutations were found to stabilize Ta1b by 247 and 8.6-fold, respectively. See Table 3.

TABLE 3

Basic amino acid alanine scan digestion analysis.

| | Half Life (min) | | | |
| Mutant | Bovine Trypsin | Manduca Gut Extract (MGE) | Fold Change (Trypsin) | Fold Change (MGE) |
|---|---|---|---|---|
| WT Ta1b | 288 | 1.5 | — | — |
| R7A | 132 | not tested | 0.5 | not tested |
| R9A | >6000 | 370 | >20 | 247 |
| K13A | 294 | not tested | 1.0 | not tested |
| K18A | 1194 | not tested | 4.1 | not tested |
| R38A | 1860 | 19 | 6.5 | 8.6 |

Example 3: Combinatorial Peptide Screen for Sequences Resistant to Insect Gut Proteases A FRET based peptide library screen to identify positions that may reduce digestion in the presence of lepidopteran gut proteases. The FRET analysis was performed using a commercially available FRET kit (Cat. No. PSREPLI005, Mimotopes, Victoria, Australia). The FRET analysis is follows: a peptide library coupled to FRET molecules (a dye and a quencher) was used as reporter assays for the identification of peptides that cleave in either insect gut environment or in simulated human gastrointestinal environment. Briefly, a FRET kit contains pools of FRET molecules with a stretch of 3 variable amino acid sequences bracketed by a series of glycine amino acids attached to either a dye or a quencher. Each FRET molecule gives no signal if the variable region is not cleaved, but can be excited if the molecule is cleaved. The speed at which the cleavage occurs (i.e., the specificity of the sequence for the proteases) can be ranked by the rate at which the fluorescent signal occurs over time (i.e., the slope).

The FRET kit used contains 512 pools of up to 8 different FRET molecules per pool. The FRET reaction is very high-throughput, with the enzymes added to the plate of pooled material with a multichannel loading pipet and then the plate is read once a minute for detectable fluorescence. The output of fluorescence detection is recorded for each reaction.

FRET samples were prepared immediately prior to assay as recommended by the manufacturer (add 5 µL 50% acetonitrile in water to each well and agitate plate on shaker for 5 minutes; then add 45 µL of assay buffer and agitate again for 5 minutes). At this point, the FRET pools were ready of the addition of 50 µL of the working enzyme stock to start the reactions. Using a multichannel, repeat pipetter, 50 µL of the working enzyme stock (for each of the enzyme types tested) was added to each well and then the plate was immediately placed into a plate reader (SpectraMax plate reader with SoftMax Pro 6.0 software, Molecular Devices, Sunnyvale CA) and emissions were read using the setting of Excitation 320 nm, Emission 420 nm, with a cut-off of 420 nm. Readings were taken every 1 minute for 15 minutes. Once the plates were completed, they were sealed with an aluminum sealer and stored at −80° C.

To test the FRET pool cleavage by gut enzymes of a lepidopteran pest, gut enzymes were isolated from Corn Earworm (*Helicoverpa zea*). Corn Earworm insects were obtained commercially from Benzon Research (Carlisle, PA) as eggs. Hatched larvae were raised on artificial diet until $4/5^{th}$ instar (20 mm long) before guts were isolated. Before gut extract, larvae were anesthetized using $CO_2$. The larva was then pinned on the dissection plate at both the head and the tail. Using dissection scissors, the cuticle was nicked. The dissection scissors were then inserted into the nick and the cuticle was lengthwise along the insect. The cuticle was then carefully pulled back and pinned open to reveal the digestive track. Using DI water, the insect was thoroughly rinsed to remove hemolymph. The gut was then excised with tweezers and placed in a solution of 500 µL of 200 mM Tris-HCl, pH 8.1, 150 mM NaCl (assay buffer). The tube was pre-weighed and post-weighed to calculate the total amount of gut added. Corn Earworm gut was diluted to a stock concentration of 7 mg/mL (10×) in 200 mM Tris-HCl, pH 8.1, 150 mM NaCl. This was diluted fresh each plate by 20× with the assay buffer. Using a multichannel, repeat pipetter, 50 µL of 1× gut extract was added to each well and read immediately as described above.

Next, the FRET kits was tested against the lepidopteran gut simulated protease environment, and data was recovered. Table 11 shows the results of the combinatorial peptide screen, highlighting the amino acid substitutions at position P2, P1, P1', and P2', where P1 corresponds to the R9 position. The library does not contain methionine, so the similar amino acids leucine and isoleucine were assumed to approximate cleavability of M10 (position P1'). Several mutations (shown in Table 4 in bold) displayed enhanced stability in the presence of lepidopteran proteases, and several of these were further characterized for stability and activity in Ta1b.

TABLE 4

| Fold reduction in peptide digestion rate. | | | |
| --- | --- | --- | --- |
| P2 | P1 | P1' | P2' |
| A | R | M | T |
| A/V — | 5.1 | 0.9 | 0.9 |
| D/E 3.4 | 58.1 | 0.9 | 3.0 |
| F/Y 1.7 | 2.7 | 0.5 | 0.7 |
| I/L 1.8 | 33.9 | — | 0.7 |
| K/R 3.0 | — | 0.6 | 0.6 |
| N/Q 3.6 | 10.8 | 0.7 | 1.4 |
| P 305.3 | 5.1 | 18.5 | 9.9 |
| S/T 3.3 | 9.0 | 0.6 | — |

Mutant Stability and Activity Profiling

FRET based mutations were incorporated into TVPs and assessed for protease stability and activity. Because position R9 appeared to be a pharmacophore residue important for activity, we prioritized conservative mutations with large polar side chains that would more likely retain a similar activity profile at this position. An exemplary method of FRET screening is disclosed in U.S. patent application Ser. No. 15/727,277, entitled "Cleavable Peptides and Insecticidal and Nematicidal Proteins Comprising Same," the disclosure of which is incorporated herein by reference in its entirety.

The combinatorial library contains three randomized amino acids surrounded by glycines, with a FRET dye/quencher pair on the N- and C-termini. Cleavage of the peptide results in an increase in signal proportional to the amount of cleavage and allows for rank-ordering of the susceptibility of various peptide sequences to gut proteases. The combinatorial library was subjected to digestion in the presence of *Helicoverpa zea* gut extract that was isolated in an identical manner as the aforementioned MGE technique.

TVPs were assessed for stability in the presence of MGE (as described above). Activity was assessed by injection into houseflies (*Musca domestica*): 0.5 was injected intrathoracically into houseflies with an average mass of 18 mg. The dose required for 50% knockdown and mortality was determined at 24 hour post-injection.

Of the TVPs tested, several mutants adversely affected activity. However, several TVPs were able to maintain activity similar to the native Ta1b, e.g., TVPs with the following substitutions: A8S, R9N, R9Q, and T11P, showed significant reduction in digestibility by *Manduca* Gut Extract (MGE), consistent with the combinatorial peptide library results.

To assess the activity of alanine mutations, TVPs with mutations R38A and R9A were injected into the dorsal intrathoracic region of adult houseflies. R38A did not show any reduction in activity relative to wild-type Ta1b, but R9A had a 9-fold reduction in activity. See Table 5.

TABLE 5

| | | Fold |
| | Fold Stability | Activity |
| Mutant | Improvement | Reduction |
|---|---|---|
| A8D | not tested | >10 |
| A8N | 1.8 | not tested |
| A8P | not tested | >10 |
| A8S | 12.1 | 1.3 |
| R9A | 247 | 8.7 |
| R9E | not tested | >10 |
| R9H | 16.2 | 2.5 |
| R9N | >50 | 1.5 |
| R9Q | >50 | 0.8 |
| T11D | not tested | >10 |
| T11P | 92.9 | 1.4 |
| R38A | 8.6 | 1.0 |

Mutant stability and activity profiling.

Example 4: Housefly Injection Assay

Figure 2:
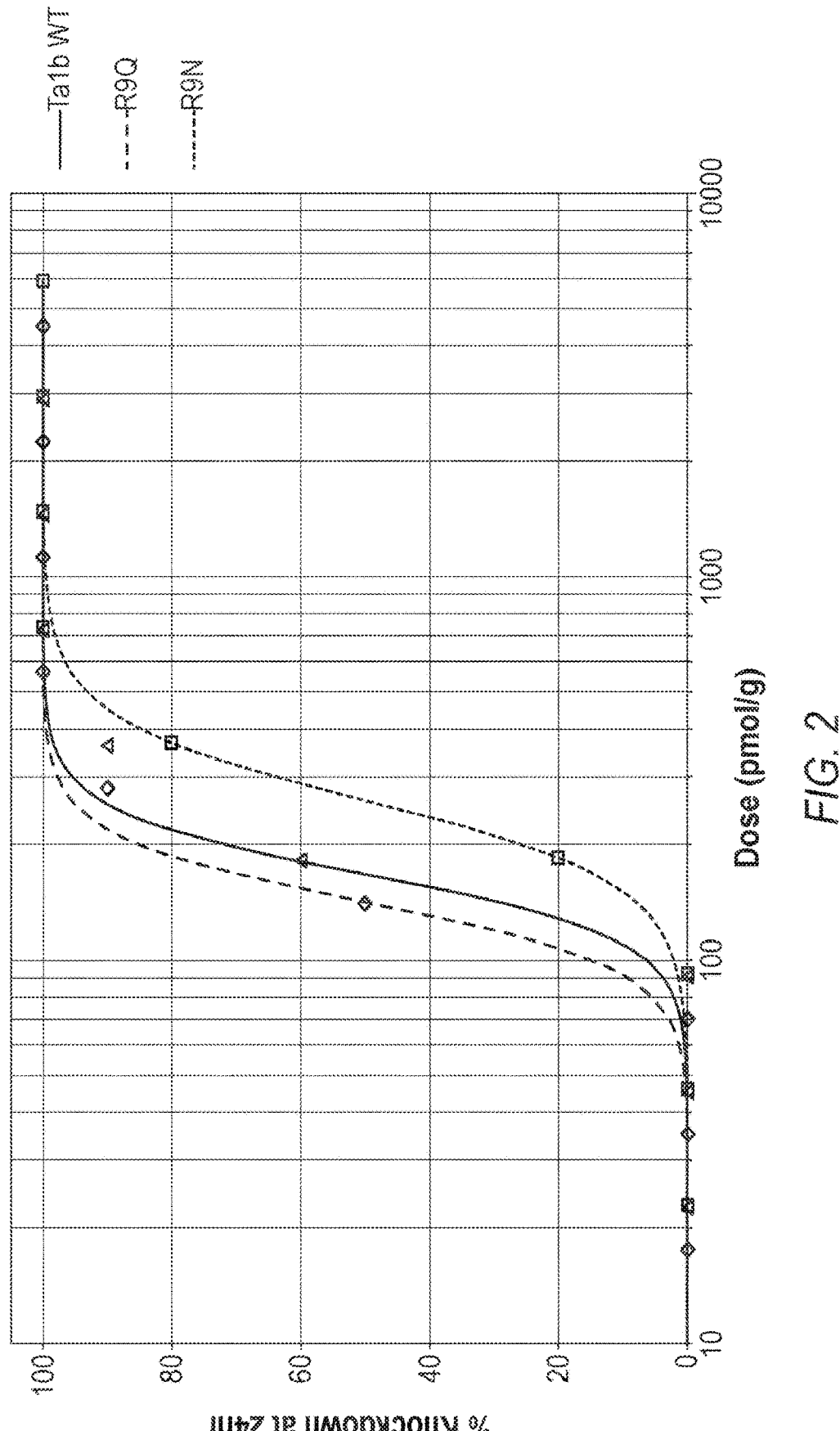
FIG. 2 depicts the results of a housefly injection assay where activity of Wild-type Ta1b, and the TVPs with amino acid substitutions at positions R9Q and R9N were injected intrathoracically into houseflies, and the dose of TVP required for 50% knockdown ($KD_{50}$) was then determined at 24-hours post-injection.

Activity of the TVPs identified in the mutant stability assay were assessed by injection into houseflies (*Musca domestica*). Wild-type Ta1b and the TVPs with amino acid substitutions at positions R9Q and R9N were injected intrathoracically into houseflies with an average mass of 18 mg, at an injection dose of 0.5 μL of toxin or control. The dose of TVP required for 50% knockdown ($KD_{50}$) was then determined at 24-hours post-injection. The results of this experiment illustrate that the R9Q TVP is more active compared to wild-type Ta1b, as indicated by the lower dose required to reach $KD_{50}$ and in houseflies (controls using water and $CO_2$ showed no knockdown effect). FIG. 2.

Example 5: Thrip Survival Assay

A wild population of western flower *thrips* (*Frankliniella occidentalis*) were collected from greenhouse grown *Phlox paniculata*. Untreated control (UTC) of water, or 400 μg of toxin, were applied to 8×33 mm filter paper (85.6 μg/cm²) and placed inside sealed containers with *thrips* and 10% sucrose as food. Thrip mortality was then measured at four days.

Figure 3:
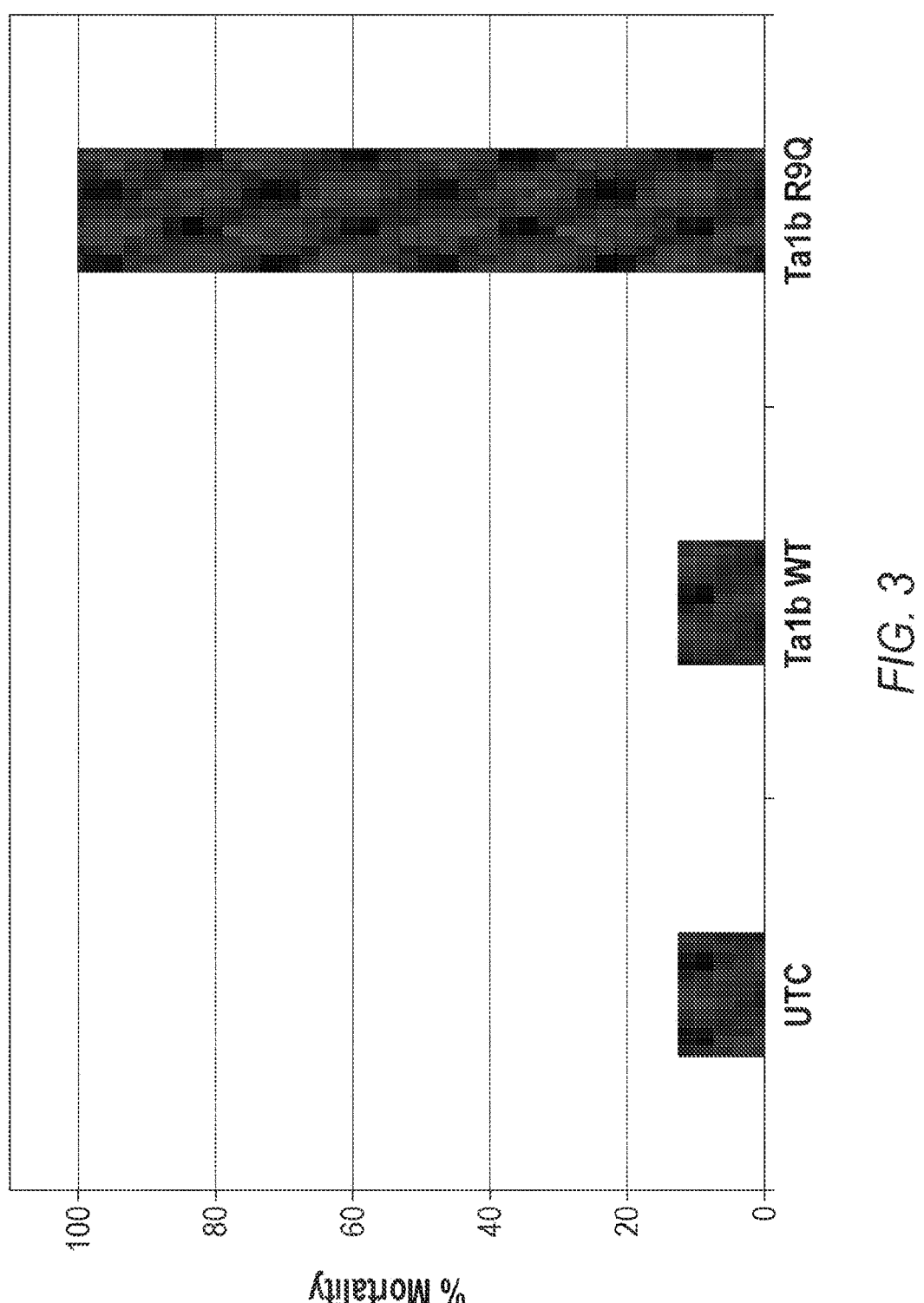
FIG. 3 depicts the results of the Thrip survival assay evaluating percent mortality (% Mortality) of untreated control (UTC), wild-type U1-agatoxin-Ta1b (Ta1bWT), and a TVP with an amino acid substitution at position R9Q.

The Thrip survival assay revealed that there was 12.5% mortality in the untreated control (UTC) and wild-type U1-agatoxin-Ta1b; however, using the TVPs with amino acid substitutions at positions R9Q resulted in 100% mortality. FIG. 3.

Example 6: Post-Translational Modification of TVPs in *K. lactis*

TVPs expressed and secreted from *K. lactis* undergo post-translational modifications. To better understand this post-translational modification, TVP-R9Q was injected onto a Chromolith C18 column (4.6×100 mm) and eluted at a flow rate of 2 mL min-1 and a gradient of 15-33% acetonitrile over 8 min. Mass spectra were then collected on an ESI LC-TOF Micromass LCT instrument (Waters).

Figure 4:
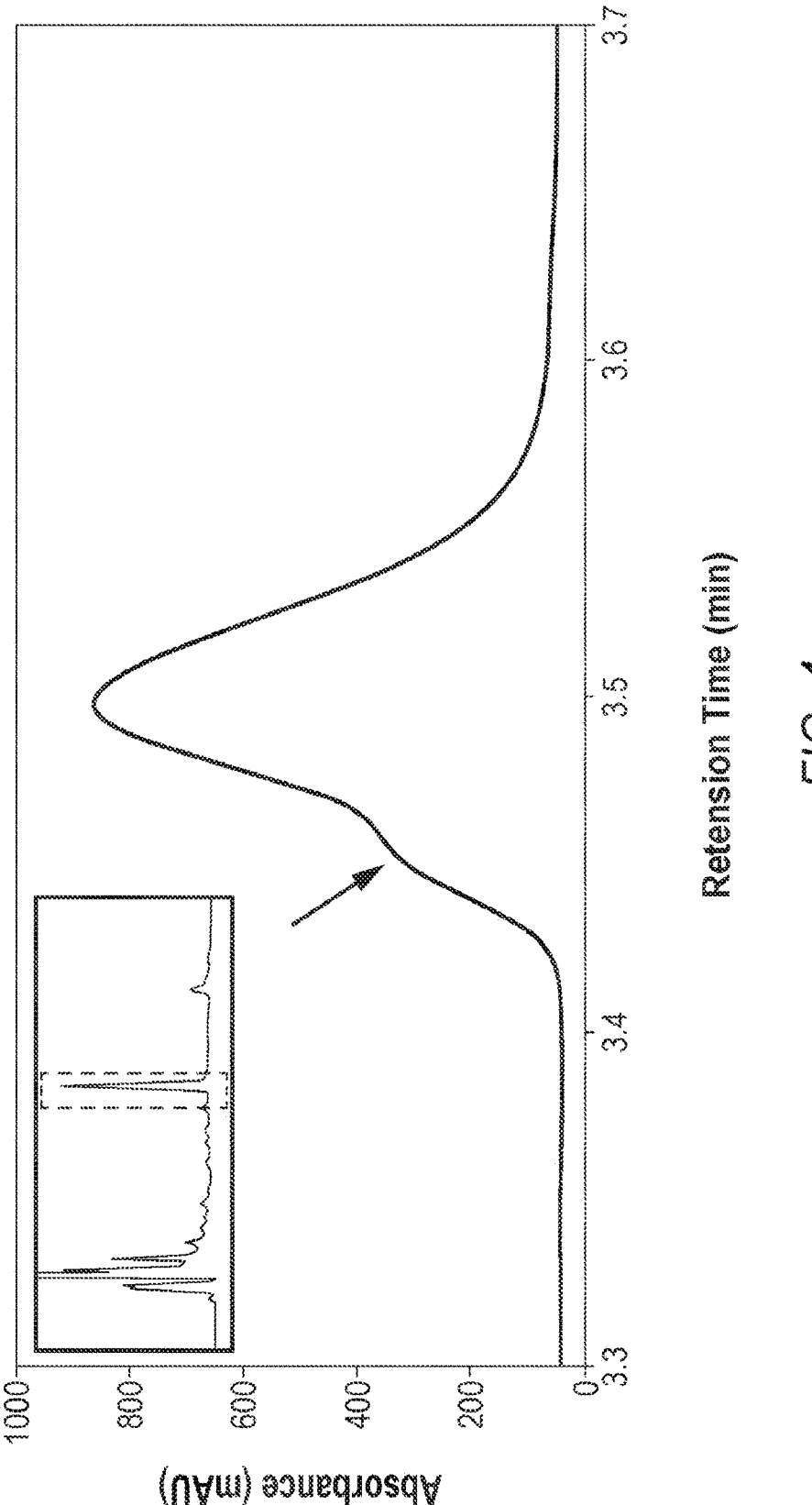
FIG. 4 depicts an HPLC chromatogram of a TVP with an amino acid substitution at position R9Q (TVP-R9Q), showing a putative glycosylation species as a "shoulder" on the left side of the main TVP peak (as indicated by a black arrow).
Figures 5, 6:
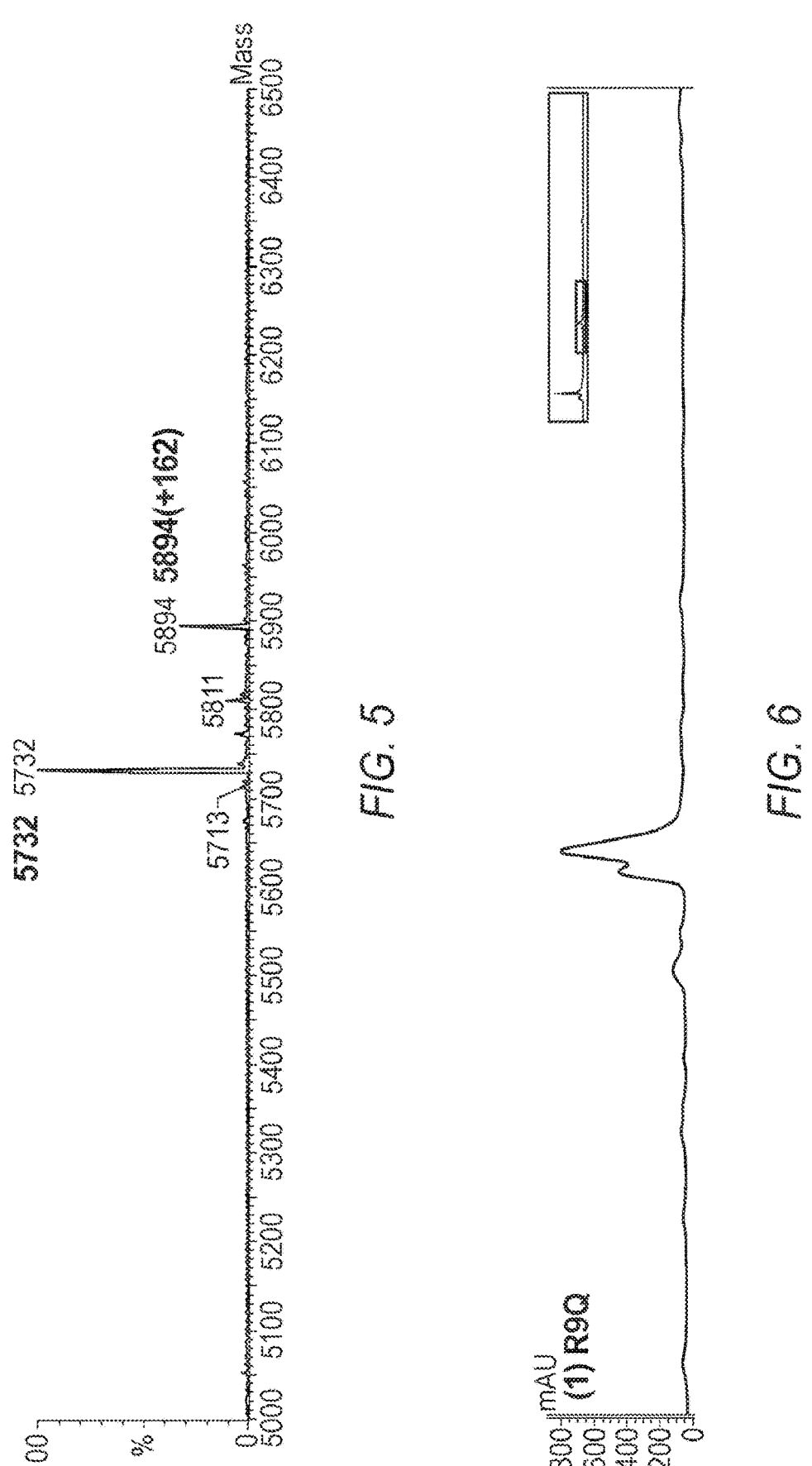
FIG. 5 depicts the results of ESI-MS showing the mass spectra of TVP-R9Q. The inset depicts a deconvolution of the multiply charged species, and calculates masses of 5732 and 5894 Da. Expected molecular weight of fully oxidized TVP-R9Q is 5731.3.
FIG. 6 depicts an HPLC chromatogram results of TVP-R9Q. The glycosylation is shown by the smaller "shoulder" on the left side of the main peak.

The post-translational modification that occurs in TVPs is evidenced by a mass shift of +162 Da. FIG. 4. There is a strong possibility that this post-translational event is a glycosylation, specifically, an O-linked mannosylation of a serine or threonine residue. FIG. 4 depicts the readout of an HPLC chromatogram of TVP-R9Q, showing a shoulder on the TVP peak (indicated by a black arrow). FIG. 5 depicts the Mass spectra of TVP-R9Q. Deconvolution of the multiply charged species (inset) calculates masses of 5732 and 5894 Da. Expected molecular weight of fully oxidized TVP-R9Q is 5731.3 Da. FIG. 5.

Example 7: Removal of Glycosylation Site and Protection of C-Terminus

To further characterize TVP variants, the effect of removing the putative glycosylation site, and protective effects the C-terminal amino acid affords, were analyzed. TVP variants were injected onto a Chromolith C18 column (4.6×100 mm) and eluted at a flow rate of 2 mL min-1 and a gradient of 15-33% acetonitrile over 8 min. Mass spectra were collected on an ESI LC-TOF Micromass LCT instrument (Waters).

The following TVPs were analyzed: (1) TVP-R9Q; (2) TVP-R9QΔG; (3) TVP-R9Q/T43A/ΔG; (4) TVP-R9Q/T43A; and (5) TVP-R9Q/T43A/ΔK-G. The expected/observed mass spectra results for the molecular weights of the foregoing TVPs is reported in Table 6.

TABLE 6

Expected/Observed molecular weight for TVPs.

| Sequence | Expected Molecular Weight | Observed Molecular Weight |
|---|---|---|
| (1) TVP-R9Q | 5731.3 | 5732 |
| (2) TVP-R9QΔG | | |
| (3) TVP-R9Q/T43A/ΔG | 5644.2 | 5645 |
| (4) TVP-R9Q/T43A | 5701.3 | 5702 |
| (5) TVP-R9Q/T43A/ΔK-G | 5516.0 | 5516 |

Figures 7, 8:
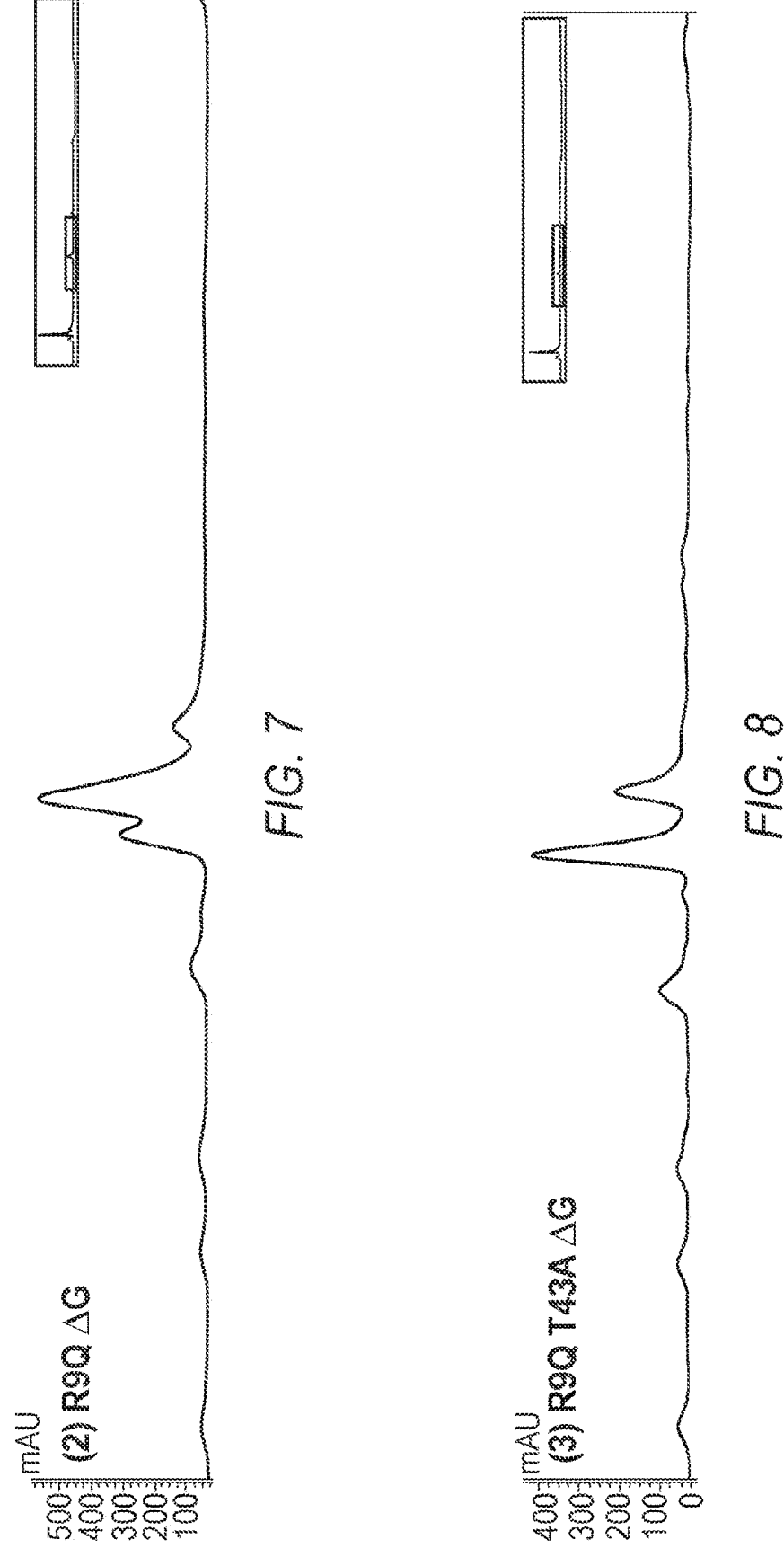
FIG. 7 depicts an HPLC chromatogram results of TVP-R9QΔG. The glycosylation is shown by the smaller "shoulder" on the left side of the main peak. The partial proteolyzation is shown by the right shoulder.
FIG. 8 depicts an HPLC chromatogram results of TVP-R9Q/T43A/ΔG. The proteolysis event is demonstrated by the presence of two shoulders: the smaller "shoulder" on the left side of the main peak indicates the partial proteolyzation event.

The putative glycosylation event is confirmed, as shown by the HPLC of TVP-R9Q, and as indicated by the left shoulder peak. FIG. 6. Removal of the C-terminal glycine from Ta1b (e.g., TVP-R9QΔG and TVP-R9Q/T43A/ΔG) results in the terminal lysine (K50) to be partially proteolyzed during expression in *K. lactis*. FIGS. 7-8.

Figures 9, 10:
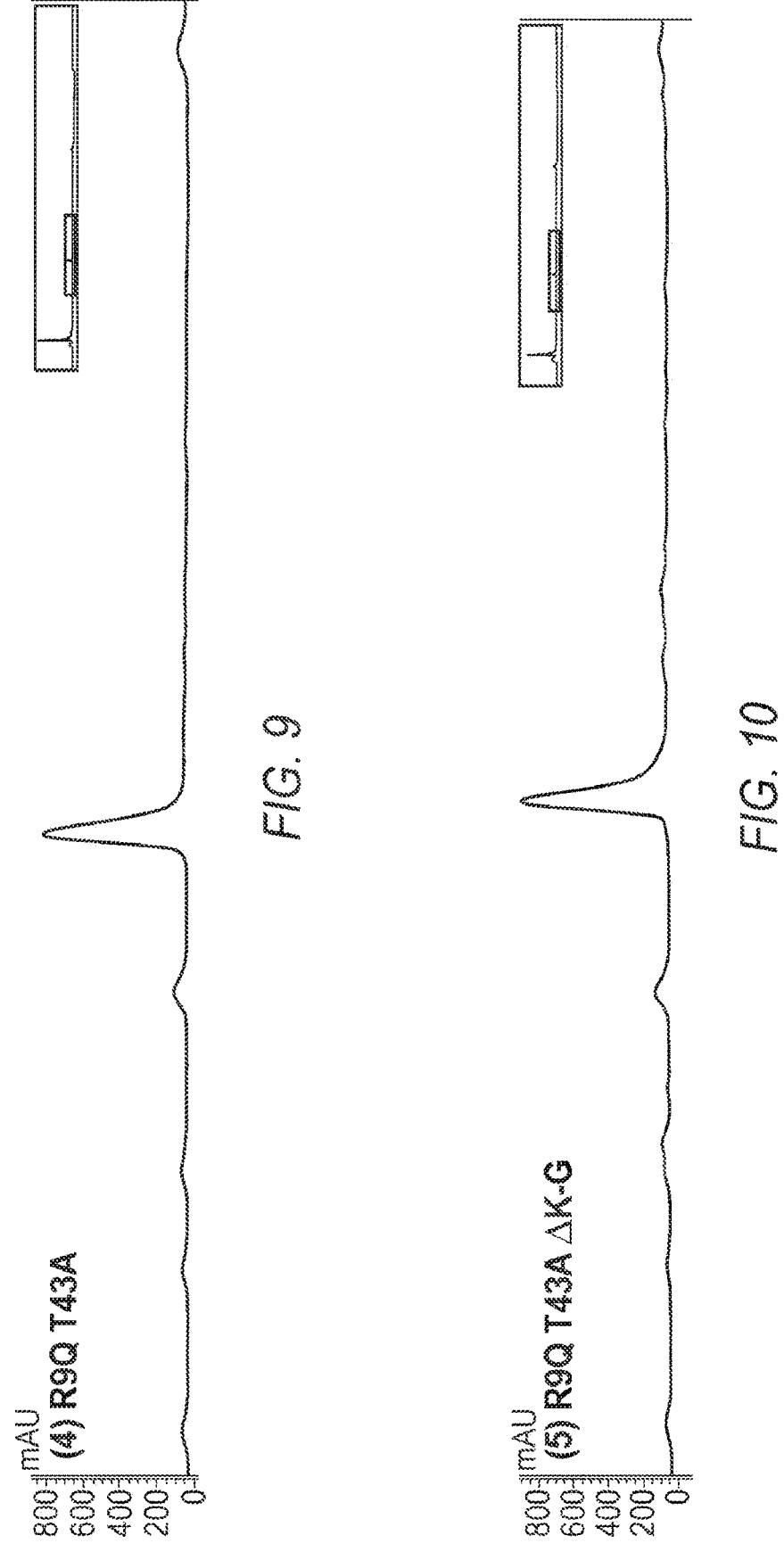
FIG. 9 depicts an HPLC chromatogram results of TVP-R9Q/T43A. Here, a single species of TVP is present.
FIG. 10 depicts an HPLC chromatogram results of TVP-R9Q/T43A/ΔK-G. Here, a single species of TVP is present.
Figures 11, 12:
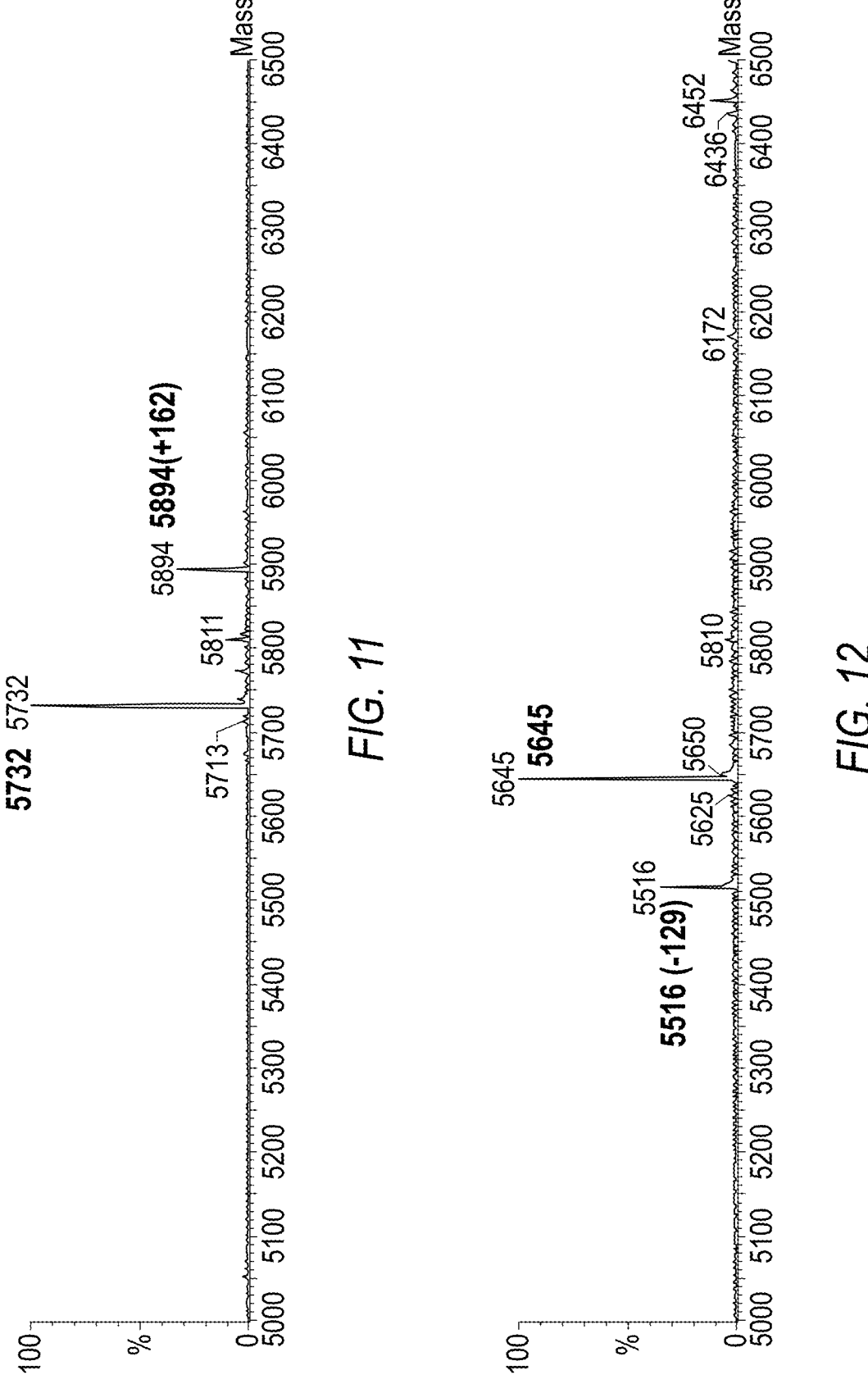
FIG. 11 depicts the results of ESI-MS showing the mass spectra of TVP-R9Q.
FIG. 12 depicts the results of ESI-MS showing the mass spectra of TVP-R9Q/T43A/ΔG.
Figures 13, 14:
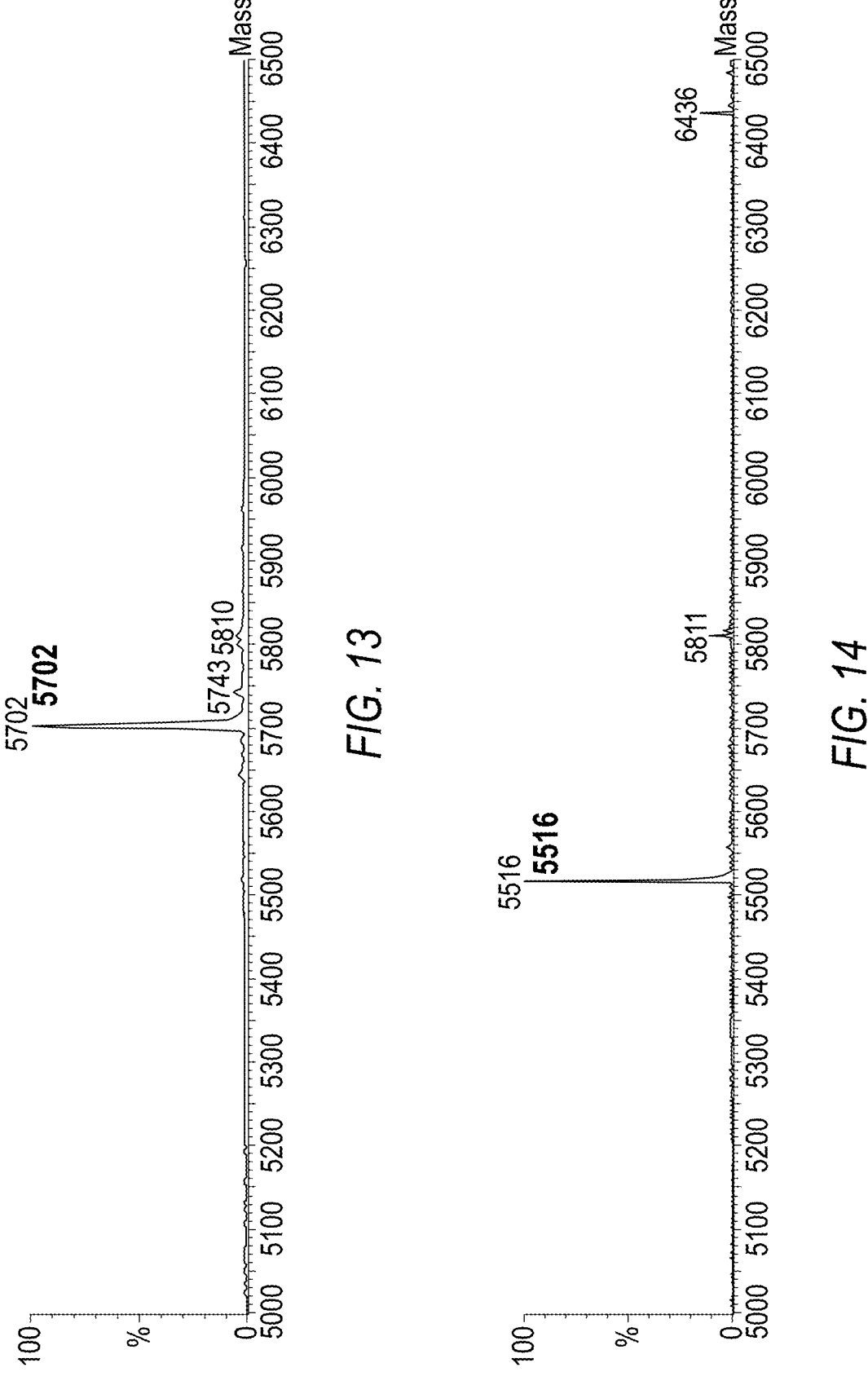
FIG. 13 depicts the results of ESI-MS showing the mass spectra of TVP-R9Q/T43A.
FIG. 14 depicts the results of ESI-MS showing the mass spectra of TVP-R9Q/T43A/ΔK-G.

A single species of TVP can be expressed when the terminal glycine is added back (e.g., TVP-R9Q/T43A) or the terminal lysine is also removed (TVP-R9Q/T43A/ΔK-G). FIGS. 9 and 10.

FIGS. 11-14 show the results of the ESI-MS analysis, showing the mass spectra of (1) TVP-R9Q; (2) TVP-R9QΔG; (3) TVP-R9Q/T43A/ΔG; (4) TVP-R9Q/T43A; and (5) TVP-R9Q/T43A/ΔK-G.

Example 8: Housefly Injection Assay Using TVPs after Removal of Glycosylation Site The TVPs: (1) TVP-R9Q; (2) TVP-R9QΔG; (3) TVP-R9Q/T43A/ΔG; (4) TVP-R9Q/T43A; and (5) TVP-R9Q/T43A/ΔK-G, were analyzed in a housefly injection assay. Housefly injections were performed as previously described herein. Table 7 shows the results of the housefly injection assay. Here, all the TVPs showed higher activity when compared to WT Ta1b.

TABLE 7

Housefly injection assay results.

| Peptide tested | Fly $KD_{50}$ (pmol/g) |
|---|---|
| Wild-type | 167 |
| TVP-R9Q | 149 |
| TVP-R9Q/ΔG | 136 |

TABLE 7-continued

| Housefly injection assay results. | |
|---|---|
| Peptide tested | Fly KD$_{50}$ (pmol/g) |
| TVP-R9Q/T43A/ΔG | 157 |
| TVP-R9Q/T43A | 180 |
| TVP-R9Q/T43A/ΔK-G | 157 |

Figure 15:
FIG. 15 depicts the results of the Housefly injection assay using TVPs after removal of glycosylation site and/or the C-terminal amino acids.

Here, removal of the glycosylation site and C-terminal amino acids (i.e., ΔG and/or ΔK-G) resulted in peptides with higher activity when compared to WT Ta1b. FIG. 15.

Example 9: Corn Earworm Bioassay

To compare the WT Ta1b and TVP-R9Q, an injection and oral foliar bioassay was performed. Here, the affect that WT Ta1b and TVP-R9Q had on mortality in corn earworms was evaluated. The results of the injection and oral bioassays are shown in the table below.

First, WT Ta1b (WT) and the R9Q mutant of Ta1b (TVP-R9Q) were evaluated in a lepidopteran injection assay. The experimental unit consisted of 8 injected individual corn earworm (*Helicoverpa zea*) per peptide dose. There were four experimental replicates per peptide. Prior to injection, corn earworm larvae were reared to their fourth instar on standard lepidoptera diet. The larvae were weighed to determine accurate dose calculations. The exact doses varied slightly between replicates because of variations in corn earworm larvae mass, but the approximate doses injected were: 1000, 2000, 4000, and 8000 pmol/g. Injections were performed using a hand microapplicator and a syringe fitted with a 30 gauge needle. Larvae were injected at the base of one of their most posterior prolegs. Larvae were injected with 1 μL of treatment solution.

After injection, larvae were placed in a well of a 32-well tray filled with 5 mL of standard lepidoptera diet. The trays were then placed in a 28° C. Incubator. The condition of the larvae were evaluated 24 hours after injection. Larvae were evaluated as either "alive" or "knockdown" where alive individuals moved normally, fed normally, and reacted to probing normally; knockdown individuals did not have coordinated movement, were unable to feed, and did not react to probing.

In the oral foliar bioassay, the experimental unit consisted of 12 leaf discs (per peptide concentration) sprayed (front and back) with a total spray volume of 5.5 mL (2.75 mL for each side) on which neonate corn earworm (*Helicoverpa zea*) were allowed to feed. There were four experimental replicates per peptide.

Romaine lettuce was cut into 30 mm diameter disks, and then sterilized using a 140 ppm bleach solution; the disks were then triple rinsed in water. The romaine lettuce disks were then pinned to a Styrofoam board and sprayed with a given treatment; the disks were flipped, sprayed again, allowed to dry, and placed in the arena.

The arena was 32-well rearing tray containing 5 mL of 1% agar. One romaine lettuce disk was placed in each well, with a single first instar corn earworm (*Helicoverpa zea*) per leaf disk. The trays were then placed in a 28° C. Incubator.

Mortality of the corn earworms was evaluated on the fourth day after spraying and larvae application to the leaf discs. Larvae were scored as either alive (moving and feeding normally) or dead (immobile, discolored).

The results of the injection and oral bioassays are presented in the table below.

TABLE 8

| Injection and oral mortality assay. WT = wild type. Error is shown as standard error of the mean (n = 3). "ppt" = part per thousand. | | |
|---|---|---|
| Name | Injection LD$_{50}$ (pmol/g) | Oral Bioassay % Mortality at 3 ppt |
| WT | 2933 ± 827 | 6 ± 3 |
| TVP-R9Q | 3406 ± 516 | 21 ± 7 |

Example 10: Stability Formulations

Liquid Concentrate Stability

A liquid concentrate (LC) formulation was evaluated at different temperatures over time. An LC formulation comprising 2% TVP-R9Q/T43A; 0.03% benzisothiazolinone (BIT); 2% sorbitol; and the remaining amount of the LC formulation was fermentation beer, i.e., a concentrate of cell separated fermentation beer, was evaluated using HPLC to determine the stability of TVP-R9Q/T43A at different temperature and over time. The temperatures evaluated were 4° C., 21° C., 37° C., 45° C., and 54° C. The times evaluated were 0, 16, 31, 42, 98, and 114 days.

Figure 16:
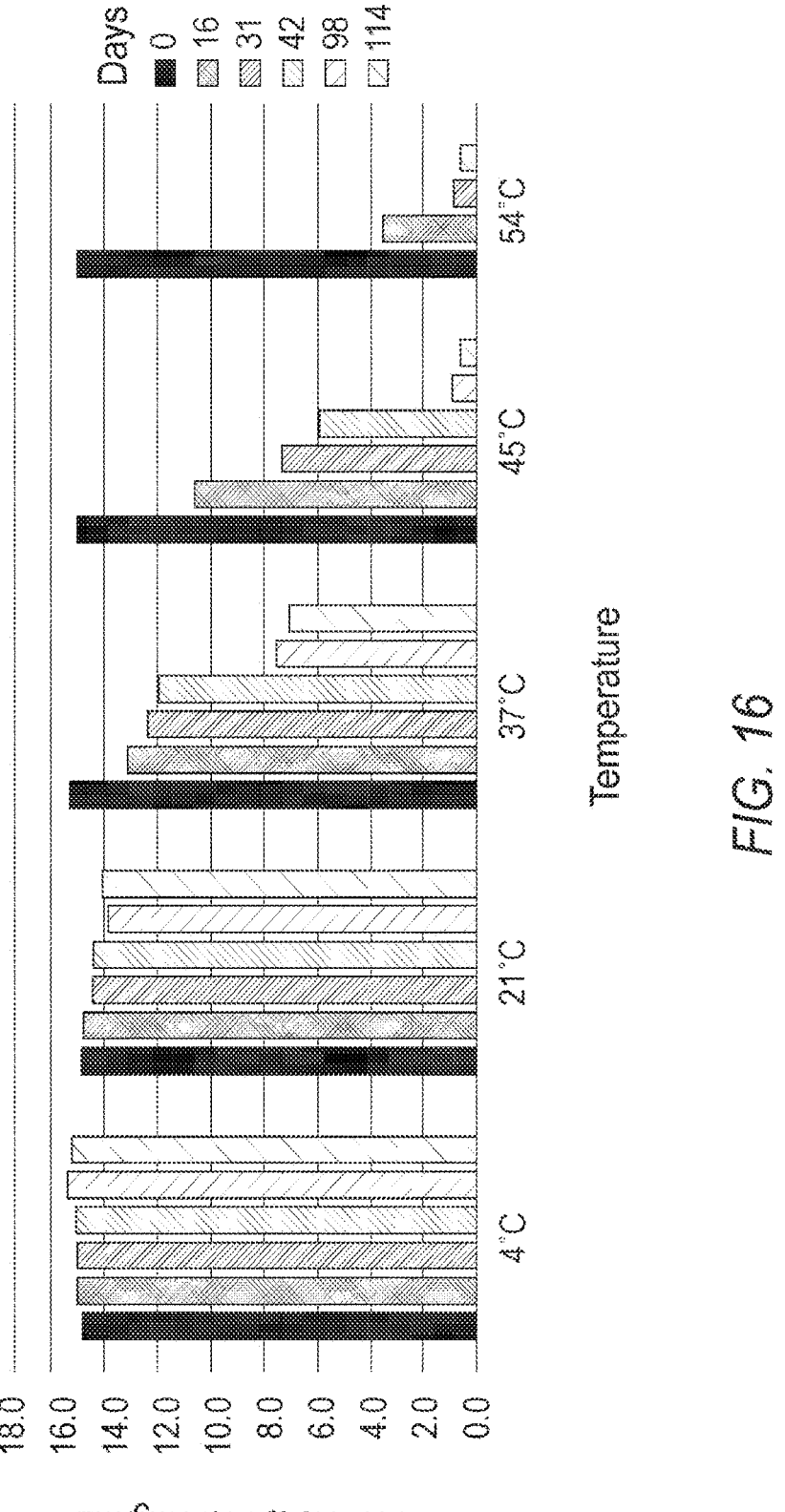
FIG. 16 shows the results of a stability assay of a liquid concentrate (LC) formulation, evaluated at different temperatures over time. The LC formulation comprised 2% TVP-R9Q/T43A; 0.03% benzisothiazolinone (BIT); 2% sorbitol; and the remaining amount of the LC formulation was fermentation beer, i.e., a concentrate of cell separated fermentation beer, was evaluated using HPLC to determine the stability of TVP-R9Q/T43A at different temperature and over time. The temperatures evaluated were 4° C., 21° C., 37° C., 45° C., and 54° C. The times evaluated were 0, 16, 31, 42, 98, and 114 days.

As shown in FIG. 16, liquid formulations degrades rapidly in field relevant temperatures.

Spray Dried Powder (SDP) Stability Assay

The stability of TVP-R9Q/T43A was next evaluated in a spray dried powder (SDP) form. Here, the SDP formulation was created from dried fermentation beer: briefly, fermentation beer was taken from reactor, concentrated, and spray dried, removing all water. TVP-R9Q/T43A stability in a SDP was evaluated using HPLC to quantify the amount of TVP-R9Q/T43A in mg/mL, at 21° C., 37° C., and 45° C., with and without an oxygen/moisture scavenger packet (Mitsubishi Gas Chemical America, Inc., Product No. AS-100; 655 3rd Ave #24, New York, NY 10017 USA), at 0, 7, 14, 28, 42, and 62 days.

Figure 17:
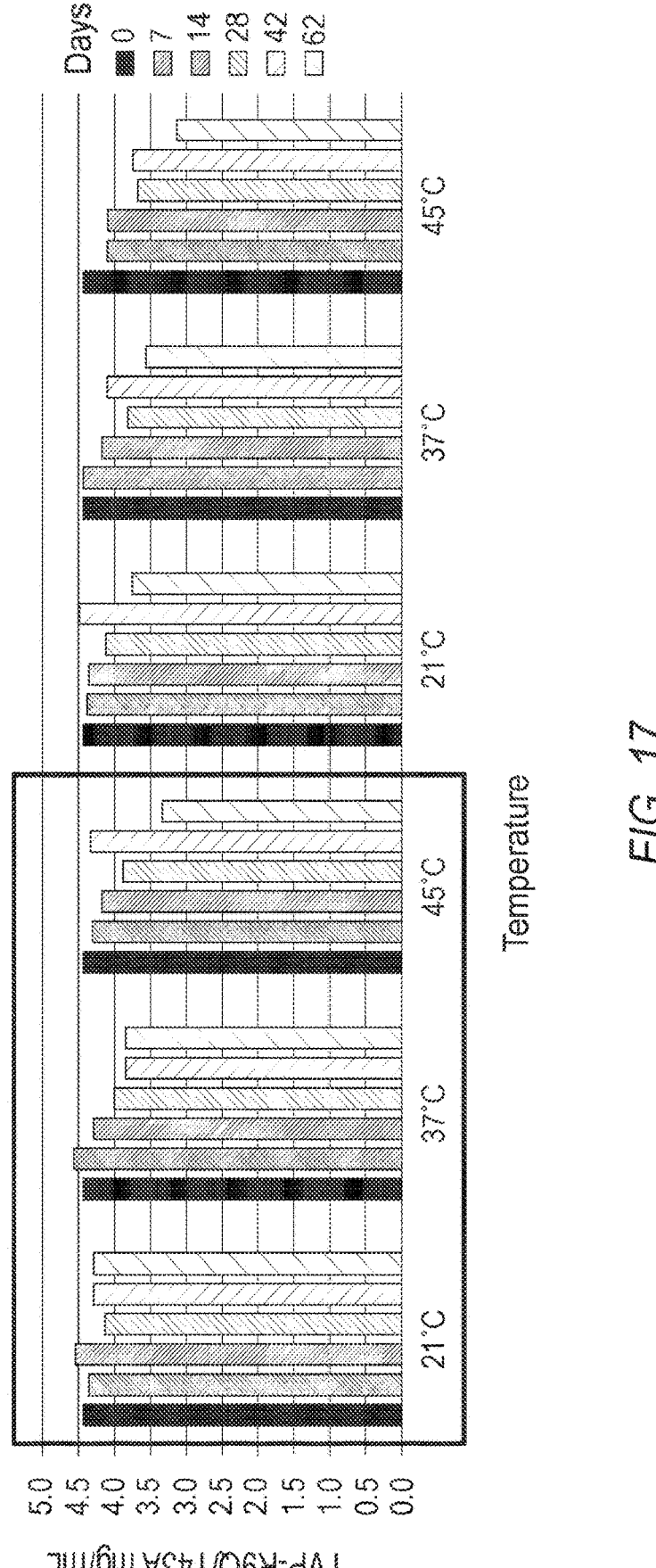
FIG. 17 shows the results of a stability assay of TVP-R9Q/T43A in a spray dried powder (SDP) form. Here, the SDP formulation was created from dried fermentation beer. TVP-R9Q/T43A stability in a SDP was evaluated using HPLC to quantify the amount of TVP-R9Q/T43A in mg/mL, at 21° C., 37° C., and 45° C., with and without an oxygen/moisture scavenger packet. The results enclosed by the black square show the results obtained when using the oxygen/moisture scavenger packet.

As shown in FIG. 17, TVP-R9Q/T43A in a solid state is significantly more stable relative to the liquid state (compare to FIG. 16, above). Moreover, incubation with the oxygen/moisture scavenger packets further increased the stability of TVP-R9Q/T43A. FIG. 17.

The use of an oxygen/moisture scavenger packet during further increased stability. Here, the packet was sealed inside a Mylar bag with the sample prior to testing. After incubation for 62 days at 21° C., the amount of TVP-R9Q/T43A (mg/mL) with an oxygen/moisture scavenger packet decreased by 3.5%, compared to the 15.4% decrease observed in TVP-R9Q/T43A without an oxygen/moisture scavenger packet. FIG. 17. Similarly, after 62 days at 37° C., the decrease in TVP-R9Q/T43A with an oxygen/moisture scavenger packet was 13.0%, compared to the 19.5% decrease observed without an oxygen/moisture scavenger packet. Finally, after 62 days at 45° C. the decrease in TVP-R9Q/T43A with an oxygen/moisture scavenger packet was 24.7%, compared to the 29.5% decrease observed without an oxygen/moisture scavenger packet. Here, degradation of peptide increases as temperature increases. FIG. 17.

Example 11: Preliminary Stability Assay with Additional Excipients

Stability Formulations

Those having ordinary skill in the art will recognize that a combination of long and short chain saccharides with high glass transition temperatures (Tg) promotes low mobility (e.g., α relaxation and β relaxation). See Mensink et al., How sugars protect proteins in the solid state and during drying (review): Mechanisms of stabilization in relation to stress conditions. Eur J Pharm Biopharm. 2017 May; 114: 288-295.

Figure 18:
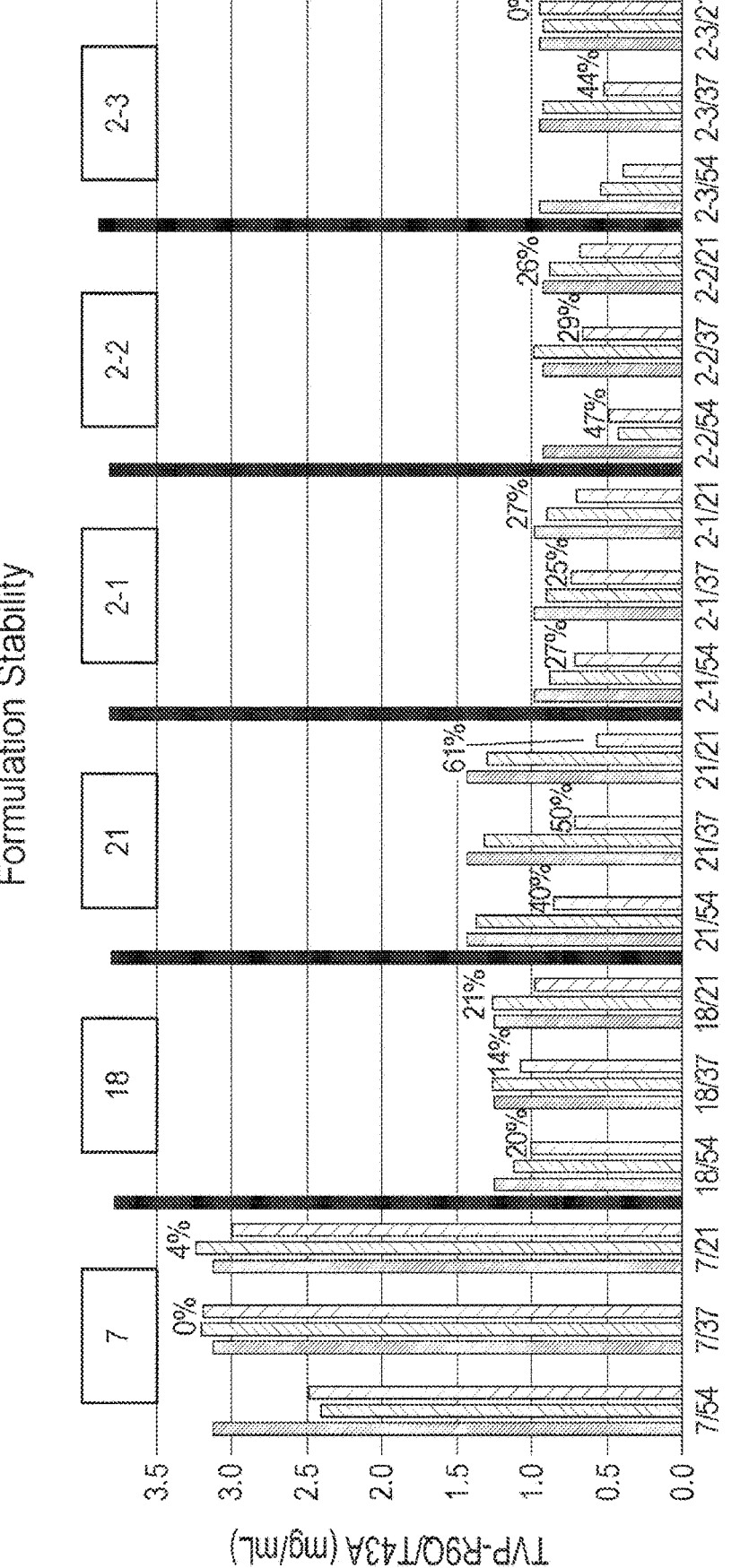
FIG. 18 shows the results of a degradation assay performed to evaluate preliminary stability formulations. The formulations were tested at 54° C., 37° C., and 21° C. for 2 weeks. Each group of formulation number (i.e., 7; 18; 21; 2-1; 2-2; and 2-3) are indicated by Formulation No. followed by a dash "/" and then the temperature tested, i.e., 54° C., 37° C., and 21° C.
Figure 21:
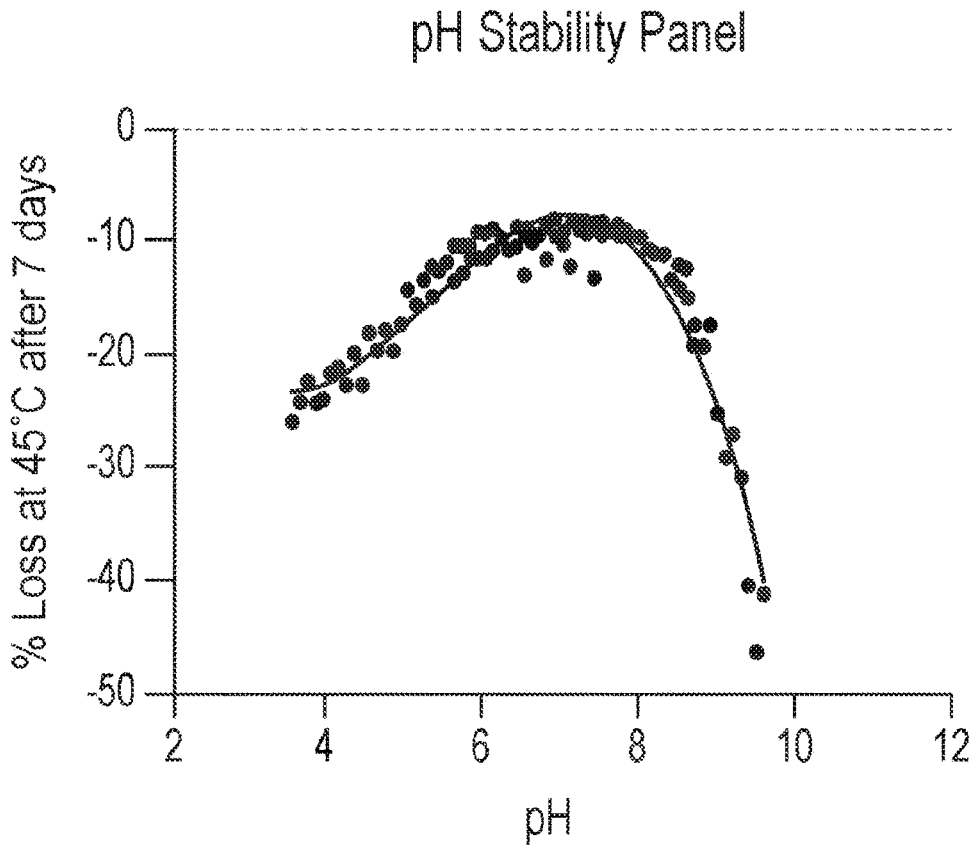
FIG. 21 depicts the results of a pH stability assay. Here, a pH stability screen was performed to determine the effect of pH on the stability of TVP-R9Q/T43A; 1 part per thousand (ppt) of TVP-R9Q/T43A was incubated at varying pH values. TVP-R9Q/T43A was incubated at 45° C. for 7 days and analyzed by HPLC to determine the percent of peptide remaining. As shown here, an optimal pH was determined to be between 6.5 and 7.5.

A degradation assay was performed to evaluate preliminary stability formulations. The components of the preliminary stability formulations are provided in the table below. The formulations were tested at 54° C., 37° C., and 21° C. for 2 weeks. The results of the preliminary stability assay are shown in FIG. 18.

peptide remaining. As shown in FIG. 21, an optimal pH was determined to be between 6.5 and 7.5.

Common preservatives used to prevent microbial contamination include, inter alia, benzoates, propionates, and sorbates. The choice of preservative is highly dependent on pH. Typically, the effective upper pH limit is about 4.5 for benzoates; about 5.5 for propionates; and about 6.5 for sorbates. In some embodiments, when used at the pH levels of, e.g., mildly acidic products (pH 5.5-6.0), sorbates (as opposed to benzoates or propionates) are more effective against a wider spectrum deleterious microorganisms.

TABLE 9

Preliminary stability formulations. Amounts are in grams
(% w/w); "—" indicates the absence of an ingredient.

| Formula No. | SDP | LC w/ BIT | Lignosulfonate | Gypsum | Maltodextrin | Trehalose | Maltose | H₂O |
|---|---|---|---|---|---|---|---|---|
| 7 | 320 | — | 40 | — | 40 | — | — | 244 |
| 18 | — | 425 | — | — | 150 | 75 | — | |
| 21 | 200 | — | 40 | 40 | | 200 | — | 241 |
| 2-1 | — | 425 | — | — | 150 | 150 | — | — |
| 2-2 | — | 425 | — | — | 150 | 75 | 75 | — |
| 2-3 | — | 425 | — | — | 150 | — | 150 | — |

Example 12: Benzisothiazolinone (BIT) Compatibility with TVPs

Two dry formulations—a formulation of cell separated and concentrated fermentation beer having TVP-R9Q/T43A, and a SDP formulation—were evaluated for BIT compatibility. The cell separated and concentrated fermentation beer formulation of TVP-R9Q/T43A was obtained by as described above. The SDP formulation was obtained from fermentation beer as follows: a Buchi spray drier (Model B-290) was used under the following conditions: inlet temperature: 160° C.; outlet temperature: 65-70° C.; pump speed: 35-40 rpm; pressure drop: 45-50 psi; aspirator set to 100%; and atomization pressure of 50 psi.

Samples were evaluated at T0 (time immediately after formulation and drying with spray dryer, performed at room temperature) and after incubation for two weeks at 54° C. Peptide concentration was quantified via HPLC analysis as described herein. Each formulation was tested at 4° C., 21° C., 37° C., and 45° C.

Figure 19:
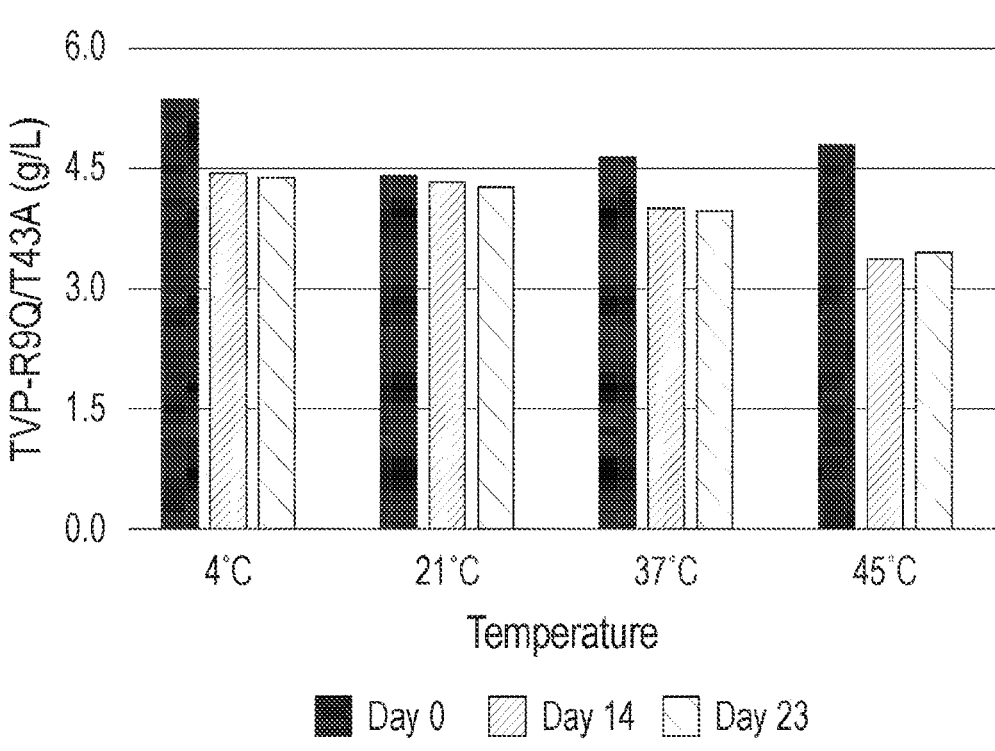
FIG. 19 shows the results of a stability assay for formulations containing Benzisothiazolinone (BIT) to determine their compatibility with TVPs. Here, the formulation was cell separated and concentrated fermentation beer obtained from cells expressing TVP-R9Q/T43A, Samples were evaluated at T0 (time immediately after formulation and drying with spray dryer, performed at room temperature) and after incubation for two weeks at 54° C. Peptide concentration was quantified via HPLC analysis as described herein. Each formulation was tested at 4° C., 21° C., 37° C., and 45° C.

As shown in FIG. 19, the use of BIT reduced the stability of TVP-R9Q/T43A when it was formulated in a solid state, and when used without other additives.

Figure 20:
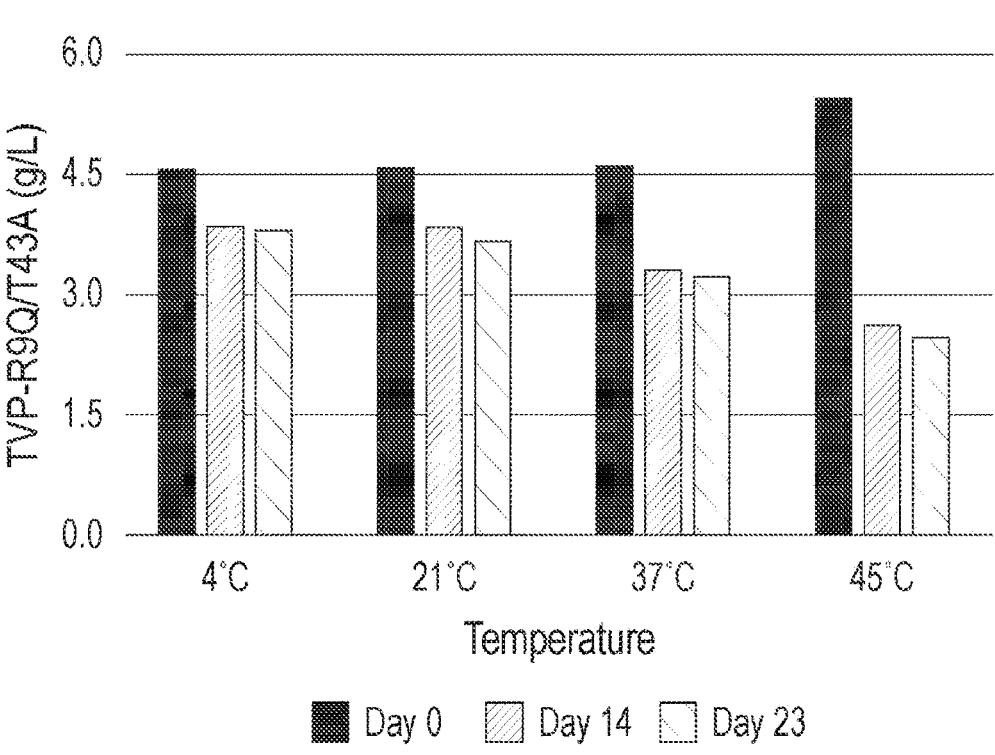
FIG. 20 shows the results of a stability assay for formulations containing Benzisothiazolinone (BIT) to determine their compatibility with TVPs. Here, the formulation a spray dried powder (SDP) containing TVP-R9Q/T43A, Samples were evaluated at T0 (time immediately after formulation and drying with spray dryer, performed at room temperature) and after incubation for two weeks at 54° C. Peptide concentration was quantified via HPLC analysis as described herein. Each formulation was tested at 4° C., 21° C., 37° C., and 45° C.

However, as shown in FIG. 20, when the formulation is spray dried and combined with BIT, there was a decrease in stability of TVP over time, which was exacerbated by higher temperatures. FIG. 20.

BIT is commonly used as an anti-microbial. However, as shown here, the use of BIT resulted in degradation of TVP upon spray drying. FIGS. 19-20.

Example 13: pH Stability Screen

A pH stability screen was performed to determine the effect of pH on the stability of TVP-R9Q/T43A. Here, 1 part per thousand (ppt) of TVP-R9Q/T43A was incubated at varying pH values using a Slice pH kit (Hampton Research, Catalog No. HR2-070; 34 Journey Aliso Viejo, CA 92656-3317 USA). TVP-R9Q/T43A was incubated at 45° C. for 7 days and analyzed by HPLC to determine the percent of

Example 14: Preservatives and Microbial Formation

Several different combinations of preservatives were evaluated to determine the effect thereof on microbial contamination. A formulation of 2% TVP-R9Q/T43A obtained from fermentation beer was combined with 2% sorbitol and other additives. The formulations were mixed in the open, and stored for 2 days at 21° C. After 2 days, the formulations were plated and evaluated for colony forming unit (CFUs).

Based on the information gleaned from the previous example, sorbates were used in the following table to understand if a replacing BIT was possible. The ingredients used in the formulations described in the table below are as follows: Sorbitol (Neosorb 70/20 B; Roquette; Catalog No. 421112980; 1347 Beaver Channel Parkway Clinton, IA 52732-5933 USA); Sodium Benzoate (Alfa Aesar; Catalog No. A15946; 2 Radcliff Rd, Tewksbury, MA 01876 USA); Potassium Sorbate (Alfa Aesar; Catalog No. A12844); Sodium Citrate (Fisher Scientific; Catalog No. BP327-500).

The table below provides a summary of the different formulations, and their effect on colony forming unit (CFUs).

TABLE 10

Preservatives and microbial contamination. The TVP
evaluated was TVP-R9Q/T43A. "Na" means sodium.
"K" means potassium, and is an amount of 0.2% w/w.

| Temp (° C.) | Formulation | CFUs | pH |
|---|---|---|---|
| 4 | 2% TVP + 2% Sorbitol + 0.03% BIT | 0 | n/a |
| 4 | 2% TVP + 2% Sorbitol + 0.2% Na Benzoate + K Sorbate | 0 | n/a |
| 4 | 2% TVP + 2% Sorbitol + 0.2% Na Benzoate + K Sorbate + 0.2% EDTA | 0 | n/a |
| 4 | 2% TVP + 2% Sorbitol + 0.2% Na Benzoate + K Sorbate + 0.2% EDTA | 0 | n/a |
| 21 | 2% TVP + 2% Sorbitol + 0.03% BIT | 0 | 5.12 |
| 21 | 2% TVP + 2% Sorbitol + 0.2% Na Benzoate + K Sorbate | 0 | 5.2 |

TABLE 10-continued

Preservatives and microbial contamination. The TVP
evaluated was TVP-R9Q/T43A. "Na" means sodium.
"K" means potassium, and is an amount of 0.2% w/w.

| Temp (° C.) | Formulation | CFUs | pH |
|---|---|---|---|
| 21 | 2% TVP + 2% Sorbitol + 0.2% Na Benzoate + K Sorbate + 0.2% EDTA | 5 | 5.22 |
| 21 | 2% TVP + 2% Sorbitol + 0.2% Na Benzoate + K Sorbate + 0.2% EDTA | 0 | 5.3 |
| 37 | 2% TVP + 2% Sorbitol + 0.03% BIT | 0 | n/a |
| 37 | 2% TVP + 2% Sorbitol + 0.2% Na Benzoate + K Sorbate | 0 | n/a |
| 37 | 2% TVP + 2% Sorbitol + 0.2% Na Benzoate + K Sorbate + 0.2% EDTA | 0 | n/a |
| 37 | 2% TVP + 2% Sorbitol + 0.2% Na Benzoate + K Sorbate + 0.2% EDTA | 0 | n/a |
| 45 | 2% TVP + 2% Sorbitol + 0.03% BIT | 0 | n/a |
| 45 | 2% TVP + 2% Sorbitol + 0.2% Na Benzoate + K Sorbate | 0 | n/a |
| 45 | 2% TVP + 2% Sorbitol + 0.2% Na Benzoate + K Sorbate + 0.2% EDTA | 0 | n/a |
| 45 | 2% TVP + 2% Sorbitol + 0.2% Na Benzoate + K Sorbate + 0.2% EDTA | 0 | n/a |

As shown above, only the formulation consisting of 2% TVP+2% Sorbitol+0.2 Na Benzoate+K Sorbate+0.2 EDTA, at 21° C., resulted in any CFUs; accordingly, with this exception, the foregoing formulations prevent microbial growth.

Example 15: Stability Panel Part I

In light of the results shown in Example 10, concerning the stability of TVP in liquid concentrate and SDP forms, work was pursued to identify formulations that would stabilize the TVP. The formulations evaluated are found in the table below. Ingredients tested include the following: TVP-R9Q/T43A in the form of liquid concentrate (LC), i.e., a concentrate of cell-separated fermentation beer; $H_2O$ (reverse osmosis); maltodextrin (MALTRIN®; Grain Processing Corporation, Catalog No. M100; 1600 Oregon Street Muscatine, Iowa 52761-1494, USA); trehalose; maltose; $K_2HPO_4$ (dipotassium phosphate, anhydrous; ICL Food Specialties; CAS No. 7758-11-4; 622 Emerson Road, Suite 500, St. Louis, MO 63141 USA); $KH_2PO_4$ (mono potassium phosphate; ICL Specialty Fertilizers; CAS No. 7778-77-0; 2755 W 5th N St N, Summerville, SC 29483); and BIT (Lonza; PROXEL® AQ Preservative; 9.25% aqueous solution of 1,2-benzisothiazolin-3-one; Lonza Group Ltd. Muenchensteinerstrasse 38, CH-4002 Basel, Switzerland).

The spray dry parameters were as follows: inlet temperature: 160° C.; outlet temperature: 65-70° C.; pump speed: 35-40 rpm; pressure drop: 45-50 psi; aspirator set to 100%; and atomization pressure of 50 psi.

Samples were evaluated at T0 (time immediately after formulation and drying with spray dryer, performed at room temperature) and after incubation for two weeks at 54° C. Peptide concentration was quantified via HPLC analysis as described herein.

TABLE 11

Stability Formulations Part I.

| Formula No. | Dilution | H₂O | LC (mL) | Maltodextrin | Trehalose | Maltose | K₂HPO₄ | KH₂PO₄ | BIT (%) | pH | Theor. Conc. (%) | T0 Moist. (%) |
|---|---|---|---|---|---|---|---|---|---|---|---|---|
| 1 | 2x | 200.0 | 100.0 | 108.9 | — | — | 0.0 | 0.0 | 0.014 | 5.2 | 3.74 | 10.00 |
| 2 | 2x | 200.0 | 100.0 | 81.7 | 27.2 | — | 0.0 | 0.0 | 0.014 | 5.2 | 3.74 | 9.60 |
| 3 | 2x | 200.0 | 100.0 | 81.7 | — | 27.2 | 0.0 | 0.0 | 0.014 | 5.2 | 3.74 | 8.00 |
| 4 | 2x | 200.0 | 100.0 | 71.9 | 35.9 | — | 0.0 | 0.0 | 0.014 | 5.2 | 3.77 | 8.00 |
| 5 | 2x | 200.0 | 100.0 | 81.7 | 27.2 | — | 2.15 | 1.04 | 0.014 | 7.2 | 3.74 | 8.00 |
| 6 | 2x | 200.0 | 100.0 | 71.9 | 35.9 | — | 2.15 | 1.04 | 0.014 | 7.8 | 3.77 | 8.00 |
| 7 | 2x | 200.0 | 100.0 | 51.7 | 17.22 | — | 2.15 | 1.04 | 0.000 | 7.2 | 5.38 | 8.00 |
| 8 | 2x | 200.0 | 100.0 | 51.7 | — | 17.22 | 2.15 | 1.04 | 0.000 | 5.2 | 5.38 | 8.00 |
| 9 | 4x | 150.0 | 50.0 | 45.5 | 22.7 | — | 0.00 | 0.00 | 0.000 | 5.2 | 2.06 | 10.00 |
| 10 | 4x | 150.0 | 50.0 | 45.5 | 22.7 | — | 2.15 | 1.04 | 0.000 | 7.2 | 2.06 | 8.00 |
| 11 | 4x | 150.0 | 50.0 | 0.0 | 68.2 | — | 7.20 | 1.00 | 0.000 | 7.2 | 2.06 | 10.00 |
| 12 | 4x | 150.0 | 50.0 | 0.0 | 68.2 | — | 17.00 | 1.04 | 0.000 | 7.8 | 2.06 | 7.80 |
| 13 | 4x | 150.0 | 50.0 | 0.0 | 68.2 | 0.0 | 17.00 | 1.00 | 0.000 | 7.8 | 2.06 | 10.00 |
| 14 | 8x | 175.0 | 25.0 | 50.0 | 0 | 0.0 | 0.25 | 0.13 | 0.000 | 7.2 | 1.45 | 10.00 |
| 15 | 2x | 100.0 | 100.0 | 50.0 | 0 | 0.0 | 0.50 | 0.25 | 0.000 | 7.2 | 4.84 | 10.00 |
| 16 | 1x | 0.0 | 200.0 | 50.0 | 0 | 0.0 | 1.00 | 0.50 | 0.000 | 7.2 | 7.93 | 10.00 |
| 17 | 1x | 0.0 | 200.0 | 50.0 | 0 | 0.0 | 1.00 | 0.50 | 0.000 | 7.2 | 7.93 | 7.80 |

This table shows the formulations used to stabilize TVP.

Here, amounts are shown in grams unless otherwise indicated.

"LC" means liquid concentrate, and is a concentrate of cell separated fermentation beer of cells expressing TVP-R9Q/T43A.

"Theor. Conc." Means theoretical concentration.

"T0 Moist." means Time zero (T0) moisture percentage.

A "—" indicates that the given ingredient is not present.

The formulations presented in table above were evaluated at T0 (time immediately after formulation, drying through spray dryer, and performed at room temperature) and after incubation for two weeks at 54° C. Peptide concentration was quantified via HPLC analysis as described herein. The results of the analysis are shown in FIG. 22.

Figure 22:
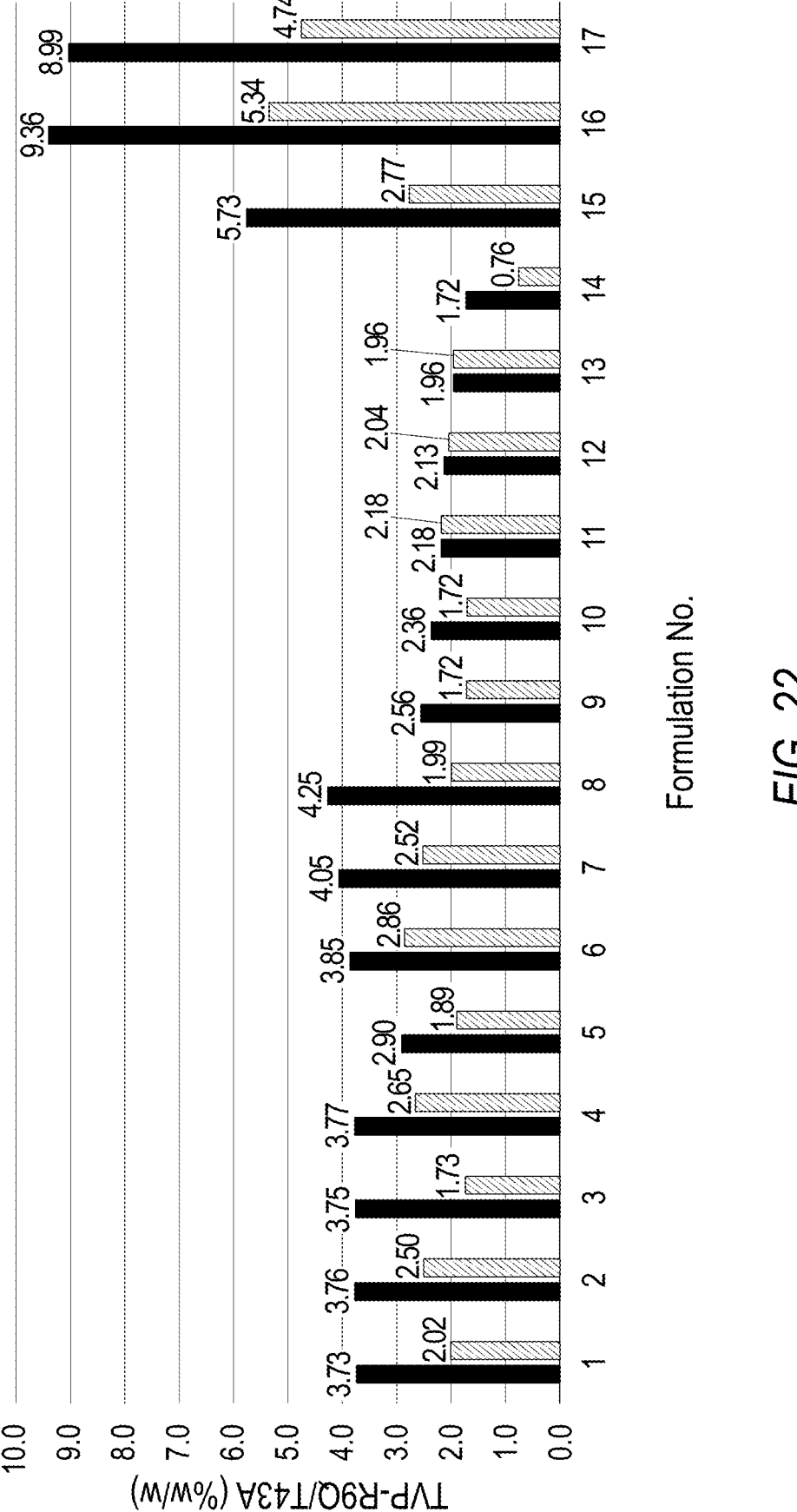
FIG. 22 shows the results of Stability Panel Part I, which includes Formulations Nos. 1-17. Ingredients tested include the following: TVP-R9Q/T43A in the form of liquid concentrate (LC), i.e., a concentrate of cell-separated fermentation beer; $H_2O$ (reverse osmosis); maltodextrin; trehalose; maltose; $K_2HPO_4$; $KH_2PO_4$; and BIT (9.25% aqueous solution of 1,2-benzisothiazolin-3-one). Samples were evaluated at T0 (time immediately after formulation and drying with spray dryer, performed at room temperature) and after incubation for two weeks at 54° C. Peptide concentration was quantified via HPLC analysis.

As shown in FIG. 22, significant degradation was observed in formulations comprising maltose or maltodextrin. However, combinations of trehalose and phosphate were shown to stabilize TVP-R9Q/T43A. Here, neither maltodextrin nor maltose alone (Formulations No. 1, 3, Trehalose manufacturers tested were Bulk Supplements (B) (Catalog No. TREH100; 7511 Eastgate Rd, Henderson, NV 89011 USA), and Swanson® (S) (Catalog No. 478; P.O. Box 2803. Fargo, ND 58108-2803 USA).

The spray dry parameters are as follows: inlet temperature: 160° C.; outlet temperature: 65-70° C.; pump speed: 35-40 rpm; pressure drop: 45-50 psi; aspirator set to 100%; and atomization pressure of 50 psi.

Samples were evaluated at T0 and after incubation for two weeks at 54° C. Peptide concentration was quantified via HPLC analysis as described herein.

TABLE 12

| | | | | | | | | | | Theor. |
|---|---|---|---|---|---|---|---|---|---|---|
| Formula No. | $H_2O$ | LC (mL) | Trehalose | Mfg. | $K_2HPO_4$ | $KH_2PO_4$ | Lignosulfonate | BIT | pH | Peptide % |
| 18 | 150.0 | 50.0 | 68.2 | S | 7.20 | 1.00 | 0.00 | − | 7.2 | 1.88 |
| 19 | 150.0 | 50.0 | 68.2 | B | 7.20 | 1.00 | 0.0 | − | 7.2 | 1.88 |
| 20 | 100.0 | 100.0 | 68.2 | S | 7.20 | 1.00 | 0.00 | − | 7.2 | 3.46 |
| 21 | 100.0 | 100.0 | 68.2 | B | 7.20 | 1.00 | 0.0 | − | 7.2 | 3.46 |
| 22 | 50.0 | 150.0 | 68.2 | B | 7.20 | 1.00 | 0.00 | − | 7.2 | 4.82 |
| 23 | 25.0 | 175.0 | 68.2 | B | 17.00 | 1.00 | 0.0 | − | 7.8 | 4.94 |
| 24 | 150.0 | 50.0 | 68.2 | B | 0.00 | 0.00 | 0.00 | − | 5.2 | 2.06 |
| 25 | 100.0 | 100.0 | 68.2 | B | 7.20 | 1.00 | 0.00 | + | 7.2 | 5.02 |
| 26 | 100.0 | 100.0 | 68.2 | S | 7.20 | 1.00 | 0.00 | + | 7.2 | 5.02 |
| 27 | 100 | 100 | 68.2 | B | 7.20 | 1.00 | 0.00 | + | 7.2 | 5.02 |
| 28 | 100.0 | 100.0 | 68.2 | B | 0.00 | 0.00 | 5.00 | + | 5.2 | 5.42 |

Stability Formulations Part II.

This table shows the formulations used to evaluate: (1) whether trehalose from different manufacturers impacted the stability; (2) the amount of peptide that could be stabilized with a set amount of trehalose; and (3) whether $KH_2PO_4$ was necessary for stabilization. Amounts are shown in grams unless otherwise indicated.

"LC" means liquid concentrate, and is a concentrate of cell separated fermentation beer of cells expressing TVP-R9Q/T43A.

"Mfg" means manufacturer, and refers to the manufacturer of trehalose: B = Bulk Supplements; S = Swanson.

"Theor. Peptide" means theoretical peptide percentage.

The amount of BIT was 0.03% wt/wt and its presence or absence in a formulation is indicated by a "+" or "−", respectively.

15-17) provide stability; however, using trehalose and phosphates showed improved stability (Formulas No. 11-13). FIG. 22.

Example 16: Stability Panel Part II

An additional set of tests were performed to determine the following: (1) whether trehalose from different manufacturers impacted the stability; (2) the amount of peptide that could be stabilized with a set amount of trehalose; (3) whether $KH_2PO_4$ was necessary for stabilization; and (4) whether lignosulfonate would prevent physical stability issues; and (5) the effect of BIT.

In this example, each formulation was created according the descriptions provided in the table below; here, the components were combined, thoroughly mixed and/or dissolved, then spray dried. Ingredients tested include the following: TVP-R9Q/T43A in the form of liquid concentrate (LC), i.e., a concentrate of cell-separated fermentation beer; $H_2O$ (reverse osmosis); maltodextrin (MALTRIN®; Grain Processing Corporation, Catalog No. M100; 1600 Oregon Street Muscatine, Iowa 52761-1494, USA); trehalose; maltose; $K_2HPO_4$ (dipotassium phosphate, anhydrous; ICL Food Specialties; CAS No. 7758-11-4; 622 Emerson Road, Suite 500, St. Louis, MO 63141 USA); $KH_2PO_4$ (mono potassium phosphate; ICL Specialty Fertilizers; CAS No. 7778-77-0; 2755 W 5th N St N, Summerville, SC 29483); and BIT (Lonza; PROXEL® AQ Preservative; 9.25% aqueous solution of 1,2-benzisothiazolin-3-one; Lonza Group Ltd. Muenchensteinerstrasse 38, CH-4002 Basel, Switzerland); and Lignosulfonate (Borregaard LignoTech; Vanisperse CB; CAS No. 8061-51-6; Borregaard AS, P.O BOX 162, NO-1701 Sarpsborg, Norway).

Figure 23:
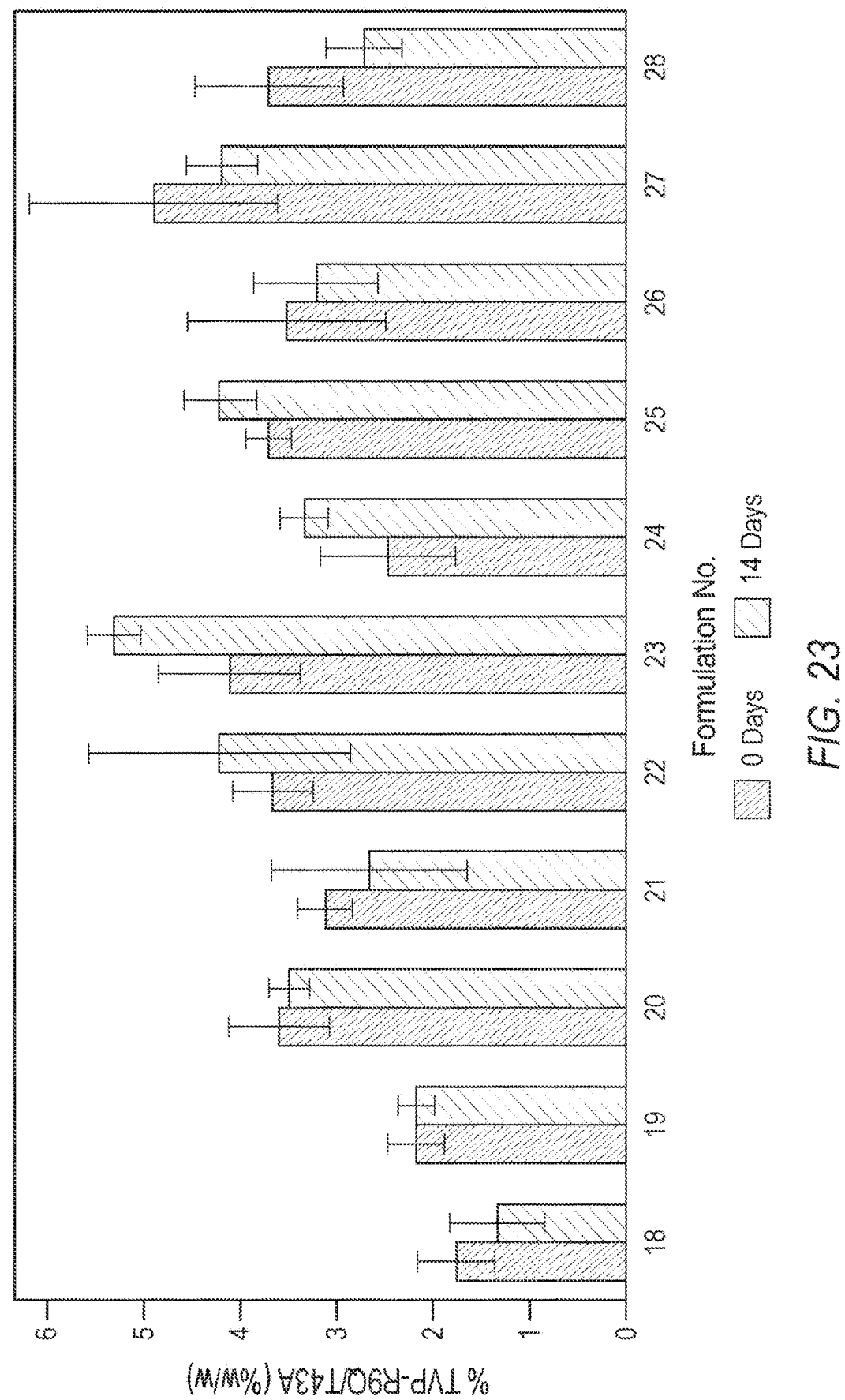
FIG. 23 shows the results of Stability Panel Part II, which includes Formulations Nos. 18-28. Ingredients tested include the following: TVP-R9Q/T43A in the form of liquid concentrate (LC), i.e., a concentrate of cell-separated fermentation beer; $H_2O$ (reverse osmosis); maltodextrin; trehalose; maltose; $K_2HPO_4$; $KH_2PO_4$; BIT (9.25% aqueous solution of 1,2-benzisothiazolin-3-one); and lignosulfonate. Samples were evaluated at T0 and after incubation for two weeks at 54° C. Peptide concentration was quantified via HPLC analysis as described herein.

Trehalose obtained from different manufacturers did not impact the stability of TVP-R9Q/T43A (see, e.g., Formulations Nos. 20, 21, 26, 27). FIG. 23.

The amount of peptide that could be stabilized was increased from 2% (see formulations in previous example) to about 5% (see Formulation Nos. 25-28). FIG. 23.

Figure 24:
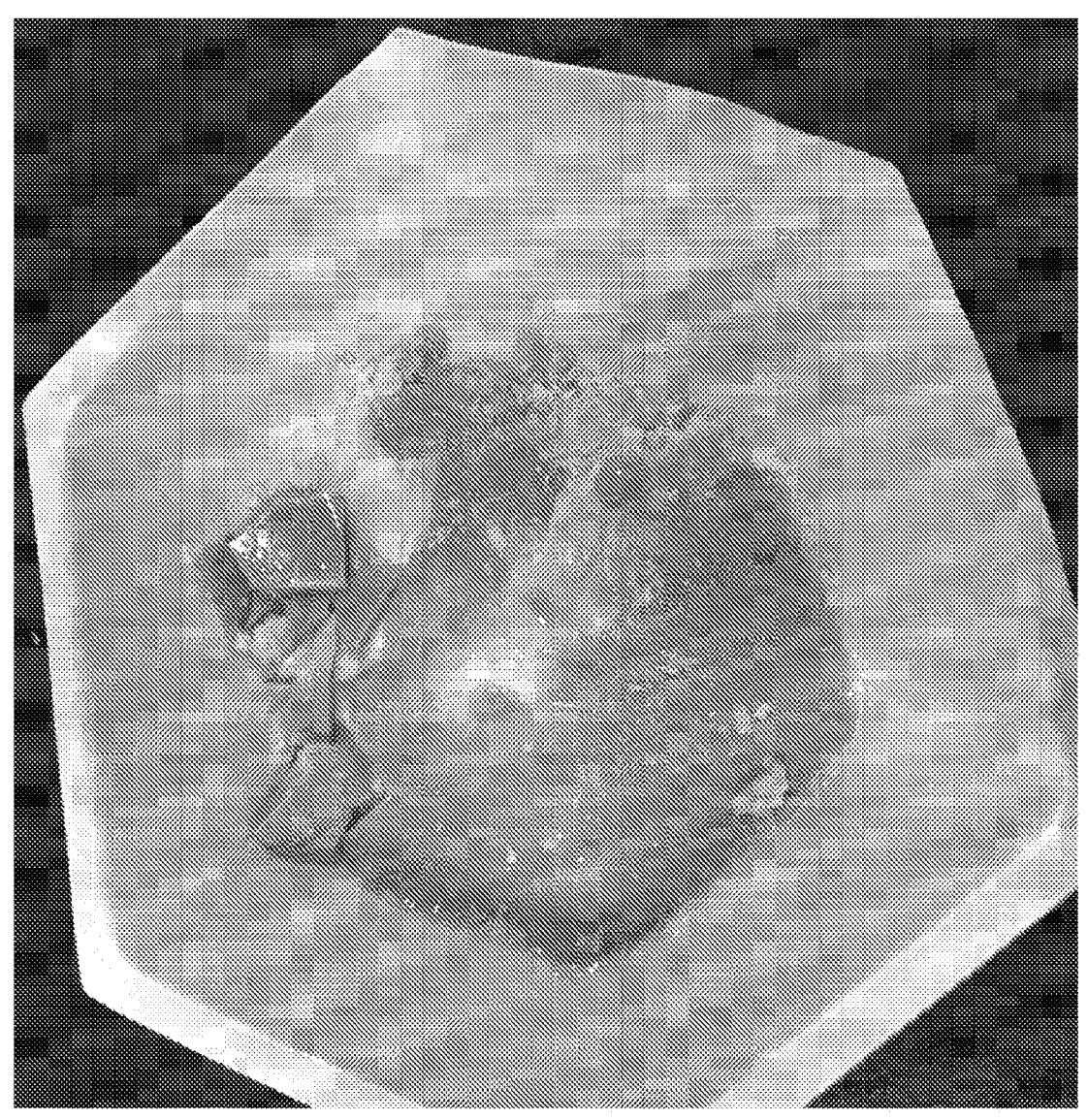
FIG. 24 shows a photo demonstrating the brittle solid agglomeration that formed during storage at 54° C. after 2 weeks.

Here, whether $KH_2PO_4$ was necessary for stabilization was inconclusive. The last row in the table above shows the only formulation having lignosulfonate (Formulation No. 28). Lignosulfonate was added due to an unexpected physical stability issue that occurred: during storage at 54° C., Formulation Nos. 18-27 had a physical form that changed from a light powder into a brittle solid agglomeration. FIG. 24.

Figure 25:
FIG. 25 shows a photo demonstrating the physical form that resulted after the addition of lignosulfonate. As shown here, while the addition of lignosulfonate did prevent the formation of a brittle solid, it nevertheless did not prevent clumping after incubation at 54° C. for 2 weeks.

Lignosulfonate was added to Formulation No. 28 in order to prevent this agglomeration, thereby keeping the formulations in a dry flowable powder form. While the addition of lignosulfonate did prevent the formation of a brittle solid, it nevertheless did not prevent clumping. FIG. 25.

Finally, as demonstrated by Formulation Nos. 8-11, the addition of BIT did not have an effect on the stability of TVP-R9Q/T43A.

Some samples revealed an apparent increase in peptide; this result is likely an artifact resulting from unexpected physical stability issues that occurred. FIG. 23. As mentioned above, storage at 54° C. resulted in a change in the physical form from a light powder into a brittle solid agglomeration. Consequently, the agglomeration of the powder made accurate measurements difficult, and the apparent increase in peptide (e.g., Formula No. 22) can be attributed to problems in acquiring a representative sample.

Example 17: Stability Panel Part III

Based on the information gleaned from Examples 15 and 16, additional spray dry experiments were performed: here, the intent was to stabilize the peptide while also maintaining physical stability (i.e., a dry flowable powder form).

Formulations were prepared using ingredients according to the table below, and evaluated using HPLC as described herein. Components were combined, thoroughly mixed and/or dissolved, and then spray dried. Ingredients tested include the following: TVP-R9Q/T43A in the form of liquid concentrate (LC), i.e., a concentrate of cell-separated fermentation beer; H₂O (reverse osmosis); trehalose; lignosulfate (Borregaard LignoTech; Vanisperse CB; CAS No. 8061-51-6; Borregaard AS, P.O BOX 162, NO-1701 Sarpsborg, Norway); maltodextrin (MALTRIN®; Grain Processing Corporation, Catalog No. M100; 1600 Oregon Street Muscatine, Iowa 52761-1494, USA); K₂HPO₄ (dipotassium phosphate, anhydrous; ICL Food Specialties; CAS No. 7758-11-4; 622 Emerson Road, Suite 500, St. Louis, MO 63141 USA); KH₂PO₄ (mono potassium phosphate; ICL Specialty Fertilizers; CAS No. 7778-77-0; 2755 W 5th N St N, Summerville, SC 29483); and BIT (Lonza; PROXEL® AQ Preservative; 9.25% aqueous solution of 1,2-benzisothiazolin-3-one; Lonza Group Ltd. Muenchensteinerstrasse 38, CH-4002 Basel, Switzerland). Trehalose manufacturers tested were Swanson® (S) (Catalog No. 478; P.O. Box 2803. Fargo, ND 58108-2803 USA); and Nagase America LLC. (N) (TREHA®; non-reducing disaccharide consisting of two glucose molecules bound in an α,α-1,1 linkage; 546 5th Avenue, Floor 19, New York, NY 10036-5000 USA).

The spray dry parameters are as follows: inlet temperature: 160° C.; outlet temperature: 65-70° C.; pump speed: 35-40 rpm; pressure drop: 45-50 psi; aspirator set to 100%; and atomization pressure of 50 psi.

Samples were evaluated at T0 and after incubation for two weeks at 54° C. Peptide concentration was quantified via HPLC analysis as described herein.

The equation for calculation theoretical peptide concentration is as follows:

$$\text{Peptide Concentration } (\% \, wt/wt) = \frac{\text{Peptide weight (g)}}{\text{Dry solids weight (g)}} \times 100 \qquad \text{(Formula IV)}$$

Figure 26:
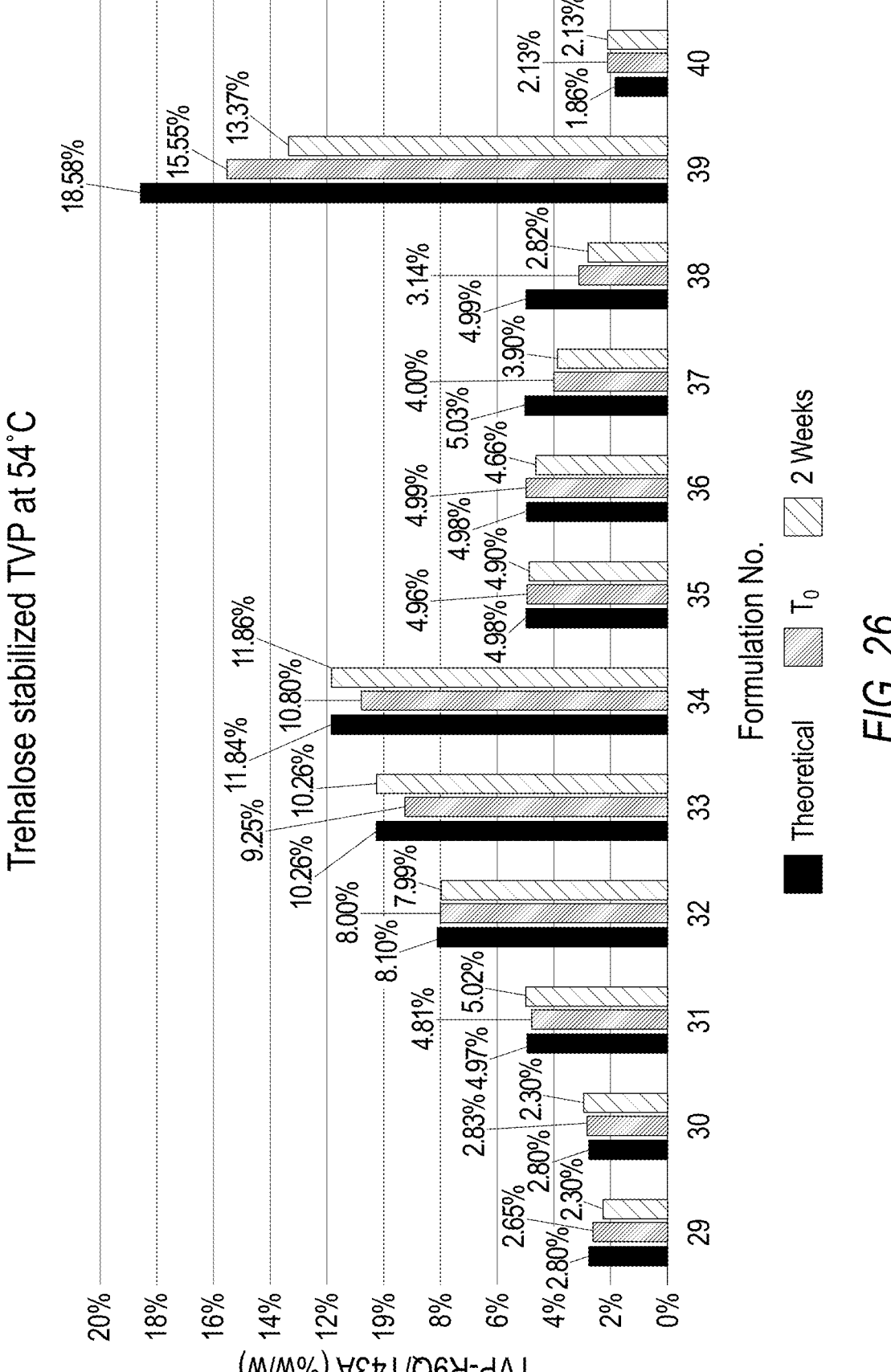
FIG. 26 shows the results of Stability Panel Part III, which includes Formulations Nos. 18-28. Ingredients tested include the following: TVP-R9Q/T43A in the form of liquid concentrate (LC), i.e., a concentrate of cell-separated fermentation beer; $H_2O$ (reverse osmosis); trehalose; lignosulfate; maltodextrin; $K_2HPO_4$; $KH_2PO_4$; and BIT (9.25% aqueous solution of 1,2-benzisothiazolin-3-one). Here, the bar graph shows the theoretical peptide concentration based on the composition design described in the table above (black bar). The actual percentage of peptide at T0 is shown in the grey bar. The actual percentage of peptide after two weeks incubation at 54° C. for 2 weeks shown in the hatched bar.

As shown in FIG. 26, the bar graph shows the theoretical peptide concentration based on the composition design described in the table above (black bar). The actual percentage of peptide at T0 is shown in the grey bar. The actual percentage of peptide after two weeks incubation at 54° C. is shown in the hatched bar. FIG. 26.

Figure 27:
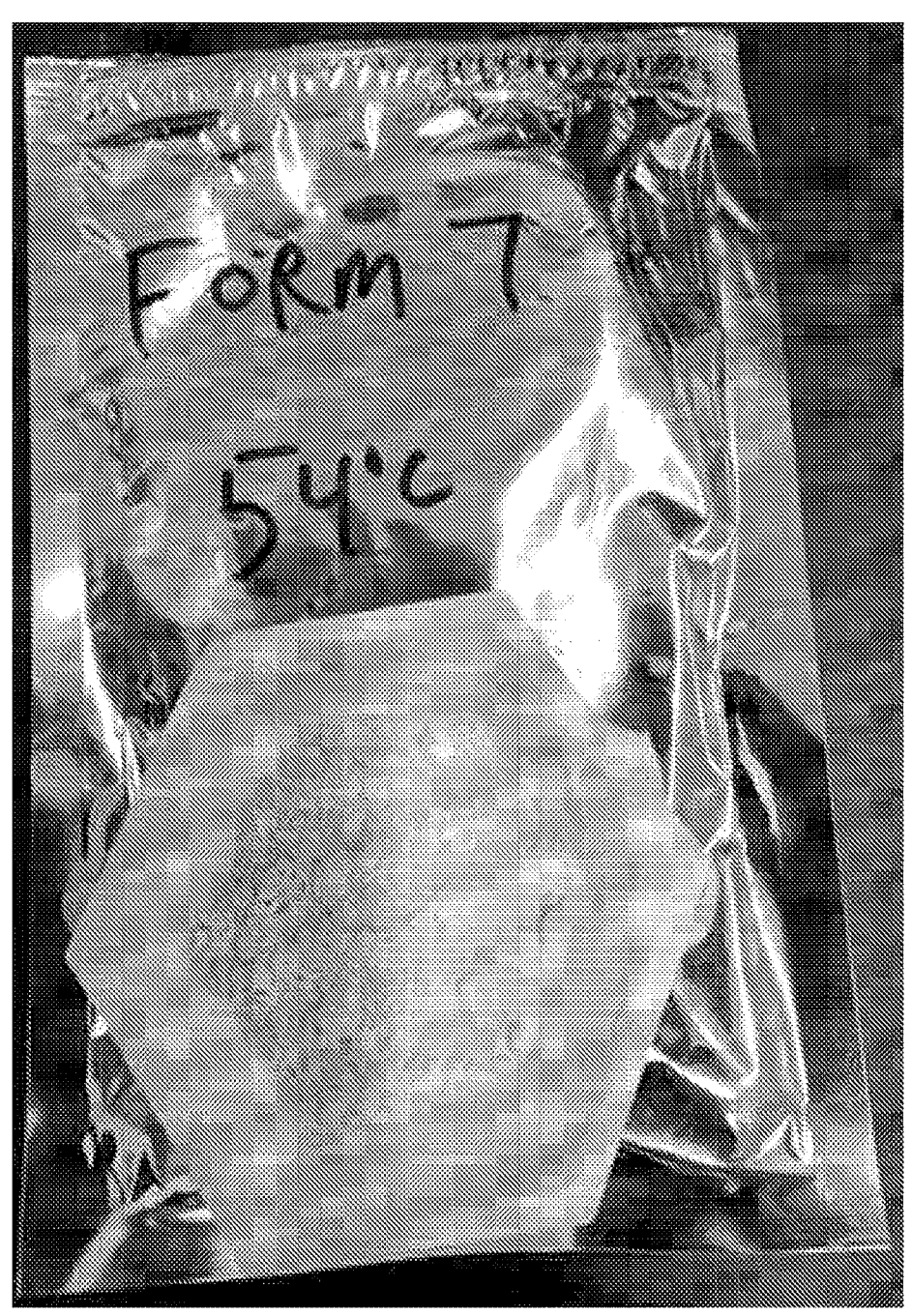
FIG. 27 shows a photo demonstrating the physical form of Formulation No. 35 (in a tray resting on a bag marked "Form 7"). As shown here, Formulation No. 35 was able to maintain a dry flowable powder form after incubation at 54° C. for 2 weeks.
Figure 28:
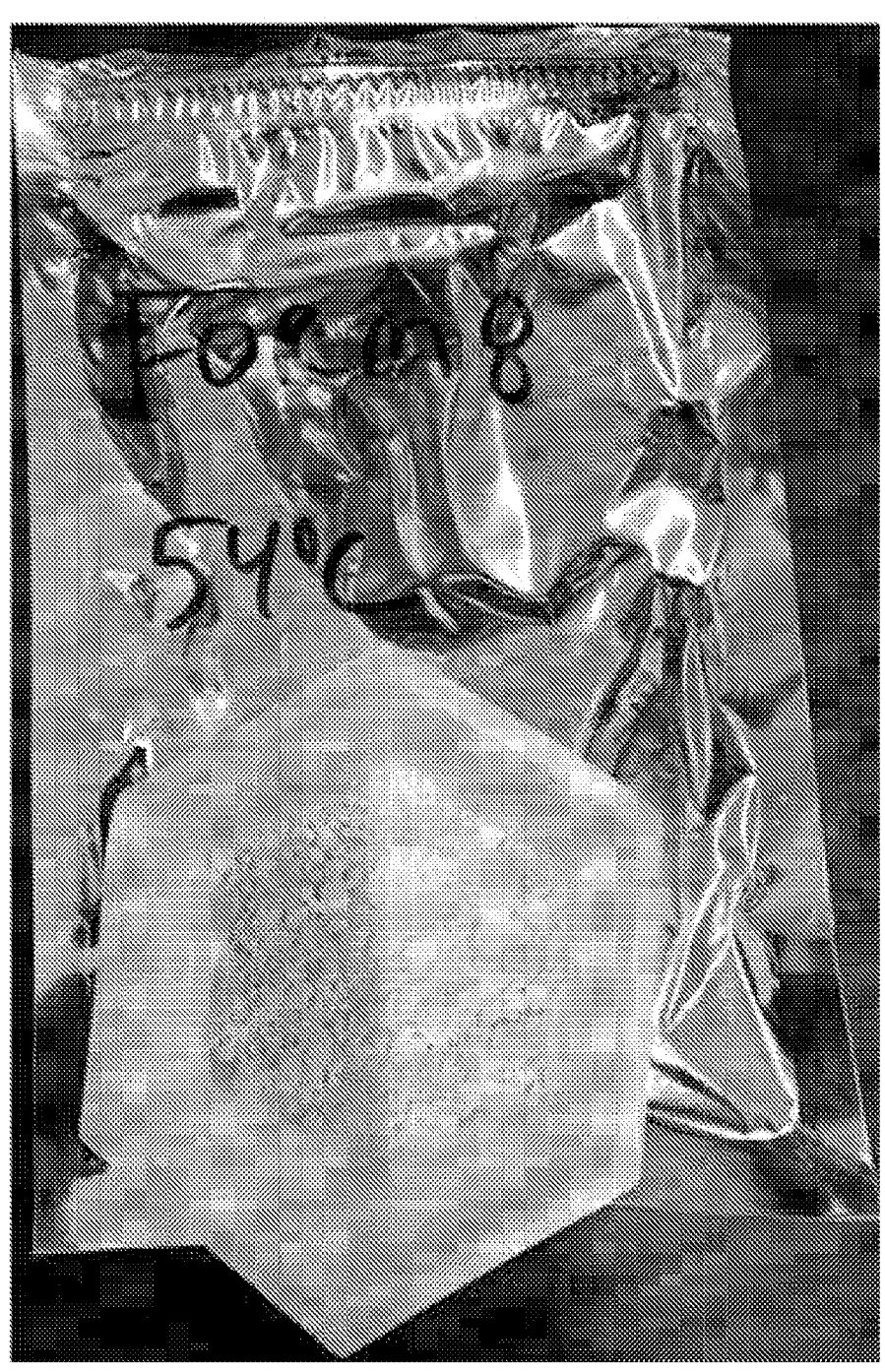
FIG. 28 shows a photo demonstrating the physical form of Formulation No. 36 (in a tray resting on a bag marked "Form 8"). As shown here, Formulation No. 36 was able to maintain a dry flowable powder form after incubation at 54° C. for 2 weeks.

Here, the addition of lignosulfonate did not prevent physical instability. However, the formulations in this example were able to stabilize peptide and also maintain physical stability in a dry flowable powder form. Formulation Nos. 35 and 36 showed good peptide stability and resulted in a dry flowable powder form. FIGS. 27-28.

Formulation Nos. 31-34 showed good peptide stability, however, they nevertheless resulted in clumping and/or agglomeration.

Example 18: Dry and Granular Formulations

Designing a Dry Formulation

Four prototype formulations were generated on pilot scale using fluid bed dryers with the purpose of creating a granular product that conferred stability to the unstable TVP active ingredient.

The prototype formulations were created with varying amounts of trehalose being added to liquid concentrate (LC) containing TVP-R9Q/T43A prior to drying.

The trial setup appears in the table below. All ingredient except maltodextrin were added prior to the fluid bed process. During the fluid bed drying process, the formulated liquid was sprayed onto a fluidized bed of maltodextrin to create the granule. Ingredients used are the same as those described in the examples above.

TABLE 14

Prototype formulations. "LC" means liquid concentrate. "LC DS" means liquid concentrate dissolved solids.

| Trial No. | LC Peptide (g/L) | LC DS (g/kg) | LC (mL) | Trehalose (g) | Malto-dextrin (g) | K₂HPO₄ (g) | KH2PO₄ (g) |
|---|---|---|---|---|---|---|---|
| 1 | 58 | 226 | 4000 | 697.2 | 1000 | 73.4 | 9.96 |
| 2 | 58 | 226 | 1000 | 300 | 100 | 29 | 4 |

TABLE 13

Stability Formulations Part III.

| Formula No. | H₂O | LC (mL) | Trehalose | Mfg. | Lignosulfonate | M100 | K₂HPO₄ | KH₂PO₄ | BIT | pH | Theor. Peptide % |
|---|---|---|---|---|---|---|---|---|---|---|---|
| 29 | 150.0 | 50.0 | 68.2 | S | 0.0 | 0.0 | 7.20 | 1.00 | + | 7.2 | 2.8 |
| 30 | 150.0 | 50.0 | 68.2 | N | 0.0 | 0.0 | 7.20 | 1.00 | + | 7.2 | 2.8 |
| 31 | 100.0 | 100.0 | 68.2 | N | 0.0 | 0.0 | 7.20 | 1.00 | + | 7.2 | 5.0 |
| 32 | 50.0 | 200.0 | 68.2 | N | 0.0 | 0.0 | 7.20 | 1.00 | + | 7.2 | 8.1 |
| 33 | 0.0 | 300.0 | 68.2 | N | 0.0 | 0.0 | 7.20 | 1.00 | + | 7.2 | 10.3 |
| 34 | 0.0 | 200.0 | 34.1 | N | 0.0 | 0.0 | 3.60 | 0.50 | + | 7.2 | 11.8 |
| 35 | 155.0 | 145.0 | 68.2 | N | 0.0 | 34.1 | 7.20 | 1.00 | + | 7.2 | 5.0 |
| 36 | 110.0 | 190.0 | 68.2 | N | 0.0 | 68.2 | 7.20 | 1.00 | + | 7.2 | 5.0 |
| 37 | 110.0 | 115.0 | 68.2 | N | 10.0 | 0.0 | 7.20 | 1.00 | + | 7.2 | 5.0 |
| 38 | 110 | 127 | 68.2 | N | 20.0 | 0.0 | 7.20 | 1.00 | + | 7.2 | 5.0 |
| 39 | 0.0 | 200.0 | 0 | N | 0.0 | 0.0 | 7.20 | 1.00 | + | 7.2 | 18.6 |
| 40 | 150 | 50 | 68.2 | S | 0.0 | 0.0 | 7.20 | 1.00 | − | 7.2 | 1.9 |

This table shows the formulations used to evaluate a compositions effect on peptide stabilization and physical stability.
Amounts are shown in grams unless otherwise indicated.
"LC" means liquid concentrate, and is a concentrate of cell separated fermentation beer of cells expressing TVP-R9Q/T43A.
"Mfg" means manufacturer, and refers to the manufacturer of trehalose: S = Swanson; N = Nagase.
"M100" refers to maltodextrin.
"Theor. Peptide" means theoretical peptide percentage.

TABLE 14-continued

Prototype formulations. "LC" means liquid concentrate. "LC DS" means liquid concentrate dissolved solids.

| Trial No. | LC Peptide (g/L) | LC DS (g/kg) | LC (mL) | Trehalose (g) | Malto-dextrin (g) | $K_2HPO_4$ (g) | KH2PO4 (g) |
|---|---|---|---|---|---|---|---|
| 3 | 58 | 226 | 1000 | 200 | 100 | 29 | 4 |
| 4 | 58 | 226 | 1000 | 100 | 100 | 29 | 4 |

The theoretical end % w/w for the prototypes subsequent to the fluid bed drying process are presented in the table below. The percent of TVP-R9Q/T43A active ingredient (% AI) is considered to be in the liquid concentrate dissolved solids (% LC DS).

TABLE 15

Theoretical end % w/w for prototype formulations. "% AI" refers to percent active ingredient (TVP-R9Q/T43A). "LC DS" means liquid concentrate dissolved solids. Amounts are shown in % w/w.

| Trial No. | % AI | % LC DS | % Trehalose | % Maltodextrin | % $K_2HPO_4$ | % $KH_2PO_4$ | % BIT |
|---|---|---|---|---|---|---|---|
| 1 | 8.42 | 35.37 | 25.29 | 36.27 | 2.66 | 0.36 | 0.05 |
| 2 | 8.57 | 36.00 | 44.31 | 14.77 | 4.28 | 0.59 | 0.05 |
| 3 | 10.05 | 42.24 | 34.66 | 17.33 | 5.03 | 0.69 | 0.06 |
| 4 | 12.16 | 51.09 | 20.96 | 20.96 | 6.08 | 0.84 | 0.07 |

Figure 29:
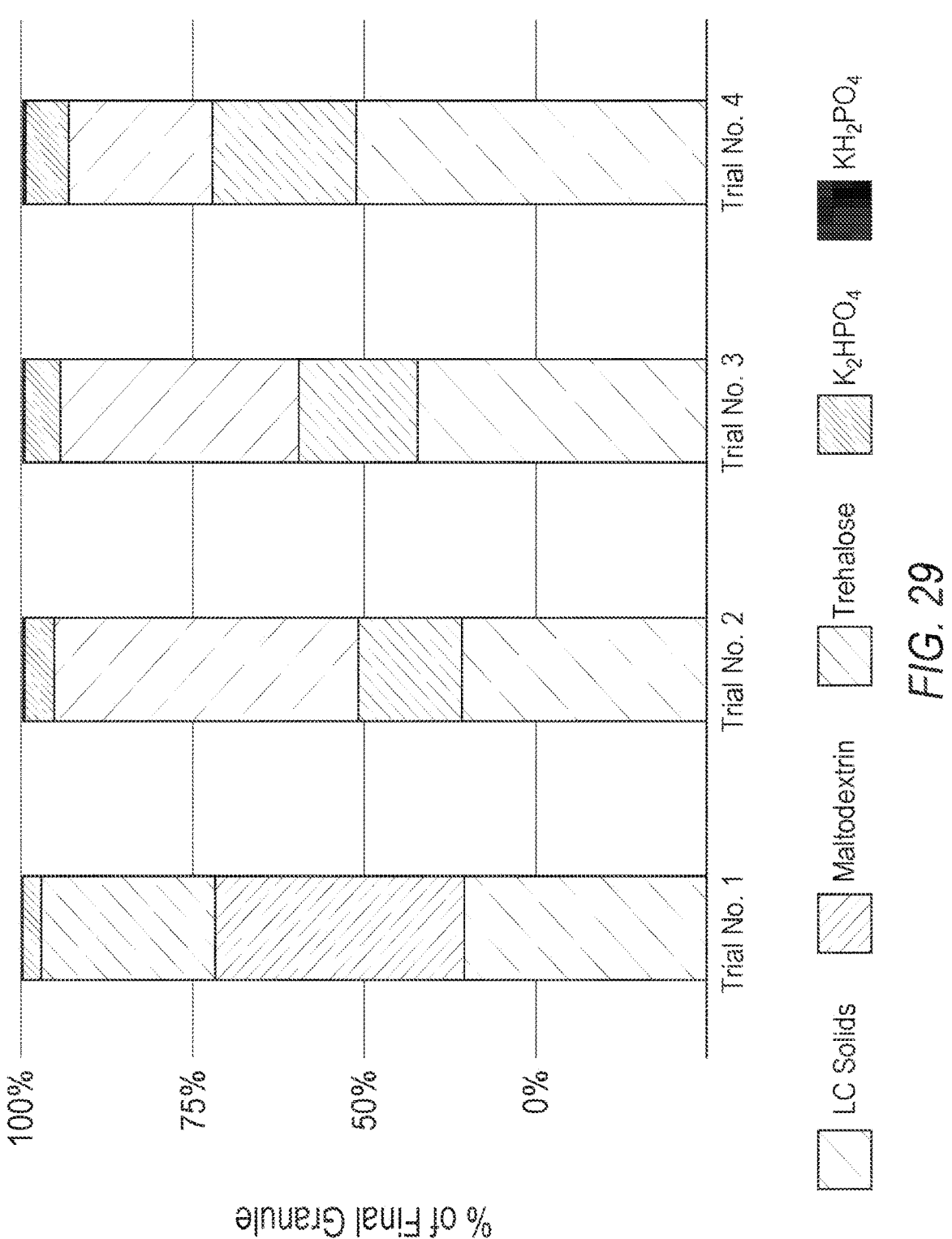
FIG. 29 depicts a summary of the theoretical formulations (average values) of the four, dry granular prototype formulations.

Theoretical formulations (average values) of the four prototypes are presented in FIG. 29, based on the data presented in the table below.

TABLE 16

Theoretical formulation data. "R" means replicate, and refers to a replication of the assay for peptide measurement (i.e., not technical replicates). "Avg." means average. T0 means Time zero. T2w means time at two weeks. Std. Dev. means standard deviation.

| Trial No. | T0 TVP (% wt/wt) | Avg. T0 (% wt/wt) | Std Dev. | T2w TVP (% wt/wt) | Avg. T2w (% wt/wt) | Std. Dev. of T2w Samples | Expected TVP % wt/wt at T0 |
|---|---|---|---|---|---|---|---|
| Trial No. 1 R1 | 7.99 | 8.22 | 0.23 | 8.24 | 8.15 | 0.06 | 8.64% |
| Trial No. 1 R2 | 8.13 | | | 8.10 | | | |
| Trial No. 1 R3 | 8.53 | | | 8.12 | | | |
| Trial No. 2 R1 | 7.92 | 7.85 | 0.09 | 8.43 | 8.39 | 0.04 | 8.80% |
| Trial No. 2 R2 | 7.72 | | | 8.39 | | | |
| Trial No. 2 R3 | 7.92 | | | 8.33 | | | |
| Trial No. 3 R1 | 9.94 | 9.52 | 0.30 | 9.80 | 9.62 | 0.15 | 10.32% |
| Trial No. 3 R2 | 9.38 | | | 9.44 | | | |
| Trial No. 3 R3 | 9.24 | | | 9.61 | | | |
| Trial No. 4 R1 | 10.85 | 11.01 | 0.22 | 11.05 | 10.99 | 0.05 | 12.64% |
| Trial No. 4 R2 | 11.31 | | | 10.93 | | | |
| Trial No. 4 R3 | 10.86 | | | 10.99 | | | |

The four prototypes were evaluated for high temperature stability via incubation at 54° C. for two weeks, in the presence of an oxygen/moisture scavenger packet (Mitsubishi Gas Chemical America, Inc., Product No. AS-100; 655 3rd Ave #24, New York, NY 10017 USA). Measurement of the TVP-R9Q/T43A peptide was performed using HPLC-UV at t=0 (after formulation and drying) and t=14 days.

Figure 30:
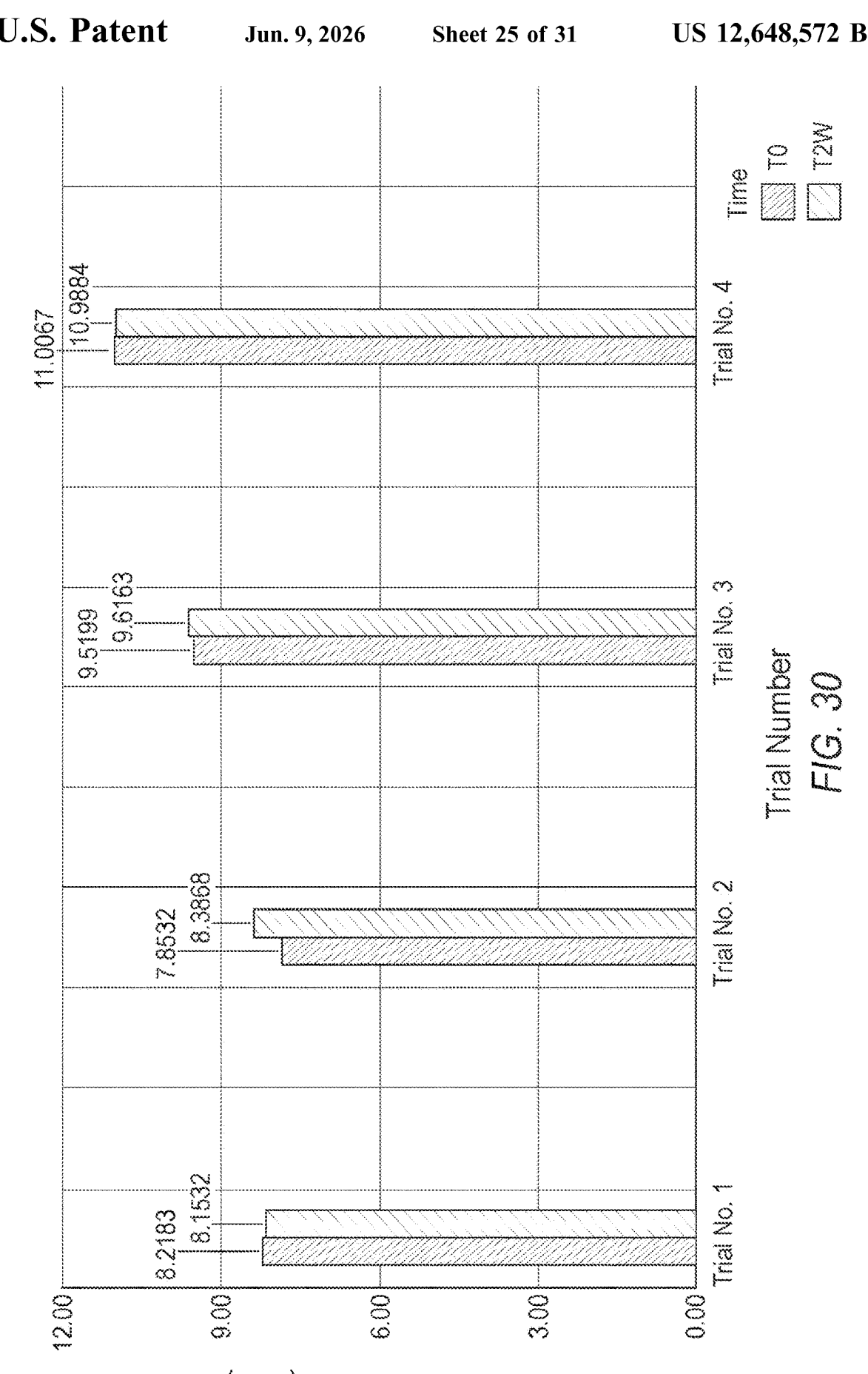
FIG. 30 depicts the results of a stability assay testing the four prototype trials, Trial Nos. 1-4. The four prototypes were evaluated for high temperature stability via incubation at 54° C. for two weeks, in the presence of an oxygen/moisture scavenger packet. Measurement of the TVP-R9Q/T43A peptide was performed using HPLC-UV at T0 (after formulation and drying) and T2W (time after 2 weeks).
Figure 31:
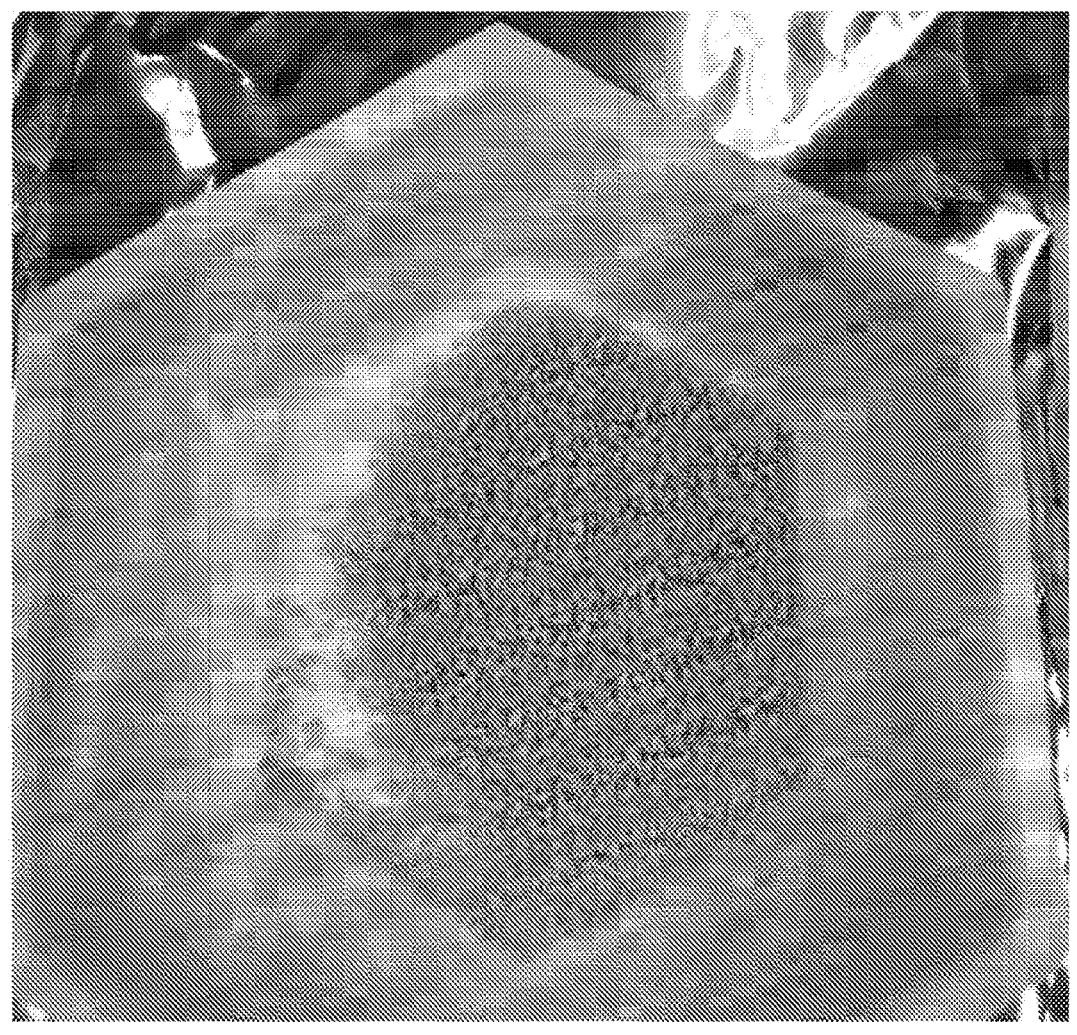
FIG. 31 shows a photo demonstrating the physical form that resulted from Trial No. 1, after incubation at 54° C. for 2 weeks Here, the physical form is a dry flowable granular form.
Figure 32:
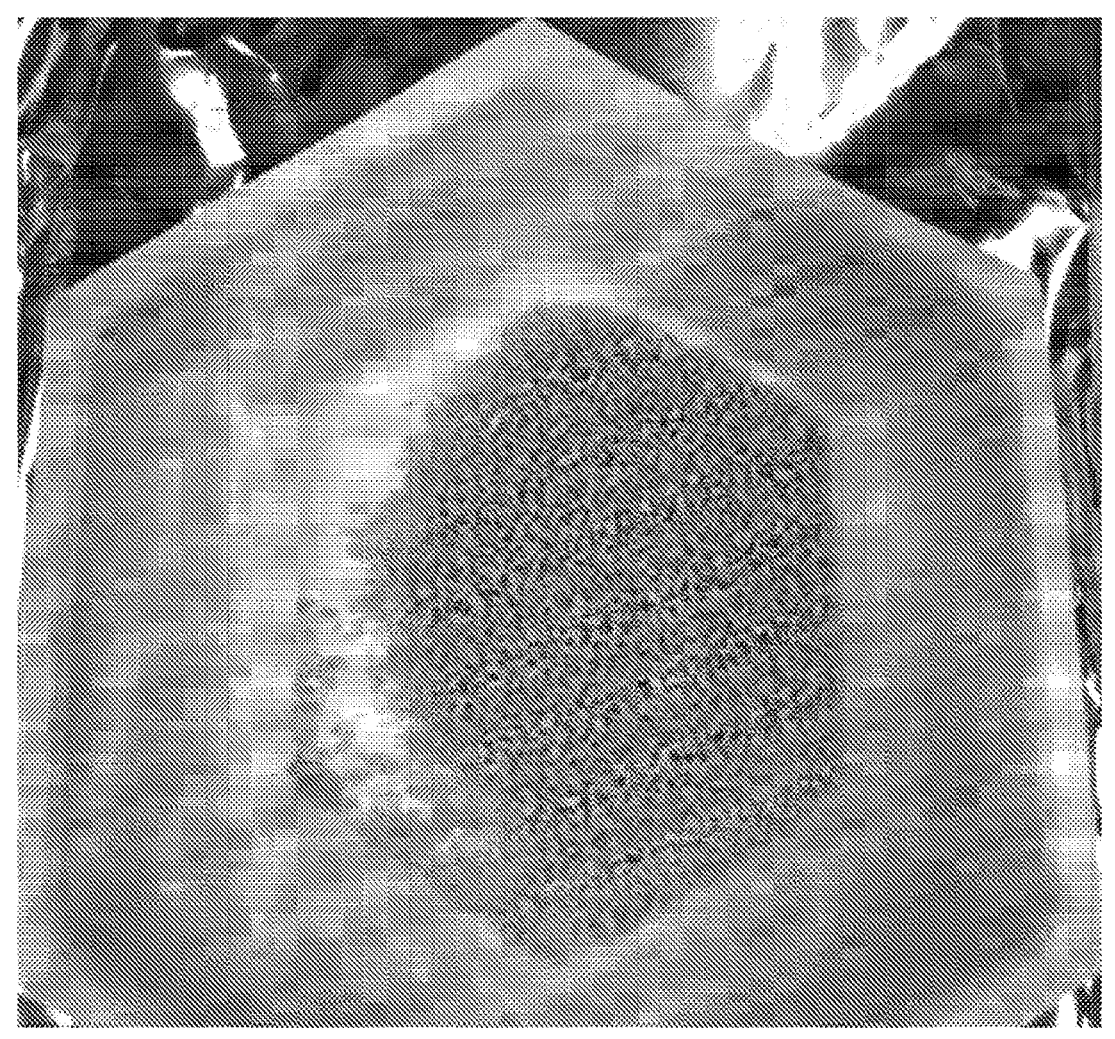
FIG. 32 shows a photo demonstrating the physical form that resulted from Trial No. 2, after incubation at 54° C. for 2 weeks Here, the physical form is a dry flowable granular form.
Figure 33:
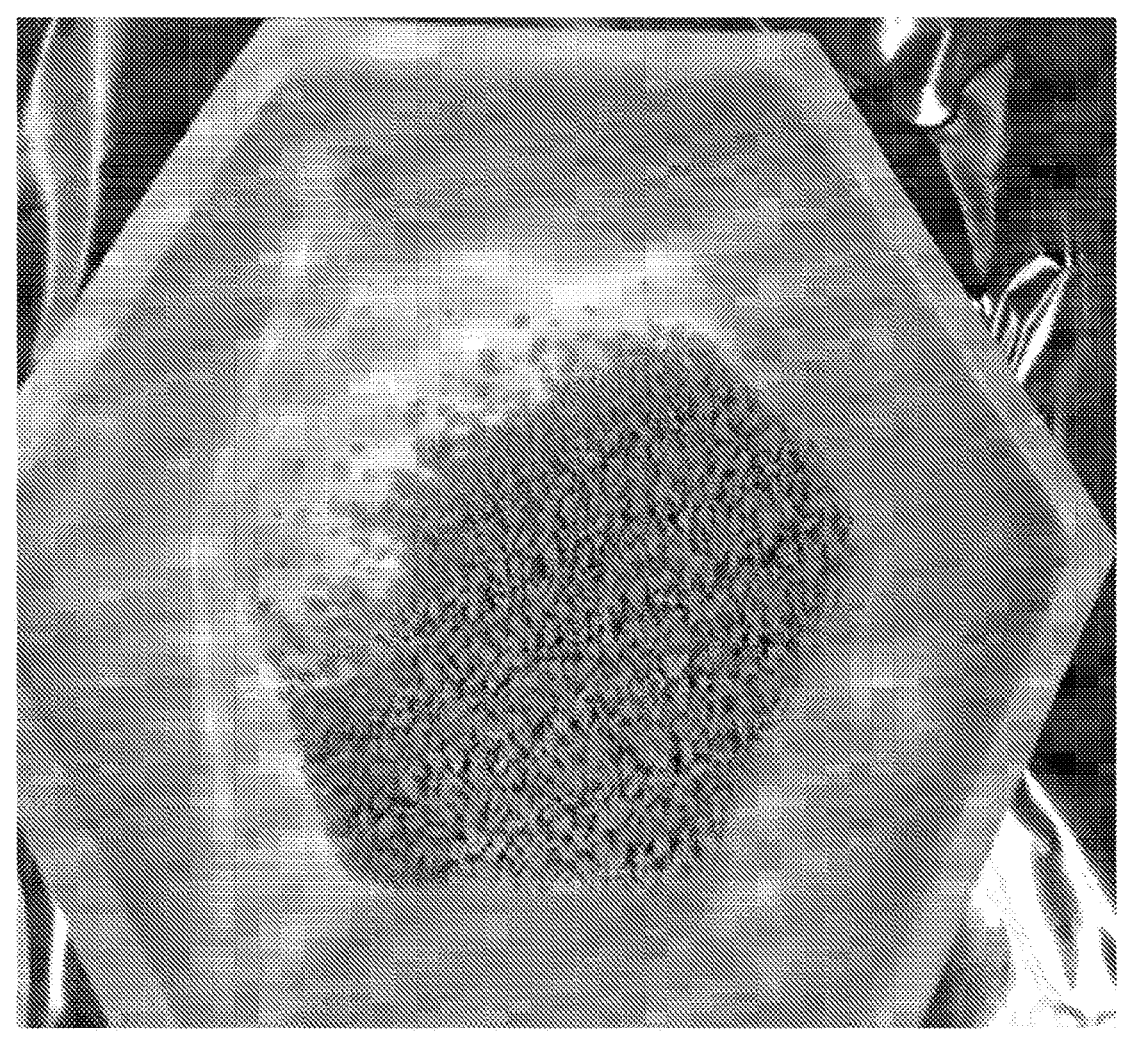
FIG. 33 shows a photo demonstrating the physical form that resulted from Trial No. 3, after incubation at 54° C. for 2 weeks Here, the physical form is a dry flowable granular form.
Figure 34:
FIG. 34 shows a photo demonstrating the physical form that resulted from Trial No. 1, after incubation at 54° C. for 2 weeks Here, the physical form is a dry flowable granular form.

As shown in FIG. 30, all four prototypes were stable after incubation for two weeks at 54° C.

A subsequent formulation process was developed based on the foregoing set of experiments. The formulation process measures the liquid concentrate, dissolved solids (LC DS) in the fermentation, i.e., downstream process, and adds trehalose to an appropriate ratio to confer stability to the unstable TVP-R9Q/T43A peptide following drying.

The tested ratio ranges evaluated was about 0.81 to about 2.44 LC DS per trehalose (0.81-2.44 LC DS:Trehalose) and is presented in the table below.

TABLE 17

Ratio ranges of TVP to Trehalose. "LC DS" means liquid concentrate, dissolved solids. Matrix DS refers to the dissolved solids remaining from the fermentation/downstream processing steps upstream of formulation.

| Trial No. | Trehalose (g) | Calculated LC DS (g) | Matrix DS:Trehalose |
|---|---|---|---|
| 1 | 697 | 975 | 1.40 |
| 2 | 300 | 244 | 0.81 |
| 3 | 200 | 244 | 1.22 |
| 4 | 100 | 244 | 2.44 |

The foregoing trials were also physically stable, insofar that they were in a dry flowable granular form. The results of the physical form for Trial Nos. 1, 2, 3, and 4, are shown in FIGS. 31-34.

Example 19: Circular Dichroism (CD) Assay of Trehalose Stabilization

Circular Dichroism (CD) is an absorption spectroscopy method. CD employs the differential absorption of left and right circularly polarized light. The spectrum obtained due to this phenomenon is called CD spectrum in which the CD signal is represented in terms of millidegrees (mdeg).

An optically active chiral molecule will absorb one direction of the circularly polarized light in a preferential manner; and, the difference in this absorption—i.e., of the left or right circularly polarized light—can be measured and quantified. Ultraviolet (UV) CD can be used to determine aspects of protein secondary structures, e.g., alpha-helix, beta-sheet, random coil, etc. For example, one of the most widely used applications of CD is to evaluate whether a protein is folded correctly, and/or whether a given mutation affects that protein's stability or conformation. See N. Greenfield, Using circular dichroism spectra to estimate protein secondary structure, Nat Protoc. 2006; 1(6): 2876-2890.

To further evaluate the effect that trehalose has on the stabilization of TVPs, and the biophysical characteristics thereof, a composition containing minimal and highly pure components were investigated using CD. Here, the composition comprised 10% trehalose and 0.5 ppt (0.05% w/v) TVP-R9Q/T43A. Other than trehalose and Ta1b, the only other component is the 10 mM sodium phosphate buffer. CD spectra were recorded on a Jasco J-1500 spectrometer (JASCO Inc., 28600 Mary's Court, Easton, MD 21601 USA). TVP-R9Q/T43A was diluted into 10 mM sodium phosphate, pH 7.0, at 0.5 mg/mL in a 0.1 cm quartz cuvette. Spectra were recorded at 0.1 nm intervals at a scan rate of 100 nm min$^{-1}$ at 20° C. Fixed wavelength melting curves were generated for every 1° C. with a temperature ramp of 10° C. min$^{-1}$. Melt curves were fit to a Boltzmann sigmoid to determine the melting point ($T_m$).

Figure 35:
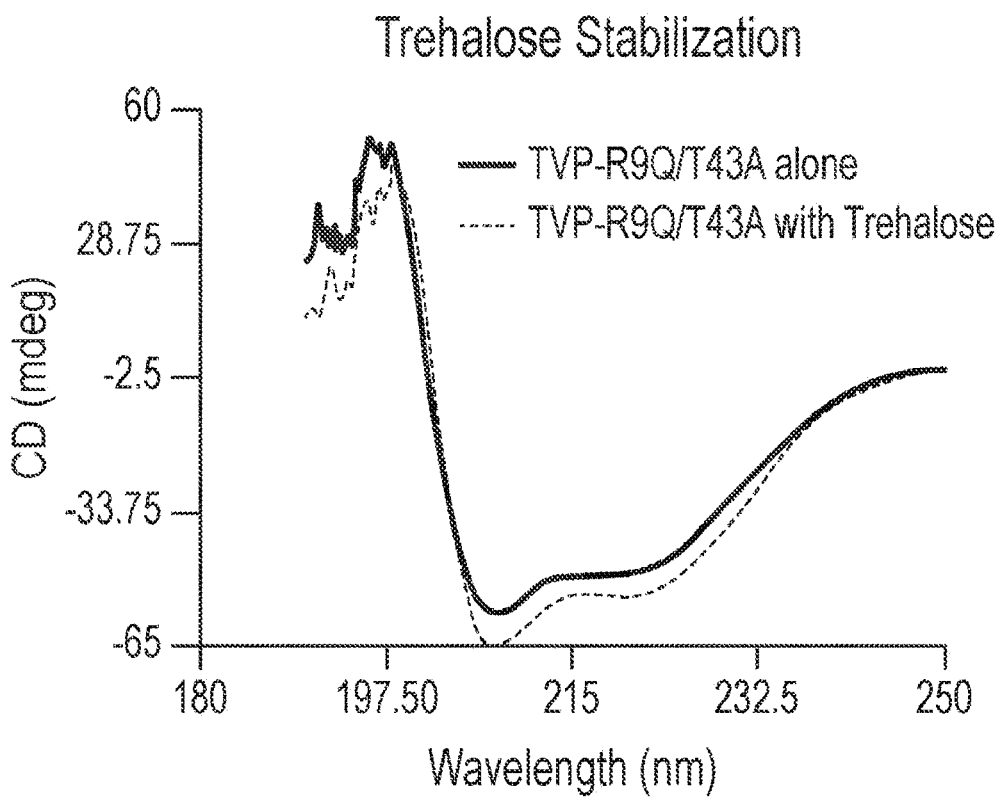
FIG. 35 shows the results of Circular Dichroism (CD) assay. Addition of 10% trehalose stabilizes the tertiary structure of TVP-R9Q/T43A as indicated by the deepening CD spectra at 214 nm and 220 nm that shows the peptide has become more alpha helical, consistent with its 3D structure.
Figure 36:
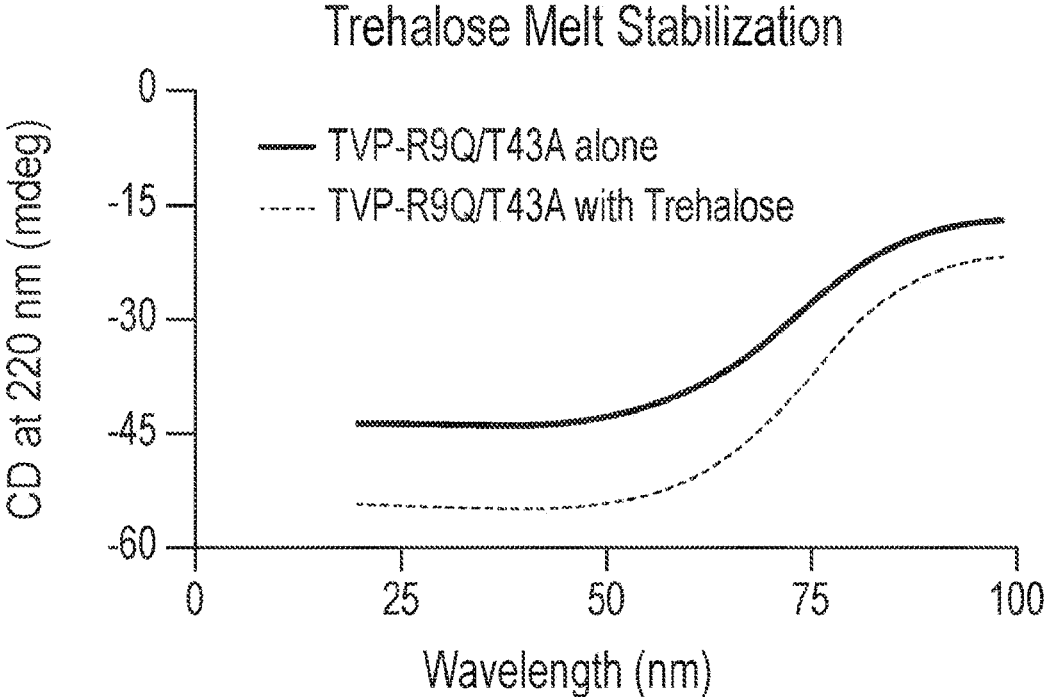
FIG. 36 shows the results of Circular Dichroism (CD) assay evaluating melt characteristics. Here addition of 10% trehalose increases the melting point of TVP-R9Q/T43A from 71.6° C. to 73.6° C. supporting its increased stability in the presence of trehalose.

Addition of 10% trehalose stabilizes the secondary structure of TVP-R9Q/T43A as indicated by the deepening CD spectra at 214 nm and 220 nm that shows the peptide has become more alpha helical, consistent with its 3D structure. FIG. 35. Further, addition of 10% trehalose increases the melting point of TVP-R9Q/T43A from 71.6° C. to 73.6° C. supporting its increased stability in the presence of trehalose. FIG. 36.

Example 20: Summary of the Stable Formulation

The table below provides a summary of the components used to create a stable formulation of TVP.

TABLE 18

Illustrative formulation. The % w/w amounts described below are a summary of an illustrative formulation based on the results obtained from the Example section.

| Component | % w/w |
|---|---|
| TVP | 8.50% |
| 1,2-Benzisothiazolin-3-one | 0.05% |
| Maltodextrin (M100) | 36.30% |
| Trehalose | 25.30% |
| Potassium Phosphate Dibasic Anhydrous (K$_2$HPO$_4$) | 2.60% |
| Potassium Phosphate Monobasic (KH$_2$PO$_4$) | 0.40% |
| Fermentation solid | 26.85% |

Example 21: Position Scan and Gut Environment Assay

TVPs were exposed to lepidopteran gut proteases in order to determine their stability in a simulated lepidopteran gut environment.

Generation of the TVP Expression Vector

A DNA construct of various TVPs were codon optimized and synthesized as a fusion with *Kluyveromyces lactis* alpha mating factor pre/pro sequence (αMF) and ligated into the NotI and HindIII restriction sites of pKlac1 (New England Biolabs®). The vector was digested with SacII to linearize and remove the bacterial Ori and selection marker, then electroporated into electrocompetent *Kluyveromyces lactis* cells. Multiple gene copy transformants were selected on selection plates containing acetamide as the sole nitrogen source. Clones expressing TVPs were assessed by HPLC on a Chromolith C18 column (4.6×25 mm) and eluted at a flow rate of 2 mL min$^{-1}$ and gradient of 10-30% acetonitrile over 2 min.

Digestion of TVPs

To determine the stability of TVPs when exposed to lepidopteran gut proteases, early fifth instar *Helicoverpa zea* larvae were dissected to remove the intact digestive tract from other tissues and hemolymph. To obtain the *Helicoverpa* gut extract (HGE), a small incision was made to the intestinal lining such that gut contents could be collected in a tube. Multiple dissections were pooled and kept on ice for immediate use, or stored at −80° C. for future use.

Wild-type Ta1b (SEQ ID NO: 1) was used as a template, and mutated at amino acid substitution at position 9, (i.e., R9; SEQ ID NO: 1) to produce the TVPs evaluated here; these TVPs have a substitution of the arginine at position 9 (i.e., R9) of the wild-type amino acid sequence (SEQ ID NO: 1), with one of the amino acids F, P, Y, K, W, H, A, G, N, L, D, V, M, I, Q, C, E, T, and S; in addition, a TVP with an R9Q+T43A mutation (relative to wild-type Ta1b) was likewise evaluated (SEQ ID NO: 85). Each TVP tested here, and its amino acid substitution(s), are shown in Table 19.

The TVPs described above and shown in Table 19 were confronted with *Helicoverpa* gut extract (HGE) to simulate digestion in the lepidopteran gut environment. Here, the TVPs were incubated with 6× diluted amount of HGE obtained from *Helicoverpa* deep well cell growths. The 6× diluted UGE was supplemented with 30 mM Tris-HCl, pH 8.8, to maintain the alkaline pH of the *Helicoverpa* gut environment.

Samples of the digested TVPs were collected at time points of 0, 3, and 22.5 hours. To quench the digestion process, 30 mM Glycine, pH 2.0 was added to the samples, and the samples of the digested TVPs were immediately analyzed using reverse-phase HPLC to quantify the TVP peak area. As shown in Table 19, When WT Ta1b is incubated with the 6× diluted UGE, it is completely digested between 3 and 22.5 hours, with a half-life of 1.9 hours.

As shown in Table 19 below, substituting R9 with the amino acids A, G, N, L, D, V, M, I, Q+T43A, Q, C, E, T, or S (as illustrated in SEQ ID NOs: 77-90), completely abolished UGE digestion. In contrast, substituting R9 with the amino acids F, P, Y, K, W, or H (as illustrated in SEQ ID NOs: 71-76) did not provide a substantial increase in stability relative to the stability observed in wild type Ta1b.

TABLE 19

Complete Amino Acid scan digestion analysis.

| Amino Acid (Position 9) | Half-Life (hours) | SEQ ID NO. | Sequence | Result |
|---|---|---|---|---|
| R (WT) | 1.9 | 1 | EPDEICRARMTNKEFT YKSNVCNNCGDQVAAC EAECFRNDVYTACHEA QKG | NA |
| F | 2.0 | 71 | EPDEICRAFMTNKEFT YKSNVCNNCGDQVAAC EAECFRNDVYTACHEA QKG | Unstable |
| P | 2.1 | 72 | EPDEICRAPMTNKEFT YKSNVCNNCGDQVAAC EAECFRNDVYTACHEA QKG | |
| Y | 4.4 | 73 | EPDEICRAYMTNKEFT YKSNVCNNCGDQVAAC EAECFRNDVYTACHEA QKG | |
| K | 6.3 | 74 | EPDEICRAKMTNKEFT YKSNVCNNCGDQVAAC EAECFRNDVYTACHEA QKG | |

TABLE 19-continued

Complete Amino Acid scan digestion analysis.

| Amino Acid (Position 9) | Half-Life (hours) | SEQ ID NO. | Sequence | Result |
|---|---|---|---|---|
| W | 9.1 | 75 | EPDEICRAWMTNKEFT YKSNVCNNCGDQVAAC EAECFRNDVYTACHEA QKG | |
| H | 9.6 | 76 | EPDEICRAHMTNKEFT YKSNVCNNCGDQVAAC EAECFRNDVYTACHEA QKG | |
| A | 10.7 | 77 | EPDEICRAAMTNKEFT YKSNVCNNCGDQVAAC EAECFRNDVYTACHEA QKG | Stable |
| G | 12.7 | 78 | EPDEICRAGMTNKEFT YKSNVCNNCGDQVAAC EAECFRNDVYTACHEA QKG | |
| N | 13.8 | 79 | EPDEICRANMTNKEFT YKSNVCNNCGDQVAAC EAECFRNDVYTACHEA QKG | |
| L | 17.5 | 80 | EPDEICRALMTNKEFT YKSNVCNNCGDQVAAC EAECFRNDVYTACHEA QKG | |
| D | 22.6 | 81 | EPDEICRADMTNKEFT YKSNVCNNCGDQVAAC EAECFRNDVYTACHEA QKG | |
| V | 23.6 | 82 | EPDEICRAVMTNKEFT YKSNVCNNCGDQVAAC EAECFRNDVYTACHEA QKG | |
| M | 26.4 | 83 | EPDEICRAMMTNKEFT YKSNVCNNCGDQVAAC EAECFRNDVYTACHEA QKG | |
| I | 31.8 | 84 | EPDEICRAIMTNKEFT YKSNVCNNCGDQVAAC EAECFRNDVYTACHEA QKG | |
| Q + T43A | 36.8 | 85 | EPDEICRAQMTNKEFT YKSNVCNNCGDQVAAC EAECFRNDVYAACHEA QKG | |
| Q | 42.2 | 86 | EPDEICRAQMTNKEFT YKSNVCNNCGDQVAAC EAECFRNDVYTACHEA QKG | |
| C | 63.4 | 87 | EPDEICRACMTNKEFT YKSNVCNNCGDQVAAC EAECFRNDVYTACHEA QKG | |
| E | 67.9 | 88 | EPDEICRAEMTNKEFT YKSNVCNNCGDQVAAC EAECFRNDVYTACHEA QKG | |
| T | 95.8 | 89 | EPDEICRATMTNKEFT YKSNVCNNCGDQVAAC EAECFRNDVYTACHEA QKG | |
| S | 139.4 | 90 | EPDEICRASMTNKEFT YKSNVCNNCGDQVAAC EAECFRNDVYTACHEA QKG | |

Example 22: Removal of a Glycosylation Site

Generation of the TVP Expression Vector

A DNA construct of various TVPs were codon optimized and synthesized as a fusion with *Kluyveromyces lactis* alpha mating factor pre/pro sequence (αMF) and ligated into the NotI and HindIII restriction sites of pKlac1 (New England Biolabs). The vector was digested with SacII to linearize and remove the bacterial Ori and selection marker, then electroporated into electrocompetent *Kluyveromyces lactis* cells. Multiple gene copy transformants were selected on selection plates containing acetamide as the sole nitrogen source. Clones expressing TVPs were assessed by HPLC on a Chromolith C18 column (4.6×25 mm) and eluted at a flow rate of 2 mL min-1 and gradient of 10-30% acetonitrile over 2 min. TVPs were assessed for glycosylation (+162 to MW) by LC-MS on a Chromolith C18 column (4.6×100 mm) and eluted at a flow rate of 1 mL min$^{-1}$ and analyzed via mass spectrometry as described in the examples above.

As shown in Table 20, of the amino acids substituted at position 43, only Threonine (T) and Serine (S) (SEQ ID NOs. 108 and 109) produced glycosylation species while the other 18 different amino acids (SEQ ID NOs: 91-107, and 110) did not produce any glycosylated species.

TABLE 20

Results of glycosylation site removal.

| Amino Acid (Position 43) | Glycosylation (Y/N) | SEQ ID NO. | Sequence |
|---|---|---|---|
| F | No | 91 | EPDEICRARMTNKEFTYK SNVCNNCGDQVAACEAEC FRNDVYFACHEAQKG |
| P | No | 92 | EPDEICRARMTNKEFTYK SNVCNNCGDQVAACEAEC FRNDVYPACHEAQKG |
| Y | No | 93 | EPDEICRARMTNKEFTYK SNVCNNCGDQVAACEAEC FRNDVYYACHEAQKG |
| K | No | 94 | EPDEICRARMTNKEFTYK SNVCNNCGDQVAACEAEC FRNDVYKACHEAQKG |
| W | No | 95 | EPDEICRARMTNKEFTYK SNVCNNCGDQVAACEAEC FRNDVYWACHEAQKG |
| H | No | 96 | EPDEICRARMTNKEFTYK SNVCNNCGDQVAACEAEC FRNDVYHACHEAQKG |
| A | No | 97 | EPDEICRARMTNKEFTYK SNVCNNCGDQVAACEAEC FRNDVYAACHEAQKG |
| G | No | 98 | EPDEICRARMTNKEFTYK SNVCNNCGDQVAACEAEC FRNDVYGACHEAQKG |
| N | No | 99 | EPDEICRARMTNKEFTYK SNVCNNCGDQVAACEAEC FRNDVYNACHEAQKG |
| L | No | 100 | EPDEICRARMTNKEFTYK SNVCNNCGDQVAACEAEC FRNDVYLACHEAQKG |
| D | Not Tested | 101 | EPDEICRARMTNKEFTYK SNVCNNCGDQVAACEAEC FRNDVYDACHEAQKG |
| V | No | 102 | EPDEICRARMTNKEFTYK SNVCNNCGDQVAACEAEC FRNDVYVACHEAQKG |

TABLE 20-continued

Results of glycosylation site removal.

| Amino Acid (Position 43) | Glycosylation (Y/N) | SEQ ID NO. | Sequence |
|---|---|---|---|
| M | No | 103 | EPDEICRARMTNKEFTYK SNVCNNCGDQVAACEAEC FRNDVYMACHEAQKG |
| I | No | 104 | EPDEICRARMTNKEFTYK SNVCNNCGDQVAACEAEC FRNDVYIACHEAQKG |
| Q | No | 105 | EPDEICRARMTNKEFTYK SNVCNNCGDQVAACEAEC FRNDVYQACHEAQKG |
| C | No | 106 | EPDEICRARMTNKEFTYK SNVCNNCGDQVAACEAEC FRNDVYCACHEAQKG |

TABLE 20-continued

Results of glycosylation site removal.

| Amino Acid (Position 43) | Glycosylation (Y/N) | SEQ ID NO. | Sequence |
|---|---|---|---|
| E | No | 107 | EPDEICRARMTNKEFTYK SNVCNNCGDQVAACEAEC FRNDVYEACHEAQKG |
| T (WT) | Yes | 108 | EPDEICRARMTNKEFTYK SNVCNNCGDQVAACEAEC FRNDVYTACHEAQKG |
| S | Yes | 109 | EPDEICRARMTNKEFTYK SNVCNNCGDQVAACEAEC FRNDVYSACHEAQKG |
| R | No | 110 | EPDEICRARMTNKEFTYK SNVCNNCGDQVAACEAEC FRNDVYRACHEAQKG |

The invention claimed is:

1. A pesticidal U1-agatoxin-Ta1b variant polypeptide (TVP) comprising the amino acid sequence set forth in any one of SEQ ID NO: 2, 49, or 51; or an agriculturally acceptable salt thereof.

2. A pesticidal U1-agatoxin-Ta1b variant polypeptide (TVP) consisting of the amino acid sequence set forth in any one of SEQ ID NO: 2, 49, or 51; or an agriculturally acceptable salt thereof.

3. A pesticidal U1-agatoxin-Ta1b variant polypeptide (TVP) comprising the amino acid sequence set forth in SEQ ID NO: 51, or an agriculturally acceptable salt thereof.

4. A pesticidal U1-agatoxin-Ta1b variant polypeptide (TVP) consisting of the amino acid sequence set forth in SEQ ID NO: 51, or an agriculturally acceptable salt thereof.

5. A pesticidal U1-agatoxin-Ta1b variant polypeptide (TVP) comprising the amino acid sequence set forth in SEQ ID NO: 2, or an agriculturally acceptable salt thereof.

6. A pesticidal U1-agatoxin-Ta1b variant polypeptide (TVP) consisting of the amino acid sequence set forth in SEQ ID NO: 2, or an agriculturally acceptable salt thereof.

7. A pesticidal U1-agatoxin-Ta1b variant polypeptide (TVP) comprising the amino acid sequence set forth in SEQ ID NO: 49, or an agriculturally acceptable salt thereof.

8. A pesticidal U1-agatoxin-Ta1b variant polypeptide (TVP) consisting of the amino acid sequence set forth in SEQ ID NO: 49, or an agriculturally acceptable salt thereof.

9. A composition comprising a pesticidal U1-agatoxin-Ta1b variant polypeptide (TVP) and at least one excipient; wherein the TVP comprises the amino acid sequence set forth in any one of SEQ ID NO: 2, 49, or 51, or an agriculturally acceptable salt thereof.

10. A kit comprising: (1) a pesticidal U1-agatoxin-Ta1b variant polypeptide (TVP) comprising the amino acid sequence set forth in any one of SEQ ID NO: 2, 49, or 51, or an agriculturally acceptable salt thereof; and (2) at least one excipient.

\* \* \* \* \*

SEQUENCE LISTING

<160> NUMBER OF SEQ ID NOS: 152

<210> SEQ ID NO 1
<211> LENGTH: 51
<212> TYPE: PRT
<213> ORGANISM: Eratigena agrestis

<400> SEQUENCE: 1

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 2
<211> LENGTH: 51
<212> TYPE: PRT
<213> ORGANISM: Artificial sequence
<220> FEATURE:
<223> OTHER INFORMATION: TVP-R9Q

<400> SEQUENCE: 2

Glu Pro Asp Glu Ile Cys Arg Ala Gln Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 3
<211> LENGTH: 50
<212> TYPE: PRT
<213> ORGANISM: Artificial sequence
<220> FEATURE:
<223> OTHER INFORMATION: TVP-R9QdG

<400> SEQUENCE: 3

-continued

```
Glu Pro Asp Glu Ile Cys Arg Ala Gln Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys
    50

<210> SEQ ID NO 4
<211> LENGTH: 51
<212> TYPE: PRT
<213> ORGANISM: Artificial sequence
<220> FEATURE:
<223> OTHER INFORMATION: TVP-K18A

<400> SEQUENCE: 4

Glu Pro Asp Glu Ile Cys Arg Ala Arg Met Thr Asn Lys Glu Phe Thr
1               5                   10                  15

Tyr Ala Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 5
<211> LENGTH: 50
<212> TYPE: PRT
<213> ORGANISM: Artificial sequence
<220> FEATURE:
<223> OTHER INFORMATION: TVP-K18AdG

<400> SEQUENCE: 5

Glu Pro Asp Glu Ile Cys Arg Ala Arg Met Thr Asn Lys Glu Phe Thr
1               5                   10                  15

Tyr Ala Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys
    50

<210> SEQ ID NO 6
<211> LENGTH: 51
<212> TYPE: PRT
<213> ORGANISM: Artificial sequence
<220> FEATURE:
<223> OTHER INFORMATION: TVP-R38A

<400> SEQUENCE: 6

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Ala Asn Asp Val Tyr Thr Ala Cys His Glu Ala
        35                  40                  45

Gln Lys Gly
    50
```

-continued

```
<210> SEQ ID NO 7
<211> LENGTH: 50
<212> TYPE: PRT
<213> ORGANISM: Artificial sequence
<220> FEATURE:
<223> OTHER INFORMATION: TVP-R38AdG

<400> SEQUENCE: 7

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Ala Asn Asp Val Tyr Thr Ala Cys His Glu Ala
        35                  40                  45

Gln Lys
    50

<210> SEQ ID NO 8
<211> LENGTH: 51
<212> TYPE: PRT
<213> ORGANISM: Artificial sequence
<220> FEATURE:
<223> OTHER INFORMATION: TVP-A8N

<400> SEQUENCE: 8

Glu Pro Asp Glu Ile Cys Arg Asn Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 9
<211> LENGTH: 50
<212> TYPE: PRT
<213> ORGANISM: Artificial sequence
<220> FEATURE:
<223> OTHER INFORMATION: TVP-A8NdG

<400> SEQUENCE: 9

Glu Pro Asp Glu Ile Cys Arg Asn Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys
    50

<210> SEQ ID NO 10
<211> LENGTH: 51
<212> TYPE: PRT
<213> ORGANISM: Artificial sequence
<220> FEATURE:
<223> OTHER INFORMATION: TVP-A8S

<400> SEQUENCE: 10

Glu Pro Asp Glu Ile Cys Arg Ser Arg Met Thr Asn Lys Glu Phe Thr
1               5                   10                  15
```

```
Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50
```

```
<210> SEQ ID NO 11
<211> LENGTH: 50
<212> TYPE: PRT
<213> ORGANISM: Artificial sequence
<220> FEATURE:
<223> OTHER INFORMATION: TVP-A8SdG

<400> SEQUENCE: 11

Glu Pro Asp Glu Ile Cys Arg Ser Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys
    50
```

```
<210> SEQ ID NO 12
<211> LENGTH: 51
<212> TYPE: PRT
<213> ORGANISM: Artificial sequence
<220> FEATURE:
<223> OTHER INFORMATION: TVP-R9N

<400> SEQUENCE: 12

Glu Pro Asp Glu Ile Cys Arg Ala Asn Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50
```

```
<210> SEQ ID NO 13
<211> LENGTH: 50
<212> TYPE: PRT
<213> ORGANISM: Artificial sequence
<220> FEATURE:
<223> OTHER INFORMATION: TVP-R9NdG

<400> SEQUENCE: 13

Glu Pro Asp Glu Ile Cys Arg Ala Asn Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys
    50
```

```
<210> SEQ ID NO 14
<211> LENGTH: 51
<212> TYPE: PRT
```

<213> ORGANISM: Artificial sequence
<220> FEATURE:
<223> OTHER INFORMATION: TVP-T11P

<400> SEQUENCE: 14

Glu Pro Asp Glu Ile Cys Arg Ala Arg Met Pro Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 15
<211> LENGTH: 50
<212> TYPE: PRT
<213> ORGANISM: Artificial sequence
<220> FEATURE:
<223> OTHER INFORMATION: TVP-T11PdG

<400> SEQUENCE: 15

Glu Pro Asp Glu Ile Cys Arg Ala Arg Met Pro Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys
    50

<210> SEQ ID NO 16
<211> LENGTH: 153
<212> TYPE: DNA
<213> ORGANISM: Eratigena agrestis

<400> SEQUENCE: 16
gaaccagacg agatatgcag agcaaggatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 17
<211> LENGTH: 153
<212> TYPE: DNA
<213> ORGANISM: Artificial sequence
<220> FEATURE:
<223> OTHER INFORMATION: TVP-R9Q

<400> SEQUENCE: 17
gaaccagacg agatatgcag agcacaaatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 18
<211> LENGTH: 150
<212> TYPE: DNA
<213> ORGANISM: Artificial sequence
<220> FEATURE:
<223> OTHER INFORMATION: TVP-R9QdG

<400> SEQUENCE: 18

-continued

```
gaaccagacg agatatgcag agcacaaatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa                                      150

<210> SEQ ID NO 19
<211> LENGTH: 153
<212> TYPE: DNA
<213> ORGANISM: Artificial sequence
<220> FEATURE:
<223> OTHER INFORMATION: TVP-K18A

<400> SEQUENCE: 19
gaaccagacg agatatgcag agcaaggatg accaacaaag aatttaccta tgcttccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 20
<211> LENGTH: 150
<212> TYPE: DNA
<213> ORGANISM: Artificial sequence
<220> FEATURE:
<223> OTHER INFORMATION: TVP-K18AdG

<400> SEQUENCE: 20
gaaccagacg agatatgcag agcaaggatg accaacaaag aatttaccta tgcttccaac      60
gtatgcaata attgtggcga ccaggtggca gcctgcgagg cagagtgctt tcgtaatgac     120
gtttacacag cttgtcacga ggctcagaaa                                      150

<210> SEQ ID NO 21
<211> LENGTH: 153
<212> TYPE: DNA
<213> ORGANISM: Artificial sequence
<220> FEATURE:
<223> OTHER INFORMATION: TVP-R38A

<400> SEQUENCE: 21
gaaccagacg agatatgcag agcaaggatg accaacaaag aatttaccta taagtccaac      60
gtatgcaata attgtggcga ccaggtggca gcctgcgagg cagagtgctt tgctaatgac     120
gtttacacag cttgtcacga ggctcagaaa ggt                                  153

<210> SEQ ID NO 22
<211> LENGTH: 150
<212> TYPE: DNA
<213> ORGANISM: Artificial sequence
<220> FEATURE:
<223> OTHER INFORMATION: TVP-R38AdG

<400> SEQUENCE: 22
gaaccagacg agatatgcag agcaaggatg accaacaaag aatttaccta taagtccaac      60
gtatgcaata attgtggcga ccaggtggca gcctgcgagg cagagtgctt tgctaatgac     120
gtttacacag cttgtcacga ggctcagaaa                                      150

<210> SEQ ID NO 23
<211> LENGTH: 153
<212> TYPE: DNA
<213> ORGANISM: Artificial sequence
<220> FEATURE:
<223> OTHER INFORMATION: TVP-A8N
```

<400> SEQUENCE: 23
gaaccagacg agatatgcag aaacaggatg accaacaaag aatttaccta taagtccaac    60
gtatgcaata attgtggcga ccaggtggca gcctgcgagg cagagtgctt tcgtaatgac   120
gtttacacag cttgtcacga ggctcagaaa ggt                                153

<210> SEQ ID NO 24
<211> LENGTH: 150
<212> TYPE: DNA
<213> ORGANISM: Artificial sequence
<220> FEATURE:
<223> OTHER INFORMATION: TVP-A8NdG

<400> SEQUENCE: 24
gaaccagacg agatatgcag aaacaggatg accaacaaag aatttaccta taagtccaac    60
gtatgcaata attgtggcga ccaggtggca gcctgcgagg cagagtgctt tcgtaatgac   120
gtttacacag cttgtcacga ggctcagaaa                                    150

<210> SEQ ID NO 25
<211> LENGTH: 153
<212> TYPE: DNA
<213> ORGANISM: Artificial sequence
<220> FEATURE:
<223> OTHER INFORMATION: TVP-A8S

<400> SEQUENCE: 25
gaaccagacg agatatgcag atcaaggatg accaacaaag aatttaccta taagtccaac    60
gtatgcaata attgtggcga ccaggtggca gcctgcgagg cagagtgctt tcgtaatgac   120
gtttacacag cttgtcacga ggctcagaaa ggt                                153

<210> SEQ ID NO 26
<211> LENGTH: 150
<212> TYPE: DNA
<213> ORGANISM: Artificial sequence
<220> FEATURE:
<223> OTHER INFORMATION: TVP-A8SdG

<400> SEQUENCE: 26
gaaccagacg agatatgcag atcaaggatg accaacaaag aatttaccta taagtccaac    60
gtatgcaata attgtggcga ccaggtggca gcctgcgagg cagagtgctt tcgtaatgac   120
gtttacacag cttgtcacga ggctcagaaa                                    150

<210> SEQ ID NO 27
<211> LENGTH: 153
<212> TYPE: DNA
<213> ORGANISM: Artificial sequence
<220> FEATURE:
<223> OTHER INFORMATION: TVP-R9N

<400> SEQUENCE: 27
gaaccagacg agatatgcag agcaaacatg accaacaaag aatttaccta taagtccaac    60
gtatgcaata attgtggcga ccaggtggca gcctgcgagg cagagtgctt tcgtaatgac   120
gtttacacag cttgtcacga ggctcagaaa ggt                                153

<210> SEQ ID NO 28
<211> LENGTH: 150
<212> TYPE: DNA
<213> ORGANISM: Artificial sequence
<220> FEATURE:
<223> OTHER INFORMATION: TVP-R9NdG -continued

<400> SEQUENCE: 28

```
gaaccagacg agatatgcag agcaaacatg accaacaaag aatttaccta taagtccaac     60
gtatgcaata attgtggcga ccaggtggca gcctgcgagg cagagtgctt tcgtaatgac    120
gtttacacag cttgtcacga ggctcagaaa                                     150
```

<210> SEQ ID NO 29
<211> LENGTH: 153
<212> TYPE: DNA
<213> ORGANISM: Artificial sequence
<220> FEATURE:
<223> OTHER INFORMATION: TVP-T11P

<400> SEQUENCE: 29

```
gaaccagacg agatatgcag agcaaggatg cctaacaaag aatttaccta taagtccaac     60
gtatgcaata attgtggcga ccaggtggca gcctgcgagg cagagtgctt tcgtaatgac    120
gtttacacag cttgtcacga ggctcagaaa ggt                                 153
```

<210> SEQ ID NO 30
<211> LENGTH: 150
<212> TYPE: DNA
<213> ORGANISM: Artificial sequence
<220> FEATURE:
<223> OTHER INFORMATION: TVP-T11PdG

<400> SEQUENCE: 30

```
gaaccagacg agatatgcag agcaaggatg cctaacaaag aatttaccta taagtccaac     60
gtatgcaata attgtggcga ccaggtggca gcctgcgagg cagagtgctt tcgtaatgac    120
gtttacacag cttgtcacga ggctcagaaa                                     150
```

<210> SEQ ID NO 31
<211> LENGTH: 4
<212> TYPE: PRT
<213> ORGANISM: Artificial sequence
<220> FEATURE:
<223> OTHER INFORMATION: IGER

<400> SEQUENCE: 31

```
Ile Gly Glu Arg
1
```

<210> SEQ ID NO 32
<211> LENGTH: 5
<212> TYPE: PRT
<213> ORGANISM: Artificial sequence
<220> FEATURE:
<223> OTHER INFORMATION: EEKKN

<400> SEQUENCE: 32

```
Glu Glu Lys Lys Asn
1               5
```

<210> SEQ ID NO 33
<211> LENGTH: 8
<212> TYPE: PRT
<213> ORGANISM: Artificial sequence
<220> FEATURE:
<223> OTHER INFORMATION: ETMFKHGL

<400> SEQUENCE: 33

```
Glu Thr Met Phe Lys His Gly Leu
1               5
```

255

256

```
<210> SEQ ID NO 34
<211> LENGTH: 238
<212> TYPE: PRT
<213> ORGANISM: Aequorea victoria

<400> SEQUENCE: 34

Ala Ser Lys Gly Glu Glu Leu Phe Thr Gly Val Val Pro Ile Leu Val
1               5                   10                  15

Glu Leu Asp Gly Asp Val Asn Gly His Lys Phe Ser Val Ser Gly Glu
            20                  25                  30

Gly Glu Gly Asp Ala Thr Tyr Gly Lys Leu Thr Leu Lys Phe Ile Cys
        35                  40                  45

Thr Thr Gly Lys Leu Pro Val Pro Trp Pro Thr Leu Val Thr Thr Phe
    50                  55                  60

Ser Tyr Gly Val Gln Cys Phe Ser Arg Tyr Pro Asp His Met Lys Arg
65                  70                  75                  80

His Asp Phe Phe Lys Ser Ala Met Pro Glu Gly Tyr Val Gln Glu Arg
                85                  90                  95

Thr Ile Ser Phe Lys Asp Asp Gly Asn Tyr Lys Thr Arg Ala Glu Val
            100                 105                 110

Lys Phe Glu Gly Asp Thr Leu Val Asn Arg Ile Glu Leu Lys Gly Ile
        115                 120                 125

Asp Phe Lys Glu Asp Gly Asn Ile Leu Gly His Lys Leu Glu Tyr Asn
    130                 135                 140

Tyr Asn Ser His Asn Val Tyr Ile Thr Ala Asp Lys Gln Lys Asn Gly
145                 150                 155                 160

Ile Lys Ala Asn Phe Lys Ile Arg His Asn Ile Glu Asp Gly Ser Val
                165                 170                 175

Gln Leu Ala Asp His Tyr Gln Gln Asn Thr Pro Ile Gly Asp Gly Pro
            180                 185                 190

Val Leu Leu Pro Asp Asn His Tyr Leu Ser Thr Gln Ser Ala Leu Ser
        195                 200                 205

Lys Asp Pro Asn Glu Lys Arg Asp His Met Val Leu Leu Glu Phe Val
    210                 215                 220

Thr Ala Ala Gly Ile Thr His Gly Met Asp Glu Leu Tyr Lys
225                 230                 235

<210> SEQ ID NO 35
<211> LENGTH: 157
<212> TYPE: PRT
<213> ORGANISM: Galanthus nivalis

<400> SEQUENCE: 35

Met Ala Lys Ala Ser Leu Leu Ile Leu Ala Thr Ile Phe Leu Gly Val
1               5                   10                  15

Ile Thr Pro Ser Cys Leu Ser Glu Asn Ile Leu Tyr Ser Gly Glu Thr
            20                  25                  30

Leu Pro Thr Gly Gly Phe Leu Ser Ser Gly Ser Phe Val Phe Ile Met
        35                  40                  45

Gln Glu Asp Cys Asn Leu Val Leu Tyr Asn Val Asp Lys Pro Ile Trp
    50                  55                  60

Ala Thr Asn Thr Gly Gly Leu Ser Ser Asp Cys Ser Leu Ser Met Gln
65                  70                  75                  80

Asn Asp Gly Asn Leu Val Val Phe Thr Pro Ser Asn Lys Pro Ile Trp
                85                  90                  95
```

Ala Ser Asn Thr Asp Gly Gln Asn Gly Asn Tyr Val Cys Ile Leu Gln
            100                 105                 110

Lys Asp Arg Asn Val Val Ile Tyr Gly Thr Asn Arg Trp Ala Thr Gly
            115                 120                 125

Thr Tyr Thr Gly Ala Val Gly Ile Pro Glu Ser Pro Pro Ser Glu Lys
    130                 135                 140

Tyr Pro Ser Ala Gly Lys Ile Lys Leu Val Thr Ala Lys
145                 150                 155

<210> SEQ ID NO 36
<211> LENGTH: 224
<212> TYPE: PRT
<213> ORGANISM: Juniperus ashei

<400> SEQUENCE: 36

Met Ala Arg Val Ser Glu Leu Ala Phe Leu Leu Ala Ala Thr Leu Ala
1               5                   10                  15

Ile Ser Leu His Met Gln Glu Ala Gly Val Val Lys Phe Asp Ile Lys
            20                  25                  30

Asn Gln Cys Gly Tyr Thr Val Trp Ala Ala Gly Leu Pro Gly Gly Gly
            35                  40                  45

Lys Arg Leu Asp Gln Gly Gln Thr Trp Thr Val Asn Leu Ala Ala Gly
    50                  55                  60

Thr Ala Ser Ala Arg Phe Trp Gly Arg Thr Gly Cys Thr Phe Asp Ala
65                  70                  75                  80

Ser Gly Lys Gly Ser Cys Gln Thr Gly Asp Cys Gly Gly Gln Leu Ser
                85                  90                  95

Cys Thr Val Ser Gly Ala Val Pro Ala Thr Leu Ala Glu Tyr Thr Gln
            100                 105                 110

Ser Asp Gln Asp Tyr Tyr Asp Val Ser Leu Val Asp Gly Phe Asn Ile
            115                 120                 125

Pro Leu Ala Ile Asn Pro Thr Asn Ala Gln Cys Thr Ala Pro Ala Cys
    130                 135                 140

Lys Ala Asp Ile Asn Ala Val Cys Pro Ser Glu Leu Lys Val Asp Gly
145                 150                 155                 160

Gly Cys Asn Ser Ala Cys Asn Val Phe Lys Thr Asp Gln Tyr Cys Cys
                165                 170                 175

Arg Asn Ala Tyr Val Asp Asn Cys Pro Ala Thr Asn Tyr Ser Lys Ile
            180                 185                 190

Phe Lys Asn Gln Cys Pro Gln Ala Tyr Ser Tyr Ala Lys Asp Asp Thr
            195                 200                 205

Ala Thr Phe Ala Cys Ala Ser Gly Thr Asp Tyr Ser Ile Val Phe Cys
    210                 215                 220

<210> SEQ ID NO 37
<211> LENGTH: 24
<212> TYPE: PRT
<213> ORGANISM: Hordeum vulgare

<400> SEQUENCE: 37

Met Ala Asn Lys His Leu Ser Leu Ser Leu Phe Leu Val Leu Leu Gly
1               5                   10                  15

Leu Ser Ala Ser Leu Ala Ser Gly
            20

<210> SEQ ID NO 38

```
<211> LENGTH: 27
<212> TYPE: PRT
<213> ORGANISM: Nicotiana plumbaginifolia

<400> SEQUENCE: 38

Glu Met Gly Lys Met Ala Ser Leu Phe Ala Ser Leu Leu Val Val Leu
1               5                   10                  15

Val Ser Leu Ser Leu Ala Ser Glu Ser Ser Ala
            20                  25

<210> SEQ ID NO 39
<211> LENGTH: 26
<212> TYPE: PRT
<213> ORGANISM: Nicotiana plumbaginifolia

<400> SEQUENCE: 39

Met Gly Lys Met Ala Ser Leu Phe Ala Thr Phe Leu Val Val Leu Val
1               5                   10                  15

Ser Leu Ser Leu Ala Ser Glu Ser Ser Ala
            20                  25

<210> SEQ ID NO 40
<211> LENGTH: 78
<212> TYPE: DNA
<213> ORGANISM: Nicotiana plumbaginifolia

<400> SEQUENCE: 40
atgggtaaga tggcttctct gtttgcttct ctgctggttg ttctggtttc tctgtctctg      60
gcttctgaat cttctgct                                                    78

<210> SEQ ID NO 41
<211> LENGTH: 78
<212> TYPE: DNA
<213> ORGANISM: Nicotiana plumbaginifolia

<400> SEQUENCE: 41
atgggtaaga tggcttctct gtttgctact tttctggttg ttctggtttc tctgtctctg      60
gcttctgaat cttctgct                                                    78

<210> SEQ ID NO 42
<211> LENGTH: 224
<212> TYPE: PRT
<213> ORGANISM: Juniperus ashei

<400> SEQUENCE: 42

Lys Phe Asp Ile Lys Asn Gln Cys Gly Tyr Thr Val Trp Ala Ala Gly
1               5                   10                  15

Leu Pro Gly Gly Gly Lys Arg Leu Asp Gln Gly Gln Thr Trp Thr Val
            20                  25                  30

Asn Leu Ala Ala Gly Thr Ala Ser Ala Arg Phe Trp Gly Arg Thr Gly
        35                  40                  45

Cys Thr Phe Asp Ala Ser Gly Lys Gly Ser Cys Gln Thr Gly Asp Cys
    50                  55                  60

Gly Gly Gln Leu Ser Cys Thr Val Ser Gly Ala Val Pro Ala Thr Leu
65                  70                  75                  80

Ala Glu Tyr Thr Gln Ser Asp Gln Asp Tyr Tyr Asp Val Ser Leu Val
                85                  90                  95

Asp Gly Phe Asn Ile Pro Leu Ala Ile Asn Pro Thr Asn Ala Gln Cys
            100                 105                 110
```

-continued

Thr Ala Pro Ala Cys Lys Ala Asp Ile Asn Ala Val Cys Pro Ser Glu
        115                 120                 125

Leu Lys Val Asp Gly Gly Cys Asn Ser Ala Cys Asn Val Phe Lys Thr
        130                 135                 140

Asp Gln Tyr Cys Cys Arg Asn Ala Tyr Val Asp Asn Cys Pro Ala Thr
145                 150                 155                 160

Asn Tyr Ser Lys Ile Phe Lys Asn Gln Cys Pro Gln Ala Tyr Ser Tyr
                165                 170                 175

Ala Lys Asp Asp Thr Ala Thr Phe Ala Cys Ala Ser Gly Thr Asp Tyr
                180                 185                 190

Ser Ile Val Phe Cys Met Ala Arg Val Ser Glu Leu Ala Phe Leu Leu
                195                 200                 205

Ala Ala Thr Leu Ala Ile Ser Leu His Met Gln Glu Ala Gly Val Val
        210                 215                 220

<210> SEQ ID NO 43
<211> LENGTH: 105
<212> TYPE: PRT
<213> ORGANISM: Galanthus nivalis

<400> SEQUENCE: 43

Asp Asn Ile Leu Tyr Ser Gly Glu Thr Leu Ser Thr Gly Glu Phe Leu
1                   5                   10                  15

Asn Tyr Gly Ser Phe Val Phe Ile Met Gln Glu Asp Cys Asn Leu Val
                20                  25                  30

Leu Tyr Asp Val Asp Lys Pro Ile Trp Ala Thr Asn Thr Gly Gly Leu
        35                  40                  45

Ser Arg Ser Cys Phe Leu Ser Met Gln Thr Asp Gly Asn Leu Val Val
        50                  55                  60

Tyr Asn Pro Ser Asn Lys Pro Ile Trp Ala Ser Asn Thr Gly Gly Gln
65                  70                  75                  80

Asn Gly Asn Tyr Val Cys Ile Leu Gln Lys Asp Arg Asn Val Val Ile
                85                  90                  95

Tyr Gly Thr Asp Arg Trp Ala Thr Gly
                100                 105

<210> SEQ ID NO 44
<211> LENGTH: 68
<212> TYPE: PRT
<213> ORGANISM: Eratigena agrestis

<400> SEQUENCE: 44

Met Lys Leu Gln Leu Met Ile Cys Leu Val Leu Leu Pro Cys Phe Phe
1                   5                   10                  15

Cys Glu Pro Asp Glu Ile Cys Arg Ala Arg Met Thr Asn Lys Glu Phe
                20                  25                  30

Thr Tyr Lys Ser Asn Val Cys Asn Asn Cys Gly Asp Gln Val Ala Ala
            35                  40                  45

Cys Glu Ala Glu Cys Phe Arg Asn Asp Val Tyr Thr Ala Cys His Glu
        50                  55                  60

Ala Gln Lys Gly
65

<210> SEQ ID NO 45
<211> LENGTH: 68
<212> TYPE: PRT
<213> ORGANISM: Eratigena agrestis -continued

```
<400> SEQUENCE: 45

Met Lys Leu Gln Leu Met Ile Cys Leu Val Leu Leu Pro Cys Phe Phe
1               5                   10                  15

Cys Glu Pro Asp Glu Ile Cys Arg Ala Arg Met Thr Asn Lys Glu Phe
            20                  25                  30

Thr Tyr Lys Ser Asn Val Cys Asn Asn Cys Gly Asp Gln Val Ala Ala
        35                  40                  45

Cys Glu Ala Glu Cys Phe Arg Asn Asp Val Tyr Thr Ala Cys His Glu
    50                  55                  60

Ala Gln Lys Gly
65

<210> SEQ ID NO 46
<211> LENGTH: 68
<212> TYPE: PRT
<213> ORGANISM: Eratigena agrestis

<400> SEQUENCE: 46

Met Lys Leu Gln Leu Met Ile Cys Leu Val Leu Leu Pro Cys Phe Phe
1               5                   10                  15

Cys Glu Pro Asp Glu Ile Cys Arg Ala Arg Met Thr Asn Lys Glu Phe
            20                  25                  30

Thr Tyr Lys Ser Asn Val Cys Asn Asn Cys Gly Asp Gln Val Ala Ala
        35                  40                  45

Cys Glu Ala Glu Cys Phe Arg Asn Asp Val Tyr Thr Ala Cys His Glu
    50                  55                  60

Ala Gln Lys Gly
65

<210> SEQ ID NO 47
<211> LENGTH: 68
<212> TYPE: PRT
<213> ORGANISM: Eratigena agrestis

<400> SEQUENCE: 47

Met Lys Leu Gln Leu Met Ile Cys Leu Val Leu Leu Pro Cys Phe Phe
1               5                   10                  15

Cys Glu Pro Asp Glu Ile Cys Arg Ala Arg Met Thr Asn Lys Glu Phe
            20                  25                  30

Thr Tyr Lys Ser Asn Val Cys Asn Asn Cys Gly Asp Gln Val Ala Ala
        35                  40                  45

Cys Glu Ala Glu Cys Phe Arg Asn Asp Val Tyr Thr Ala Cys His Glu
    50                  55                  60

Ala Gln Lys Gly
65

<210> SEQ ID NO 48
<211> LENGTH: 68
<212> TYPE: PRT
<213> ORGANISM: Eratigena agrestis

<400> SEQUENCE: 48

Met Lys Leu Gln Leu Met Ile Cys Leu Val Leu Leu Pro Cys Phe Phe
1               5                   10                  15

Cys Glu Pro Asp Glu Ile Cys Arg Ala Arg Met Thr Asn Lys Glu Phe
            20                  25                  30

Thr Tyr Lys Ser Asn Val Cys Asn Asn Cys Gly Asp Gln Val Ala Ala
        35                  40                  45
```

```
Cys Glu Ala Glu Cys Phe Arg Asn Asp Val Tyr Thr Ala Cys His Glu
    50                  55                  60

Ala Gln Lys Gly
65

<210> SEQ ID NO 49
<211> LENGTH: 51
<212> TYPE: PRT
<213> ORGANISM: Artificial sequence
<220> FEATURE:
<223> OTHER INFORMATION: TVP-T43A

<400> SEQUENCE: 49

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Ala Ala Cys His Glu Ala
        35                  40                  45

Gln Lys Gly
    50

<210> SEQ ID NO 50
<211> LENGTH: 50
<212> TYPE: PRT
<213> ORGANISM: Artificial sequence
<220> FEATURE:
<223> OTHER INFORMATION: TVP-T43AdG

<400> SEQUENCE: 50

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Ala Ala Cys His Glu Ala
        35                  40                  45

Gln Lys
    50

<210> SEQ ID NO 51
<211> LENGTH: 51
<212> TYPE: PRT
<213> ORGANISM: Artificial sequence
<220> FEATURE:
<223> OTHER INFORMATION: TVP-R9Q/T43A

<400> SEQUENCE: 51

Glu Pro Asp Glu Ile Cys Arg Ala Gln Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Ala Ala Cys His Glu Ala
        35                  40                  45

Gln Lys Gly
    50

<210> SEQ ID NO 52
<211> LENGTH: 50
<212> TYPE: PRT
<213> ORGANISM: Artificial sequence
<220> FEATURE:
```

-continued

```
<223> OTHER INFORMATION: TVP-R9Q/T43A/dG

<400> SEQUENCE: 52

Glu Pro Asp Glu Ile Cys Arg Ala Gln Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Ala Ala Cys His Glu Ala
        35                  40                  45

Gln Lys
    50

<210> SEQ ID NO 53
<211> LENGTH: 49
<212> TYPE: PRT
<213> ORGANISM: Artificial sequence
<220> FEATURE:
<223> OTHER INFORMATION: TVP-R9Q/T43A/dK-G

<400> SEQUENCE: 53

Glu Pro Asp Glu Ile Cys Arg Ala Gln Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Ala Ala Cys His Glu Ala
        35                  40                  45

Gln

<210> SEQ ID NO 54
<211> LENGTH: 153
<212> TYPE: DNA
<213> ORGANISM: Artificial sequence
<220> FEATURE:
<223> OTHER INFORMATION: TVP-T43A

<400> SEQUENCE: 54
gaaccagacg agatatgcag agcaaggatg accaacaaag aatttaccta taagtccaac      60
gtatgcaata attgtggcga ccaggtggca gcctgcgagg cagagtgctt tcgtaatgac     120
gtttacgctg cttgtcacga ggctcagaaa ggt                                  153

<210> SEQ ID NO 55
<211> LENGTH: 150
<212> TYPE: DNA
<213> ORGANISM: Artificial sequence
<220> FEATURE:
<223> OTHER INFORMATION: TVP-T43AdG

<400> SEQUENCE: 55
gaaccagacg agatatgcag agcaaggatg accaacaaag aatttaccta taagtccaac      60
gtatgcaata attgtggcga ccaggtggca gcctgcgagg cagagtgctt tcgtaatgac     120
gtttacgctg cttgtcacga ggctcagaaa                                      150

<210> SEQ ID NO 56
<211> LENGTH: 153
<212> TYPE: DNA
<213> ORGANISM: Artificial sequence
<220> FEATURE:
<223> OTHER INFORMATION: TVP-R9Q/T43A

<400> SEQUENCE: 56
```
gaaccagacg agatatgcag agcacaaatg accaacaaag aatttaccta taagtccaac        60
gtatgcaata attgtggcga ccaggtggca gcctgcgagg cagagtgctt tcgtaatgac        120
gtttacgcag cttgtcacga ggctcagaaa ggt        153

<210> SEQ ID NO 57
<211> LENGTH: 150
<212> TYPE: DNA
<213> ORGANISM: Artificial sequence
<220> FEATURE:
<223> OTHER INFORMATION: TVP-R9Q/T43A/dG

<400> SEQUENCE: 57
gaaccagacg agatatgcag agcacaaatg accaacaaag aatttaccta taagtccaac        60
gtatgcaata attgtggcga ccaggtggca gcctgcgagg cagagtgctt tcgtaatgac        120
gtttacgctg cttgtcacga ggctcagaaa        150

<210> SEQ ID NO 58
<211> LENGTH: 147
<212> TYPE: DNA
<213> ORGANISM: Artificial sequence
<220> FEATURE:
<223> OTHER INFORMATION: TVP-R9Q/T43A/dK-G

<400> SEQUENCE: 58
gaaccagacg agatatgcag agcacaaatg accaacaaag aatttaccta taagtccaac        60
gtatgcaata attgtggcga ccaggtggca gcctgcgagg cagagtgctt tcgtaatgac        120
gtttacgctg cttgtcacga ggctcag        147

<210> SEQ ID NO 59
<211> LENGTH: 17
<212> TYPE: PRT
<213> ORGANISM: Eratigena agrestis

<400> SEQUENCE: 59

Met Lys Leu Gln Leu Met Ile Cys Leu Val Leu Leu Pro Cys Phe Phe
1               5                   10                  15

Cys

<210> SEQ ID NO 60
<211> LENGTH: 50
<212> TYPE: PRT
<213> ORGANISM: Eratigena agrestis

<400> SEQUENCE: 60

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys
    50

<210> SEQ ID NO 61
<211> LENGTH: 6
<212> TYPE: PRT
<213> ORGANISM: Artificial Sequence
<220> FEATURE:
<223> OTHER INFORMATION: ALKFLV -continued

```
<400> SEQUENCE: 61

Ala Leu Lys Phe Leu Val
1               5

<210> SEQ ID NO 62
<211> LENGTH: 6
<212> TYPE: PRT
<213> ORGANISM: Artificial Sequence
<220> FEATURE:
<223> OTHER INFORMATION: ALKLFV

<400> SEQUENCE: 62

Ala Leu Lys Leu Phe Val
1               5

<210> SEQ ID NO 63
<211> LENGTH: 6
<212> TYPE: PRT
<213> ORGANISM: Artificial Sequence
<220> FEATURE:
<223> OTHER INFORMATION: IFVRLR

<400> SEQUENCE: 63

Ile Phe Val Arg Leu Arg
1               5

<210> SEQ ID NO 64
<211> LENGTH: 6
<212> TYPE: PRT
<213> ORGANISM: Artificial Sequence
<220> FEATURE:
<223> OTHER INFORMATION: LFAAPF

<400> SEQUENCE: 64

Leu Phe Ala Ala Pro Phe
1               5

<210> SEQ ID NO 65
<211> LENGTH: 8
<212> TYPE: PRT
<213> ORGANISM: Artificial Sequence
<220> FEATURE:
<223> OTHER INFORMATION: ALKFLVGS

<400> SEQUENCE: 65

Ala Leu Lys Phe Leu Val Gly Ser
1               5

<210> SEQ ID NO 66
<211> LENGTH: 8
<212> TYPE: PRT
<213> ORGANISM: Artificial Sequence
<220> FEATURE:
<223> OTHER INFORMATION: ALKLFVGS

<400> SEQUENCE: 66

Ala Leu Lys Leu Phe Val Gly Ser
1               5

<210> SEQ ID NO 67
<211> LENGTH: 8
<212> TYPE: PRT
<213> ORGANISM: Artificial Sequence
<220> FEATURE:
<223> OTHER INFORMATION: IFVRLRGS

<400> SEQUENCE: 67
```

Ile Phe Val Arg Leu Arg Gly Ser
1               5

<210> SEQ ID NO 68
<211> LENGTH: 8
<212> TYPE: PRT
<213> ORGANISM: Artificial Sequence
<220> FEATURE:
<223> OTHER INFORMATION: LFAAPFGS

<400> SEQUENCE: 68

Leu Phe Ala Ala Pro Phe Gly Ser
1               5

<210> SEQ ID NO 69
<211> LENGTH: 8
<212> TYPE: PRT
<213> ORGANISM: Artificial Sequence
<220> FEATURE:
<223> OTHER INFORMATION: LFVRLRGS

<400> SEQUENCE: 69

Leu Phe Val Arg Leu Arg Gly Ser
1               5

<210> SEQ ID NO 70
<211> LENGTH: 6
<212> TYPE: PRT
<213> ORGANISM: Artificial Sequence
<220> FEATURE:
<223> OTHER INFORMATION: LGERGS

<400> SEQUENCE: 70

Leu Gly Glu Arg Gly Ser
1               5

<210> SEQ ID NO 71
<211> LENGTH: 51
<212> TYPE: PRT
<213> ORGANISM: Artificial Sequence
<220> FEATURE:
<223> OTHER INFORMATION: TVP-R9F

<400> SEQUENCE: 71

Glu Pro Asp Glu Ile Cys Arg Ala Phe Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 72
<211> LENGTH: 51
<212> TYPE: PRT
<213> ORGANISM: Artificial sequence
<220> FEATURE:
<223> OTHER INFORMATION: TVP-R9P

<400> SEQUENCE: 72

Glu Pro Asp Glu Ile Cys Arg Ala Pro Met Thr Asn Lys Glu Phe Thr
1               5                   10                  15

Tyr Lys Ser Asn Val Cys Asn Asn Cys Gly Asp Gln Val Ala Ala Cys

-continued

```
              20              25              30

Glu Ala Glu Cys Phe Arg Asn Asp Val Tyr Thr Ala Cys His Glu Ala
        35              40              45

Gln Lys Gly
    50

<210> SEQ ID NO 73
<211> LENGTH: 51
<212> TYPE: PRT
<213> ORGANISM: Artificial sequence
<220> FEATURE:
<223> OTHER INFORMATION: TVP-R9Y

<400> SEQUENCE: 73

Glu Pro Asp Glu Ile Cys Arg Ala Tyr Met Thr Asn Lys Glu Phe Thr
1               5               10              15

Tyr Lys Ser Asn Val Cys Asn Asn Cys Gly Asp Gln Val Ala Ala Cys
            20              25              30

Glu Ala Glu Cys Phe Arg Asn Asp Val Tyr Thr Ala Cys His Glu Ala
        35              40              45

Gln Lys Gly
    50

<210> SEQ ID NO 74
<211> LENGTH: 51
<212> TYPE: PRT
<213> ORGANISM: Artificial sequence
<220> FEATURE:
<223> OTHER INFORMATION: TVP-R9K

<400> SEQUENCE: 74

Glu Pro Asp Glu Ile Cys Arg Ala Lys Met Thr Asn Lys Glu Phe Thr
1               5               10              15

Tyr Lys Ser Asn Val Cys Asn Asn Cys Gly Asp Gln Val Ala Ala Cys
            20              25              30

Glu Ala Glu Cys Phe Arg Asn Asp Val Tyr Thr Ala Cys His Glu Ala
        35              40              45

Gln Lys Gly
    50

<210> SEQ ID NO 75
<211> LENGTH: 51
<212> TYPE: PRT
<213> ORGANISM: Artificial sequence
<220> FEATURE:
<223> OTHER INFORMATION: TVP-R9W

<400> SEQUENCE: 75

Glu Pro Asp Glu Ile Cys Arg Ala Trp Met Thr Asn Lys Glu Phe Thr
1               5               10              15

Tyr Lys Ser Asn Val Cys Asn Asn Cys Gly Asp Gln Val Ala Ala Cys
            20              25              30

Glu Ala Glu Cys Phe Arg Asn Asp Val Tyr Thr Ala Cys His Glu Ala
        35              40              45

Gln Lys Gly
    50

<210> SEQ ID NO 76
<211> LENGTH: 51
<212> TYPE: PRT
<213> ORGANISM: Artificial sequence
```

```
<220> FEATURE:
<223> OTHER INFORMATION: TVP-R9H

<400> SEQUENCE: 76

Glu Pro Asp Glu Ile Cys Arg Ala His Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 77
<211> LENGTH: 51
<212> TYPE: PRT
<213> ORGANISM: Artificial sequence
<220> FEATURE:
<223> OTHER INFORMATION: TVP-R9A

<400> SEQUENCE: 77

Glu Pro Asp Glu Ile Cys Arg Ala Ala Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 78
<211> LENGTH: 51
<212> TYPE: PRT
<213> ORGANISM: Artificial sequence
<220> FEATURE:
<223> OTHER INFORMATION: TVP-R9G

<400> SEQUENCE: 78

Glu Pro Asp Glu Ile Cys Arg Ala Gly Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 79
<211> LENGTH: 51
<212> TYPE: PRT
<213> ORGANISM: Artificial sequence
<220> FEATURE:
<223> OTHER INFORMATION: TVP-R9N

<400> SEQUENCE: 79

Glu Pro Asp Glu Ile Cys Arg Ala Asn Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45
```

Gln Lys Gly
    50

<210> SEQ ID NO 80
<211> LENGTH: 51
<212> TYPE: PRT
<213> ORGANISM: Artificial sequence
<220> FEATURE:
<223> OTHER INFORMATION: TVP-R9L

<400> SEQUENCE: 80

Glu Pro Asp Glu Ile Cys Arg Ala Leu Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 81
<211> LENGTH: 51
<212> TYPE: PRT
<213> ORGANISM: Artificial sequence
<220> FEATURE:
<223> OTHER INFORMATION: TVP-R9D

<400> SEQUENCE: 81

Glu Pro Asp Glu Ile Cys Arg Ala Asp Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 82
<211> LENGTH: 51
<212> TYPE: PRT
<213> ORGANISM: Artificial sequence
<220> FEATURE:
<223> OTHER INFORMATION: TVP-R9V

<400> SEQUENCE: 82

Glu Pro Asp Glu Ile Cys Arg Ala Val Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 83
<211> LENGTH: 51
<212> TYPE: PRT
<213> ORGANISM: Artificial sequence
<220> FEATURE:
<223> OTHER INFORMATION: TVP-R9M

<400> SEQUENCE: 83

```
Glu Pro Asp Glu Ile Cys Arg Ala Met Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 84
<211> LENGTH: 51
<212> TYPE: PRT
<213> ORGANISM: Artificial sequence
<220> FEATURE:
<223> OTHER INFORMATION: TVP-R9I

<400> SEQUENCE: 84

Glu Pro Asp Glu Ile Cys Arg Ala Ile Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 85
<211> LENGTH: 51
<212> TYPE: PRT
<213> ORGANISM: Artificial sequence
<220> FEATURE:
<223> OTHER INFORMATION: TVP-R9Q/ T43A

<400> SEQUENCE: 85

Glu Pro Asp Glu Ile Cys Arg Ala Gln Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Ala Ala Cys His Glu Ala
        35                  40                  45

Gln Lys Gly
    50

<210> SEQ ID NO 86
<211> LENGTH: 51
<212> TYPE: PRT
<213> ORGANISM: Artificial sequence
<220> FEATURE:
<223> OTHER INFORMATION: TVP-R9Q

<400> SEQUENCE: 86

Glu Pro Asp Glu Ile Cys Arg Ala Gln Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50
```

<210> SEQ ID NO 87
<211> LENGTH: 51
<212> TYPE: PRT
<213> ORGANISM: Artificial sequence
<220> FEATURE:
<223> OTHER INFORMATION: TVP-R9C

<400> SEQUENCE: 87

Glu Pro Asp Glu Ile Cys Arg Ala Cys Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 88
<211> LENGTH: 51
<212> TYPE: PRT
<213> ORGANISM: Artificial sequence
<220> FEATURE:
<223> OTHER INFORMATION: TVP-R9E

<400> SEQUENCE: 88

Glu Pro Asp Glu Ile Cys Arg Ala Glu Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 89
<211> LENGTH: 51
<212> TYPE: PRT
<213> ORGANISM: Artificial sequence
<220> FEATURE:
<223> OTHER INFORMATION: TVP-R9T

<400> SEQUENCE: 89

Glu Pro Asp Glu Ile Cys Arg Ala Thr Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Thr Ala Cys His Glu Ala
        35                  40                  45

Gln Lys Gly
    50

<210> SEQ ID NO 90
<211> LENGTH: 51
<212> TYPE: PRT
<213> ORGANISM: Artificial sequence
<220> FEATURE:
<223> OTHER INFORMATION: TVP-R9S

<400> SEQUENCE: 90

Glu Pro Asp Glu Ile Cys Arg Ala Ser Met Thr Asn Lys Glu Phe Thr
1               5                   10                  15

-continued

```
Tyr Lys Ser Asn Val Cys Asn Asn Cys Gly Asp Gln Val Ala Ala Cys
        20                  25                  30

Glu Ala Glu Cys Phe Arg Asn Asp Val Tyr Thr Ala Cys His Glu Ala
        35                  40                  45

Gln Lys Gly
    50

<210> SEQ ID NO 91
<211> LENGTH: 51
<212> TYPE: PRT
<213> ORGANISM: Artificial sequence
<220> FEATURE:
<223> OTHER INFORMATION: TVP-T43F

<400> SEQUENCE: 91

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
        20                  25                  30

Glu Ala Glu Cys Phe Arg Asn Asp Val Tyr Phe Ala Cys His Glu Ala
        35                  40                  45

Gln Lys Gly
    50

<210> SEQ ID NO 92
<211> LENGTH: 51
<212> TYPE: PRT
<213> ORGANISM: Artificial sequence
<220> FEATURE:
<223> OTHER INFORMATION: TVP-T43P

<400> SEQUENCE: 92

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
        20                  25                  30

Glu Ala Glu Cys Phe Arg Asn Asp Val Tyr Pro Ala Cys His Glu Ala
        35                  40                  45

Gln Lys Gly
    50

<210> SEQ ID NO 93
<211> LENGTH: 51
<212> TYPE: PRT
<213> ORGANISM: Artificial sequence
<220> FEATURE:
<223> OTHER INFORMATION: TVP-T43Y

<400> SEQUENCE: 93

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
        20                  25                  30

Glu Ala Glu Cys Phe Arg Asn Asp Val Tyr Tyr Ala Cys His Glu Ala
        35                  40                  45

Gln Lys Gly
    50

<210> SEQ ID NO 94
<211> LENGTH: 51
<212> TYPE: PRT
```

-continued

```
<213> ORGANISM: Artificial sequence
<220> FEATURE:
<223> OTHER INFORMATION: TVP-T43K

<400> SEQUENCE: 94

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Lys Ala Cys His Glu Ala
        35                  40                  45

Gln Lys Gly
    50

<210> SEQ ID NO 95
<211> LENGTH: 51
<212> TYPE: PRT
<213> ORGANISM: Artificial sequence
<220> FEATURE:
<223> OTHER INFORMATION: TVP-T43W

<400> SEQUENCE: 95

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Trp Ala Cys His Glu Ala
        35                  40                  45

Gln Lys Gly
    50

<210> SEQ ID NO 96
<211> LENGTH: 51
<212> TYPE: PRT
<213> ORGANISM: Artificial sequence
<220> FEATURE:
<223> OTHER INFORMATION: TVP-T43H

<400> SEQUENCE: 96

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr His Ala Cys His Glu Ala
        35                  40                  45

Gln Lys Gly
    50

<210> SEQ ID NO 97
<211> LENGTH: 51
<212> TYPE: PRT
<213> ORGANISM: Artificial sequence
<220> FEATURE:
<223> OTHER INFORMATION: TVP-T43A

<400> SEQUENCE: 97

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Ala Ala Cys His Glu Ala
```

```
            35                  40                  45

Gln Lys Gly
    50

<210> SEQ ID NO 98
<211> LENGTH: 51
<212> TYPE: PRT
<213> ORGANISM: Artificial sequence
<220> FEATURE:
<223> OTHER INFORMATION: TVP-T43G

<400> SEQUENCE: 98

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Gly Ala Cys His Glu Ala
        35                  40                  45

Gln Lys Gly
    50

<210> SEQ ID NO 99
<211> LENGTH: 51
<212> TYPE: PRT
<213> ORGANISM: Artificial sequence
<220> FEATURE:
<223> OTHER INFORMATION: TVP-T43N

<400> SEQUENCE: 99

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Asn Ala Cys His Glu Ala
        35                  40                  45

Gln Lys Gly
    50

<210> SEQ ID NO 100
<211> LENGTH: 51
<212> TYPE: PRT
<213> ORGANISM: Artificial sequence
<220> FEATURE:
<223> OTHER INFORMATION: TVP-T43L

<400> SEQUENCE: 100

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Leu Ala Cys His Glu Ala
        35                  40                  45

Gln Lys Gly
    50

<210> SEQ ID NO 101
<211> LENGTH: 51
<212> TYPE: PRT
<213> ORGANISM: Artificial sequence
<220> FEATURE:
<223> OTHER INFORMATION: TVP-T43D
```

```
<400> SEQUENCE: 101

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Asp Ala Cys His Glu Ala
        35                  40                  45

Gln Lys Gly
    50

<210> SEQ ID NO 102
<211> LENGTH: 51
<212> TYPE: PRT
<213> ORGANISM: Artificial sequence
<220> FEATURE:
<223> OTHER INFORMATION: TVP-T43V

<400> SEQUENCE: 102

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Val Ala Cys His Glu Ala
        35                  40                  45

Gln Lys Gly
    50

<210> SEQ ID NO 103
<211> LENGTH: 51
<212> TYPE: PRT
<213> ORGANISM: Artificial sequence
<220> FEATURE:
<223> OTHER INFORMATION: TVP-T43M

<400> SEQUENCE: 103

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Met Ala Cys His Glu Ala
        35                  40                  45

Gln Lys Gly
    50

<210> SEQ ID NO 104
<211> LENGTH: 51
<212> TYPE: PRT
<213> ORGANISM: Artificial sequence
<220> FEATURE:
<223> OTHER INFORMATION: TVP-T43I

<400> SEQUENCE: 104

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Ile Ala Cys His Glu Ala
        35                  40                  45

Gln Lys Gly
    50
```

<210> SEQ ID NO 105
<211> LENGTH: 51
<212> TYPE: PRT
<213> ORGANISM: Artificial sequence
<220> FEATURE:
<223> OTHER INFORMATION: TVP-T43Q

<400> SEQUENCE: 105

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Gln Ala Cys His Glu Ala
        35                  40                  45

Gln Lys Gly
    50

<210> SEQ ID NO 106
<211> LENGTH: 51
<212> TYPE: PRT
<213> ORGANISM: Artificial sequence
<220> FEATURE:
<223> OTHER INFORMATION: TVP-T43C

<400> SEQUENCE: 106

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Cys Ala Cys His Glu Ala
        35                  40                  45

Gln Lys Gly
    50

<210> SEQ ID NO 107
<211> LENGTH: 51
<212> TYPE: PRT
<213> ORGANISM: Artificial sequence
<220> FEATURE:
<223> OTHER INFORMATION: TVP-T43E

<400> SEQUENCE: 107

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Glu Ala Cys His Glu Ala
        35                  40                  45

Gln Lys Gly
    50

<210> SEQ ID NO 108
<211> LENGTH: 51
<212> TYPE: PRT
<213> ORGANISM: Artificial sequence
<220> FEATURE:
<223> OTHER INFORMATION: TVP-T43T

<400> SEQUENCE: 108

Glu Pro Asp Glu Ile Cys Arg Ala Arg Met Thr Asn Lys Glu Phe Thr
1               5                   10                  15

Tyr Lys Ser Asn Val Cys Asn Asn Cys Gly Asp Gln Val Ala Ala Cys
         20                  25                  30

Glu Ala Glu Cys Phe Arg Asn Asp Val Tyr Thr Ala Cys His Glu Ala
     35                  40                  45

Gln Lys Gly
     50

<210> SEQ ID NO 109
<211> LENGTH: 51
<212> TYPE: PRT
<213> ORGANISM: Artificial sequence
<220> FEATURE:
<223> OTHER INFORMATION: TVP-T43S

<400> SEQUENCE: 109

Glu Pro Asp Glu Ile Cys Arg Ala Arg Met Thr Asn Lys Glu Phe Thr
1               5                  10                  15

Tyr Lys Ser Asn Val Cys Asn Asn Cys Gly Asp Gln Val Ala Ala Cys
         20                  25                  30

Glu Ala Glu Cys Phe Arg Asn Asp Val Tyr Ser Ala Cys His Glu Ala
     35                  40                  45

Gln Lys Gly
     50

<210> SEQ ID NO 110
<211> LENGTH: 51
<212> TYPE: PRT
<213> ORGANISM: Artificial sequence
<220> FEATURE:
<223> OTHER INFORMATION: TVP-T43R

<400> SEQUENCE: 110

Glu Pro Asp Glu Ile Cys Arg Ala Arg Met Thr Asn Lys Glu Phe Thr
1               5                  10                  15

Tyr Lys Ser Asn Val Cys Asn Asn Cys Gly Asp Gln Val Ala Ala Cys
         20                  25                  30

Glu Ala Glu Cys Phe Arg Asn Asp Val Tyr Arg Ala Cys His Glu Ala
     35                  40                  45

Gln Lys Gly
     50

<210> SEQ ID NO 111
<211> LENGTH: 153
<212> TYPE: DNA
<213> ORGANISM: Artificial sequence
<220> FEATURE:
<223> OTHER INFORMATION: TVP-R9F

<400> SEQUENCE: 111
gaaccagacg agatatgcag agcattcatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 112
<211> LENGTH: 153
<212> TYPE: DNA
<213> ORGANISM: Artificial sequence
<220> FEATURE:
<223> OTHER INFORMATION: TVP-R9P

<400> SEQUENCE: 112

-continued

```
gaaccagacg agatatgcag agcacccatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                 153
```

```
<210> SEQ ID NO 113
<211> LENGTH: 153
<212> TYPE: DNA
<213> ORGANISM: Artificial sequence
<220> FEATURE:
<223> OTHER INFORMATION: TVP-R9Y

<400> SEQUENCE: 113
```

```
gaaccagacg agatatgcag agcatatatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                 153
```

```
<210> SEQ ID NO 114
<211> LENGTH: 153
<212> TYPE: DNA
<213> ORGANISM: Artificial sequence
<220> FEATURE:
<223> OTHER INFORMATION: TVP-R9K

<400> SEQUENCE: 114
```

```
gaaccagacg agatatgcag agcaaaaatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                 153
```

```
<210> SEQ ID NO 115
<211> LENGTH: 153
<212> TYPE: DNA
<213> ORGANISM: Artificial sequence
<220> FEATURE:
<223> OTHER INFORMATION: TVP-R9W

<400> SEQUENCE: 115
```

```
gaaccagacg agatatgcag agcatggatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                 153
```

```
<210> SEQ ID NO 116
<211> LENGTH: 153
<212> TYPE: DNA
<213> ORGANISM: Artificial sequence
<220> FEATURE:
<223> OTHER INFORMATION: TVP-R9H

<400> SEQUENCE: 116
```

```
gaaccagacg agatatgcag agcacatatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                 153
```

```
<210> SEQ ID NO 117
<211> LENGTH: 153
<212> TYPE: DNA
<213> ORGANISM: Artificial sequence
<220> FEATURE:
<223> OTHER INFORMATION: TVP-R9A
```

-continued

```
<400> SEQUENCE: 117
gaaccagacg agatatgcag agcagcaatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 118
<211> LENGTH: 153
<212> TYPE: DNA
<213> ORGANISM: Artificial sequence
<220> FEATURE:
<223> OTHER INFORMATION: TVP-R9G

<400> SEQUENCE: 118
gaaccagacg agatatgcag agcaggaatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 119
<211> LENGTH: 153
<212> TYPE: DNA
<213> ORGANISM: Artificial sequence
<220> FEATURE:
<223> OTHER INFORMATION: TVP-R9N

<400> SEQUENCE: 119
gaaccagacg agatatgcag agcaaatatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 120
<211> LENGTH: 153
<212> TYPE: DNA
<213> ORGANISM: Artificial sequence
<220> FEATURE:
<223> OTHER INFORMATION: TVP-R9L

<400> SEQUENCE: 120
gaaccagacg agatatgcag agcactaatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 121
<211> LENGTH: 153
<212> TYPE: DNA
<213> ORGANISM: Artificial sequence
<220> FEATURE:
<223> OTHER INFORMATION: TVP-R9D

<400> SEQUENCE: 121
gaaccagacg agatatgcag agcagatatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 122
<211> LENGTH: 153
<212> TYPE: DNA
<213> ORGANISM: Artificial sequence
<220> FEATURE:
<223> OTHER INFORMATION: TVP-R9V
```

-continued

<400> SEQUENCE: 122

```
gaaccagacg agatatgcag agcagtcatg accaacaaag aatttaccta taagtccaac     60
gtatgcaata attgtggcga ccaggtggca gcctgcgagg cagagtgctt tcgtaatgac    120
gtttacacag cttgtcacga ggctcagaaa ggt                                 153
```

<210> SEQ ID NO 123
<211> LENGTH: 153
<212> TYPE: DNA
<213> ORGANISM: Artificial sequence
<220> FEATURE:
<223> OTHER INFORMATION: TVP-R9M

<400> SEQUENCE: 123

```
gaaccagacg agatatgcag agcaatgatg accaacaaag aatttaccta taagtccaac     60
gtatgcaata attgtggcga ccaggtggca gcctgcgagg cagagtgctt tcgtaatgac    120
gtttacacag cttgtcacga ggctcagaaa ggt                                 153
```

<210> SEQ ID NO 124
<211> LENGTH: 153
<212> TYPE: DNA
<213> ORGANISM: Artificial sequence
<220> FEATURE:
<223> OTHER INFORMATION: TVP-R9I

<400> SEQUENCE: 124

```
gaaccagacg agatatgcag agcaattatg accaacaaag aatttaccta taagtccaac     60
gtatgcaata attgtggcga ccaggtggca gcctgcgagg cagagtgctt tcgtaatgac    120
gtttacacag cttgtcacga ggctcagaaa ggt                                 153
```

<210> SEQ ID NO 125
<211> LENGTH: 153
<212> TYPE: DNA
<213> ORGANISM: Artificial sequence
<220> FEATURE:
<223> OTHER INFORMATION: TVP-R9Q/ T43A

<400> SEQUENCE: 125

```
gaaccagacg agatatgcag agcacaaatg accaacaaag aatttaccta taagtccaac     60
gtatgcaata attgtggcga ccaggtggca gcctgcgagg cagagtgctt tcgtaatgac    120
gtttacgcag cttgtcacga ggctcagaaa ggt                                 153
```

<210> SEQ ID NO 126
<211> LENGTH: 153
<212> TYPE: DNA
<213> ORGANISM: Artificial sequence
<220> FEATURE:
<223> OTHER INFORMATION: TVP-R9Q

<400> SEQUENCE: 126

```
gaaccagacg agatatgcag agcacaaatg accaacaaag aatttaccta taagtccaac     60
gtatgcaata attgtggcga ccaggtggca gcctgcgagg cagagtgctt tcgtaatgac    120
gtttacacag cttgtcacga ggctcagaaa ggt                                 153
```

<210> SEQ ID NO 127
<211> LENGTH: 153
<212> TYPE: DNA
<213> ORGANISM: Artificial sequence
<220> FEATURE:

-continued

303

<223> OTHER INFORMATION: TVP-R9C

<400> SEQUENCE: 127
gaaccagacg agatatgcag agcatctatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 128
<211> LENGTH: 153
<212> TYPE: DNA
<213> ORGANISM: Artificial sequence
<220> FEATURE:
<223> OTHER INFORMATION: TVP-R9E

<400> SEQUENCE: 128
gaaccagacg agatatgcag agcagaaatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 129
<211> LENGTH: 153
<212> TYPE: DNA
<213> ORGANISM: Artificial sequence
<220> FEATURE:
<223> OTHER INFORMATION: TVP-R9T

<400> SEQUENCE: 129
gaaccagacg agatatgcag agcaactatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 130
<211> LENGTH: 153
<212> TYPE: DNA
<213> ORGANISM: Artificial sequence
<220> FEATURE:
<223> OTHER INFORMATION: TVP-R9S

<400> SEQUENCE: 130
gaaccagacg agatatgcag agcatctatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 131
<211> LENGTH: 153
<212> TYPE: DNA
<213> ORGANISM: Artificial sequence
<220> FEATURE:
<223> OTHER INFORMATION: TVP-T43F

<400> SEQUENCE: 131
gaaccagacg agatatgcag agcaaggatg accaacaaag aatttaccta taagtccaac      60
gtatgcaata attgtggcga ccaggtggca gcctgcgagg cagagtgctt tcgtaatgac     120
gtttactttg cttgtcacga ggctcagaaa ggt                                  153

<210> SEQ ID NO 132
<211> LENGTH: 153
<212> TYPE: DNA
<213> ORGANISM: Artificial sequence -continued

```
<220> FEATURE:
<223> OTHER INFORMATION: TVP-T43P

<400> SEQUENCE: 132
gaaccagacg agatatgcag agcaaggatg accaacaaag aatttaccta taagtccaac      60
gtatgcaata attgtggcga ccaggtggca gcctgcgagg cagagtgctt tcgtaatgac     120
gtttaccctg cttgtcacga ggctcagaaa ggt                                  153

<210> SEQ ID NO 133
<211> LENGTH: 153
<212> TYPE: DNA
<213> ORGANISM: Artificial sequence
<220> FEATURE:
<223> OTHER INFORMATION: TVP-T43Y

<400> SEQUENCE: 133
gaaccagacg agatatgcag agcaaggatg accaacaaag aatttaccta taagtccaac      60
gtatgcaata attgtggcga ccaggtggca gcctgcgagg cagagtgctt tcgtaatgac     120
gtttactatg cttgtcacga ggctcagaaa ggt                                  153

<210> SEQ ID NO 134
<211> LENGTH: 153
<212> TYPE: DNA
<213> ORGANISM: Artificial sequence
<220> FEATURE:
<223> OTHER INFORMATION: TVP-T43K

<400> SEQUENCE: 134
gaaccagacg agatatgcag agcaaggatg accaacaaag aatttaccta taagtccaac      60
gtatgcaata attgtggcga ccaggtggca gcctgcgagg cagagtgctt tcgtaatgac     120
gtttacaaag cttgtcacga ggctcagaaa ggt                                  153

<210> SEQ ID NO 135
<211> LENGTH: 153
<212> TYPE: DNA
<213> ORGANISM: Artificial sequence
<220> FEATURE:
<223> OTHER INFORMATION: TVP-T43W

<400> SEQUENCE: 135
gaaccagacg agatatgcag agcaaggatg accaacaaag aatttaccta taagtccaac      60
gtatgcaata attgtggcga ccaggtggca gcctgcgagg cagagtgctt tcgtaatgac     120
gtttactggg cttgtcacga ggctcagaaa ggt                                  153

<210> SEQ ID NO 136
<211> LENGTH: 153
<212> TYPE: DNA
<213> ORGANISM: Artificial sequence
<220> FEATURE:
<223> OTHER INFORMATION: TVP-T43H

<400> SEQUENCE: 136
gaaccagacg agatatgcag agcaaggatg accaacaaag aatttaccta taagtccaac      60
gtatgcaata attgtggcga ccaggtggca gcctgcgagg cagagtgctt tcgtaatgac     120
gtttaccatg cttgtcacga ggctcagaaa ggt                                  153

<210> SEQ ID NO 137
<211> LENGTH: 153
<212> TYPE: DNA
```

```
<213> ORGANISM: Artificial sequence
<220> FEATURE:
<223> OTHER INFORMATION: TVP-T43A

<400> SEQUENCE: 137
gaaccagacg agatatgcag agcaaggatg accaacaaag aatttaccta taagtccaac    60
gtatgcaata attgtggcga ccaggtggca gcctgcgagg cagagtgctt tcgtaatgac   120
gtttacgctg cttgtcacga ggctcagaaa ggt                                153

<210> SEQ ID NO 138
<211> LENGTH: 153
<212> TYPE: DNA
<213> ORGANISM: Artificial sequence
<220> FEATURE:
<223> OTHER INFORMATION: TVP-T43G

<400> SEQUENCE: 138
gaaccagacg agatatgcag agcaaggatg accaacaaag aatttaccta taagtccaac    60
gtatgcaata attgtggcga ccaggtggca gcctgcgagg cagagtgctt tcgtaatgac   120
gtttacggtg cttgtcacga ggctcagaaa ggt                                153

<210> SEQ ID NO 139
<211> LENGTH: 153
<212> TYPE: DNA
<213> ORGANISM: Artificial sequence
<220> FEATURE:
<223> OTHER INFORMATION: TVP-T43N

<400> SEQUENCE: 139
gaaccagacg agatatgcag agcaaggatg accaacaaag aatttaccta taagtccaac    60
gtatgcaata attgtggcga ccaggtggca gcctgcgagg cagagtgctt tcgtaatgac   120
gtttacaatg cttgtcacga ggctcagaaa ggt                                153

<210> SEQ ID NO 140
<211> LENGTH: 153
<212> TYPE: DNA
<213> ORGANISM: Artificial sequence
<220> FEATURE:
<223> OTHER INFORMATION: TVP-T43L

<400> SEQUENCE: 140
gaaccagacg agatatgcag agcaaggatg accaacaaag aatttaccta taagtccaac    60
gtatgcaata attgtggcga ccaggtggca gcctgcgagg cagagtgctt tcgtaatgac   120
gtttacttag cttgtcacga ggctcagaaa ggt                                153

<210> SEQ ID NO 141
<211> LENGTH: 153
<212> TYPE: DNA
<213> ORGANISM: Artificial sequence
<220> FEATURE:
<223> OTHER INFORMATION: TVP-T43D

<400> SEQUENCE: 141
gaaccagacg agatatgcag agcaaggatg accaacaaag aatttaccta taagtccaac    60
gtatgcaata attgtggcga ccaggtggca gcctgcgagg cagagtgctt tcgtaatgac   120
gtttacgatg cttgtcacga ggctcagaaa ggt                                153

<210> SEQ ID NO 142
<211> LENGTH: 153
```

<212> TYPE: DNA
<213> ORGANISM: Artificial sequence
<220> FEATURE:
<223> OTHER INFORMATION: TVP-T43V

<400> SEQUENCE: 142
gaaccagacg agatatgcag agcaaggatg accaacaaag aatttaccta taagtccaac          60
gtatgcaata attgtggcga ccaggtggca gcctgcgagg cagagtgctt tcgtaatgac         120
gtttacgtcg cttgtcacga ggctcagaaa ggt                                      153

<210> SEQ ID NO 143
<211> LENGTH: 153
<212> TYPE: DNA
<213> ORGANISM: Artificial sequence
<220> FEATURE:
<223> OTHER INFORMATION: TVP-T43M

<400> SEQUENCE: 143
gaaccagacg agatatgcag agcaaggatg accaacaaag aatttaccta taagtccaac          60
gtatgcaata attgtggcga ccaggtggca gcctgcgagg cagagtgctt tcgtaatgac         120
gtttacatgg cttgtcacga ggctcagaaa ggt                                      153

<210> SEQ ID NO 144
<211> LENGTH: 153
<212> TYPE: DNA
<213> ORGANISM: Artificial sequence
<220> FEATURE:
<223> OTHER INFORMATION: TVP-T43I

<400> SEQUENCE: 144
gaaccagacg agatatgcag agcaaggatg accaacaaag aatttaccta taagtccaac          60
gtatgcaata attgtggcga ccaggtggca gcctgcgagg cagagtgctt tcgtaatgac         120
gtttacattg cttgtcacga ggctcagaaa ggt                                      153

<210> SEQ ID NO 145
<211> LENGTH: 153
<212> TYPE: DNA
<213> ORGANISM: Artificial sequence
<220> FEATURE:
<223> OTHER INFORMATION: TVP-T43Q

<400> SEQUENCE: 145
gaaccagacg agatatgcag agcaaggatg accaacaaag aatttaccta taagtccaac          60
gtatgcaata attgtggcga ccaggtggca gcctgcgagg cagagtgctt tcgtaatgac         120
gtttaccaag cttgtcacga ggctcagaaa ggt                                      153

<210> SEQ ID NO 146
<211> LENGTH: 153
<212> TYPE: DNA
<213> ORGANISM: Artificial sequence
<220> FEATURE:
<223> OTHER INFORMATION: TVP-T43C

<400> SEQUENCE: 146
gaaccagacg agatatgcag agcaaggatg accaacaaag aatttaccta taagtccaac          60
gtatgcaata attgtggcga ccaggtggca gcctgcgagg cagagtgctt tcgtaatgac         120
gtttactctg cttgtcacga ggctcagaaa ggt                                      153

<210> SEQ ID NO 147

```
<211> LENGTH: 153
<212> TYPE: DNA
<213> ORGANISM: Artificial sequence
<220> FEATURE:
<223> OTHER INFORMATION: TVP-T43E

<400> SEQUENCE: 147
gaaccagacg agatatgcag agcaaggatg accaacaaag aatttaccta taagtccaac      60
gtatgcaata attgtggcga ccaggtggca gcctgcgagg cagagtgctt tcgtaatgac     120
gtttacgaag cttgtcacga ggctcagaaa ggt                                  153

<210> SEQ ID NO 148
<211> LENGTH: 153
<212> TYPE: DNA
<213> ORGANISM: Artificial sequence
<220> FEATURE:
<223> OTHER INFORMATION: TVP-T43T

<400> SEQUENCE: 148
gaaccagacg agatatgcag agcaaggatg accaacaaag aatttaccta taagtccaac      60
gtatgcaata attgtggcga ccaggtggca gcctgcgagg cagagtgctt tcgtaatgac     120
gtttacacag cttgtcacga ggctcagaaa ggt                                  153

<210> SEQ ID NO 149
<211> LENGTH: 153
<212> TYPE: DNA
<213> ORGANISM: Artificial sequence
<220> FEATURE:
<223> OTHER INFORMATION: TVP-T43S

<400> SEQUENCE: 149
gaaccagacg agatatgcag agcaaggatg accaacaaag aatttaccta taagtccaac      60
gtatgcaata attgtggcga ccaggtggca gcctgcgagg cagagtgctt tcgtaatgac     120
gtttactcag cttgtcacga ggctcagaaa ggt                                  153

<210> SEQ ID NO 150
<211> LENGTH: 153
<212> TYPE: DNA
<213> ORGANISM: Artificial sequence
<220> FEATURE:
<223> OTHER INFORMATION: TVP-T43R

<400> SEQUENCE: 150
gaaccagacg agatatgcag agcaaggatg accaacaaag aatttaccta taagtccaac      60
gtatgcaata attgtggcga ccaggtggca gcctgcgagg cagagtgctt tcgtaatgac     120
gtttacagag cttgtcacga ggctcagaaa ggt                                  153

<210> SEQ ID NO 151
<211> LENGTH: 51
<212> TYPE: PRT
<213> ORGANISM: Artificial sequence
<220> FEATURE:
<223> OTHER INFORMATION: Artificial sequence
<220> FEATURE:
<221> NAME/KEY: VARIANT
<222> LOCATION: (8)..(8)
<223> OTHER INFORMATION: X1 is A, S, or N
<220> FEATURE:
<221> NAME/KEY: VARIANT
<222> LOCATION: (9)..(9)
<223> OTHER INFORMATION: X2 is R, Q, N, A, G, N, L, D, V, M, I, C, E, T,
      or S
<220> FEATURE:
```

-continued

```
<221> NAME/KEY: VARIANT
<222> LOCATION: (11)..(11)
<223> OTHER INFORMATION: X3 is T or P
<220> FEATURE:
<221> NAME/KEY: VARIANT
<222> LOCATION: (18)..(18)
<223> OTHER INFORMATION: X4 is K or A
<220> FEATURE:
<221> NAME/KEY: VARIANT
<222> LOCATION: (38)..(38)
<223> OTHER INFORMATION: X5 is R or A
<220> FEATURE:
<221> NAME/KEY: VARIANT
<222> LOCATION: (43)..(43)
<223> OTHER INFORMATION: X (Z1) is T, S, A, F, P, Y, K, W, H, A, G, N,
      L, V, M, I, Q, C, E, or R
<220> FEATURE:
<221> NAME/KEY: VARIANT
<222> LOCATION: (50)..(50)
<223> OTHER INFORMATION: X6 is K or absent
<220> FEATURE:
<221> NAME/KEY: VARIANT
<222> LOCATION: (51)..(51)
<223> OTHER INFORMATION: X7 is G or absent

<400> SEQUENCE: 151

Glu Pro Asp Glu Ile Cys Arg Xaa Xaa Met Xaa Asn Lys Glu Phe Thr
1               5                   10                  15

Tyr Xaa Ser Asn Val Cys Asn Asn Cys Gly Asp Gln Val Ala Ala Cys
            20                  25                  30

Glu Ala Glu Cys Phe Xaa Asn Asp Val Tyr Xaa Ala Cys His Glu Ala
        35                  40                  45

Gln Xaa Xaa
    50

<210> SEQ ID NO 152
<211> LENGTH: 51
<212> TYPE: PRT
<213> ORGANISM: Artificial sequence
<220> FEATURE:
<223> OTHER INFORMATION: Formula (II)
<220> FEATURE:
<221> NAME/KEY: VARIANT
<222> LOCATION: (9)..(9)
<223> OTHER INFORMATION: X1 is R or Q
<220> FEATURE:
<221> NAME/KEY: VARIANT
<222> LOCATION: (43)..(43)
<223> OTHER INFORMATION: X (Z1) is T or A

<400> SEQUENCE: 152

Glu Pro Asp Glu Ile Cys Arg Ala Xaa Met Thr Asn Lys Glu Phe Thr
1               5                   10                  15

Tyr Lys Ser Asn Val Cys Asn Asn Cys Gly Asp Gln Val Ala Ala Cys
            20                  25                  30

Glu Ala Glu Cys Phe Arg Asn Asp Val Tyr Xaa Ala Cys His Glu Ala
        35                  40                  45

Gln Lys Gly
    50
```